United States Patent
Geierstanger et al.

(10) Patent No.: US 10,392,421 B2
(45) Date of Patent: Aug. 27, 2019

(54) CYTOTOXIC PEPTIDES AND CONJUGATES THEREOF

(71) Applicant: NOVARTIS AG, Basel (CH)

(72) Inventors: Bernhard Hubert Geierstanger, Solana Beach, CA (US); Jan Grunewald, San Diego, CA (US); Yunho Jin, San Diego, CA (US); Weijia Ou, San Diego, CA (US); Tetsuo Uno, San Diego, CA (US); Yongqin Wan, San Diego, CA (US); Xing Wang, San Diego, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/961,531

(22) Filed: Apr. 24, 2018

(65) Prior Publication Data

US 2018/0244717 A1    Aug. 30, 2018

Related U.S. Application Data

(63) Continuation of application No. 15/104,727, filed as application No. PCT/US2014/070800 on Dec. 17, 2014, now Pat. No. 9,988,420.

(60) Provisional application No. 61/917,293, filed on Dec. 17, 2013.

(51) Int. Cl.
| | |
|---|---|
| *C07K 5/02* | (2006.01) |
| *A61K 47/68* | (2017.01) |
| *C07K 7/02* | (2006.01) |
| *C07K 16/32* | (2006.01) |

(52) U.S. Cl.
CPC ........ *C07K 5/0205* (2013.01); *A61K 47/6817* (2017.08); *A61K 47/6851* (2017.08); *C07K 7/02* (2013.01); *C07K 16/32* (2013.01)

(58) Field of Classification Search
CPC ............ A61K 47/6803; A61K 47/6851; A61K 47/545; A61K 47/68; C07K 5/0205; C07K 7/02
See application file for complete search history.

(56) References Cited

U.S. PATENT DOCUMENTS

| | | | |
|---|---|---|---|
| 5,595,756 A | 1/1997 | Bally | |
| 5,654,399 A | 8/1997 | Sakakibara et al. | |
| 5,767,237 A | 6/1998 | Sakakibara et al. | |
| 5,840,699 A | 11/1998 | Sakakibara et al. | |
| 6,004,934 A | 12/1999 | Sakakibara et al. | |
| 6,124,431 A | 9/2000 | Sakakibara et al. | |
| 7,498,298 B2 | 3/2009 | Doronina et al. | |
| 7,745,394 B2 | 6/2010 | Doronina et al. | |
| 7,749,504 B2 | 7/2010 | Cairns et al. | |
| 7,750,116 B1 | 7/2010 | Doronina et al. | |
| 7,803,915 B2 | 9/2010 | Cairns et al. | |
| 7,964,566 B2 | 6/2011 | Doronina et al. | |
| 7,964,567 B2 | 6/2011 | Doronina et al. | |
| 7,968,687 B2 | 6/2011 | McDonagh et al. | |
| 7,994,135 B2 | 8/2011 | Doronina et al. | |
| 8,242,252 B2 | 8/2012 | McDonagh et al. | |
| 8,288,352 B2 | 10/2012 | Doronina | |
| 8,512,707 B2 | 8/2013 | Doronina et al. | |
| 8,557,780 B2 | 10/2013 | Doronina et al. | |
| 8,609,105 B2 | 12/2013 | Senter et al. | |
| 8,703,714 B2 | 4/2014 | Doronina et al. | |
| 8,828,401 B2 | 9/2014 | Doroski et al. | |
| 8,987,209 B2 | 3/2015 | Lerchen et al. | |
| 8,992,932 B2 | 3/2015 | Lerchen et al. | |
| 9,029,406 B2 | 5/2015 | Lerchen et al. | |

(Continued)

FOREIGN PATENT DOCUMENTS

| | | | |
|---|---|---|---|
| WO | 2007103288 | 9/2007 | |
| WO | WO-2013072813 A2 * | 5/2013 | ............... C07K 7/02 |

(Continued)

OTHER PUBLICATIONS

Junutula, et al., "Site-specific conjugation of a cytotoxic drug to an antibody improves the therapeutic index", Nature Biotechnology, Aug. 2008, pp. 925-932, vol. 26, No. 8, Nature Publishing Group, US.

(Continued)

*Primary Examiner* — Kaipeen E Yang
(74) *Attorney, Agent, or Firm* — Daniel E. Raymond; Genomics Institute of the Novartis Research Foundation

(57) ABSTRACT

Disclosed herein are novel cytotoxic peptides of formula (I) as described herein:

Formula (I)

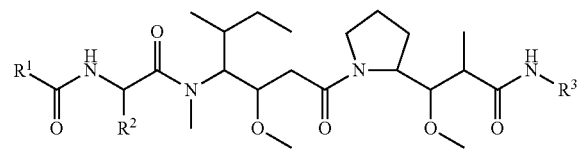

and the use of such peptides in making immunoconjugates (i.e Antibody Drug Conjugates) Also described herein are immunoconjugates (i.e Antibody Drug Conjugates) comprising such novel cytotoxic peptide linked to an antigen binding moiety, such as an antibody; where such immunoconjugates are useful for treating cell proliferative disorders. The invention further provides pharmaceutical compositions comprising these immunoconjugates, compositions comprising the immunoconjugates with a therapeutic co-agent, and methods to use these immunoconjugates and compositions for treating cell proliferation disorders.

12 Claims, 16 Drawing Sheets
Specification includes a Sequence Listing.

(56) References Cited

U.S. PATENT DOCUMENTS

| | | |
|---|---|---|
| 9,073,993 B2 | 7/2015 | McDonagh et al. |
| 9,109,035 B2 | 8/2015 | Liang et al. |
| 9,138,486 B2 | 9/2015 | Doroski et al. |
| 9,249,186 B2 | 2/2016 | Doroski et al. |
| 9,272,052 B2 | 3/2016 | Lewis et al. |
| 9,463,252 B2 | 10/2016 | Senter et al. |
| 2007/0160617 A1 | 7/2007 | Ma et al. |
| 2008/0305044 A1 | 12/2008 | McDonagh et al. |
| 2009/0068178 A1 | 3/2009 | Crowley et al. |
| 2011/0070243 A1 | 3/2011 | Crowley et al. |
| 2016/0052966 A1 | 2/2016 | Miao et al. |

FOREIGN PATENT DOCUMENTS

| | | |
|---|---|---|
| WO | 2013093809 | 6/2013 |
| WO | 2013184514 | 12/2013 |
| WO | 2014124316 | 8/2014 |

OTHER PUBLICATIONS

Strop, et al., "Location Mailers: Site of Conjugation Modulates Stability and Pharmacokinetics of Antibody Drug Conjugates", Chemistry & Biology, Feb. 1, 2013, pp. 161-167, vol. 20, No. 2, Elsevier Ltd.

Junutula, et al., "Supplementary Materials for Site-specific conjugation of a cytotoxic drug to an antibody improves the therapeutic index", Nature Biotechnology, Aug. 2008, pp. 925-932, vol. 26, No. 8, Nature Publishing Group, US.

Axup, et al., "Synthesis of site-specific antibody-drug conjugates using unnatural amino acids", Proceedings of the National Academy of Sciences, Oct. 2, 2012, pp. 16101-16106, vol. 109, No. 40.

Trail, "Antibody Drug conjugates as Cancer Therapeutics", Antibodies, Feb. 27, 2013, pp. 113-129, vol. 2.

Hait, "Anticancer drug development: the grand challenges", Nature Reviews, Apr. 2010, pp. 253-254, vol. 9, Macmillan Publishers Limited.

Sporn, et al., "Chemoprevention of cancer", Carcinogenesis, 2000, pp. 525-530, vol. 21, No. 3, Oxford University Press.

"Cellular and Molecular Basis of Cancer", Merck Manual, Nov. 7, 2012, pp. 1-5.

Pubchem, SID104326166, Feb. 18, 2011, available online at https://pubchem.ncbi.nlm.nih.gov/substance/104326166.

Gravanis, et al., "The changing world of cancer drug development: the regulatory bodies' perspective", Chinese Clinical Oncology, 2014, pp. 1-5, vol. 3, No. 2, Chinese Clinical Oncology.

Neidle, "Failure MOdes in Anticancer Drug Discovery and Development", Cancer Drug Design and Discovery, 2008, pp. 427-431, Elsevier/Academic Press.

Enablement Decision Tree, Example F, situation 1.

* cited by examiner

SEQUENCE LISTING

<160> NUMBER OF SEQ ID NOS: 31

<210> SEQ ID NO 1
<211> LENGTH: 450
<212> TYPE: PRT
<213> ORGANISM: Artificial Sequence
<220> FEATURE:

<223> OTHER INFORMATION: anti-Her2 heavy chain wild type

<400> SEQUENCE: 1

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

```
Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 2
<211> LENGTH: 214
<212> TYPE: PRT
<213> ORGANISM: Artificial Sequence
<220> FEATURE:
<223> OTHER INFORMATION: anti-Her2 light chain wild type

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 108
<212> TYPE: PRT
<213> ORGANISM: Artificial Sequence
<220> FEATURE:
<223> OTHER INFORMATION: constant region of the mutant light chain of
      anti-Her2 LS-S159C and antibody 20507 LC-S159C

<400> SEQUENCE: 3

Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
```

```
                20              25                  30
Phe Tyr Pro Arg Glu Ala Lys Val Gln Trp Lys Val Asp Asn Ala Leu
            35                  40                  45

Gln Ser Gly Asn Cys Gln Glu Ser Val Thr Glu Gln Asp Ser Lys Asp
        50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105
```

<210> SEQ ID NO 4
<211> LENGTH: 331
<212> TYPE: PRT
<213> ORGANISM: Artificial Sequence
<220> FEATURE:
<223> OTHER INFORMATION: constant region of the mutant heavy chain of
      antibody 20507 HC-E155C

<400> SEQUENCE: 4

```
Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Cys Pro Val Thr Val Ser Trp Asn Ser Gly Ala Leu Thr
            35                  40                  45

Ser Gly Val His Thr Phe Pro Ala Val Leu Gln Ser Ser Gly Leu Tyr
        50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
            115                 120                 125

Pro Lys Pro Lys Asp Thr Leu Met Ile Ser Arg Thr Pro Glu Val Thr
        130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270
```

```
Asn Asn Tyr Lys Thr Thr Pro Pro Val Leu Asp Ser Asp Gly Ser Phe
            275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 5
<211> LENGTH: 331
<212> TYPE: PRT
<213> ORGANISM: Artificial Sequence
<220> FEATURE:
<223> OTHER INFORMATION: constant region of the mutant heavy chain of
      antibody 20507 HC-S376C

<400> SEQUENCE: 5

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Cys Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300
```

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 6
<211> LENGTH: 331
<212> TYPE: PRT
<213> ORGANISM: Artificial Sequence
<220> FEATURE:
<223> OTHER INFORMATION: constant region of the mutant light chain of
      anti-Her2-HC-E152C-S375C and antibody 20507-HC-E152C-S375C

<400> SEQUENCE: 6

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Cys Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Cys Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys

```
                    325                 330

<210> SEQ ID NO 7
<211> LENGTH: 108
<212> TYPE: PRT
<213> ORGANISM: Artificial Sequence
<220> FEATURE:
<223> OTHER INFORMATION: constant region of the mutant light chain of
      antibody 20507 LC-K107C

<400> SEQUENCE: 7

Cys Arg Thr Val Ala Ala Pro Ser Val Phe Ile Phe Pro Pro Ser Asp
1               5                  10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105

<210> SEQ ID NO 8
<211> LENGTH: 342
<212> TYPE: PRT
<213> ORGANISM: Artificial Sequence
<220> FEATURE:
<223> OTHER INFORMATION: constant region of the heavy chain of anti-Her2
      HC-ins388-ybbR

<400> SEQUENCE: 8

Ser Ala Ser Thr Lys Gly Pro Ser Val Phe Pro Leu Ala Pro Ser Ser
1               5                  10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
```

```
                    180               185                   190
Leu His Gln Asp Trp Leu Asn Gly Lys Glu Tyr Lys Cys Lys Val Ser
            195                 200                 205

Asn Lys Ala Leu Pro Ala Pro Ile Glu Lys Thr Ile Ser Lys Ala Lys
            210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asp Ser Leu Glu Phe Ile Ala Ser Lys Leu Ala Asn Asn Tyr Lys Thr
            275                 280                 285

Thr Pro Pro Val Leu Asp Ser Asp Gly Ser Phe Phe Leu Tyr Ser Lys
            290                 295                 300

Leu Thr Val Asp Lys Ser Arg Trp Gln Gln Gly Asn Val Phe Ser Cys
305                 310                 315                 320

Ser Val Met His Glu Ala Leu His Asn His Tyr Thr Gln Lys Ser Leu
                325                 330                 335

Ser Leu Ser Pro Gly Lys
            340

<210> SEQ ID NO 9
<211> LENGTH: 343
<212> TYPE: PRT
<213> ORGANISM: Artificial Sequence
<220> FEATURE:
<223> OTHER INFORMATION: constant region of the mutant heavy chain
      HC-ins388-A1 in anti-Her2 and antibody 20507

<400> SEQUENCE: 9

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
            35                  40                  45

Ser Gly Val His Thr Phe Pro Ala Val Leu Gln Ser Ser Gly Leu Tyr
        50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
            130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190
```

Leu His Gln Asp Trp Leu Asn Gly Lys Glu Tyr Lys Cys Lys Val Ser
            195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Gly Asp Ser Leu Asp Met Leu Glu Trp Ser Leu Met Asn Asn Tyr Lys
        275                 280                 285

Thr Thr Pro Pro Val Leu Asp Ser Asp Gly Ser Phe Phe Leu Tyr Ser
    290                 295                 300

Lys Leu Thr Val Asp Lys Ser Arg Trp Gln Gln Gly Asn Val Phe Ser
305                 310                 315                 320

Cys Ser Val Met His Glu Ala Leu His Asn His Tyr Thr Gln Lys Ser
                325                 330                 335

Leu Ser Leu Ser Pro Gly Lys
            340

<210> SEQ ID NO 10
<211> LENGTH: 331
<212> TYPE: PRT
<213> ORGANISM: Artificial Sequence
<220> FEATURE:
<223> OTHER INFORMATION: constant region of the heavy chain wild type of
      antibody 20507

<400> SEQUENCE: 10

Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190

Leu His Gln Asp Trp Leu Asn Gly Lys Glu Tyr Lys Cys Lys Val Ser
        195                 200                 205

```
Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Glu
225                 230                 235                 240

Glu Met Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330

<210> SEQ ID NO 11
<211> LENGTH: 108
<212> TYPE: PRT
<213> ORGANISM: Artificial Sequence
<220> FEATURE:
<223> OTHER INFORMATION: constant region of the light chain wild type of
      antibody 20507

<400> SEQUENCE: 11

Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105

<210> SEQ ID NO 12
<211> LENGTH: 24
<212> TYPE: PRT
<213> ORGANISM: Artificial Sequence
<220> FEATURE:
<223> OTHER INFORMATION: Expression Vector

<400> SEQUENCE: 12

Met Lys Thr Phe Ile Leu Leu Leu Trp Val Leu Leu Trp Val Ile
1               5                   10                  15

Phe Leu Leu Pro Gly Ala Thr Ala
            20

<210> SEQ ID NO 13
<211> LENGTH: 41
<212> TYPE: DNA
<213> ORGANISM: Artificial Sequence
<220> FEATURE:
```

<223> OTHER INFORMATION: primer sequence

<400> SEQUENCE: 13
agcggcaact gtcaggagag cgtcaccgag caggacagca a                41

<210> SEQ ID NO 14
<211> LENGTH: 40
<212> TYPE: DNA
<213> ORGANISM: Artificial Sequence
<220> FEATURE:
<223> OTHER INFORMATION: primer sequence

<400> SEQUENCE: 14
ctctcctgac agttgccgct ctgcagggcg ttgtccacct                  40

<210> SEQ ID NO 15
<211> LENGTH: 39
<212> TYPE: DNA
<213> ORGANISM: Artificial Sequence
<220> FEATURE:
<223> OTHER INFORMATION: primer sesquence

<400> SEQUENCE: 15
tacttcccct gtcccgtgac cgtgtcctgg aacagcgga                   39

<210> SEQ ID NO 16
<211> LENGTH: 38
<212> TYPE: DNA
<213> ORGANISM: Artificial Sequence
<220> FEATURE:
<223> OTHER INFORMATION: primer sequence

<400> SEQUENCE: 16
ggtcacggga caggggaagt agtccttcac caggcagc                    38

<210> SEQ ID NO 17
<211> LENGTH: 40
<212> TYPE: DNA
<213> ORGANISM: Artificial Sequence
<220> FEATURE:
<223> OTHER INFORMATION: primer sequence

<400> SEQUENCE: 17 ttctaccct gcgacatcgc cgtggagtgg gagagcaacg                   40

<210> SEQ ID NO 18
<211> LENGTH: 41
<212> TYPE: DNA
<213> ORGANISM: Artificial Sequence
<220> FEATURE:
<223> OTHER INFORMATION: primer sequence

<400> SEQUENCE: 18
ggcgatgtcg cagggtaga agcccttcac cagacaggtc a                 41

<210> SEQ ID NO 19
<211> LENGTH: 40
<212> TYPE: DNA
<213> ORGANISM: Artificial Sequence
<220> FEATURE:
<223> OTHER INFORMATION: primer sequence

<400> SEQUENCE: 19
gtggagatct gtcgaacggt ggccgctccc agcgtgttca                  40

```
<210> SEQ ID NO 20
<211> LENGTH: 39
<212> TYPE: DNA
<213> ORGANISM: Artificial Sequence
<220> FEATURE:
<223> OTHER INFORMATION: primer sequence

<400> SEQUENCE: 20
accgttcgac agatctccac cttggtaccc tgtccgaac                                39

<210> SEQ ID NO 21
<211> LENGTH: 52
<212> TYPE: DNA
<213> ORGANISM: Artificial Sequence
<220> FEATURE:
<223> OTHER INFORMATION: primer sequence

<400> SEQUENCE: 21
ctggagttca tcgccagcaa gctggccaac aactacaaga ccacacctcc ag                 52

<210> SEQ ID NO 22
<211> LENGTH: 46
<212> TYPE: DNA
<213> ORGANISM: Artificial Sequence
<220> FEATURE:
<223> OTHER INFORMATION: primer sequence

<400> SEQUENCE: 22
cttgctggcg atgaactcca ggctgtcctc gggctggccg ttgctc                        46

<210> SEQ ID NO 23
<211> LENGTH: 52
<212> TYPE: DNA
<213> ORGANISM: Artificial Sequence
<220> FEATURE:
<223> OTHER INFORMATION: primer sequence

<400> SEQUENCE: 23
ctggacatgc tggagtggag cctgatgaac aactacaaga ccacacctcc ag                 52

<210> SEQ ID NO 24
<211> LENGTH: 46
<212> TYPE: DNA
<213> ORGANISM: Artificial Sequence
<220> FEATURE:
<223> OTHER INFORMATION: primer sequence

<400> SEQUENCE: 24
ccactccagc atgtccaggc tgtcgccctc gggctggccg ttgctc                        46

<210> SEQ ID NO 25
<211> LENGTH: 45
<212> TYPE: DNA
<213> ORGANISM: Artificial Sequence
<220> FEATURE:
<223> OTHER INFORMATION: B. subtilis Sfp pET22b primer

<400> SEQUENCE: 25
gaaggagata tacatatgaa aatttatggg atttacatgg atcgc                         45

<210> SEQ ID NO 26
<211> LENGTH: 44
<212> TYPE: DNA
<213> ORGANISM: Artificial Sequence
<220> FEATURE:
<223> OTHER INFORMATION: B. subtilis Sfp pET22b primer
```

<400> SEQUENCE: 26
gtggtggtgg tggtggtgca gcaattcttc ataggagacc atcg        44

<210> SEQ ID NO 27
<211> LENGTH: 22
<212> TYPE: DNA
<213> ORGANISM: Artificial Sequence
<220> FEATURE:
<223> OTHER INFORMATION: pET22b primer

<400> SEQUENCE: 27
caccaccacc accaccactg ag        22

<210> SEQ ID NO 28
<211> LENGTH: 41
<212> TYPE: DNA
<213> ORGANISM: Artificial Sequence
<220> FEATURE:
<223> OTHER INFORMATION: pET22b primer

<400> SEQUENCE: 28
catatgtata tctccttctt aaagttaaac aaaattattt c        41

<210> SEQ ID NO 29
<211> LENGTH: 43
<212> TYPE: DNA
<213> ORGANISM: Artificial Sequence
<220> FEATURE:
<223> OTHER INFORMATION: TEV into B. subtilis Sfp pET22b primer

<400> SEQUENCE: 29
gagaacctgt acttccaagg ccaccaccac caccaccact gag        43

<210> SEQ ID NO 30
<211> LENGTH: 47
<212> TYPE: DNA
<213> ORGANISM: Artificial Sequence
<220> FEATURE:
<223> OTHER INFORMATION: TEV into B. subtilis Sfp pET22b primer

<400> SEQUENCE: 30
gccttggaag tacaggttct ccagcaattc ttcataggag accatcg        47

<210> SEQ ID NO 31
<211> LENGTH: 237
<212> TYPE: PRT
<213> ORGANISM: Artificial Sequence
<220> FEATURE:
<223> OTHER INFORMATION: Bacillus subtilis Sfp PPTase with C-terminal
    TEV cleavage site and His6 tag

<400> SEQUENCE: 31

Met Lys Ile Tyr Gly Ile Tyr Met Asp Arg Pro Leu Ser Gln Glu Glu
1               5                   10                  15

Asn Glu Arg Phe Met Ser Phe Ile Ser Pro Glu Lys Arg Glu Lys Cys
            20                  25                  30

Arg Arg Phe Tyr His Lys Glu Asp Ala His Arg Thr Leu Leu Gly Asp
        35                  40                  45

Val Leu Val Arg Ser Val Ile Ser Arg Gln Tyr Gln Leu Asp Lys Ser
    50                  55                  60

Asp Ile Arg Phe Ser Thr Gln Glu Tyr Gly Lys Pro Cys Ile Pro Asp
65                  70                  75                  80

Leu Pro Asp Ala His Phe Asn Ile Ser His Ser Gly Arg Trp Val Ile

|   |   |   |   |   | 85 |   |   |   |   | 90 |   |   |   |   | 95 |   |   |
|---|---|---|---|---|----|---|---|---|---|----|---|---|---|---|----|---|---|

Cys Ala Phe Asp Ser Gln Pro Ile Gly Ile Asp Ile Glu Lys Thr Lys
            100                 105                 110

Pro Ile Ser Leu Glu Ile Ala Lys Arg Phe Phe Ser Lys Thr Glu Tyr
            115                 120                 125

Ser Asp Leu Leu Ala Lys Asp Lys Asp Glu Gln Thr Asp Tyr Phe Tyr
130                 135                 140

His Leu Trp Ser Met Lys Glu Ser Phe Ile Lys Gln Glu Gly Lys Gly
145                 150                 155                 160

Leu Ser Leu Pro Leu Asp Ser Phe Ser Val Arg Leu His Gln Asp Gly
            165                 170                 175

Gln Val Ser Ile Glu Leu Pro Asp Ser His Ser Pro Cys Tyr Ile Lys
            180                 185                 190

Thr Tyr Glu Val Asp Pro Gly Tyr Lys Met Ala Val Cys Ala Ala His
            195                 200                 205

Pro Asp Phe Pro Glu Asp Ile Thr Met Val Ser Tyr Glu Glu Leu Leu
            210                 215                 220

Glu Asn Leu Tyr Phe Gln Gly His His His His His His
225                 230                 235

CYTOTOXIC PEPTIDES AND CONJUGATES THEREOF

CROSS-REFERENCE TO RELATED APPLICATIONS

This application is a continuation of prior application U.S. application Ser. No. 15/104,727, filed Jun. 15, 2016, which is a 371 U.S. national phase application of international application number PCT/US2014/070800 filed 17 Dec. 2014, which application claims the benefit of priority under 35 U.S.C. § 119(e) to U.S. Provisional Application No. 61/917,293, filed 17 Dec. 2013. The disclosures of which are incorporated herein by reference in their entirety and for all purposes.

FIELD OF THE INVENTION

The invention provides compounds that are anti-mitotic cytotoxic peptides, and are useful to treat cellular proliferative disorders. The invention also includes conjugates that comprise such cytotoxic peptides linked to an antigen-binding moiety, and pharmaceutical compositions containing these conjugates. Also included are methods of using these compounds and conjugates to treat cell proliferation disorders, including cancers.

BACKGROUND

The use of antibody-drug conjugates (ADCs) for the targeted delivery of cell proliferation inhibitors and/or cytotoxic agents to specific cells has been the focus of significant research. Antibody-Drug Conjugate, Methods in Molecular Biology, Vol. 1045, Editor L. Ducry, Humana Press (2013). ADCs include an antibody selected for its ability to bind to a cell targeted for therapeutic intervention, linked to a drug selected for its cytostatic or cytotoxic activity. Binding of the antibody to the targeted cell thereby delivers the drug to the site where its therapeutic effect is needed.

Many antibodies that recognize and selectively bind to targeted cells, like cancer cells, have been disclosed for use in ADCs, and many methods for attaching payload (drug) compounds such as cytotoxins to antibodies have also been described. In spite of the extensive work on ADCs, though, only a few classes of cell proliferation inhibitors have been used extensively as ADC payloads. Even though the first ADC approved for use in humans in the U.S. was launched in 2000 (and later withdrawn from the market), a decade later only a few chemical classes of drug compounds (maytansinoids, auristatins, calicheamycins and duocarmycins) had reached clinical trials as payloads for ADCs. *Antibody-Drug Conjugates: the Next Generation of Moving Parts*, A. Lash, *Start-Up*, December 2011, 1-6. Given the widely acknowledged value of ADCs as therapeutics, particularly for treating cancer, there thus remains a need for cytotoxic peptides with improved properties for use as payloads in ADCs.

SUMMARY OF THE INVENTION

The invention provided herein includes cytotoxic peptides and methods of using such cytotoxic peptides as the drug component of an antibody-drug conjugate (ADC). The present invention includes novel cytotoxic peptides and the use of such novel cytotoxic peptides as payloads for ADCs. The invention further includes methods and intermediates useful for incorporating such novel cytotoxic peptides into ADCs, and methods to use the novel compounds and conjugates to treat cell proliferation disorders. Such cytotoxic peptides are anti-mitotic agents that inhibit cell division by blocking the polymerization of tubulin and thereby blocking nuclear migration and nuclear and cellular division.

In one aspect of the invention are cytotoxic peptides, or stereoisomer thereof, and pharmaceutically acceptable salts thereof, having the structure of Formula (I) wherein:

(Formula (I))

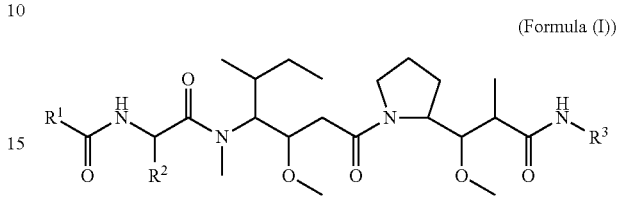

$R^1$ is a C-linked 6 membered heterocycloalkyl containing 1-2 N heteroatoms and a $C_1$-$C_2$alkylene bridge or $R^1$ is a C-linked 5-8 membered fused bicyclic heterocycloalkyl containing 1-2 N heteroatoms, wherein each is unsubstituted, or each is substituted with an $R^7$ and 0 to 3 substituents independently selected from $R^5$ and $R^6$, or each is substituted with 1 to 3 substituents independently selected from $R^5$ and $R^6$;

$R^2$ is —$C_1$-$C_6$alkyl;

$R^3$ is

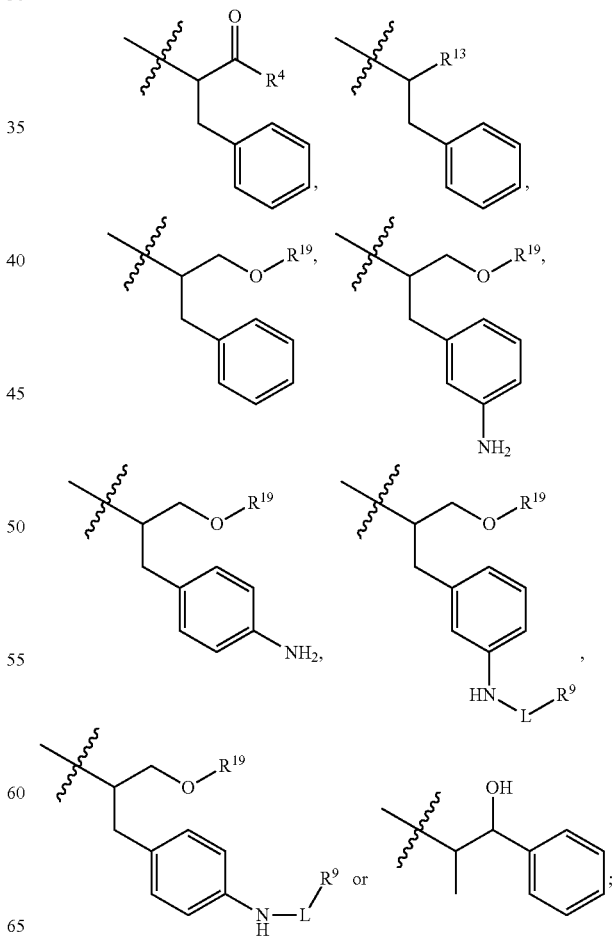

$R^4$ is —OH, $C_1$-$C_6$alkoxy, —N($R^{14}$)$_2$, —$R^{16}$, —$NR^{12}$(CH$_2$)$_m$ N($R^{14}$)$_2$, —$NR^{12}$(CH$_2$)$_m$$R^{16}$, -$LR^9$, —NHS(O)$_2$ $R_{11}$, —NHS(O)$_2$(CH$_2$)$_m$N$_3$, —NHS(=O)$_2$$LR^9$,

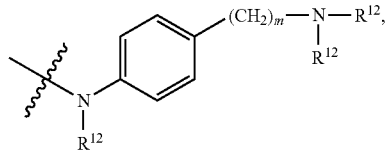

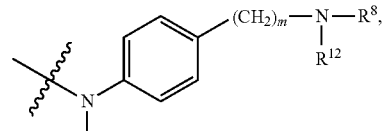

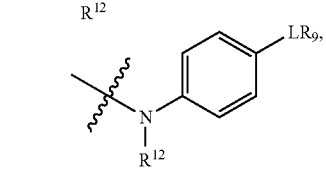

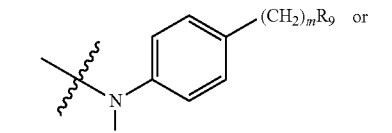

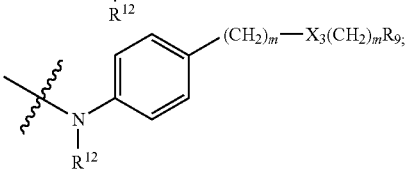

$R^5$ is $C_1$-$C_6$alkyl, —C(=O)$R^{11}$, —(CH$_2$)$_m$OH, —C(=O)(CH$_2$)$_m$OH, —C(=O)((CH$_2$)$_m$O)$_n$$R^{12}$, —((CH$_2$)$_m$O)$_n$$R^{12}$, or $C_1$-$C_6$alkyl which is optionally substituted with —CN, —C(=O)NH$_2$ or 1 to 5 hydroxyl;

$R^6$ is halo, oxo, OH, $C_1$-$C_6$alkyl, —N($R^{14}$)$_2$, —$R^{16}$ and —$NR^{12}$C(=O)$R^{11}$;

$R^7$ is $LR^9$;

$R^8$ is H or $LR^9$;

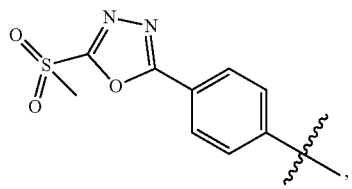

each L is independently selected from -L$_1$L$_2$L$_3$L$_4$L$_5$L$_6$-, -L$_6$L$_5$L$_4$L$_3$L$_2$L$_1$-, -L$_1$L$_2$L$_3$L$_4$L$_5$-, -L$_5$L$_4$L$_3$L$_2$L$_1$-,-L$_1$L$_2$L$_3$L$_4$-, -L$_4$L$_3$L$_2$L$_1$-,-L$_1$L$_2$L$_3$-, -L$_3$L$_2$L$_1$-,-L$_1$L$_2$-, -L$_2$L$_1$- and -L$_1$, wherein -L$_1$, L$_2$, L$_3$, L$_4$, L$_5$, and L$_6$ are as defined herein;

$R^9$ is

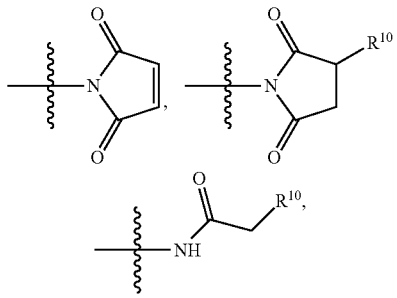

—$NR_{12}$C(=O)CH=CH$_2$, —N$_3$,

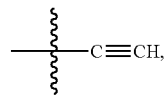

SH, —SS$R^{15}$, —S(=O)$_2$(CH=CH$_2$), —(CH$_2$)$_2$S(=O)$_2$(CH=CH$_2$), —$NR_{12}$S(=O)$_2$(CH=CH$_2$), —$NR_{12}$C(=O)CH$_2$$R^{10}$, —$NR_{12}$C(=O)CH$_2$Br, —$NR_{12}$C(=O)CH$_2$I, —NHC(=O)CH$_2$Br, —NHC(=O)CH$_2$I, —ONH$_2$, —C(O)NHNH$_2$,

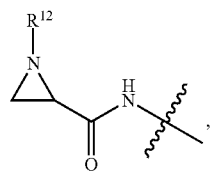

—CO$_2$H, —NH$_2$, —NCO, —NCS,

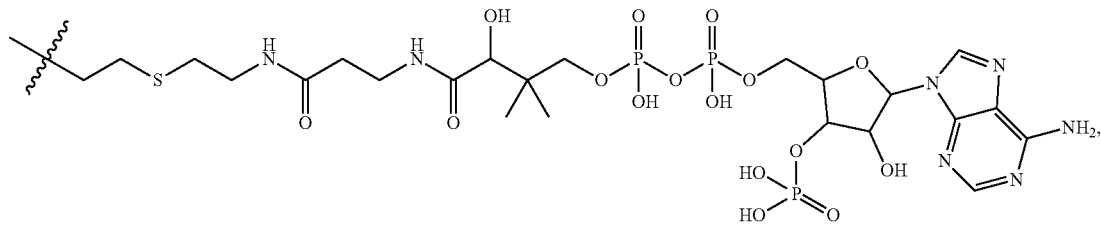

-continued
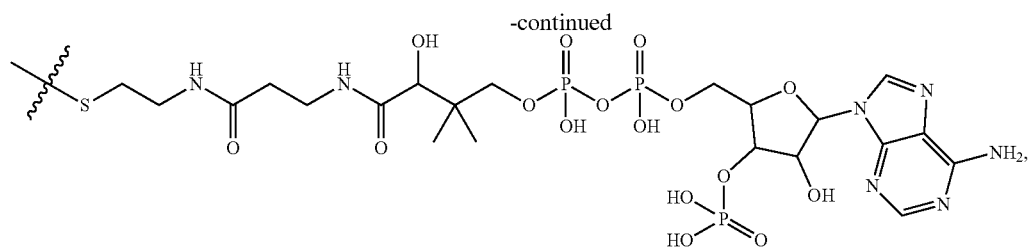
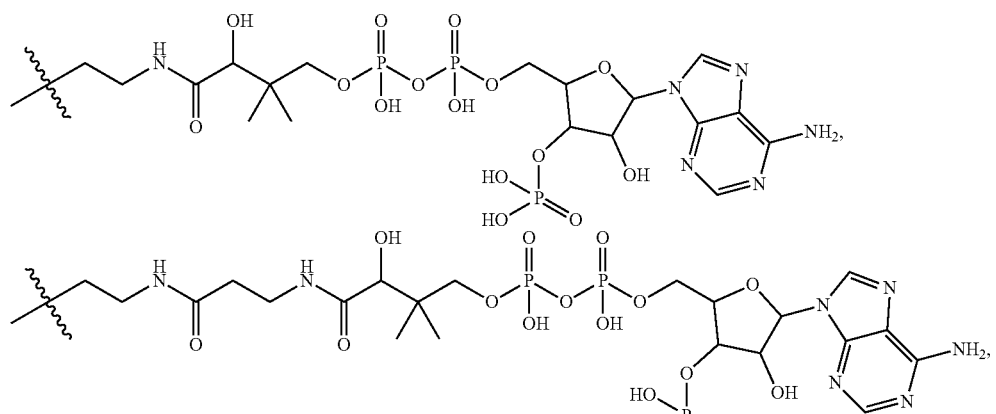
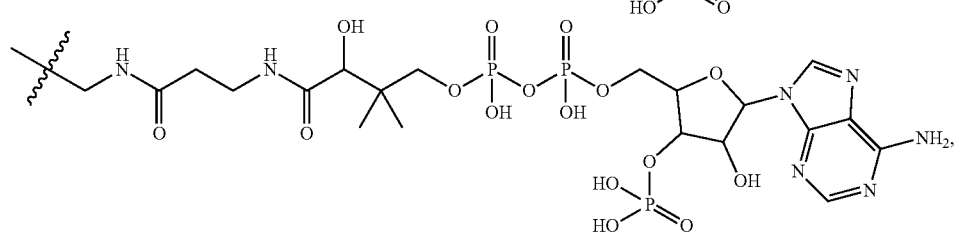
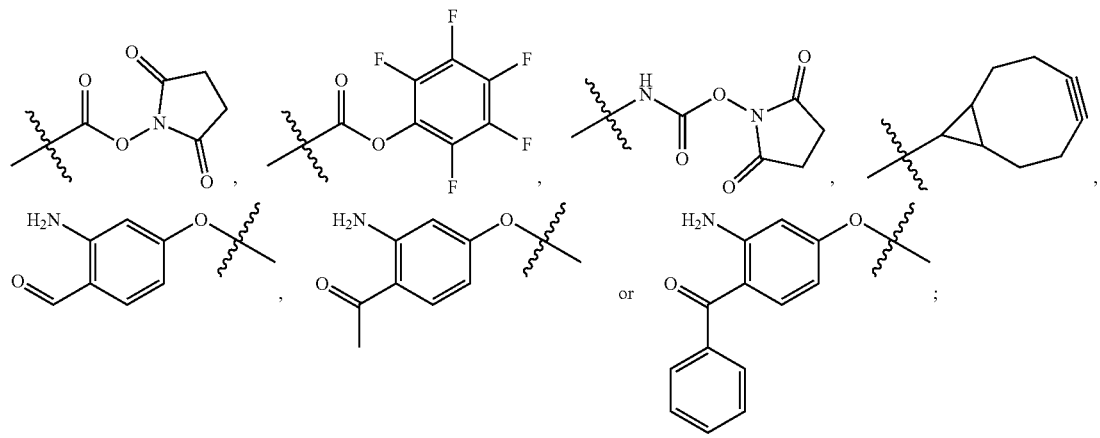
R¹⁰ is
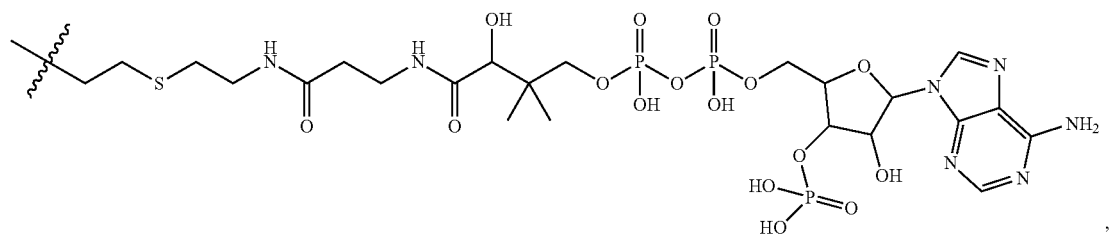

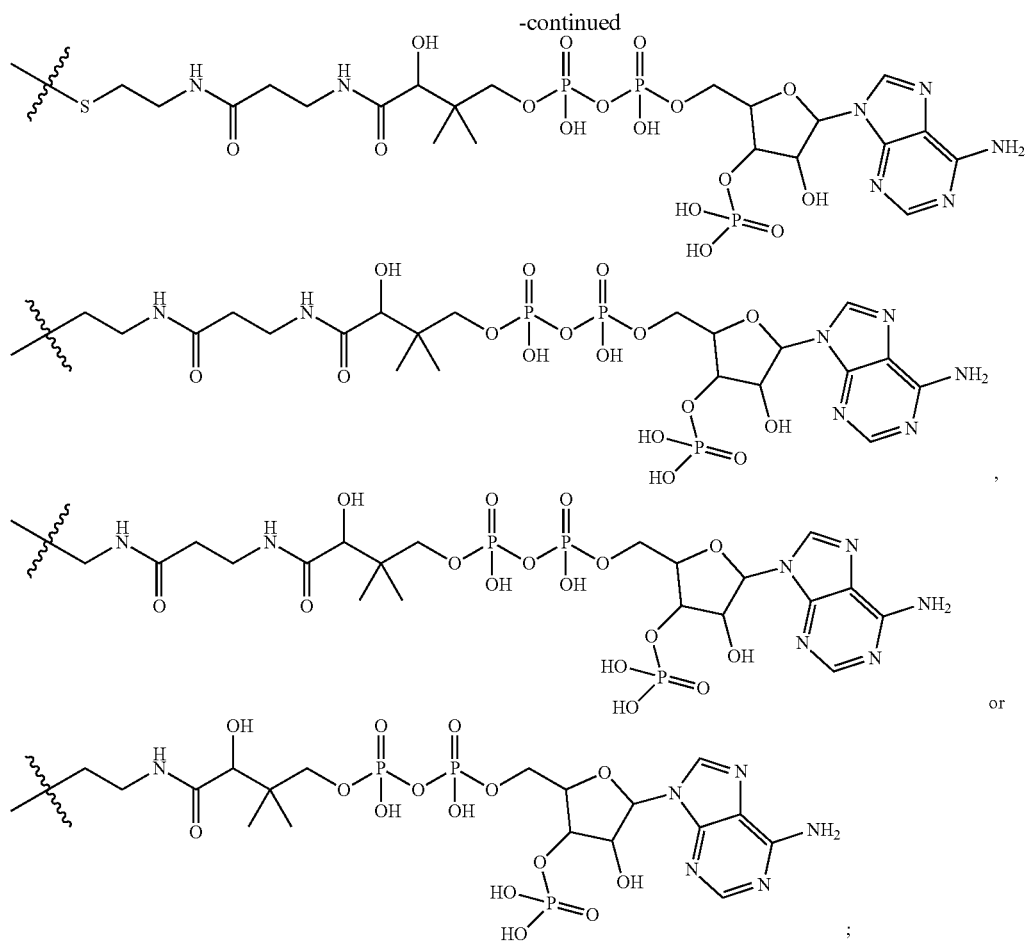

each $R^{11}$ is independently selected from $C_1$-$C_6$alkyl and $C_1$-$C_6$alkyl which is optionally substituted with 1 to 5 hydroxyl;

each $R^{12}$ is independently selected from H and $C_1$-$C_6$alkyl;

$R^{13}$ is tetrazolyl, imidazolyl substituted with phenyl, oxadiazolyl substituted with phenyl, pyrazolyl, pyrimidinyl,

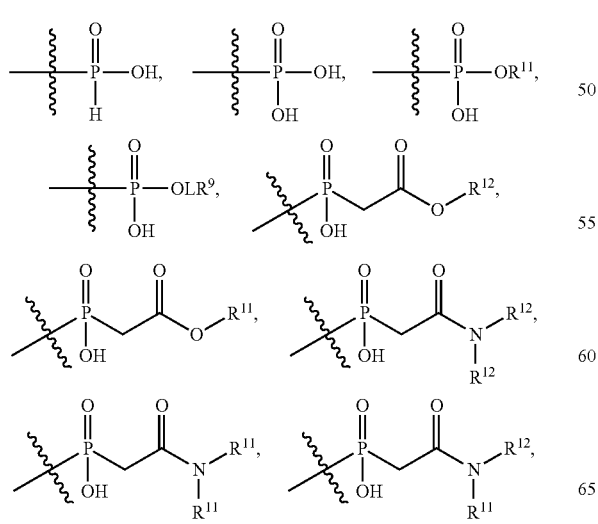

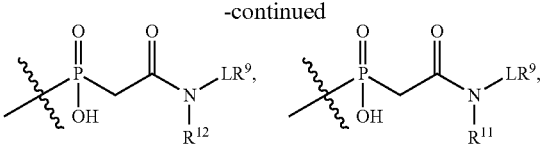

—$CH_2S(=O)_2NH_2$, —$CH_2S(=O)_2NHLR^9$, -$LR^9$ or —$X_4LR^9$;

each $R^{14}$ is independently selected from H and $C_1$-$C_6$alkyl;

$R^{15}$ is 2-pyridyl or 4-pyridyl;

$R^{16}$ is an N-linked 4-8 membered heterocycloalkyl containing 1-2 heteroatoms independently selected from N and O, which is unsubstituted or substituted with -$LR^9$;

each $R^{19}$ is H or $C_1$-$C_6$alkyl;

$X_3$ is

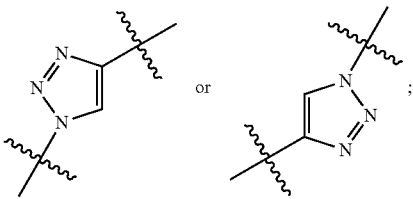 [SMILES: *c1cn(*)nn1 ; *c1cn(*)nn1]

$X_4$ is

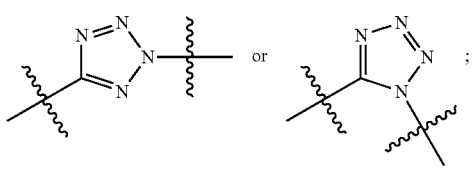 [SMILES: *c1nnn(*)n1 ; *c1nnnn1*]

each m is independently selected from 1, 2, 3, 4, 5, 6, 7, 8, 9 and 10; and each n is independently selected from 1, 2, 3, 4, 5, 6, 7, 8, 9, 10, 11, 12, 13, 14, 15, 16, 17 and 18.

In an embodiment of this aforementioned aspect, $R^1$ is a C-linked 6 membered heterocycloalkyl containing 1-2 N heteroatoms and a $C_1$-$C_2$alkylene bridge or $R^1$ is a C-linked 5-8 membered fused bicyclic heterocycloalkyl containing 1-2 N heteroatoms, wherein each is unsubstituted, or each is substituted with an $R^7$ and 0 to 3 substituents independently selected from $R^5$ and $R^6$, or each is substituted with 1 to 3 substituents independently selected from $R^5$ and $R^6$;

$R^2$ is —$C_1$-$C_6$alkyl;

$R^3$ is

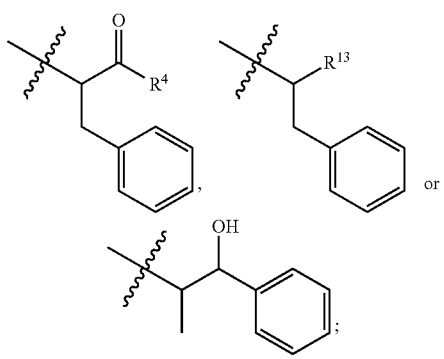

$R^4$ is —OH, $C_1$-$C_6$alkoxy, —N($R^{14}$)$_2$, —$R^{16}$, —$NR^{12}$(CH$_2$)$_m$N($R^{14}$)$_2$, —$NR^{12}$(CH$_2$)$_m$$R^{16}$, -$LR^9$, —NHS(O)$_2$$R_{11}$, —NHS(O)$_2$(CH$_2$)$_m$N$_3$, —NHS(=O)$_2$$LR^9$,

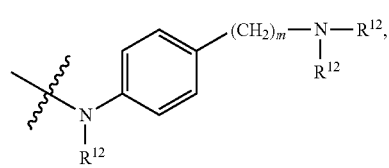

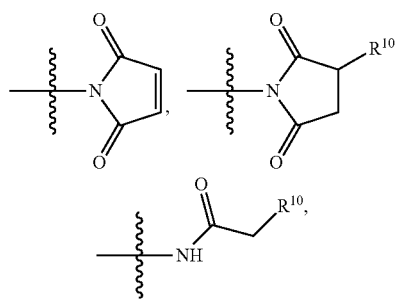

$R^5$ is $C_1$-$C_6$alkyl, $C_1$-$C_6$alkyl which is optionally substituted with 1 to 5 hydroxyl, —C(=O)$R^{11}$, —(CH$_2$)$_m$OH, —C(=O)(CH$_2$)$_m$OH, —C(=O)((CH$_2$)$_m$O)$_n$$R^{12}$, or —((CH$_2$)$_m$O)$_n$$R^{12}$;

$R^6$ is halo, oxo, OH, $C_1$-$C_6$alkyl, —N($R^{14}$)$_2$, —$R^{16}$ and —$NR^{12}$C(=O)$R^{11}$;

$R^7$ is $LR^9$;

$R^8$ is H or $LR^9$;

each L is independently selected from -$L_1L_2L_3L_4L_5L_6$-, -$L_6L_5L_4L_3L_2L_1$-, -$L_1L_2L_3L_4L_5$-, -$L_5L_4L_3L_2L_1$-,-$L_1L_2L_3L_4$-, -$L_4L_3L_2L_1$-,-$L_1L_2L_3$-, -$L_3L_2L_1$-,-$L_1L_2$-, -$L_2L_1$- and -$L_1$, wherein -$L_1$, $L_2$, $L_3$, $L_4$, $L_5$, and $L_6$ are as defined herein;

$R^9$ is

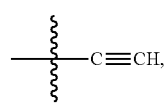

—$NR_{12}$C(=O)CH=CH$_2$, —N$_3$,

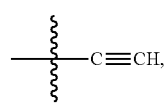

SH, —SS$R^{15}$, —S(=O)$_2$(CH=CH$_2$), —(CH$_2$)$_2$S(=O)$_2$(CH=CH$_2$), —$NR_{12}$S(=O)$_2$(CH=CH$_2$), —$NR_{12}$C(=O)CH$_2$$R^{10}$, —$NR_{12}$C(=O)CH$_2$Br, —$NR_{12}$C(=O)CH$_2$I, —NHC(=O)CH$_2$Br, —NHC(=O)CH$_2$I, —ONH$_2$, —C(O)NHNH$_2$,

11
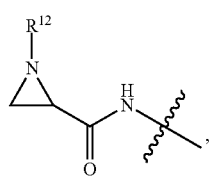
—CO₂H, —NH₂, —NCO, —NCS,
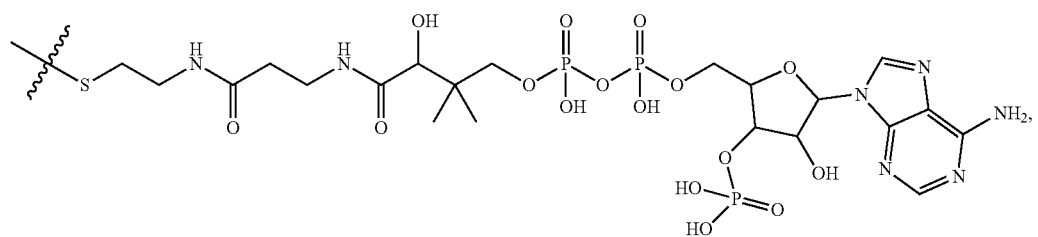
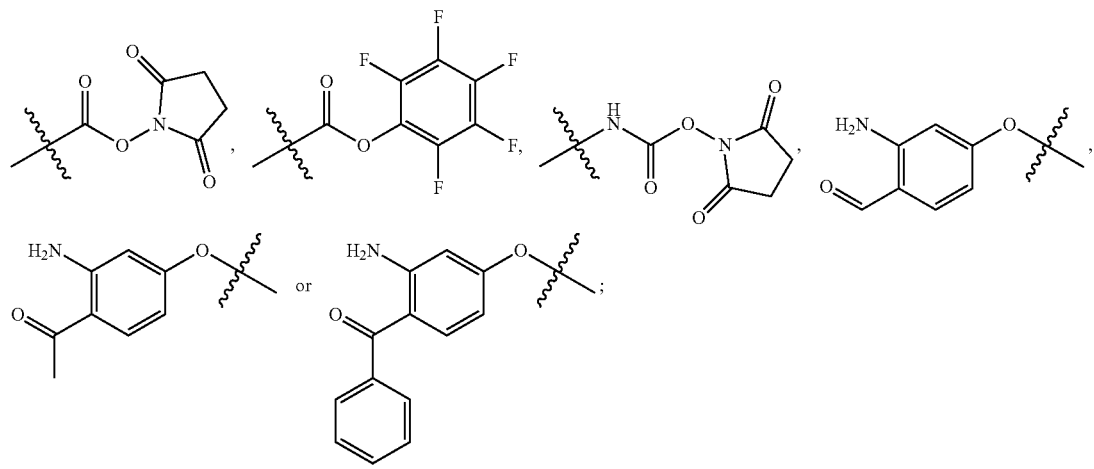
$R^{10}$ is
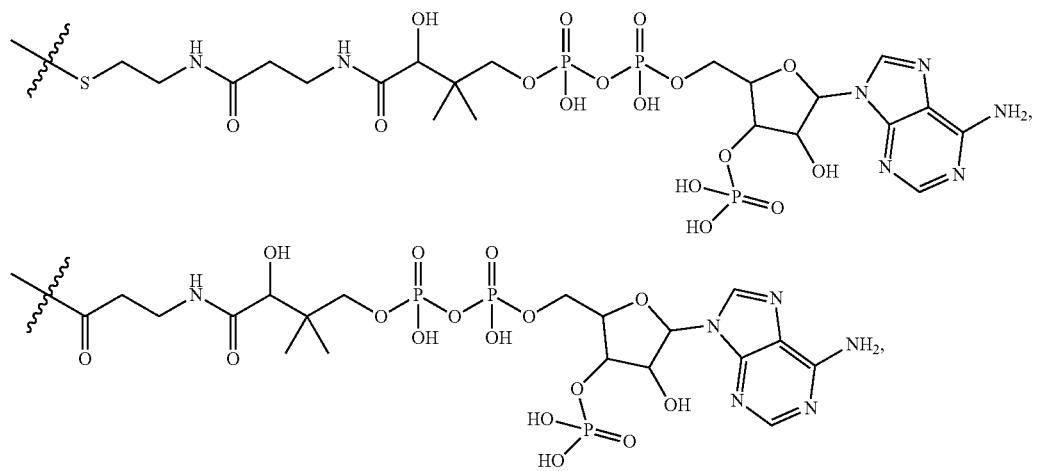
12
each $R^{11}$ is independently selected from $C_1$-$C_6$alkyl and $C_1$-$C_6$alkyl which is optionally substituted with 1 to 5 hydroxyl;
each $R^{12}$ is independently selected from H and $C_1$-$C_6$alkyl;
$R^{13}$ is tetrazolyl,
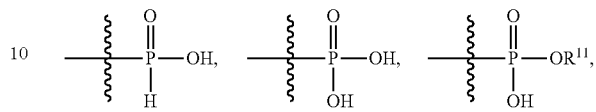

-continued

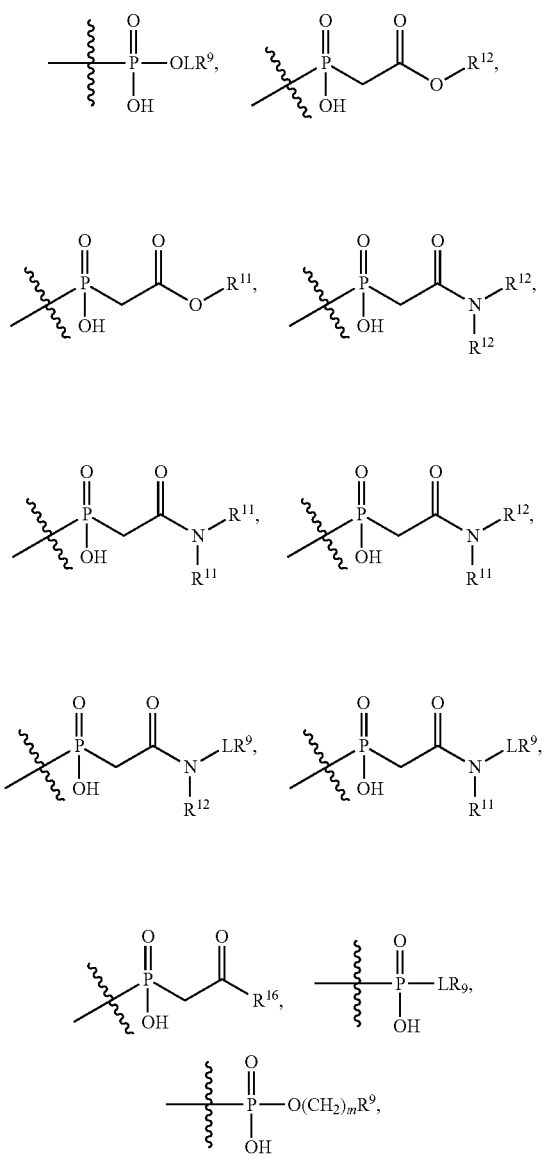

LR⁹ or —X₄LR⁹;

each $R^{14}$ is independently selected from H and $C_1$-$C_6$alkyl;

$R^{15}$ is 2-pyridyl or 4-pyridyl;

$R^{16}$ is an N-linked 4-8 membered heterocycloalkyl containing 1-2 heteroatoms independently selected from N and O, which is unsubstituted or substituted with -LR⁹;

$X_3$ is

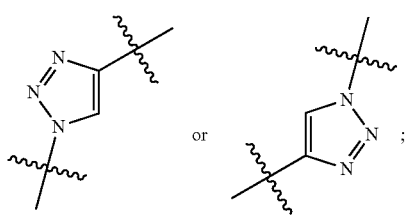 [SMILES: *c1cn(*)nn1 ; "or" ; *c1cn(*)nn1]

$X_4$ is

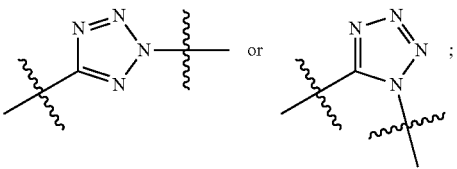 [SMILES: *c1nnn(*)n1 ; *c1nnnn1*]

each m is independently selected from 1, 2, 3, 4, 5, 6, 7, 8, 9 and 10; and each n is independently selected from 1, 2, 3, 4, 5, 6, 7, 8, 9, 10, 11, 12, 13, 14, 15, 16, 17 and 18.

In certain embodiments of this aspect of the cytotoxic peptides having the structure of Formula (I), $R^1$ is a C-linked 6 membered heterocycloalkyl containing 1-2 N heteroatoms and a $C_1$-$C_2$alkylene bridge, or $R^1$ is a C-linked 5-8 membered fused bicyclic heterocycloalkyl containing 1-2 N heteroatoms, wherein each is unsubstituted or each is substituted with 1 to 3 substituents independently selected from $R^5$ and $R^6$;

$R^2$ is —$C_1$-$C_6$alkyl;

$R^3$ is

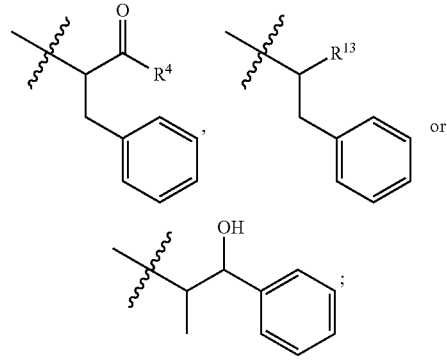

$R^4$ is —OH, $C_1$-$C_6$alkoxy, —N($R^{14}$)₂, —$R^{16}$, —$NR^{12}$ $(CH_2)_m$ N($R^{14}$)₂, —$NR^{12}(CH_2)_mR^{16}$, —NHS(O)₂$R^{11}$,

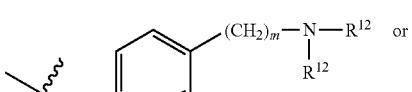

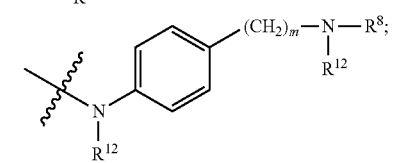

$R^5$ is $C_1$-$C_6$alkyl, $C_1$-$C_6$alkyl which is optionally substituted with 1 to 5 hydroxyl, —C(=O)$R^{11}$, —$(CH_2)_m$OH, —C(=O)$(CH_2)_m$OH, —C(=O)$((CH_2)_mO)_nR^{12}$, or —$((CH_2)_mO)_nR^{12}$;

$R^6$ is halo, oxo, OH, $C_1$-$C_6$alkyl, —$N(R^{14})_2$, —$R^{16}$ and —$NR^{12}C(=O)R^{11}$;

$R^8$ is H;

each $R^{11}$ is independently selected from $C_1$-$C_6$alkyl and $C_1$-$C_6$alkyl which is optionally substituted with 1 to 5 hydroxyl;

each $R^{12}$ is independently selected from H and $C_1$-$C_6$alkyl;

$R^{13}$ is tetrazolyl,

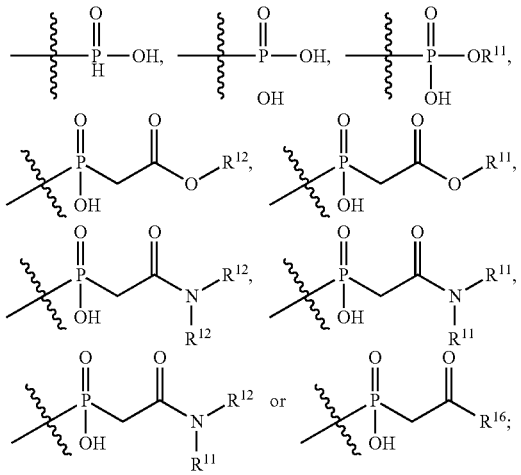

each $R^{14}$ is independently selected from H and $C_1$-$C_6$alkyl;

$R^{15}$ is 2-pyridyl or 4-pyridyl;

$R^{16}$ is an unsubstituted N-linked 4-8 membered heterocycloalkyl containing 1-2 heteroatoms independently selected from N and O;

each m is independently selected from 1, 2, 3, 4, 5, 6, 7, 8, 9 and 10, and each n is independently selected from 1, 2, 3, 4, 5, 6, 7, 8, 9, 10, 11, 12, 13, 14, 15, 16, 17 and 18.

In certain embodiments of this aspect of the cytotoxic peptides having the structure of Formula (I), are cytotoxic peptides having the structure of Formula (Ia):

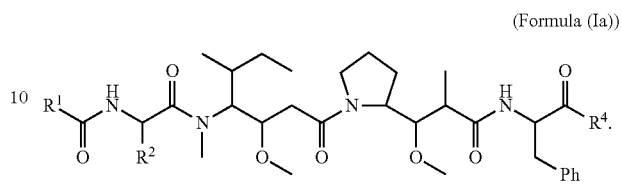

(Formula (Ia))

In other embodiments of the aspect of the cytotoxic peptides having the structure of Formula (I) or Formula (Ia), are cytotoxic peptides having the structure of Formula (Ib):

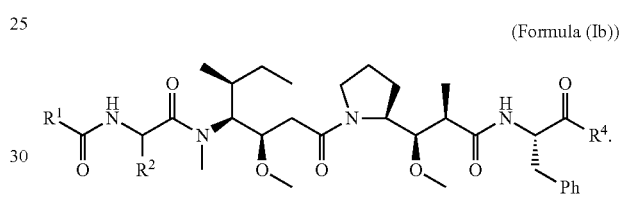

(Formula (Ib))

In certain embodiments of the aspect of the cytotoxic peptides having the structure of Formula (I), are cytotoxic peptides having the structure of Formula (Ic):

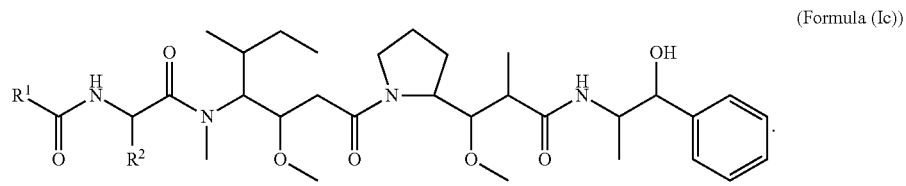

(Formula (Ic))

In other embodiments of the aspect of the cytotoxic peptides having the structure of Formula (I) or Formula (Ic), are cytotoxic peptides having the structure of Formula (Id):

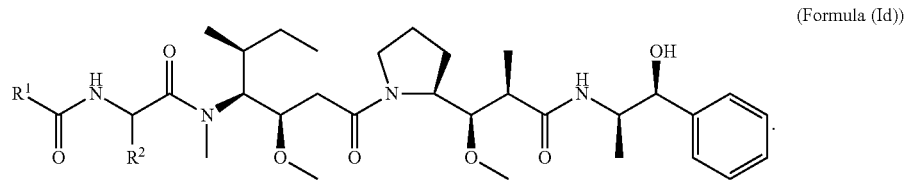

(Formula (Id))

In certain embodiments of the aspect of the cytotoxic peptides having the structure of Formula (I), are cytotoxic peptides having the structure of Formula (Ie):

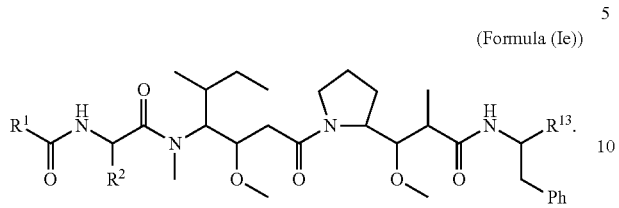
(Formula (Ie))

In other embodiments of the aspect of the cytotoxic peptides having the structure of Formula (I) or Formula (Ie), are cytotoxic peptides having the structure of Formula (If):

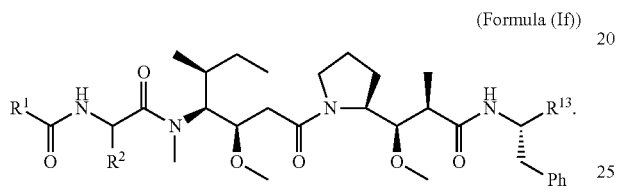
(Formula (If))

The present invention provides immunoconjugates, also referred to herein as ADCs, containing cytotoxic peptides linked to an antigen binding moiety, such as an antibody or antibody fragment. These conjugates comprising cytotoxic peptides are useful to treat cell proliferation disorders, particularly when the cytotoxic peptides is linked to an antibody that recognizes cancer cells and thus promotes delivery of the cytotoxic peptides to a cell targeted for attack. The immunoconjugates are especially useful for treating certain cancers as further detailed herein. Data provided herein demonstrate that these immunoconjugates are effective inhibitors of cell proliferation; without being bound by theory, it is believed their activity is due to inhibition of the polymerization of tubulin in cells.

In one aspect of the immunoconjugates of the invention include immunoconjugates of Formula (II):

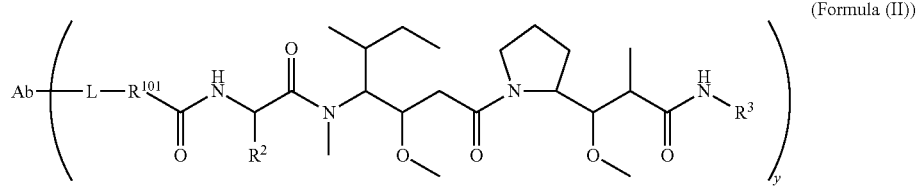
(Formula (II))

wherein:

Ab represents an antigen binding moiety;

L is selected from $-L_1L_2L_3L_4L_5L_6-$, $-L_6L_5L_4L_3L_2L_1-$, $-L_1L_2L_3L_4L_5-$, $-L_5L_4L_3L_2L_1-$,$-L_1L_2L_3L_4-$, $-L_4L_3L_2L_1-$,$-L_1L_2L_3-$, $-L_3L_2L_1-$,$-L_1L_2-$, $-L_2L_1-$ and $-L_1$, wherein $-L_1$, $L_2$, $L_3$, $L_4$, $L_5$, and $L_6$ are as defined herein;

y is an integer from 1 to 16;

$R^{101}$ is a 6 membered heterocycloalkyl divalent radical containing 1-2 N heteroatoms and a $C_1$-$C_2$alkylene bridge, wherein the 6 membered heterocycloalkyl divalent radical is C-linked to the

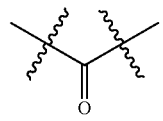 [SMILES: *C(*)=O]

group and is N-linked to $L_1$ or is C-linked to $L_1$, and the 6 membered heterocycloalkyl divalent radical is unsubstituted or substituted with 1 to 3 substituents independently selected from $R^5$ and $R^6$;

or $R^{101}$ is a 5-8 membered fused bicyclic heterocycloalkyl divalent radical containing 1-2 N heteroatoms, wherein the 5-8 membered fused bicyclic heterocycloalkyl divalent radical is C-linked to the

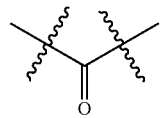 [SMILES: *C(*)=O]

group and is N-linked to $L_1$ or is C-linked to $L_1$, and the 5-8 membered fused bicyclic heterocycloalkyl divalent radical is unsubstituted or substituted with 1 to 3 substituents independently selected from $R^5$ and $R^6$;

$R^2$ is $-C_1$-$C_6$alkyl;

$R^3$ is

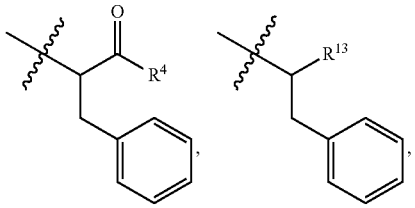

-continued

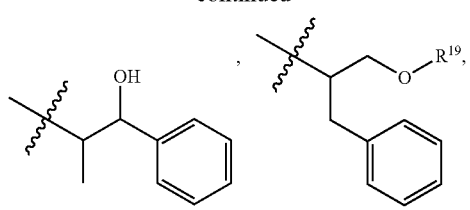

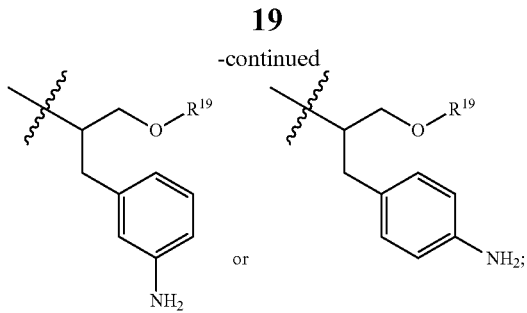

$R^4$ is —OH, $C_1$-$C_6$alkoxy, —N($R^{14}$)$_2$, —$R^{16}$, —$NR^{12}$(CH$_2$)$_m$N($R^{14}$)$_2$, or —$NR^{12}$(CH$_2$)$_m R^{16}$, —NHS(O)$_2 R_{11}$ or

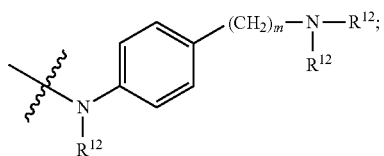

$R^5$ is $C_1$-$C_6$alkyl, —C(=O)$R^{11}$, —(CH$_2$)$_m$OH, —C(=O)(CH$_2$)$_m$OH, —C(=O)((CH$_2$)$_m$O)$_n R^{12}$, —((CH$_2$)$_m$O)$_n R^{12}$, or $C_1$-$C_6$alkyl which is optionally substituted with —CN, —C(=O)NH$_2$ or 1 to 5 hydroxyl, $R^6$ is halo, oxo, OH, $C_1$-$C_6$alkyl, —N($R^{14}$)$_2$, —$R^{16}$ and —$NR^{12}$C(=O)$R^{11}$;

$R^{11}$ is $C_1$-$C_6$alkyl or $C_1$-$C_6$alkyl which is optionally substituted with 1 to 5 hydroxyl;

each $R^{12}$ is independently selected from H and $C_1$-$C_6$alkyl;

$R^{13}$ is tetrazolyl, imidazolyl substituted with phenyl, oxadiazolyl substituted with phenyl, pyrazolyl, pyrimidinyl,

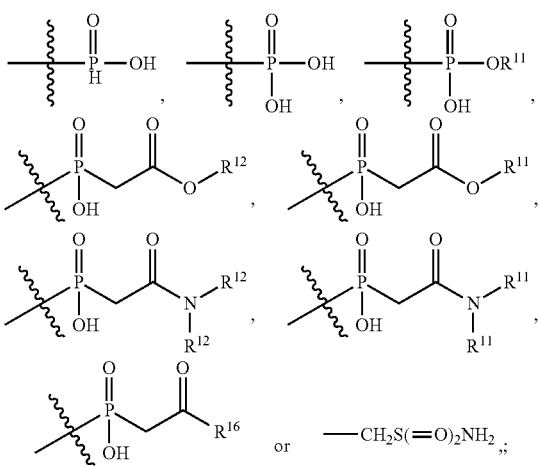

each $R^{14}$ is independently selected from H and $C_1$-$C_6$alkyl;

$R^{16}$ is an N-linked 4-8 membered heterocycloalkyl containing 1-2 heteroatoms independently selected from N and O;

$R^{19}$ is H or $C_1$-$C_6$alkyl;

each m is independently selected from 1, 2, 3, 4, 5, 6, 7, 8, 9 and 10, and each n is independently selected from 1, 2, 3, 4, 5, 6, 7, 8, 9, 10, 11, 12, 13, 14, 15, 16, 17 and 18.

In one aspect of the immunoconjugates of the invention include immunoconjugates of Formula (II):

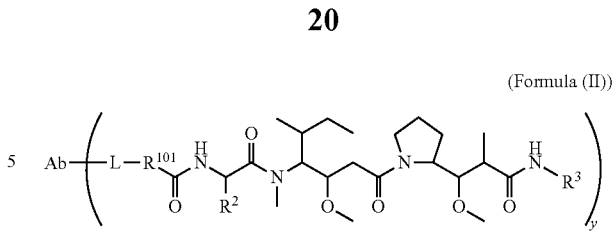

(Formula (II))

wherein:

Ab represents an antigen binding moiety;

L is selected from -L$_1$L$_2$L$_3$L$_4$L$_5$L$_6$-, -L$_6$L$_5$L$_4$L$_3$L$_2$L$_1$-, -L$_1$L$_2$L$_3$L$_4$L$_5$-, -L$_5$L$_4$L$_3$L$_2$L$_1$-,-L$_1$L$_2$L$_3$L$_4$-, -L$_4$L$_3$L$_2$L$_1$-,-L$_1$L$_2$L$_3$-, -L$_3$L$_2$L$_1$-,-L$_1$L$_2$-, -L$_2$L$_1$- and -L$_1$, wherein -L$_1$, L$_2$, L$_3$, L$_4$, L$_5$, and L$_6$ are as defined herein;

y is an integer from 1 to 16;

$R^{101}$ is a 6 membered heterocycloalkyl divalent radical containing 1-2 N heteroatoms and a $C_1$-$C_2$alkylene bridge, wherein the 6 membered heterocycloalkyl divalent radical is C-linked to the

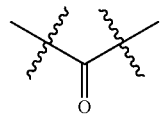

group and is N-linked to L$_1$ or is C-linked to L$_1$, and the 6 membered heterocycloalkyl divalent radical is unsubstituted or substituted with 1 to 3 substituents independently selected from $R^5$ and $R^6$;

or $R^{101}$ is a 5-8 membered fused bicyclic heterocycloalkyl divalent radical containing 1-2 N heteroatoms, wherein the 5-8 membered fused bicyclic heterocycloalkyl divalent radical is C-linked to the

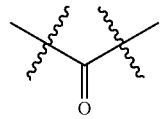 [SMILES: *C(*)=O]

group and is N-linked to L$_1$ or is C-linked to L$_1$, and the 5-8 membered fused bicyclic heterocycloalkyl divalent radical is unsubstituted or substituted with 1 to 3 substituents independently selected from $R^5$ and $R^6$;

$R^2$ is —$C_1$-$C_6$alkyl;

$R^3$ is

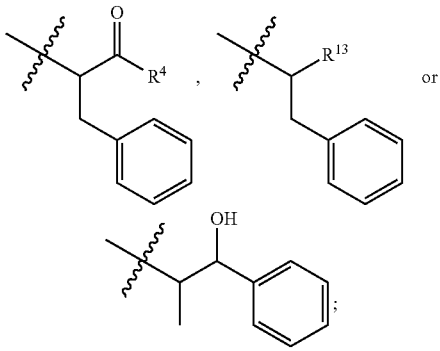

R⁴ is —OH, C₁-C₆alkoxy, —N(R¹⁴)₂, —R¹⁶, —NR¹²(CH₂)ₘN(R¹⁴)₂, or —NR¹²(CH₂)ₘR¹⁶, —NHS(O)₂R₁₁ or

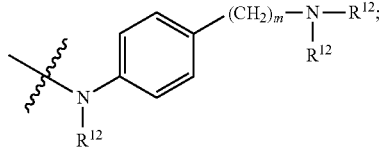

R⁵ is C₁-C₆alkyl, C₁-C₆alkyl which is optionally substituted with 1 to 5 hydroxyl, —C(=O)R¹¹, —(CH₂)ₘOH, —C(=O)(CH₂)ₘOH, —C(=O)((CH₂)ₘO)ₙR¹², or —((CH₂)ₘO)ₙR¹²;

R⁶ is halo, oxo, OH, C₁-C₆alkyl, —N(R¹⁴)₂, —R¹⁶ and —NR¹²C(=O)R¹¹;

R¹¹ is C₁-C₆alkyl or C₁-C₆alkyl which is optionally substituted with 1 to 5 hydroxyl;

each R¹² is independently selected from H and C₁-C₆alkyl;

R¹³ is tetrazolyl,

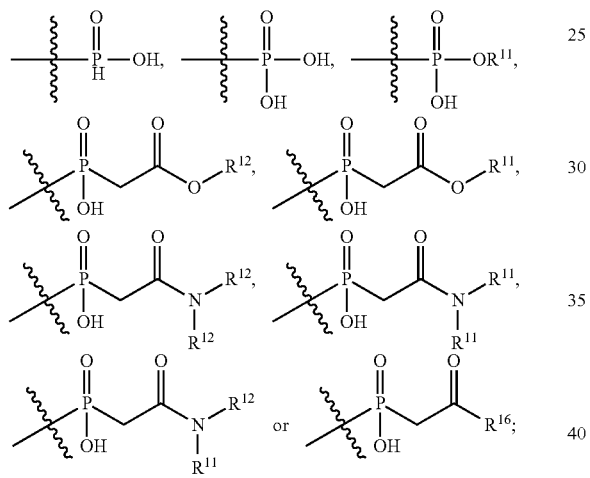

each R¹⁴ is independently selected from H and C₁-C₆alkyl;

R¹⁶ is an N-linked 4-8 membered heterocycloalkyl containing 1-2 heteroatoms independently selected from N and O;

each m is independently selected from 1, 2, 3, 4, 5, 6, 7, 8, 9 and 10, and each n is independently selected from 1, 2, 3, 4, 5, 6, 7, 8, 9, 10, 11, 12, 13, 14, 15, 16, 17 and 18.

In another aspect of the immunoconjugates of the invention are immunoconjugates having the structure of Formula (III):

(Formula (III))

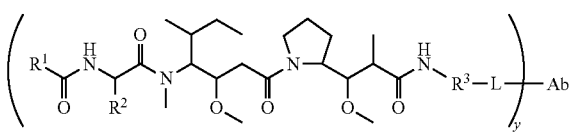

wherein:
Ab represents an antigen binding moiety;
L is selected from -L₁L₂L₃L₄L₅L₆-, -L₆L₅L₄L₃L₂L₁-, -L₁L₂L₃L₄L₅-, -L₅L₄L₃L₂L₁-,-L₁L₂L₃L₄-, -L₄L₃L₂L₁-,- L₁L₂L₃-, -L₃L₂L₁-,-L₁L₂-, -L₂L₁- and -L₁-, wherein -L₁, L₂, L₃, L₄, L₅, and L₆ are as defined herein;

y is an integer from 1 to 16;

R¹ is a 6 membered heterocycloalkyl containing 1-2 N heteroatoms and a C₁-C₂alkylene bridge, wherein the 6 membered heterocycloalkyl is unsubstituted or substituted with 1 to 3 substituents independently selected from R⁵ and R⁶;

or R¹ is a 5-8 membered fused bicyclic heterocycloalkyl containing 1-2 N heteroatoms, wherein the 5-8 membered fused bicyclic heterocycloalkyl is unsubstituted or substituted with 1 to 3 substituents independently selected from R⁵ and R⁶;

R² is —C₁-C₆alkyl;

R³ is

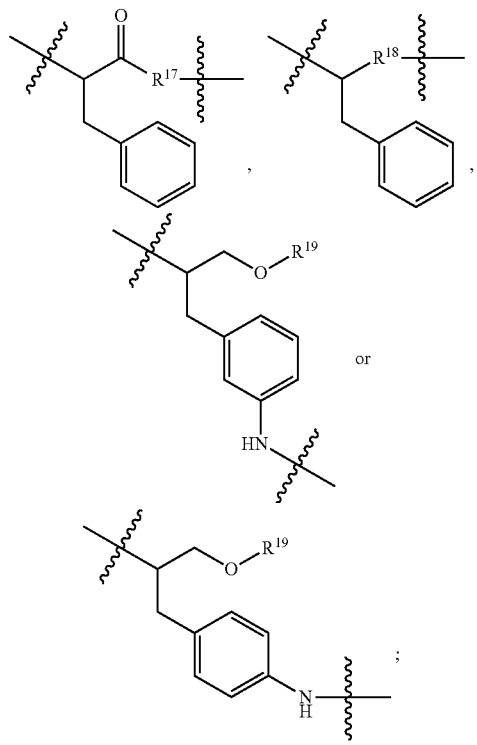

R⁵ is C₁-C₆alkyl, C₁-C₆alkyl which is optionally substituted with 1 to 5 hydroxyl, —C(=O)R¹¹, —(CH₂)ₘOH, —C(=O)(CH₂)ₘOH, —C(=O)((CH₂)ₘO)ₙR¹², or —((CH₂)ₘO)ₙR¹²;

R⁶ is halo, oxo, OH, C₁-C₆alkyl, —N(R¹⁴)₂, —R¹⁶ and —NR¹²C(=O)R¹¹;

R¹¹ is C₁-C₆alkyl or C₁-C₆alkyl which is optionally substituted with 1 to 5 hydroxyl;

each R¹² is independently selected from H and C₁-C₆alkyl;

each R¹⁴ is independently selected from H and C₁-C₆alkyl;

R¹⁶ is an N-linked 4-8 membered heterocycloalkyl containing 1-2 heteroatoms independently selected from N and O;

R¹⁷ is a bond, —NH—, —NHS(=O)₂—, $R^3$ is

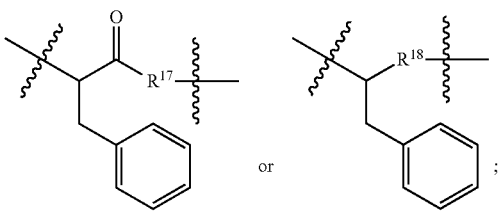

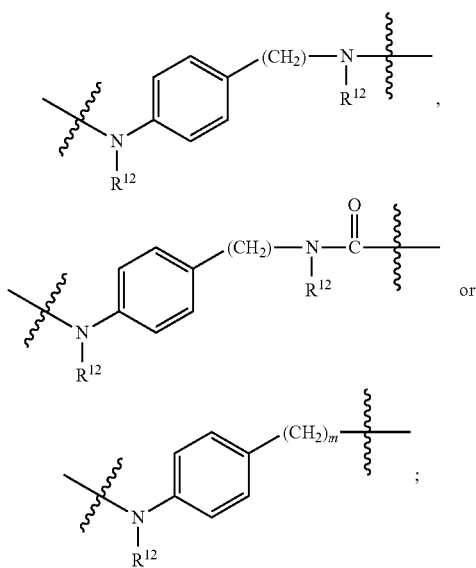

$R^5$ is $C_1$-$C_6$alkyl, $C_1$-$C_6$alkyl which is optionally substituted with 1 to 5 hydroxyl, —C(=O)$R^{11}$, —(CH$_2$)$_m$OH, —C(=O)(CH$_2$)$_m$OH, —C(=O)((CH$_2$)$_m$O)$_n$$R^{12}$, or —((CH$_2$)$_m$O)$_n$$R^{12}$;

$R^6$ is halo, oxo, OH, $C_1$-$C_6$alkyl, —N($R^{14}$)$_2$, —$R^{16}$ and —N$R^{12}$C(=O)$R^{11}$;

$R^{11}$ is $C_1$-$C_6$alkyl or $C_1$-$C_6$alkyl which is optionally substituted with 1 to 5 hydroxyl;

each $R^{12}$ is independently selected from H and $C_1$-$C_6$alkyl;

each $R^{14}$ is independently selected from H and $C_1$-$C_6$alkyl;

$R^{16}$ is an N-linked 4-8 membered heterocycloalkyl containing 1-2 heteroatoms independently selected from N and O;

$R^{17}$ is a bond, —NH—, —NHS(=O)$_2$—,

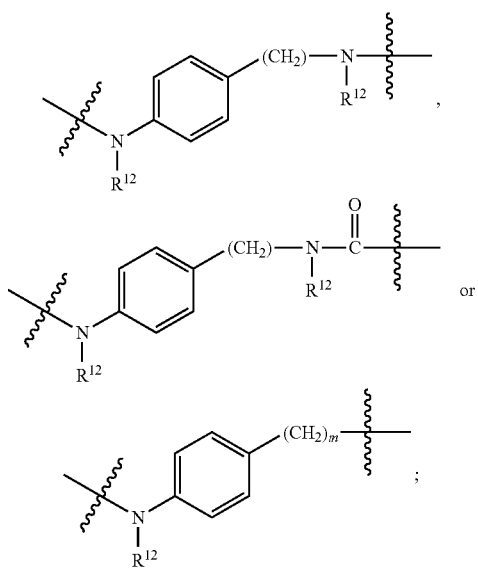

$R^{18}$ is a bond,

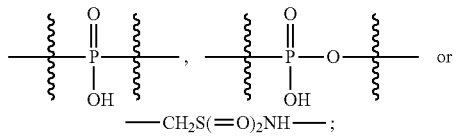

—CH$_2$S(=O)$_2$NH—;

$R^{19}$ is H or $C_1$-$C_6$alkyl;

each m is independently selected from 1, 2, 3, 4, 5, 6, 7, 8, 9 and 10, and each n is independently selected from 1, 2, 3, 4, 5, 6, 7, 8, 9, 10, 11, 12, 13, 14, 15, 16, 17 and 18.

In another aspect of the immunoconjugates of the invention are immunoconjugates having the structure of Formula (III):

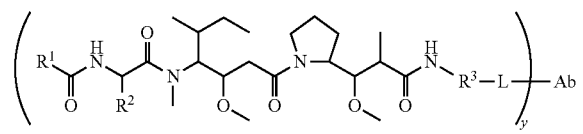

wherein:

Ab represents an antigen binding moiety;

L is selected from -L$_1$L$_2$L$_3$L$_4$L$_5$L$_6$-, -L$_6$L$_5$L$_4$L$_3$L$_2$L$_1$-, -L$_1$L$_2$L$_3$L$_4$L$_5$-, -L$_5$L$_4$L$_3$L$_2$L$_1$-,-L$_1$L$_2$L$_3$L$_4$-, -L$_4$L$_3$L$_2$L$_1$-,-L$_1$L$_2$L$_3$-, -L$_3$L$_2$L$_1$-,-L$_1$L$_2$-, -L$_2$L$_1$- and -L$_1$, wherein -L$_1$, L$_2$, L$_3$, L$_4$, L$_5$, and L$_6$ are as defined herein;

y is an integer from 1 to 16;

$R^1$ is a 6 membered heterocycloalkyl containing 1-2 N heteroatoms and a $C_1$-$C_2$alkylene bridge, wherein the 6 membered heterocycloalkyl is unsubstituted or substituted with 1 to 3 substituents independently selected from $R^5$ and $R^6$;

or $R^1$ is a 5-8 membered fused bicyclic heterocycloalkyl containing 1-2 N heteroatoms, wherein the 5-8 membered fused bicyclic heterocycloalkyl is unsubstituted or substituted with 1 to 3 substituents independently selected from $R^5$ and $R^6$;

$R^2$ is —$C_1$-$C_6$alkyl;

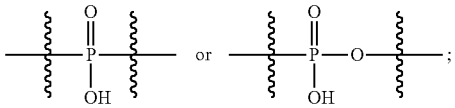 [SMILES: *P(*)(=O)O ; *OP(*)(=O)O]

each m is independently selected from 1, 2, 3, 4, 5, 6, 7, 8, 9 and 10, and each n is independently selected from 1, 2, 3, 4, 5, 6, 7, 8, 9, 10, 11, 12, 13, 14, 15, 16, 17 and 18.

The invention provides methods for making such ADCs using cytotoxic peptides of Formula (I) as the payload (drug) to be delivered. In such cytotoxic peptides the cytotoxic peptide N-terminus or C-terminus has been modified to have a reactive functional group, and optionally one or more linker components, to facilitate connecting the cytotoxic peptide either directly or indirectly to the antibody or antigen binding fragment, for instance the above described second and third aspects of the cytotoxic peptides of Formula (I). In addition, the invention provides methods to use these ADCs to treat cell proliferation disorders.

In another aspect, the invention provides pharmaceutical compositions comprising an immunoconjugate of Formula (II) or Formula (III), or subformulae thereof, admixed with at least one pharmaceutically acceptable carrier or excipient, optionally admixed with two or more pharmaceutically acceptable carriers or excipients, and methods to use these compositions to treat cell proliferation disorders.

In another aspect, the invention provides a method to treat a condition characterized by excessive or undesired cell proliferation, which comprises administering to a subject in need of such treatment an effective amount of an immunoconjugate of Formula (II) or Formula (III). The subject for treatment can be a mammal, and is preferably a human. Conditions treatable by the immunoconjugates and methods described herein include various forms of cancer, such as gastric, myeloid, colon, nasopharyngeal, esophageal, and prostate tumors, glioma, neuroblastoma, breast cancer, lung cancer, ovarian cancer, colorectal cancer, thyroid cancer, leukemia (e.g., myelogenous leukemia, lymphocytic leukemia, acute myelogenous leukemia (AML), chronic myeloid leukemia (CML), acute lymphoblastic leukemia (ALL), T-lineage acute lymphoblastic leukemia or T-ALL chronic lymphocytic leukemia (CLL), myelodysplastic syndrome (MDS), hairy cell leukemia), lymphoma (Hodgkin's lymphoma (HL), non-Hodgkin's lymphoma (NHL)), multiple myeloma, bladder, renal, gastric (e.g., gastrointestinal stromal tumors (GIST)), liver, melanoma and pancreatic cancer, and sarcoma. Other cell proliferation disorders that can be treated with these methods and compositions include diabetic retinopathy, liver and lung fibrosis, Sjogren's syndrome, and lupus erythematous.

The invention includes compositions of Formulas (I)-(III) and the subformulae thereof as described herein, and all stereoisomers (including diastereoisomers and enantiomers), tautomers, and isotopically enriched versions thereof (including deuterium substitutions) as well as pharmaceutically acceptable salts of these compounds. The present invention also comprises polymorphs of Formula (I) (or sub-formulas thereof) and salts, particularly pharmaceutically acceptable salts, thereof.

DETAILED DESCRIPTION

Figure 1A:
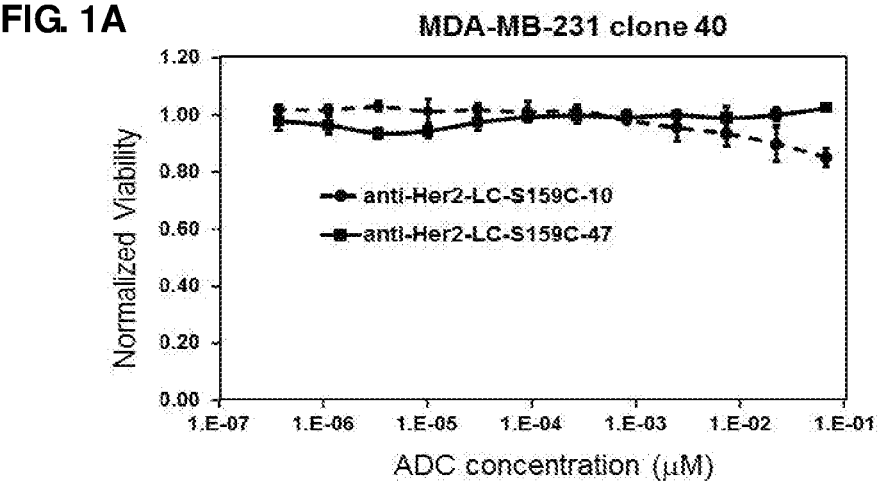
FIG. 1. In vitro cell proliferation assays of anti-Her2 Cys (A) and A1/ybbR tag (B) mutant ADCs with MDA-MB-231 clone 40, anti-Her2 Cys (C) and A1/ybbR tag (D) mutant ADCs with MDA-MB-231 clone 16, anti-Her2 Cys (E) and A1/ybbR tag (F) mutant ADCs with HCC1954, and anti-Her2 Cys (G) and A1/ybbR tag (H) mutant ADCs with JimT-1 cells.
Figure 1B:
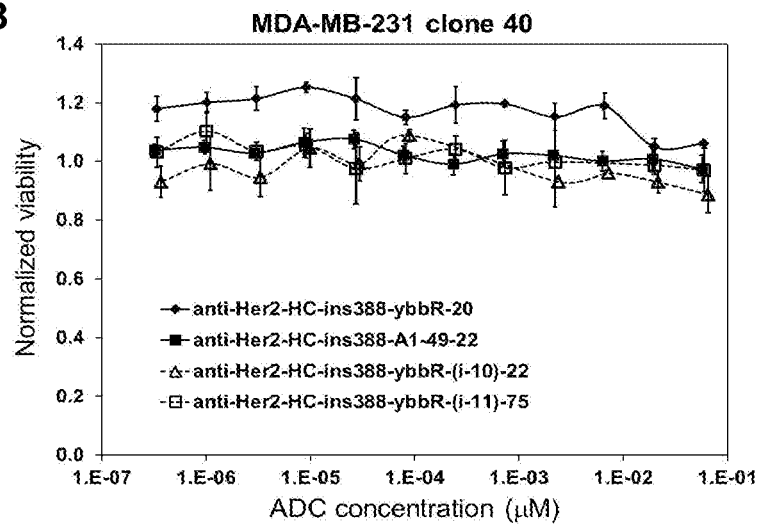
Figure 1C:
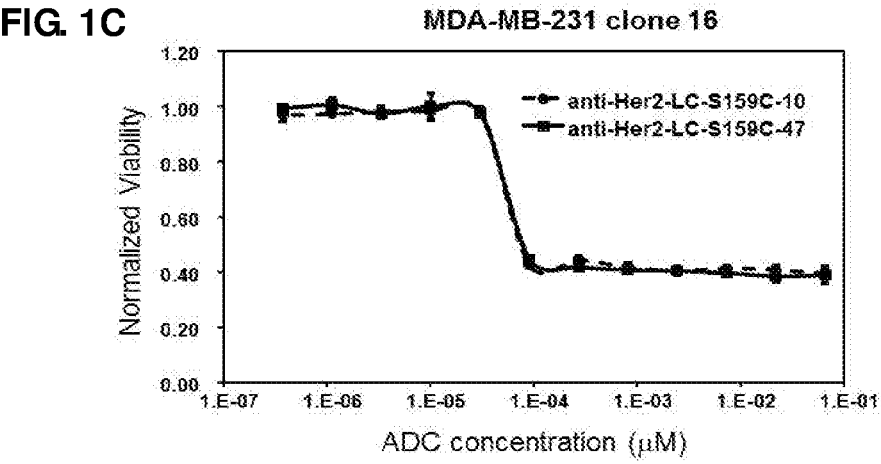
Figure 1D:
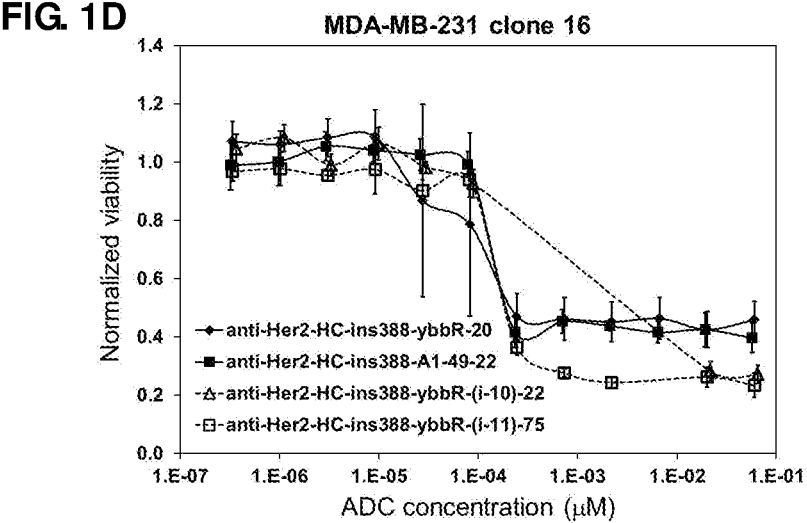
Figure 1E:
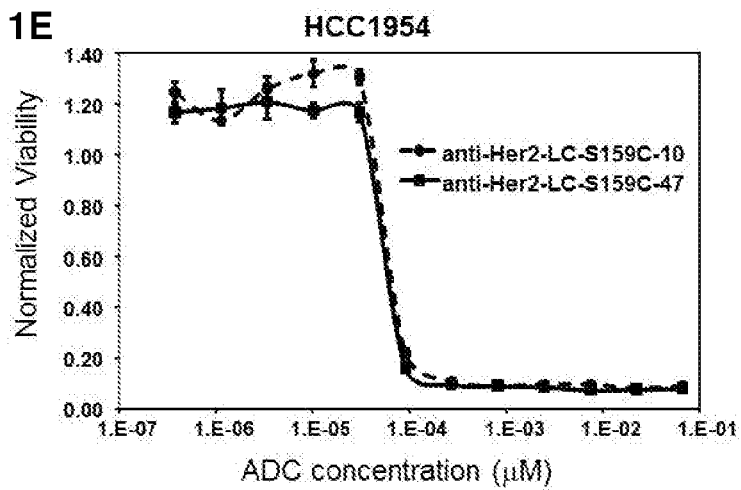
Figure 1F:
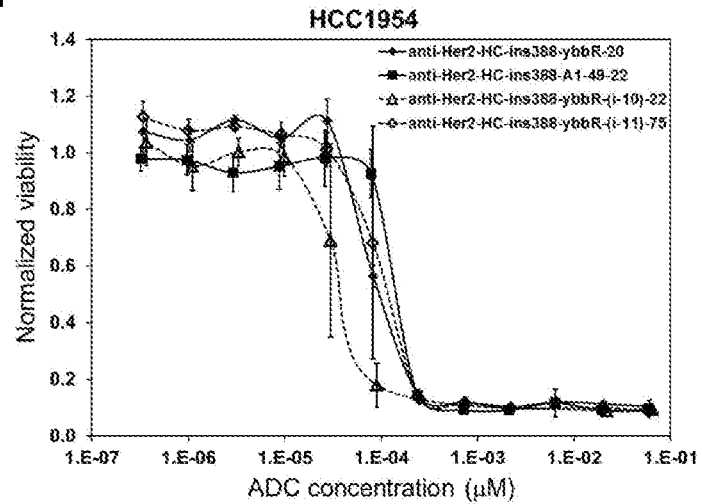
Figure 1G:
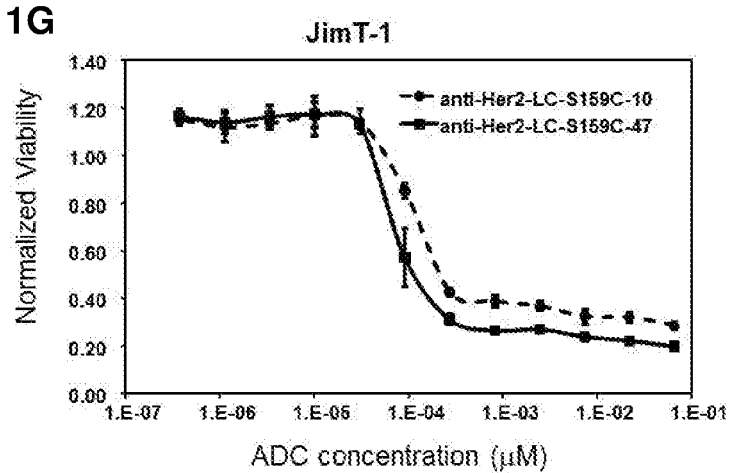
Figure 1H:
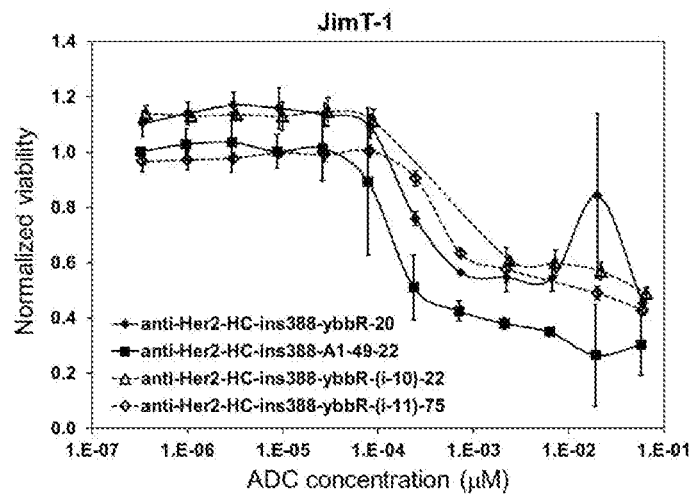
Figure 2A:
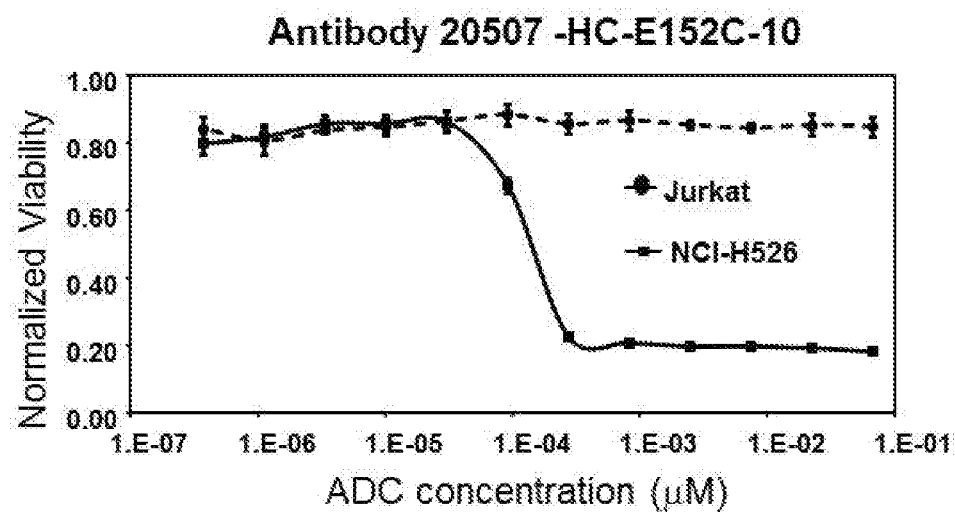
FIG. 2. In vitro cell proliferation assays of antibody 20507-HC-E152C-10 (A), antibody 20507-HC-S375C-47 (B), antibody 20507-HC-ins388-A1-20 (C), and antibody 20507-HC-ins388-A1-49-22 (D) ADCs.
Figure 2B:
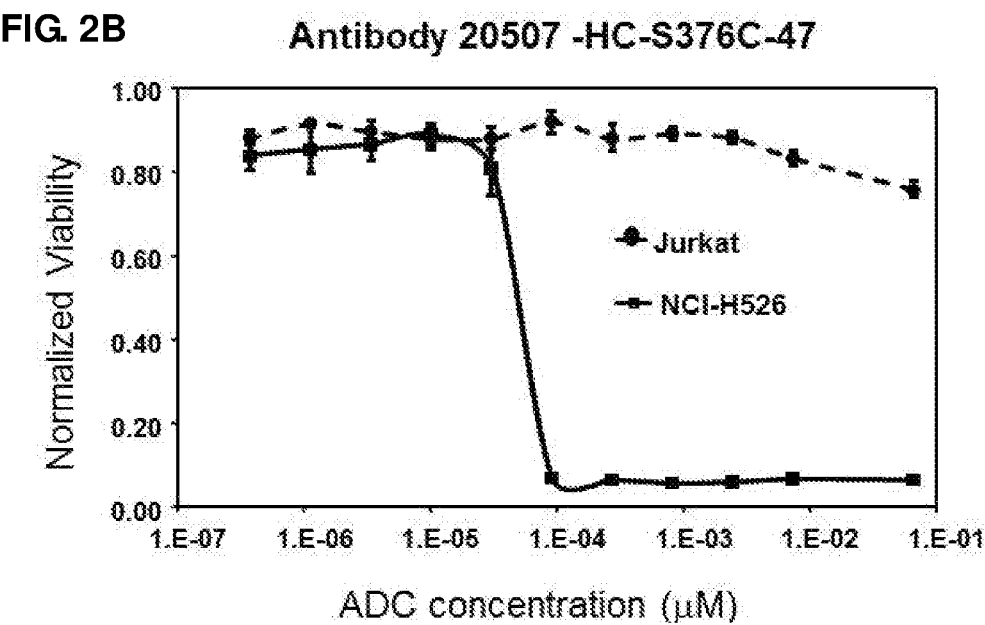
Figure 2C:
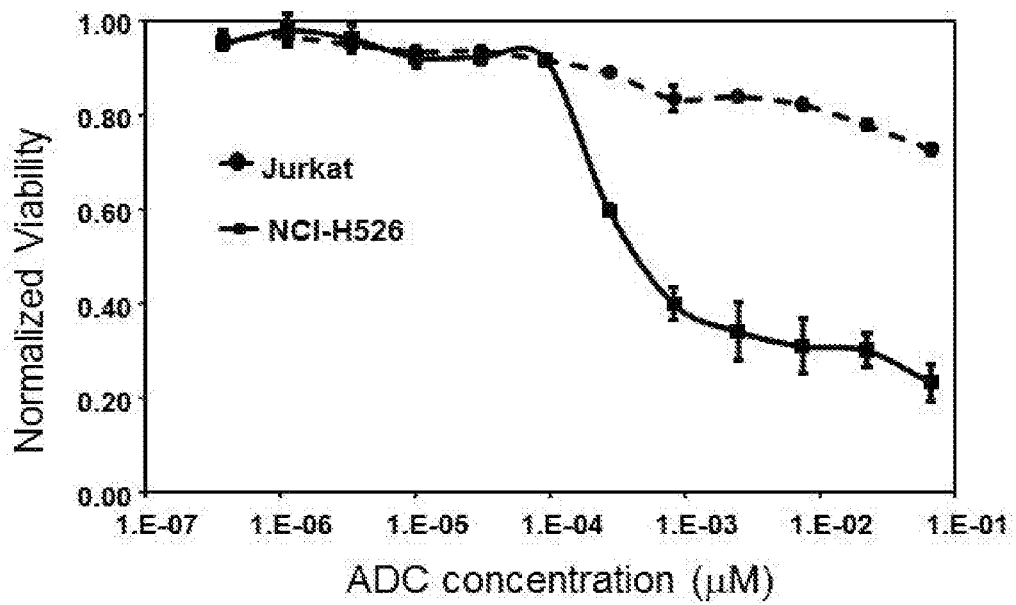
Figure 2D:
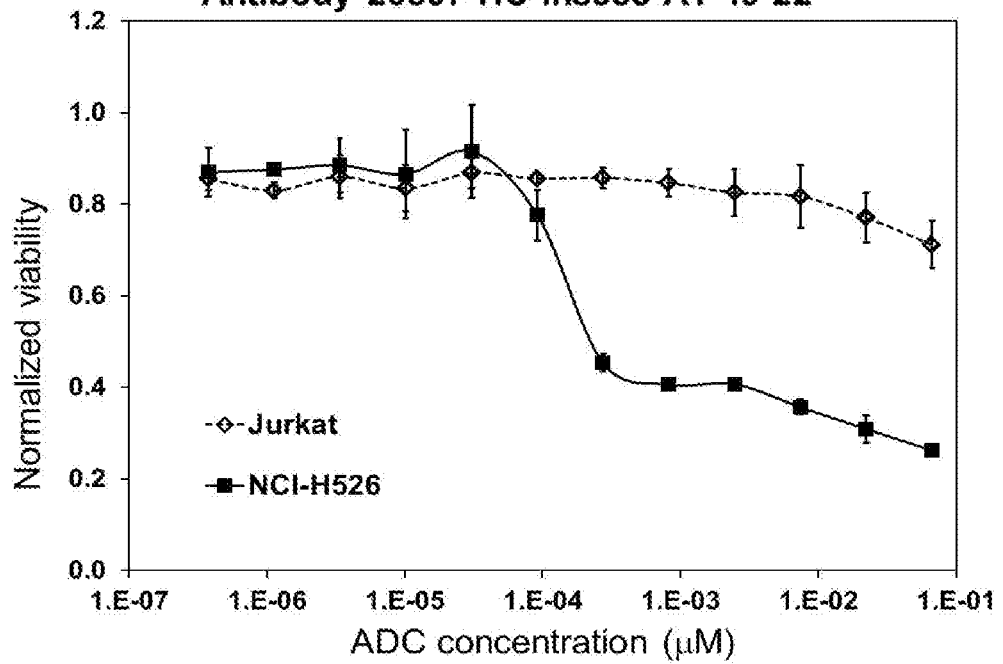
Figure 3A:
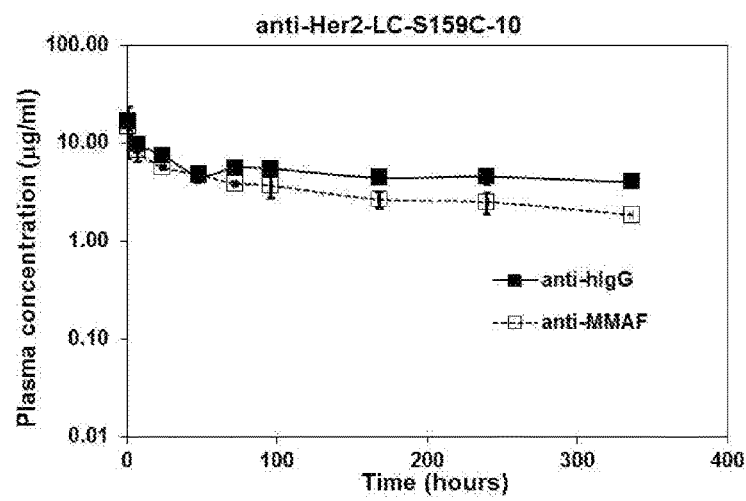
FIG. 3. Pharmacokinetic studies of anti-Her2-LC-S159C-10 (A), anti-Her2-LC-S159C-47 (B), anti-Her2-LC-S159C-77 (C), anti-Her2-LC-S159C-80 (D), anti-Her2-LC-S159C-79 (E), anti-Her2-LC-S159C-78 (F), anti-Her2-LC-S159C-14 (G), anti-Her2-HC-E152C-S375C-10 (H), and anti-Her2-10 (I) in naïve mice.
Figure 3B:
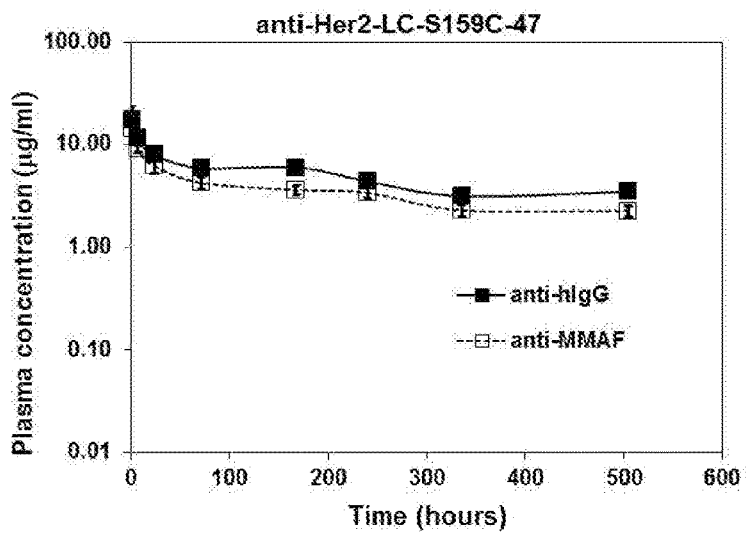
Figure 3C:
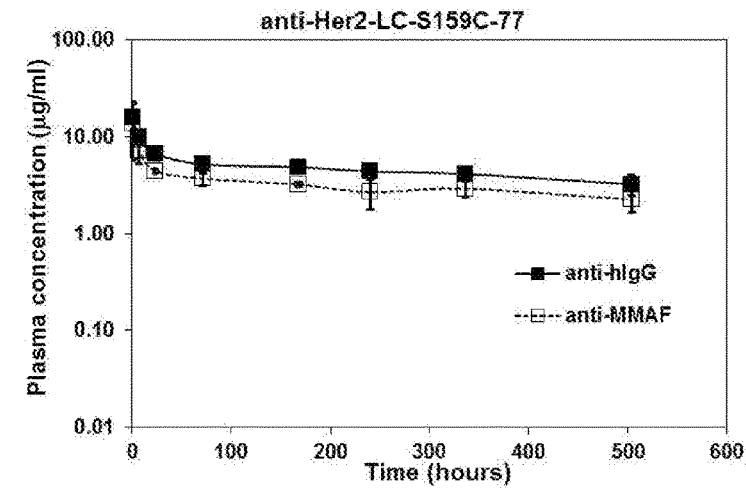
Figure 3D:
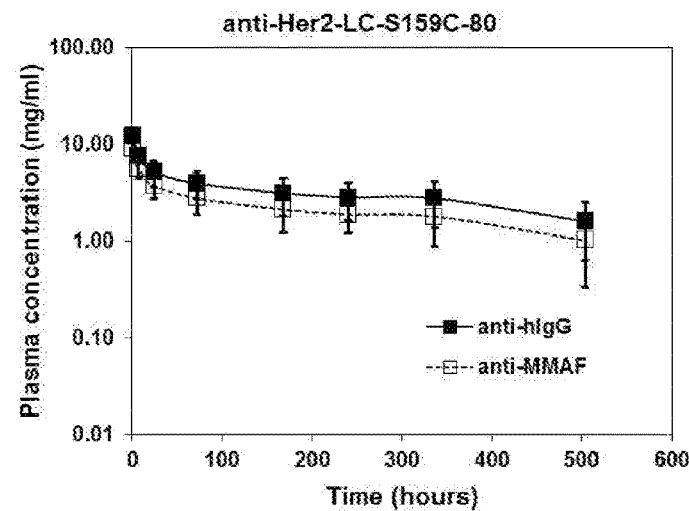
Figure 3E:
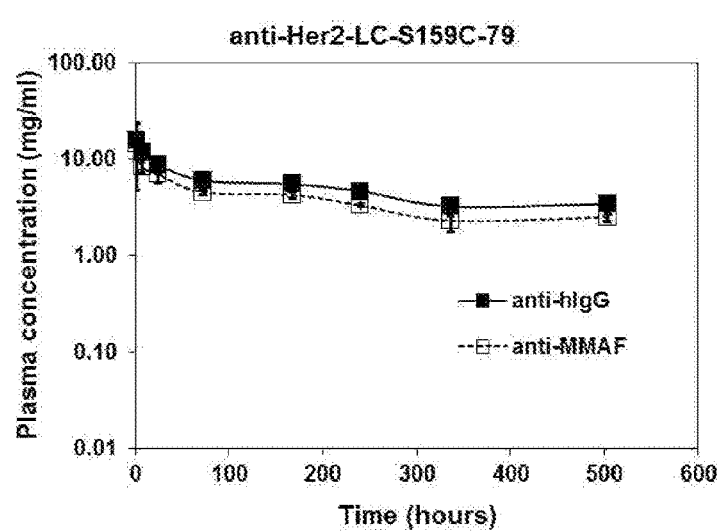
Figure 3F:
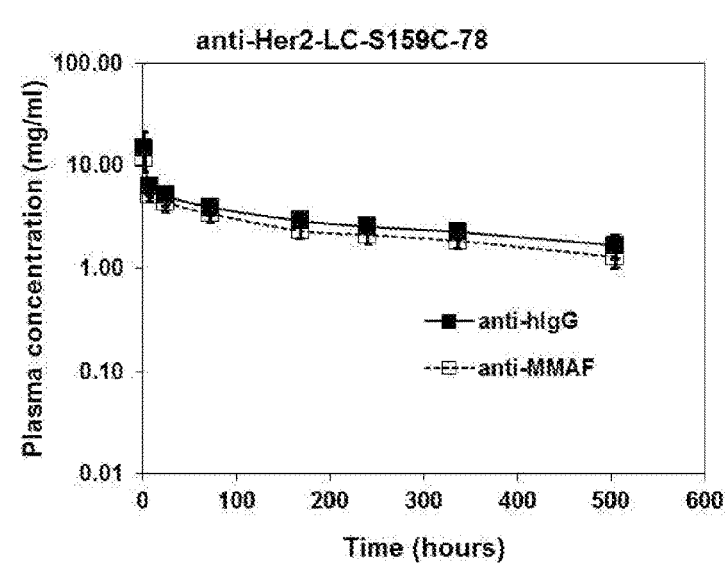
Figure 3G:
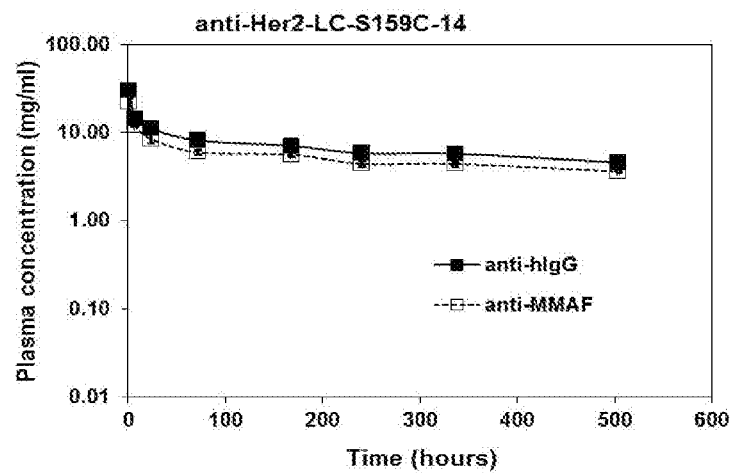
Figure 3H:
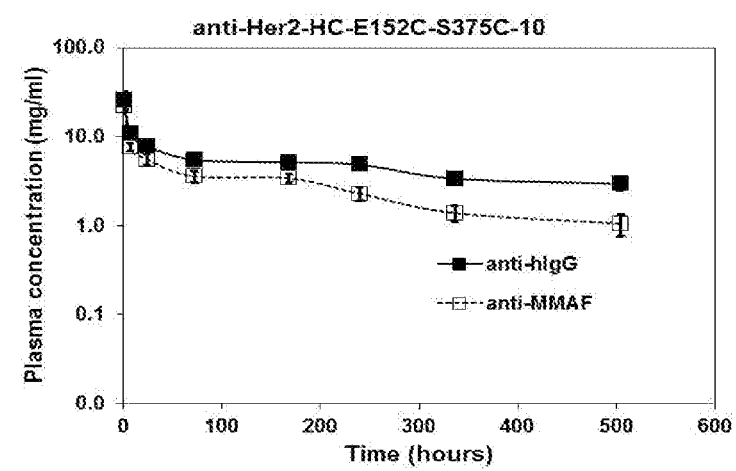
Figure 3I:
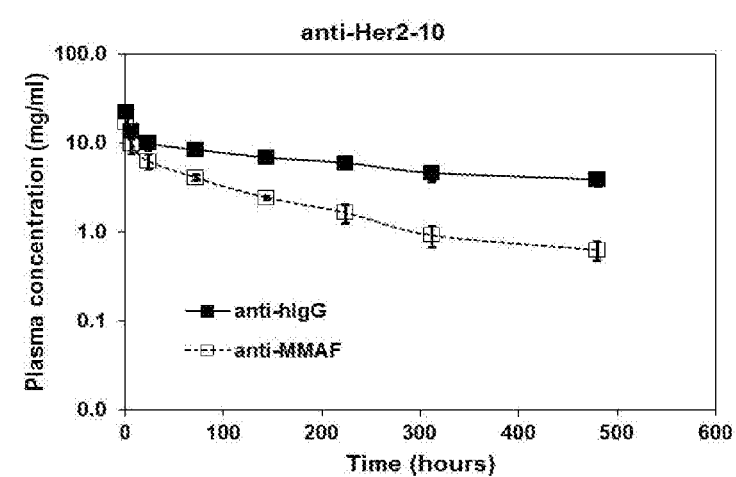
Figure 4A:
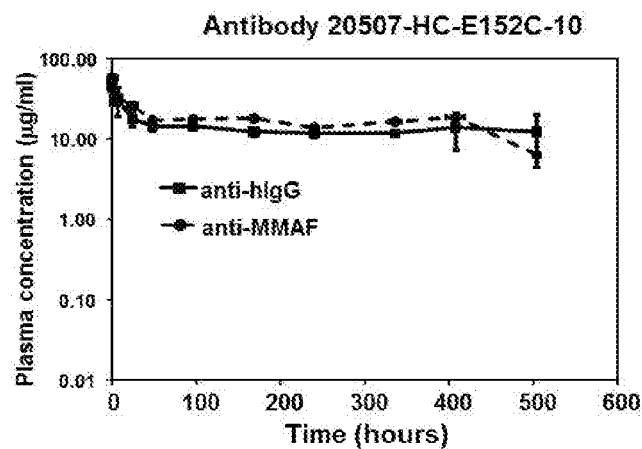
FIG. 4. Pharmacokinetic studies of antibody 20507-HC-E152C-10 (A), antibody 20507-LC-K107C-47 (B), antibody 20507-HC-ins388-A1-20 (C), antibody 20507-HC-E152C-S375C-10 (D), antibody 20507-10 (E), anti-Her2-HC-S375C-10 (D), antibody 20507-10 (E), anti-Her2-HC-ins388-ybbR-20 (G), antibody 20507-HC-ins388-A1-49-22 (H), anti-Her2-HC-ins388-A1-49-22 (I), and anti-Her2-HC-ins388-ybbR-(i-11)-75 (J) ADCs in naïve mice at a dose of 1 mg/kg. The pharmacokinetic study of antibody 20507-HC-ins388-A1-20 (F) was performed in tumor-bearing mice at a dose of 10 mg/kg.
Figure 4B:
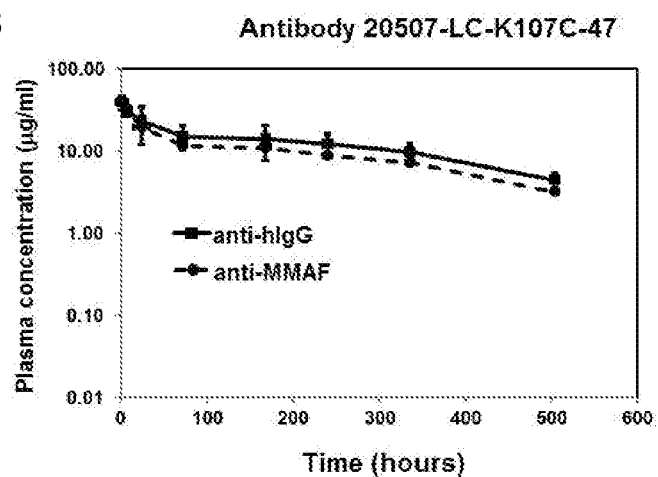
Figure 4C:
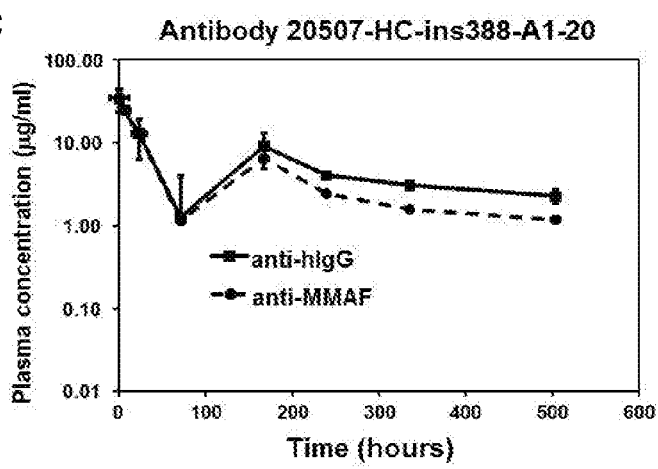
Figure 4D:
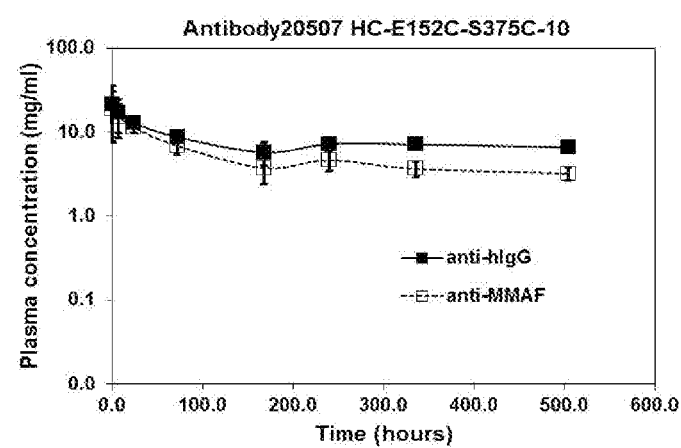
Figure 4E:
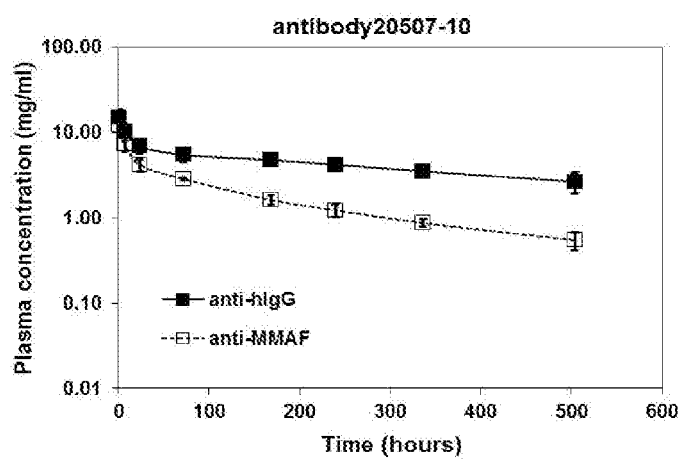
Figure 4F:
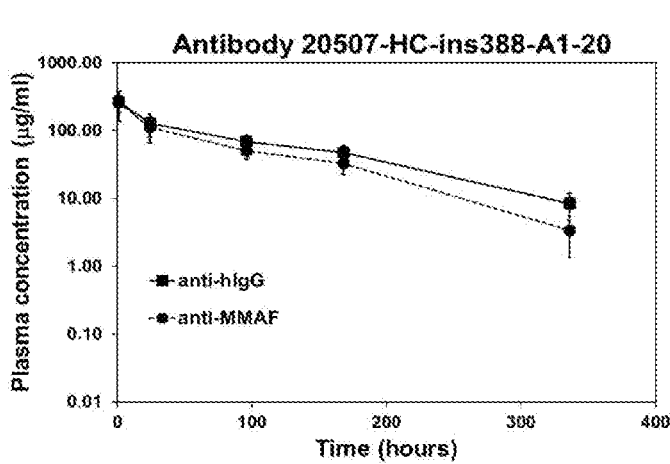
Figure 4G:
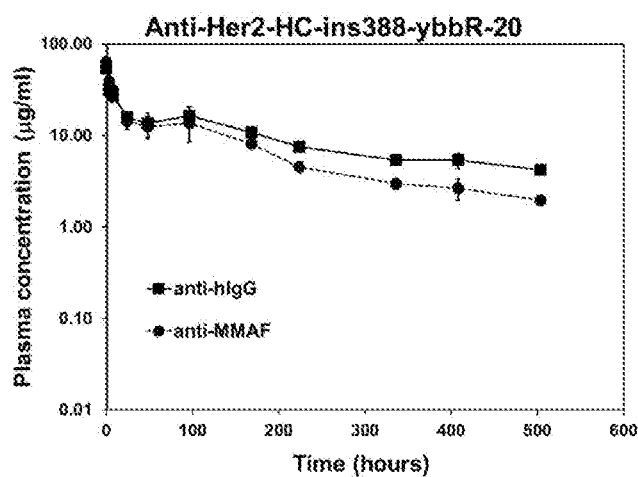
Figure 4H:
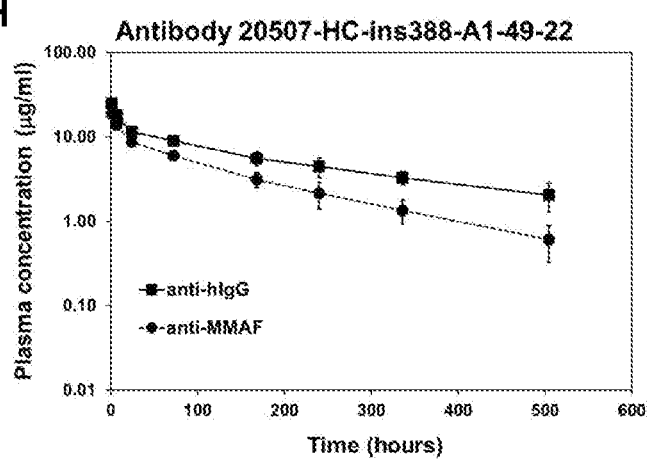
Figure 4I:
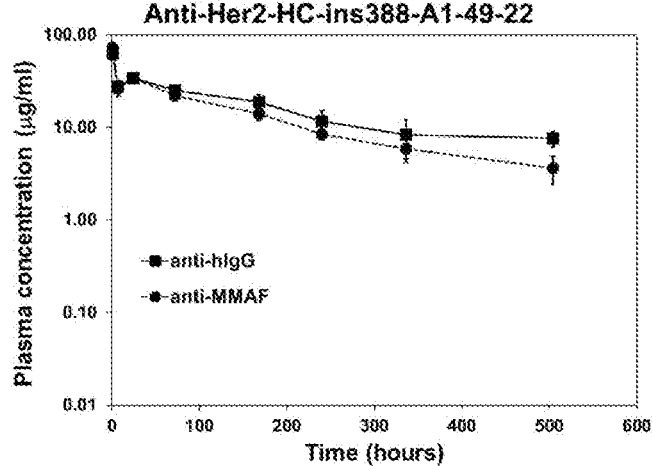
Figure 4J:
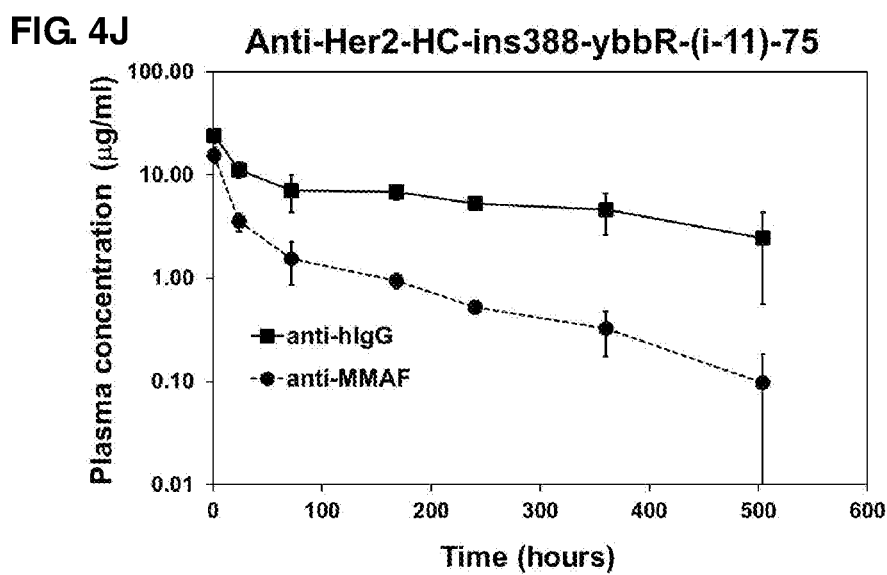

The following definitions apply unless otherwise expressly provided.

The term "amino acid" refers to canonical, synthetic, and unnatural amino acids, as well as amino acid analogs and amino acid mimetics that function in a manner similar to the canonical amino acids. Canonical amino acids are proteinogenous amino acids encoded by the genetic code and include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, as well as selenocysteine, pyrrolysine and pyrroline-carboxy-lysine. Amino acid analogs refer to compounds that have the same basic chemical structure as a canonical amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a canonical amino acid.

The term "antigen binding moiety" as used herein refers to a moiety capable of binding specifically to an antigen, and includes but is not limited to antibodies and antibody fragments.

The term "antibody" as used herein refers to a polypeptide of the immunoglobulin family that is capable of binding a corresponding antigen non-covalently, reversibly, and in a specific manner. For example, a naturally occurring IgG antibody is a tetramer comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hyper variability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antibody" includes, but is not limited to, monoclonal antibodies, human antibodies, humanized antibodies, camelid antibodies, chimeric antibodies, and anti-idiotypic (anti-Id) antibodies (including, e.g., anti-Id antibodies to antibodies of the invention). The antibodies can be of any isotype/class (e.g., IgG, IgE, IgM, IgD, IgA and IgY), or subclass (e.g., IgG1, IgG2, IgG3, IgG4, IgA1 and IgA2).

Both the light and heavy chains are divided into regions of structural and functional homology. The terms "constant" and "variable" are used functionally. In this regard, it will be appreciated that the variable domains of both the light ($V_L$) and heavy ($V_H$) chain portions determine antigen recognition and specificity. Conversely, the constant domains of the light chain ($C_L$) and the heavy chain (CH1, CH2 or CH3) confer important biological properties such as secretion, transplacental mobility, Fc receptor binding, complement binding, and the like. By convention, the numbering of the constant region domains increases as they become more distal from the antigen binding site or amino-terminus of the antibody. The N-terminus is a variable region and at the C-terminus is a constant region; the CH3 and $C_L$ domains actually comprise the carboxy-terminal domains of the heavy and light chain, respectively.

The term "antigen binding fragment", as used herein, refers to one or more portions of an antibody that retain the ability to specifically interact with (e.g., by binding, steric hindrance, stabilizing/destabilizing, spatial distribution) an epitope of an antigen. Examples of binding fragments include, but are not limited to, single-chain Fvs (scFv), disulfide-linked Fvs (sdFv), Fab fragments, F(ab') fragments, a monovalent fragment consisting of the VL, VH, CL and CH1 domains; a F(ab)2 fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., Nature 341:544-546, 1989), which consists of a VH domain; and an isolated complementarity determining region (CDR), or other epitope-binding fragments of an antibody.

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv ("scFv"); see, e.g., Bird et al., Science 242:423-426, 1988; and Huston et al., Proc. Natl. Acad. Sci. 85:5879-5883, 1988). Such single chain antibodies are also intended to be encompassed within the term "antigen binding fragment." These antigen binding fragments are obtained using conventional techniques known to those of skill in the art, and the fragments are screened for utility in the same manner as are intact antibodies.

Antigen binding fragments can also be incorporated into single domain antibodies, maxibodies, minibodies, nanobodies, intrabodies, diabodies, triabodies, tetrabodies, v-NAR and bis-scFv (see, e.g., Hollinger and Hudson, Nature Biotechnology 23:1126-1136, 2005). Antigen binding fragments can be grafted into scaffolds based on polypeptides such as fibronectin type III (Fn3) (see U.S. Pat. No. 6,703,199, which describes fibronectin polypeptide monobodies).

Antigen binding fragments can be incorporated into single chain molecules comprising a pair of tandem Fv segments (VH-CH1-VH-CH1) which, together with complementary light chain polypeptides, form a pair of antigen binding regions (Zapata et al., Protein Eng. 8:1057-1062, 1995; and U.S. Pat. No. 5,641,870).

The term "monoclonal antibody" or "monoclonal antibody composition" as used herein refers to polypeptides, including antibodies and antigen binding fragments that have substantially identical amino acid sequence or are derived from the same genetic source. This term also includes preparations of antibody molecules of single molecular composition. A monoclonal antibody composition displays a single binding specificity and affinity for a particular epitope.

The term "human antibody", as used herein, includes antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik et al., J. Mol. Biol. 296:57-86, 2000).

The human antibodies of the invention may include amino acid residues not encoded by human sequences (e.g., mutations introduced by random or site-specific mutagenesis in vitro or by somatic mutation in vivo, or a substitution to promote stability or manufacturing).

The term "humanized" antibody, as used herein, refers to an antibody that retains the reactivity of a non-human antibody while being less immunogenic in humans. This can be achieved, for instance, by retaining the non-human CDR regions and replacing the remaining parts of the antibody with their human counterparts. See, e.g., Morrison et al., Proc. Natl. Acad. Sci. USA, 81:6851-6855 (1984); Morrison and Oi, Adv. Immunol., 44:65-92 (1988); Verhoeyen et al., Science, 239:1534-1536 (1988); Padlan, Molec. Immun., 28:489-498 (1991); Padlan, Molec. Immun., 31(3):169-217 (1994).

The term "specifically binds" or "selectively binds," when used in the context of describing the interaction between an antigen (e.g., a protein or a glycan) and an antibody, antibody fragment, or antibody-derived binding agent, refers to a binding reaction that is determinative of the presence of the antigen in a heterogeneous population of proteins and other biologics, e.g., in a biological sample, e.g., a blood, serum, plasma or tissue sample. Thus, under certain designated immunoassay conditions, the antibodies or binding agents with a particular binding specificity bind to a particular antigen at least two times the background and do not substantially bind in a significant amount to other antigens present in the sample. In one embodiment, under designated immunoassay conditions, the antibody or binding agents with a particular binding specificity bind to a particular antigen at least ten (10) times the background and do not substantially bind in a significant amount to other antigens present in the sample. Specific binding to an antibody or binding agent under such conditions may require the antibody or agent to have been selected for its specificity for a particular protein. As desired or appropriate, this selection may be achieved by subtracting out antibodies that cross-react with molecules from other species (e.g., mouse or rat) or other subtypes. Alternatively, in some embodiments, antibodies or antibody fragments are selected that cross-react with certain desired molecules.

A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998), for a description of immunoassay formats and conditions that can be used to determine specific immunoreactivity). Typically a specific or selective binding reaction will produce a signal at least twice over the background signal and more typically at least than 10 to 100 times over the background.

The term "affinity" as used herein refers to the strength of interaction between antibody and antigen at single antigenic sites. Within each antigenic site, the variable region of the antibody "arm" interacts through weak non-covalent forces with antigen at numerous sites; the more interactions, the stronger the affinity.

The term "isolated antibody" refers to an antibody that is substantially free of other antibodies having different antigenic specificities. An isolated antibody that specifically binds to one antigen may, however, have cross-reactivity to other antigens. Moreover, an isolated antibody may be substantially free of other cellular material and/or chemicals.

The terms "polypeptide" and "protein" are used interchangeably herein to refer to a polymer of amino acid residues. The terms apply to canonical amino acid polymers as well as to non-canonical amino acid polymers. Unless otherwise indicated, a particular polypeptide sequence also implicitly encompasses modified variants thereof.

The term "immunoconjugate" or "antibody-drug-conjugate" as used herein refers to the linkage of an antigen binding moiety such as an antibody or an antigen binding fragment thereof with an cytotoxic peptide of Formula (I). The linkage can be covalent bonds, or non-covalent interactions, and can include chelation. Various linkers, known in the art, can be employed in order to form the immunoconjugate.

The term "cytotoxin", or "cytotoxic agent" as used herein, refer to any agent that is detrimental to the growth and proliferation of cells and may act to reduce, inhibit, or destroy a cell or malignancy.

The term "anti-cancer agent" as used herein refers to any agent that can be used to treat a cell proliferative disorder such as cancer, including but not limited to, cytotoxic agents, chemotherapeutic agents, radiotherapy and radiotherapeutic agents, targeted anti-cancer agents, and immunotherapeutic agents.

The term "drug moiety" or "payload" as used herein, refers to a chemical moiety that is or can be conjugated to an antibody or antigen binding fragment to form an immunoconjugate, and can include any moiety that is useful to attach to the antibody or antigen binding fragment. For example, "drug moiety" or "payload" includes, but is not limited to, the cytotoxic peptides described herein. The immunoconjugates of the invention comprise one or more cytotoxic peptides described herein as a payload, but may also include one or more other payloads. Other payloads include, for example, a drug moiety or payload can be an anti-cancer agent, an anti-inflammatory agent, an antifungal agent, an antibacterial agent, an anti-parasitic agent, an anti-viral agent, or an anesthetic agent. In certain embodiments a drug moiety is selected from an Eg5 inhibitor, a HSP90 inhibitor, an IAP inhibitor, an mTor inhibitor, a microtubule stabilizer, a microtubule destabilizer, an auristatin, a dolastatin, a maytansinoid, a MetAP (methionine aminopeptidase), an inhibitor of nuclear export of proteins CRM1, a DPPIV inhibitor, an inhibitor of phosphoryl transfer reactions in mitochondria, a protein synthesis inhibitor, a kinase inhibitor, a CDK2 inhibitor, a CDK9 inhibitor, a proteasome inhibitor, a kinesin inhibitor, an HDAC inhibitor, a DNA damaging agent, a DNA alkylating agent, a DNA intercalator, a DNA minor groove binder and a DHFR inhibitor. Suitable examples include calicheamycins such as gamma-calicheamycin; and maytansinoids such as DM1, DM3 and DM4. Methods for attaching each of these to a linker compatible with the antibodies and method of the invention are known in the art. See, e.g., Singh et al., (2009) Therapeutic Antibodies: Methods and Protocols, vol. 525, 445-457.

"Tumor" refers to neoplastic cell growth and proliferation, whether malignant or benign, and all pre-cancerous and cancerous cells and tissues.

The term "anti-tumor activity" means a reduction in the rate of tumor cell proliferation, viability, or metastatic activity. A possible way of showing anti-tumor activity is to show a decline in growth rate of abnormal cells that arises during therapy or tumor size stability or reduction. Such activity can be assessed using accepted in vitro or in vivo tumor models, including but not limited to xenograft models, allograft models, MMTV models, and other known models known in the art to investigate anti-tumor activity.

The term "malignancy" refers to a non-benign tumor or a cancer. As used herein, the term "cancer" includes a malignancy characterized by deregulated or uncontrolled cell growth. Exemplary cancers include: carcinomas, sarcomas, leukemias, and lymphomas.

The term "cancer" includes primary malignant tumors (e.g., those whose cells have not migrated to sites in the subject's body other than the site of the original tumor) and secondary malignant tumors (e.g., those arising from metastasis, the migration of tumor cells to secondary sites that are different from the site of the original tumor).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to at least partially alleviate, inhibit, prevent and/or ameliorate a condition, or a disorder or a disease.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In specific embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

In certain embodiments, the modified immunoconjugates of the invention are described according to an "cytotoxic peptide-to-antibody" ratio of, e.g., 1, 2, 3, 4, 5, 6, 7, or 8, or 12 or 16; this ratio corresponds to "y" in Formula (II) and Formula (III). While this ratio has an integer value for a specific conjugate molecule, it is understood that an average value is typically used to describe a sample containing many molecules, due to some degree of inhomogeneity within a sample of an immunoconjugate. The average loading for a sample of an immunoconjugate is referred to herein as the "drug to antibody ratio," or DAR. In some embodiments, the DAR is between about 1 and about 16, and typically is about 1, 2, 3, 4, 5, 6, 7, or 8. In some embodiments, at least 50% of a sample by weight is compound having the average DAR plus or minus 2, and preferably at least 50% of the sample is a product that contains the average DAR plus or minus 1.5. Preferred embodiments include immunoconjugates wherein the DAR is about 2 to about 8, e.g., about 2, about 3, about 4, about 5, about 6, about 7, or about 8. In these embodiments, a DAR of "about q" means the measured value for DAR is within ±20% of q, or preferably within ±10% of q.

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non- superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)− or (S)−.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms, unless otherwise stated, e.g., where a specific isomer is identified. Optically active (R)− and (S)− isomers may be prepared using chiral synthons or chiral reagents, or resolved using conventional techniques. If the compound contains a double bond, the substituent may be E or Z configuration. If the compound contains a di-substituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlorotheophyllinate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^{3}H$ and $^{14}C$, or those into which non-radioactive isotopes, such as $^{2}H$ and $^{13}C$ are present. Such isotopically labeled compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d^6$-acetone, $d^6$-DMSO, as well as solvates with non-enriched solvents.

Compounds of the invention, i.e. compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO 2004/078163. Hence the invention further provides co-crystals comprising a compound of formula (I).

Any asymmetric atom (e.g., carbon or the like) of the compound(s) of the present invention can be present in racemic or enantiomerically enriched, for example the (R)–, (S)– or (R,S)– configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess of either the (R)– or (S)– configuration; i.e., for optically active compounds, it is often preferred to use one enantiomer to the substantial exclusion of the other enantiomer. Substituents at atoms with unsaturated double bonds may, if possible, be present in cis- (Z)- or trans- (E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof. "Substantially pure" or "substantially free of other isomers" as used herein means the product contains less than 5%, and preferably less than 2%, of other isomers relative to the amount of the preferred isomer, by weight.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of Formula (I) of the present invention, including salts, hydrates and solvates thereof, may inherently or by design form polymorphs.

The term "thiol-maleimide" as used herein refers to a group formed by reaction of a thiol with maleimide, having this general formula

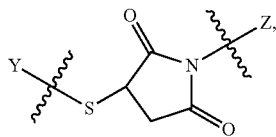

where Y and Z are groups to be connected via the thiol-maleimide linkage and can comprise linker components, antibodies or payloads.

"Cleavable" as used herein refers to a linker or linker component that connects two moieties by covalent connections, but breaks down to sever the covalent connection between the moieties under physiologically relevant conditions, typically a cleavable linker is severed in vivo more rapidly in an intracellular environment than when outside a cell, causing release of the payload to preferentially occur inside a targeted cell. Cleavage may be enzymatic or non-enzymatic, but generally releases a payload from an antibody without degrading the antibody. Cleavage may leave some portion of a linker or linker component attached to the payload, or it may release the payload without any residual part or component of the linker.

"Pcl" as used herein refers to pyrroline carboxy lysine, e.g.,

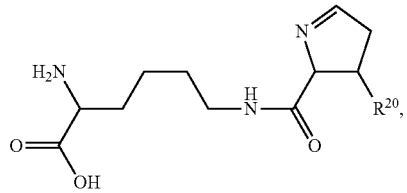

where $R^{20}$ is H, which has the following formula when incorporated into a peptide:

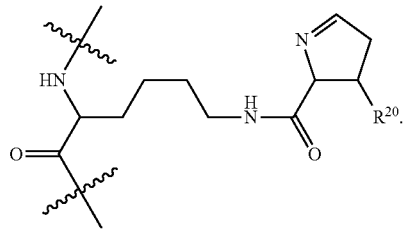

The corresponding compound wherein $R^{20}$ is methyl is pyrrolysine.

"Non-cleavable" as used herein refers to a linker or linker component that is not especially susceptible to breaking down under physiological conditions, e.g., it is at least as stable as the antibody or antigen binding fragment portion of the immunoconjugate. Such linkers are sometimes referred to as "stable", meaning they are sufficiently resistant to degradation to keep the payload connected to the antigen binding moiety Ab until Ab is itself at least partially degraded, i.e., the degradation of Ab precedes cleavage of the linker in vivo. Degradation of the antibody portion of an ADC having a stable or non-cleavable linker may leave some or all of the linker, and one or more amino acid groups from an antibody, attached to the payload or drug moiety that is delivered in vivo.

The terms "$C_1$-$C_3$alkyl", "$C_2$-$C_3$alkyl", "$C_1$-$C_4$alkyl", "$C_1$-$C_5$alkyl", "$C_1$-$C_6$alkyl" and "$C_2$-$C_6$alkyl", as used herein, refer to a fully saturated branched or straight chain hydrocarbon containing 1-3 carbon atoms, 2-3 carbon atoms, 1-4 carbon atoms, 1-5 carbon atoms, 1-6 carbon atoms or 2-6 carbon atoms, respectively. Non-limiting examples of "$C_1$-$C_3$alkyl" groups include methyl, ethyl, n-propyl and isopropyl. Non-limiting examples of "$C_2$-$C_3$alkyl" groups include ethyl, n-propyl and isopropyl. Non-limiting examples of "$C_1$-$C_4$alkyl" groups include methyl, ethyl, n-propyl, isopropyl, n-butyl, isobutyl, sec-butyl and tert-butyl. Non-limiting examples of "$C_1$-$C_5$alkyl" groups include methyl, ethyl, n-propyl, isopropyl, n-butyl, isobutyl, sec-butyl, tert-butyl, n-pentyl and isopentyl. Non-limiting examples of "$C_1$-$C_6$alkyl" groups include methyl, ethyl, n-propyl, isopropyl, n-butyl, isobutyl, sec-butyl, tert-butyl, n-pentyl, isopentyl and hexyl. Non-limiting examples of "$C_2$-$C_6$alkyl" groups include ethyl, n-propyl, isopropyl, n-butyl, isobutyl, sec-butyl, tert-butyl, n-pentyl, isopentyl and hexyl.

As used herein, the term "alkylene" refers to a divalent alkyl group having 1 to 10 carbon atoms, and two open valences to attach to other features. Unless otherwise provided, alkylene refers to moieties having 1 to 10 carbon atoms, 1 to 6 carbon atoms, or 1 to 4 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene and the like.

The terms "$C_1$-$C_3$alkoxy", "$C_2$-$C_3$alkoxy", "$C_1$-$C_4$alkoxy", "$C_1$-$C_5$alkoxy", "$C_1$-$C_6$alkoxy" and "$C_2$-$C_6$alkoxy, as used herein, refer to the groups —O—$C_1$-$C_3$alkyl, —O—$C_2$-$C_3$alkyl, —O—$C_1$-$C_4$alkyl, —O—$C_1$-$C_5$alkyl, —O-$C_1$-$C_6$alkyl and —O—$C_2$-$C_6$alkyl, respectively, wherein the groups "$C_1$-$C_3$alkyl", "$C_2$-$C_3$alkyl", "$C_1$-$C_4$alkyl", "$C_1$-$C_5$alkyl", "$C_1$-$C_6$alkyl" and "$C_2$-$C_6$alkyl" are as defined herein. Non-limiting examples of "$C_1$-$C_3$alkoxy" groups include methoxy, ethoxy, n-propoxy and isopropoxy. Non-limiting examples of "$C_2$-$C_3$alkoxy" groups include ethoxy, n-propoxy and isopropoxy. Non-limiting examples of "$C_1$-$C_4$alkoxy" groups include methoxy, ethoxy, n-propoxy, isopropoxy, n-butoxy, isobutoxy, sec-butoxy and tert-butoxy. Non-limiting examples of "$C_1$-$C_5$alkoxy" groups include methoxy, ethoxy, n-propoxy, isopropoxy, n-butoxy, isobutoxy, sec-butoxy, tert-butoxy, n-pentyloxy and isopentyloxy. Non-limiting examples of "$C_1$-$C_6$alkoxy" groups include methoxy, ethoxy, n-propoxy, isopropoxy, n-butoxy, isobutoxy, sec-butoxy, tert-butoxy, n-pentyloxy, isopentyloxy and hexyloxy. Non-limiting examples of "$C_2$-$C_6$alkoxy" groups include ethoxy, n-propoxy, isopropoxy, n-butoxy, isobutoxy, sec-butoxy, tert-butoxy, n-pentyloxy, isopentyloxy and hexyloxy.

As used herein, the term "halogen" (or halo) refers to fluorine, bromine, chlorine or iodine, in particular fluorine or chlorine. Halogen-substituted groups and moieties, such as alkyl substituted by halogen (haloalkyl) can be mono-, poly- or per-halogenated.

As used herein, the term "heteroatoms" refers to nitrogen (N), oxygen (O) or sulfur (S) atoms, in particular nitrogen or oxygen, unless otherwise provided.

The term "4-8 membered heterocycloalkyl," as used herein refers to a saturated 4-8 membered monocyclic hydrocarbon ring structure wherein one to two of the ring carbons of the hydrocarbon ring structure are replaced by one to two NR groups, wherein R is hydrogen, a bond, an $R^5$ group as defined herein or an $R^7$ group as defined herein. Non-limiting examples of 4-8 membered heterocycloalkyl groups, as used herein, include azatadinyl, azetadin-1-yl, azetadin-2-yl, azetadin-3-yl, pyrrolidinyl, pyrrolidin-1-yl, pyrrolidin-2-yl, pyrrolidin-3-yl, pyrrolidin-4-yl, pyrrolidin-5-yl, piperidinyl, piperidin-1-yl, piperidin-2-yl, piperidin-3-yl, piperidin-4-yl, piperidin-5-yl, piperidin-6-yl, piperazinyl, piperazin-1-yl, piperazin-2-yl, piperazin-3-yl, piperazin-4-yl, piperazin-5-yl, piperazin-6-yl, azepanyl, azepan-1-yl, azepan-2-yl, azepan-3-yl, azepan-4-yl, azepan-5-yl, azepan-6-yl, and azepan-7-yl.

The term "6 membered heterocycloalkyl," as used herein refers to a saturated 6 membered monocyclic hydrocarbon ring structure wherein one to two of the ring carbons of the hydrocarbon ring structure are replaced by one to two NR groups, wherein R is hydrogen, a bond, an $R^5$ group as defined herein or an $R^7$ group as defined herein. Non-limiting examples of 6 membered heterocycloalkyl groups, as used herein, include piperidinyl, piperidin-1-yl, piperidin-2-yl, piperidin-3-yl, piperidin-4-yl, piperidin-5-yl, piperidin-6-yl, piperazinyl, piperazin-1-yl, piperazin-2-yl, piperazin-3-yl, piperazin-4-yl, piperazin-5-yl and piperazin-6-yl.

The term "5-8 membered fused bicyclic heterocycloalkyl," as used herein refers to a saturated 5-8 membered fused bicyclic hydrocarbon ring structure, wherein one to two of the ring carbons of the hydrocarbon ring structure are replaced by one to two NR groups, R is hydrogen, a bond, an $R^5$ group as defined herein or an $R^7$ group as defined herein. Non-limiting examples of 5-8 membered fused bicyclic heterocycloalkyl groups, as used herein, include 3-azabicyclo[3.1.0]hexanyl and 3-azabicyclo[4.1.0]heptanyl.

The immunoconjugate naming convention used herein is antibody-Compound Number, where Compound Number refers to the compound of Formula (I) used for conjugation to the particular antibody.

Linkers

The cytotoxic peptides provided herein for use as ADC payloads can be attached to a linker, L, or directly to an antigen binding moiety. Suitable linkers for use in such ADCs are well known in the art, and can be used in the conjugates of the invention. The linker, L, can be attached to the antigen binding moiety at any suitable available position on the antigen binding moiety: typically, L is attached to an available amino nitrogen atom (i.e., a primary or secondary amine, rather than an amide) or a hydroxylic oxygen atom, or to an available sulfhydryl, such as on a cysteine. The attachment of the linker, L, to the cytotoxic peptides provided herein can be at the N-terminus of the cytotoxic peptide or at the C-terminus of the cytotoxic peptide. A wide variety of linkers for use in ADCs are known (see, e.g., Lash, *Antibody-Drug Conjugates: the Next Generation of Moving Parts, Start-Up*, December 2011, 1-6), and can be used in conjugates within the scope of the invention.

The linker, L, in Formula (I), Formula (II) and Formula (III) is a linking moiety comprising one or more linker components $L_1$, $L_2$, $L_3$, $L_4$, $L_5$, $L_6$, etc. In certain embodiments a linker component can represent a bond connecting the groups flanking it together. In certain embodiments, L is —*$L_1L_2L_3L_4L_5L_6$-, where the * denotes the site of attachment to the cytotoxic peptide of the invention. In certain embodiments a linker component can represent a bond connecting the groups flanking it together. In certain embodiments, L is —*$L_1L_2L_3L_4L_5$-, where the * denotes the site of attachment to the cytotoxic peptide of the invention. In certain embodiments a linker component can represent a bond connecting the groups flanking it together. In certain embodiments, L is —*$L_1L_2L_3L_4$-, where the * denotes the site of attachment to the cytotoxic peptide of the invention. In certain embodiments a linker component can represent a bond connecting the groups flanking it together. In certain embodiments, L is —*$L_1L_2L_3$-, where the * denotes the site of attachment to the cytotoxic peptide of the invention. In a preferred embodiment L is —*$L_1L_2$-, where the * denotes the site of attachment to the cytotoxic peptide of the invention. In certain embodiment L is —$L_1$-. Some preferred linkers and linker components are depicted herein.

The linker, L, in Formula (I), Formula (II) and Formula (III) may be divalent, meaning it can used to link only one payload per linker to an antigen binding moiety, or it can be trivalent an is able to link two payloads per linker to an antigen binding moiety, or it can be polyvalent. Trivalent, tetravalent, and polyvalent linkers can be used to increase the loading of a payload (drug) on an antigen binding moiety (e.g. an antibody), thereby increasing the drug to antibody ratio (DAR) without requiring additional sites on the antibody for attaching multiple linkers. Examples of such linkers given in Bioconjugate Chem., 1999 March-April; 10(2): 279-88; U.S. Pat. No. 6,638,499; Clin Cancer Res Oct. 15, 2004 10; 7063; and WO2012/113847A1.

A linker, L, for use in the compounds of Formula (I) and the immunoconjugates of Formula (II) and Formula (III) can be cleavable or non-cleavable. Cleavable linkers, such as those containing a hydrazone, a disulfide, the dipeptide Val-Cit, and ones containing a glucuronidase-cleavable p-aminobenzyloxycarbonyl moiety, are well known in the art, and can be used. See, e.g., Ducry, et al., *Bioconjugate Chem.*, vol. 21, 5-13 (2010). For the immunoconjugates of comprising a cleavable linker, the linker is substantially stable in vivo until the immunoconjugate binds to or enters a cell, at which point either intracellular enzymes or intracellular chemical conditions (pH, reduction capacity) cleave the linker to free the cytotoxic peptide.

Alternatively, non-cleavable linkers can be used in compounds of Formula (I) and the immunoconjugates of Formula (II) and Formula (III). Non-cleavable linkers lack structural components designed to degrade in cells, and thus their structures can vary substantially. See, e.g., Ducry, et al., *Bioconjugate Chem.*, vol. 21, 5-13 (2010). These immunoconjugates are believed to enter a targeted cell and undergo proteolytic degradation of the antibody rather than linker decomposition; thus at least a portion, or all, of the linker and even some of the antibody or antibody fragment may remain attached to the payload.

The linker, L, in the compounds of Formula (I) and the immunoconjugates of Formula (II) and Formula (III) typically commonly contain two or more linker components, which may be selected for convenience in assembly of the conjugate, or they may be selected to impact properties of the conjugate. Suitable linker components for forming linker, L, are known in the art, as are methods for constructing the linker L. Linker components can include the groups commonly used to attach a group to an amino acid, spacers such as alkylene groups and ethylene oxide oligomers, amino acids and short peptides up to about 4 amino acids in length; a bond; and carbonyl, carbamate, carbonate, urea, ester and amide linkages, and the like. Linker components can comprise thiol-maleimide groups, thioethers, amides, and esters; groups that are easily cleaved in vivo under conditions found in, on or around targeted cells, such as disulfides, hydrazones, dipeptides like Val-Cit, substituted benzyloxycarbonyl groups, and the like; spacers to orient the payload in a suitable position relative to the antigen binding moiety, such as phenyl, heteroaryl, cycloalkyl or heterocyclyl rings, and alkylene chains; and/or pharmacokinetic property-enhancing groups, such as alkylene substituted with one or more polar groups (carboxy, sulfonate, hydroxyl, amine, amino acid, saccharide), and alkylene chains containing one or more —NH— or —O— in place of methylene group(s), such as glycol ethers (—$CH_2CH_2O$—)$_p$ where p is 1-10, which may enhance solubility or reduce intermolecular aggregation, for example.

In addition, linker components can comprise chemical moieties that are readily formed by reaction between two reactive groups. Non-limiting examples of such chemical moieties are given in Table 1.

TABLE 1

| Reactive Group 1 | Reactive Group 2 | Chemical Moiety |
| --- | --- | --- |
| a thiol | a thiol | —S—S— |
| a thiol | a maleimide | (succinimide thioether structure) |
| a thiol | a haloacetamide | (thioether acetamide structure) |
| an azide | an alkyne | (1,2,3-triazole, 1,4- or 1,5-isomer) |

TABLE 1-continued

| Reactive Group 1 | Reactive Group 2 | Chemical Moiety |
| --- | --- | --- |
| an azide | a triaryl phosphine | |
| an azide | a cyclooctene | |
| an azide | an oxanobornadiene | |
| a triaryl phosphine | an azide | |
| an oxanobornadiene | an azide | |
| an alkyne | an azide | |

TABLE 1-continued
| Reactive Group 1 | Reactive Group 2 | Chemical Moiety |
|---|---|---|
| a cyclooctene | azide | 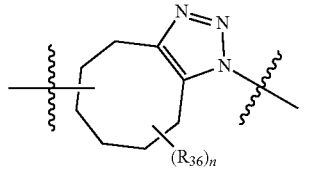 or 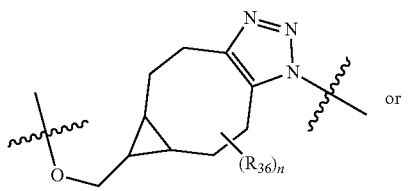 or 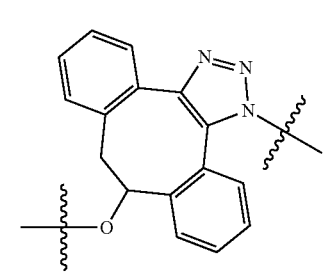 [SMILES: *OC1Cc2ccccc2-c2nnn(*)c2-c2ccccc21] |
| a cyclooctene | a diaryl tetrazine | 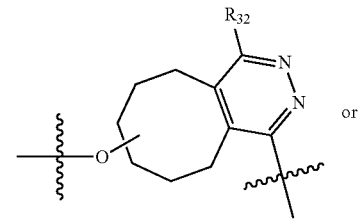 or 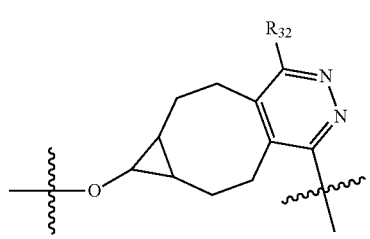 |
| a diaryl tetrazine | a cyclooctene | 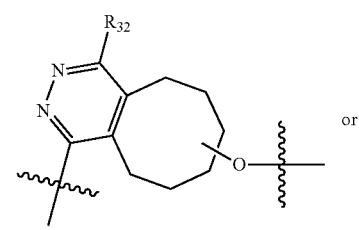 or 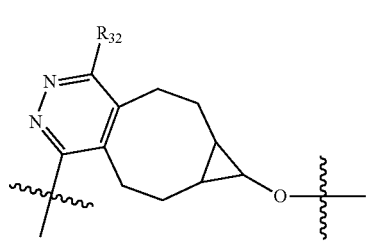 |

TABLE 1-continued
| Reactive Group 1 | Reactive Group 2 | Chemical Moiety |
|---|---|---|
| a monoaryl tetrazine | a norbornene | 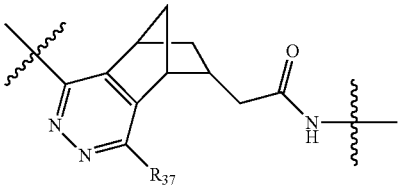 |
| a norbornene | a monoaryl tetrazine | 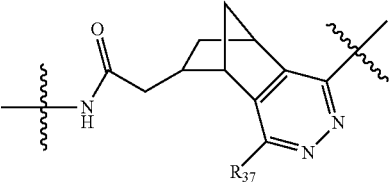 |
| an aldehyde | a hydroxylamine | 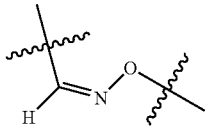 [SMILES: */C=N\O*] |
| an aldehyde | a hydrazine | 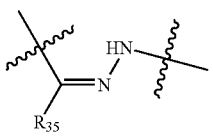 |
| an aldehyde | $NH_2-NH-C(=O)-$ | 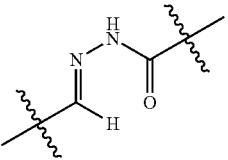 [SMILES: */C=N/NC(*)=O] |
| a ketone | a hydroxylamine | 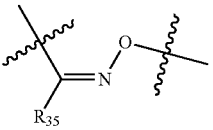 |
| a ketone | a hydrazine | 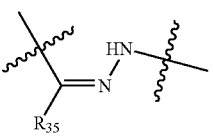 |
| a ketone | $NH_2-NH-C(=O)-$ | 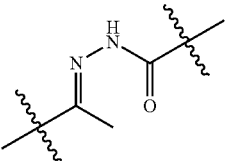 [SMILES: *C(=O)N/N=C(/*)C] |
| a hydroxylamine | an aldehyde | 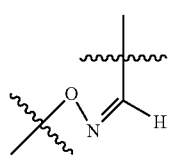 [SMILES: */C=N\O*] |

TABLE 1-continued

| Reactive Group 1 | Reactive Group 2 | Chemical Moiety |
|---|---|---|
| a hydroxylamine | a ketone | (structure: oxime) |
| a hydrazine | an aldehyde | (structure: hydrazone from aldehyde) |
| a hydrazine | a ketone | (structure: hydrazone from ketone with $R_{35}$) |
| $NH_2-NH-C(=O)-$ | an aldehyde | (structure: acyl hydrazone from aldehyde) |
| $NH_2-NH-C(=O)-$ | a ketone | (structure: acyl hydrazone from ketone with $R_{35}$) |
| a haloacetamide | a thiol | (structure: –NH–C(=O)–CH$_2$–S–) |
| a maleimide | a thiol | (structure: succinimide thioether) |
| a vinyl sulfone | a thiol | (structure: –SO$_2$–CH$_2$CH$_2$–S–) |
| a thiol | a vinyl sulfone | (structure: –S–CH$_2$CH$_2$–SO$_2$–) |
| an aziridine | a thiol | (structure: –NH–CH$_2$CH$_2$–S– or –NH–CH$_2$CH$_2$–S–) |

TABLE 1-continued

| Reactive Group 1 | Reactive Group 2 | Chemical Moiety |
|---|---|---|
| a thiol | an aziridine | | where: $R^{32}$ in Table 1 is H, $C_{1-4}$ alkyl, phenyl, pyrimidine or pyridine; $R^{35}$ in Table 1 is H, $C_{1-6}$alkyl, phenyl or $C_{1-4}$alkyl substituted with 1 to 3 —OH groups; each $R^{36}$ in Table 1 is independently selected from H, $C_{1-6}$alkyl, fluoro, benzyloxy substituted with —C(=O)OH, benzyl substituted with —C(=O)OH, $C_{1-4}$alkoxy substituted with —C(=O)OH and $C_{1-4}$alkyl substituted with —C(=O)OH; $R^{37}$ in Table 1 is independently selected from H, phenyl and pyridine, each $R^5$ in Table 1 is independently selected from H or $C_{1-6}$alkyl; $R^{12}$ in Table 1 is H, —CH$_3$ or phenyl; $R^{50}$ in Table 1 is H or nitro.

In some embodiments, a linker component of linker, L, of immunoconjugates of Formula (II) ans Formula (III) is a group formed upon reaction of a reactive functional group with one of the amino acid side chains commonly used for conjugation, e.g., the thiol of cysteine, or the free —NH$_2$ of lysine, or a Pcl or Pyl group engineered into an antibody. See e.g., Ou, et al., PNAS 108(26), 10437-42 (2011). Linker components formed by reaction with a cysteine residue of the antigen binding moiety include, but are not limited to,

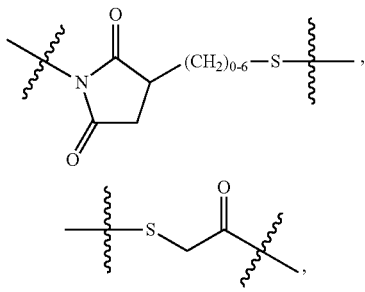

-continued

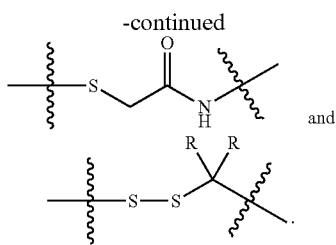 and

Linker components formed by reaction with the —NH$_2$ of a lysine residue of the antigen binding moiety, where each p is 1-10, and each R is independently H or C$_{1-4}$ alkyl (preferably methyl) include, but are not limited to,

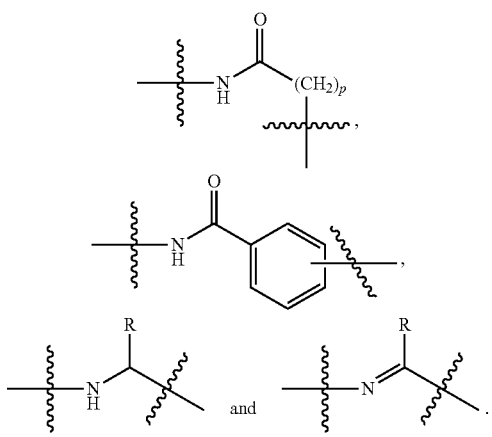

Linker components formed by reaction with a Pcl or Pyl group include, but are not limited to,

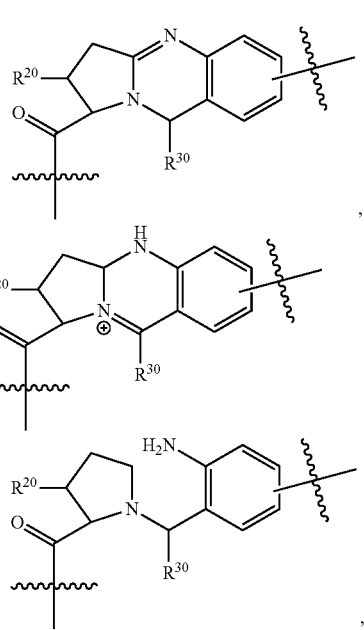

wherein R$^{20}$ is H or Me, and R$^{30}$ is H, Me or Phenyl, for linking, where the acyl group shown attaches to the lysine portion of a Pcl or Pyl in an engineered antibody. A linker component formed upon reaction of an Ab disulfide bridge,

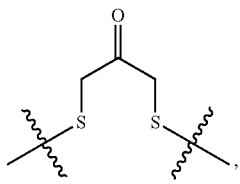 [SMILES: *SCC(=O)CS*]

and a compound of Formula (I) which contains an hydroxylamine is

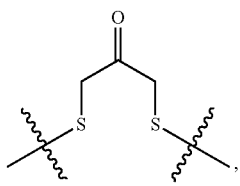 [SMILES: *SCC(=O)CS*]

A linker component formed upon reaction of an Ab disulfide bridge,

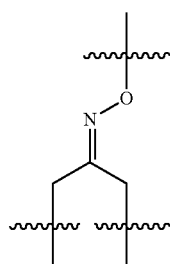

and a compound of Formula (I) which contains an hydroxylamine is

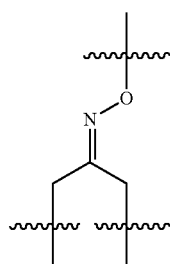

In some embodiments, a linker component of linker, L, of immunoconjugates of Formula (II) ans Formula (III) include, for example, alkylene groups —(CH$_2$)$_n$— (where n is typically 1-10 or 1-6), ethylene glycol units (—CH$_2$CH$_2$O—)$_n$ (where n is 1-20, typically 1-10 or 1-6), —O—, —S—, carbonyl (—C(=O)—), amides —C(=O)—NH— or —NH—C(=O)—, esters —C(=O)—O— or —O—C(=O)—, ring systems having two available points of attachment such as a divalent ring selected from phenyl (including 1,2- 1,3- and 1,4- di-substituted phenyls), C$_{5-6}$ heteroaryl, C$_{3-8}$ cycloalkyl including 1,1-disubstituted cyclopropyl, cyclobutyl, cyclopentyl or cyclohexyl, and 1,4-disubstituted cyclohexyl, and C$_{4-8}$ heterocyclyl rings, and specific examples depicted below;

amino acids —NH—CHR*—C(=O)— or —C(=O)—CHR*—NH—, or groups derived from amino acids that attach to N of an adjacent structure (e.g., to a maleimide nitrogen) having the formula [N]—CHR*—C(=O)— where R* is the side chain of a known amino acid (frequently one of the canonical amino acids, e.g., trp, ala, asp, lys, gly, and the like, but also including e.g. norvaline, norleucine, homoserine, homocysteine, phenylglycine, citrulline, and other commonly named alpha-amino acids), polypeptides of known amino acids (e.g., dipeptides, tripeptides, tetrapeptides, etc.), thiol-maleimide linkages (from addition of —SH to maleimide), —S—CR$_2$— and other thiol ethers such as —S—CR$_2$—C(=O)— or —C(=O)—CR$_2$—S— where R is independently at each occurrence H or C$_{1-4}$ alkyl, —CH$_2$—C(=O)—, and disulfides (—S—S—), as well as combinations of any of these with other linker components described below, e.g., a bond, a non-enzymatically cleavable linker, a non-cleavable linker, an enzymatically cleavable linker, a photo-stable linker, a photo-cleavable linker or a linker that comprises a self-immolative spacer.

In certain embodiments, Linker, L, of compounds of Formula (I) and immunoconjugates of Formula (II) and Formula (III) is —*L$_1$L$_2$L$_3$L$_4$L$_5$L$_6$-, where the * denotes the site of attachment to the cytotoxic peptide of the invention. In certain embodiments, Linker, L, of compounds of Formula (I) and immunoconjugates of Formula (II) and Formula (III) is —*L$_1$L$_2$L$_3$L$_4$L$_5$-, where the * denotes the site of attachment to the cytotoxic peptide of the invention. In certain embodiments, Linker, L, of compounds of Formula (I) and immunoconjugates of Formula (II) and Formula (III) is —*L$_1$L$_2$L$_3$L$_4$-, where the * denotes the site of attachment to the cytotoxic peptide of the invention. In certain embodiments, Linker, L, of compounds of Formula (I) and immunoconjugates of Formula (II) and Formula (III) is —*L$_1$L$_2$L$_3$-, where the * denotes the site of attachment to the cytotoxic peptide of the invention. In a preferred embodiment Linker, L, of compounds of Formula (I) and immunoconjugates of Formula (II) and Formula (III) is —*L$_1$L$_2$-, where the * denotes the site of attachment to the cytotoxic peptide of the invention. In certain embodiments Linker, L, of compounds of Formula (I) is —L$_1$-.

Linker component L$_1$ of compounds of Formula (I) and immunoconjugates of Formula (II) and Formula (III) is selected from —(CH$_2$)$_m$—, —C(=O)(CH$_2$)$_m$—, —C(=O)X$_1$X$_2$C(=O)(CH$_2$)$_m$—, —C(=O)X$_1$X$_2$C(=O)(CH$_2$)$_m$NR$^{12}$C(=O)(CH$_2$)$_m$—, —C(=O)X$_1$X$_2$C(=O)(CH$_2$)$_m$X$_3$(CH$_2$)$_m$—, —C(=O)X$_1$X$_2$C(=O)((CH$_2$)$_m$O)$_n$(CH$_2$)$_m$—, —C(=O)X$_1$X$_2$C(=O)((CH$_2$)$_m$O)$_n$(CH$_2$)$_m$NR$^{12}$C(=O)(CH$_2$)$_m$—, —C(=O)X$_1$X$_2$C(=O)((CH$_2$)$_m$O)$_n$(CH$_2$)$_m$NR$^{12}$C(=O)(CH$_2$)$_m$X$_3$(CH$_2$)$_m$—, —C(=O)X$_1$X$_2$C(=O)((CH$_2$)$_m$O)$_n$(CH$_2$)$_m$X$_3$(CH$_2$)$_m$—, —C(=O)X$_1$X$_2$C(=O)(CH$_2$)$_m$NR$^{12}$C(=O)((CH$_2$)$_m$O)$_n$(CH$_2$)$_m$—, —C(=O)X$_1$X$_2$C(=O)(CH$_2$)$_m$NR$^{12}$C(=O)((CH$_2$)$_m$O)$_n$(CH$_2$)$_m$X$_3$(CH$_2$)$_m$—, —C(=O)X$_1$X$_2$(CH$_2$)$_m$X$_3$(CH$_2$)$_m$—, —C(=O)X$_1$X$_2$((CH$_2$)$_m$O)$_n$(CH$_2$)$_m$—, —C(=O)X$_1$X$_2$((CH$_2$)$_m$O)$_n$(CH$_2$)$_m$NR$^{12}$C(=O)(CH$_2$)$_m$—, —C(=O)X$_1$X$_2$((CH$_2$)$_m$O)$_n$(CH$_2$)$_m$NR$^{12}$C(=O)(CH$_2$)$_m$X$_3$(CH$_2$)$_m$—, —C(=O)X$_1$X$_2$((CH$_2$)$_m$O)$_n$(CH$_2$)$_m$X$_3$(CH$_2$)$_m$—, —C(=O)X$_1$X$_2$(CH$_2$)$_m$NR$^{12}$((CH$_2$)$_m$O)$_n$(CH$_2$)$_m$—, —C(=O)X$_1$X$_2$C(=O)(CH$_2$)$_m$NR$^{12}$((CH$_2$)$_m$O)$_n$(CH$_2$)$_m$X$_3$(CH$_2$)$_m$—, —(CH$_2$)$_m$NR$^{12}$C(=O)(CH$_2$)$_m$—, —C(=O)((CH$_2$)$_m$O)$_n$(CH$_2$)$_m$—, —(CH$_2$)$_m$S(=O)$_2$((CH$_2$)$_m$O)$_n$(CH$_2$)$_m$—, —C(=O)(CH$_2$)$_m$NR$^{12}$(CH$_2$)$_m$—, —C(=O)NR$^{12}$(CH$_2$)$_m$—, —C(=O)NR$^{12}$(CH$_2$)$_m$X$_3$(CH$_2$)$_m$—, —C(=O)NH(CH$_2$)$_m$NR$^{12}$C(=O)X$_1$X$_2$C(=O)(CH$_2$)$_m$—, —C(=O)(CH$_2$)$_m$X$_3$((CH$_2$)$_m$O)$_n$—, —C(=O)X$_1$C(=O)NR$^{12}$(CH$_2$)$_m$NR$^{12}$C(=O)(CH$_2$)$_m$—, —C(=O)X$_1$C(=O)NR$^{12}$(CH$_2$)$_m$X$_3$(CH$_2$)$_m$—, —C(=O)NR$^{12}$(CH$_2$)$_m$NR$^{12}$C(=O)(CH$_2$)$_m$—, —C(=O)NR$^{12}$(CH$_2$)$_m$NR$^{12}$C(=O)(CH$_2$)$_m$X$_3$(CH$_2$)$_m$—,

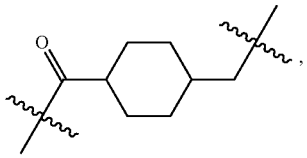

—(CH$_2$)$_m$C(=O)NR$^{12}$(CH$_2$)$_m$NR$^{12}$C(=O)(CH$_2$)$_m$—, —(CH$_2$)$_m$C(=O)—, —(CH$_2$)$_m$C(=O)X$_2$X$_1$C(=O)—, —(CH$_2$)$_m$X$_3$(CH$_2$)$_m$C(=O)X$_2$X$_1$C(=O)—, —(CH$_2$)$_m$C(=O)NR$^{12}$(CH$_2$)$_m$—, —(CH$_2$)$_m$X$_3$(CH$_2$)$_m$C(=O)NR$^{12}$(CH$_2$)$_m$—, —(CH$_2$)$_m$NR$^{12}$C(=O)(CH$_2$)$_m$X$_3$(CH$_2$)$_m$—, —(CH$_2$)$_m$(O(CH$_2$)$_m$)$_n$C(=O)—, —(CH$_2$)$_m$(O(CH$_2$)$_m$)$_n$S(=O)$_2$(CH$_2$)$_m$—, —(CH$_2$)$_m$NR$^{12}$(CH$_2$)$_m$C(=O)—, —(CH$_2$)$_m$NR$^{12}$C(=O)—, —(CH$_2$)$_m$C(=O)X$_2$X$_1$C(=O)NR$^{12}$(CH$_2$)$_m$NHC(=O)—, —(CH$_2$)$_m$C(=O)NR$^{12}$(CH$_2$)$_m$NR$^{12}$C(=O)X$_1$—, —(CH$_2$)$_m$C(=O)NR$^{12}$(CH$_2$)$_m$NR$^{12}$C(=O)—,

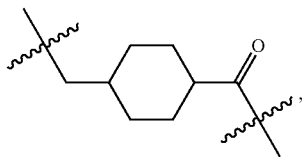 [SMILES: *CC1CCC(C(*)=O)CC1]

—((CH$_2$)$_m$O)$_n$(CH$_2$)$_m$—, —(CH$_2$)$_m$(O(CH$_2$)$_m$)$_n$—, —(CH$_2$)$_m$(O(CH$_2$)$_m$)$_n$X$_3$(CH$_2$)$_m$—, —(CH$_2$)$_m$X$_3$((CH$_2$)$_m$O)$_n$(CH$_2$)$_m$—, —(CH$_2$)$_m$X$_3$(CH$_2$)$_m$C(=O)—, —C(=O)(CH$_2$)$_m$X$_3$(CH$_2$)$_m$—, —(CH$_2$)$_m$X$_3$(CH$_2$)$_m$(O(CH$_2$)$_m$)$_n$C(=O)—, —C(=O)((CH$_2$)$_m$O)$_n$(CH$_2$)$_m$X$_3$(CH$_2$)$_m$—, —(CH$_2$)$_m$C(=O)NR$^{12}$(CH$_2$)$_m$C(=O)—, —C(=O)(CH$_2$)$_m$NR$^{12}$C(=O)(CH$_2$)$_m$—, —(CH$_2$)$_m$C(=O)NR$^{12}$(CH$_2$)$_m$(O(CH$_2$)$_m$)$_n$C(=O)—, —C(=O)((CH$_2$)$_m$O)$_n$(CH$_2$)$_m$NR$^{12}$C(=O)(CH$_2$)$_m$—, —(CH$_2$)$_m$C(=O)NR$^{12}$(CH$_2$)$_m$C(=O)NR$^{12}$(CH$_2$)$_m$—, —(CH$_2$)$_m$NR$^{12}$C(=O)(CH$_2$)$_m$NR$^{12}$C(=O)(CH$_2$)$_m$—, —C(=O)NR$^{12}$(CH$_2$)$_m$NR$^{12}$C(=O)—, —(CH$_2$)$_m$S(CH$_2$)$_m$—, —NR$^{12}$C(=O)(CH$_2$)$_m$—, —NR$^{12}$C(=O)(CH$_2$)$_m$X$_3$(CH$_2$)$_m$—, —(CH$_2$)$_m$X$_3$(CH$_2$)$_m$C(=O)NR$^{12}$—, —(CH$_2$)$_m$C(=O)NR$^{12}$—, —(CH$_2$)$_m$NR$^{12}$(CH$_2$)$_m$—, —(CH$_2$)$_m$X$_3$(CH$_2$)$_m$—, —((CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$—, —NR$^{12}$(CH$_2$)$_m$—, —NR$^{12}$C(R$^{12}$)$_2$(CH$_2$)$_m$—, —(CH$_2$)$_m$C(R$^{12}$)$_2$NR$^{12}$—, —(CH$_2$)$_m$C(=O)NR$^{12}$(CH$_2$)$_m$NR$^{12}$—, —NR$^{12}$(CH$_2$)$_m$NR$^{12}$C(=O)(CH$_2$)$_m$—, —NR$^{12}$C(R$^{12}$)$_2$(CH$_2$)$_m$NR$^{12}$C(=O)(CH$_2$)$_m$—, —(CH$_2$)$_m$C(=O)NR$^{12}$(CH$_2$)$_m$C(R$^{12}$)$_2$NR$^{12}$—, —NR$^{12}$(CH$_2$)$_m$X$_3$(CH$_2$)$_m$—, —NR$^{12}$C(R$^{12}$)$_2$(CH$_2$)$_m$X$_3$(CH$_2$)$_m$—, —(CH$_2$)$_m$X$_3$(CH$_2$)$_m$C(R$^{12}$)$_2$NR$^{12}$—, —NR$^{12}$C(R$^{12}$)$_2$(CH$_2$)$_m$OC(=O)NR$^{12}$(CH$_2$)$_m$—, —(CH$_2$)$_m$NR$^{12}$C(=O)O(CH$_2$)$_m$C(R$^{12}$)$_2$NR$^{12}$—, —NR$^{12}$C(R$^{12}$)$_2$(CH$_2$)$_m$OC(=O)NR$^{12}$(CH$_2$)$_m$X$_3$(CH$_2$)$_m$—, —(CH$_2$)$_m$X$_3$(CH$_2$)$_m$NR$^{12}$C(=O)O(CH$_2$)$_m$C(R$^{12}$)$_2$NR$^{12}$—, —NR$^{12}$C(R$^{12}$)$_2$(CH$_2$)$_m$OC(=O)NR$^{12}$((CH$_2$)$_m$O)$_n$(CH$_2$)$_m$—, —(CH$_2$)$_m$(O(CH$_2$)$_m$)$_n$NR$^{12}$C(=O)O(CH$_2$)$_m$C(R$^{12}$)$_2$NR$^{12}$—, —NR$^{12}$C(R$^{12}$)$_2$(CH$_2$)$_m$OC(=O)NR$^{12}$((CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NR$^{12}$C(=O)O(CH$_2$)$_m$C(R$^{12}$)$_2$NR$^{12}$—, —(CH$_2$)$_m$X$_3$(CH$_2$)$_m$NR$^{12}$—, —NR$^{12}$((CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NR$^{12}$—, —(CH$_2$)$_m$NR$^{12}$—, —NR$^{12}$((CH$_2$)$_m$O)$_n$(CH$_2$)$_m$—, —NR$^{12}$ $-((CH_2)_mO)_n(CH_2)_mNR^{12}C(=O)(CH_2)_m-$, $-(CH_2)_mC(=O)NR^{12}(CH_2)_m(O(CH_2)_m)_nNR^{12}-$, $-(CH_2)_m(O(CH_2)_m)_nNR^{12}-$, $-(C(R_{12})_2)_m-$, $-(CH_2CH_2O)_n-$, $-(OCH_2CH_2)_n-$, $-(CH_2)_mO(CH_2)_m-$, $-S(=O)_2(CH_2)_m-$, $-(CH_2)_mS(=O)_2-$, $-S(=O)_2(CH_2)_mNR^{12}C(=O)(CH_2)_m-$, $-(CH_2)_mC(=O)NR^{12}(CH_2)_mS(=O)_2-$, $-S(=O)_2(CH_2)_mX_3(CH_2)_m-$, $-(CH_2)_mX_3(CH_2)_mS(=O)_2-$, $-(CH_2)_mX_2X_1C(=O)-$, $-C(=O)X_1X_2(CH_2)_m-$, $-(CH_2)_m(O(CH_2)_m)_nC(=O)X_2X_1C(=O)-$, $-C(=O)X_1X_2C(=O)((CH_2)_mO)_n(CH_2)_m-$, $-(CH_2)_m(O(CH_2)_m)_nX_2X_1C(=O)-$, $-(CH_2)_mX_3(CH_2)_mX_2X_1C(=O)-$, $-C(=O)X_1X_2(CH_2)_mX_3(CH_2)_m-$, $-(CH_2)_mX_3(CH_2)_m(O(CH_2)_m)_nX_2X_1C(=O)-$, $-(CH_2)_mX_3(CH_2)_mC(=O)NR^{12}(CH_2)_mNR^{12}C(=O)-$, $-(CH_2)_mX_3(CH_2)_mC(=O)NR^{12}(CH_2)_mC(=O)-$, $-C(=O)(CH_2)_mNR^{12}C(=O(CH_2)_mX_3(CH_2)_m-$, $-(CH_2)_mX_3(CH_2)_mC(=O)NR^{12}(CH_2)_m(O(CH_2)_m)_nC(=O)-$, $-C(=O)((CH_2)_mO)_n(CH_2)_mNR^{12}C(=O)(CH_2)_mX_3(CH_2)_m-$, $-(CH_2)_mNR^{12}C(=O)X_1X_2C(=O)(CH_2)_m-$, $-(CH_2)_mC(=O)X_2X_1C(=O)NR^{12}(CH_2)_m-$, $-X_4X_1X_2C(=O)(CH_2)_m-$, $-(CH_2)_mC(=O)X_2X_1X_4-$, $-X_1C(=O)(CH_2)_mNHC(=O)(CH_2)_m-$, $-(CH_2)_mC(=O)NH(CH_2)_mC(=O)X_1-$, $-C(=O)CHR^{aa}NR^{12}-$, $-CHR^{aa}C(=O)-$, $-C(=O)NR^{12}-$, $-C(=O)O-$, $-S-$, $-SCH_2C(=O)NR^{12}-$, $-NR^{12}C(=O)CH_2S-$, $-S(=O)_2CH_2CH_2S-$, $-SCH_2CH_2S(=O)_2-$, $-(CH_2)_2S(=O)_2CH_2CH_2S-$, $-SCH_2CH_2S(=O)_2CH_2CH_2-$, $-NR^{12}C(=S)-$, $-(CH_2)_mX_3(O(CH_2)_m)_nC(=O)-$, $-C(=O)((CH_2)_mO)_nX_3(CH_2)_m-$, $-(CH_2)_mNR^{12}C(=O)((CH_2)_mO)_n(CH_2)_m-$, $-(CH_2)_m(O(CH_2)_m)_nC(=O)NR^{12}(CH_2)_m-$, $-(CH_2)_mNHC(=O)NR^{12}(CH_2)_m-$, $-(CH_2)_mX_3(CH_2)_mNR^{12}C(=O)-$, $-C(=O)NR^{12}(CH_2)_mX_3(CH_2)_m-$, $-NR_{12}S(=O)_2(CH_2)_mX_3(CH_2)_m-$, $-(CH_2)_mX_3(CH_2)_mS(=O)_2NR_{12}-$,

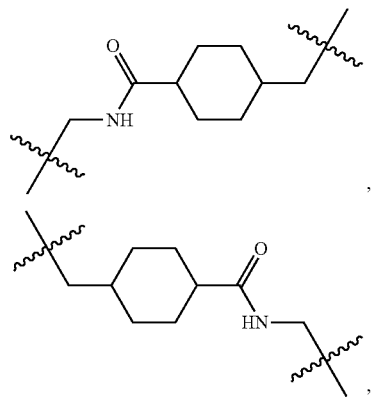

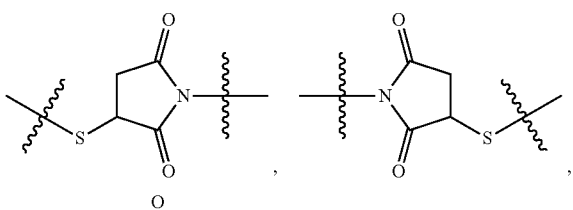

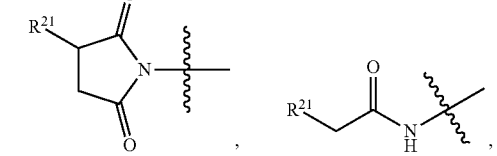

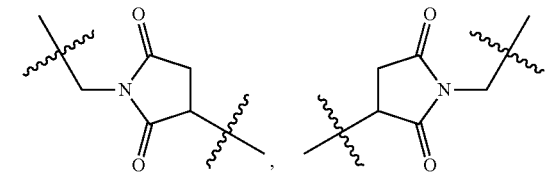

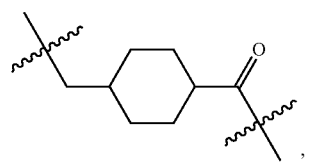

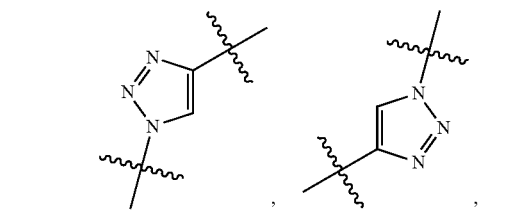

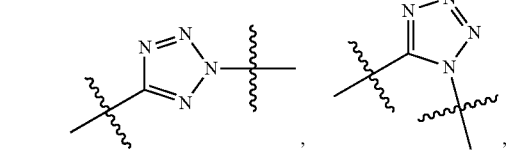

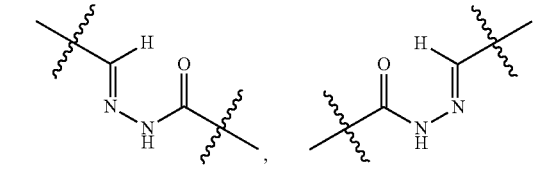

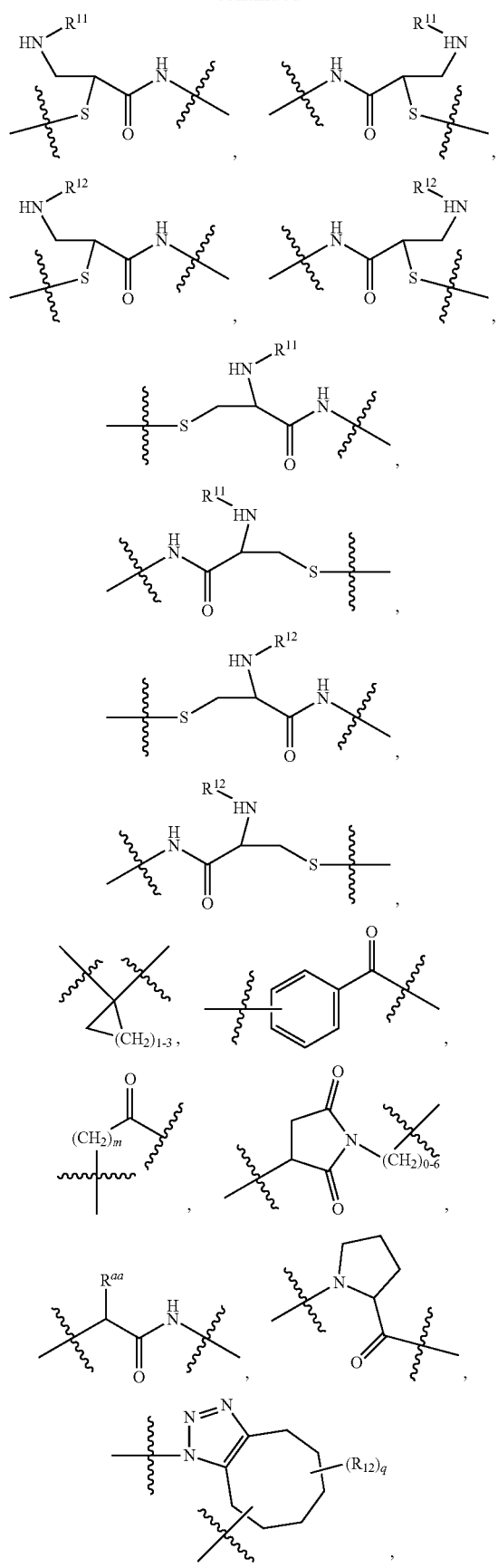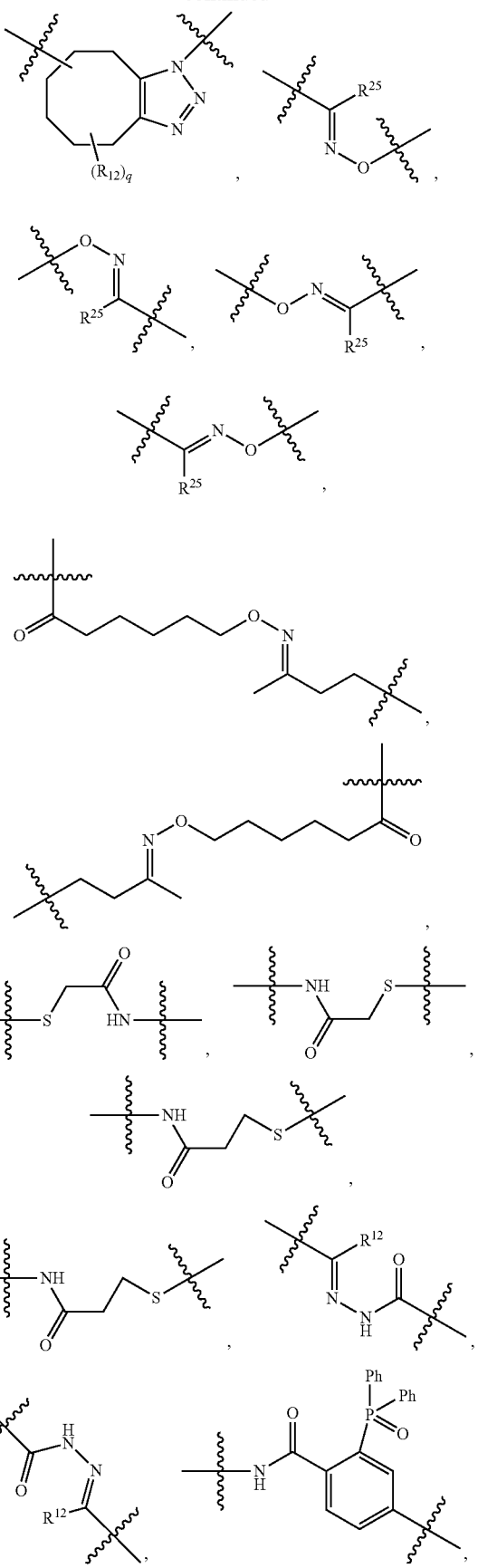

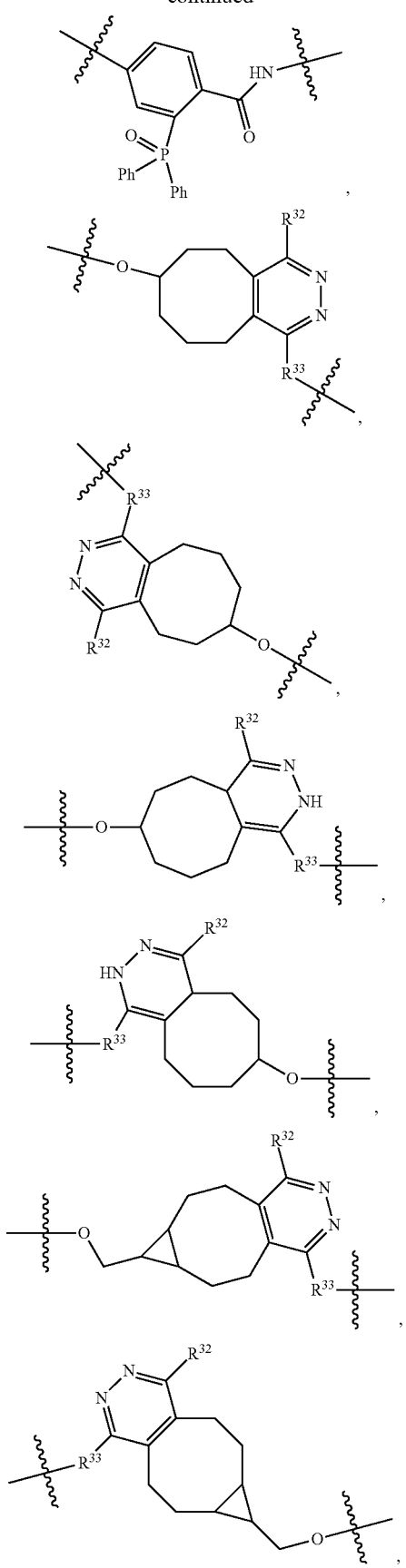
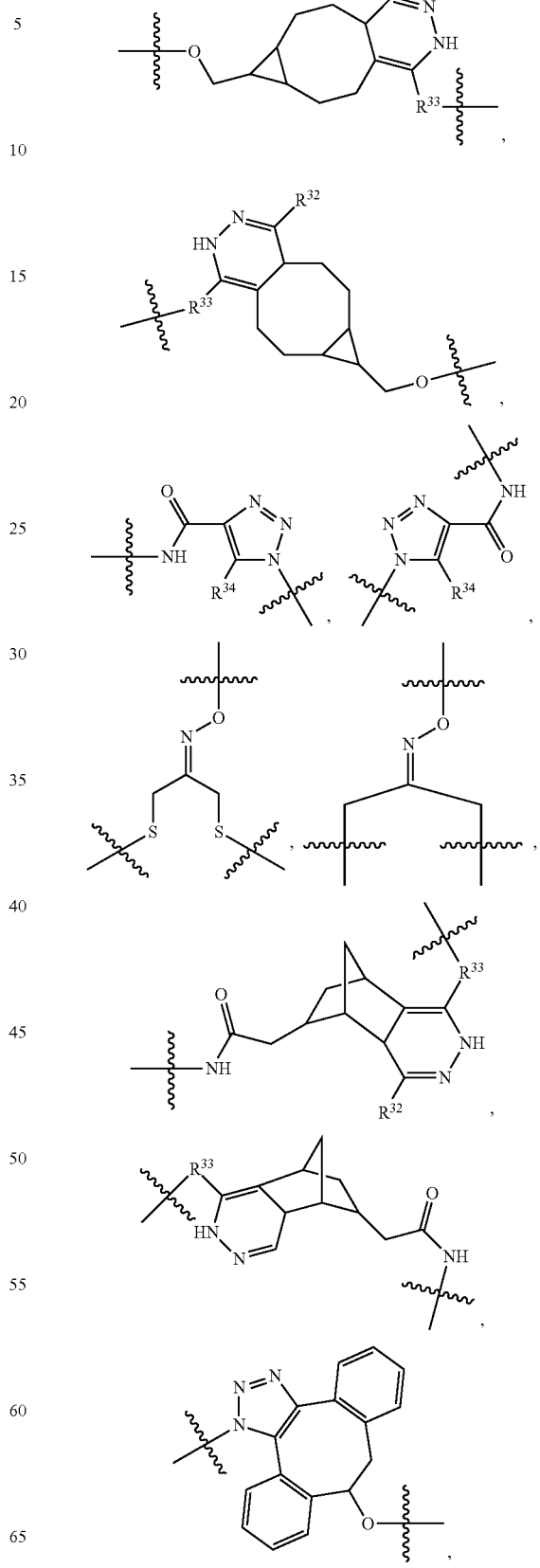

-continued

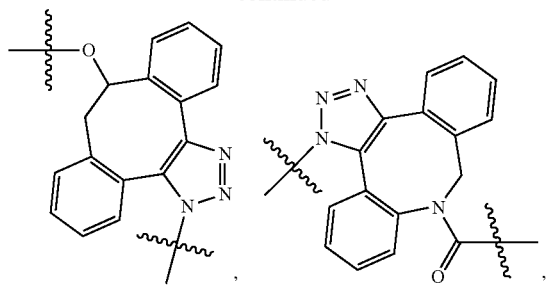

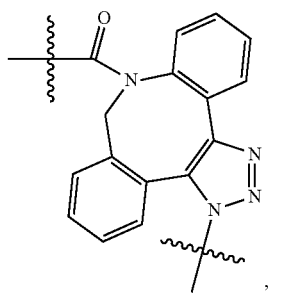

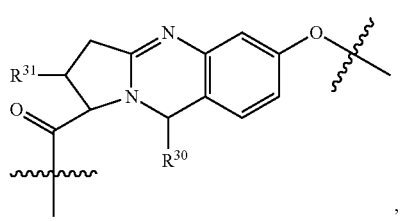

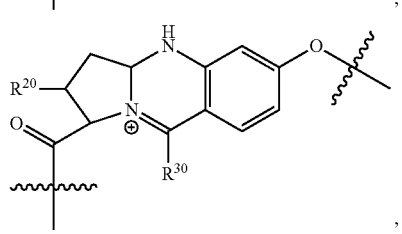

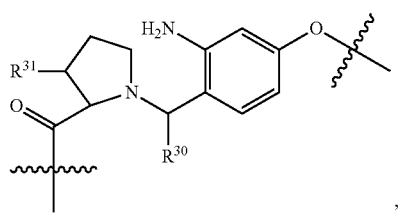

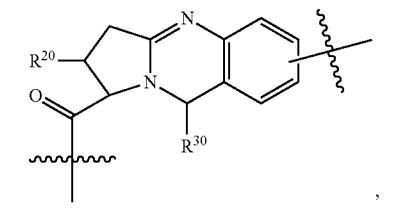

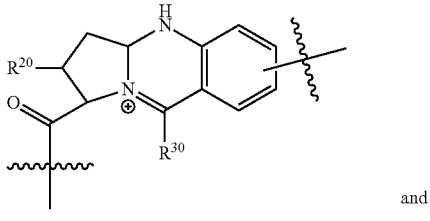

and

-continued

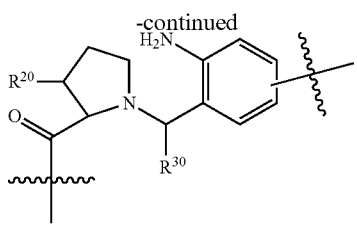

wherein:
$R^{20}$ is H or Me, and $R^{30}$ is H, —CH$_3$ or phenyl;
$R^{21}$ is

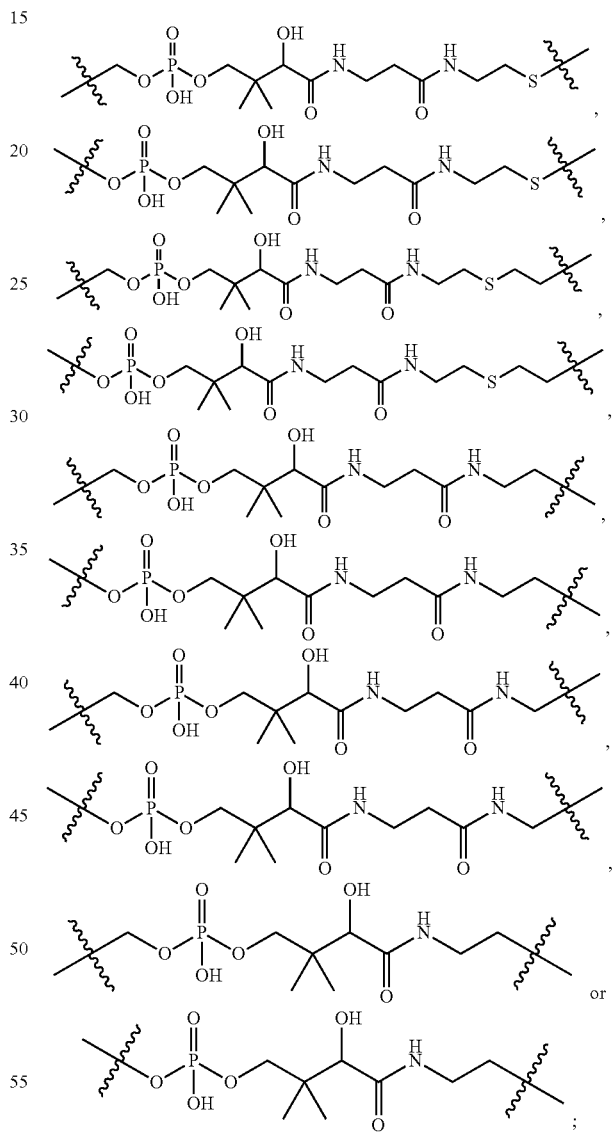

each $R^{25}$ is independently selected from H or $C_{1-4}$ alkyl;
$R^{aa}$ is a side chain of an amino acid selected from glycine, alanine, tryptophan, tyrosine, phenylalanine, leucine, isoleucine, valine, asparagine, glutamic acid, glutamine, aspatic acid, histidine, arginine, lysine, cysteine, methionine, serine, threonine, phenylglycine and t-butylglycine;
$R^{32}$ is independently selected from H, $C_{1-4}$ alkyl, phenyl, pyrimidine and pyridine;

$R^{33}$ is independently selected from
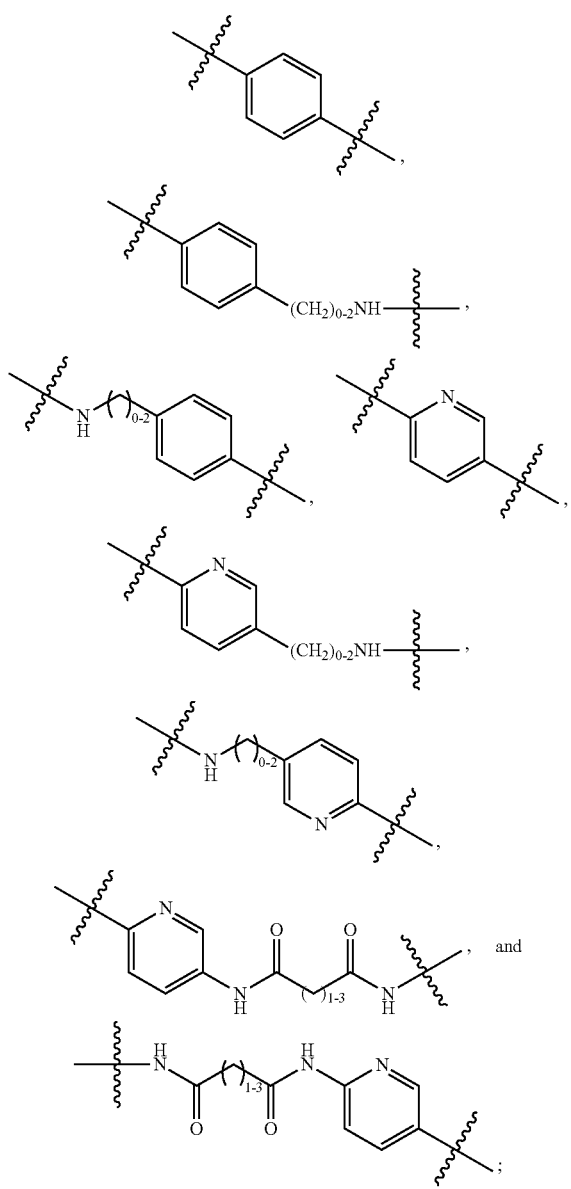
and
$R^{34}$ is independently selected from H, $C_{1-4}$ alkyl, and $C_{1-6}$ haloalkyl;
$X_1$ is self immolative spacer selected from
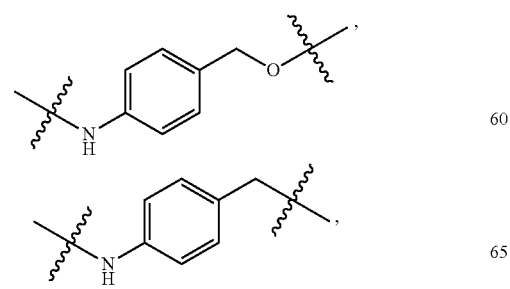
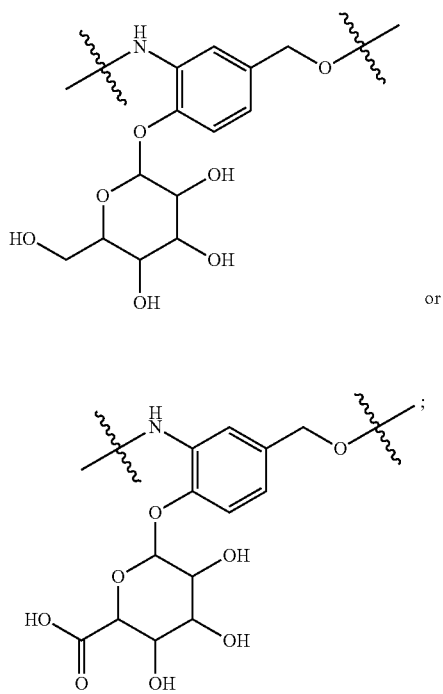
$X_2$ is dipeptide selected from
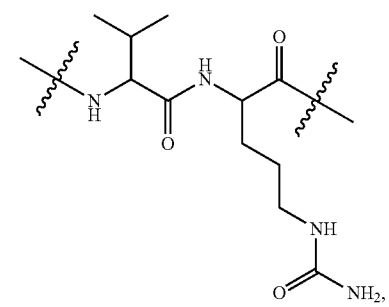
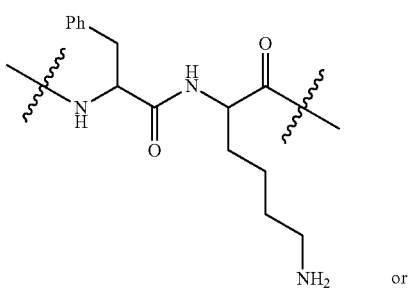
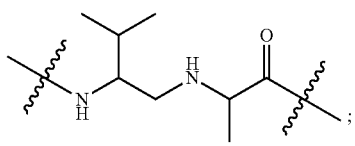

$X_3$ is

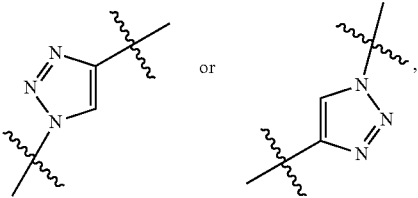 [SMILES: *c1cn(*)nn1 ; *c1cn(*)nn1]

or $X_4$ is

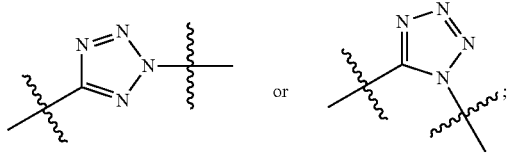 [SMILES: *c1nnn(*)n1 ; *c1nnnn1*]

or ;

each m is independently selected from 1, 2, 3, 4, 5, 6, 7, 8, 9 and 10, and each n is independently selected from 1, 2, 3, 4, 5, 6, 7, 8, 9, 10, 11, 12, 13, 14, 15, 16, 17 and 18.

Linker components $L_2$, $L_3$, $L_4$, $L_5$, and $L_6$ of compounds of Formula (I) and immunoconjugates of Formula (II) and Formula (III) are each independently selected from a bond, —(CH$_2$)$_m$—, —C(=O)(CH$_2$)$_m$—, —C(=O)X$_1$X$_2$C(=O)(CH$_2$)$_m$—, —C(=O)X$_1$X$_2$C(=O)(CH$_2$)$_m$NR$^{12}$C(=O)(CH$_2$)$_m$—, —C(=O)X$_1$X$_2$C(=O)(CH$_2$)$_m$X$_3$(CH$_2$)$_m$—, —C(=O)X$_1$X$_2$C(=O)((CH$_2$)$_m$O)$_n$(CH$_2$)$_m$—, —C(=O)X$_1$X$_2$C(=O)((CH$_2$)$_m$O)$_n$(CH$_2$)$_m$NR$^{12}$C(=O)(CH$_2$)$_m$—, —C(=O)X$_1$X$_2$C(=O)((CH$_2$)$_m$O)$_n$(CH$_2$)$_m$NR$^{12}$C(=O)(CH$_2$)$_m$X$_3$(CH$_2$)$_m$—, —C(=O)X$_1$X$_2$C(=O)((CH$_2$)$_m$O)$_n$(CH$_2$)$_m$X$_3$(CH$_2$)$_m$—, —C(=O)X$_1$X$_2$C(=O)(CH$_2$)$_m$NR$^{12}$C(=O)((CH$_2$)$_m$O)$_n$(CH$_2$)$_m$—, —C(=O)X$_1$X$_2$C(=O)(CH$_2$)$_m$NR$^{12}$C(=O)((CH$_2$)$_m$O)$_n$(CH$_2$)$_m$X$_3$(CH$_2$)$_m$—, —C(=O)X$_1$X$_2$(CH$_2$)$_m$X$_3$(CH$_2$)$_m$—, —C(=O)X$_1$X$_2$((CH$_2$)$_m$O)$_n$(CH$_2$)$_m$—, —C(=O)X$_1$X$_2$((CH$_2$)$_m$O)$_n$(CH$_2$)$_m$NR$^{12}$C(=O)(CH$_2$)$_m$—, —C(=O)X$_1$X$_2$((CH$_2$)$_m$O)$_n$(CH$_2$)$_m$NR$^{12}$C(=O)(CH$_2$)$_m$X$_3$(CH$_2$)$_m$—, —C(=O)X$_1$X$_2$((CH$_2$)$_m$O)$_n$(CH$_2$)$_m$X$_3$(CH$_2$)$_m$—, —C(=O)X$_1$X$_2$(CH$_2$)$_m$NR$^{12}$((CH$_2$)$_m$O)$_n$(CH$_2$)$_m$—, —C(=O)X$_1$X$_2$C(=O)(CH$_2$)$_m$NR$^{12}$((CH$_2$)$_m$O)$_n$(CH$_2$)$_m$X$_3$(CH$_2$)$_m$—, —(CH$_2$)$_m$NR$^{12}$C(=O)(CH$_2$)$_m$—, —C(=O)((CH$_2$)$_m$O)$_n$(CH$_2$)$_m$—, —(CH$_2$)$_m$S(=O)$_2$((CH$_2$)$_m$O)$_n$(CH$_2$)$_m$—, —C(=O)(CH$_2$)$_m$NR$^{12}$(CH$_2$)$_m$—, —C(=O)NR$^{12}$(CH$_2$)$_m$—, —C(=O)NR$^{12}$(CH$_2$)$_m$X$_3$(CH$_2$)$_m$—, —C(=O)NH(CH$_2$)$_m$NR$^{12}$C(=O)X$_1$X$_2$C(=O)(CH$_2$)$_m$—, —C(=O)(CH$_2$)$_m$X$_3$((CH$_2$)$_m$O)$_n$—, —C(=O)X$_1$C(=O)NR$^{12}$(CH$_2$)$_m$NR$^{12}$C(=O)(CH$_2$)$_m$—, —C(=O)X$_1$C(=O)NR$^{12}$(CH$_2$)$_m$X$_3$(CH$_2$)$_m$—, —C(=O)NR$^{12}$(CH$_2$)$_m$NR$^{12}$C(=O)(CH$_2$)$_m$—, —C(=O)NR$^{12}$(CH$_2$)$_m$NR$^{12}$C(=O)(CH$_2$)$_m$X$_3$(CH$_2$)$_m$—,

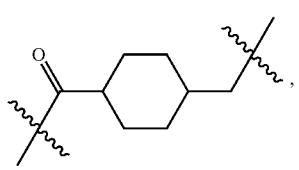 [SMILES: *CC1CCC(C(*)=O)CC1]

—(CH$_2$)$_m$C(=O)NR$^{12}$(CH$_2$)$_m$NR$^{12}$C(=O)(CH$_2$)$_m$—, —(CH$_2$)$_m$C(=O)—, —(CH$_2$)$_m$C(=O)X$_2$X$_1$C(=O)—, —(CH$_2$)$_m$X$_3$(CH$_2$)$_m$C(=O)X$_2$X$_1$C(=O)—, —(CH$_2$)$_m$C(=O)NR$^{12}$(CH$_2$)$_m$—, —(CH$_2$)$_m$X$_3$(CH$_2$)$_m$C(=O)NR$^{12}$(CH$_2$)$_m$—, —(CH$_2$)$_m$NR$^{12}$C(=O)(CH$_2$)$_m$X$_3$(CH$_2$)$_m$—, —(CH$_2$)$_m$(O(CH$_2$)$_m$)$_n$C(=O)—, —(CH$_2$)$_m$(O(CH$_2$)$_m$)$_n$S(=O)$_2$(CH$_2$)$_m$—, —(CH$_2$)$_m$NR$^{12}$(CH$_2$)$_m$C(=O)—, —(CH$_2$)$_m$NR$^{12}$C(=O)—, —(CH$_2$)$_m$C(=O)X$_2$X$_1$C(=O)NR$^{12}$(CH$_2$)$_m$NHC(=O)—, —(CH$_2$)$_m$C(=O)NR$^{12}$(CH$_2$)$_m$NR$^{12}$C(=O)X$_1$—, —(CH$_2$)$_m$C(=O)NR$^{12}$(CH$_2$)$_m$NR$^{12}$C(=O)—,

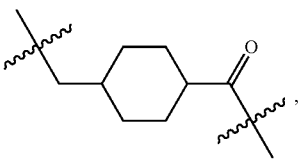 [SMILES: *CC1CCC(C(*)=O)CC1]

—((CH$_2$)$_m$O)$_n$(CH$_2$)$_m$—, —(CH$_2$)$_m$(O(CH$_2$)$_m$)$_n$—, —(CH$_2$)$_m$(O(CH$_2$)$_m$)$_n$X$_3$(CH$_2$)$_m$—, —(CH$_2$)$_m$X$_3$((CH$_2$)$_m$O)$_n$(CH$_2$)$_m$—, —(CH$_2$)$_m$X$_3$(CH$_2$)$_m$C(=O)—, —C(=O)(CH$_2$)$_m$X$_3$(CH$_2$)$_m$—, —(CH$_2$)$_m$X$_3$(CH$_2$)$_m$(O(CH$_2$)$_m$)$_n$C(=O)—, —C(=O)((CH$_2$)$_m$O)$_n$(CH$_2$)$_m$X$_3$(CH$_2$)$_m$—, —(CH$_2$)$_m$C(=O)NR$^{12}$(CH$_2$)$_m$C(=O)—, —C(=O)(CH$_2$)$_m$NR$^{12}$C(=O)(CH$_2$)$_m$—, —(CH$_2$)$_m$C(=O)NR$^{12}$(CH$_2$)$_m$(O(CH$_2$)$_m$)$_n$C(=O)—, —C(=O)((CH$_2$)$_m$O)$_n$(CH$_2$)$_m$NR$^{12}$C(=O)(CH$_2$)$_m$—, —(CH$_2$)$_m$C(=O)NR$^{12}$(CH$_2$)$_m$C(=O)NR$^{12}$(CH$_2$)$_m$—, —(CH$_2$)$_m$NR$^{12}$C(=O)(CH$_2$)$_m$NR$^{12}$C(=O)(CH$_2$)$_m$—, —C(=O)NR$^{12}$(CH$_2$)$_m$NR$^{12}$C(=O)—, —(CH$_2$)$_m$S(CH$_2$)$_m$—, —NR$^{12}$C(=O)(CH$_2$)$_m$—, —NR$^{12}$C(=O)(CH$_2$)$_m$X$_3$(CH$_2$)$_m$—, —(CH$_2$)$_m$X$_3$(CH$_2$)$_m$C(=O)NR$^{12}$—, —(CH$_2$)$_m$C(=O)NR$^{12}$—, —(CH$_2$)$_m$NR$^{12}$(CH$_2$)$_m$—, —(CH$_2$)$_m$X$_3$(CH$_2$)$_m$—, —((CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$—, —NR$^{12}$(CH$_2$)$_m$—, —NR$^{12}$C(R$^{12}$)$_2$(CH$_2$)$_m$—, —(CH$_2$)$_m$C(R$^{12}$)$_2$NR$^{12}$—, —(CH$_2$)$_m$C(=O)NR$^{12}$(CH$_2$)$_m$NR$^{12}$—, —NR$^{12}$(CH$_2$)$_m$NR$^{12}$C(=O)(CH$_2$)$_m$—, —NR$^{12}$C(R$^{12}$)$_2$(CH$_2$)$_m$NR$^{12}$C(=O)(CH$_2$)$_m$—, —(CH$_2$)$_m$C(=O)NR$^{12}$(CH$_2$)$_m$C(R$^{12}$)$_2$NR$^{12}$—, —NR$^{12}$(CH$_2$)$_m$X$_3$(CH$_2$)$_m$—, —NR$^{12}$C(R$^{12}$)$_2$(CH$_2$)$_m$X$_3$(CH$_2$)$_m$—, —(CH$_2$)$_m$X$_3$(CH$_2$)$_m$C(R$^{12}$)$_2$NR$^{12}$—, —NR$^{12}$C(R$^{12}$)$_2$(CH$_2$)$_m$OC(=O)NR$^{12}$(CH$_2$)$_m$—, —(CH$_2$)$_m$NR$^{12}$C(=O)O(CH$_2$)$_m$C(R$^{12}$)$_2$NR$^{12}$—, —NR$^{12}$C(R$^{12}$)$_2$(CH$_2$)$_m$OC(=O)NR$^{12}$(CH$_2$)$_m$X$_3$(CH$_2$)$_m$—, —(CH$_2$)$_m$X$_3$(CH$_2$)$_m$NR$^{12}$C(=O)O(CH$_2$)$_m$C(R$^{12}$)$_2$NR$^{12}$—, —NR$^{12}$C(R$^{12}$)$_2$(CH$_2$)$_m$OC(=O)NR$^{12}$((CH$_2$)$_m$O)$_n$(CH$_2$)$_m$—, —(CH$_2$)$_m$(O(CH$_2$)$_m$)$_n$NR$^{12}$C(=O)O(CH$_2$)$_m$C(R$^{12}$)$_2$NR$^{12}$—, —NR$^{12}$C(R$^{12}$)$_2$(CH$_2$)$_m$OC(=O)NR$^{12}$((CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NR$^{12}$C(=O)O(CH$_2$)$_m$C(R$^{12}$)$_2$NR$^{12}$—, —(CH$_2$)$_m$X$_3$(CH$_2$)$_m$NR$^{12}$—, —NR$^{12}$((CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NR$^{12}$—, —(CH$_2$)$_m$NR$^{12}$—, —NR$^{12}$((CH$_2$)$_m$O)$_n$(CH$_2$)$_m$—, —NR$^{12}$((CH$_2$)$_m$O)$_n$(CH$_2$)$_m$NR$^{12}$C(=O)(CH$_2$)$_m$—, —(CH$_2$)$_m$C(=O)NR$^{12}$(CH$_2$)$_m$(O(CH$_2$)$_m$)$_n$NR$^{12}$—, —(CH$_2$)$_m$(O(CH$_2$)$_m$)$_n$NR$^{12}$—, —C(R$_{12}$)$_2)_m$—, —(CH$_2$CH$_2$O)$_n$—, —(OCH$_2$CH$_2$)$_n$—, —(CH$_2$)$_m$O(CH$_2$)$_m$—, —S(=O)$_2$(CH$_2$)$_m$—, —(CH$_2$)$_m$S(=O)$_2$—, —S(=O)$_2$(CH$_2$)$_m$NR$^{12}$C(=O)(CH$_2$)$_m$—, —(CH$_2$)$_m$C(=O)NR$^{12}$(CH$_2$)$_m$S(=O)$_2$—, —S(=O)$_2$(CH$_2$)$_m$X$_3$(CH$_2$)$_m$—, —(CH$_2$)$_m$X$_3$(CH$_2$)$_m$S(=O)$_2$—, —(CH$_2$)$_m$X$_2$X$_1$C(=O)—, —C(=O)X$_1$X$_2$(CH$_2$)$_m$—, —(CH$_2$)$_m$(O(CH$_2$)$_m$)$_n$C(=O)X$_2$X$_1$C(=O)—, —C(=O)X$_1$X$_2$C(=O)((CH$_2$)$_m$O)$_n$(CH$_2$)$_m$—, —(CH$_2$)$_m$(O(CH$_2$)$_m$)$_n$X$_2$X$_1$C(=O)—, —(CH$_2$)$_m$X$_3$(CH$_2$)$_m$X$_2$X$_1$C(=O)—, —C(=O)X$_1$X$_2$(CH$_2$)$_m$X$_3$(CH$_2$)$_m$—, —(CH$_2$)$_m$X$_3$(CH$_2$)$_m$(O(CH$_2$)$_m$)$_n$X$_2$X$_1$C(=O)—, —(CH$_2$)$_m$X$_3$(CH$_2$)$_m$C (=O)NR¹²(CH₂)ₘNR¹²C(=O)—, —(CH₂)ₘX₃(CH₂)ₘC(=O)NR¹²(CH₂)ₘC(=O)—, —C(=O)(CH₂)ₘNR¹²C(=O(CH₂)ₘX₃(CH₂)ₘ—, —(CH₂)ₘX₃(CH₂)ₘC(=O)NR¹²(CH₂)ₘ(O(CH₂)ₘ)ₙC(=O)—, —C(=O)((CH₂)ₘO)ₙ(CH₂)ₘNR¹²C(=O)(CH₂)ₘX₃(CH₂)ₘ—, —(CH₂)ₘNR¹²C(=O)X₁X₂C(=O)(CH₂)ₘ—, —(CH₂)ₘC(=O)X₂X₁C(=O)NR¹²(CH₂)ₘ—, —X₄X₁X₂C(=O)(CH₂)ₘ—, —(CH₂)ₘC(=O)X₂X₁X₄—, —X₁C(=O)(CH₂)ₘNHC(=O)(CH₂)ₘ—, —(CH₂)ₘC(=O)NH(CH₂)ₘC(=O)X₁—, —C(=O)CHR^aa NR¹²—, —CHR^aa C(=O)—, —C(=O)NR¹²—, —C(=O)O—, —S—, —SCH₂C(=O)NR¹²—, —NR¹²C(=O)CH₂S—, —S(=O)₂CH₂CH₂S—, —SCH₂CH₂S(=O)₂—, —(CH₂)₂S(=O)₂CH₂CH₂S—, —SCH₂CH₂S(=O)₂CH₂CH₂—, —NR¹²C(=S)-, —(CH₂)ₘX₃(O(CH₂)ₙ)ₙC(=O)—, —C(=O)((CH₂)ₘO)ₙX₃(CH₂)ₘ—, —(CH₂)ₘNR¹²C(=O)((CH₂)ₘO)ₙ(CH₂)ₘ—, —(CH₂)ₘ(O(CH₂)ₙ)ₙC(=O)NR¹²(CH₂)ₘ—, —(CH₂)ₘNR¹²C(=O)NR¹²(CH₂)ₘ—, —(CH₂)ₘX₃(CH₂)ₘNR¹²C(=O)—, —C(=O)NR¹²(CH₂)ₘX₃(CH₂)ₘ—, —NR₁₂S(=O)₂(CH₂)ₘX₃(CH₂)ₘ—, —(CH₂)ₘX₃(CH₂)ₘS(=O)₂NR₁₂—,

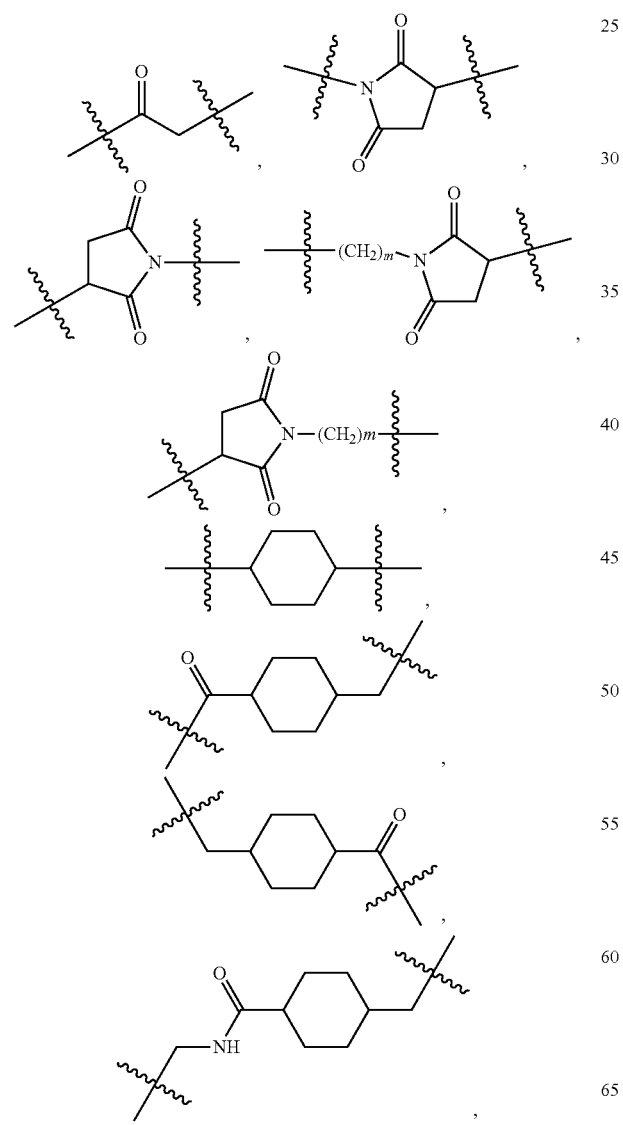

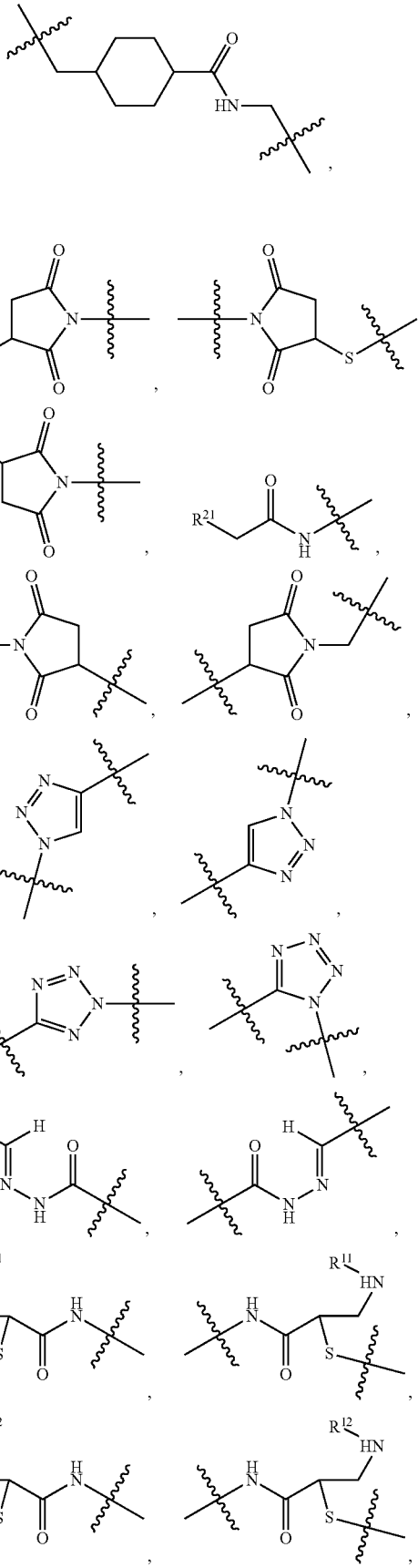

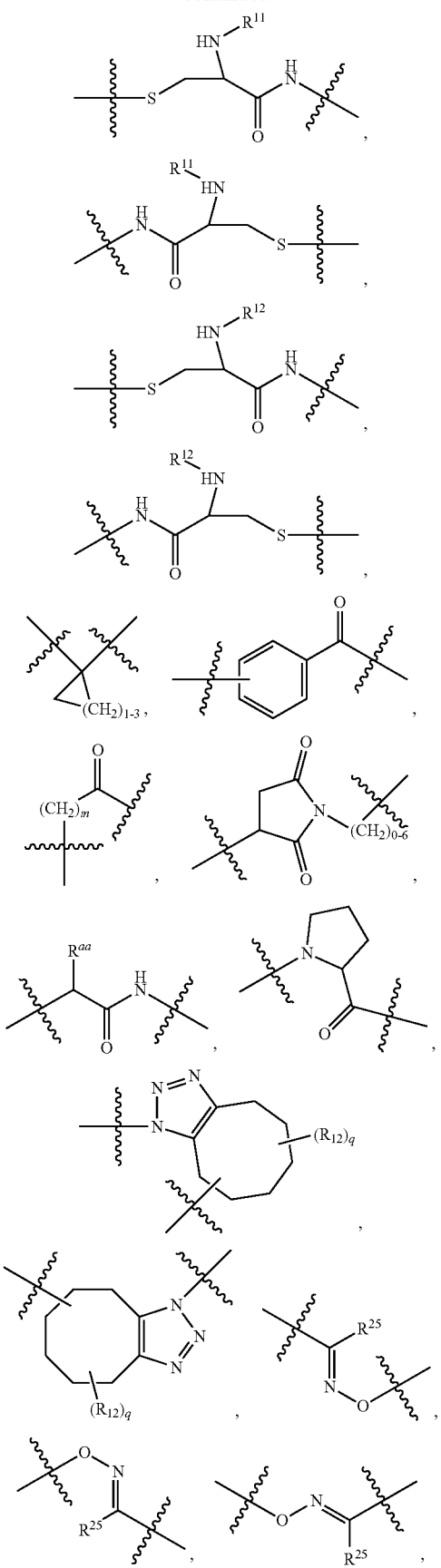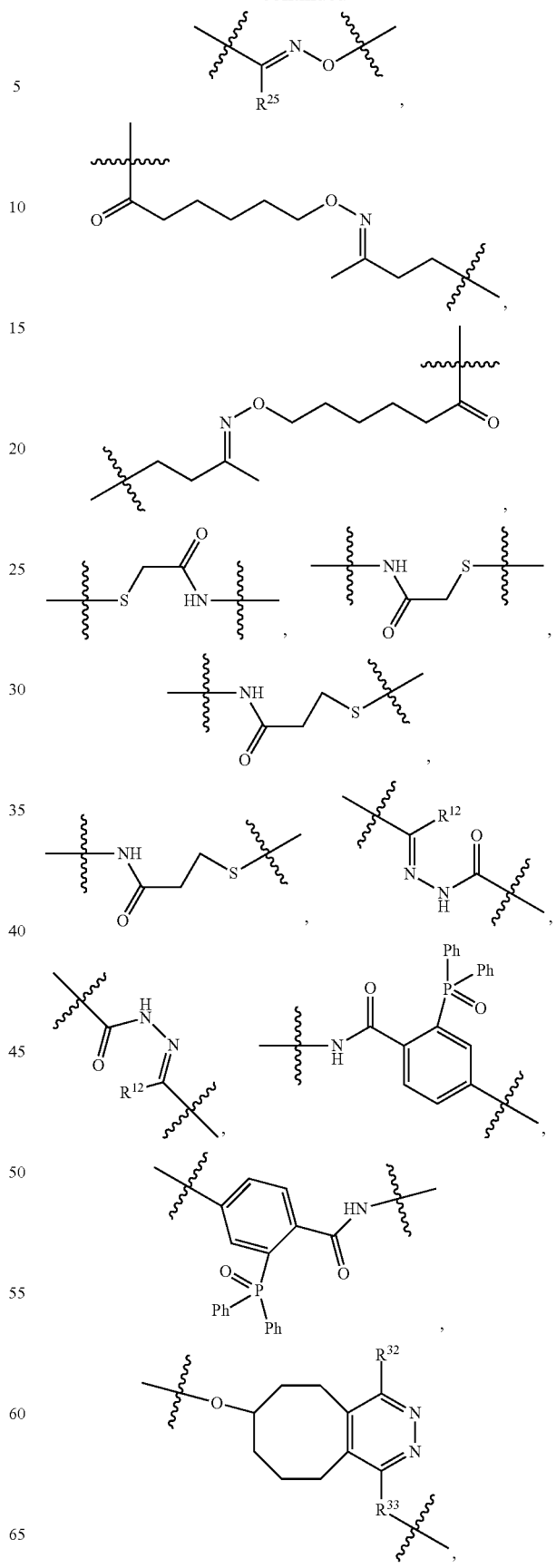

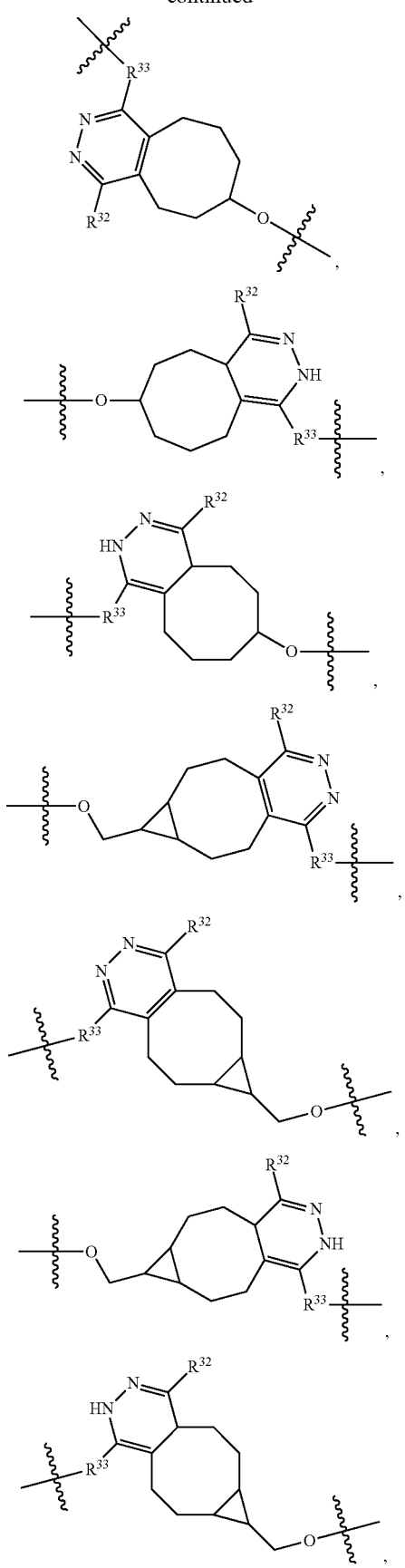
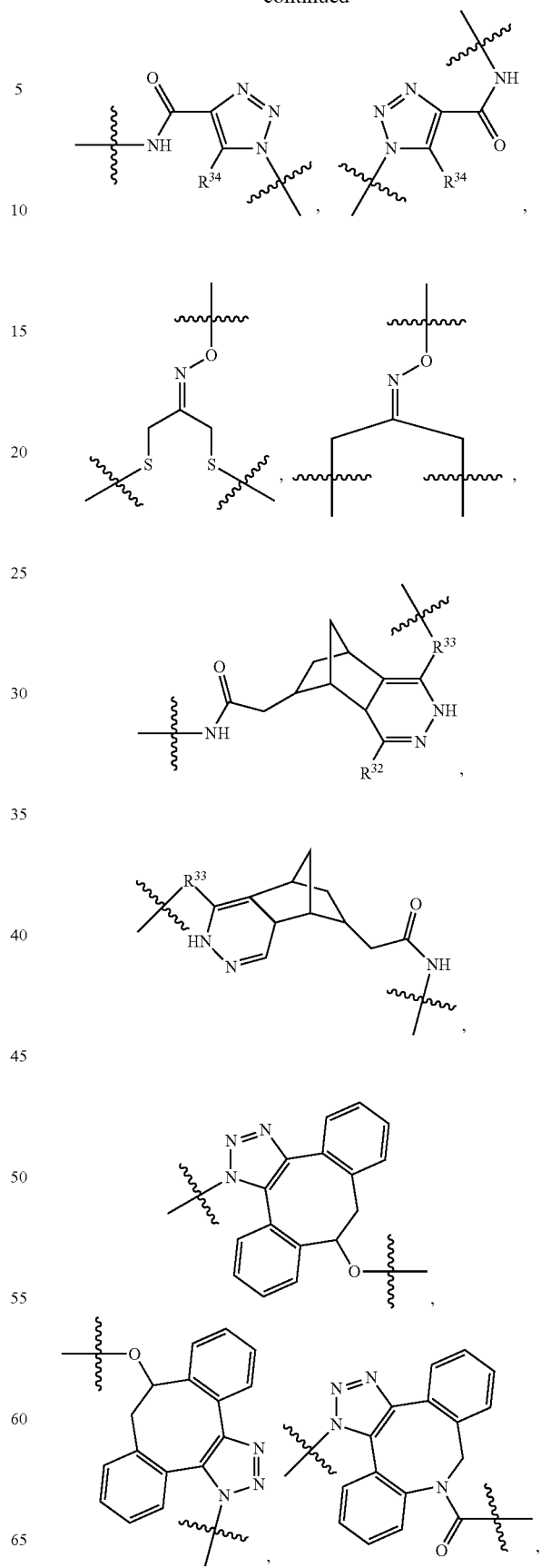

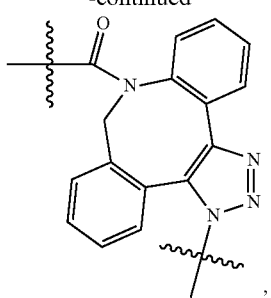

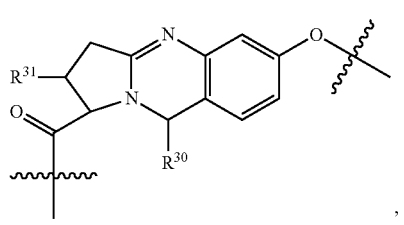

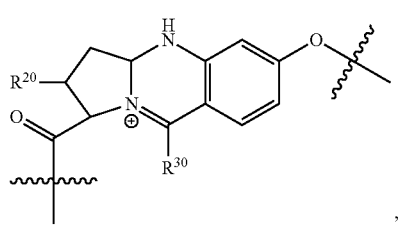

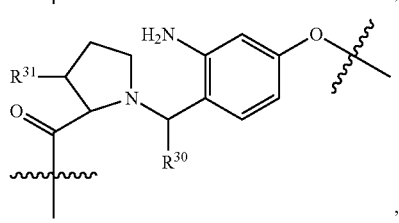

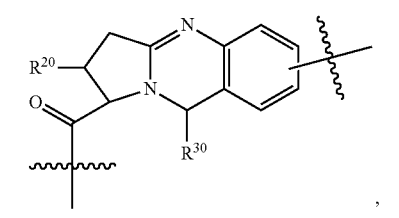

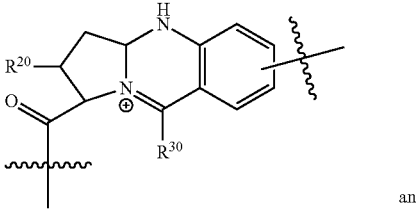

and

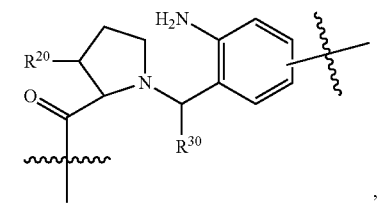

wherein:
R²⁰ is H or Me, and R³⁰ is H, —CH₃ or phenyl;
R²¹ is

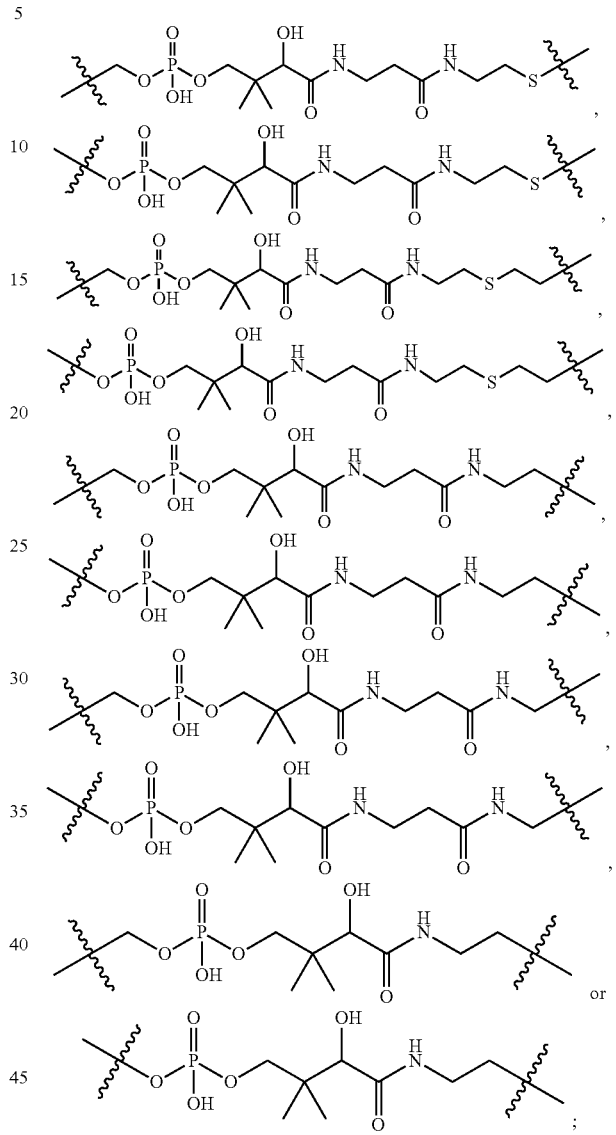

each R²⁵ is independently selected from H or C₁₋₄ alkyl;
Rᵃᵃ is a side chain of an amino acid selected from glycine, alanine, tryptophan, tyrosine, phenylalanine, leucine, isoleucine, valine, asparagine, glutamic acid, glutamine, aspatic acid, histidine, arginine, lysine, cysteine, methionine, serine, threonine, phenylglycine and t-butylglycine;
R³² is independently selected from H, C₁₋₄ alkyl, phenyl, pyrimidine and pyridine;
R³³ is independently selected from

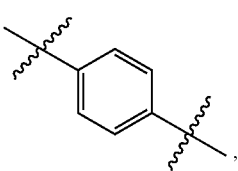

75
-continued
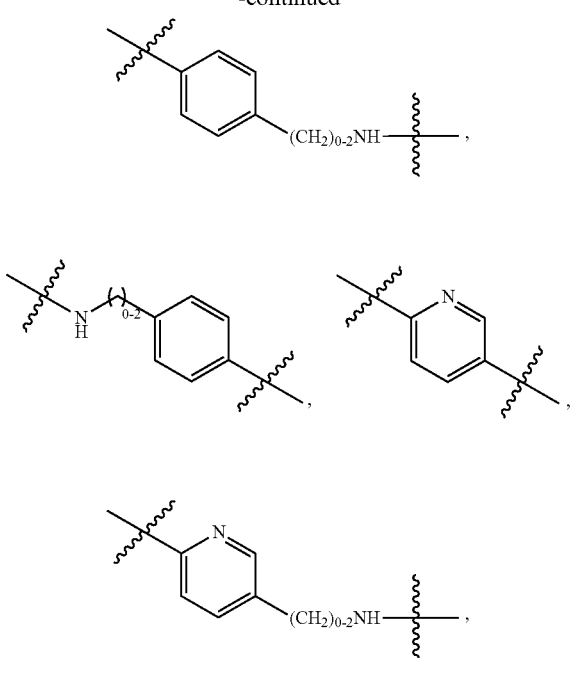
and
R[34] is independently selected from H, $C_{1-4}$ alkyl, and $C_{1-6}$ haloalkyl;
$X_1$ is self immolative spacer selected from
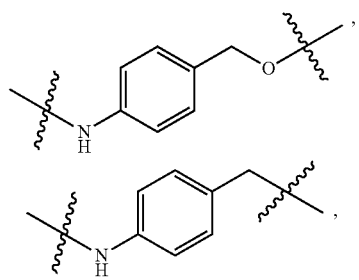
76
-continued
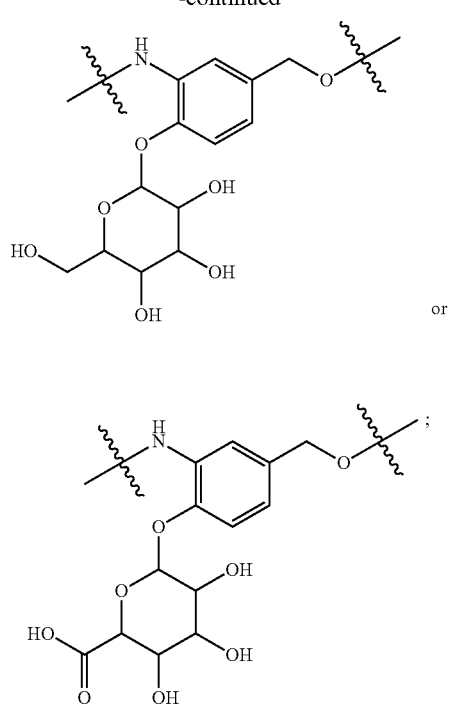
$X_2$ is dipeptide selected from
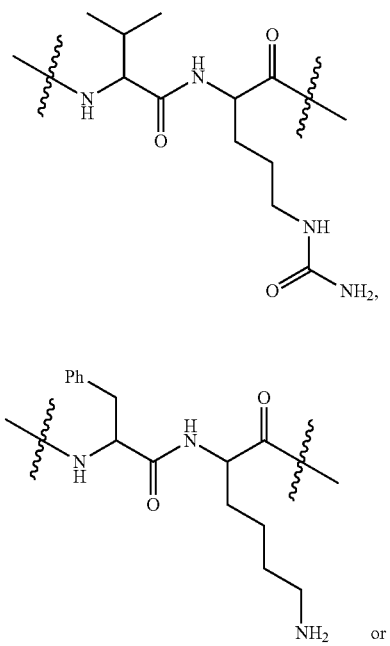
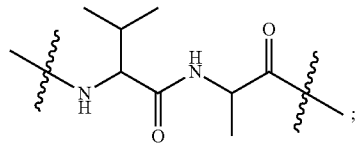

X₃ is

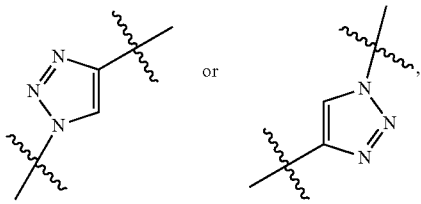 [SMILES: *c1cn(*)nn1 ; *c1cn(*)nn1] or , and X₄ is

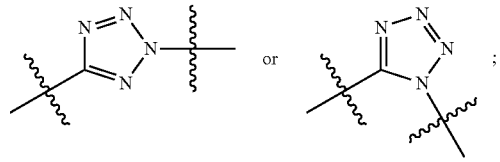 [SMILES: *c1nnn(*)n1 ; *c1nnnn1*] or ;

each m is independently selected from 1, 2, 3, 4, 5, 6, 7, 8, 9 and 10, and each n is independently selected from 1, 2, 3, 4, 5, 6, 7, 8, 9, 10, 11, 12, 13, 14, 15, 16, 17 and 18.

Cytotoxic Peptides

The cytotoxic peptides of the invention, or stereoisomer thereof, and pharmaceutically acceptable salts thereof, are compounds having the structure of Formula (I)

(Formula (I))

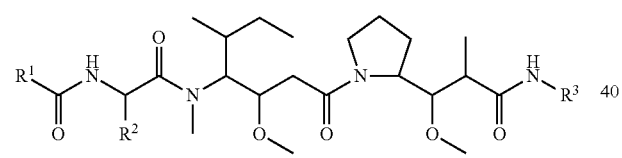

wherein:

$R^1$ is a C-linked 6 membered heterocycloalkyl containing 1-2 N heteroatoms and a $C_1$-$C_2$alkylene bridge or $R^1$ is a C-linked 5-8 membered fused bicyclic heterocycloalkyl containing 1-2 N heteroatoms, wherein each is unsubstituted, or each is substituted with an $R^7$ and 0 to 3 substituents independently selected from $R^5$ and $R^6$, or each is substituted with 1 to 3 substituents independently selected from $R^5$ and $R^6$;

$R^2$ is —$C_1$-$C_6$alkyl;

$R^3$ is

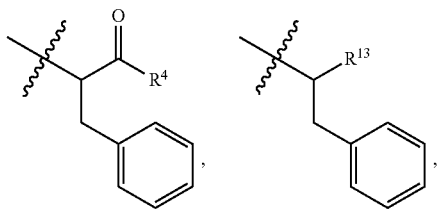 , $R^4$ is —OH, $C_1$-$C_6$alkoxy, —N$(R^{14})_2$, —$R^{16}$, —N$R^{12}$$(CH_2)_m$N$(R^{14})_2$, —N$R^{12}$$(CH_2)_m$$R^{16}$, -L$R^9$, —NHS(O)$_2$$R_{11}$, —NHS(O)$_2$$(CH_2)_m$$N_3$, —NHS(=O)$_2$L$R^9$,

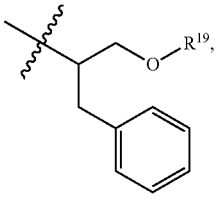

or

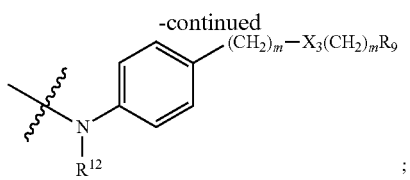

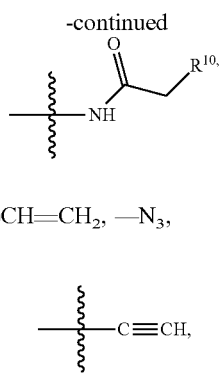

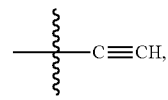

$R^5$ is $C_1$-$C_6$alkyl, —C(=O)$R^{11}$, —(CH$_2$)$_m$OH, —C(=O)(CH$_2$)$_m$OH, —C(=O)((CH$_2$)$_m$O)$_n$$R^{12}$, —((CH$_2$)$_m$O)$_n$$R^{12}$, or $C_1$-$C_6$alkyl which is optionally substituted with —CN, —C(=O)NH$_2$ or 1 to 5 hydroxyl;

$R^6$ is halo, oxo, OH, $C_1$-$C_6$alkyl, —N($R^{14}$)$_2$, —$R^{16}$ and —NR$^{12}$C(=O)$R^{11}$;

$R^7$ is L$R^9$;

$R^8$ is H or L$R^9$;

each L is independently selected from -L$_1$L$_2$L$_3$L$_4$L$_5$L$_6$-, -L$_6$L$_5$L$_4$L$_3$L$_2$L$_1$-, -L$_1$L$_2$L$_3$L$_4$L$_5$-, -L$_5$L$_4$L$_3$L$_2$L$_1$-, -L$_1$L$_2$L$_3$L$_4$-, -L$_4$L$_3$L$_2$L$_1$-, -L$_1$L$_2$L$_3$-, -L$_3$L$_2$L$_1$-, -L$_1$L$_2$-, -L$_2$L$_1$- and -L$_1$, wherein -L$_1$, L$_2$, L$_3$, L$_4$, L$_5$, and L$_6$ are as defined herein;

$R^9$ is

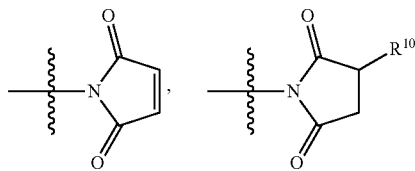

—NR$_{12}$C(=O)CH=CH$_2$, —N$_3$,

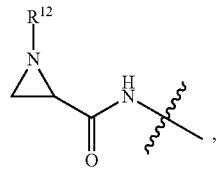

SH, —SSR$^{15}$, —S(=O)$_2$(CH=CH$_2$), —(CH$_2$)$_2$S(=O)$_2$(CH=CH$_2$), —NR$_{12}$S(=O)$_2$(CH=CH$_2$), —NR$_{12}$C(=O)CH$_2$R$^{10}$, —NR$_{12}$C(=O)CH$_2$Br, —NR$_{12}$C(=O)CH$_2$I, —NHC(=O)CH$_2$Br, —NHC(=O)CH$_2$I, —ONH$_2$, —C(O)NHNH$_2$,

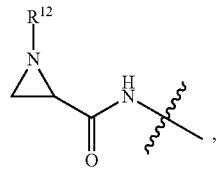

—CO$_2$H, —NH$_2$, —NCO, —NCS,

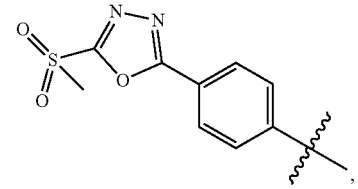

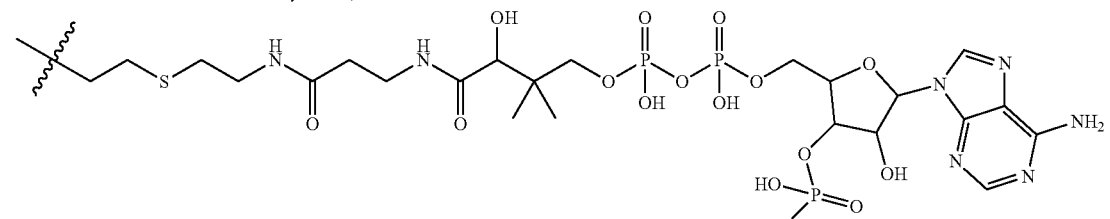

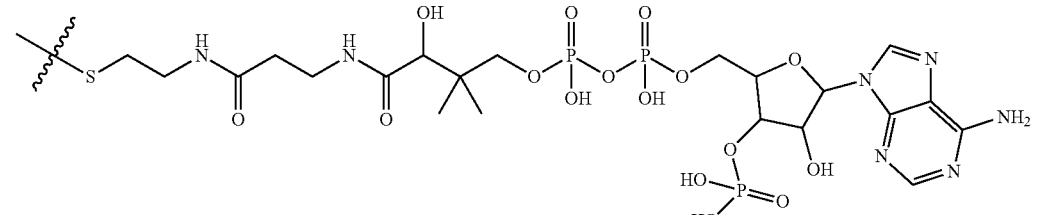

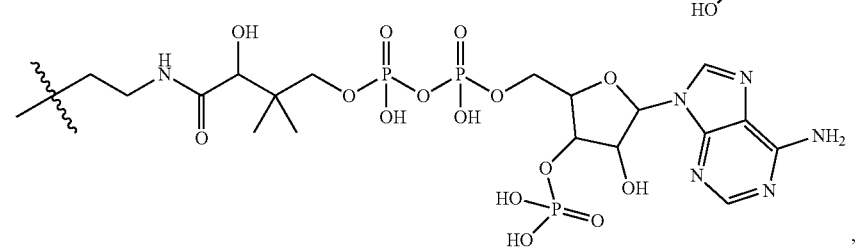

-continued
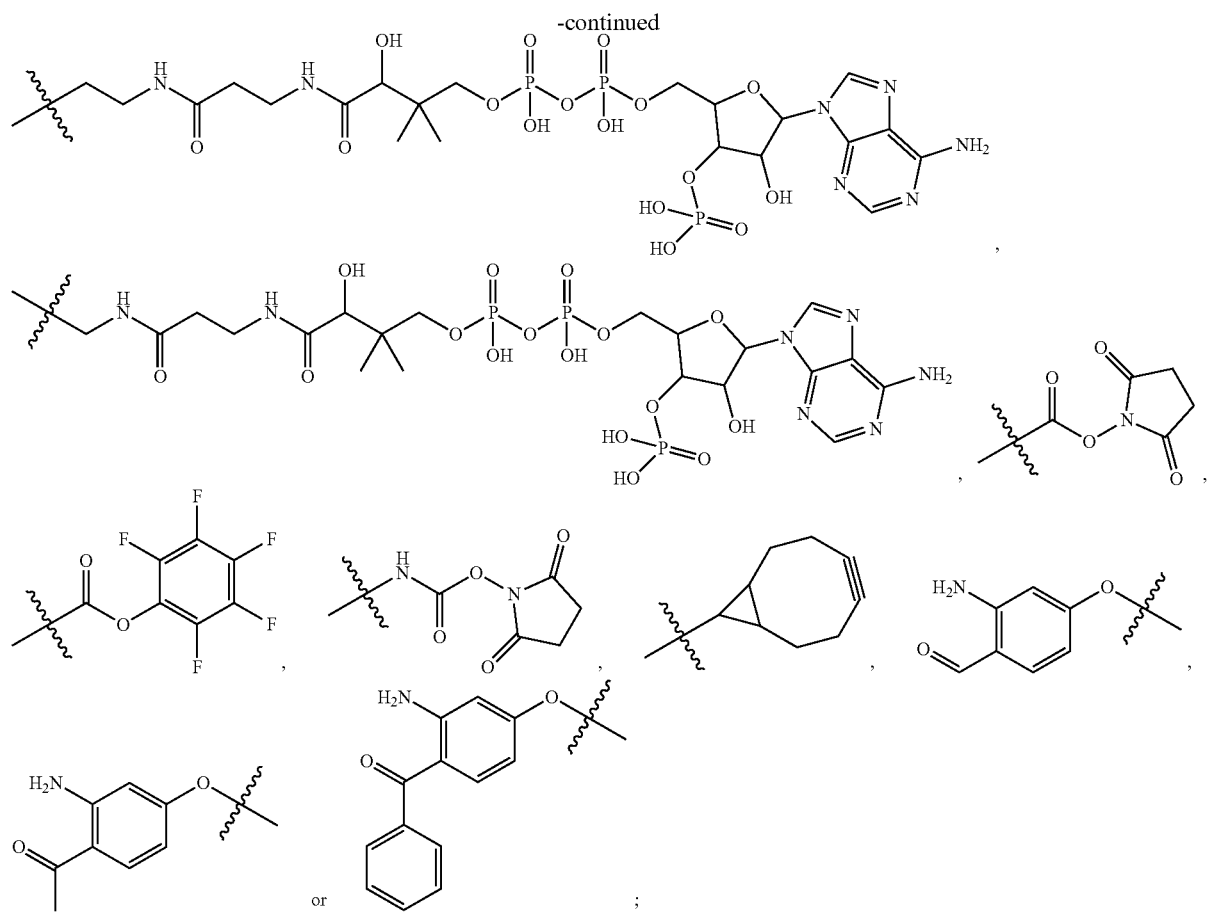
R¹⁰ is
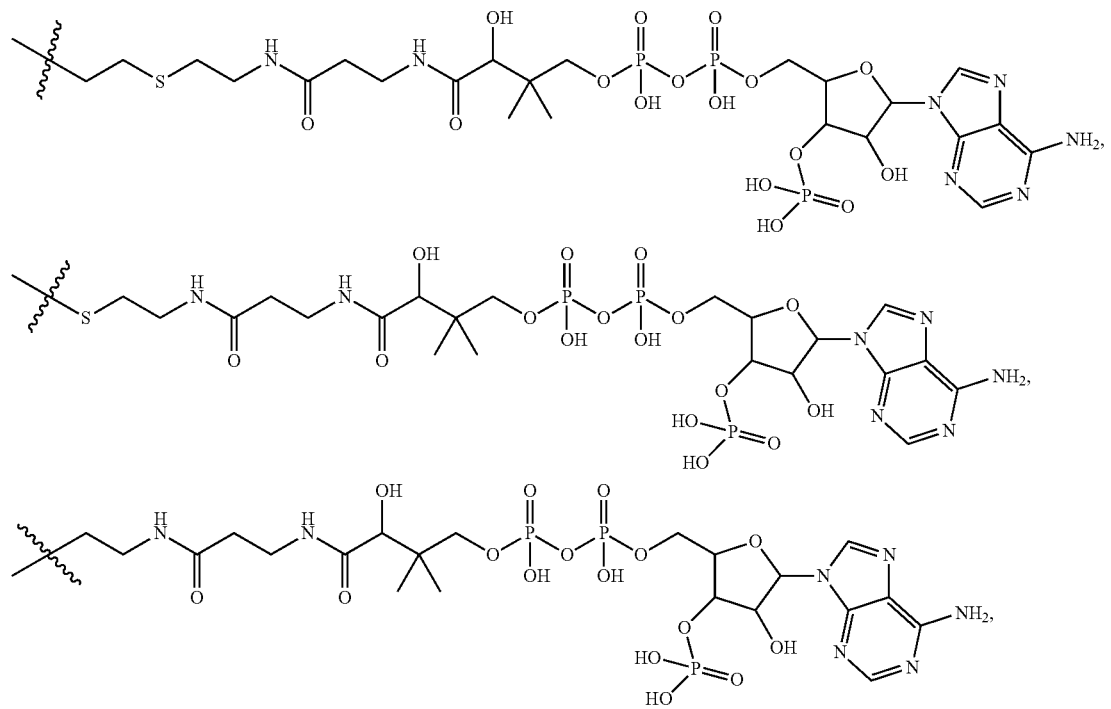

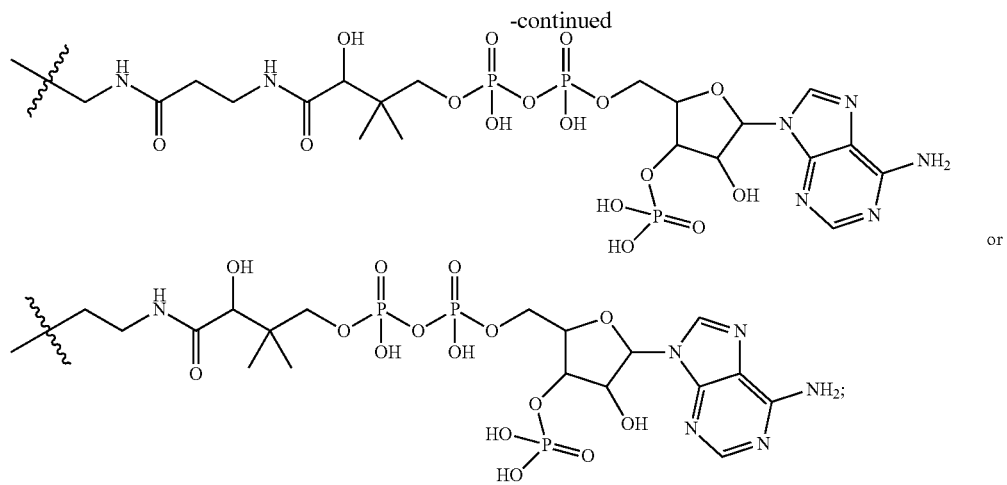
or each $R^{11}$ is independently selected from $C_1$-$C_6$alkyl and $C_1$-$C_6$alkyl which is optionally substituted with 1 to 5 hydroxyl;

each $R^{12}$ is independently selected from H and $C_1$-$C_6$alkyl;

$R^{13}$ is tetrazolyl, imidazolyl substituted with phenyl, oxadiazolyl substituted with phenyl, pyrazolyl, pyrimidinyl,

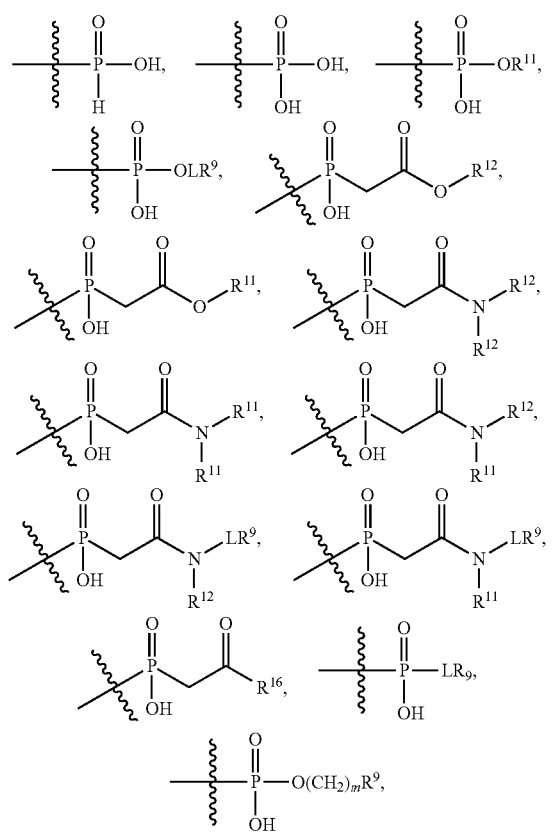

—$CH_2S(=O)_2NH_2$, —$CH_2S(=O)_2NHLR^9$, -$LR^9$ or —$X_4LR^9$;

each $R^{14}$ is independently selected from H and $C_1$-$C_6$alkyl;
$R^{15}$ is 2-pyridyl or 4-pyridyl;

$R^{16}$ is an N-linked 4-8 membered heterocycloalkyl containing 1-2 heteroatoms independently selected from N and O, which is unsubstituted or substituted with -$LR^9$;

each $R^{19}$ is H or $C_1$-$C_6$alkyl;

$X_3$ is

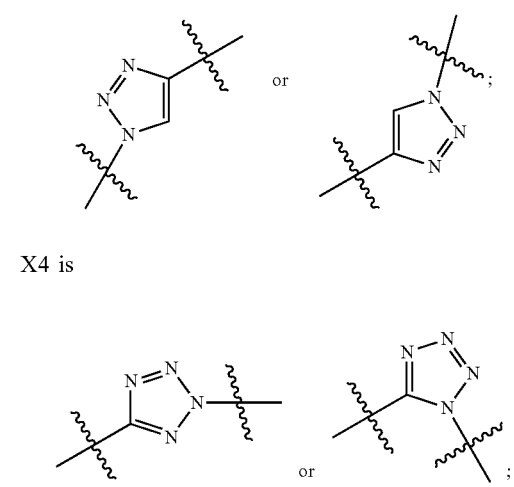

$X_4$ is

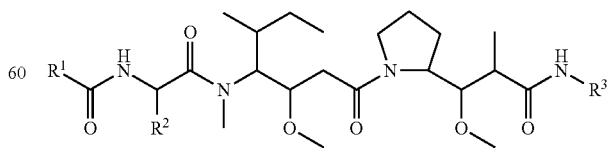

each m is independently selected from 1, 2, 3, 4, 5, 6, 7, 8, 9 and 10; and each n is independently selected from 1, 2, 3, 4, 5, 6, 7, 8, 9, 10, 11, 12, 13, 14, 15, 16, 17 and 18.

In one aspect of the invention are cytotoxic peptides, or stereoisomer thereof, and pharmaceutically acceptable salts thereof, having the structure of Formula (I)

(Formula (I))

wherein:
$R^1$ is a C-linked 6 membered heterocycloalkyl containing 1-2 N heteroatoms and a $C_1$-$C_2$alkylene bridge or $R^1$ is a C-linked 5-8 membered fused bicyclic heterocycloalkyl containing 1-2 N heteroatoms, wherein each is unsubstituted, or each is substituted with an $R^7$ and 0 to 3 substituents independently selected from $R^5$ and $R^6$, or each is substituted with 1 to 3 substituents independently selected from $R^5$ and $R^6$;

$R^2$ is —$C_1$-$C_6$alkyl;

$R^3$ is

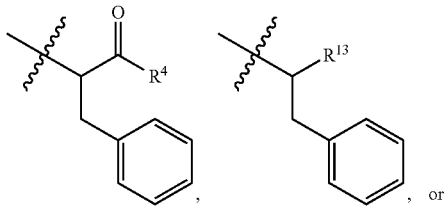

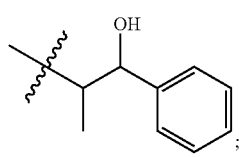

$R^4$ is —OH, $C_1$-$C_6$alkoxy, —$N(R^{14})_2$, —$R^{16}$, —$NR^{12}(CH_2)_mN(R^{14})_2$, —$NR^{12}(CH_2)_mR^{16}$, -$LR^9$, —$NHS(O)_2R_{11}$, —$NHS(O)_2(CH_2)_mN_3$, —$NHS(=O)_2LR^9$,

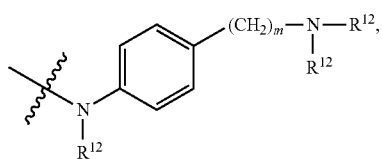

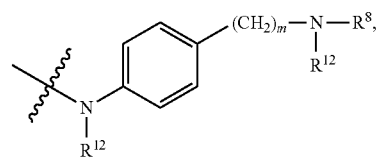

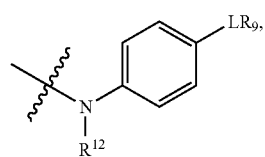

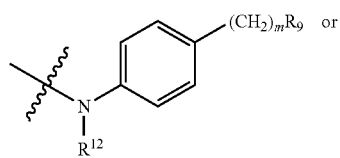

-continued

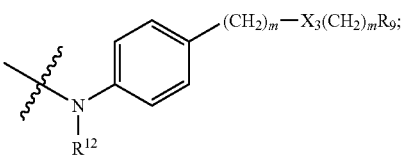

$R^5$ is $C_1$-$C_6$alkyl, $C_1$-$C_6$alkyl which is optionally substituted with 1 to 5 hydroxyl, —$C(=O)R^{11}$, —$(CH_2)_mOH$, —$C(=O)(CH_2)_mOH$, —$C(=O)((CH_2)_mO)_nR^{12}$, or —$((CH_2)_mO)_nR^{12}$;

$R^6$ is halo, oxo, OH, $C_1$-$C_6$alkyl, —$N(R^{14})_2$, —$R^{16}$ and —$NR^{12}C(=O)R^{11}$;

$R^7$ is $LR^9$;

$R^8$ is H or $LR^9$;

each L is a linker independently selected from -$L_1L_2L_3L_4L_5L_6$-, -$L_6L_5L_4L_3L_2L_1$-, -$L_1L_2L_3L_4L_5$-, -$L_5L_4L_3L_2L_1$-, -$L_1L_2L_3L_4$-, -$L_4L_3L_2L_1$-, -$L_1L_2L_3$-, -$L_3L_2L_1$-, -$L_1L_2$-, -$L_2L_1$- and -$L_1$, wherein -$L_1$, $L_2$, $L_3$, $L_4$, $L_5$, and $L_6$ are as defined herein;

$R^9$ is

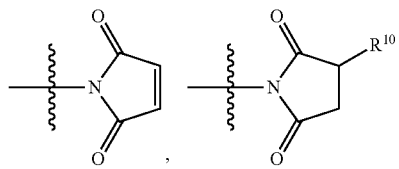

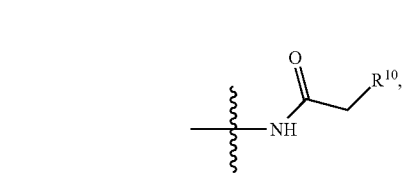

—$NR_{12}C(=O)CH=CH_2$, —$N_3$,

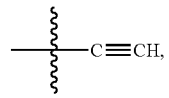

SH, —$SSR^{15}$, —$S(=O)_2(CH=CH_2)$, —$(CH_2)_2S(=O)_2(CH=CH_2)$, —$NR_{12}S(=O)_2(CH=CH_2)$, —$NR_{12}C(=O)CH_2R^{10}$, —$NR_{12}C(=O)CH_2Br$, —$NR_{12}C(=O)CH_2I$, —$NHC(=O)CH_2Br$, —$NHC(=O)CH_2I$, —$ONH_2$, —$C(O)NHNH_2$,

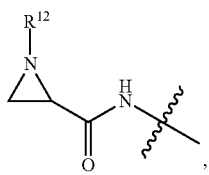

—$CO_2H$, —$NH_2$, —NCO, —NCS,

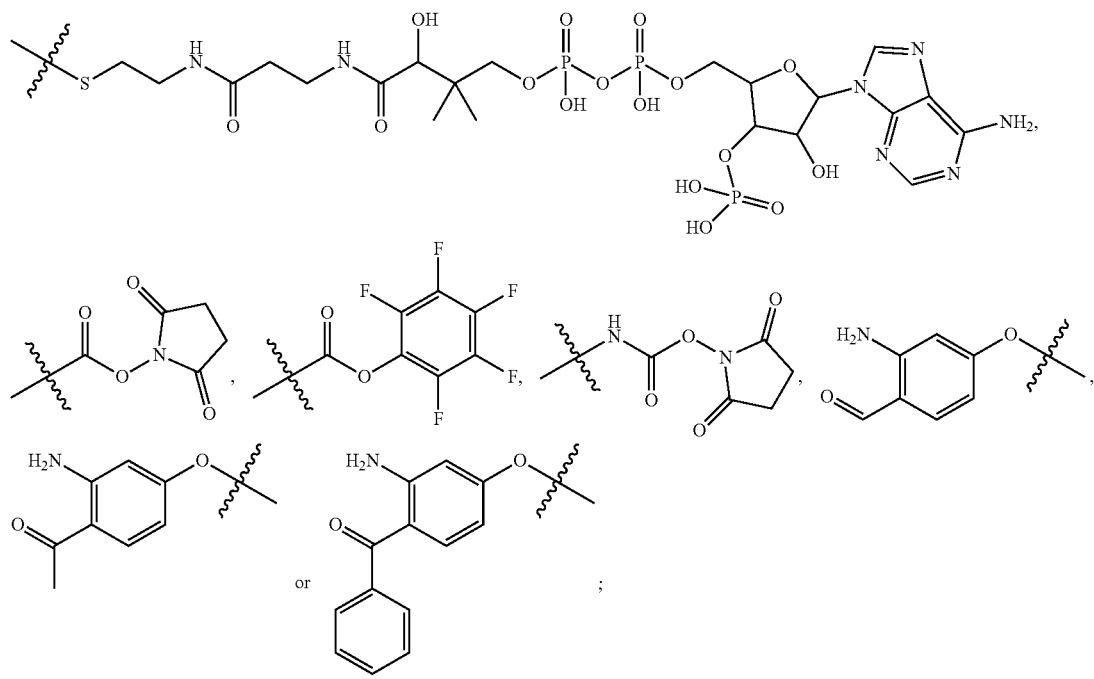
$R^{10}$ is
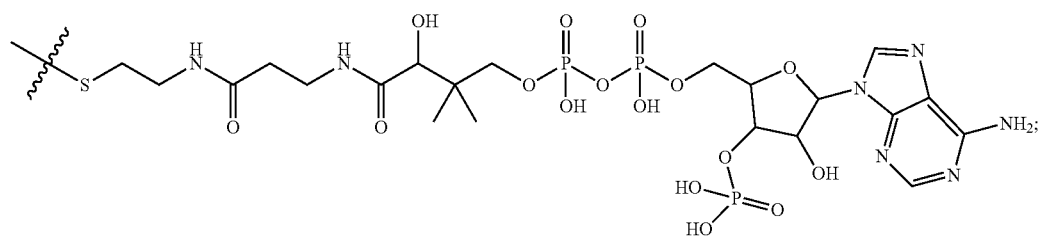 [SMILES: *SCCNC(=O)CCNC(=O)C(O)C(C)(C)COP(=O)(O)OP(=O)(O)OCC1OC(n2cnc3c(N)ncnc32)C(O)C1OP(=O)(O)O]
each $R^{11}$ is independently selected from $C_1$-$C_6$alkyl and $C_1$-$C_6$alkyl which is optionally substituted with 1 to 5 hydroxyl;
each $R^{12}$ is independently selected from H and $C_1$-$C_6$alkyl;
$R^{13}$ is tetrazolyl,
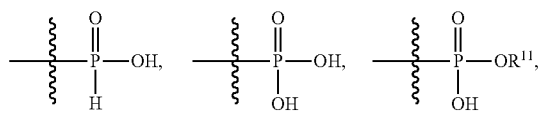
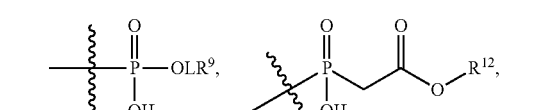
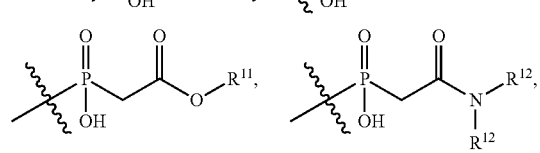
-continued
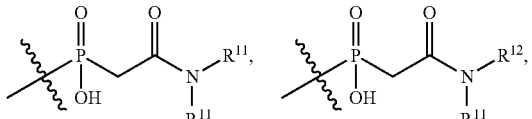
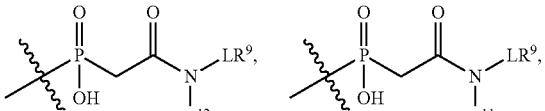
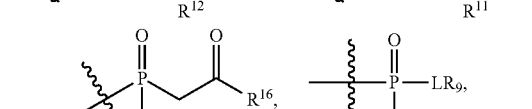
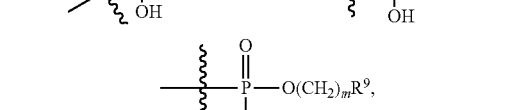
-$LR^9$ or —$X_4LR^9$;
each $R^{14}$ is independently selected from H and $C_1$-$C_6$alkyl;
$R^{15}$ is 2-pyridyl or 4-pyridyl;

R[16] is an N-linked 4-8 membered heterocycloalkyl containing 1-2 heteroatoms independently selected from N and O, which is unsubstituted or substituted with -LR[9];

$X_3$ is

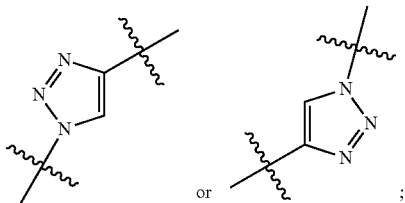 [SMILES: *c1cn(*)nn1 ; *c1cn(*)nn1]

or ;

$X_4$ is

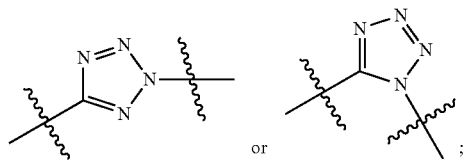 [SMILES: *c1nnn(*)n1 ; *c1nnnn1*]

or ;

each m is independently selected from 1, 2, 3, 4, 5, 6, 7, 8, 9 and 10;

each n is independently selected from 1, 2, 3, 4, 5, 6, 7, 8, 9, 10, 11, 12, 13, 14, 15, 16, 17 and 18.

Synthetic Methods

All starting materials, building blocks, reagents, acids, bases, dehydrating agents, solvents, and catalysts utilized to synthesize the compounds of the present invention are either commercially available or can be produced by organic synthesis methods known to one of ordinary skill in the art (see e.g., Houben-Weyl 4th Ed. 1952, *Methods of Organic Synthesis*, Thieme, Volume 21). Further, the compounds of the present invention can be produced by organic synthesis methods known to one of ordinary skill in the art in view of the following examples.

Illustrative examples of synthetic approaches to the compound of Formula (I), and subformulae thereof, are provided in the following general Schemes. In the following schemes R[1], R[2], R[3], R[4], R[5], R[6] and L are as defined herein. Although the general schemes show specific reagents used for various synthetic steps, it is understood that other known reagents can be used to accomplish such synthetic steps.

Synthetic approaches for compounds of Formula (I), and sub formulae thereof, wherein R[1] is a C-linked 6 membered heterocycloalkyl containing 1-2 N heteroatoms and a $C_1$-$C_2$alkylene bridge or R[1] is a C-linked 5-8 membered fused bicyclic heterocycloalkyl containing 1-2 N heteroatoms, wherein each is unsubstituted or each is substituted with 1 to 3 substituents independently selected from R[5] and R[6] are shown below in Schemes 1 to 3.

Scheme 1

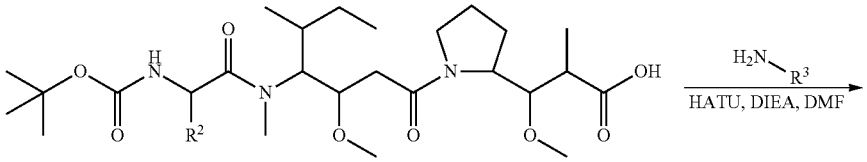

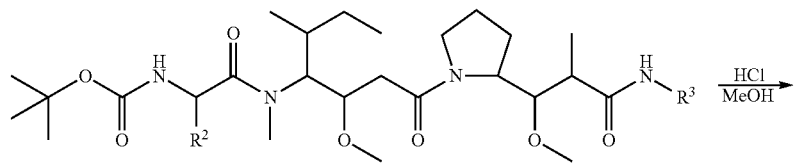

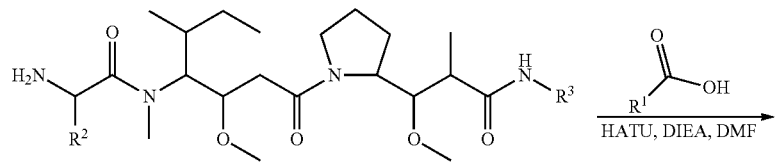

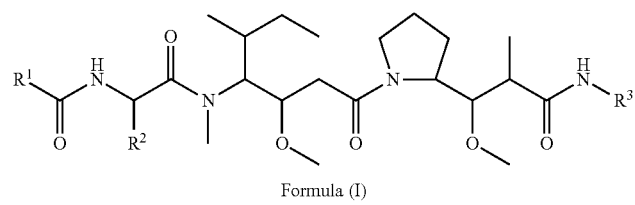

Formula (I)

In Scheme 1, R³ is coupled to a short peptide via amide bond formation followed by a deprotection step with subsequent coupling of R¹ via amide bond formation. In Scheme 1, by way of example,
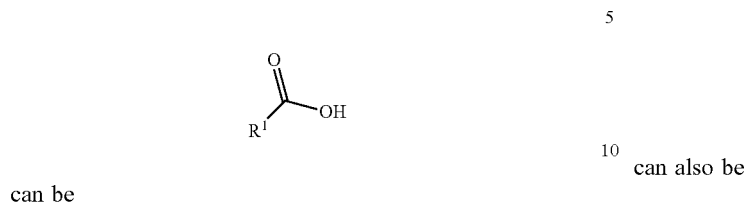
can be
which are subsequently deprotected after coupling. In Scheme 1, by way of example,
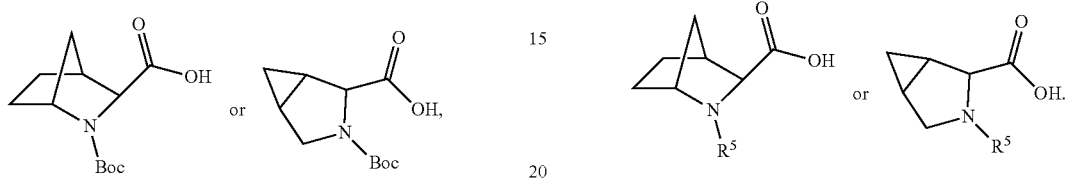
can also be
Scheme 2
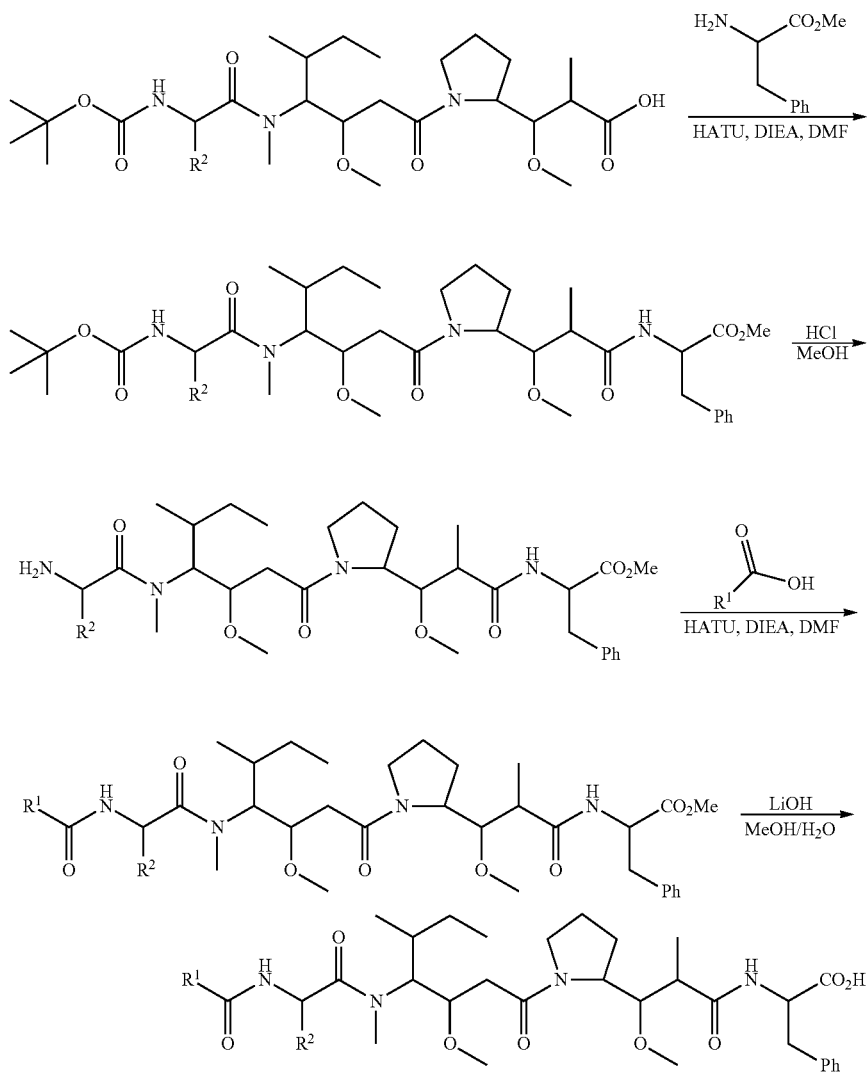

Scheme 2 illustrates one exemplary synthetic approach to compounds of Formula (I), and sub formulae thereof, wherein R³ is

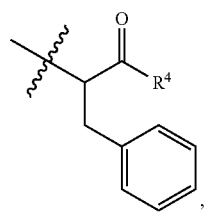

and R⁴ is —OH or —OCH₃. In Scheme 2, R³ is coupled to a short peptide via amide bond formation followed by a deprotection step with subsequent coupling of R¹ via amide bond formation. In Scheme 2, by way of example,

can be

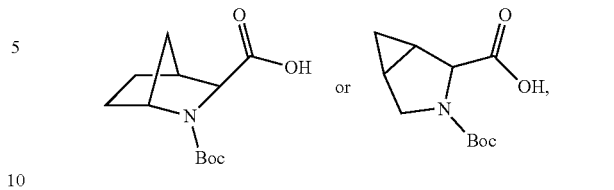

which are subsequently deprotected after coupling. In Scheme 1, by way of example,

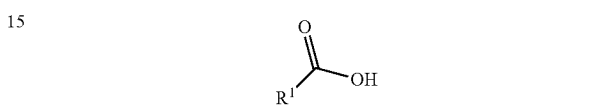

can also be

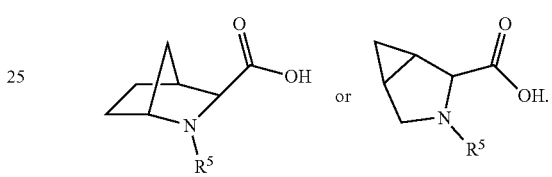

Scheme 3

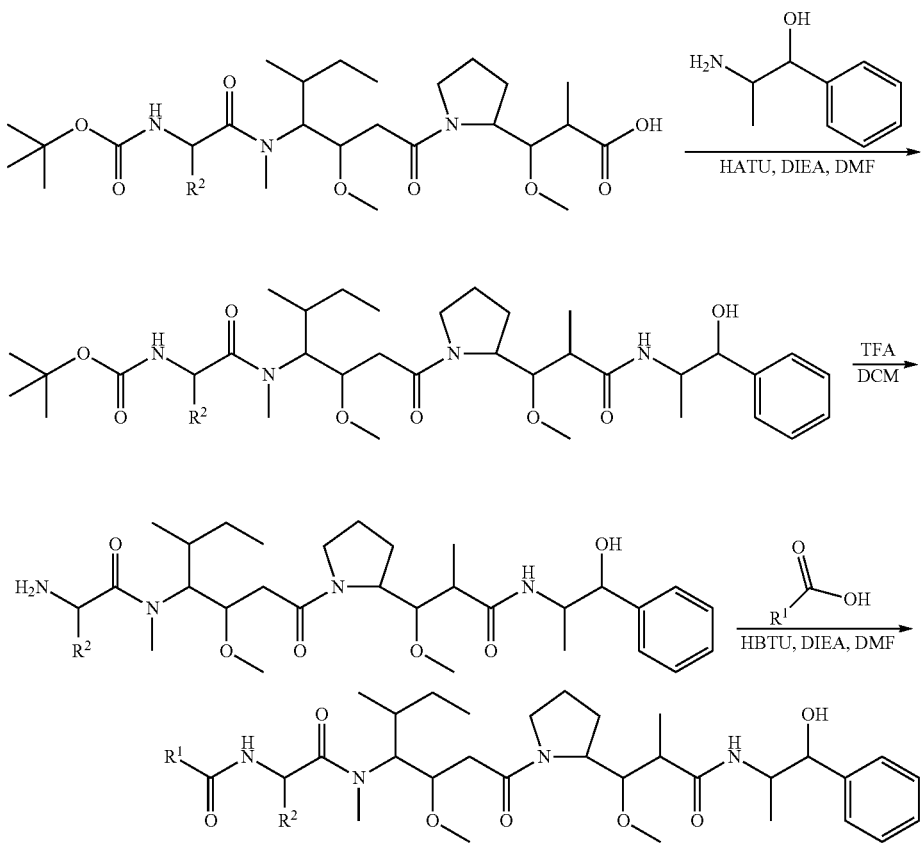

Scheme 3 illustrates one exemplary synthetic approach to compounds of Formula (I), and sub formulae thereof, wherein R³ is

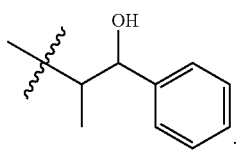

In Scheme 3, R³ is coupled to a short peptide via amide bond formation followed by a deprotection step with subsequent coupling of R¹ via amide bond formation. In Scheme 3, by way of example,

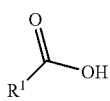

can be

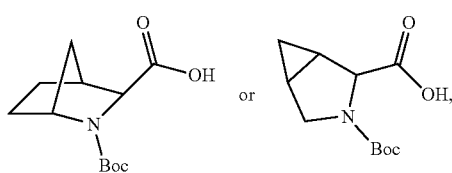 [SMILES: CC(C)(C)OC(=O)N1C2CCC(C2)C1C(=O)O ; CC(C)(C)OC(=O)N1CC2CC2C1C(=O)O]

which are subsequently deprotected after coupling. In Scheme 1, by way of example,

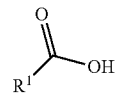

can also be

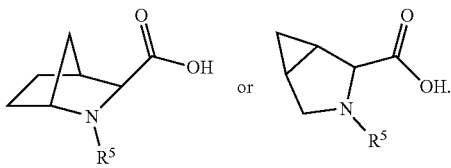

Synthetic approaches for N-terminal linked compounds of Formula (I), and sub formulae thereof, wherein R¹ is a C-linked 6 membered heterocycloalkyl containing 1-2 N heteroatoms and a $C_1$-$C_2$alkylene bridge or R¹ is a C-linked 5-8 membered fused bicyclic heterocycloalkyl containing 1-2 N heteroatoms, wherein each is substituted with an R⁷ and 0 to 3 substituents independently selected from R⁵ and R⁶ are shown below in Schemes 4 to 6.

Scheme 4

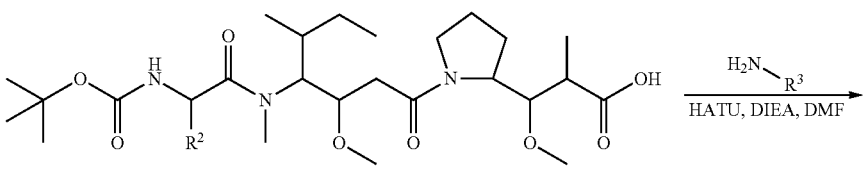

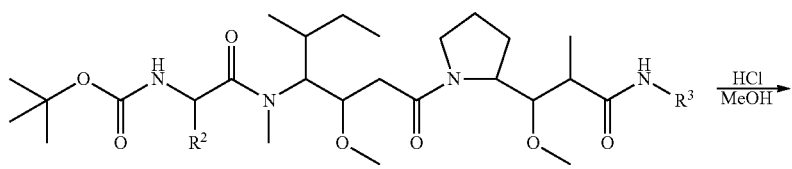

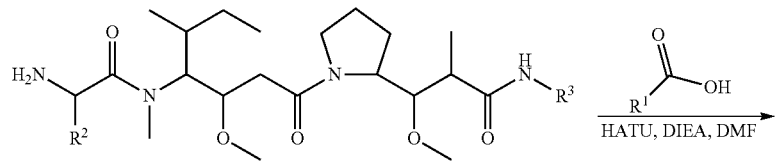

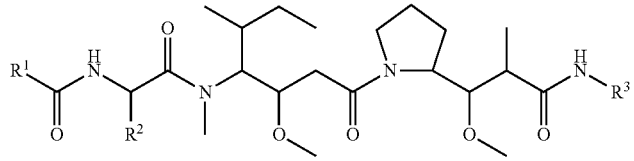

Formula (I)

In Scheme 4, $R^3$ is coupled to a short peptide via amide bond formation followed by a deprotection step with subsequent coupling of $R^1$ via amide bond formation. In Scheme 3, by way of example,

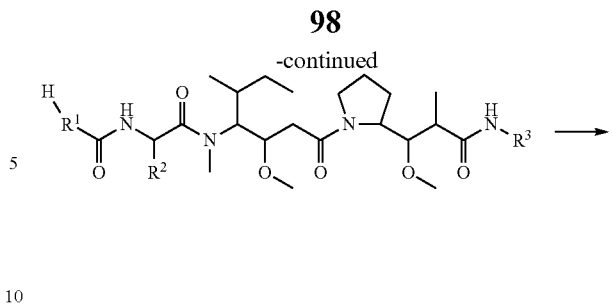

can be

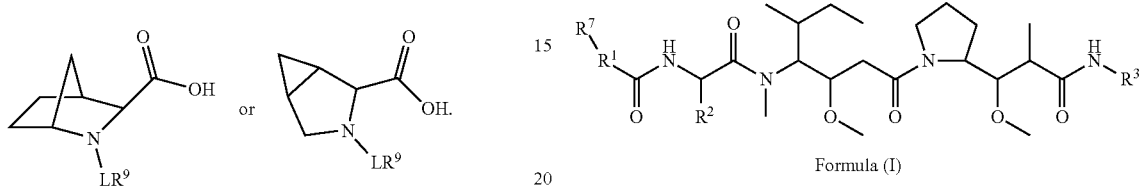

Scheme 5

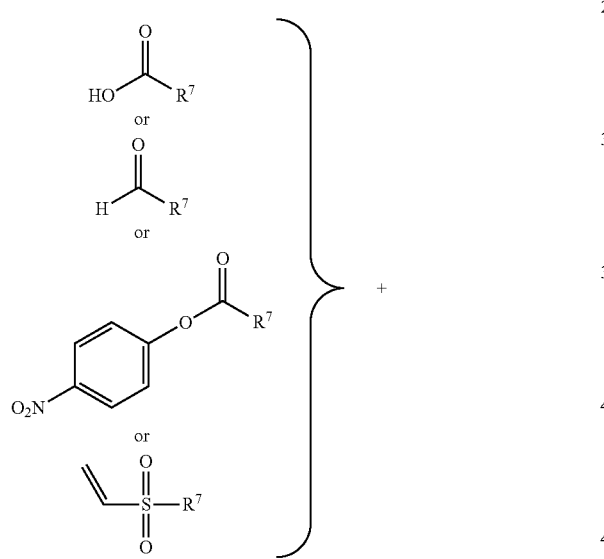

In Scheme 5, $R^1$ is initially a C-linked 6 membered heterocycloalkyl containing 1-2 N heteroatoms and a $C_1$-$C_2$alkylene bridge or $R^1$ is a C-linked 5-8 membered fused bicyclic heterocycloalkyl containing 1-2 N heteroatoms, wherein each is unsubstituted or each is substituted with 1 to 3 substituents independently selected from $R^5$ and $R^6$ (see Schemes 1 to 3) and then $R^7$ is subsequently attached to obtain a C-linked 6 membered heterocycloalkyl containing 1-2 N heteroatoms and a $C_1$-$C_2$alkylene bridge or $R^1$ is a C-linked 5-8 membered fused bicyclic heterocycloalkyl containing 1-2 N heteroatoms, wherein each is substituted with an $R^7$ and 0 to 3 substituents independently selected from $R^5$ and $R^6$. Illustrative examples are shown in the scheme below:

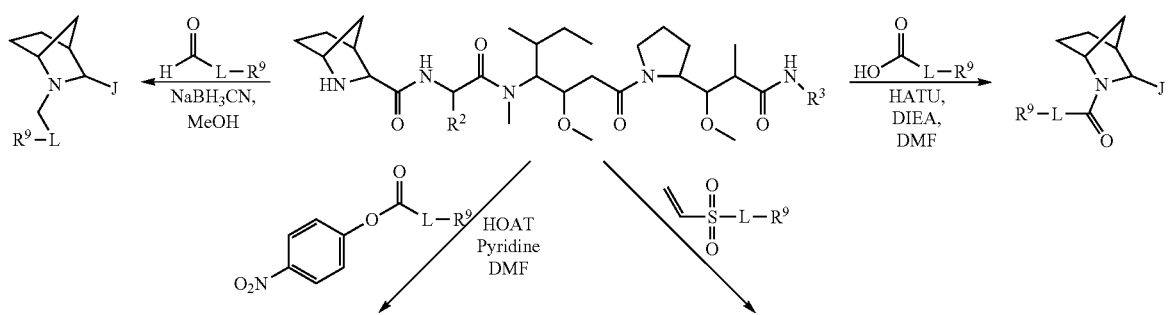

-continued

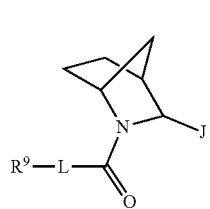 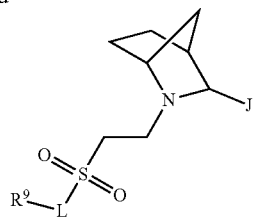

*where J is

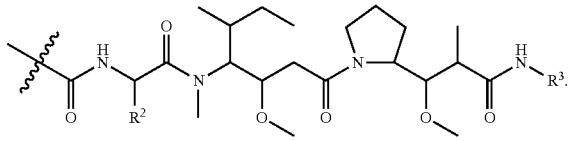

Alternatively, compounds of Formula (I), and sub formulae thereof, wherein $R^1$ is a C-linked 5-8 membered fused bicyclic heterocycloalkyl containing 1-2 N heteroatoms, wherein each is unsubstituted or each is substituted with 1 to 3 substituents independently selected from $R^5$ and $R^6$ (see Schemes 1 to 3) and then $R^7$ is subsequently attached to obtain a C-linked 6 membered heterocycloalkyl containing 1-2 N heteroatoms and a $C_1$-$C_2$alkylene bridge or $R^1$ is a C-linked 5-8 membered fused bicyclic heterocycloalkyl containing 1-2 N heteroatoms, wherein each is substituted with an $R^7$ and 0 to 3 substituents independently selected from $R^5$ and $R^6$ are obtained by a two step process as seen in Scheme 6.

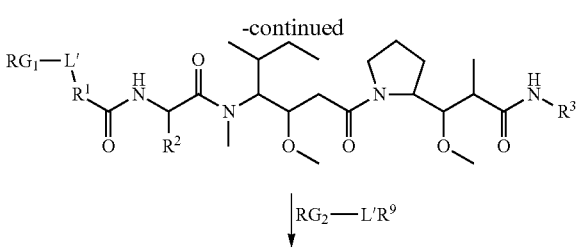

Scheme 6

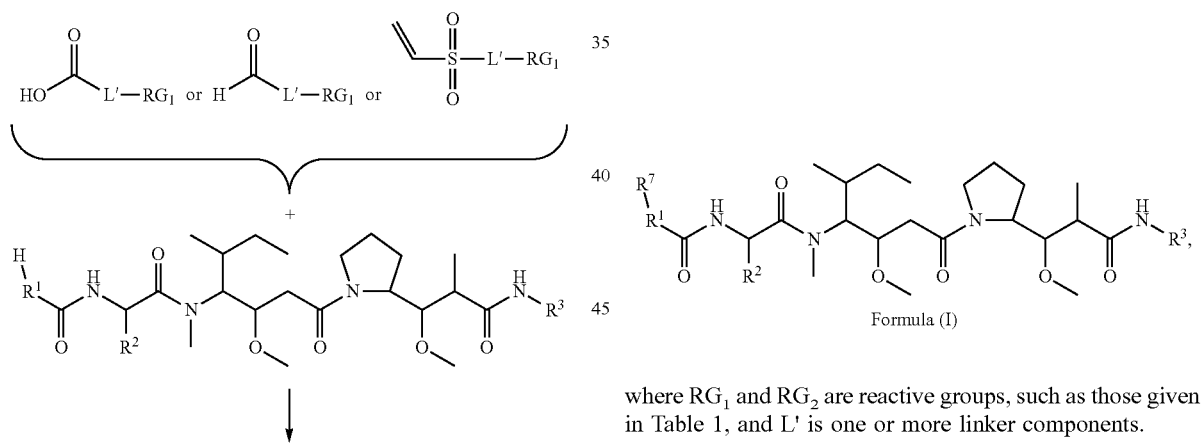

where $RG_1$ and $RG_2$ are reactive groups, such as those given in Table 1, and L' is one or more linker components.

Illustrative examples are shown in the scheme below:

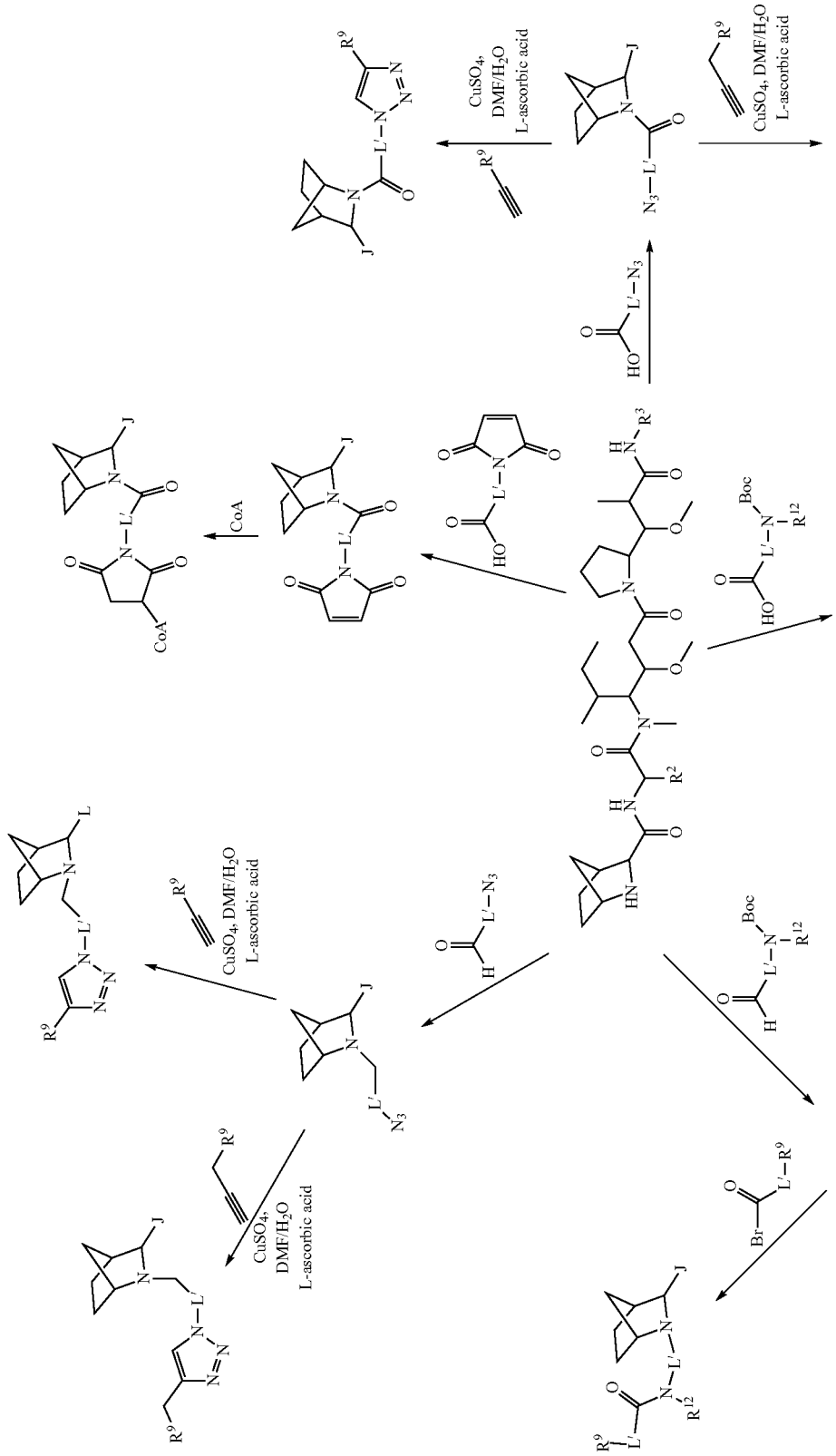

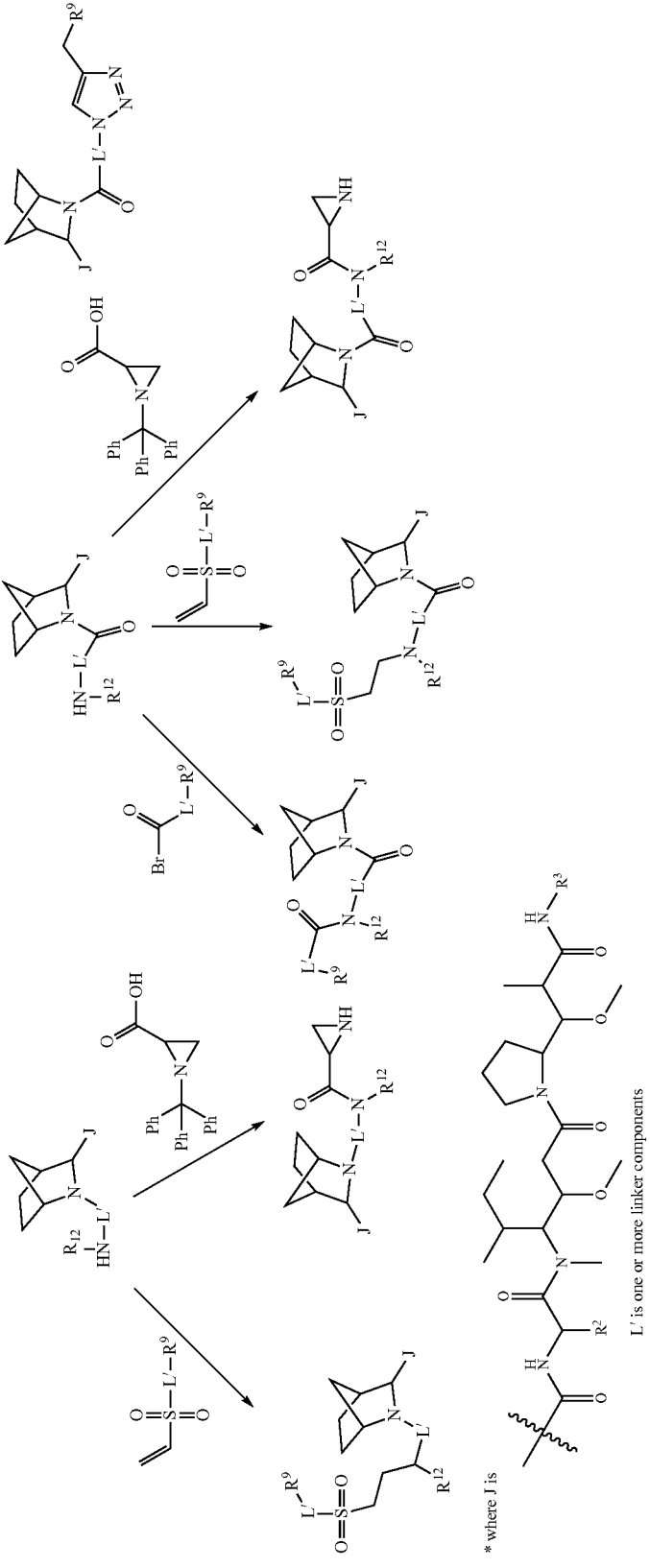

One synthetic approach for C-terminal linked compounds of Formula (I), and sub formulae thereof, wherein $R^1$ is a C-linked 6 membered heterocycloalkyl containing 1-2 N heteroatoms and a $C_1$-$C_2$alkylene bridge or $R^1$ is a C-linked 5-8 membered fused bicyclic heterocycloalkyl containing 1-2 N heteroatoms, wherein each is substituted with an $R^7$ and 0 to 3 substituents independently selected from $R^5$ and $R^6$ is shown below in Scheme 7.

Scheme 7

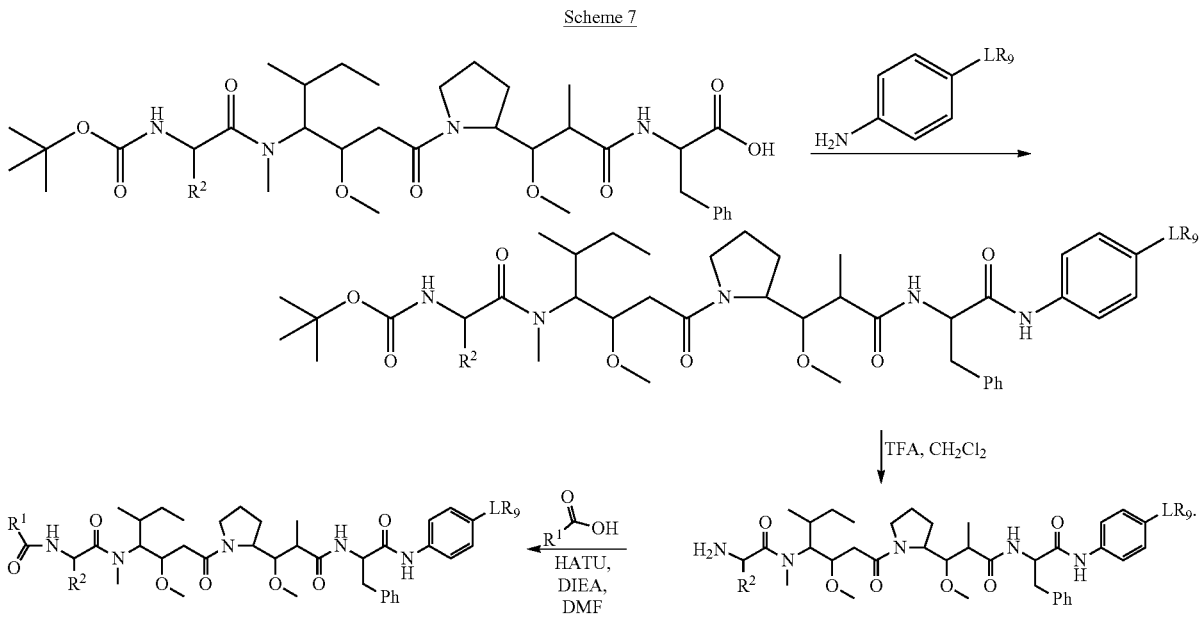

An alternative synthetic approach for C-terminal linked compounds of Formula (I), and sub formulae thereof, wherein $R^1$ is a C-linked 6 membered heterocycloalkyl containing 1-2 N heteroatoms and a $C_1$-$C_2$alkylene bridge or $R^1$ is a C-linked 5-8 membered fused bicyclic heterocycloalkyl containing 1-2 N heteroatoms, wherein each is substituted with an $R^7$ and 0 to 3 substituents independently selected from $R^5$ and $R^6$ is shown below in Scheme 8.

Scheme 8

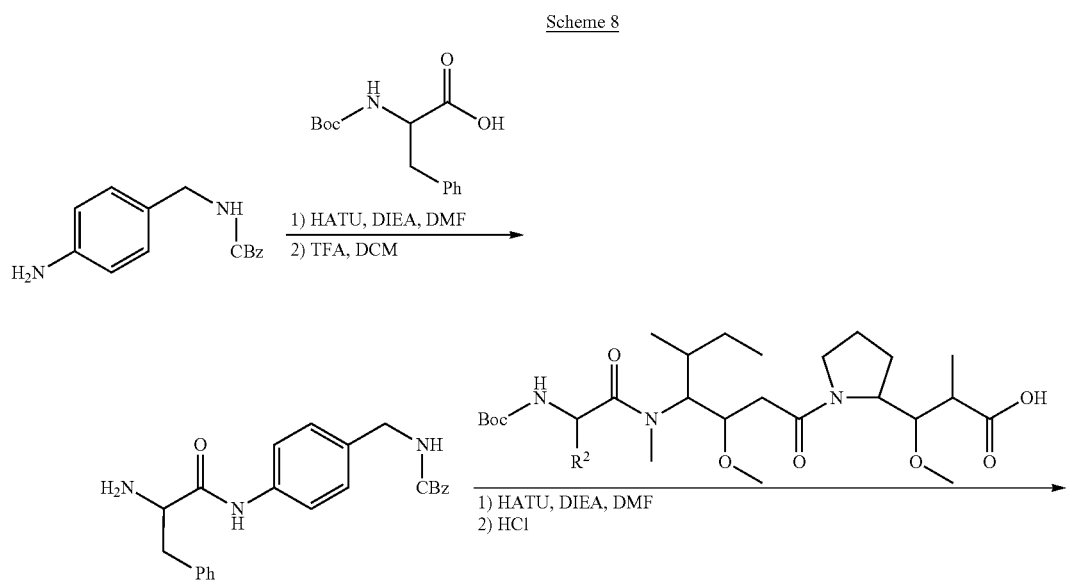

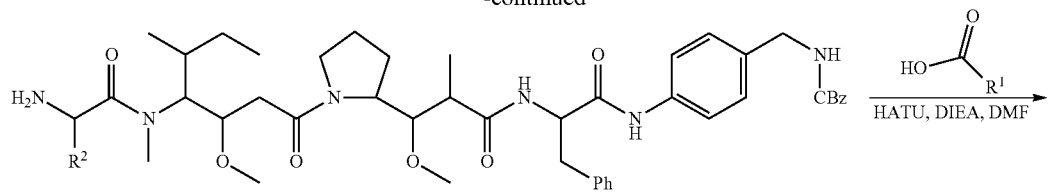

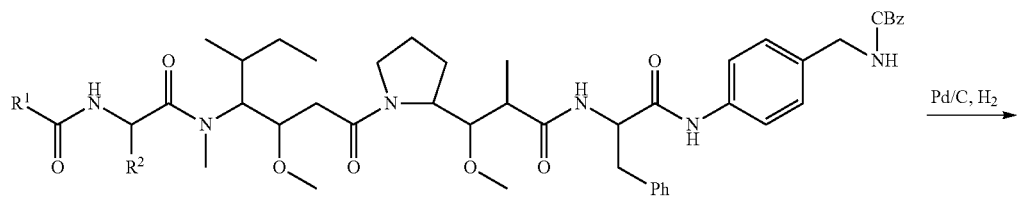

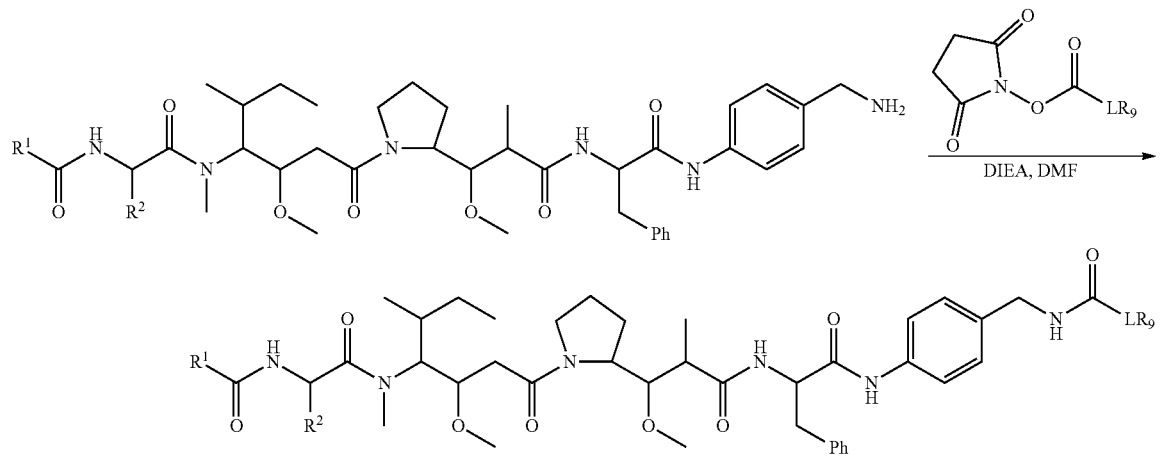

An alternative synthetic approach for C-terminal linked compounds of Formula (I), and sub formulae thereof, wherein $R^1$ is a C-linked 6 membered heterocycloalkyl containing 1-2 N heteroatoms and a $C_1$-$C_2$alkylene bridge or $R^1$ is a C-linked 5-8 membered fused bicyclic heterocycloalkyl containing 1-2 N heteroatoms, wherein each is substituted with an $R^7$ and 0 to 3 substituents independently selected from $R^5$ and $R^6$ is shown below in Scheme 9.

Scheme 9

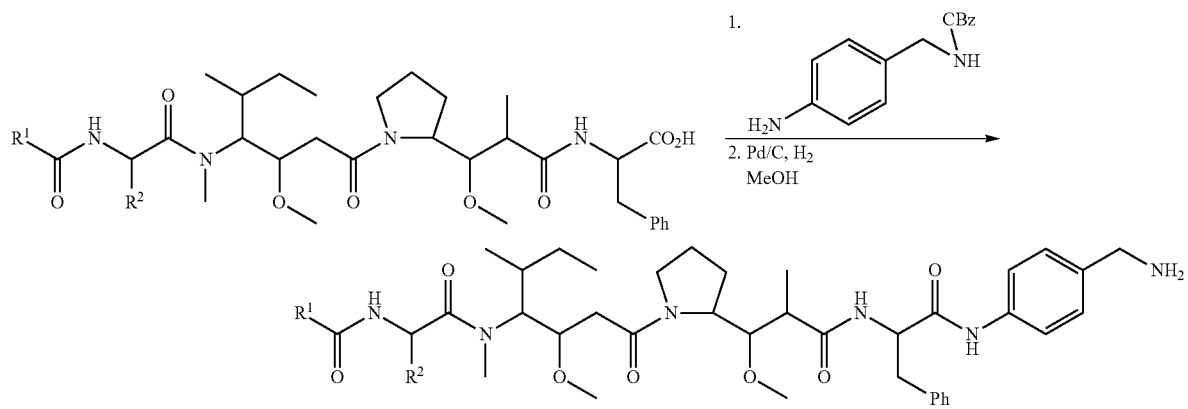

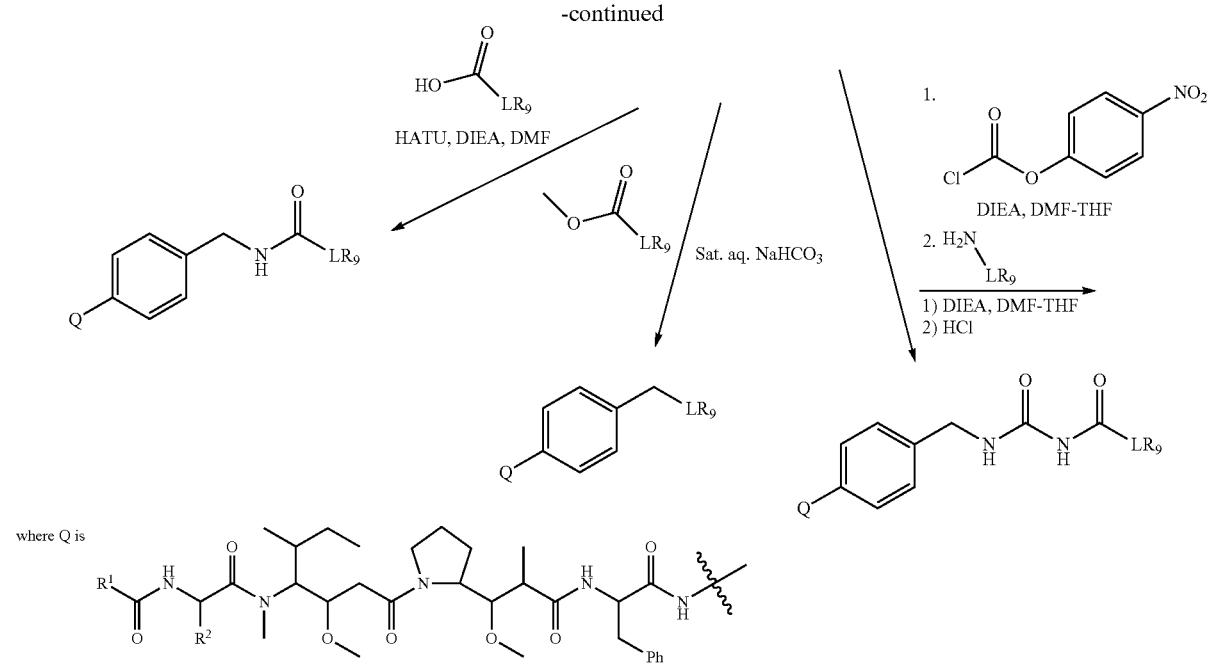

An alternative synthetic approach for C-terminal linked compounds of Formula (I), and sub formulae thereof, wherein $R^1$ is a C-linked 6 membered heterocycloalkyl containing 1-2 N heteroatoms and a $C_1$-$C_2$alkylene bridge or $R^1$ is a C-linked 5-8 membered fused bicyclic heterocycloalkyl containing 1-2 N heteroatoms, wherein each is substituted with an $R^7$ and 0 to 3 substituents independently selected from $R^5$ and $R^6$ is shown below in Scheme 10.

Scheme 10

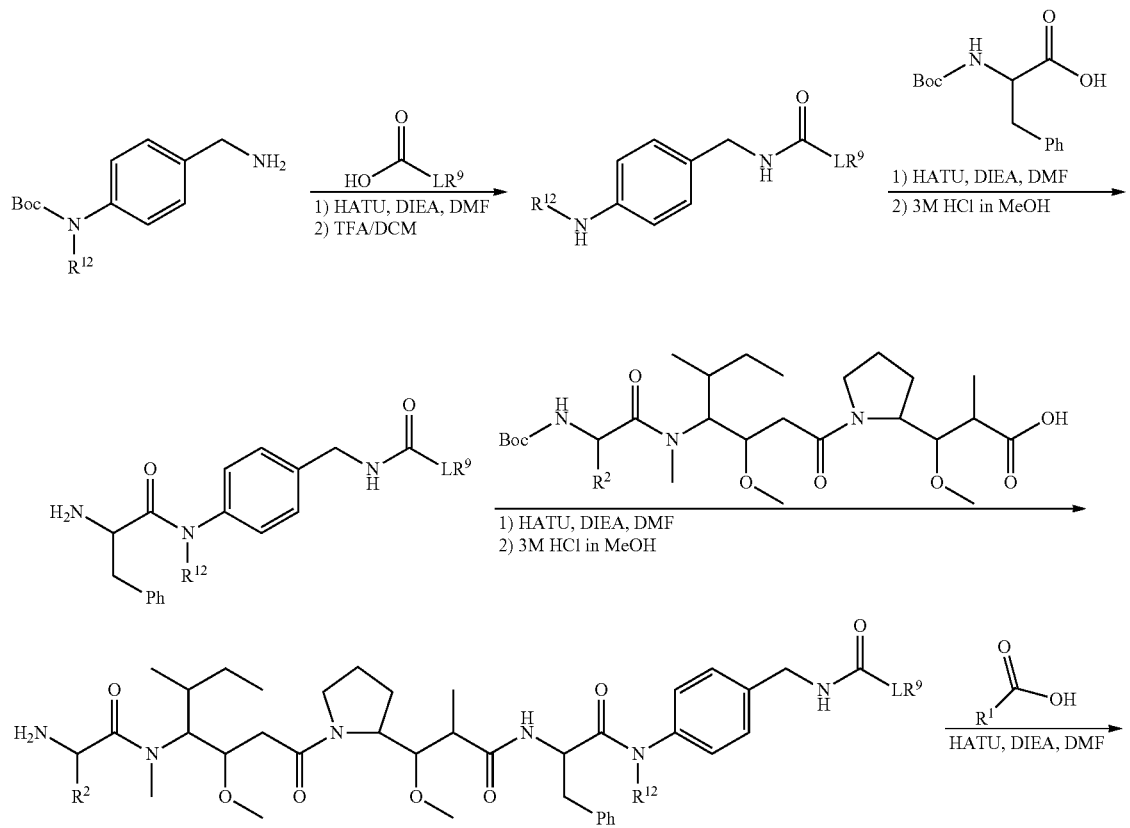

-continued

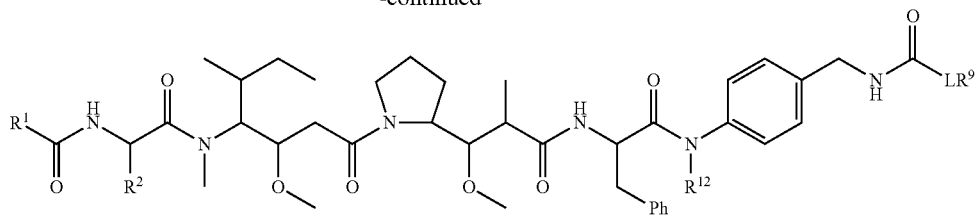

An alternative synthetic approach for C-terminal linked compounds of Formula (I), and sub formulae thereof, wherein $R^1$ is a C-linked 6 membered heterocycloalkyl containing 1-2 N heteroatoms and a $C_1$-$C_2$alkylene bridge or $R^1$ is a C-linked 5-8 membered fused bicyclic heterocycloalkyl containing 1-2 N heteroatoms, wherein each is substituted with an $R^7$ and 0 to 3 substituents independently selected from $R^5$ and $R^6$ is shown below in Scheme 11.

Scheme 11

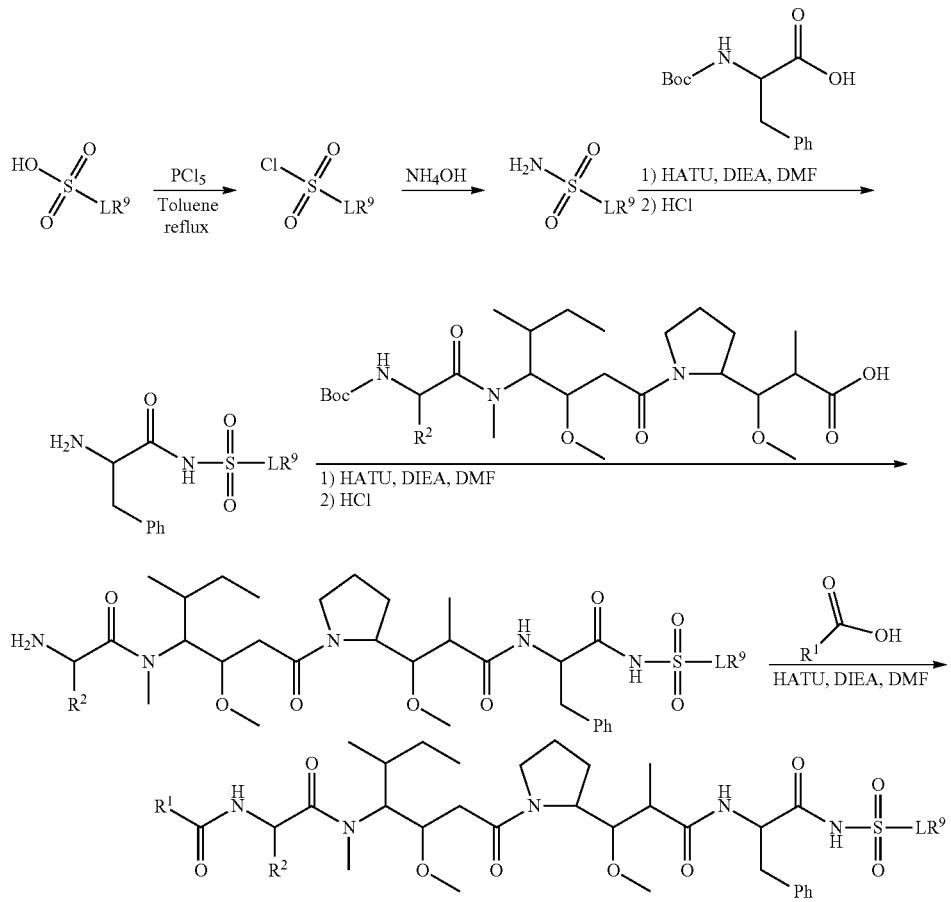

An alternative synthetic approach for C-terminal linked compounds of Formula (I), and sub formulae thereof, wherein $R^1$ is a C-linked 6 membered heterocycloalkyl containing 1-2 N heteroatoms and a $C_1$-$C_2$alkylene bridge or $R^1$ is a C-linked 5-8 membered fused bicyclic heterocycloalkyl containing 1-2 N heteroatoms, wherein each is substituted with an $R^7$ and 0 to 3 substituents independently selected from $R^5$ and $R^6$ is shown below in Scheme 12.

Scheme 12
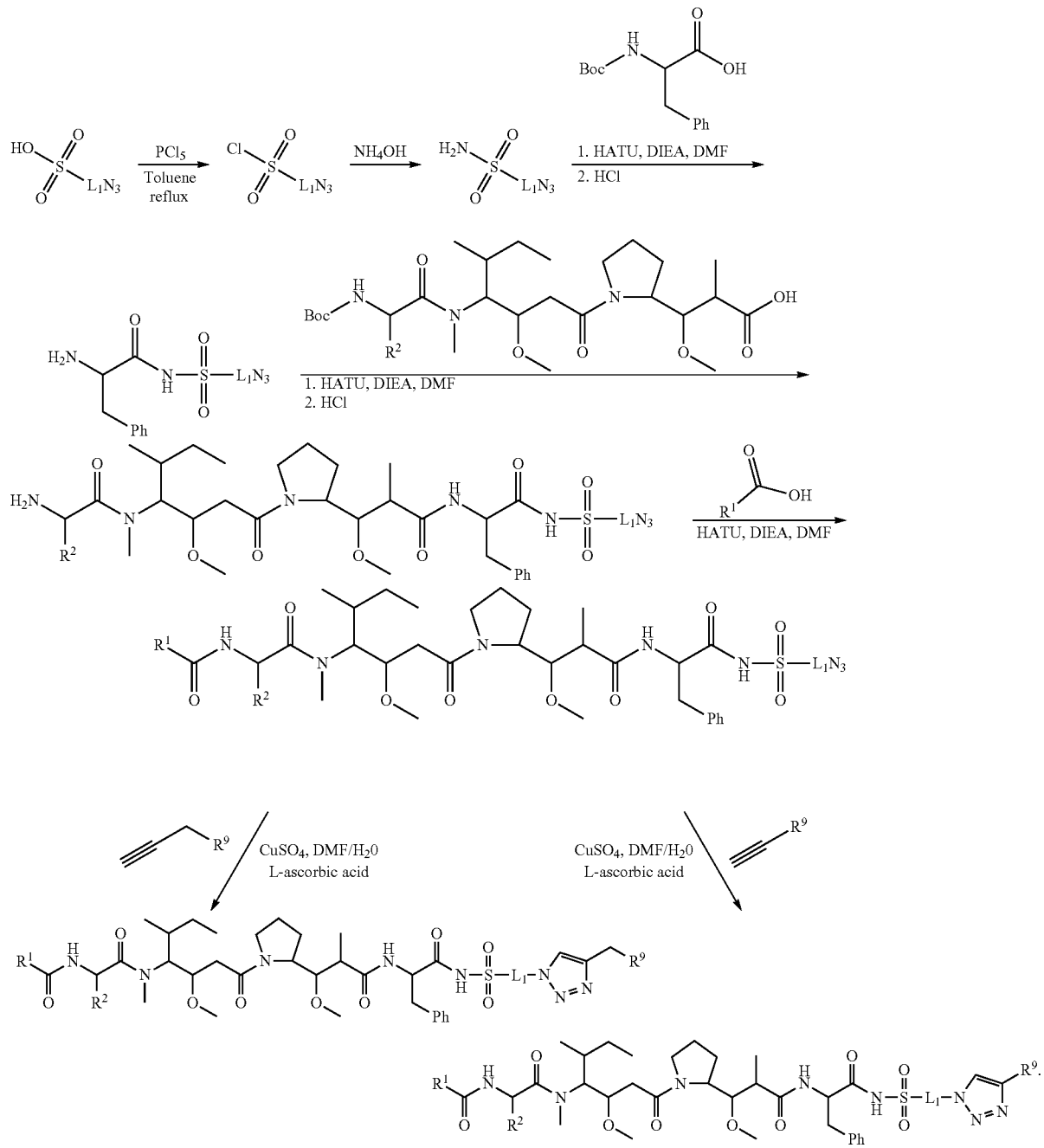
In Schemes 7 to 12, by way of example,
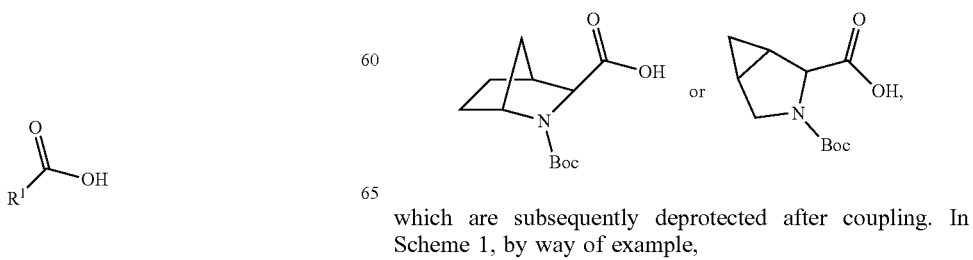
can be
which are subsequently deprotected after coupling. In Scheme 1, by way of example,

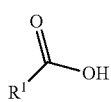

can also be

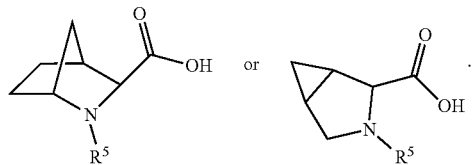

Alternatively, in Schemes 7 to 12 $R^5$ can be attached, after deprotection of the unsubstituted C-linked 6 membered heterocycloalkyl containing 1-2 N heteroatoms and a $C_1$-$C_2$alkylene bridge or the unsubstituted $R^1$ is a C-linked 5-8 membered fused bicyclic heterocycloalkyl containing 1-2 N heteroatoms, by subsequent reaction with either

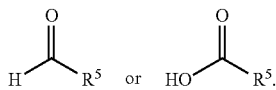

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (=20-133 mbar). Abbreviations used are those conventional in the art. All reactions were carried out under nitrogen using commercial grade solvents without any further distillation. Reagents were used as commercial grade without further purification. Thin layer chromatography was carried out using TLC silica gel plates. Column chromatography was carried out using an ISCO Combiflash Companion system, using flash grade prepacked Redisep® columns.

Preparative HPLC was performed on Waters Autopurification system using the following conditions: Column Sunfire C18 30×100 mm, 5 μm, gradient elution with $CH_3CN$ in water+0.05% TFA-$CH_3CN$ at 30 ml/min.

Analytical Methods

Unless otherwise indicated, the following HPLC and HPLC/MS methods were used in the preparation of Intermediates and Examples.

LC/MS analysis was performed on an Agilent 1200sl/ 6140 system.

Column: Waters Acquity HSS T3 C18, 50×2.0, 1.8 μm

Mobile Phase: A) $H_2O$+0.05% TFA; B: acetonitrile+ 0.035% TFA

Pump Method:

| Time | A % | B % | Flow (mL/min) |
|------|-----|-----|---------------|
| 0    | 90  | 10  | 0.9 |
| 1.35 | 0   | 100 | 0.9 |
| 1.36 | 0   | 100 | 0.9 |
| 1.95 | 0   | 100 | 0.9 |
| 1.96 | 90  | 10  | 0.9 |
| 2.0  | 90  | 10  | 0.9 |

Detection: UV Diode Array at 190 nm-400 nm
MS Scan: 200-1350 amu
ELSD: 60° C.
MS Parameters:

| Polarity | Positive |
|----------|----------|
| Drying Gas | 12 |
| Nebulizer Pressure | 50 |
| Drying Gas Temperature | 350 |
| Capillary Voltage | 3000 |

Synthetic Procedure for Intermediates

Synthesis of (S)-2-phenyl-1-(5-phenyl-1,3,4-oxadiazol-2-yl)ethanamine (i-1)

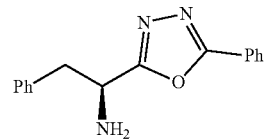

Step 1: (S)-2-((t-Butoxycarbonyl)amino)-3-phenylpropanoic acid (200 mg, 0.754 mmol) was added to dichloromethane (5.5 ml) at 0° C., followed by carbonyldiimidazole (128 mg, 0.792 mmol). After stirring at 0° C. for 30 min, benzohydrazide (103 mg, 0.754 mmol) was added. After additional 45 min at 0° C., carbon tetrabromide (497 mg, 1.5 mmol) and triphenylphosphine (198 mg, 0.754 mmol) were added. The mixture was stirred for 2 h at 0° C. and then at rt for 16 h. Water was added to the mixture and extracted with DCM (5 ml×3). The organic layers were combined, dried with $Na_2SO_4$, filtered and concentrated. The crude product was purified by a silica gel column (20-40% ethyl acetate in hexanes) to obtain t-butyl [(1S)-2-phenyl-1-(5-phenyl-1,3,4-oxadiazol-2-yl) ethyl] carbamate. MS m/z 366 (M+H), Retention time 1.351 min. 1H NMR (400 MHz, Chloroform-d) δ 8.03-7.85 (m, 2H), 7.62-7.38 (m, 3H), 7.33-7.16 (m, 3H), 7.18-7.04 (m, 2H), 5.35 (d, J=7.9 Hz, 1H), 5.15 (d, J=9.1 Hz, 1H), 3.28 (d, J=6.6 Hz, 2H), 1.54 (s, 9H).

Step 2: To the compound obtained in step 1, (548 mg, 1.5 mmol) in DCM (5 ml) was added TFA (1.5 ml). The resulting solution was stirred at room temperature for 18 h and then concentrated to obtain (S)-2-phenyl-1-(5-phenyl-1,3,4-oxadiazol-2-yl)ethanamine (i-1) TFA salt. It was used without further purification. MS m/z 266 (M+H). Retention time 0.858 min.

Synthesis of 2-phenyl-1-(pyrimidin-2-yl)ethanamine (i-2)

Benzylmagnesium chloride (1.2 ml, 2.4 mmol) (2M in THF) was added dropwise to 2-cyanopyrimidine (210 mg, 2.00 mmol) in toluene (10 ml) at 0° C. The reaction was stirred at this temperature for 1 h. Then 2-butanol (10 ml) was added, followed by sodium borohydride (106 mg, 2.80 mmol). The reaction was stirred at rt for 1 h, and then quenched with MeOH (3 ml) and water. The mixture was extracted with EtOAc (2×30 ml). The organic layer was dried with Na$_2$SO$_4$, filtered and concentrated. The crude product was purified by preparative HPLC (10-30% acetonitrile in water with 0.05% TFA) to obtain 2-phenyl-1-(pyrimidin-2-yl)ethanamine (i-2). MS m/z 200.2 (M+H). Retention time 0.637 min. $^1$H NMR (400 MHz, Acetonitrile-d3) δ 8.75 (d, J=5.0 Hz, 2H), 7.41 (t, J=4.9 Hz, 1H), 7.27 (m, 3H), 7.14-7.05 (m, 2H), 4.84 (t, J=6.7 Hz, 1H), 3.45 (dd, J=14.1, 6.3 Hz, 1H), 3.33 (dd, J=14.1, 7.1 Hz, 1H).

Synthesis of (S)-2-phenyl-1-(1H-pyrazol-3-yl)ethanamine (i-3)

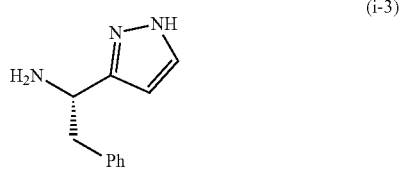 [SMILES: N[C@@H](Cc1ccccc1)c1cc[nH]n1]

(i-3)

Step 1: Hydrazine monohydrate (0.034 ml, 0.69 mmol) was added to (S,E)-t-butyl (5-(diethylamino)-3-oxo-1-phenylpent-4-en-2-yl)carbamate (60 mg, 0.17 mmol) in MeOH (5 ml). The reaction was heated at 70° C. for 2 h and then 50° C. for 3 days. The reaction mixture was concentrated, taken up in water, and extracted with DCM (5 ml×2). The DCM layers were combined, dried with Na$_2$SO$_4$, filtered and concentrated. The residue was purified by silica gel preparative TLC (4% MeOH in DCM) to obtain (S)-t-butyl (2-phenyl-1-(1H-pyrazol-3-yl)ethyl)carbamate. MS m/z 288.2 (M+H). Retention time 1.310 min. 1H NMR (400 MHz, Chloroform-d) δ 7.53-7.35 (m, 1H), 7.28-6.90 (m, 5H), 6.01 (s, 1H), 5.47-5.25 (m, 0.3 H), 5.15-4.84 (m, 0.7H), 3.40 (s, 1H), 3.09 (d, J=8.0 Hz, 2H), 1.34 (d, J=31.2 Hz, 9H).

Step 2: A solution of the compound obtained in step 1 (38 mg, 0.13 mmol) in DCM (2 ml) was treated with TFA (0.5 ml) at rt for 2 h and then concentrated to give (S)-2-phenyl-1-(1H-pyrazol-3-yl)ethanamine TFA salt (i-3). The product was used in the next step without further purification. MS m/z 188.2 (M+H). Retention time 0.616 min.

Synthesis of (S)-t-butyl (3-(2-amino-3-hydroxypropyl)phenyl)carbamate (i-4)

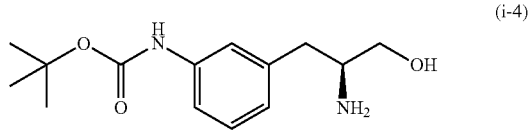 [SMILES: CC(C)(C)OC(=O)Nc1cccc(C[C@H](N)CO)c1]

(i-4)

Step 1: BH$_3$ in THF (1M, 10 ml) was added to (S)-2-((t-butoxycarbonyl)amino)-3-(3-nitrophenyl)propanoic acid (562 mg, 1.81 mmol) in THF (10 ml) with stirring at 0° C. Then the reaction was stirred at 50° C. for 1 h. The reaction mixture was cooled at 0° C., quenched with water, diluted with EtOAc and washed with 10% aqueous K$_2$CO$_3$, dried over MgSO$_4$, filtered and concentrated. The crude was purified by a silica gel column (30-70% EtOAc-hexanes) to obtain (S)-t-butyl (1-hydroxy-3-(3-nitrophenyl)propan-2-yl)carbamate as white solid. MS m/z 319.1 (M+Na). Retention time 1.183 minute. 1H NMR (600 MHz, Chloroform-d) δ 8.13-8.04 (m, 2H), 7.57 (d, J=7.7 Hz, 1H), 7.46 (dd, J=8.9, 7.6 Hz, 1H), 4.76 (s, 1H), 3.87 (dq, J=8.0, 4.6, 4.1 Hz, 1H), 3.69 (dd, J=10.9, 3.9 Hz, 1H), 3.58 (dd, J=10.8, 4.7 Hz, 1H), 2.97 (td, J=13.1, 12.5, 7.3 Hz, 2H), 1.37 (s, 9H).

Step 2: To (S)-t-butyl (1-hydroxy-3-(3-nitrophenyl)propan-2-yl)carbamate (0.31 g, 1.0 mmol) in acetonitrile (5 ml) was added 10% hydrochloric acid (5 ml). The reaction mixture was stirred at rt for 48 h and then concentrated to give (S)-2-amino-3-(3-nitrophenyl)propan-1-ol as HCl salt. MS m/z 197.2 (M+H). Retention time 0.775 min.

Step 3: (S)-2-Amino-3-(3-nitrophenyl)propan-1-ol HCl salt (0.243 g, 1.046 mmol) was dissolved in MeOH (10 ml) and 10% palladium on carbon (50 mg, 0.047 mmol) was added. A 2 L hydrogen balloon was attached. The reaction was flushed with H$_2$ three times and then stirred at rt for 1 h. LCMS indicated the reaction was complete. The reaction was filtered through a celite pad and concentrated to give (S)-2-amino-3-(3-aminophenyl)propan-1-ol as HCl salt. MS m/z 167.2 (M+H). Retention time 0.373 min.

Step 4: (S)-2-Amino-3-(3-aminophenyl)propan-1-ol HCl salt (0.212 g, 1.046 mmol) and Boc$_2$O (228 mg, 1.05 mmol) and dioxane-water-AcOH (10:9:1, 20 ml) were combined and stirred at rt for 3 days. LCMS indicated the reaction was 75% complete. Additional Boc$_2$O (150 mg) was added and the reaction was further stirred for 6 h. The reaction mixture was then concentrated and purified with preparative HPLC (10-40% acetonitrile in water with 0.05% TFA) to give (S)-t-butyl (3-(2-amino-3-hydroxypropyl)phenyl)carbamate (i-4) as an oil. MS m/z 267.2 (M+H). Retention time 1.011 min.

Synthesis of (S)-t-butyl (4-(2-amino-3-hydroxypropyl)phenyl)carbamate (i-5)

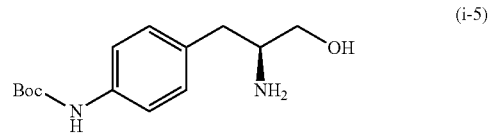 [SMILES: CC(C)(C)OC(=O)Nc1ccc(C[C@H](N)CO)cc1]

(i-5)

Step 1: To (S)-2-((t-butoxycarbonyl)amino)-3-(4-nitrophenyl)propanoic acid (0.80 g, 2.58 mmol) in THF (10 ml) was added borane dimethyl sulfide complex (1.00 ml, 10.5 mmol) at 0° C. The reaction was stirred for 10 min at 0° C. and then at rt for 5 h. The reaction was then quenched with water at 0° C. The quenched mixture was partitioned between DCM and 1M aqueous Na$_2$CO$_3$. The DCM layer was separated, dried over Na$_2$SO$_4$, filtered and concentrated to give (S)-t-butyl (1-hydroxy-3-(4-nitrophenyl)propan-2-yl)carbamate as white solid. MS m/z 319.1(M+Na). Retention time 1.031 min. 1H NMR (400 MHz, Chloroform-d) δ 8.10 (d, J=8.8 Hz, 2H), 7.33 (d, J=8.7 Hz, 2H), 4.73 (s, 1H), 3.83 (s, 1H), 3.70-3.56 (m, 1H), 3.50 (d, J=4.6 Hz, 1H), 2.91 (d, J=7.1 Hz, 2H), 1.32 (s, 9H).

Step 2: (S)-t-Butyl (1-hydroxy-3-(4-nitrophenyl)propan-2-yl)carbamate (300 mg, 1.01 mmol) in acetonitrile (5 ml) and 10% hydrochloric acid (5 ml) was stirred at rt for 4 h and then concentrated. The residue was treated with saturated aqueous Na$_2$CO$_3$, and extracted with DCM-iPrOH (10:1, 10 mlx3). The organic layers were combined, dried and concentrated to give (S)-2-amino-3-(4-nitrophenyl)propan-1-ol. MS m/z 197.2 (M+H). Retention time 0.512 min. $^1$H NMR (400 MHz, Chloroform-d) δ 8.32-7.92 (m, 2H), 7.41-7.21 (m, 2H), 4.18-4.00 (m, 1H), 3.66-3.49 (m, 2H), 3.49-3.36 (m, 1H), 3.25-3.00 (m, 1H), 3.01-2.74 (m, 2H), 2.70-2.65 (m, 1H).

Step 3: (S)-2-Amino-3-(4-nitrophenyl)propan-1-ol (200 mg, 1.019 mmol) was dissolved in MeOH (10 ml) and 10% Pd/C (50 mg) was added. A 2 L hydrogen balloon was attached. The reaction was flushed with H2 three times and then stirred at rt for 3 h. The reaction mixture was filtered through a celite pad and then concentrated to give (S)-2-amino-3-(4-aminophenyl)propan-1-ol. MS m/z 167.2 (M+H). Retention time 0.240 min.

Step 4: (S)-2-Amino-3-(4-aminophenyl)propan-1-ol (168 mg, 1.012 mmol) was dissolved in dioxane (10 ml)-water (9 ml)-AcOH (1 ml) and t-butyl dicarbonate (0.28 g, 1.28 mmol) were combined and stirred at rt for 16 h. The reaction mixture was then concentrated and purified with ISCO using C18 column, eluted with 10-40% acetonitrile in water with 0.05% TFA to give (S)-t-butyl (4-(2-amino-3-hydroxypropyl)phenyl)carbamate TFA (i-5). MS m/z 267.2 (M+H). Retention time 0.764 min. $^1$H NMR (400 MHz, Acetonitrile-d3) δ 7.59 (s, 1H), 7.36 (d, J=8.5 Hz, 2H), 7.16 (d, J=8.5 Hz, 2H), 6.14 (s, 3H), 3.69 (dd, J=11.7, 3.2 Hz, 1H), 3.57-3.36 (m, 2H), 2.86 (d, J=7.1 Hz, 2H), 1.47 (s, 9H).

Synthesis of (S)-t-butyl (3-(2-amino-3-methoxypropyl)phenyl)carbamate (i-6)

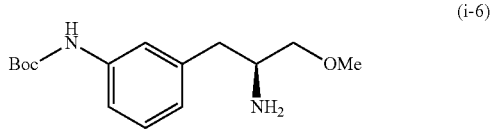 [SMILES: COC[C@@H](N)Cc1cccc(NC(=O)OC(C)(C)C)c1]

Step 1: Borane dimethyl sulfide complex (3.00 ml, 31.6 mmol) was added to (S)-2-((t-butoxycarbonyl)amino)-3-(3-nitrophenyl)propanoic acid (1.5 g, 4.83 mmol) in THF (10 ml) at 0° C. The reaction was stirred for 10 min at 0° C. and then at rt for 6 h. The reaction was then quenched with water at 0° C. The quenched reaction mixture was partitioned between DCM and 1M aqueous Na$_2$CO$_3$. The DCM layer was separated, dried over Na$_2$SO$_4$, filtered and concentrated to give (S)-t-butyl (1-hydroxy-3-(3-nitrophenyl)propan-2-yl)carbamate as white solid. MS m/z 319.1(M+Na). Retention time 1.031 min. $^1$H NMR (400 MHz, Chloroform-d) δ 8.14-7.97 (m, 2H), 7.57 (dt, J=7.7, 1.4 Hz, 1H), 7.46 (dd, J=8.8, 7.6 Hz, 1H), 4.77 (d, J=14.5 Hz, 1H), 3.87 (s, 1H), 3.69 (dd, J=10.9, 3.8 Hz, 1H), 3.58 (dd, J=10.9, 4.7 Hz, 1H), 2.95 (t, J=6.8 Hz, 2H), 1.37 (s, 9H).

Step 2: To (S)-t-butyl (1-hydroxy-3-(3-nitrophenyl)propan-2-yl)carbamate (0.200 g, 0.675 mmol) in THF/DMF 4:1 (10 ml) at 0° C. was added NaH (60% in mineral oil, 0.048 g, 1.2 mmol) slowly, followed by methyl iodide (0.19 g, 1.3 mmol). The resulting mixture was stirred at rt for 1 h. The reaction was quenched carefully by slow addition of water until no bubbling (H$_2$) was observed. The crude product was extracted with EtOAc (10 mlx3). The combined organic phases was dried over Na$_2$SO$_4$, filtered and concentrated. The residue was purified by ISCO using C18 column and eluted with 30-67% ACN in water with 0.05% TFA to give (S)-t-butyl (1-methoxy-3-(3-nitrophenyl)propan-2-yl)carbamate as white solid. MS m/z 333.1 (M+Na). Retention time 1.205 min. $^1$H NMR (400 MHz, Chloroform-d) d 8.10 (dd, J=4.5, 2.5 Hz, 2H), 7.59 (d, J=7.5 Hz, 1H), 7.48 (dd, J=8.8, 7.6 Hz, 1H), 4.96 (d, J=8.7 Hz, 1H), 4.07-3.88 (m, 1H), 3.43-3.28 (m, 5H), 2.98 (d, J=7.2 Hz, 2H), 1.40 (s, 9H).

Step 3: (S)-t-Butyl (1-methoxy-3-(3-nitrophenyl)propan-2-yl)carbamate (124 mg, 0.400 mmol) in acetonitrile (3 ml) and 10% hydrochloric acid (3 ml) was stirred at rt for 4 h and then concentrated. Saturated aqueous Na$_2$CO$_3$ was added to the residue and the resulting mixture was extracted with DCM-iPrOH (10:1, 10 mlx3). The organic layers were combined, dried and concentrated to give (S)-1-methoxy-3-(3-nitrophenyl)propan-2-amine. MS m/z 211.2 (M+H). Retention time 0.622 min.

Step 4: (S)-1-Methoxy-3-(3-nitrophenyl)propan-2-amine was dissolved in MeOH (10 ml) and 10% Pd/C (50 mg) was added. A 2 L hydrogen balloon was attached. The reaction was flushed with H$_2$ three times and then stirred at rt for 3 h. The reaction mixture was filtered through a celite pad and then concentrated to give (S)-3-(2-amino-3-methoxypropyl) aniline. MS m/z 181.2 (M+H). Retention time 0.282 min.

Step 5: (S)-3-(2-Amino-3-methoxypropyl)aniline (62.6 mg, 0.347 mmol) in dioxane (3 ml)-water (3 ml)-AcOH (0.6 ml) and t-butyl dicarbonate (0.093 ml, 0.4 mmol) were combined and stirred at rt for 16 h. The reaction mixture was then concentrated and purified with ISCO using C18 column, eluted with 10-40% acetonitrile in water with 0.05% TFA to give (S)-t-butyl (3-(2-amino-3-methoxypropyl)phenyl)carbamate TFA salt (i-6). MS m/z 281.2 (M+H). Retention time 0.856 min. $^1$H NMR (400 MHz, Acetonitrile-d3) d 7.61 (s, 1H), 7.40-7.12 (m, 3H), 6.89 (dt, J=7.4, 1.5 Hz, 1H), 6.78 (s, 3H), 3.59 (m, 1H), 3.50 (dd, J=10.6, 3.4 Hz, 1H), 3.38 (dd, J=10.6, 6.9 Hz, 1H), 3.33 (s, 3H), 2.90 (d, J=7.5 Hz, 3H), 1.48 (s, 9H).

Synthesis of (3R,4S,5S)-4-((S)-N,3-dimethyl-2-((1R,3S,4S)-2-methyl-2-azabicyclo[2.2.1]heptane-3-carboxamido)butanamido)-3-methoxy-5-methylheptanoic acid (i-7)

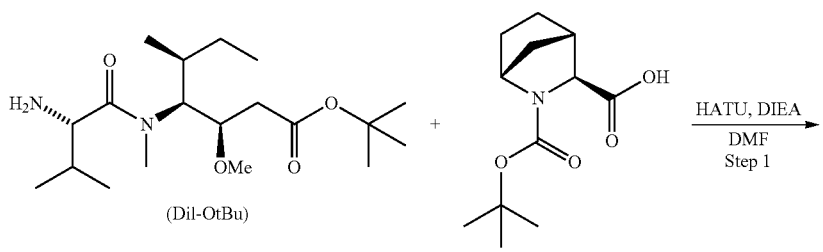

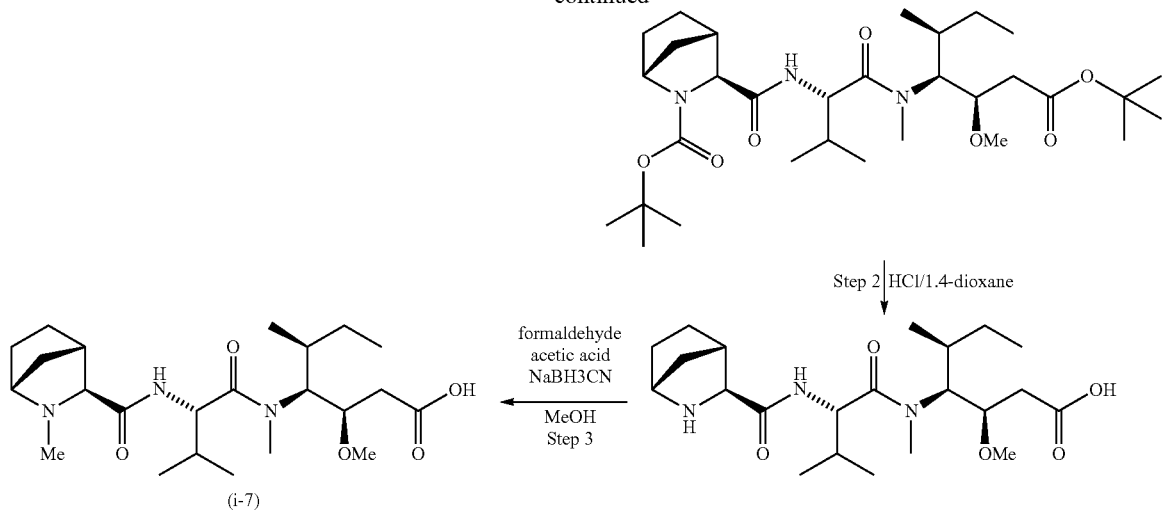

Step 2 | HCl/1,4-dioxane formaldehyde
acetic acid
NaBH3CN
———————
MeOH
Step 3

(i-7)

Step 1: DiI-OtBu HCl salt (388 mg, 0.982 mmol), (1R, 3S,4S)-2-(t-butoxycarbonyl)-2-azabicyclo[2.2.1]heptane-3-carboxylic acid (287 mg, 1.19 mmol), HATU (411 mg, 1.08 mmol) and DIEA (0.42 ml, 2.38 mmol) and DMF (5 ml) were combined and stirred at rt for 30 min. The reaction mixture was diluted with water (10 ml) and purified by RP-C18 ISCO to give (3R,4S,5S)-t-butyl 4-((S)-N,3-dimethyl-2-((1R,3S,4S)-2-methyl-2-azabicyclo[2.2.1]heptane-3-carboxamido)butanamido)-3-methoxy-5-methylheptanoate. MS (m+1)=582.5, HPLC Peak RT=1.542 min Step 2: The product obtained in step 1 (540 mg, 0.93 mmol) in 4M HCl in 1,4-dioxane (10 ml) was stirred at rt overnight. The reaction mixture was concentrated in to give (3R,4S,5S)-4-((S)-N,3-dimethyl-2-((1R,3S,4S)-2-methyl-2-azabicyclo[2.2.1]heptane-3-carboxamido)butanamido)-3-methoxy-5-methylheptanoic acid. MS (m+1)=426.2, HPLC Peak RT=0.736 min Step 3: The product obtained in step 2 (430 mg, 0.93 mmol), 37% formaldehyde solution (0.38 ml, 4.7 mmol), acetic acid (0.27 ml, 4.65 mmol), NaBH3CN (585 mg, 9.31 mmol) and MeOH (10 ml) were combined and stirred at rt for 30 min and then concentrated. The residue was purified by RP-C18 ISCO to give 450 mg of (3R,4S,5S)-4-((S)-N,3-dimethyl-2-((1R,3S,4S)-2-methyl-2-azabicyclo[2.2.1]heptane-3-carboxamido)butanamido)-3-methoxy-5-methylheptanoic acid as a TFA salt. The TFA salt was treated with 10 ml of 12N HCl solution and concentrated twice to give (3R,4S,5S)-4-((S)-N,3-dimethyl-2-((1R,3S,4S)-2-methyl-2-azabicyclo[2.2.1]heptane-3-carboxamido)butanamido)-3-methoxy-5-methylheptanoic acid HCl salt (i-7). MS (m+1)=440.2, HPLC Peak RT=0.754 min Synthesis of Boc-Dap-OMe: ((S)-tert-butyl 2-((1R, 2R)-1,3-dimethoxy-2-methyl-3-oxopropyl)pyrrolidine-1-carboxylate) (i-8)

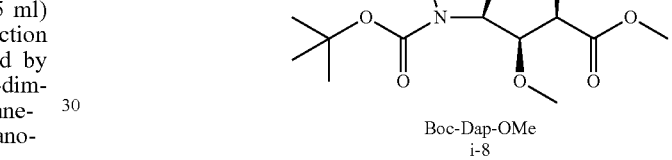

Boc-Dap-OMe
i-8

Boc-Dap-OH (Small Molecules Inc., 3.11 g, 10.8 mmol), K2CO3 (2.99 g, 21.6 mmol), iodomethane (2.95 g) and acetone (55 mL) were combined. The reaction was stirred at 20° C. for 2 h. An additional methyliodide (2.28 g) was added to the reaction and the reaction was stirred at 40° C. for 3 h. The reaction mixture was concentrated. The residue was partitioned between 200 mL EtOAc and 100 mL H2O. The organic layer was separated, washed with 50 mL saturated aq NaCl, dryed over MgSO4, filtered and concentrated, affording Boc-Dap-OMe (i-8) as a yellow oil. MS (ESI+) m/z calc 324.2, found 324.2 (M+23). Retention time 1.245 min.

Synthesis of Dap-OMe: ((2R,3R)-methyl 3-methoxy-2-methyl-3-((S)-pyrrolidin-2-yl)propanoate) (i-9)

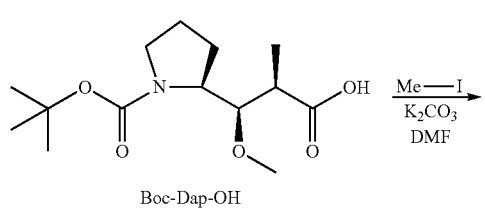

Boc-Dap-OH

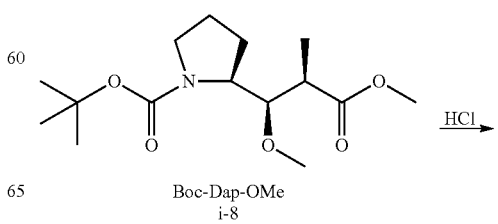

Boc-Dap-OMe
i-8

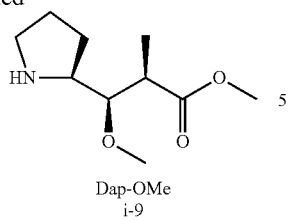

Dap-OMe
i-9

Boc-Dap-OMe (3.107 g, 10.3 mmol) was combined with HCl in diethyl ether (2 M, 10 mL) and concentrated. This operation was repeated. The reaction was complete after the 7th treatment. HCl salt of Dap-OMe (i-9) was obtained as a white solid after being concentrated. MS (ESI+) m/z calc 202.1, found 202.2 (M+1). Retention time 0.486 min. $^1$H NMR (400 MHz, CDCl$_3$): δ 4.065-4.041 (m, 1H), 3.732 (br.s, 1H), 3.706 (s, 3H), 3.615 (s, 3H), 3.368 (br.s, 1H), 3.314 (br.s, 1H), 2.795 (q, 1H, J=6.8 Hz), 2.085-1.900 (m, 4H), 1.287 (d, 3H, J=7.2 Hz).

Synthesis of (R)-2,4-dihydroxy-3,3-dimethyl-N-(3-oxo-3-((2-oxopropyl)amino)propyl)butanamide (i-10)

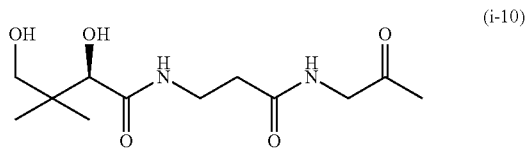 [SMILES: CC(=O)CNC(=O)CCNC(=O)[C@H](O)C(C)(C)CO]

(i-10)

Step 1: Panthotheic acid (50 mg, 0.23 mmol) was dissolved in DMF (5 mL) and diphenylphosphoryl azide (98 μL, 0.46 mmol) and 2-(2-methyl-1,3-dioxolan-2-yl)ethanamine (40 mg, 0.34 mmol) were added. The reaction mixture was cooled to 0° C. and triethylamine (79 μL, 0.57 mmol) was added. The reaction mixture was stirred at 0° C. for 10 min, and then stirred at rt for 24 h. EtOAc (50 mL) was added and washed with 0.1N HCl solution (20 mL), 0.1N NaOH solution (20 mL), brine (20 mL), dried over Na$_2$SO$_4$ and filtered. The filtrate was concentrated in vacuo and the residue was purified by HPLC and lyopylized to give (R)-2,4-dihydroxy-3,3-dimethyl-N-(3-(((2-methyl-1,3-dioxolan-2-yl)methyl)amino)-3-oxopropyl)butanamide. MS (m+1)=319.2, HPLC Peak RT=0.466 min Step 2: (R)-2,4-dihydroxy-3,3-dimethyl-N-(3-(((2-methyl-1,3-dioxolan-2-yl)methyl)amino)-3-oxopropyl)butanamide (46 mg, 0.14 mmol) was dissolved in THF (5 mL) and 3N HCl solution (3 mL) and stirred at rt for 4 h. After cooling to 0° C., the reaction mixture was neutralized with 1N NaOH solution and concentrated half volume in vacuo. The reaction mixture was purified by ISCO RP-C18 and lyophilized to give (R)-2,4-dihydroxy-3,3-dimethyl-N-(3-oxo-3-((2-oxopropyl)amino)propyl)butanamide (i-10). MS (m+1)=275.2, HPLC Peak RT=0.337 min, 1H-NMR (MeOD, 400 MHz) δ 3.99 (s, 2H), 3.84 (s, 1H), 3.42~4.47 (m, 2H), 3.42 (d, 1H, J=11.2 Hz), 3.34 (d, 1H, J=11.2 Hz), 2.45 (t, 2H, J=6.8 Hz), 2.10 (s, 3H), 0.87 (s, 6H).

Synthesis of (R)-N-(3-((2-azidoethyl)amino)-3-oxopropyl)-2,4-dihydroxy-3,3-dimethylbutanamide (i-11)

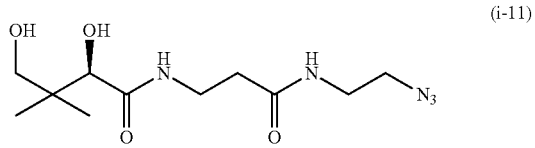 [SMILES: CC(C)(CO)[C@@H](O)C(=O)NCCC(=O)NCCN=[N+]=[N-]]

(i-11)

Panthotheic acid (50 mg, 0.23 mmol) was dissolved in DMF (5 mL) and diphenylphosphoryl azide (98 μL, 0.46 mmol) and 2-azidoethanamine (30 mg, 0.34 mmol) were added. The reaction mixture was cooled to 0° C. and triethylamine (79 μL, 0.57 mmol) was added. The reaction mixture was stirred at 0° C. for 10 min, and then stirred at rt for 24 h. EtOAc (50 mL) was added and washed with 0.1N HCl solution (20 mL), 0.1N NaOH solution (20 mL), brine (20 mL), dried over Na$_2$SO$_4$ and filtered. The filtrate was concentrated in vacuo and the residue was purified by HPLC and lyopylized to give (R)-N-(3-((2-azidoethyl)amino)-3-oxopropyl)-2,4-dihydroxy-3,3-dimethylbutanamide (i-11). MS (m+1)=288.2, HPLC Peak RT=0.504 min, 1H-NMR (MeOD, 400 MHz) δ 3.84 (s, 1H), 3.41~4.47 (m, 3H), 3.31~3.35 (m, 5H), 2.40 (t, 2H, J=6.8 Hz), 0.87 (s, 6H).

Synthesis of (R)-2,4-dihydroxy-3,3-dimethyl-N-(3-oxo-3-((3-oxobutyl)amino)propyl)butanamide (i-12)

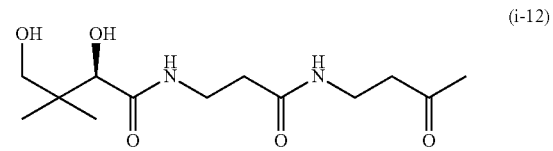 [SMILES: CC(=O)CCNC(=O)CCNC(=O)[C@H](O)C(C)(C)CO]

(i-12)

Step 1: Panthotheic acid hemicalcium salt (100 mg, 0.390 mmol) was dissolved in CH$_3$CN (10 mL) and exchanged to panthotheic acid using sulfuric acid resin. Panthotheic acid (10 mg, 0.046 mmol) was dissolved in DMF (2 mL) and diphenylphosphoryl azide (20 μL, 0.091 mmol) and 2-(2-methyl-1,3-dioxolan-2-yl)ethanamine (7 mg, 0.005 mmol) were added. The reaction mixture was cooled to 0° C. and triethylamine (16 μL, 0.114 mmol) was added. The reaction mixture was stirred at 0° C. for 10 min, and then stirred at rt for 24 h. EtOAc (50 mL) was added and washed with 0.1N HCl solution (20 mL), 0.1N NaOH solution (20 mL), brine (20 mL), dried over Na$_2$SO$_4$ and filtered. The filtrate was concentrated in vacuo and the residue was purified by HPLC and lyopylized to give (R)-2,4-dihydroxy-3,3-dimethyl-N-(3-((2-(2-methyl-1,3-dioxolan-2-yl)ethyl)amino)-3-oxopropyl)butanamide. MS (m+1)=333.2, HPLC Peak RT=0.512 min Step 2: (R)-2,4-dihydroxy-3,3-dimethyl-N-(3-((2-(2-methyl-1,3-dioxolan-2-yl)ethyl)amino)-3-oxopropyl)butanamide (6 mg, 0.018 mmol) was dissolved in THF (2 mL) and 3N HCl solution (1 mL) and stirred at rt for 4 h. After cooling to 0° C., the reaction mixture was neutralized with 1N NaOH solution and concentrated half volume in vacuo. The reaction mixture was purified by ISCO RP-C18 and lyophilized to give (R)-2,4-dihydroxy-3,3-dimethyl-N-(3-oxo-3-((3-0xobutyl)amino)propyl) butanamide (i-12). MS (m+1)=289.2, HPLC Peak RT=0.362 min, 1H-NMR (MeOD, 400 MHz) δ 3.83 (s, 1H), 3.37~4.45 (m, 3H), 3.34 (d, 2H, J=7.2 Hz), 3.32 (d, 1H, J=3.2 Hz), 2.65 (t, 2H, J=6.4 Hz), 2.34 (t, 2H, J=6.8 Hz), 2.10 (s, 3H), 0.87 (s, 6H).

Synthesis of 2,4-dihydroxy-3,3-dimethyl-N-(3-oxobutyl)butanamide (i-13)

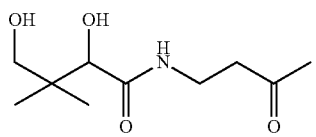

(i-13)

Step 1: Lithium aluminum hydride (583 mg, 15 mmol) was dissolved in THF (100 mL) and cooled to 0° C. A solution of (±)-pantolactone (1 g, 8 mmol) in THF (50 mL) was added at 0° C. and stirred at rt for 4 h. To the reaction mixture was added anhydrous sodium sulfate slowly, followed by EtOAc (50 mL). The reaction mixture was filtered over a short celite pad and the filtrate was concentrated. The residue was purified by ISCO (5% to 20% of MeOH in $CH_2Cl_2$) to give 3,3-dimethylbutane-1,2,4-triol. 1H-NMR ($CDCl_3$, 400 MHz) δ 3.71~3.74 (m, 1H), 3.65 (dd, 1H, J=4.8 and 7.6 Hz), 3.57 (dd, 1H, J=2.4 and 4.8 Hz), 3.54 (d, 1H, J=7.2 Hz), 3.48 (d, 1H, J=7.2 Hz), 0.95 (s, 3H), 0.93 (s, 3H).

Step 2: 3,3-dimethylbutane-1,2,4-triol (570 mg, 4 mmol) and 1-(dimethoxymethyl)-4-methoxybenzene (1.16 g, 6 mmol) were dissolved in $CH_2Cl_2$ (50 mL) and (7,7-dimethyl-2-oxobicyclo[2.2.1]heptan -1-yl) methanesulfonic acid (99 mg, 0.4 mmol) was added. The reaction mixture was stirred at rt for 2 h and triethylamine (0.29 mL, 2 mmol) was added. After concentration, the residue was purified by ISCO (0% to 30% of EtOAc in n-Hexane) to give 2-(4-methoxyphenyl)-5,5-dimethyl-1,3-dioxan-4-yl)methanol. 1H-NMR ($CDCl_3$, 400 MHz) δ 7.44 (d, 2H, J=6.0 Hz), 6.91 (d, 2H, J=6.0 Hz), 5.47 (s, 1H), 3.90 (s, 1H), 3.81 (s, 3H), 3.59~3.70 (m, 5H), 1.14 (s, 3H), 0.84 (s, 3H).

Step 3: DMSO (0.27 mL, 4 mmol) was dissolved in anhydrous $CH_2Cl_2$ (20 mL) and oxalyl chloride (0.25 mL, 3 mmol) was added at −78° C. The reaction mixture was stirred for 15 min at −78° C. and a solution of 2-(4-methoxyphenyl)-5,5-dimethyl-1,3-dioxan-4-yl)methanol (485 mg, 2 mmol) in anhydrous $CH_2Cl_2$ (1 mL) was added slowly. The reaction mixture was stirred at −78° C. for 30 min and triethylamine (1.34 mL, 10 mmol) was added. The reaction mixture was allowed to warm up to rt and stirred for 1 h. The reaction mixture was partitioned between water (50 mL) and $CH_2Cl_2$ (100 mL), and the organic layer was washed with sat. $NaHCO_3$ (50 mL) and brine (50 mL), dried over $Na_2SO_4$, filtered and concentrated. The residue was purified by ISCO (20% to 50% of EtOAc in n-Hexane) to give 2-(4-methoxyphenyl)-5,5-dimethyl-1,3-dioxane-4-carbaldehyde. MS (m+1)=251.2, HPLC Peak RT=1.105 min.

Step 4: 2-(4-methoxyphenyl)-5,5-dimethyl-1,3-dioxane-4-carbaldehyde (289 mg, 1 mmol) was dissolved in acetone/$CH_2Cl_2$ (3:1, 20 mL) and freshly prepared solution of $NaH_2PO_4 \cdot H_2O$ (1593 mg, 12 mmol) and $NaCl_2O$ (528 mg, 6 mmol) in water (5 mL) was added at rt. The reaction mixture was stirred for 30 min at rt and concentrated. The residue was purified by ISCO (C18) to give 2-(4-methoxyphenyl)-5,5-dimethyl-1,3-dioxane-4-carboxylic acid. MS (m+1)=267.2, HPLC Peak RT=0.957 min.

Step 5: 2-(4-methoxyphenyl)-5,5-dimethyl-1,3-dioxane-4-carboxylic acid (40 mg, 0.2 mmol) was dissolved in DMF (3 mL) and HATU (39 mg, 0.2 mmol) and DIEA (0.05 mL, 0.3 mmol) were added. The reaction mixture was stirred for 10 min at rt and 2-(2-methyl-1,3-dioxolan-2-yl)ethanamine (40 mg, 0.3 mmol) was added. The reaction mixture was stirred at rt for 1 h and purified by preparative HPLC to give 2-(4-methoxyphenyl)-5,5-dimethyl-N-(2-(2-methyl-1,3-dioxolan-2-yl)ethyl)-1,3-dioxane-4-carboxamide. MS (m+1)=380.2, HPLC Peak RT=1.102 min, 1H-NMR ($CDCl_3$, 400 MHz) δ 7.44 (d, 2H, J=5.6 Hz), 7.33 (bs, 1H), 6.90 (d, 2H, J=5.2 Hz), 5.46 (s, 1H), 4.08 (s, 1H), 3.82~3.88 (m, 2H), 3.81 (s, 3H), 3.75 (m, 1H), 3.68 (dd, 2H, J=7.6 and 16.0 Hz), 3.38 (m, 2H), 1.86 (m, 4H), 1.31 (s, 3H), 1.11 (s, 3H), 1.09 (s, 3H).

Step 5: 2-(4-methoxyphenyl)-5,5-dimethyl-N-(2-(2-methyl-1,3-dioxolan-2-yl)ethyl)-1,3-dioxane-4-carboxamide (10 mg, 0.03 mmol) was dissolved in 3M HCl in MeOH (1 mL) and water (0.1 mL) was added. The reaction mixture was concentrated in vacuo and purified by ISCO (C18) to give 2,4-dihydroxy-3,3-dimethyl-N-(3-oxobutyl)butanamide (i-13). MS (m+1)=218.2, HPLC Peak RT=0.400 min, 1H-NMR (MeOD-$d_4$, 400 MHz) δ 3.84 (s, 1H), 3.31~3.44 (m, 4H), 2.70 (t, 2H, J=4.0 Hz), 2.12 (s, 3H), 0.88 (s, 3H).

Synthetic Procedure for Non-linked Peptides

EXAMPLE 1

(S)-Methyl 2-((2R,3R)-3-((S)-1-((3R,4S,5S)-4-((S)-2-((1R,3S,4S)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoate (1)

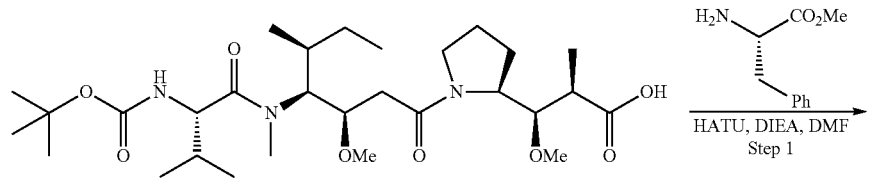

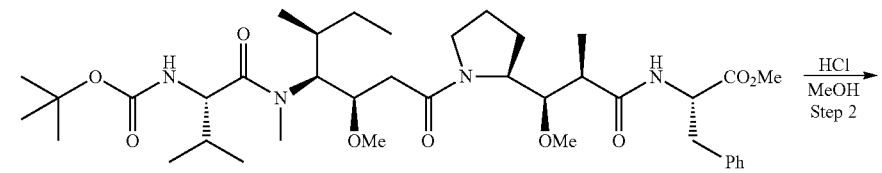

-continued

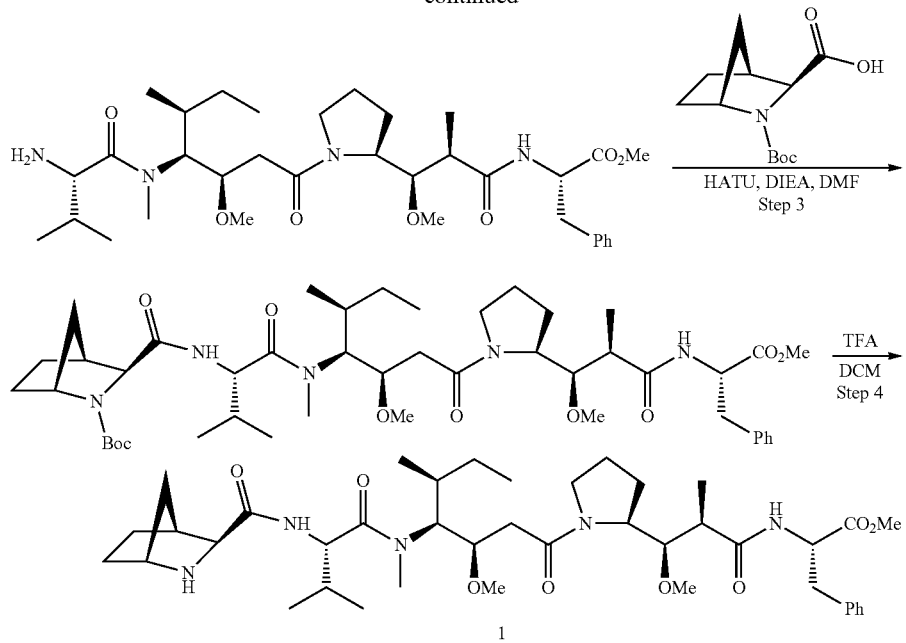

Step 1: To a solution of BocVal-Dil-Dap-OH (1.00 g, 1.75 mmol) in N,N-dimethylformamide (DMF, 20.0 mL) at 0° C. were added N,N-diisopropyl ethylamine (DIEA, 0.677 g, 5.25 mmol) and 1-[bis(dimethylamino)methylene]-1H-1,2,3-triazolo[4,5-b]pyridinium 3-oxid hexafluorophosphate (HATU) (0.731 g, 1.93 mmol). The resulting solution was then stirred for 5 minutes and added to a solution of L-phenylalanine methyl ester HCl salt (0.377 g, 1.75 mmol) and DIEA (0.226 g, 1.75 mmol) in DMF (5.0 mL) at 0° C. The reaction mixture was warmed to room temperature, stirred for an additional 30 minutes and then concentrated. The residue was purified by reverse phase HPLC using the ISCO system, C18 column, eluted with 20-90% acetonitrile-water to obtain BocVal-Dil-Dap-PheOMe: MS m/z 733.4 (M+1); retention time 1.47 minutes.

Step 2: To a solution of BocVal-Dil-Dap-PheOMe (0.683 g, 0.932 mmol) obtained in step 1 in methanol (20 mL) was added HCl (4N in 1,4-dioxane, 16 mL). The reaction mixture was stirred at room temperature for 7 hours and concentrated. The residue was dissolved in dioxane and lyophilized to obtain Val-Dil-Dap-PheOMe HCl salt: MS m/z 633.4 (M+1); retention time 0.96 minutes.

Step 3: (1R,3S,4S)-N-Boc-2-azabicyclo[2.2.1]heptane-3-carboxylic acid (12.6 mg, 0.052 mmol) was dissolved in DMF (1 mL) in a 15 ml round bottom flask. DIEA (12.3 mg, 0.095 mmol) and HATU (19 mg, 0.050 mmol) were added. The reaction mixture was stirred for 10 minutes and Val-Dil-Dap-PheOMe HCl salt (30 mg, 0.090 mmol) in DMF (1.0 mL) was added. The reaction mixture was stirred for 1 hour. LCMS analysis indicated the reaction was complete. The crude was purified by reverse phase HPLC using C18 column, eluted with 20-90% acetonitrile-H$_2$O containing 0.05% trifluoroacetic acid (TFA). The fractions containing the desired product were pooled and concentrated to obtain (1R,3S,4S)-tert-butyl 3-(((S)-1-(((3R,4S,5S)-3-methoxy-1-((S)-2-((1R,2R)-1-methoxy-3-(((S)-1-methoxy-1-oxo-3-phenylpropan-2-yl)amino)-2-methyl-3-oxopropyl)pyrrolidin-1-yl)-5-methyl-1-oxoheptan-4-yl)(methyl)amino)-3-methyl-1-oxobutan-2-yl)carbamoyl)-2-azabicyclo[2.2.1]heptane-2-carboxylate: MS m/z 856.6 (M+1); retention time 1.67 minutes.

Step 4: The product obtained in step 3 was dissolved in dichloromethane (DCM) (2.0 mL) and treated with TFA (0.5 mL). The reaction mixture was stirred at room temperature for 1 hour. LCMS analysis showed the reaction was complete. The reaction mixture was concentrated by rotary evaporator to give compound 1 as a TFA salt: MS m/z 756.6 (M+1); retention time 1.22 minutes.

EXAMPLE 2

(S)-2-((2R,3R)-3-((S)-1-((3R,4S,5S)-4-((S)-2-((1R,3S,4S)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (2)

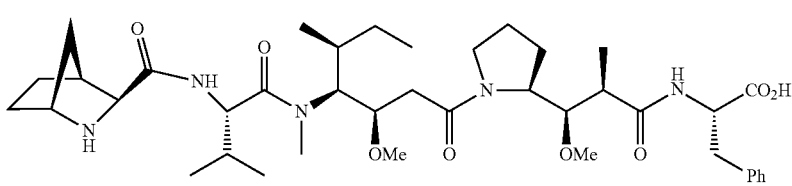

In a 25 mL round bottom flask were added (S)-methyl 2-((2R,3R)-3-((S)-1-((3R,4S,5S)-4-((S)-2-((1R,3S,4S)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoate TFA salt (1) (38.4 mg, 0.044 mmol), LiOHmonohydrate (50.0 mg, 1.19 mmol) and a solvent mixture of MeOH—H₂O (2:1, 4.0 mL). The mixture was stirred at room temperature for 60 hours. The LC-MS analysis indicated the reaction was complete. The reaction mixture was concentrated and purified by reverse phase HPLC, C18 column, eluted with acetonitrile-H₂O (10-70%) containing 0.05% TFA. The fractions containing the desired product were combined and concentrated to give compound 2 as a TFA salt, MS m/z 742.5 (M+1). Retention time 1.15 minutes.

EXAMPLE 3

(1R,3S,4S)-N-((S)-1-(((3R,4S,5S)-1-((S)-2-((1R,2R)-3-(((1S,2R)-1-Hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-azabicyclo[2.2.1]heptane-3-carboxamide (3)

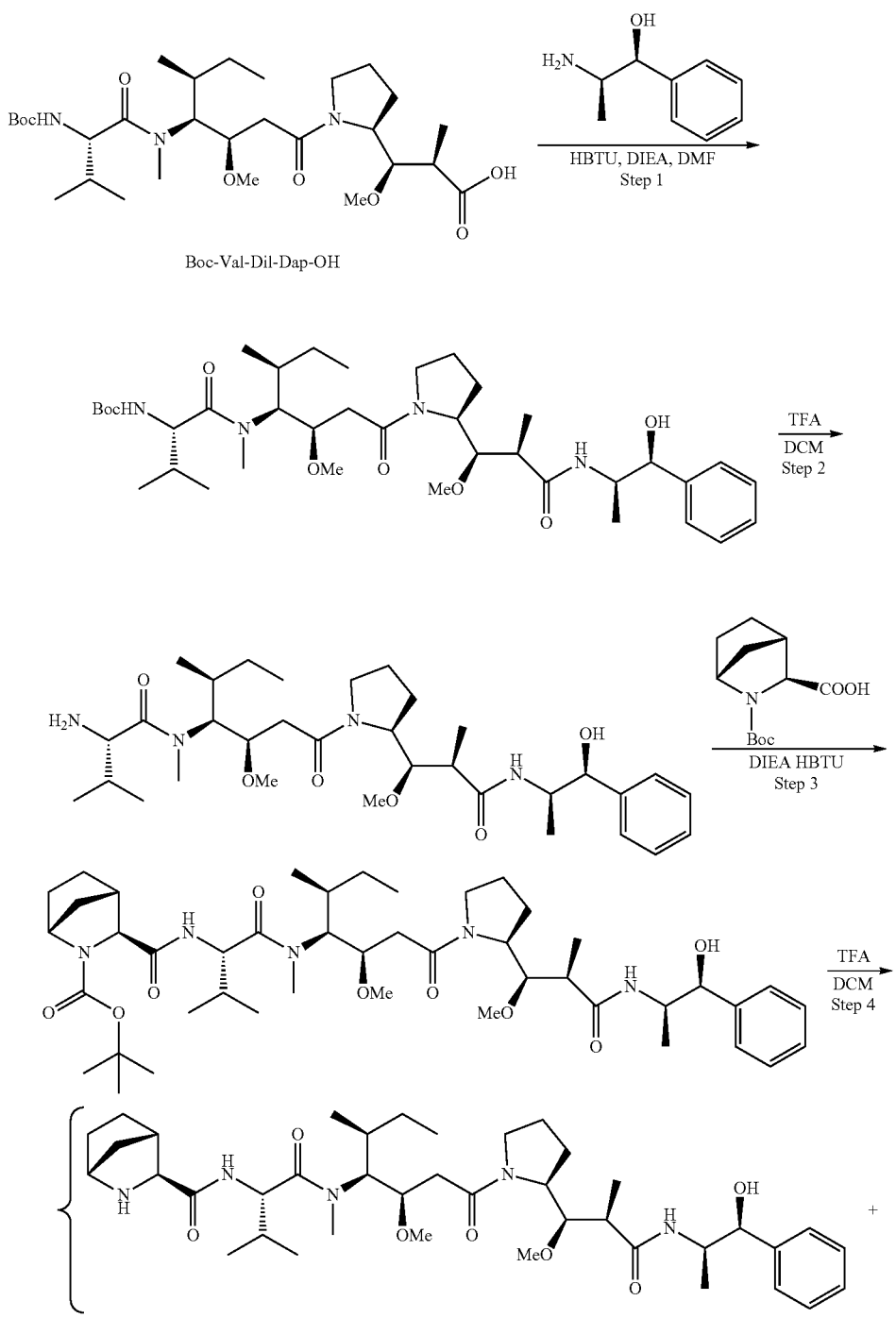

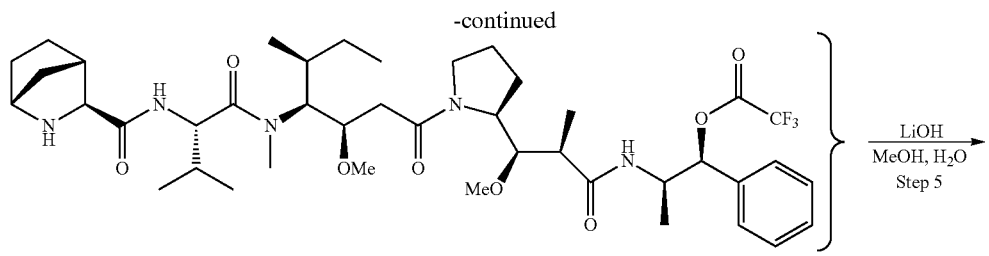

-continued

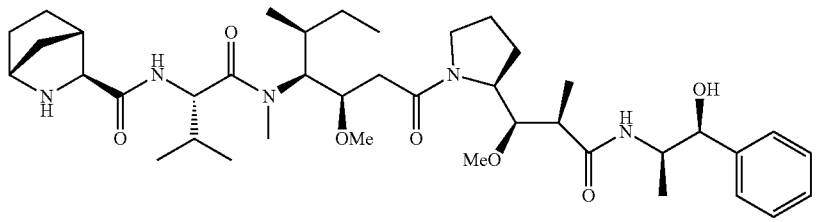

3

Step 1: To a solution of Boc-Val-Dil-Dap-OH (20.0 mg, 0.035 mmol) in DMF (1.0 mL) in a 15 mL round bottom flask was added DIEA (9.0 mg, 0.070 mmol), followed by N,N,N',N'-tetramethyl-O-(1H-benzotriazol-1-yl)uronium hexafluorophosphate (HBTU) (13.3 mg, 0.035 mmol). The reaction mixture was stirred for 10 minutes before (1S,2R)-2-amino-1-phenylpropan-1-ol (6.4 mg, 0.042 mmol) in DMF (1.0 mL) was added to the reaction mixture. The reaction was stirred for 1 hour. LCMS analysis indicated the reaction was complete. The crude was purified by reverse phase HPLC, C18 column, eluted with 20-70% acetonitrile-H$_2$O containing 0.05% TFA. The fractions containing the desired product were pooled and concentrated to obtain tert-butyl ((S)-1-(((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)carbamate, MS m/z 705.4 (M+1). Retention time 1.39 minutes.

Step 2: To a solution of tert-butyl ((S)-1-(((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)carbamate (24.7 mg, 0.035 mmol) in DCM (2.0 mL) was added TFA (1.0 mL). The reaction mixture was stirred at room temperature for 2 hours and concentrated to obtain a mixture of (S)-2-amino-N-((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethylbutanamide (MS m/z 605.4 (M+1) Retention time 0.96 minutes and the TFA ester thereof (MS m/z 701.4 (M+1)), Retention time 1.17 minutes. The mixture was used in the next step without further purification.

Step 3: To a solution of (1R,3S,4S)-2-(tert-butoxycarbonyl)-2-azabicyclo[2.2.1]heptane-3-carboxylic acid (8.4 mg, 0.035 mmol) in DMF (1.0 mL) were added DIEA (0.024 ml, 0.14 mmol) and HBTU (13.3 mg, 0.035 mmol). The reaction mixture was stirred for 10 minutes and added to a solution of the product mixture obtained in step 2 (25.2 mg, 0.035 mmol) (containing TFA ester) in DMF (0.5 mL). The reaction mixture was kept at room temperature for 18 hours and then the crude was purified by reverse phase HPLC, C18 column, eluted with 30-90% acetonitrile-H$_2$O, containing 0.05% TFA. The fractions containing the desired products were concentrated to obtain a mixture of (1R,3S,4S)-tert-butyl 3-(((S)-1-(((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)carbamoyl)-2-azabicyclo[2.2.1]heptane-2-carboxylate (MS m/z 828.5 (M+1)) Retention time 1.42 minutes and the TFA ester thereof (MS m/z 924.4 (M+1)) Retention time 1.61 minutes.

Step 4: To a solution of the mixture obtained in step 3 in DCM (1.5 mL) was added TFA (1.0 mL). The reaction mixture was stirred at room temperature for 1 hour and then concentrated to obtain a mixture of (1R,3S,4S)-N-((S)-1-(((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-azabicyclo[2.2.1]heptane-3-carboxamide (MS m/z 728.4 (M+1)), retention time 0.99 minutes and (1S,2R)-2-((2R,3R)-3-((S)-1-((3R,4S,5S)-4-((S)-2-((1R,3S,4S)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-1-phenylpropyl 2,2,2-trifluoroacetate (MS m/z 824.5 (M+1)), retention time 1.31 minutes. This mixture was used in the next step without further purification.

Step 5: To a solution of the mixture obtained in step 4 in MeOH—H$_2$O (1:1, 3.0 mL) was added LiOH (10.0 mg, 0.418 mmol). The reaction mixture was stirred at room temperature for 18 hours and then concentrated to a total volume of approximately 1 mL. The crude mixture was purified by reverse phase HPLC, C18 column, eluted with 20-35% acetonitrile-H$_2$O, containing 0.05% TFA. The fractions containing the desired product were pooled and concentrated to obtain compound 3, MS m/z 728.4 (M+1). Retention time 0.99 minutes.

EXAMPLE 4

(1R,3S,4S)-N-((S)-1-(((3R,4S,5S)-1-((S)-2-((1R,2R)-3-(((S)-N-1-(Methylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-azabicyclo[2.2.1]heptane-3-carboxamide (4)

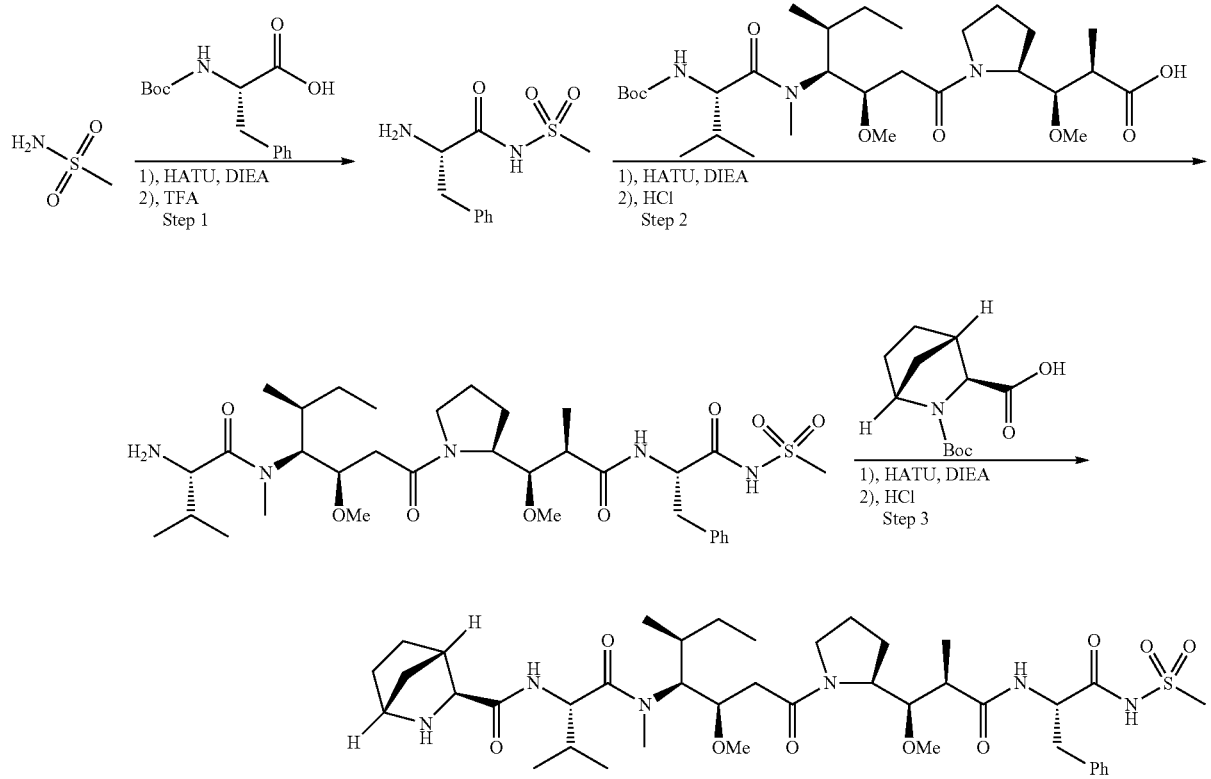

4

Step 1: (S)-2-((tert-butoxycarbonyl)amino)-3-phenylpropanoic acid (132.5 mg, 0.50 mmol) was dissolved in DMF (4 mL). DIEA (0.523 mL, 3.0 mmol) and HATU (475 mg, 1.25 mmol) were added. After 15 minutes, methanesulfonamide (143 mg) was added and The reaction mixture was stirred for 2 hours. LC/MS analysis indicated the completion of the reaction. The product was purified by Prep-HPLC, C18 column, eluted with 20-70% acetonitrile-H₂O containing 0.05% TFA. The fractions containing the desired product were pooled and lyophilized to obtain a white solid. MS m/z 243.1 (M+1). Retention time 1.023 minutes. The product was dissolved in DCM (2 mL). TFA (2 mL) was added and stirred for 1 hour at room temperature. LC/MS analysis indicated the reaction was completed. The deprotected product was purified by Prep-HPLC too, eluted with 10-40% acetonitrile-H₂O containing 0.05% TFA. The fractions containing the desired product were pooled and lyophilized to obtain a white solid. MS m/z 243.1 (M+1). Retention time 0.403 minutes. NMR (400 MHz, CD₃OD): δ 7.41-7.30 (m, 5H), 4.10-4.06 (m, 1H), 3.32-3.25 (m, 1H), 3.19 (s, 3H), 3.12-3.07 (m, 1H).

Step 2: Boc-Val-Dil-Dap (65.5 mg, 0.115 mmol) was dissolved in DMF (2 mL). DIEA (59.2 mg, 80 uL) and HATU (27.7 mg, 0.099 mmol) were added. After 10 minutes, (S)-2-amino-N-(methylsulfonyl)-3-phenylpropanamide (18.5 mg, 0.076 mmol) was added and The reaction mixture was stirred for 1 hour at room temperature. LC/MS analysis indicated the completion of the reaction. The product was purified by Prep-HPLC, C18 column, eluted with 10-90% acetonitrile-H₂O containing 0.05% TFA. The fractions containing the desired product were pooled and lyophilized to obtain a white solid. MS m/z 796.4 (M+1). Retention time 1.388 minutes. The product was dissolved in HCl in MeOH (3M, 3 mL). The solvent was removed slowly. LC/MS analysis indicated the completion of the reaction. MS m/z 696.3 (M+1). Retention time 1.046 minutes.

Step 3: (1R,3S,4S)-2-(tert-butoxycarbonyl)-2-azabicyclo[2.2.1]heptane-3-carboxylic acid (14.23 mg, 0.059 mmol) was dissolved in DMF (2 mL). DIEA (22.9 mg, 0.177 mmol) and HATU (20.19 mg, 0.053 mmol) were added. After 10 minutes, the product from the previous step (21.6 mg, 0.029 mmol) was added and The reaction mixture was stirred for 2 hours at room temperature. LC/MS analysis indicated the completion of the reaction. The product was purified by Prep-HPLC, C18 column, eluted with 10-90% acetonitrile-H₂O containing 0.05% TFA. The The fractions containing the desired product were pooled and lyophilized to obtain a white solid. MS m/z 919.5 (M+1). Retention time 1.370 minutes. The product was dissolved in HCl in MeOH (3M, 3 mL). The solvent was removed slowly. LC/MS analysis indicated the completion of the reaction. MS m/z 819.5 (M+1). Retention time 1.096 minutes.

EXAMPLE 5

(1R,3S,4S)-N-((S)-1-(((3R,4S,5S)-1-((S)-2-((1R,2R)-3-(((S)-N-1-(Methylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (5)

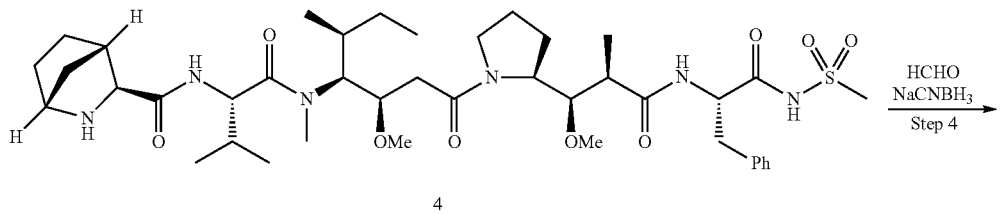

Compound 4 (5 mg, 0.00584 mmol) was dissolved in MeOH (2.0 mL). Paraformaldehyde (5.97 mg, 0.199 mmol) and acetic acid (6.0 uL) were added. Sodium cyanoborohydride (12.5 mg, 0.199 mmol) was added and the reaction mixture was heated to 50° C. and stirred for 1 hour. LC/MS analysis indicated the completion of the reaction. The product was purified by Prep-HPLC, C18 column, eluted with 10-90% acetonitrile-H$_2$O containing 0.05% TFA. The fractions containing the desired product were pooled and lyophilized to obtain a white solid. MS m/z 833.5 (M+1). Retention time 0.983 minutes.

EXAMPLE 6

(1R,3S,4S)-N-((S)-1-(((3R,4S,5S)-3-methoxy-1-((S)-2-((1R,2R)-1-Methoxy-2-methyl-3-oxo-3-(((S)-2-phenyl-1-(1H-tetrazol-5-yl)ethyl)amino)propyl)pyrrolidin-1-yl)-5-methyl-1-oxoheptan-4-yl)(methyl)amino)-3-methyl-1-oxobutan-2-yl)-2-azabicyclo[2.2.1]heptane-3-carboxamide (6)

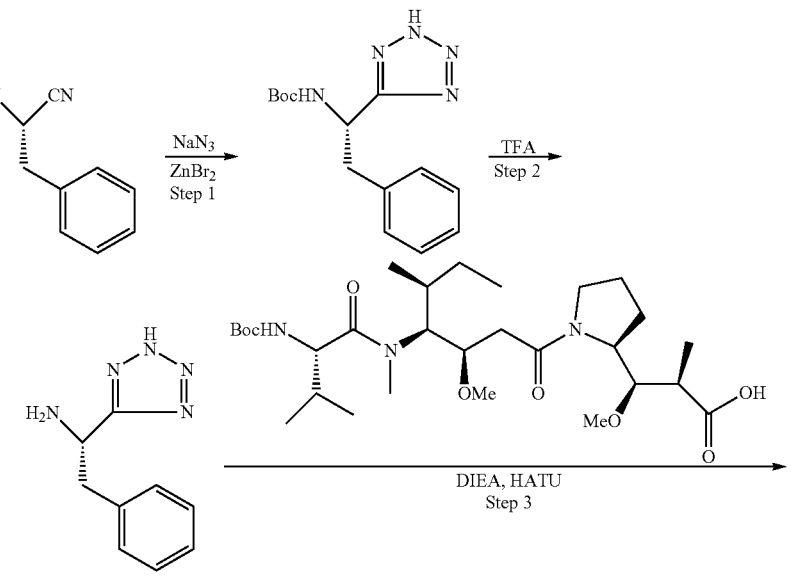

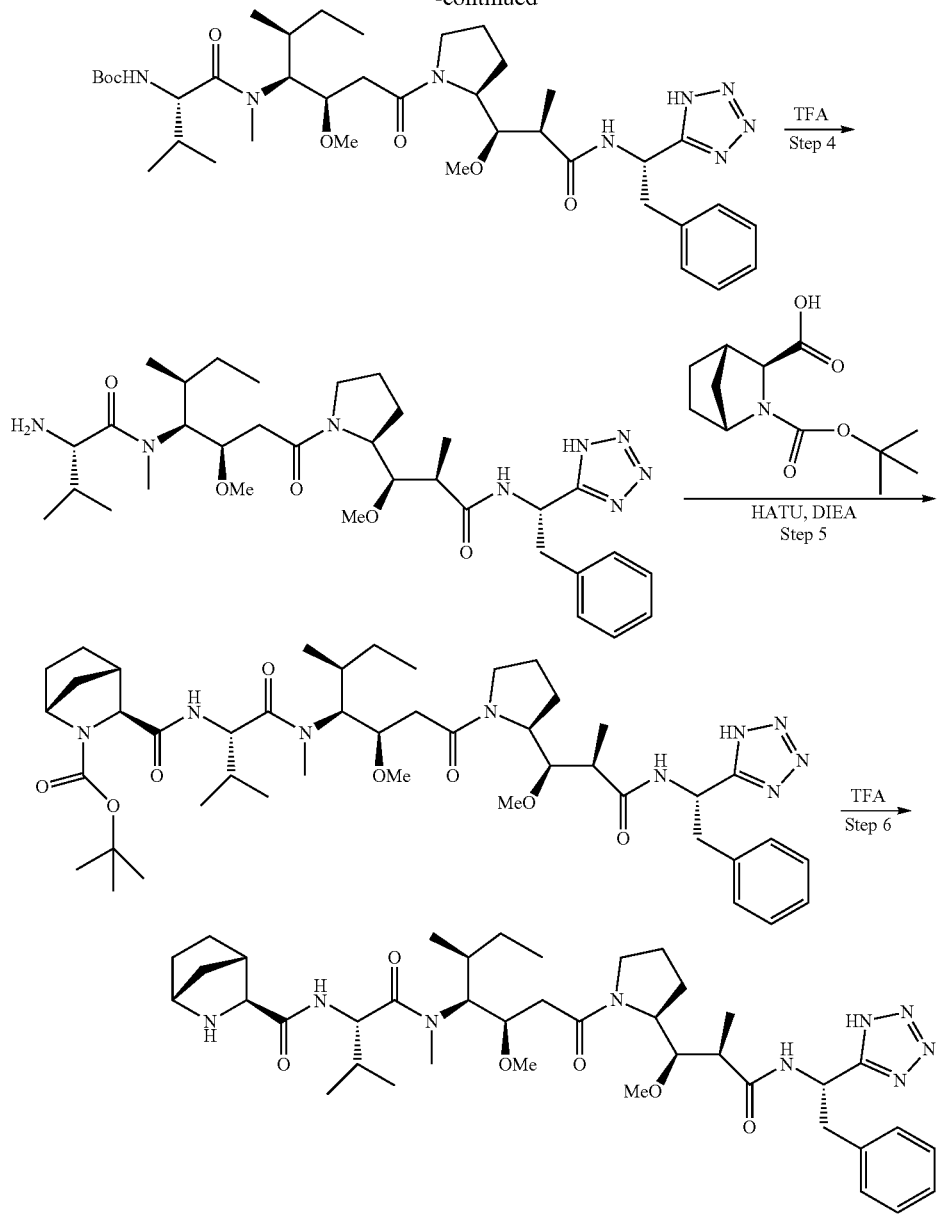

Step 1: N-Boc-amino nitrile (0.5 g, 2.03 mmol), sodium azide (0.264 g, 4.06 mmol) and zinc bromide (0.229 g, 1.02 mmol) were dissolved in a mixture of 2-propanol-water solvent mixture (1:1, 60 ml) and The reaction mixture was stirred at reflux for 16 hours. After completion of the reaction, 5 ml of 10% citric acid and 30 ml ethyl acetate were added and stirring was continued until no solid remained. The aqueous layer was extracted twice with ethyl acetate. The combined organic layer was washed with water and dried over anhydrous $Na_2SO_4$. The solvent was removed and the residue was purified by silica gel column, eluted with 10% methanol in DCM. Fractions containing the desired product were concentrated, re-dissolved in ethyl acetate, washed with brine, dried and concentrated to give (S)-tert-butyl (2-phenyl-1-(2H-tetrazol-5-yl)ethyl)carbamate MS m/z 290.2 (M+1). $^1$H NMR (400 MHz, $CDCl_3$) δ 7.40-7.24 (m, 3H), 7.22-7.12 (m, 2H), 5.22-5.02 (m, 2H), 3.49-3.24 (m, 2H), 1.40 (s, 9H).

Step 2: In a 15 ml round bottom flask was added (S)-tert-butyl (2-phenyl-1-(2H-tetrazol-5-yl)ethyl)carbamate (30 mg, 0.104 mmol), TFA (2 ml) and DCM (4 ml) to give a clear solution which was stirred at room temperature for 1 hour. LCMS showed the Boc group was cleaved. The solution was concentrated to obtain crude (S)-2-phenyl-1-(2H-tetrazol-5-yl)ethanamine as TFA salt (M+1 190.2), which was used without further purification in the next step.

Step 3: In a 15 ml round bottom flask was added Boc-Val-Dil-Dap-OH (59.3 mg, 0.104 mmol) and DIEA (0.072 ml, 0.415 mmol) in DMF (2 ml) give a clear solution. HATU (43.4 mg, 0.114 mmol) was added and the reaction mixture was then stirred for 5 minutes and then (S)-2-phenyl-1-(2H-tetrazol-5-yl)ethanamine TFA salt obtained in step 2 (0.104 mmol) was added. The solution was stirred at room temperature for 72 hours. The crude was purified by reverse phase HPLC, C18 column, eluted with 10-70% acetonitrile-H₂O, containing 0.05% TFA. Fractions containing desired product were concentrated to obtain tert-butyl ((S)-1-(((3R,4S,5S)-3-methoxy-1-((S)-2-((1R,2R)-1-methoxy-2-methyl-3-oxo-3-(((S)-2-phenyl-1-(1H-tetrazol-5-yl)ethyl)amino)propyl)pyrrolidin-1-yl)-5-methyl-1-oxoheptan-4-yl)(methyl)amino)-3-methyl-1-oxobutan-2-yl)carbamate MS m/z 743.5 (M+1). Retention time 1.325 minutes.

Step 4: In a 15 ml round bottom flask was added tert-butyl ((S)-1-(((3R,4S,5S)-3-methoxy-1-((S)-2-((1R,2R)-1-methoxy-2-methyl-3-oxo-3-(((S)-2-phenyl-1-(1H-tetrazol-5-yl)ethyl)amino)propyl)pyrrolidin-1-yl)-5-methyl-1-oxoheptan-4-yl)(methyl)amino)-3-methyl-1-oxobutan-2-yl) carbamate (46 mg, 0.056 mmol), TFA (2 ml) and DCM (4 ml) to give a clear solution which was stirred at room temperature for 1 hour. LCMS showed the Boc group was cleaved. The solution was concentrated to obtain crude (S)-2-amino-N-((3R,4S,5S)-3-methoxy-1-((S)-2-((1R,2R)-1-methoxy-2-methyl-3-oxo-3-(((S)-2-phenyl-1-(1H-tetrazol-5-yl)ethyl)amino)propyl)pyrrolidin-1-yl)-5-methyl-1-oxoheptan-4-yl)-N,3-dimethylbutanamide TFA salt. MS m/z 643.5 (M+1). Retention time 0.947 minutes, which was used in the next step without further purification.

Step 5: To a solution of (1R,3S,4S)-2-(tert-butoxycarbonyl)-2-azabicyclo[2.2.1]heptane-3-carboxylic acid (7.6 mg, 0.032 mmol) in DMF (1 ml) was added DIEA (0.014 ml, 0.079 mmol) and HATU (12 mg, 0.032 mmol), which was then added to a solution of (S)-2-amino-N-((3R,4S,5S)-3-methoxy-1-((S)-2-((1R,2R)-1-methoxy-2-methyl-3-oxo-3-(((S)-2-phenyl-1-(1H-tetrazol-5-yl)ethyl)amino)propyl)pyrrolidin-1-yl)-5-methyl-1-oxoheptan-4-yl)-N,3-dimethylbutanamide TFA salt (20 mg, 0.026 mmol). The reaction mixture was stirred at room temperature for 2 hours and then the crude was purified by reverse phase HPLC, C18 column, eluted with 30-70% acetonitrile-H₂O, containing 0.05% TFA. The fractions containing desired product were concentrated to obtain (1R,3S,4S)-tert-butyl 3-(((S)-1-(((3R,4S,5S)-3-methoxy-1-((S)-2-((1R,2R)-1-methoxy-2-methyl-3-oxo-3-(((S)-2-phenyl-1-(1H-tetrazol-5-yl)ethyl)amino)propyl)pyrrolidin-1-yl)-5-methyl-1-oxoheptan-4-yl)(methyl)amino)-3-methyl-1-oxobutan-2-yl)carbamoyl)-2-azabicyclo[2.2.1]heptane-2-carboxylate as TFA salt MS m/z 866.6 (M+1). Retention time 1.407 minutes.

Step 6: To a solution of (1R,3S,4S)-tert-butyl 3-(((S)-1-(((3R,4S,5S)-3-methoxy-1-((S)-2-((1R,2R)-1-methoxy-2-methyl-3-oxo-3-(((S)-2-phenyl-1-(1H-tetrazol-5-yl)ethyl)amino)propyl)pyrrolidin-1-yl)-5-methyl-1-oxoheptan-4-yl)(methyl)amino)-3-methyl-1-oxobutan-2-yl)carbamoyl)-2-azabicyclo[2.2.1]heptane-2-carboxylate TFA salt (10.2 mg, 0.012 mmol) in DCM (2 ml) was added TFA (1 ml). The reaction mixture was stirred at room temperature for 1 hour and then concentrated to obtain (1R,3S,4S)-N-((S)-1-(((3R,4S,5S)-3-methoxy-1-((S)-2-((1R,2R)-1-methoxy-2-methyl-3-oxo-3-(((S)-2-phenyl-1-(1H-tetrazol-5-yl)ethyl)amino)propyl)pyrrolidin-1-yl)-5-methyl-1-oxoheptan-4-yl)(methyl)amino)-3-methyl-1-oxobutan-2-yl)-2-azabicyclo[2.2.1]heptane-3-carboxamide (6) as TFA salt. MS m/z 766.6 (M+1). Retention time 0.985 minutes.

EXAMPLE 7

((R)-1-((2R,3R)-3-((S)-1-((3R,4S,5S)-4-((S)-2-((1R,3S,4S)-2-Azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-2-phenylethyl)phosphonic acid. (7)

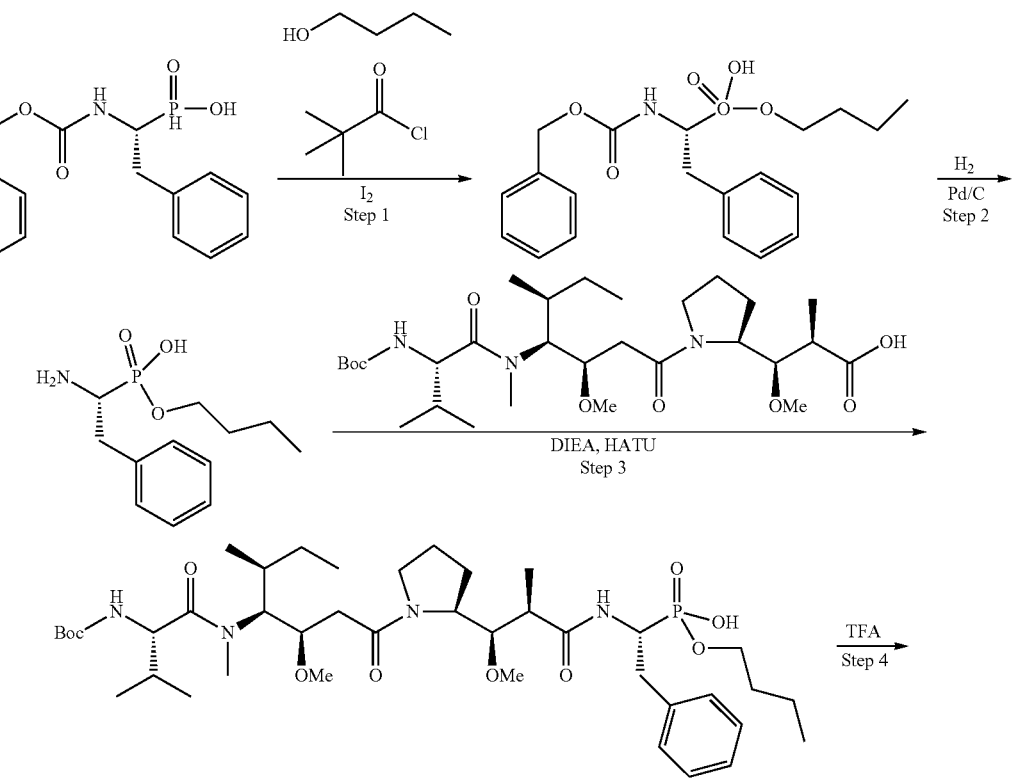

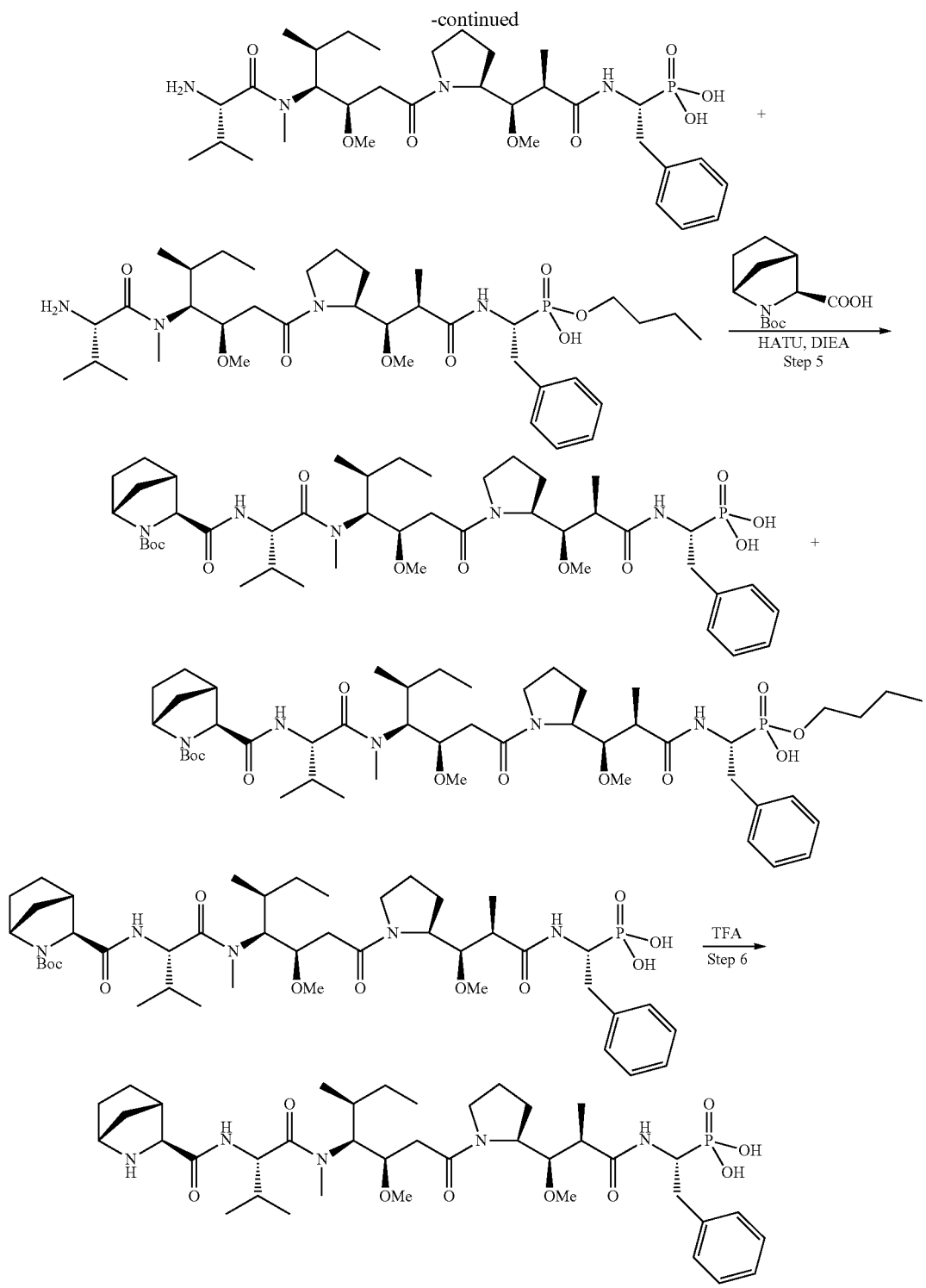

Step 1: ((R)-1-(((Benzyloxy)carbonyl)amino)-2-phenyl-ethyl)phosphinic acid (100 mg, 0.313 mmol), (synthesized by following the procedure described in J. Chem. Soc. Perkin Trans. I 1984, 2845) was dissolved in pyridine (5 ml) and n-BuOH (35 mg, 0.46 mmol) was added, followed by pivaloyl chloride (70 mg, 0.58 mmol). LCMS indicated the reaction was incomplete, therefore three other portions of n-BuOH and pivaloyl chloride were added until all of the phosphinic acid was consumed. Then a solution of iodine (160 mg, 0.630 mmol) in 2 ml pyridine-$H_2O$ (10% water) was added and the reaction misture was stirred for 20 minutes. LCMS indicated that the reaction was complete. Pyridine was removed by vacuum. Thiosulfate aqueous solution was added and the reaction mixture was extracted with EtOAc. EtOAc layer was then dried, concentrated and purified with ISCO (5.5 g C18 column), eluted with 10%-60% acetonitrile in water with 0.5% TFA to obtain benzyl ((1R)-1-(butoxy(hydroxy)phosphoryl)-2-phenylethyl)carbamate as white solid. MS m/z 392.1 (M+1). Retention time 1.179 minutes. 1H NMR (400 MHz, CD$_3$CN) d 7.42-7.18 (m, 8H), 7.18-7.00 (m, 2H), 6.10 (s, 1H), 5.07-4.59 (m, 2H), 4.20-4.35 (m, 1H), 4.13-3.93 (m, 2H), 3.15-3.30 (m, 1H), 2.85-2.75 (s, 1H), 1.71-1.47 (m, 2H), 1.47-1.23 (m, 2H), 0.89 (t, J=7.3 Hz, 3H).

Step 2: To a solution of benzyl ((1R)-1-(butoxy(hydroxy)phosphoryl)-2-phenylethyl)carbamate (84.7 mg, 0.216 mmol) in MeOH (5 ml) were added 10% Pd/C (26 mg). A hydrogen balloon was attached and the reaction mixture was stirred at room temperature for 2 hours. The catalyst was removed by filtration through Celite, and the filtrates were evaporated to dryness to give butyl hydrogen ((R)-1-amino-2-phenylethyl)phosphonate. MS m/z 258.1 (M+1). Retention time 0.789 minutes, which was used in the next step without purification.

Step 3: In a 15 mL round-bottomed flask was added Boc-Val-Dip-Dap-OH (80 mg, 0.140 mmol) and DIEA (62.9 mg, 0.487 mmol) in DMF (2 ml) to give a clear solution. HATU (53 mg, 0.139 mmol) was added and the reaction mixture was stirred for 5 minutes and then butyl hydrogen ((R)-1-amino-2-phenylethyl)phosphonate (41.9 mg, 0.163 mmol) was added. The solution was stirred at room temperature for 18 hours. The crude was purified by reverse phase HPLC, C18 column, eluted with 40-60% acetonitrile-H$_2$O, containing 0.05% TFA. The fractions containing desired product were concentrated to tert-butyl ((2S)-1-(((3R,4S,5S)-1-((2S)-2-((1R,2R)-3-(((1R)-1-(butoxy(hydroxy)phosphoryl)-2-phenylethyl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)carbamate. MS m/z 811.4 (M+1). Retention time 1.376 minutes.

Step 4: To a solution tert-butyl ((2S)-1-(((3R,4S,5S)-1-((2S)-2-((1R,2R)-3-(((1R)-1-(butoxy(hydroxy)phosphoryl)-2-phenylethyl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)carbamate (106 mg, 0.131 mmol) in DCM (3 ml) was added TFA (1 ml), and the reaction mixture was stirred at room temperature for 1 hour and then concentrated. About ⅔ converted to phosphonic acid (1-((2R,3R)-3-((S)-1-((3R,4S,5S)-4-((S)-2-amino-N,3-dimethylbutanamido)-3-methoxy-5-methylheptanoyl)pyrrolidin-2-yl)-3-methoxy-2-methylpropanamido)-2-phenylethyl)phosphonic acid. MS m/z 655.3 (M+1). Retention time 0.957 minutes. The other ⅓ was butyl hydrogen (1-((2R,3R)-3-((S)-1-((3R,4S,5S)-4-((S)-2-amino-N,3-dimethylbutanamido)-3-methoxy-5-methylheptanoyl)pyrrolidin-2-yl)-3-methoxy-2-methylpropanamido)-2-phenylethyl)phosphonate. MS m/z 711.4 (M+1). Retention time 1.038 minutes. The mixture was used in the next step without separation.

Step 5: To a solution of (1R,3S,4S)-2-(tert-butoxycarbonyl)-2-azabicyclo[2.2.1]heptane-3-carboxylic acid (3.8 mg, 0.016 mmol) in DMF (1 ml) was added DIEA (6.1 mg, 0.047 mmol) and then HATU (5.9 mg, 0.016 mmol). The reaction mixture was stirred at room temperature for 10 minutes and then added to a mixture of the amine from step 4 (12 mg, 0.016 mmol) containing mainly the phosphonic acid. The reaction mixture was stirred at room temperature for 1 hour. The crude was purified by ISCO using C18 column, 4.5 g, eluted with 10-70% acetonitrile in water with 0.05% TFA. The fractions containing desired product were concentrated to obtain ((R)-1-((2R,3R)-3-((S)-1-((3R,4S,5S)-4-((S)-2-((1R,3S,4S)-2-(tert-butoxycarbonyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-2-phenylethyl)phosphonic acid MS m/z 878.5 (M+1). Retention time 1.307 minutes, and (1R,3S,4S)-tert-butyl 3-(((2S)-1-(((3R,4S,5S)-1-((2S)-2-((1R,2R)-3-(((1R)-1-(butoxy(hydroxy)phosphoryl)-2-phenylethyl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)carbamoyl)-2-azabicyclo[2.2.1]heptane-2-carboxylate MS m/z 934.5 (M+1). Retention time 1.447 minutes.

Step 6: To a solution of ((R)-1-((2R,3R)-3-((S)-1-((3R,4S,5S)-4-((S)-2-((1R,3S,4S)-2-(tert-butoxycarbonyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-2-phenylethyl) phosphonic acid (11.0 mg, 0.012 mmol) in DCM (2 ml) was added TFA (1 ml). The reaction mixture was stirred at room temperature for 1 hour and then concentrated to obtain ((R)-1-((2R,3R)-3-((S)-1-((3R,4S,5S)-4-((S)-2-((1R,3S,4S)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-2-phenylethyl) phosphonic acid (7). MS m/z 778.4 (M+1). Retention time 0.973 minutes.

EXAMPLE 8

((R)-1-((2R,3R)-3-((S)-1-((3R,4S,5S)-4-((S)-2-((1R,3S,4S)-2-Azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-2-phenylethyl)phosphinic acid (8)

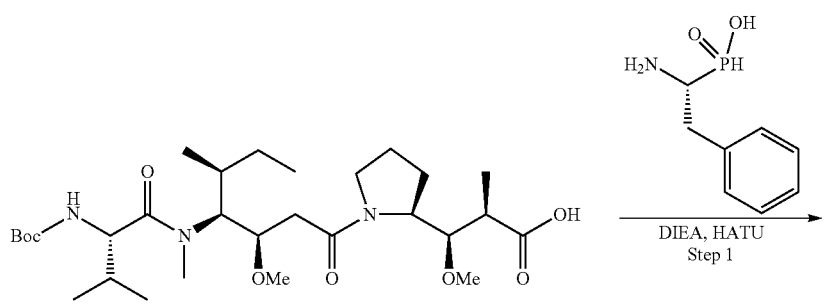

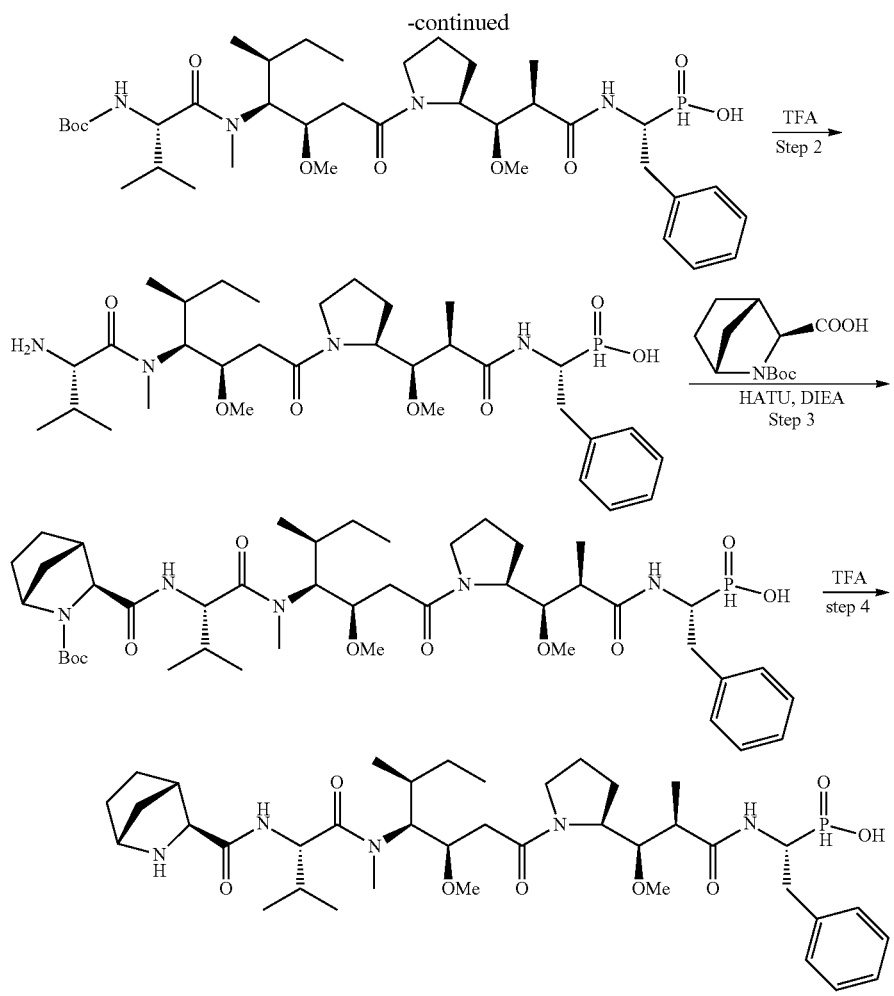

8

Step 1: In a 15 mL round-bottomed flask was added Boc-Val-Dip-Dap-OH (50 mg, 0.087 mmol) and DIEA (33.9 mg, 0.262 mmol) in DMF (2 mL) to give a clear solution. HATU (33.3 mg, 0.087 mmol) was added and the reaction mixture was stirred for 5 minutes and then added to ((R)-1-amino-2-phenylethyl)phosphinic acid (41 mg, 0.154 mmol), (synthesized by following the procedure described in J. Chem. Soc. Perkin Trans. I 1984, 2845). The solution was stirred at room temperature for 18 hours. LCMS indicated the formation of the desired product. The crude was purified by reverse phase HPLC, C18 column, eluted with 30-50% acetonitrile-H$_2$O, containing 0.05% TFA. The fractions containing desired product were concentrated to obtain ((R)-1-((2R,3R)-3-((S)-1-((3R,4S,5S)-4-((S)-2-((tert-butoxycarbonyl)amino)-N,3-dimethylbutanamido)-3-methoxy-5-methylheptanoyl)pyrrolidin-2-yl)-3-methoxy-2-methylpropanamido)-2-phenylethyl)phosphinic acid. MS m/z 739.4 (M+1). Retention time 1.248 minutes.

Step 2: To a solution of ((R)-1-((2R,3R)-3-((S)-1-((3R,4S,5S)-4-((S)-2-((tert-butoxycarbonyl)amino)-N,3-dimethylbutanamido)-3-methoxy-5-methylheptanoyl)pyrrolidin-2-yl)-3-methoxy-2-methylpropanamido)-2-phenylethyl) phosphinic acid (69.1 mg, 0.094 mmol) in DCM (2 ml) was added TFA (1 ml) and the reaction mixture was stirred at room temperature for 1 hour and then concentrated to give ((R)-1-((2R,3R)-3-((S)-1-((3R,4S,5S)-4-((S)-2-amino-N,3-dimethylbutanamido)-3-methoxy-5-methylheptanoyl)pyrrolidin-2-yl)-3-methoxy-2-methylpropanamido)-2-phenylethyl)phosphinic acid (MS m/z 639.3 (M+1); retention time 0.851 minutes) which was used without further purification in the next step.

Step 3: To a solution of (1R,3S,4S)-2-(tert-butoxycarbonyl)-2-azabicyclo[2.2.1]heptane-3-carboxylic acid (11.3 mg, 0.047 mmol) in DMF (1 ml) was added DIEA (0.033 ml, 0.188 mmol), followed by HATU (17.9 mg, 0.047 mmol). The reaction mixture was stirred for 10 minutes and then added to a solution of ((R)-1-((2R,3R)-3-((S)-1-((3R,4S,5S)-4-((S)-2-amino-N,3-dimethylbutanamido)-3-methoxy-5-methylheptanoyl)pyrrolidin-2-yl)-3-methoxy-2-methylpropanamido)-2-phenylethyl)phosphinic acid (35.4 mg, 0.047 mmol) in DMF (1 ml). LCMS indicated the reaction was complete in 10 minutes. The crude was purified by reverse phase HPLC, C18 column, eluted with 30-55% acetonitrile-H$_2$O, containing 0.05% TFA. The fractions containing desired product were concentrated to obtain ((R)-1-((2R,3R)-3-((S)-1-((3R,4S,5S)-4-((S)-2-((1R,3S,4S)-2-(tert-butoxycarbonyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-2-phenylethyl)phosphinic acid. MS m/z 862.5 (M+1). Retention time 1.372 minutes.

Step 4: To a solution of ((R)-1-((2R,3R)-3-((S)-1-((3R,4S,5S)-4-((S)-2-((1R,3S,4S)-2-(tert-butoxycarbonyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-2-phenylethyl) phosphinic acid (60 mg, 0.070 mmol) in DCM (2 ml) was added TFA (1 ml). The reaction mixture was stirred at room temperature for 1 hour and then concentrated to give ((R)-1-((2R,3R)-3-((S)-1-((3R,4S,5S)-4-((S)-2-((1R,3S,4S)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-2-phenylethyl) phosphinic acid (8). MS m/z 762.5 (M+1). Retention time 1.220 minutes.

EXAMPLE 9

((R)-1-((2R,3R)-3-((S)-1-((3R,4S,5S)-4-((S)-N,3-Dimethyl-2-((1R,3S,4S)-2-methyl-2-azabicyclo[2.2.1]heptane-3-carboxamido)butanamido)-3-methoxy-5-methylheptanoyl)pyrrolidin-2-yl)-3-methoxy-2-methylpropanamido)-2-phenylethyl) phosphinic acid (9)

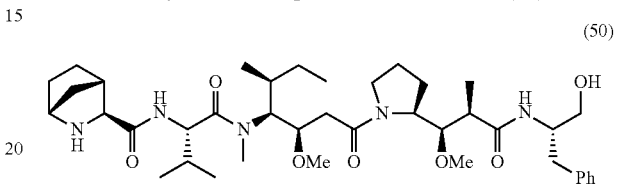

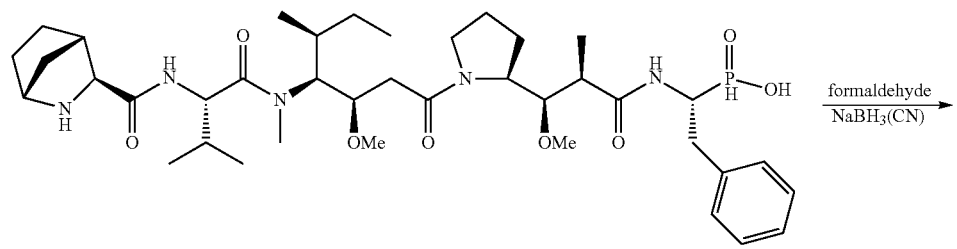

To a solution of ((R)-1-((2R,3R)-3-((S)-1-((3R,4S,5S)-4-((S)-2-((1R,3S,4S)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-2-phenylethyl)phosphinic acid (8) (20 mg, 0.023 mmol) in MeOH (2 ml) was added paraformaldehyde (10 mg, 0.33 mmol) and acetic acid (0.019 ml, 0.333 mmol), followed by sodium cyanoborohydride (20 mg, 0.32 mmol). The reaction mixture was stirred at 50° C. for 1 hour and then at room temperature for 2 days. LCMS indicated that the reaction was complete. The reaction mixture was filtered through Celite to remove the insoluble residue and the crude was purified by reverse phase HPLC, C18 column, eluted with 10-50% acetonitrile-H₂O, containing 0.05% TFA. The fractions containing desired product were concentrated to obtain ((R)-1-((2R,3R)-3-((S)-1-((3R,4S,5S)-4-((S)-N,3-dimethyl-2-((1R,3S,4S)-2-methyl-2-azabicyclo[2.2.1]heptane-3-carboxamido)butanamido)-3-methoxy-5-methylheptanoyl)pyrrolidin-2-yl)-3-methoxy-2-methylpropanamido)-2-phenylethyl)phosphinic acid (9). MS m/z 776.4 (M+1). Retention time 0.944 minutes.

EXAMPLE 10

(1R,3S,4S)-N-((S)-1-(((3R,4S,5S)-1-((S)-2-((1R,2R)-3-(((S)-1-Hydroxy-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-azabicyclo[2.2.1]heptane-3-carboxamide (50)

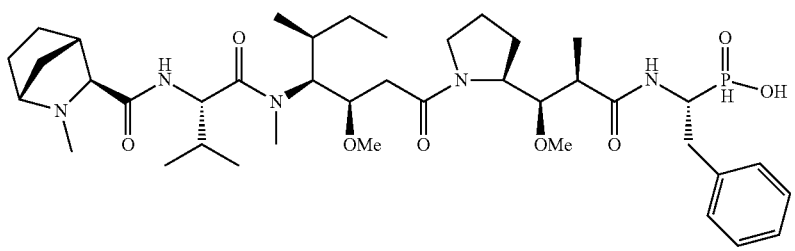

Step 1: DIEA (0.013 ml, 0.075 mmol) and HATU (18.5 mg, 0.049 mmol) were added to (1R,3S,4S)-2-(tert-butoxycarbonyl)-2-azabicyclo[2.2.1]heptane-3-carboxylic acid (9.8 mg, 0.040 mmol) in DMF (1 ml). The reaction mixture was stirred for 5 min and then added to Val-Dil-Dap-OH (17.7 mg, 0.038 mmol) in DMF. The reaction was stirred at rt for 16 h. Then the crude was purified by preparative HPLC (30-70% acetonitrile-H₂O containing 0.05% TFA) to obtain (2R,3R)-3-((S)-1-((3R,4S,5S)-4-((S)-2-((1R,3S,4S)-2-(t-butoxycarbonyl)-2-azabicyclo[2.2.1]heptane-3-carboxamido)-N,3-dimethylbutanamido)-3-methoxy-5-methylhep tanoyl)pyrrolidin-2-yl)-3-methoxy-2-methylpropanoic acid. MS m/z 695.4 (M+H). Retention time 1.376 min.

Step 2: To the product obtained in step 1 (5.9 mg, 0.008 mmol) in DMF (1 ml) were added DIEA (1.1 mg, 0.008 mmol) and HATU (3.8 mg, 0.010 mmol). After the reaction was stirred for 5 min, (S)-2-(S)-2-amino-3-phenylpropan-1-ol (1.9 mg, 0.013 mmol) in DMF was added. The reaction was stirred at rt for 1 h. The crude was purified by preparative HPLC (20-90% acetonitrile-H$_2$O containing 0.05% TFA) to obtain (1R,3S,4S)-t-butyl 3-(((S)-1-(((3R,4S,5S)-1-((S)-2-((1R,2R)-3-(((S)-1-hydroxy-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)carbamoyl)-2-azabicyclo[2.2.1]heptane-2-carboxylate. MS m/z 828.5 (M+H). Retention time 1.388 min.

Step 3: The product obtained in step 2 (4 mg, 0.005 mmol) in DCM (3 ml) was treated with TFA (1 ml) at rt for 1 h and then concentrated to give compound (50) as TFA salt. MS m/z 728.5 (M+H). Retention time 1.008 min.

bined at rt and then stirred at 50° C. for 1 h. The reaction mixture was then cooled to rt, filtered, and purified by preparative HPLC (20-40% acetonitrile-H$_2$O containing 0.05% TFA) to obtain compound (51) as TFA salt. MS m/z 742.5 (M+H). Retention time 1.008 min.

EXAMPLE 12

(1R,3S,4S)-N-((S)-1-(((3R,4S,5S)-1-((S)-2-((1R,2R)-3-(((S)-1-(3-Aminophenyl)-3-hydroxypropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (52)

(52)

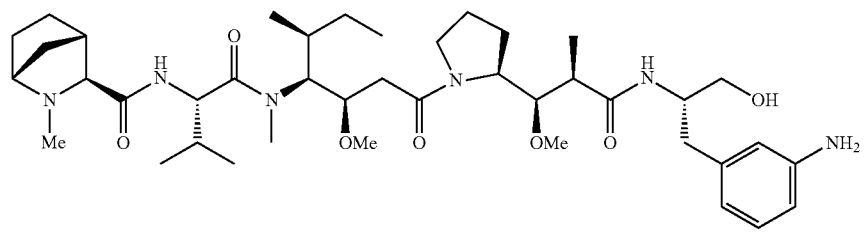

EXAMPLE 11

(1R,3S,4S)-N-((S)-1-(((3R,4S,5S)-1-((S)-2-((1R,2R)-3-(((S)-1-Hydroxy-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (51)

(51)

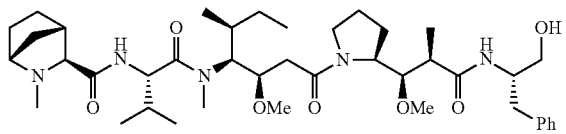

(1R,3S,4S)-N-((S)-1-(((3R,4S,5S)-1-((S)-2-((1R,2R)-3-(((S)-1-Hydroxy-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-azabicyclo[2.2.1]heptane-3-carboxamide (50) (6.1 mg, 0.008 mmol), MeOH (2 ml), acetic acid (0.005 ml, 0.09 mmol), paraformaldehyde (3 mg, 0.1 mmol), and sodium cyanoborohydride (5 mg, 0.08 mmol) were com- Step 1: DIEA (0.105 ml, 0.60 mmol) and HATU (45.5 mg, 0.12 mmol) were added to (3R,4S,5S)-4-((S)-N,3-dimethyl-2-((1R,3S,4S)-2-methyl-2-azabicyclo[2.2.1]heptane-3-carboxamido)butanamido)-3-methoxy-5-methylheptanoic acid (i-7) (57 mg, 0.12 mmol) in DMF (2 ml). The reaction mixture was stirred at rt for 5 min and then DapOMe (i-9) (28.5 mg, 0.12 mmol) in DMF (1 ml) was added. The reaction mixture was stirred at rt for 1 h and then purified by preparative HPLC (10-50% acetonitrile-H$_2$O containing 0.05% TFA) to obtain (2R,3R)-methyl 3-((S)-1-((3R,4S,5S)-4-((S)-N,3-dimethyl-2-((1R,3S,4S)-2-methyl-2-azabicyclo[2.2.1]heptane-3-carboxamido)butanamido)-3-methoxy-5-methylheptanoyl)pyrrolidin-2-yl)-3-methoxy-2-methylpropanoate. MS m/z 623.5 (M+H). Retention time 1.225 min.

Step 2: LiOH (30 mg, 1.25 mmol) was added to the product obtained in step 1 (43.2 mg, 0.059 mmol) in MeOH—H$_2$O (1:1, 4 ml). The reaction mixture was stirred at rt for 18 h, concentrated and acidified with HCl (1N, 1 ml). The crude was purified by preparative HPLC (10-38% acetonitrile-H$_2$O containing 0.05% TFA) obtain (2R,3R)-3-((S)-1-((3R,4S,5S)-4-((S)-N,3-dimethyl-2-((1R,3S,4S)-2-methyl-2-azabicyclo[2.2.1]heptane-3-carboxamido)butanamido)-3-methoxy-5-methylheptanoyl)pyrrolidin-2-yl)-3-methoxy-2-methylpropanoic acid as TFA salt. MS m/z 609.5 (M+H). Retention time 0.962 min.

Step 3: To the product obtained in step 2 (45.7 mg, 0.063 mmol) in DMF (1 ml) were added DIEA (0.055 ml, 0.32 mmol) and HATU (24.0 mg, 0.063 mmol). The reaction mixture was stirred at rt for 10 min and then added to (S)-t-butyl (3-(2-amino-3-hydroxypropyl)phenyl)carbamate TFA salt (i-4) (24.1 mg, 0.063 mmol) in DMF (1 ml). The reaction mixture was stirred at rt for 1 h and then concentrated. The crude was purified by preparative HPLC (20-70% acetonitrile-H$_2$O containing 0.05% TFA) to obtain t-butyl (3-((S)-2-((2R,3R)-3-((S)-1-((3R,4S,5S)-4-((S)-N,3-dimethyl-2-((1R,3S,4S)-2-methyl-2-azabicyclo[2.2.1]heptane-3-carboxamido)butanamido)-3-methoxy-5-methylheptanoyl)pyrrolidin-2-yl)-3-methoxy-2-methylpropanamido)-3-hydroxypropyl)phenyl)carbamate as TFA salt. MS m/z 857.5 (M+H). Retention time 1.145 min.

Step 4: A solution of the product obtained in step 3 (61.4 mg, 0.063 mmol) in acetonitrile-water (1:1, 4 ml) with 5% HCl was stirred at rt for 24 h. The reaction mixture was then concentrated and purified by preparative HPLC (10-30% acetonitrile-H$_2$O containing 0.05% TFA) to give compound (52) as TFA salt. MS m/z 757.5 (M+H). Retention time 0.744 min.

EXAMPLE 13

(S)-Methyl 2-((2R,3R)-3-((S)-1-((3R,4S,5S)-4-((S)-N,3-dimethyl-2-((1R,3S,4S)-2-methyl-2-azabicyclo[2.2.1]heptane-3-carboxamido)butanamido)-3-methoxy-5-methylheptanoyl)pyrrolidin-2-yl)-3-methoxy-2-methylpropanamido)-3-phenylpropanoate (53)

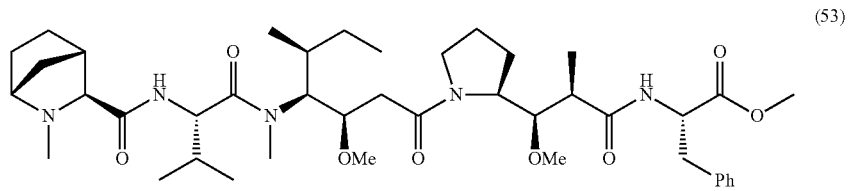 [SMILES: CC[C@H](C)[C@@H]([C@@H](CC(=O)N1CCC[C@H]1[C@H](OC)[C@@H](C)C(=O)N[C@@H](Cc1ccccc1)C(=O)OC)OC)N(C)C(=O)[C@@H](NC(=O)[C@@H]1[C@H]2CC[C@H](C2)N1C)C(C)C]

(53)

To (S)-methyl 2-((2R,3R)-3-((S)-1-((3R,4S,5S)-4-((S)-2-((1R,3S,4S)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoate TFA salt (1) (55.4 mg, 0.064 mmol) in MeOH (5 ml) were added acetic acid (0.009 ml, 0.2 mmol), paraformaldehyde (24 mg, 0.79 mmol) and then sodium cyanoborohydride (25 mg, 0.40 mmol). The reaction mixture was stirred at 40° C. for 16 h, filtered, concentrated and purified by preparative HPLC (10-45% acetonitrile-water with 0.05% TFA) to compound (53) as TFA salt. MS m/z 770.3 (M+H). Retention time 1.100 min.

EXAMPLE 14

(S)-2-((2R,3R)-3-((S)-1-((3R,4S,5S)-4-((S)-N,3-Dimethyl-2-((1R,3S,4S)-2-methyl-2-azabicyclo[2.2.1]heptane-3-carboxamido)butanamido)-3-methoxy-5-methylheptanoyl)pyrrolidin-2-yl)-3-methoxy-2-methylpropanamido)-3-phenylpropanoic acid (9d)

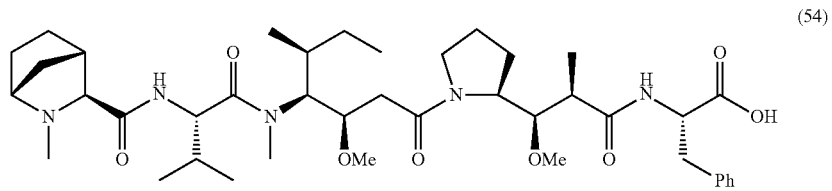 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@@H]1[C@H]2CC[C@H](C2)N1C)C(C)C]

(54)

Compound (53) TFA salt (50.8 mg, 0.057 mmol) was dissolved in MeOH—H₂O (1:1, 5 ml) and LiOH (20 mg, 0.835 mmol) was added. The reaction was stirred at 40° C. for 1 h. MeOH was removed by evaporation. Water was added to the residue, and acidified with AcOH (0.040 ml). The crude was purified by preparative HPLC (27-33% acetonitrile-H₂O containing 0.05% TFA) to obtain compound (54) as TFA salt. MS m/z 756.5 (M+H). Retention time 0.985 min.

EXAMPLE 15

(1R,3S,4S)-N-((S)-1-(((3R,4S,5S)-3-methoxy-1-((S)-2-((1R,2R)-1-Methoxy-2-methyl-3-oxo-3-(((S)-1-phenyl-3-sulfamoylpropan-2-yl)amino)propyl) pyrrolidin-1-yl)-5-methyl-1-oxoheptan-4-yl)(methyl) amino)-3-methyl-1-oxobutan-2-yl)-2-methyl-2-azabicyclo[2.2.1]heptane-3-carboxamide (55)

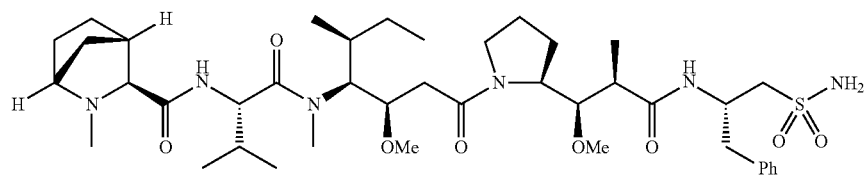

(55)

DIEA (10.2 mg, 0.014 ml) and HATU (7.7 mg, 0.020 mmol) were added to (2R,3R)-3-((S)-1-((3R,4S,5S)-4-((S)-N,3-dimethyl-2-((1R,3S,4S)-2-methyl-2-azabicyclo[2.2.1] heptane-3-carboxamido)butanamido)-3-methoxy-5-methylheptanoyl)pyrrolidin-2-yl)-3-methoxy-2-methylpropanoic acid TFA salt (Step 2, Example 12) (12.3 mg, 0.017 mmol) in DMF (1 ml). The reaction was stirred for 15 min, and then (S)-2-amino-3-phenylpropane-1-sulfonamide (4.3 mg, 0.020 mmol) in DMF (0.5 ml) was added. The reaction was stirred at rt for an additional 1 h. The crude was purified by preparative HPLC (20-70% acetonitrile-H₂O containing 0.05% TFA to obtain compound (55). MS m/z 805.5 (M+1). Retention time 0.965 min.

EXAMPLE 16

(1R,3S,4S)-N-((S)-1-(((3R,4S,5S)-3-methoxy-1-((S)-2-((1R,2R)-1-Methoxy-2-methyl-3-oxo-3-(((S)-1-phenyl-3-sulfamoylpropan-2-yl)amino)propyl) pyrrolidin-1-yl)-5-methyl-1-oxoheptan-4-yl)(methyl) amino)-3-methyl-1-oxobutan-2-yl)-2-azabicyclo [2.2.1]heptane-3-carboxamide (56)

stirred at rt for 2 h and then purified by preparative HPLC (20-70% acetonitrile-H₂O containing 0.05% TFA) to obtain (S)-t-butyl 2-((1R,2R)-1-methoxy-2-methyl-3-oxo-3-(((S)-1-phenyl-3-sulfamoylpropan-2-yl)amino)propyl)pyrrolidine-1-carboxylate. MS m/z 484.2 (M+1). Retention time 1.130 min.

Step 2; (S)-t-Butyl 2-((1R,2R)-1-methoxy-2-methyl-3-oxo-3-(((S)-1-phenyl-3-sulfamoylpropan-2-yl)amino)propyl)pyrrolidine-1-carboxylate(28.5 mg, 0.059 mmol) was dissolved in methanolic HCl (3 M, 3 ml). The solvent was slowly removed under N₂ stream followed by under reduced pressure overnight to afford (2R,3R)-3-methoxy-2-methyl-N-((S)-1-phenyl-3-sulfamoylpropan-2-yl)-3-((S)-pyrrolidin-2-yl)propanamide as HCl salt. MS m/z 384.2 (M+1). Retention time 0.630 min.

Step 3; To Cbz-Val-Dil-OH (28.7 mg, 0.066 mmol) in DMF (1 ml) were added DIEA (0.048 ml) and HATU (22.9 mg, 0.060 mmol). The reaction was stirred for 15 min, and then (2R,3R)-3-methoxy-2-methyl-N-((S)-1-phenyl-3-sulfamoylpropan-2-yl)-3-((S)-pyrrolidin-2-yl)propanamide (23 mg, 0.055 mmol) in DMF (1 ml) was added. The reaction mixture was stirred at rt for 2 h, and purified by preparative HPLC (20-70% acetonitrile-H₂O containing 0.05% TFA) to obtain benzyl ((S)-1-(((3R,4S,5S)-3-methoxy-1-((S)-2-((1R,2R)-1-methoxy-2-methyl-3-oxo-3-(((S)-1-phenyl-3-sulfamoylpropan-2-yl)amino)propyl)pyrrolidin-1-yl)-5-methyl-1-oxoheptan-4-yl)(methyl)amino)-3-methyl-1-oxobutan-2-yl)carbamate. MS m/z 802.4 (M+1). Retention time 1.298 min.

Step 4; The product obtained in step 3 (24.6 mg, 0.031 mmol), 10% Pd—C (32.7 mg) and EtOAc (3 ml) were combined and stirred under hydrogen for 8 h at rt. The reaction mixture was filtered and concentrated to give (S)-2-amino-N-((3R,4S,5S)-3-methoxy-1-((S)-2-((1R,2R)-1-methoxy-2-methyl-3-oxo-3-(((S)-1-phenyl-3-sulfamoylpropan-2-yl)amino)propyl)pyrrolidin-1-yl)-5-methyl-1-oxoheptan-4-yl)-N,3-dimethylbutanamide. MS m/z 668.4 (M+1). Retention time 0.888 min.

Step 5; (1R,3S,4S)-2-(t-Butoxycarbonyl)-2-azabicyclo[2.2.1]heptane-3-carboxylic acid (7.0 mg, 0.029 mmol),

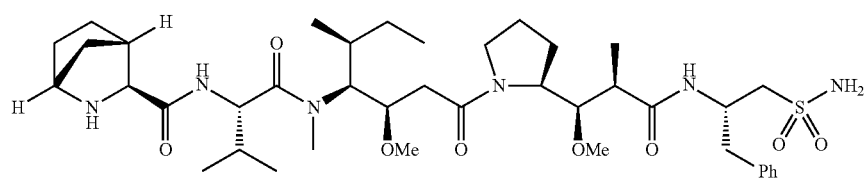

(56)

Step 1; To Boc-Dap-OH (21.6 mg, 0.075 mmol) in DMF (2 ml) were added DIEA (48.5 mg, 0.066 ml) and HATU (26.2 mg, 0.069 mmol). The reaction was stirred for 15 min, and then (S)-2-amino-3-phenylpropane-1-sulfonamide (13.4 mg, 0.063 mmol) was added. The reaction mixture was DMF (1 ml), DIEA (0.021 ml) and HATU (10.1 mg, 0.027 mmol) were combined and stirred at rt for 15 min, and then the product obtained in step 4 (16.2 mg, 0.024 mmol) in DMF (1 ml) was added. The reaction mixture was stirred at rt for 2 h and purified by preparative HPLC (30-60% acetonitrile-H$_2$O containing 0.05% TFA) to obtain (1R,3S,4S)-t-butyl 3-(((S)-1-(((3R,4S,5S)-3-methoxy-1-((S)-2-((1R,2R)-1-methoxy-2-methyl-3-oxo-3-(((S)-1-phenyl-3-sulfamoylpropan-2-yl)amino)propyl)pyrrolidin-1-yl)-5-methyl-1-oxoheptan-4-yl)(methyl)amino)-3-methyl-1-oxobutan-2-yl)carbamoyl)-2-azabicyclo[2.2.1]heptane-2-carboxylate. MS m/z 891.5 (M+1). Retention time 1.319 min.

Step 6; The product obtained in step 5 (13.2 mg, 0.015 mmol) was dissolved in methanolic HCl (3 M, 3 ml). The solvent was slowly removed under N$_2$ stream followed by under reduced pressure overnight to afford (1R,3S,4S)-N-((S)-1-(((3R,4S,5S)-3-methoxy-1-((S)-2-((1R,2R)-1-methoxy-2-methyl-3-oxo-3-(((S)-1-phenyl-3-sulfamoylpropan-2-yl)amino)propyl)pyrrolidin-1-yl)-5-methyl-1-oxoheptan-4-yl)(methyl)amino)-3-methyl-1-oxobutan-2-yl)-2-azabicyclo[2.2.1]heptane-3-carboxamide (56) as HCl salt. MS m/z 791.5 (M+1). Retention time 0.923 min.

EXAMPLE 17

(1R,3S,4S)-N-((S)-1-(((3R,4S,5S)-3-Methoxy-1-((S)-2-((1R,2R)-1-methoxy-2-methyl-3-oxo-3-(((S)-2-phenyl-1-(5-phenyl-1H-imidazol-2-yl)ethyl)amino)propyl)pyrrolidin-1-yl)-5-methyl-1-oxoheptan-4-yl)(methyl)amino)-3-methyl-1-oxobutan-2-yl)-2-azabicyclo[2.2.1]heptane-3-carboxamide (57)

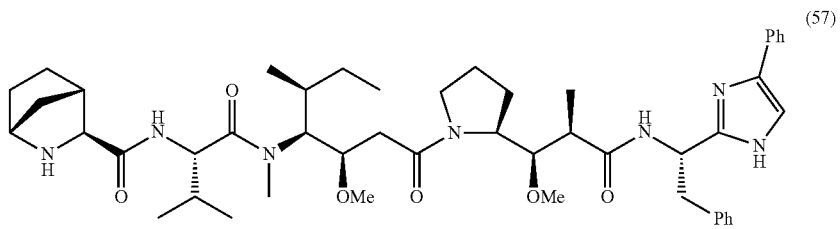 [SMILES: CC[C@H](C)[C@@H]([C@@H](CC(=O)N1CCC[C@H]1[C@H](OC)[C@@H](C)C(=O)N[C@@H](Cc1ccccc1)c1nc(-c2ccccc2)c[nH]1)OC)N(C)C(=O)[C@@H](NC(=O)[C@H]1N[C@@H]2CC[C@H]1C2)C(C)C]

(57)

DIEA (33 mg, 0.26 mmol) and HATU (19 mg, 0.051 mmol) was added to (2R,3R)-3-((S)-1-((3R,4S,5S)-4-((S)-2-((1R,3S,4S)-2-(t-butoxycarbonyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanoic acid (40 mg, 0.043 mmol) in DMF (2 ml). The reaction was stirred at rt for 15 min and then (S)-2-phenyl-1-(5-phenyl-1H-imidazol-2-yl)ethanamine (22.4 mg, 0.085 mmol) was added. The reaction was stirred at rt for 1 h. The crude was purified by preparative HPLC (20-70% acetonitrile-H$_2$O containing 0.05% TFA) to obtain (1R,3S,4S)-t-butyl 3-(((S)-1-(((3R,4S,5S)-3-methoxy-1-((S)-2-((1R,2R)-1-methoxy-2-methyl-3-oxo-3-(((S)-2-phenyl-1-(5-phenyl-1H-imidazol-2-yl)ethyl)amino)propyl)pyrrolidin-1-yl)-5-methyl-1-oxoheptan-4-yl)(methyl)amino)-3-methyl-1-oxobutan-2-yl)carbamoyl)-2-azabicyclo[2.2.1]heptane-2-carboxylate. MS m/z 940.5 (M+1). Retention time 1.333 min. This product (13.9 mg, 0.015 mmol) was dissolved in methanolic HCl (3 M, 3 ml). The solvent was slowly removed under stream of N$_2$ followed by under reduced pressure overnight to afford compound (1R,3S,4S)-N-((S)-1-(((3R,4S,5S)-3-methoxy-1-((S)-2-((1R,2R)-1-methoxy-2-methyl-3-oxo-3-(((S)-2-phenyl-1-(5-phenyl-1H-imidazol-2-yl)ethyl)amino)propyl)pyrrolidin-1-yl)-5-methyl-1-oxoheptan-4-yl)(methyl)amino)-3-methyl-1-oxobutan-2-yl)-2-azabicyclo[2.2.1]heptane-3-carboxamide (57) as HCl salt. MS m/z 840.5 (M+1). Retention time 0.936 min.

EXAMPLE 18

(1R,3S,4S)-N-((S)-1-(((3R,4S,5S)-3-Methoxy-1-((S)-2-((1R,2R)-1-methoxy-3-(((S)-1-methoxy-3-phenylpropan-2-yl)amino)-2-methyl-3-oxopropyl)pyrrolidin-1-yl)-5-methyl-1-oxoheptan-4-yl)(methyl)amino)-3-methyl-1-oxobutan-2-yl)-2-azabicyclo[2.2.1]heptane-3-carboxamide (58)

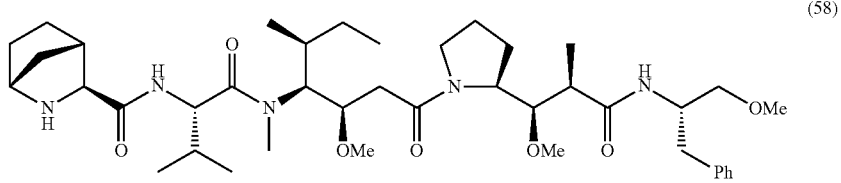 [SMILES: CC[C@H](C)[C@@H]([C@@H](CC(=O)N1CCC[C@H]1[C@H](OC)[C@@H](C)C(=O)N[C@H](COC)Cc1ccccc1)OC)N(C)C(=O)[C@@H](NC(=O)[C@H]1N[C@@H]2CC[C@H]1C2)C(C)C]

(58)

Compound (58) was prepared by the procedure described for compound (57) using (S)-1-methoxy-3-phenylpropan-2-amine HCl salt in place of (S)-2-phenyl-1-(5-phenyl-1H-imidazol-2-yl)ethanamine. MS m/z 742.5 (M+1). Retention time 0.997 min.

EXAMPLE 19

(1R,3S,4S)-N-((S)-1-(((3R,4S,5S)-3-Methoxy-1-((S)-2-((1R,2R)-1-methoxy-2-methyl-3-oxo-3-(((S)-2-phenyl-1-(1H-pyrazol-3-yl)ethyl)amino)propyl)pyrrolidin-1-yl)-5-methyl-1-oxoheptan-4-yl)(methyl)amino)-3-methyl-1-oxobutan-2-yl)-2-azabicyclo[2.2.1]heptane-3-carboxamide (59)

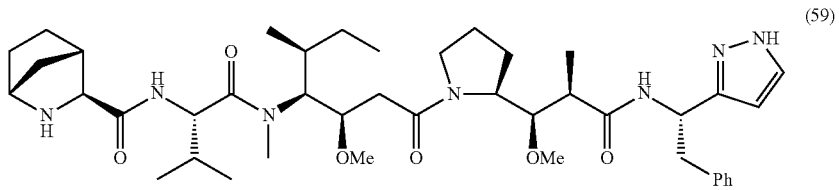 [SMILES: CC[C@H](C)[C@@H]([C@@H](CC(=O)N1CCC[C@H]1[C@H](OC)[C@@H](C)C(=O)N[C@@H](Cc1ccccc1)c1cc[nH]n1)OC)N(C)C(=O)[C@@H](NC(=O)[C@H]1N[C@@H]2CC[C@H]1C2)C(C)C]

(59)

Compound (59) was prepared by the procedure described for compound (57) using (S)-2-phenyl-1-(1H-pyrazol-3-yl)ethanamine HCl salt in place of (S)-2-phenyl-1-(5-phenyl-1H-imidazol-2-yl)ethanamine. MS m/z 764.5 (M+1). Retention time 0.959 min.

EXAMPLE 20

(1R,3S,4S)-N-((S)-1-(((3R,4S,5S)-3-Methoxy-1-((S)-2-((1R,2R)-1-methoxy-2-methyl-3-oxo-3-(((S)-2-phenyl-1-(pyrimidin-2-yl)ethyl)amino)propyl)pyrrolidin-1-yl)-5-methyl-1-oxoheptan-4-yl)(methyl)amino)-3-methyl-1-oxobutan-2-yl)-2-azabicyclo[2.2.1]heptane-3-carboxamide (60), and (1R,3S,4S)-N-((S)-1-(((3R,4S,5S)-3-methoxy-1-((S)-2-((1R,2R)-1-methoxy-2-methyl-3-oxo-3-(((R)-2-phenyl-1-(pyrimidin-2-yl)ethyl)amino)propyl)pyrrolidin-1-yl)-5-methyl-1-oxoheptan-4-yl)(methyl)amino)-3-methyl-1-oxobutan-2-yl)-2-azabicyclo[2.2.1]heptane-3-carboxamide (61)

Compounds (60) and (61) were prepared by the procedure described for compound (57) using 2-phenyl-1-(pyrimidin-2-yl)ethanamine in place of (S)-2-phenyl-1-(5-phenyl-1H-imidazol-2-yl)ethanamine. Boc protected (60) and (61) were separated on preparative HPLC (30-65% acetonitrile-H₂O containing 0.05% TFA). Removal of the Boc group from Boc protected (60) and (61) afforded ((1R,3S,4S)-N-((S)-1-(((3R,4S,5S)-3-methoxy-1-((S)-2-((1R,2R)-1-methoxy-2-methyl-3-oxo-3-(((S)-2-phenyl-1-(pyrimidin-2-yl)ethyl)amino)propyl)pyrrolidin-1-yl)-5-methyl-1-oxoheptan-4-yl)(methyl)amino)-3-methyl-1-oxobutan-2-yl)-2-azabicyclo[2.2.1]heptane-3-carboxamide (60) and (1R,3S,4S)-N-((S)-1-(((3R,4S,5S)-3-methoxy-1-((S)-2-((1R,2R)-1-methoxy-2-methyl-3-oxo-3-(((R)-2-phenyl-1-(pyrimidin-2-yl)ethyl)amino)propyl)pyrrolidin-1-yl)-5-methyl-1-oxoheptan-4-yl)(methyl)amino)-3-methyl-1-oxobutan-2-yl)-2-azabicyclo[2.2.1]heptane-3-carboxamide (61) as a HCl salt, respectively. MS m/z 776.5 (M+1). Retention time 1.001 min (60) and 1.016 min (61).

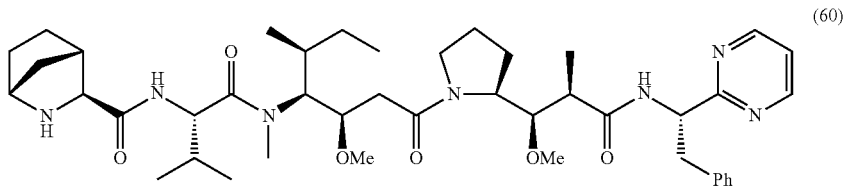

(60)

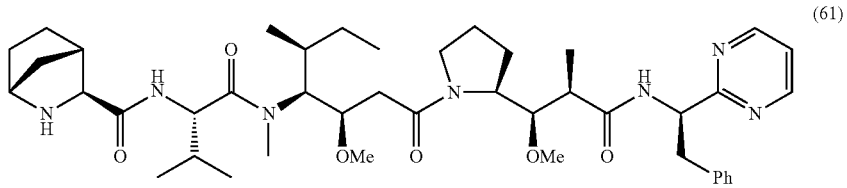

(61)

EXAMPLE 21

(1R,3S,4S)-N-((S)-1-(((3R,4S,5S)-3-Methoxy-1-((S)-2-((1R,2R)-1-methoxy-2-methyl-3-oxo-3-(((S)-2-phenyl-1-(5-phenyl-1,3,4-oxadiazol-2-yl)ethyl)amino)propyl)pyrrolidin-1-yl)-5-methyl-1-oxoheptan-4-yl)(methyl)amino)-3-methyl-1-oxobutan-2-yl)-2-azabicyclo[2.2.1]heptane-3-carboxamide (62)

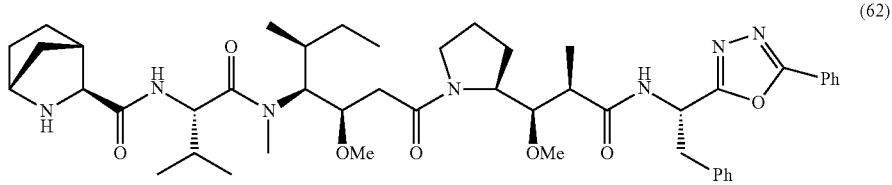 [SMILES: CC[C@H](C)[C@@H]([C@@H](CC(=O)N1CCC[C@H]1[C@H](OC)[C@@H](C)C(=O)N[C@@H](Cc1ccccc1)c1nnc(-c2ccccc2)o1)OC)N(C)C(=O)[C@@H](NC(=O)[C@H]1N[C@@H]2CC[C@H]1C2)C(C)C]

(62)

Compound (62) was prepared in the procedure described for compound (57) using (S)-2-phenyl-1-(5-phenyl-1,3,4-oxadiazol-2-yl)ethanamine in place of (S)-2-phenyl-1-(5-phenyl-1H-imidazol-2-yl)ethanamine with in step 1. After removal of the Boc group, compound (62) was obtained as HCl salt. MS m/z 842.5 (M+1). Retention time 1.112 min.

EXAMPLE 22

(1R,3S,4S)-2-(Cyanomethyl)-N-((S)-1-(((3R,4S,5S)-1-((S)-2-((1R,2R)-3-(((S)-1-hydroxy-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-azabicyclo[2.2.1]heptane-3-carboxamide (63)

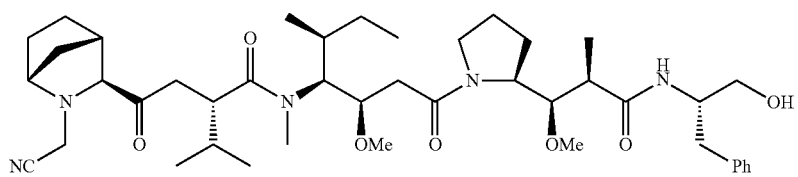

(63)

Step 1: DIEA (104 mg, 0.80 mmol) and HATU (122 mg, 0.32 mmol) were added to a solution of (1R,3S,4S)-2-(tert-butoxycarbonyl)-2-azabicyclo[2.2.1]heptane-3-carboxylic acid (78 mg, 0.32 mmol) in DMF (3 ml). The reaction mixture was stirred at rt for 5 min and then added to Val-Dil-Dap-OMe (130 mg, 0.27 mmol) in DMF (2 ml). The reaction mixture was then stirred at rt for 1 h and concentrated. Saturated sodium bicarbonate solution (5 ml) was added to the residue and the product was extracted with DCM (10 ml×3). The organic layers were combined, dried and concentrated to obtain (1R,3S,4S)-t-butyl 3-(((S)-1-(((3R,4S,5S)-1-((S)-2-((1R,2R)-1,3-dimethoxy-2-methyl-3-oxopropyl)pyrrolidin-1-yl)-3-methoxy-5-methyl-1-oxoheptan-4-yl)(methyl)amino)-3-methyl-1-oxobutan-2-yl)carbamoyl)-2-azabicyclo[2.2.1] heptane-2-carboxylate. The product was used in the next step without further purification. MS m/z 710.5 (M+H). Retention time 1.440 min.

Step 2: The product obtained in step 1 (190 mg, 0.27 mmol) in DCM (10 ml) was treated with TFA (2 ml) at rt for 3 h, and then concentrated to give (2R,3R)-methyl 3-((S)-1-((3R,4S,5S)-4-((S)-2-((1R,3S,4S)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanoate as TFA salt. MS m/z 610.5 (M+H). Retention time 1.003 min. The product was used in the next step without further purification.

Step 3: To the product obtained in step 2 (193 mg, 0.27 mmol) in MeOH (10 ml) were added acetic acid (0.015 ml, 0.27 mmol), paraformaldehyde (40 mg, 1.3 mmol) and sodium cyanoborohydride (84 mg, 1.4 mmol). The reaction was stirred at 50° C. for 16 h. LCMS indicated that approximately 90% was converted to the cyanomethylated compound and about 10% was converted to the methylated compound. The reaction mixture was filtered and purified by preparative HPLC (20-60% acetonitrile-H$_2$O containing 0.05% TFA). Fractions containing the cyano adduct were collected and concentrated to give (2R,3R)-methyl 3-((S)-1-((3R,4S,5S)-4-((S)-2-((1R,3S,4S)-2-(cyanomethyl)-2-azabicyclo[2.2.1] heptane-3-carboxamido)-N,3-dimethylbutanamido)-3-methoxy-5-methylheptanoyl)pyrrolidin-2-yl)-3-methoxy-2-methylpropanoate as TFA salt. MS m/z 648.5 (M+H). Retention time 1.261 min.

Step 4: To the product (0.12 g, 0.16 mmol) obtained in step 3 in MeOH—H$_2$O (1:1 5 ml) was added LiOH (50 mg, 2.09 mmol). The reaction mixture was stirred at rt for 16 h and then acidified with 0.2 ml 10% HCl. The cyano group was partially hydrolyzed to form a carbamoylmethylated product in addition to the cyanomethyl one. The reaction was concentrated and the two products were isolated by preparative HPLC (20-50% acetonitrile-H$_2$O containing 0.05% TFA) to obtain (2R,3R)-3-((S)-1-((3R,4S,5S)-4-((S)-2-((1R,3S,4S)-2-(cyanomethyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanoic acid, MS m/z 634.4 (M+H), retention time 1.138 min, and (2R,3R)-3-((S)-1-((3R,4S,5S)-4-((S)-2-((1R,3S,4S)-2-(2-amino-2-oxoethyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanoic acid as TFA salts. MS m/z 652.4 (M+H). Retention time 0.888 min.

Step 5: To (2R,3R)-3-((S)-1-((3R,4S,5S)-4-((S)-2-((1R,3S,4S)-2-(cyanomethyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanoic acid TFA salt (6 mg, 0.008 mmol) in DMF was added DIEA (3.1 mg, 0.024 mmol) and HATU (3.7 mg, 0.0096 mmol). The reaction was stirred at rt for 5 min and then (S)-2-amino-3-phenylpropan-1-ol (2.4 mg, 0.016 mmol) was added. The reaction was stirred at rt for 1 h. The crude was purified by preparative HPLC (10-60% acetonitrile-H₂O containing 0.05% TFA) to obtain compound (63) as TFA salt. MS m/z 767.5 (M+H). Retention time 1.189 min.

EXAMPLE 23

(1R,3S,4S)-2-(2-Amino-2-oxoethyl)-N-((S)-1-(((3R, 4S,5S)-1-((S)-2-((1R, 2R)-3-(((S)-1-hydroxy-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-azabicyclo[2.2.1]heptane-3-carboxamide (64)

Step 1: To (2R,3R)-methyl 3-((S)-1-((3R,4S,5S)-4-((S)-2-((1R,3S,4S)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanoate (step 2, Example 63) (13 mg, 0.021 mmol) TFA salt in DCM (2 ml) were added DIEA (0.014 ml, 0.082 mmol) and acetic anhydride (0.0039 ml, 0.041 mmol). The reaction was stirred at rt for 1 h. Aqueous Na₂CO₃ (2 M) was added and the reaction mixture was extracted with DCM (5 ml×3). The organic layers were combined, dried over Na₂SO₄, filtered and then concentrated to give (2R,3R)-methyl 3-((S)-1-((3R, 4S,5S)-4-((S)-2-((1R,3S,4S)-2-acetyl-2-azabicyclo[2.2.1] heptane-3-carboxamido)-N,3-dimethylbutanamido)-3-methoxy-5-methylheptanoyl)pyrrolidin-2-yl)-3-methoxy-2-methylpropanoate. The product was used in the next step without further purification. MS m/z 651.5 (M+H). Retention time 1.188 min.

(64)

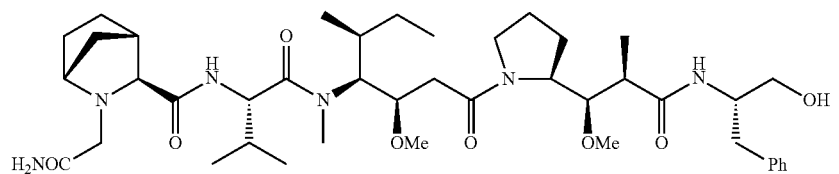

To (2R,3R)-3-((S)-1-((3R,4S,5S)-4-((S)-2-((1R,3S,4S)-2-(2-amino-2-oxoethyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanoic acid TFA salt (step 4, Example 22) (6.1 mg, 0.008 mmol) in DMF were added DIEA (3.1 mg, 0.024 mmol) and HATU (3.7 mg, 0.0096 mmol). The reaction was stirred at rt for 5 min and then (S)-2-amino-3-phenylpropan-1-ol (2.4 mg, 0.016 mmol) was added. The reaction was stirred at rt for 1 h. The crude was purified by preparative HPLC (10-60% acetonitrile-H₂O containing 0.05% TFA) to obtain compound (64) as TFA salt. MS m/z 785.5 (M+H). Retention time 0.951 min.

EXAMPLE 24

(1R,3S,4S)-2-Acetyl-N-((S)-1-(((3R,4S,5S)-1-((S)-2-((1R,2R)-3-(((S)-1-hydroxy-3-phenylpropan-2-yl) amino)-1-methoxy-2-methyl-3-oxopropyl)pyrrolidin-1-yl)-3-methoxy-5-methyl-1-oxoheptan-4-yl) (methyl)amino)-3-methyl-1-oxobutan-2-yl)-2-azabicyclo[2.2.1]heptane-3-carboxamide (65)

Step 2: To the product obtained in step 1 in MeOH:H₂O (1:1 2 ml) was added LiOH (10 mg, 0.42 mmol). The reaction was stirred at rt for 16 h. The reaction mixture was concentrated and 0.040 ml HOAc was added. The crude was purified by preparative HPLC (10-50% acetonitrile-H₂O containing 0.05% TFA) to obtain (2R,3R)-3-((S)-1-((3R,4S, 5S)-4-((S)-2-((1R,3S,4S)-2-acetyl-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanoic acid. MS m/z 637.4 (M+H). Retention time 1.158 min.

Step 3: To a solution of the product obtained in step 2, (5 mg, 0.008 mmol) in DMF (1 ml) were added DIEA (2.7 mg, 0.021 mmol) and HATU (3.9 mg, 0.010 mmol). The reaction was stirred at rt for 5 min and then (S)-2-amino-3-phenylpropan-1-ol (1.6 mg, 0.010 mmol) was added. The reaction was stirred at rt for 1 h and then the crude was purified by preparative HPLC (10-60% acetonitrile-H₂O containing 0.05% TFA) to obtain compound (65). MS m/z 770.5 (M+H). Retention time 1.121 min.

(65)

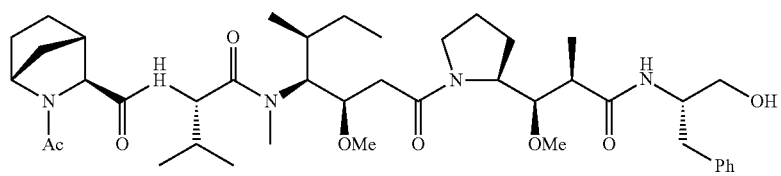

EXAMPLE 25

(1R,3S,4S)-N-((S)-1-(((3R,4S,5S)-3-Methoxy-1-((S)-2-((1R,2R)-1-methoxy-2-methyl-3-oxo-3-(((S)-2-phenyl-1-(4-phenyl-1H-imidazol-2-yl)ethyl)amino)propyl)pyrrolidin-1-yl)-5-methyl-1-oxoheptan-4-yl)(methyl)amino)-3-methyl-1-oxobutan-2-yl)-2-methyl-2-azabicyclo[2.2.1]heptane-3-carboxamide (66)

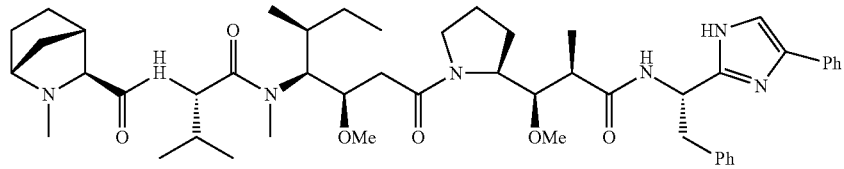

(66)

DIEA (0.0097 ml) and HATU (3.2 mg, 0.0083 mmol) were added to (2R,3R)-3-((S)-1-((3R,4S,5S)-4-((S)-N,3-dimethyl-2-((1R,3S,4S)-2-methyl-2-azabicyclo[2.2.1]heptane-3-carboxamido)butanamido)-3-methoxy-5-methylheptanoyl)pyrrolidin-2-yl)-3-methoxy-2-methylpropanoic acid TFA salt (Step 2, Example 12), 4.0 mg, 0.0055 mmol) in DMF (0.5 ml). The reaction was stirred for 15 min at rt, and (S)-2-Phenyl-1-(4-phenyl-1H-imidazol-2-yl)ethanamine (2.9 mg, 0.011 mmol) in DMF (0.5 ml) was added. The reaction mixture was stirred for 2 h at rt and then purified by preparative HPLC (20-70% acetonitrile-H$_2$O containing 0.05% TFA) to obtain (66). MS m/z 854.5 (M+1). Retention time 0.980 min.

EXAMPLE 26

(1R,3S,4S)-N-((S)-1-(((3R,4S,5S)-3-Methoxy-1-((S)-2-((1R,2R)-1-methoxy-3-(((S)-1-methoxy-3-phenylpropan-2-yl)amino)-2-methyl-3-oxopropyl)pyrrolidin-1-yl)-5-methyl-1-oxoheptan-4-yl)(methyl)amino)-3-methyl-1-oxobutan-2-yl)-2-methyl-2-azabicyclo[2.2.1]heptane-3-carboxamide (67)

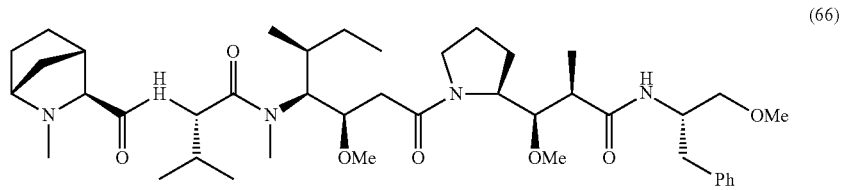

(66)

Compound (67) was obtained by the method described for compound (66) using (S)-1-methoxy-3-phenylpropan-2-amine HCl salt in place of (S)-2-phenyl-1-(5-phenyl-1H-imidazol-2-yl)ethanamine. MS m/z 756.5 (M+1). Retention time 1.046 min.

EXAMPLE 27

(1R,3S,4S)-N-((S)-1-(((3R,4S,5S)-3-Methoxy-1-
((S)-2-((1R,2R)-1-methoxy-2-methyl-3-oxo-3-(((S)-
2-phenyl-1-(1H-pyrazol-3-yl)ethyl)amino)propyl)
pyrrolidin-1-yl)-5-methyl-1-oxoheptan-4-yl)(methyl)
amino)-3-methyl-1-oxobutan-2-yl)-2-methyl-2-
azabicyclo[2.2.1]heptane-3-carboxamide (68)

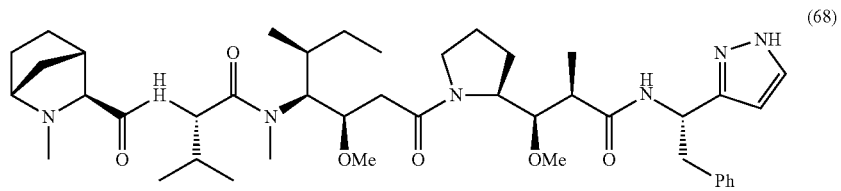
(68)

Compound (68) was obtained by the method described for compound (66) using (S)-2-phenyl-1-(1H-pyrazol-3-yl)ethanamine HCl salt in place of (S)-2-phenyl-1-(5-phenyl-1H-imidazol-2-yl)ethanamine. MS m/z 778.5 (M+1). Retention time 0.998 min.

EXAMPLE 28

(1R,3S,4S)-N-((S)-1-(((3R,4S,5S)-3-Methoxy-1-
((S)-2-((1R,2R)-1-methoxy-2-methyl-3-oxo-3-(((S)-
2-phenyl-1-(pyrimidin-2-yl)ethyl)amino)propyl)
pyrrolidin-1-yl)-5-methyl-1-oxoheptan-4-yl)(methyl)
amino)-3-methyl-1-oxobutan-2-yl)-2-methyl-2-
azabicyclo[2.2.1]heptane-3-carboxamide (69) and
(1R,3S,4S)-N-((S)-1-(((3R,4S,5S)-3-methoxy-1-
((S)-2-((1R,2R)-1-methoxy-2-methyl-3-oxo-3-(((R)-
2-phenyl-1-(pyrimidin-2-yl)ethyl)amino)propyl)
pyrrolidin-1-yl)-5-methyl-1-oxoheptan-4-yl)(methyl)
amino)-3-methyl-1-oxobutan-2-yl)-2-methyl-2-
azabicyclo[2.2.1]heptane-3-carboxamide (70)

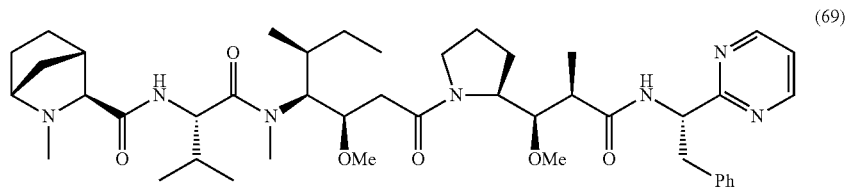
(69)

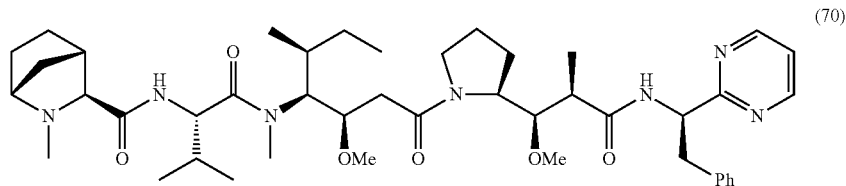
(70)

Compounds (69) and (70) were obtained by the method described for compound (66) using 2-phenyl-1-(pyrimidin-2-yl)ethanamine in place of (S)-2-phenyl-1-(5-phenyl-1H-imidazol-2-yl)ethanamine after preparative HPLC separation (30-55% acetonitrile-H$_2$O containing 0.05% TFA) of the two diasteromers. MS m/z 790.5 (M+1). Retention time 1.016 min and 1.043 min for (69) and (70), respectively.

EXAMPLE 29

(1R,3S,4S)-N-((S)-1-(((3R,4S,5S)-3-methoxy-1-((S)-2-((1R,2R)-1-Methoxy-2-methyl-3-oxo-3-(((S)-2-phenyl-1-(5-phenyl-1,3,4-oxadiazol-2-yl)ethyl)amino)propyl)pyrrolidin-1-yl)-5-methyl-1-oxoheptan-4-yl)(methyl)amino)-3-methyl-1-oxobutan-2-yl)-2-methyl-2-azabicyclo[2.2.1]heptane-3-carboxamide (71)

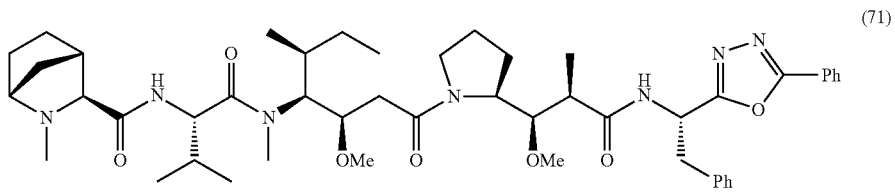 [SMILES: CC[C@H](C)[C@@H]([C@@H](CC(=O)N1CCC[C@H]1[C@H](OC)[C@@H](C)C(=O)N[C@@H](Cc1ccccc1)c1nnc(-c2ccccc2)o1)OC)N(C)C(=O)[C@@H](NC(=O)[C@@H]1[C@H]2CC[C@H](C2)N1C)C(C)C]

Compound (71) was obtained by the method described for compound (66) using (S)-2-phenyl-1-(5-phenyl-1,3,4-oxadiazol-2-yl)ethanamine in place of (S)-2-phenyl-1-(5-phenyl-1H-imidazol-2-yl)ethanamine. MS m/z 856.5 (M+1). Retention time 1.120 min.

EXAMPLE 30

(1R,3S,4S)-N-((S)-1-(((3R,4S,5S)-1-((S)-2-((1R,2R)-3-(((S)-1-(3-Aminophenyl)-3-methoxypropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (72)

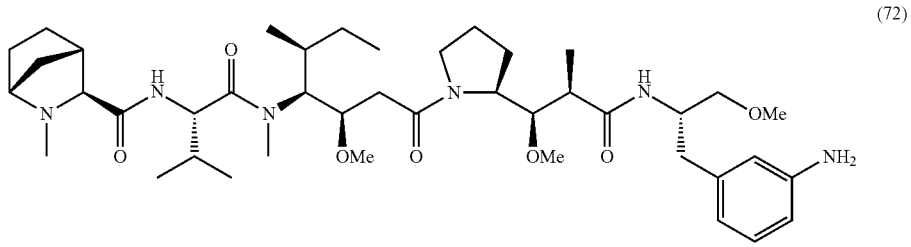 [SMILES: CC[C@H](C)[C@@H]([C@@H](CC(=O)N1CCC[C@H]1[C@H](OC)[C@@H](C)C(=O)N[C@H](COC)Cc1cccc(N)c1)OC)N(C)C(=O)[C@@H](NC(=O)[C@@H]1[C@H]2CC[C@H](C2)N1C)C(C)C]

DIEA (0.012 ml, 0.069 mmol) and HATU (7.89 mg, 0.021 mmol) were added to (2R,3R)-3-((S)-1-((3R,4S,5S)-4-((S)-N,3-dimethyl-2-((1R,3S,4S)-2-methyl-2-azabicyclo[2.2.1]heptane-3-carboxamido)butanamido)-3-methoxy-5-methylheptanoyl)pyrrolidin-2-yl)-3-methoxy-2-methylpropanoic acid (Step 2, Example 12) (10 mg, 0.014 mmol) in DMF (2 ml). The reaction was stirred at rt for 5 min and then (S)-t-butyl (3-(2-amino-3-methoxypropyl)phenyl)carbamate TFA salt (10.9 mg, 0.028 mmol) was added. The reaction was stirred at rt for 1 h and then the crude was purified by preparative HPLC (20-60% acetonitrile-H₂O containing 0.05% TFA) to obtain t-butyl (3-((S)-2-((2R,3R)-3-((S)-1-((3R,4S,5S)-4-((S)-N,3-dimethyl-2-((1R,3S,4S)-2-methyl-2-azabicyclo[2.2.1]heptane-3-carboxamido)butanamido)-3-methoxy-5-methylheptanoyl)pyrrolidin-2-yl)-3-methoxy-2-methylpropanamido)-3-methoxypropyl)phenyl)carbamate as TFA salt. MS m/z 871.5 (M+H). Retention time 1.157 min. To this product (13.6 mg, 0.014 mmol) in acetonitrile (2 ml) was added 10% hydrochloric acid (2 ml). The reaction mixture was stirred at rt for 2 h and then concentrated to give (1R,3S,4S)-N-((S)-1-(((3R,4S,5S)-1-((S)-2-((1R,2R)-3-(((S)-1-(3-aminophenyl)-3-methoxypropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (72) as HCl salt. MS m/z 771.5 (M+H). Retention time 0.883 min.

EXAMPLE 31

(1R,3S,4S)-N-((S)-1-(((3R,4S,5S)-1-((S)-2-((1R,2R)-3-(((S)-1-(4-Aminophenyl)-3-hydroxypropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (73)

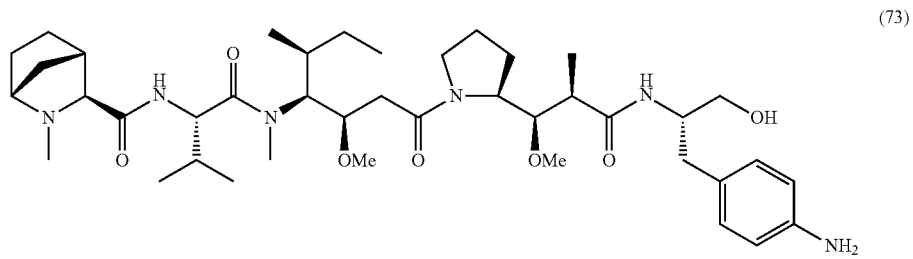 [SMILES: CC[C@H](C)[C@@H]([C@@H](CC(=O)N1CCC[C@H]1[C@H](OC)[C@@H](C)C(=O)N[C@H](CO)Cc1ccc(N)cc1)OC)N(C)C(=O)[C@@H](NC(=O)[C@@H]1[C@H]2CC[C@H](C2)N1C)C(C)C]

(73)

Compound (73) was prepared by the method described for compound (72) using (S)-t-butyl (4-(2-amino-3-hydroxypropyl)phenyl)carbamate TFA salt in place of (S)-t-butyl (3-(2-amino-3-methoxypropyl)phenyl)carbamate TFA salt. MS m/z 757.5 (M+H). Retention time 0.787 min.

EXAMPLE 32

(1R,3S,4S)-N-((S)-1-(((3R,4S,5S)-1-((S)-2-((1R,2R)-3-(((1S,2R)-1-Hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (74)

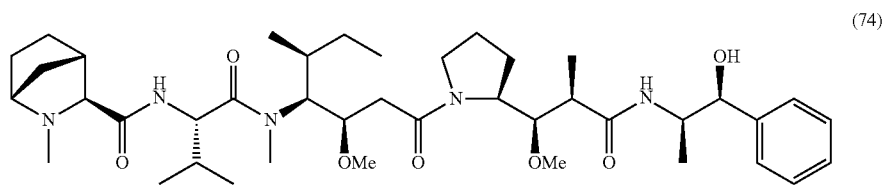 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H]1[C@H]2CC[C@H](C2)N1C)C(C)C]

(74)

DIEA (0.006 ml, 0.035 mmol) and HATU (4.0 mg, 0.010 mmol) were added to (2R,3R)-3-((S)-1-((3R,4S,5S)-4-((S)-N,3-dimethyl-2-((1R,3S,4S)-2-methyl-2-azabicyclo[2.2.1]heptane-3-carboxamido)butanamido)-3-methoxy-5-methylheptanoyl)pyrrolidin-2-yl)-3-methoxy-2-methylpropanoic acid (5 mg, 0.007 mmol) in DMF (1 ml). The reaction was stirred at rt for 5 min and then (1S,2R)-(+)-norephedrine (3 mg, 0.02 mmol) was added. The reaction mixture was stirred at rt for 1 h and then purified by preparative HPLC (20-50% acetonitrile-$H_2O$ containing 0.05% TFA). Fractions containing the desired product were combined, and 10% hydrochloric acid was added. Concentration afforded compound (74) as HCl salt. MS m/z 742.5 (M+H). Retention time 1.005 min.

Synthetic Procedure for Example N-Terminal Linked Compounds of Formula (I)

EXAMPLE 33

(S)-2-((2R,3R)-3-((S)-1-((3R,4S,5S)-4-((S)-2-((1R,3S,4S)-2-(6-(2,5-Dioxo-2,5-dihydro-1H-pyrrol-1-yl)hexanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (10)

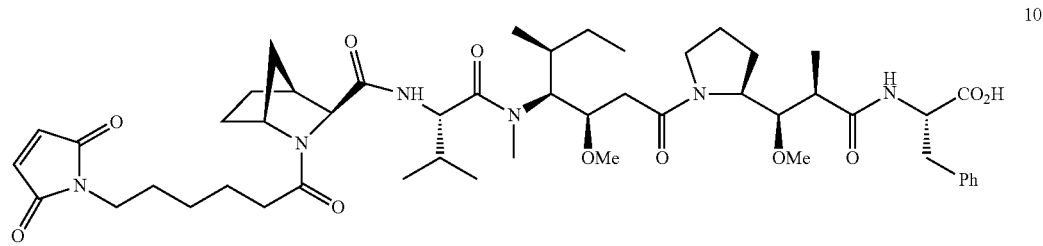 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@@H]1[C@H]2CC[C@@H](C2)N1C(=O)CCCCCN1C(=O)C=CC1=O)C(C)C]

To a solution of 6-(2,5-dioxo-2,5-dihydro-1H-pyrrol-1-yl)hexanoic acid (EMCA) (1.2 mg, 0.0058 mmol) in DMF (1.0 mL) in a 15 mL round bottom flask was added DIEA (3.0 mg, 0.023 mmol), followed by HATU (2.7 mg, 0.0070 mmol). The reaction mixture was stirred for 10 minutes before a solution of (S)-2-((2R,3R)-3-((S)-1-((3R,4S,5S)-4-((S)-2-((1R,3S,4S)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid TFA salt (2) (5.0 mg, 0.0058 mmol) in DMF (1.0 mL) was added to The reaction mixture. The reaction mixture was stirred for 1 hour. LCMS analysis indicated the reaction was complete. The crude was purified by reverse phase HPLC, C18 column, eluted with 20-80% acetonitrile-H$_2$O containing 0.05% TFA. Fractions containing product were concentrated to give compound 10, MS m/z 935.6 (M+1). Retention time 1.17 minutes.

EXAMPLE 34

(S)-2-((2R,3R)-3-((S)-1-((3R,4S,5S)-4-((S)-2-((1R,3S,4S)-2-(6-(2,5-Dioxo-2,5-dihydro-1H-pyrrol-1-yl)hexyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (11)

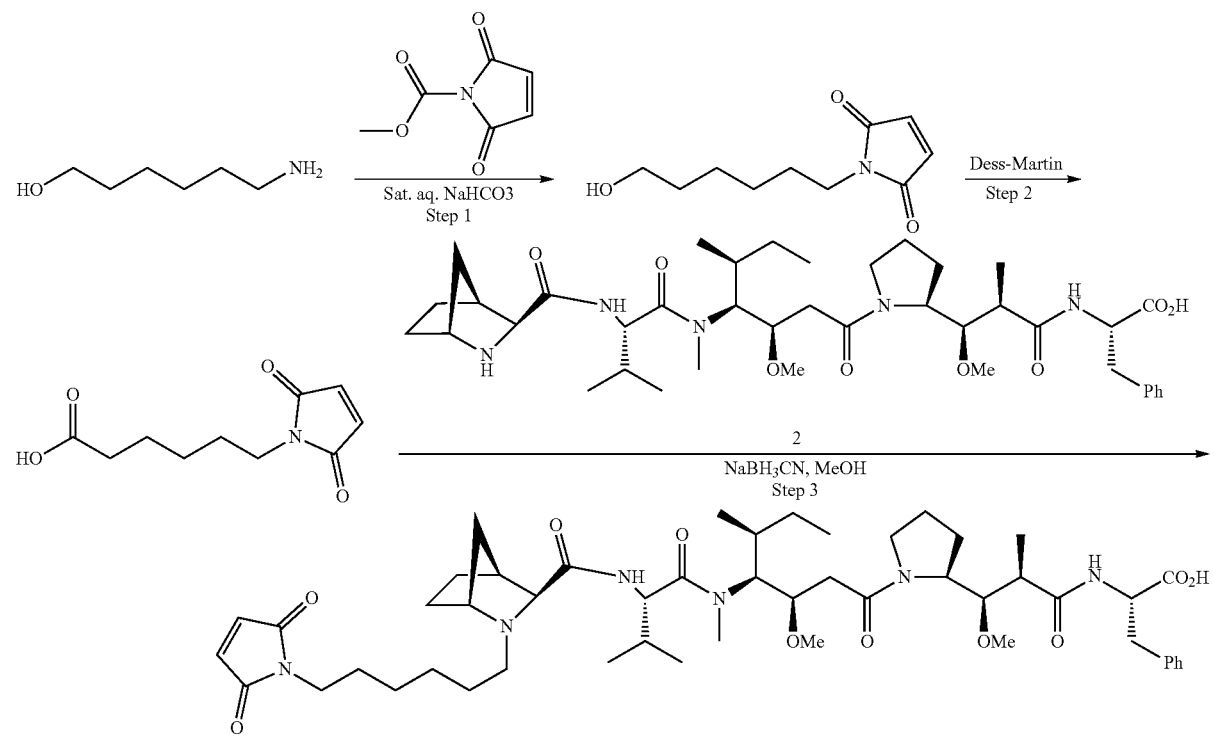

Step 1: To a 100 mL round bottom flask was added 6-amino-1-hexanol (1.00g, 6.44 mmol) in saturated NaHCO$_3$ aqueous solution (12.0 mL). The mixture was cooled at 0° C., and N-methoxycarbonylmaleimide (0.750 g, 6.44 mmol) was added. The reaction mixture was stirred at 0° C. for 1.5 hours. Then the reaction mixture was acidified at 0° C. with 2 M HCl to pH 1. The acidified reaction mixture was extracted with ethyl acetate (AcOEt). The organic layer was concentrated. The residue was dissolved in DCM, loaded onto a silica gel column, and eluted with MeOH/DCM (0-4%) to obtain 1-(6-hydroxyhexyl)-1H-pyrrole-2,5-dione as white solid, MS m/z 198.2 (M+1). $^1$H NMR (400 MHz, CDCl$_3$): δ 6.68 (s, 2H), 3.63 (t, d=6.4 Hz, 2H), 3.52 (t, d=7.2 Hz, 2H), 1.63-1.52 (m, 4H), 1.43-1.28 (m, 4H).

Step 2: To 1-(6-hydroxyhexyl)-1H-pyrrole-2,5-dione (237 mg, 1.20 mmol) in DCM (10.0 mL) was added Dess-Martin reagent (618 mg, 1.44 mmol). After 1 hour at room temperature, The reaction mixture was diluted with DCM (10 mL) and filtered. The filtrate was concentrated and purified by ISCO (silicagel, EtOAc/Hexane 0-20%) to afford 6-(2,5-dioxo-2,5-dihydro-1H-pyrrol-1-yl)hexanal as a colorless oil, MS m/z 196.2 (M+1). $^1$H NMR (400 MHz, CDCl$_3$): δ 9.76 (t, J=1.6 Hz, 1H), 6.69 (s, 2H), 3.52 (t, J=7.2 Hz, 2H), 2.43 (td, J=7.2 Hz, 1.6 Hz, 2H), 1.70-1.56 (m, 4H), 1.36-1.28 (m, 2H).

Step 3: Compound 2 (5.0 mg, 0.0067 mmol) and 6-(2,5-dioxo-2,5-dihydro-1H-pyrrol-1-yl)hexanal (6.6 mg, 0.034 mmol) were dissolved in MeOH (1.0 mL). Sodium cyanoborohydride (4.2 mg, 0.067 mmol) was added. The reaction mixture was stirred for 3 hours at room temperature. LCMS analysis indicated the completion of the reaction. The crude was purified by reverse phase HPLC using C18 column, eluted with 10-90% acetonitrile-H$_2$O containing 0.05% TFA. The factions containing the desired product were pooled and lyophilized to obtain (S)-2-((2R,3R)-3-((S)-1-((3R,4S,5S)-4-((S)-2-((1R,3S,4S)-2-(6-(2,5-dioxo-2,5-dihydro-1H-pyrrol-1-yl)hexyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid 11, MS m/z 921.6 (M+1). Retention time 1.07 minutes.

EXAMPLE 35

(S)-2-((2R,3R)-3-((S)-1-((3R,4S,5S)-4-((S)-2-((1R,3S,4S)-2-(((4-((S)-2-((S)-2-(6-(2,5-Dioxo-2,5-dihydro-1H-pyrrol-1-yl)hexanamido)-3-methylbutanamido)-5-ureidopentanamido)benzyl)oxy)carbonyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (12)

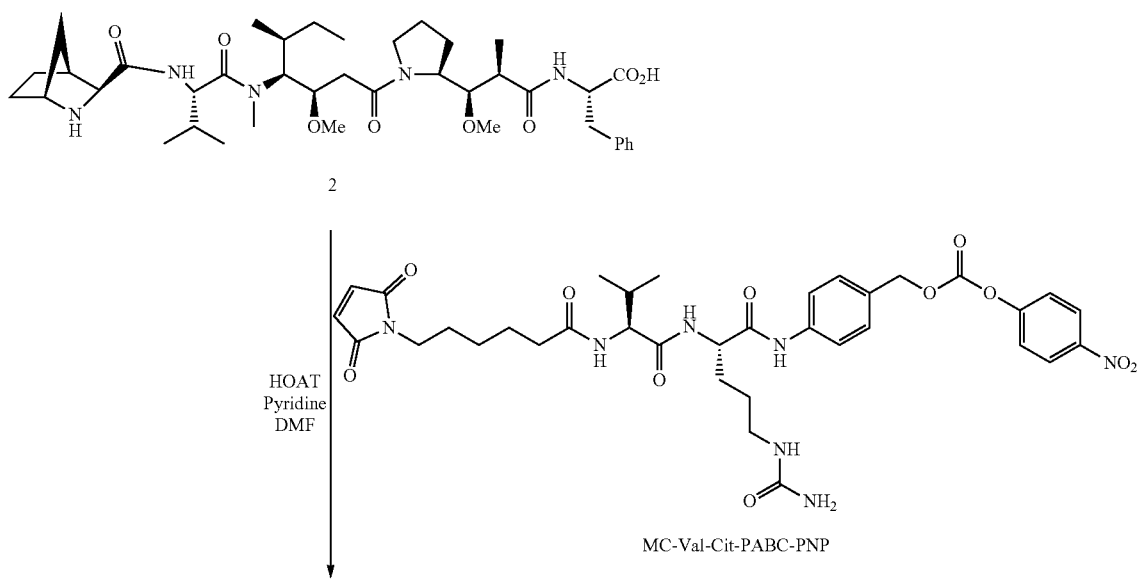

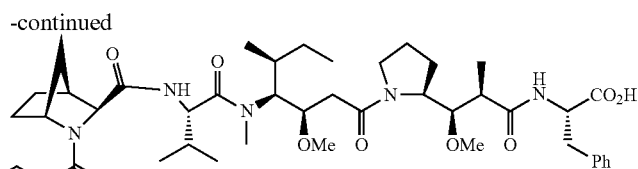

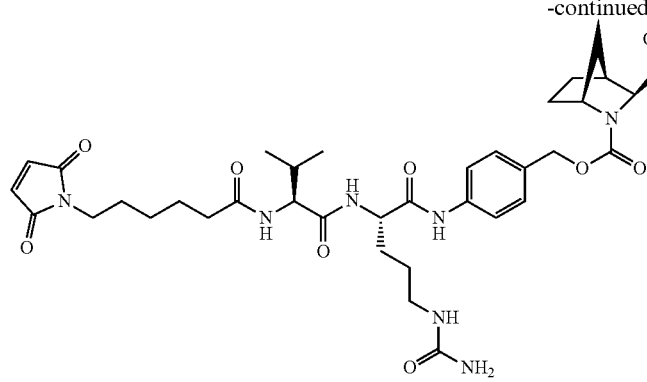

12

In a 15 mL round bottom flask at room temperature were added MC-Val-Cit-PABC-PNP (5.2 mg, 0.0070 mmol), (S)-2-((2R,3R)-3-((S)-1-((3R,4S,5S)-4-((S)-2-((1R,3S,4S)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid TFA salt (2) (5.0 mg, 0.0058 mmol) and 1-hydroxy-7-azabenzotriazole (HOAT) (0.6 mg, 0.005 mmol), followed by pyridine-DMF (1:4, 1.25 mL). To the resulting solution was added DIEA (2.3 mg, 0.018 mmol). The reaction mixture was stirred for 72 hours by which time compound 2 was consumed. The reaction mixture mixture was concentrated and the residue was purified by reverse phase HPLC, C18 column, eluted with 20-80% acetonitrile-H$_2$O, containing 0.05% TFA. The fractions containing the desired product were concentrated to give compound 12, MS m/z 1340.7 (M+1). Retention time 1.15 minutes.

EXAMPLE 36

(S)-2-((2R,3R)-3-((S)-1-((3R,4S,5S)-4-((S)-2-((1R,3S,4S)-2-(3-(2-(2-Azidoethoxy)ethoxy)propanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (13)

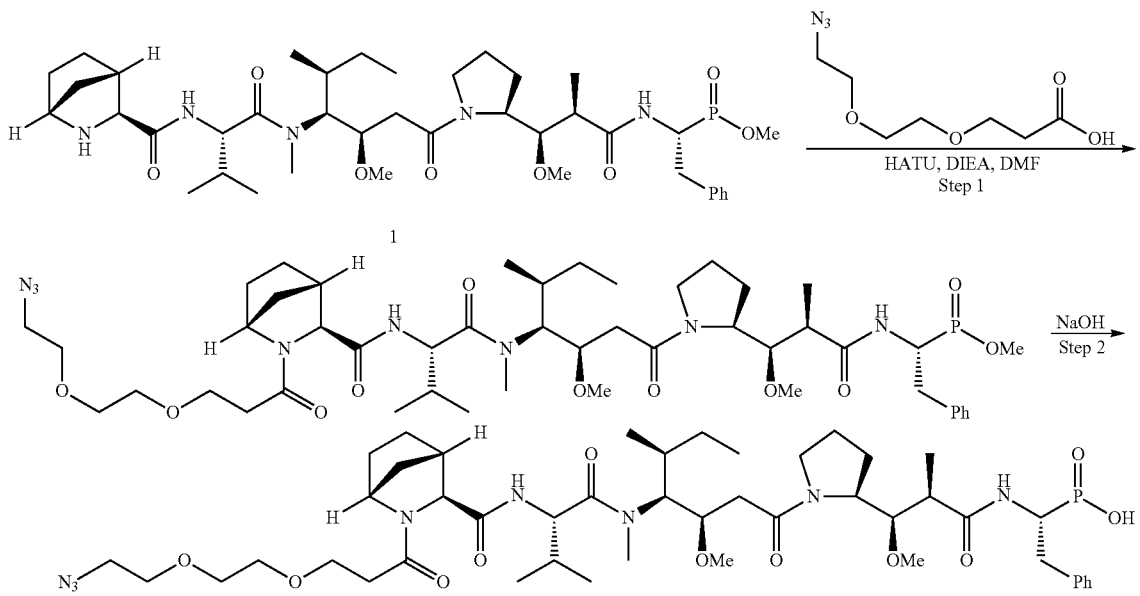

Step 1: To 3-(2-(2-Azidoethoxy)ethoxy)propanoic acid (6.6 mg, 0.033 mmol) in DMF (2 mL) were added DIEA (0.011 mL, 0.065 mmol) and HATU (10.3 mg, 0.027 mmol). After 15 minutes, compound 1 (8.2 mg, 0.010 mmol) was added. The reaction mixture was stirred for 2 hours at room temperature. LCMS analysis indicated the completion of the reaction. The crude was purified by reverse phase HPLC using C18 column, eluted with 10-90% acetonitrile-H$_2$O containing 0.05% TFA. The fractions containing the desired product were pooled and lyophilized to obtain (S)-methyl 2-((2R,3R)-3-((S)-1-((3R,4S,5S)-4-((S)-2-((1R,3S,4S)-2-

(3-(2-(2-azidoethoxy)ethoxy)propanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoate, (MS m/z 941.3 (M+1). Retention time 1.30 minutes.

Step 2: The ester product from step 1 was dissolved in acetonitrile (0.3 mL) and H$_2$O (0.2 mL). Aqueous NaOH (1.0N, 0.15 mL) was added. The reaction mixture was stirred for 30 minutes. The crude was purified by reverse phase HPLC using C18 column, eluted with 10-90% acetonitrile-H$_2$O containing 0.05% TFA. The factions containing the desired product were pooled and lyophilized to obtain compound 13 (S)-2-((2R,3R)-3-((S)-1-((3R,4S,5S)-4-((S)-2-((1R,3S,4S)-2-(3-(2-(2-azidoethoxy)ethoxy)propanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid, MS m/z 927.5 (M+1). Retention time 1.21 minutes.

EXAMPLE 37

(S)-2-((2R,3R)-3-((S)-1-((3R,4S,5S)-4-((S)-2-((1R,3S,4S)-2-(3-(2-(2-(4-((2,5-Dioxo-2,5-dihydro-1H-pyrrol-1-yl)methyl)-1H-1,2,3-triazol-1-yl)ethoxy)ethoxy)propanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (14)

14

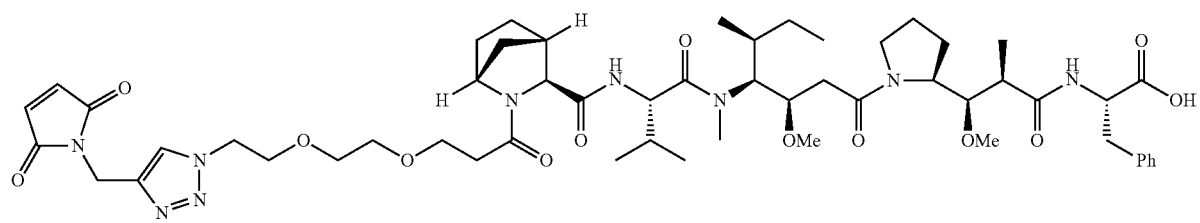

A solution of (S)-2-((2R,3R)-3-((S)-1-((3R,4S,5S)-4-((S)-2-((1R,3S,4S)-2-(3-(2-(2-azidoethoxy)ethoxy)propanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (13) (5.4 mg, 0.058 mmol), 1-(prop-2-yn-1-yl)-1H-pyrrole-2,5-dione (1.6 mg, 0.012 mmol) and CuSO$_4$ (0.7 mg, 0.005 mmol) in DMF (1.2 mL) and H$_2$O (0.3 mL) was treated with L-ascorbic acid sodium salt (2.6 mg, 0.015 mmol) and stirred at room temperature for 2 hours. LCMS analysis indicated the completion of the reaction. The crude was purified by reverse phase HPLC using C18 column, eluted with 10-90% acetonitrile-H$_2$O containing 0.05% TFA. The fractions containing the desired product were pooled and lyophilized to obtain (S)-2-((2R,3R)-3-((S)-1-((3R,4S,5S)-4-((S)-2-((1R,3S,4S)-2-(3-(2-(2-(4-((2,5-dioxo-2,5-dihydro-1H-pyrrol-1-yl)methyl)-1H-1,2,3-triazol-1-yl)ethoxy)ethoxy)propanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid 14, MS m/z 1062.5 (M+1). Retention time 1.15 minutes.

EXAMPLE 38

(S)-2-((2R,3R)-3-((S)-1-((3R,4S,5S)-4-((S)-N,3-Dimethyl-2-((1R,3S,4S)-2-(((2-(2-(2-(vinylsulfonyl)ethoxy)ethoxy)ethyl)sulfonyl)ethyl)-2-azabicyclo[2.2.1]heptane-3-carboxamido)butanamido)-3-methoxy-5-methylheptanoyl)pyrrolidin-2-yl)-3-methoxy-2-methylpropanamido)-3-phenylpropanoic acid (15)

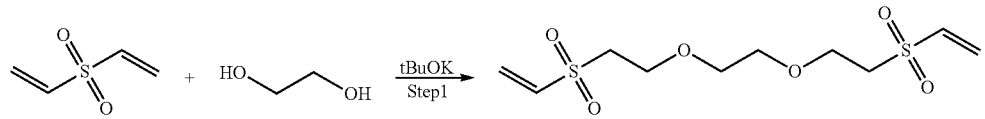

-continued

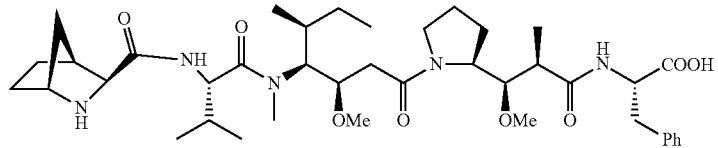 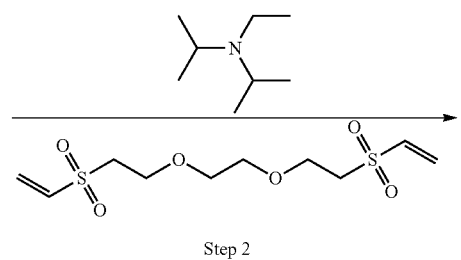

Step 2

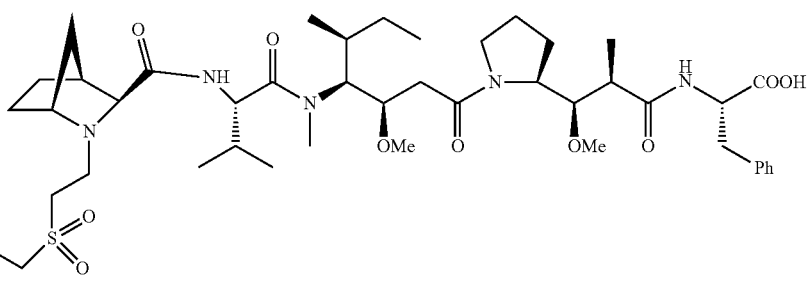

15

Step 1: t-BuOK (119 mg, 1.10 mmol) was added to a solution of divinyl sulfone (1.60 g, 13.5 mmol) and ethylene glycol (330 mg, 5.32 mmol) in THF (100 mL). The reaction mixture was stirred at room temperature for 18 hours. The solvent was removed under reduced pressure to yield a crude that was purified by silica gel column chromatography (EtOAc-Hexanes 2:1 to 3:1) to give ((2-(2-(2-vinylsulfonylethoxy)ethoxy)ethyl)sulfonyl)ethene as a colorless syrup. $^1$H NMR (400 MHz, CDCl$_3$) d 6.75 (dd, J=9.9 Hz, 16.6 Hz, 2H), 6.39 (d, J=16.6 Hz, 2H), 6.09 (d, J=9.9 Hz, 2H), 3.88 (t, J=5.7 Hz, 4H), 3.61 (s, 4H), 3.24 (t, J=5.7 Hz, 4H).

Step 2: To a solution of ((2-(2-(2-vinylsulfonylethoxy)ethoxy)ethyl)sulfonyl)ethene (13.3 mg, 0.045 mmol) in DCM-i-PrOH (2:1) were added (S)-2-((2R,3R)-3-((S)-1-((3R,4S,5S)-4-((S)-2-((1R,3S,4S)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid TFA salt (2)

(10.0 mg, 0.012 mmol) and DIEA (0.0020 mL, 0.012 mmol). The reaction mixture was heated to 80° C. for 18 hours at which time LCMS analysis indicated the reaction was 70-80% complete. The reaction mixture was concentrated, and the residue was purified by reverse phase HPLC, C18 column, eluted with 10-50% acetonitrile-H$_2$O, containing 0.05% TFA. The fractions containing he desired product were pooled and concentrated to obtain compound 15 as a TFA salt, MS m/z 1040.4 (M+1). Retention time 1.03 minutes.

EXAMPLE 39

(S)-2-((2R,3R)-3-((S)-1-((3R,4S,5S)-4-((S)-N,3-Dimethyl-2-((1R,3S,4S)-2-(3-(Methyl(2-(vinylsulfonyl)ethyl)amino)propanoyl)-2-azabicyclo[2.2.1]heptane-3-carboxamido)butanamido)-3-methoxy-5-methylheptanoyl)pyrrolidin-2-yl)-3-methoxy-2-methylpropanamido)-3-phenylpropanoic acid (16)

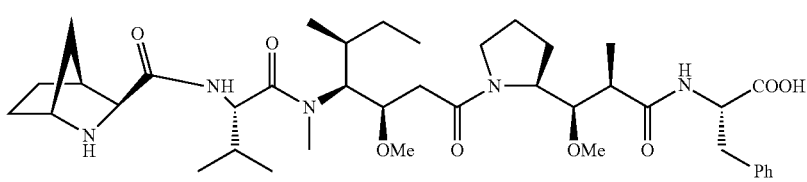 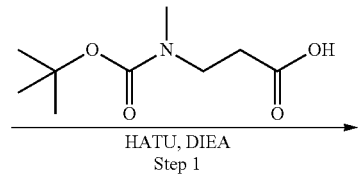

HATU, DIEA
Step 1

2

-continued

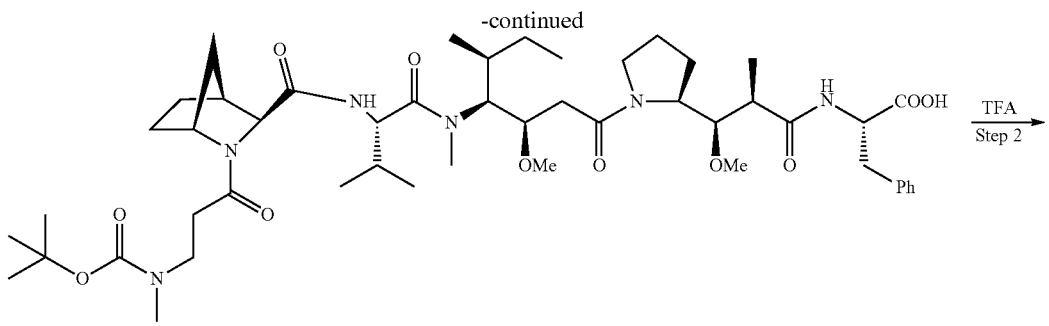

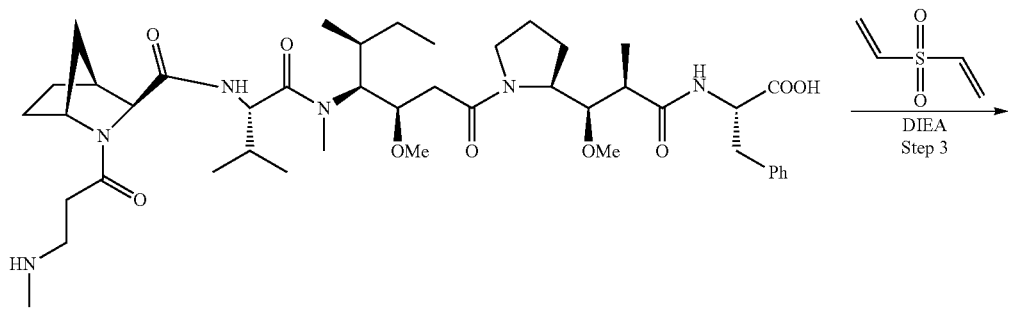

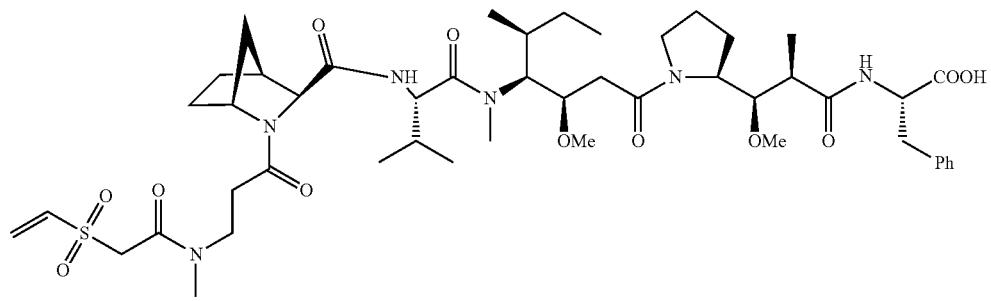

16

Step 1: To a solution of 3-((tert-butoxycarbonyl)(methyl) amino)propanoic acid (5.4 mg, 0.027 mmol) in DMF (1.0 mL) were added DIEA (0.0070 mL, 0.040 mmol) and HATU (9.1 mg, 0.024 mmol). The reaction mixture was stirred for 5 minutes and (S)-2-((2R,3R)-3-((S)-1-((3R,4S,5S)-4-((S)-2-((1R,3S,4S)-2-azabicyclo[2.2.1]heptane-3-carboxamido)-N,3-dimethylbutanamido)-3-methoxy-5-methylheptanoyl) pyrrolidin-2-yl)-3-methoxy-2-methylpropanamido)-3-phenylpropanoic acid TFA salt (2) (11.4 mg, 0.013 mmol) was added. The reaction was complete within 1 hour as judged by LCMS analysis. The crude was purified by reverse phase HPLC, C18 column, eluted with 10-70% acetonitrile-H$_2$O, containing 0.05% TFA. The fractions containing the desired product were pooled and concentrated to obtain (S)-2-((2R,3R)-3-((S)-1-((3R,4S,5S)-4-((S)-2-((1R, 3S,4S)-2-(3-((tert-butoxycarbonyl)(methyl)amino)propanoyl)-2-azabicyclo[2.2.1]heptane-3-carboxamido)-N,3-dimethylbutanamido)-3-methoxy-5-methylheptanoyl) pyrrolidin-2-yl)-3-methoxy-2-methylpropanamido)-3-phenylpropanoic acid, MS m/z 927.5 (M+1). Retention time 1.28 minutes.

Step 2: To a solution of the product obtained in step 1 (6.4 mg, 0.0069 mmol) in DCM (2.0 mL) was added TFA (1.0 mL). The reaction mixture was stirred at room temperature for 1 hour and concentrated to obtain (S)-2-((2R,3R)-3-((S)-1-((3R,4S,5S)-4-((S)-N,3-dimethyl-2-((1R,3S,4S)-2-(3-(methylamino)propanoyl)-2-azabicyclo[2.2.1]heptane-3-carboxamido)butanamido)-3-methoxy-5-methylheptanoyl) pyrrolidin-2-yl)-3-methoxy-2-methylpropanamido)-3-phenylpropanoic acid TFA salt. MS m/z 827.4 (M+1). Retention time 0.99 minutes. This product was used in the next step without further purification.

Step 3: To a solution of the product TFA salt obtained in step 2 (6.5 mg, 0.0069 mmol) in i-PrOH (2.0 mL) were added divinyl sulfone (20.0 mg, 0.169 mmol) and DIEA (0.010 mL, 0.057 mmol). The reaction mixture was stirred at 80° C. for 1 hour, at which time the reaction was complete as judged by LCMS analysis and the reaction mixture was concentrated. The residue was purified by reverse phase HPLC, C18 column, eluted with 10-60% acetonitrile-H$_2$O, containing 0.05% TFA. The fractions containing the desired product were pooled and concentrated to obtain compound 16, MS m/z 945.4 (M+1). Retention time 0.99 minutes.

EXAMPLE 40

(1R,3S,4S)-2-(6-(2,5-Dioxo-2,5-dihydro-1H-pyrrol-1-yl)hexanoyl)-N-((S)-1-(((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-azabicyclo[2.2.1]heptane-3-carboxamide (17)

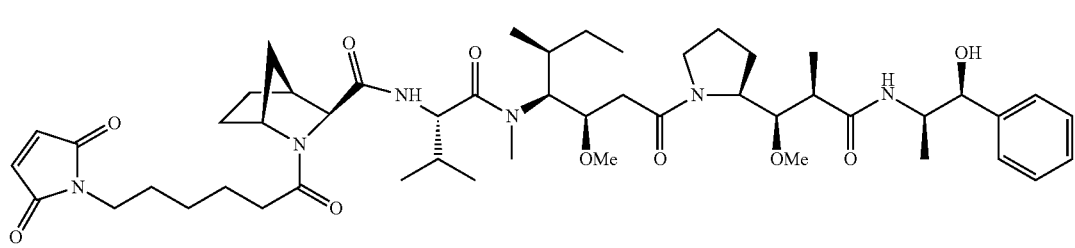

17

This compound was synthesized using the same method as described for compound (4) (in Example 4) from EMCA (5.5 mg, 0.026 mmol), DIEA (10.0 mg, 0.078 mmol), HBTU (9.8 mg, 0.026 mmol) and (1R,3S,4S)-N-((S)-1-(((3R,4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-azabicyclo[2.2.1]heptane-3-carboxamide TFA salt (3) (21.8 mg, 0.026 mmol). compound 17 was obtained after purification by reverse phase HPLC, MS m/z 921.5 (M+1). Retention time 1.25 minutes.

EXAMPLE 41

(S)-2-((2R,3R)-3-((S)-1-((3R,4S,5S)-4-((S)-2-((1R,3S,4S)-2-(6-Mercaptohexyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (18)

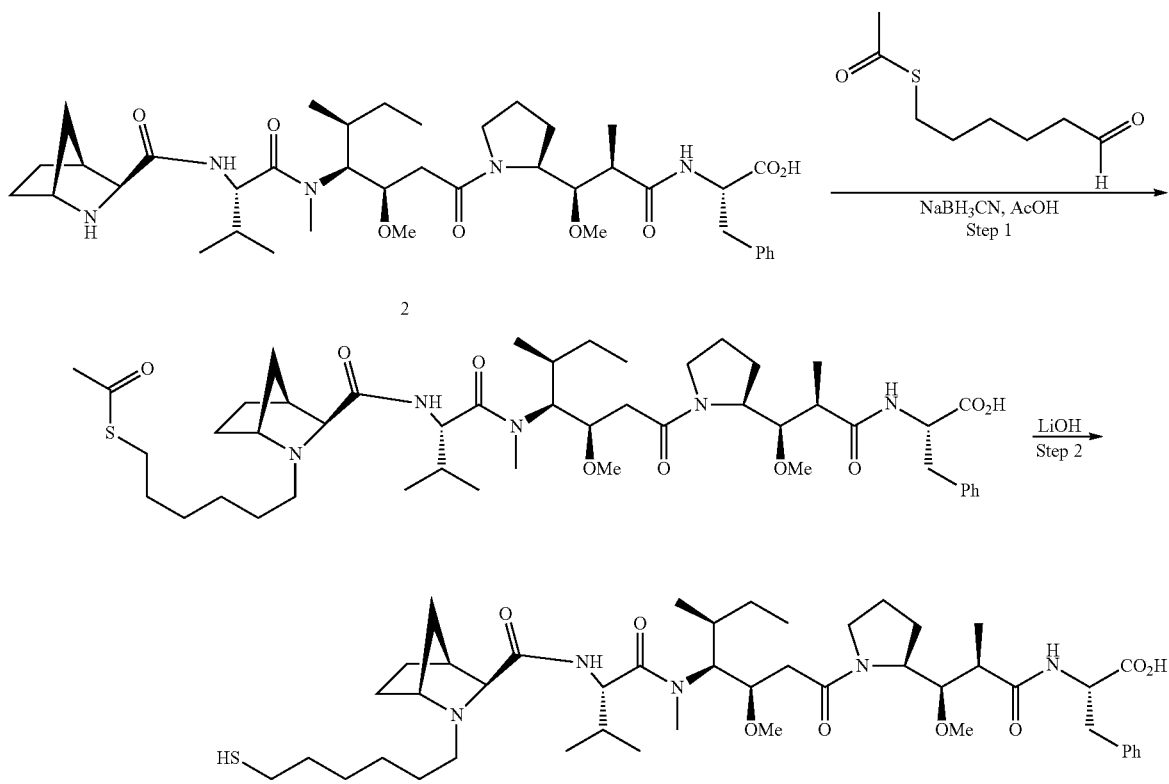

18

Step 1: To a solution of S-(6-oxohexyl) ethanethioate (4.28 mg, 0.025 mmol) and (S)-2-((2R,3R)-3-((S)-1-((3R,4S,5S)-4-((S)-2-((1R,3S,4S)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid TFA salt (2) (7.0 mg, 0.0082 mmol) in MeOH (2.0 ml) was added acetic acid (0.0050 mL, 0.083 mmol) and sodium cyanoborohydride (2.57 mg, 0.041 mmol). The reaction mixture was heated at 50° C. for 2 hours and the crude was purified by reverse phase HPLC, C18 column, eluted with 20-70% acetonitrile-H$_2$O, containing 0.05% TFA. The fractions containing the desired product were combined and concentrated, affording (S)-2-((2R,3R)-3-((S)-1-((3R,4S,5S)-4-((S)-2-((1R,3S,4S)-2-(6-(acetylthio)hexyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid, MS m/z 900.5 (M+1), retention time 1.17 minutes.

Step 2: The product obtained in step 1 was dissolved in MeOH—H$_2$O (2:1, 3.0 mL). To the solution was added lithium hydroxide (5.0 mg, 0.21 mmol). The reaction mixture was stirred at room temperature for 0.5 hour and then concentrated to approximately 1.5 mL. The crude was purified by reverse phase HPLC, C18 column, eluted with 20-60% acetonitrile-H$_2$O, containing 0.05% TFA. The fractions containing desired product were pooled and concentrated to obtain compound 18, MS m/z 858.5 (M+1). Retention time 1.16 minutes.

EXAMPLE 42

(S)-2-((2R,3R)-3-((S)-1-((3R,4S,5S)-4-((S)-2-((1R,3S,4S)-2-(6-(3-Amino-4-formylphenoxy)hexyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (19)

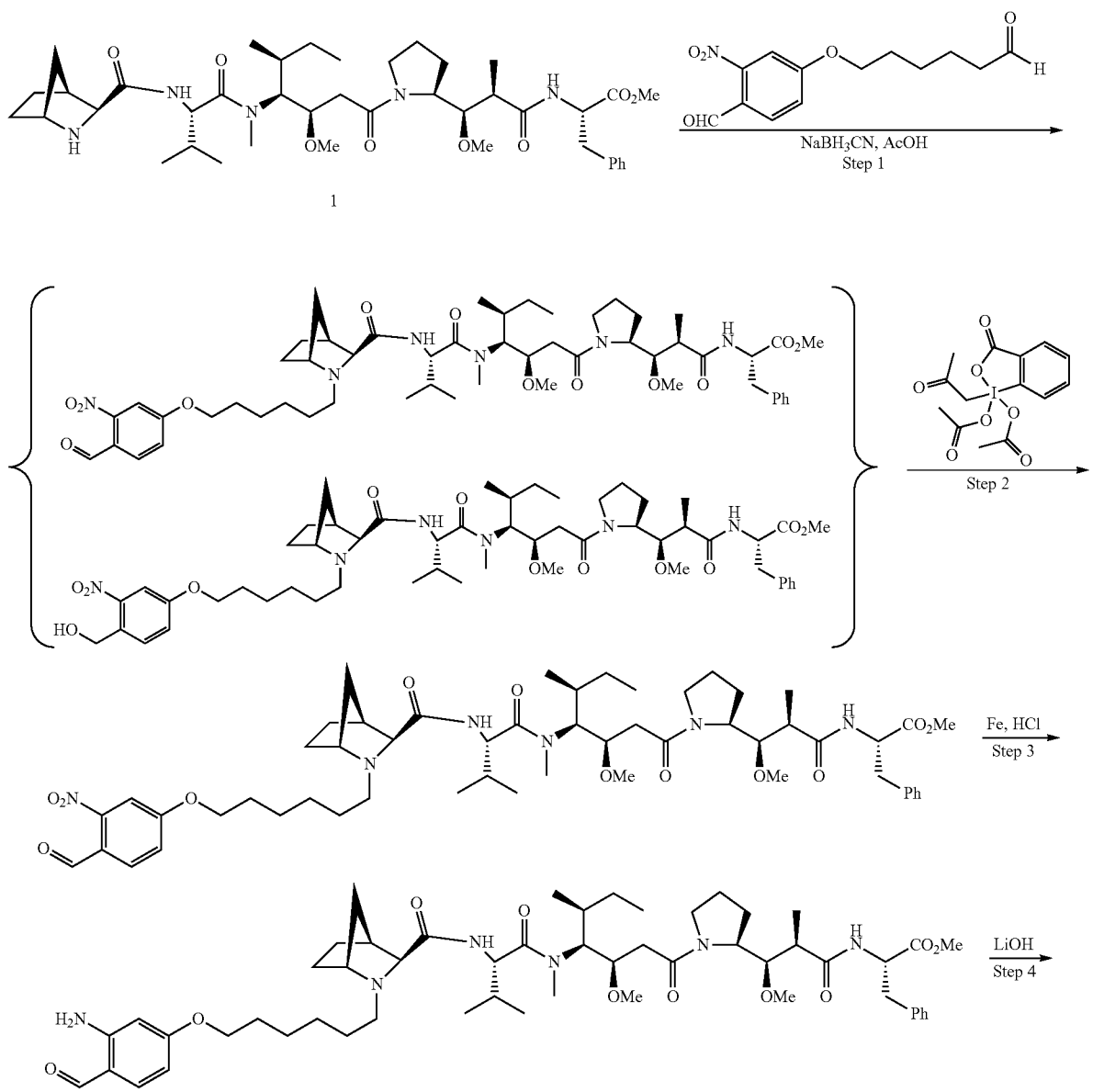

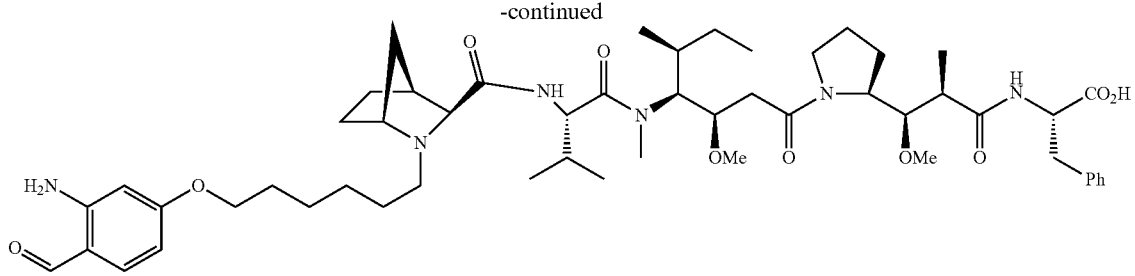

19

Step 1: To a solution of 2-nitro-4-((6-oxohexyl)oxy)benzaldehyde (20.1 mg, 0.076 mmol) and (S)-methyl 2-((2R,3R)-3-((S)-1-((3R,4S,5S)-4-((S)-2-((1R,3S,4S)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoate (1) (16.5 mg, 0.019 mmol) in DMF (2.0 mL) were added acetic acid (0.0076 mL, 0.13 mmol) and sodium cyanoborohydride (11.9 mg, 0.190 mmol). The reaction mixture was heated at 50° C. for 2 hours and the crude was purified by reverse phase HPLC, C18 column, eluted with 20-70% acetonitrile-H$_2$O, containing 0.05% TFA. The fractions containing the desired aldehyde (MS m/z 1005.5 (M+1), retention time 1.27 minutes) and the desired alcohol (MS m/z 1007.5 (M+1), retention time 1.21 minutes) intermediates were combined and concentrated and used in the next step.

Step 2: The mixture obtained from step 1 containing the aldehyde and the alcohol was dissolved in DCM (2.0 mL) and Dess-Martin periodinane (4.0 mg, 0.0095 mmol) was added. The reaction mixture was stirred at room temperature for 2 hours. The reaction mixture mixture was then washed with Na$_2$S$_2$O$_3$ aqueous solution and extracted with DCM. The DCM layer was dried over anhydrous MgSO$_4$, filtered and concentrated. The crude was purified by reverse phase HPLC, C18 column, eluted with 20-70% acetonitrile-H$_2$O, containing 0.05% TFA. The fractions containing the desired product were pooled and concentrated to give (S)-methyl 2-((2R,3R)-3-((S)-1-((3R,4S,5S)-4-((S)-2-((1R,3S,4S)-2-(6-(4-formyl-3-nitrophenoxy)hexyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoate TFA salt, MS m/z 1005.5 (M+1). Retention time 1.27 minutes. The product also contained some hydrolyzed acid, MS m/z 991.5 (M+1). Retention time 1.22 minutes.

Step 3: To a solution of the product obtained in step 2 (16.9 mg, 0.015 mmol) in 70% EtOH in water were added iron powder (0.8 mg, 0.02 mmol) and HCl (0.1N, 0.15 mL, 0.015 mmol). The reaction mixture was stirred vigorously at room temperature for 18 hours. Brown precipitate formed. The mixture was filtered through a Celite plug and the filtrate was concentrated. The crude was purified by ISCO, C18 column, eluted with 30-100% acetonitrile-H$_2$O. The fractions containing the desired product were pooled and concentrated to obtain (S)-methyl 2-((2R,3R)-3-((S)-1-((3R,4S,5S)-4-((S)-2-((1R,3S,4S)-2-(6-(3-amino-4-formylphenoxy)hexyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoate, MS m/z 975.5 (M+1). Retention time 1.23 minutes.

Step 4: To a solution of the product obtained in step 3 (4.6 mg, 0.0047 mmol) in MeOH—H$_2$O (1.5:1, 2.5 mL) was added lithium hydroxide (10.0 mg, 0.435 mmol). The reaction mixture was stirred at room temperature for 4 hours. The reaction mixture was concentrated to about 50% volume and acidified with 1N HCl to pH 5. The crude was purified by ISCO, C18 column, eluted with 30-75% acetonitrile-H$_2$O. The fractions containing the desired product were pooled, neutralized with 0.3 mg of LiOH, and lyophilized to obtain compound 19, MS m/z 961.5 (M+1). Retention time 1.15 minutes.

EXAMPLE 43

Coenzyme A adduct of (S)-2-((2R,3R)-3-((S)-1-((3R,4S,5S)-4-((S)-2-((1R,3S,4S)-2-(6-(2,5-dioxo-2,5-dihydro-1H-pyrrol-1-yl)hexanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (20)

20

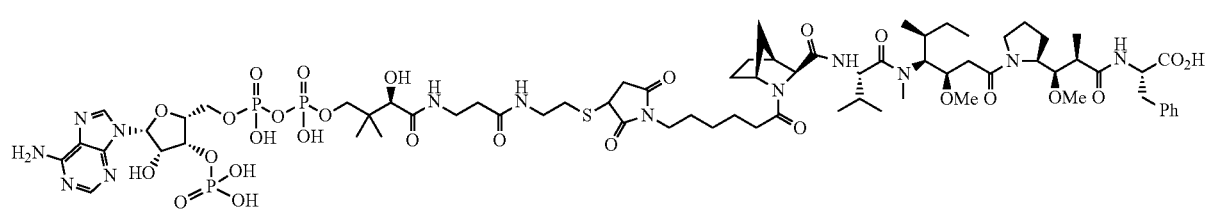

To a solution of Coenzyme A (CoA) trilithium salt (7.6 mg, 0.0096 mmol) in 100 mM phosphate buffer containing 5 mM EDTA at pH 7.5 was added a solution of (S)-2-((2R, 3R)-3-((S)-1-((3R,4S,5S)-4-((S)-2-((1R,3S,4S)-2-(6-(2,5-dioxo-2,5-dihydro-1H-pyrrol-1-yl)hexanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (17) (9.0 mg, 0.0096 mmol) in DMSO (0.048 mL). The reaction mixture was let stand at room temperature for 1 hour, at which time the reaction was complete as judged by LCMS analysis. The sample was purified by reverse phase HPLC, C18 column, eluted with 20-60% acetonitrile-H₂O, containing 0.05% TFA. The fractions containing the desired product were pooled and concentrated to obtain the CoA adduct 20, MS m/z 852 (M/2+1)). Retention time 0.98 minutes.

EXAMPLE 44

(S)-2-((2R,3R)-3-((S)-1-((3R,4S,5S)-4-((S)-2-((1R,3S,4S)-2-(6-(2-Bromoacetamido)hexanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (21)

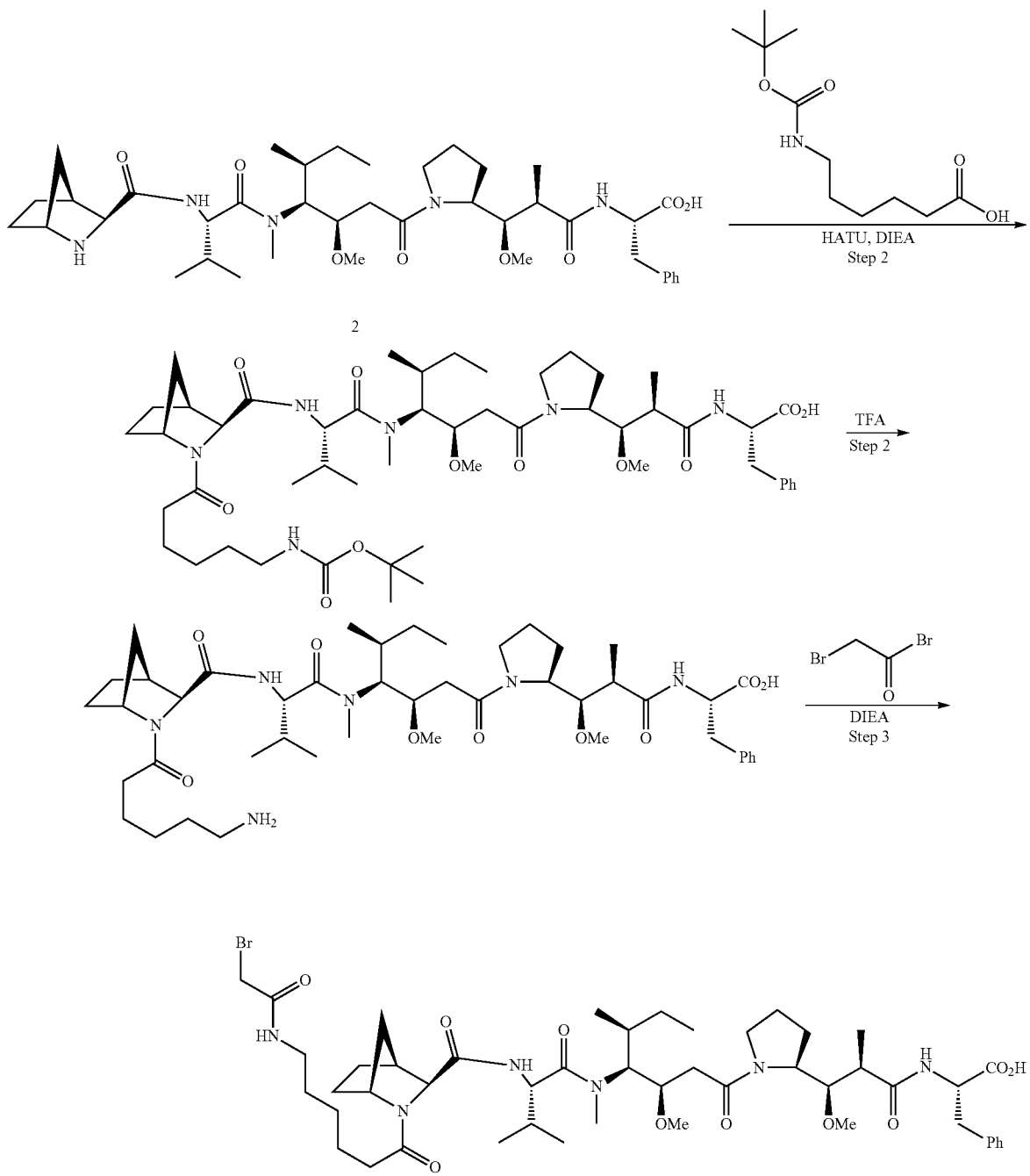

Step 1: To a solution of 6-((tert-butoxycarbonyl)amino) hexanoic acid (12 mg, 0.051 mmol) in DMF (2.0 mL) were added DIEA (18 mg, 0.14 mmol) and HATU (18 mg, 0.047 mmol). The reaction mixture was stirred at room temperature for 10 minutes before (S)-2-((2R,3R)-3-((S)-1-((3R,4S,5S)-4-((S)-2-((1R,3S,4S)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (2) (40 mg, 0.047 mmol) was added. The reaction was complete within half an hour. The crude was purified by reverse phase HPLC, C18 column, eluted with 20-70% acetonitrile-H$_2$O, containing 0.05% TFA. The factions containing the desired product were pooled and concentrated to obtain (S)-2-((2R,3R)-3-((S)-1-((3R,4S,5S)-4-((S)-2-((1R,3S,4S)-2-(6-((tert-butoxycarbonyl)amino)hexanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid, MS m/z 955.5 (M+1). Retention time 1.32 minutes.

Step 2: To a solution of the compound obtained in step 1 (15.6 mg, 0.016 mmol) in DCM (2.0 mL) was added TFA (1.0 mL). The reaction mixture was stirred at room temperature for 30 minutes and concentrated to obtain (S)-2-((2R,3R)-3-((S)-1-((3R,4S,5S)-4-((S)-2-((1R,3S,4S)-2-(6-aminohexanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid TFA salt, MS m/z 855.5 (M+1). Retention time 1.01 minutes.

Step 3: (S)-2-((2R,3R)-3-((S)-1-((3R,4S,5S)-4-((S)-2-((1R,3S,4S)-2-(6-aminohexanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid TFA salt (20 mg, 0.021 mmol) was dissolved in DCM and treated with DIEA (12 mg, 0.093 mmol). The reaction mixture was cooled to 0° C. To the reaction mixture was then added a solution of 2-bromoacetyl bromide (9.0 mg, 0.045 mmol) in DCM (0.2 mL) with stirring. The reaction mixture was stirred at 0° C. for 10 min and LCMS analysis showed that the amine starting material was consumed. Saturated aqueous NaHCO$_3$ was added to quench the reaction. The reaction mixture mixture was extracted with DCM (5 mL×3). The organic layers were combined and concentrated. The crude was purified by reverse phase HPLC, C18 column, eluted with 30-45% acetonitrile-H$_2$O, containing 0.05% TFA. The fractions were pooled and concentrated to obtain compound 21, MS m/z 975.3 (M+1). Retention time 1.19 minutes.

EXAMPLE 45

(S)-2-((2R,3R)-3-((S)-1-((3R,4S,5S)-4-((S)-2-((1R,3S,4S)-2-(6-(Aminooxy)hexanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (22)

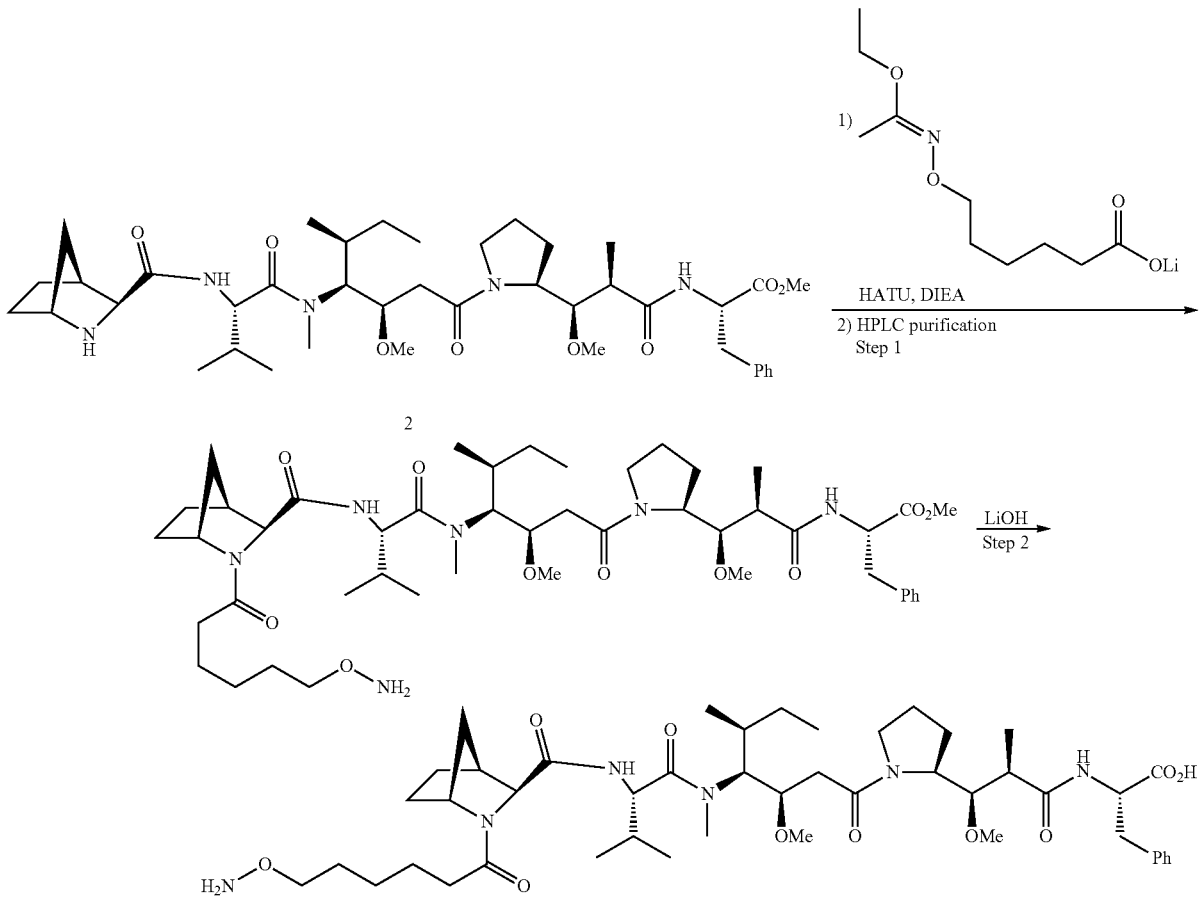

Step 1: To a solution of lithium 6-(((1-ethoxyethylidene)amino)oxy)hexanoate (6.3 mg, 0.028 mmol) in DMF (1.0 mL) was added HATU (8.9 mg, 0.023 mmol). The reaction mixture was stirred at room temperature for 20 minutes before the whole reaction mixture was added to a solution of (S)-methyl 2-((2R,3R)-3-((S)-1-((3R,4S,5S)-4-((S)-2-((1R,3S,4S)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoate TFA salt (1) (20 mg, 0.021 mmol) and DIEA (6.0 mg, 0.047 mmol) in DMF (1.0 mL). After stirring at room temperature for 2 hours, the reaction mixture was purified by reverse phase HPLC, C18 column, eluted with 40-80% acetonitrile-$H_2O$, containing 0.05% TFA. The fractions containing the desired product were pooled and concentrated. LCMS analysis revealed that the protecting group on the alkoxylamine moiety was removed to give TFA salt of (S)-methyl 2-((2R,3R)-3-((S)-1-((3R,4S,5S)-4-((S)-2-((1R,3S,4S)-2-(6-(aminooxy)hexanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoate, MS m/z 885.5 (M+1). Retention time 1.10 minutes.

Step 2: To a solution of the compound obtained in Step 1 (24.3 mg, 0.023 mmol) in MeOH—$H_2O$ (1:1, 2.0 mL) was added lithium hydroxide (20 mg, 0.84 mmol). The reaction was monitored by LCMS. Upon completion the crude was purified by reverse phase HPLC, C18 column, eluted with 20-40% acetonitrile-$H_2O$, containing 0.05% TFA. The fractions containing the desired product were concentrated to give compound 22 TFA salt, MS m/z 871.5 (M+1). Retention time 1.03 minutes.

EXAMPLE 46

(S)-2-((2R,3R)-3-((S)-1-((3R,4S,5S)-4-((S)-2-((1R,3S,4S)-2-(6-((S)-Aziridine-2-carboxamido)hexanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (23)

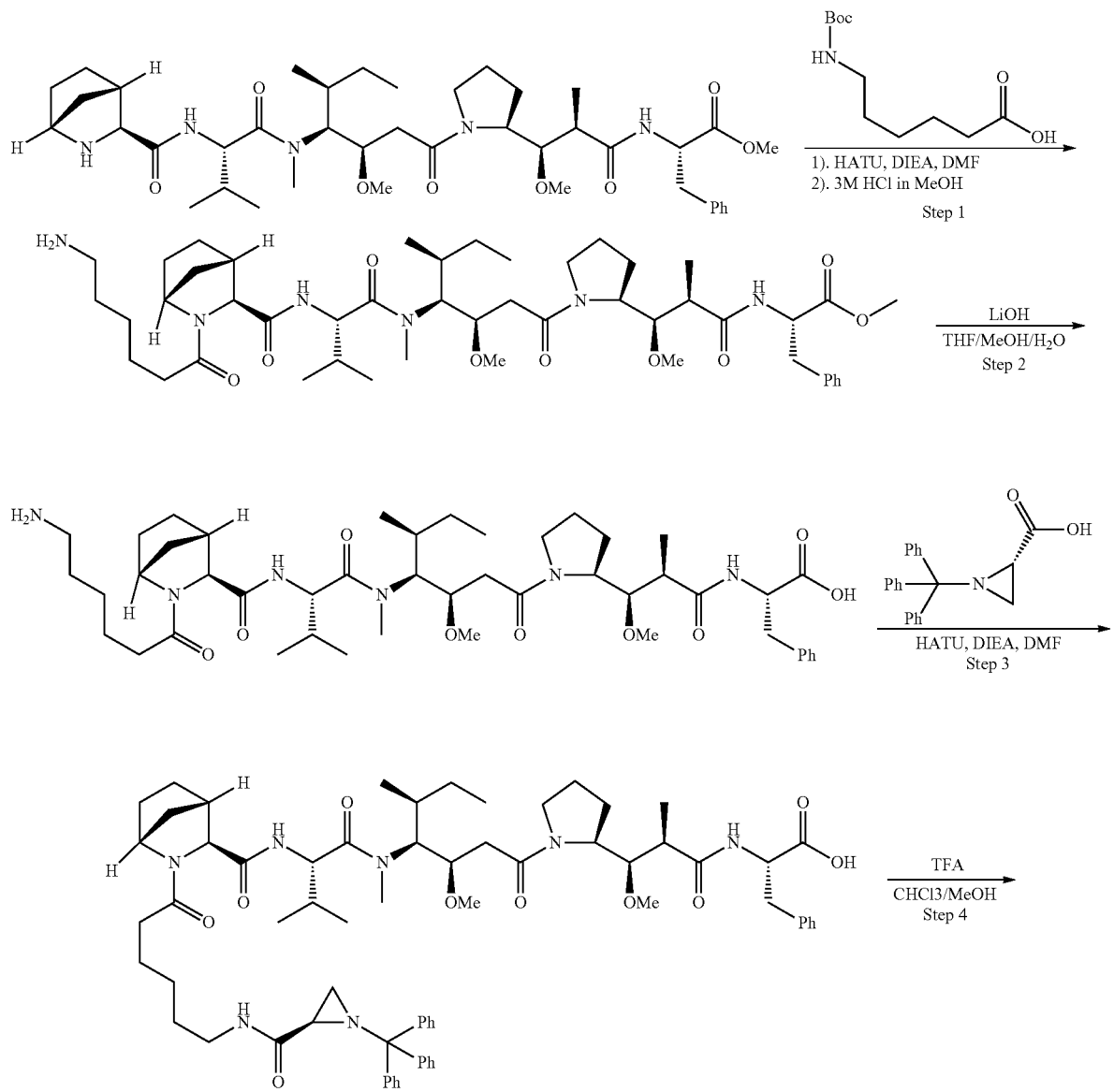

-continued

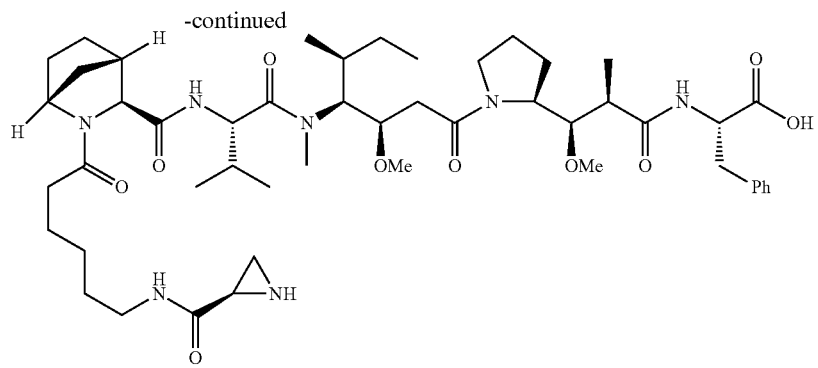

23

Step 1: In a 7 mL vial, 6-((tert-butoxycarbonyl)amino)hexanoic acid (16 mg, 0.069 mmol) was dissolved in anhydrous DMF (2 mL). DIEA (0.036 mL, 0.21 mmol) and HATU (24 mg, 0.062 mmol) were added. The reaction mixture was stirred for 10 minutes before (S)-methyl 2-((2R,3R)-3-((S)-1-((3R,4S,5S)-4-((S)-2-((1R,3S,4S)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoate (1, HCl salt, 30 mg, 0.034 mmol) was added. The reaction mixture was stirred for an additional 2 hours at room temperature. LCMS indicated the completion of the reaction. The crude was purified by reverse phase HPLC using C18 column, eluted with 10-90% ACN-H$_2$O containing 0.05% TFA. The fractions containing the desired product were pooled and lyophilized to obtain (S)-methyl 2-((2R,3R)-3-((S)-1-((3R,4S,5S)-4-((S)-2-((1R,3S,4S)-2-(6-((tert-butoxycarbonyl)amino)hexanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoate. MS m/z 969.6 (M+1). Retention time 1.42 minutes. The product thus obtained (21 mg, 0.022 mmol) was dissolved in HCl in MeOH (3M, 2 mL). The solvent was removed slowly under reduced pressure. LCMS analysis of the residue indicated the complete removal of the Boc group. The residue was taken up in acetonitrile and water and lyophilized to give (S)-methyl 2-((2R,3R)-3-((S)-1-((3R,4S,5S)-4-((S)-2-((1R,3S,4S)-2-(6-aminohexanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoate as HCl salt. MS m/z 869.5 (M+1). Retention time 1.01 minutes.

Step 2: The product from the previous step (10 mg, 0.012 mmol) was dissolved in THF (0.8 mL), MeOH (0.1 mL) and H$_2$O (0.1 mL). Lithium hydroxide monohydrate (4.83 mg, 0.115 mmol) was added. The reaction mixture was stirred for 4 hours at room temperature. LCMS indicated the completion of the reaction. The solvents were removed under reduced pressure. The residue was neutralized using 0.1N hydrochloric acid, taken up in acetonitrile and H$_2$O, and lyophilized to give (S)-2-((2R,3R)-3-((S)-1-((3R,4S,5S)-4-((S)-2-((1R,3S,4S)-2-(6-aminohexanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid containing some LiCl. MS m/z 855.6 (M+1). Retention time 0.98 minutes.

Step 3: In a 7 mL vial (S)-1-tritylaziridine-2-carboxylic acid (7.6 mg, 0.023 mmol) was dissolved in anhydrous DMF (2 mL). DIEA (0.010 mL, 0.021 mmol) and HATU (7.9 mg, 0.021 mmol) were added. The reaction mixture was stirred for 10 minutes before (S)-2-((2R,3R)-3-((S)-1-((3R,4S,5S)-4-((S)-2-((1R,3S,4S)-2-(6-aminohexanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (10 mg, 0.012 mmol). The reaction mixture was stirred at room temperature for an additional 2 hours. LCMS indicated the completion of the reaction. The solvent was removed under reduced pressure. The crude was purified by reverse phase ISCO using C18aq column (5.5 g), eluted with 10-100% acetonitrile-H$_2$O. The fractions containing the desired product were pooled and lyophilized to give (S)-2-((2R,3R)-3-((S)-1-((3R,4S,5S)-4-((S)-N,3-dimethyl-2-((1R,3S,4S)-2-(6-((S)-1-tritylaziridine-2-carboxamido)hexanoyl)-2-azabicyclo[2.2.1]heptane-3-carboxamido)butanamido)-3-methoxy-5-methylheptanoyl)pyrrolidin-2-yl)-3-methoxy-2-methylpropanamido)-3-phenylpropanoic acid. MS m/z 1166.5 (M+1). Retention time 1.49 minutes.

Step 4: The product from Step 3 (4.0 mg, 0.0034 mmol) was dissolved in MeOH/CHCl$_3$ (1:1, 1 mL) and cooled to 0° C. TFA (0.0040 mL, 0.051 mmol) was added dropwise. The reaction mixture was warmed to room temperature and stirred for 1 hour. LCMS indicated that the reaction was approximately 60% completed. TFA (0.0040 mL, 0.051 mmol) was added again. After another 1 hour at room temperature LCMS indicated the reaction was complete. The solvents were evaporated under reduced pressure. The residue was dissolved in MeOH and purified by reverse phase ISCO using C18aq column (5.5 g), eluted with 10-100% acetonitrile-H$_2$O. The fractions containing the desired product were pooled and lyophilized to give (S)-2-((2R,3R)-3-((S)-1-((3R,4S,5S)-4-((S)-2-((1R,3S,4S)-2-(6-((S)-aziridine-2-carboxamido)hexanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (23). MS m/z 924.6 (M+1). Retention time 1.012 minutes.

EXAMPLE 47

S)-2-((2R,3R)-3-((S)-1-((3R,4S,5S)-4-((S)-2-((1R,3S,4S)-2-(4-(4-((2,5-Dioxo-2,5-dihydro-1H-pyrrol-1-yl)methyl)-1H-1,2,3-triazol-1-yl)butanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (24)

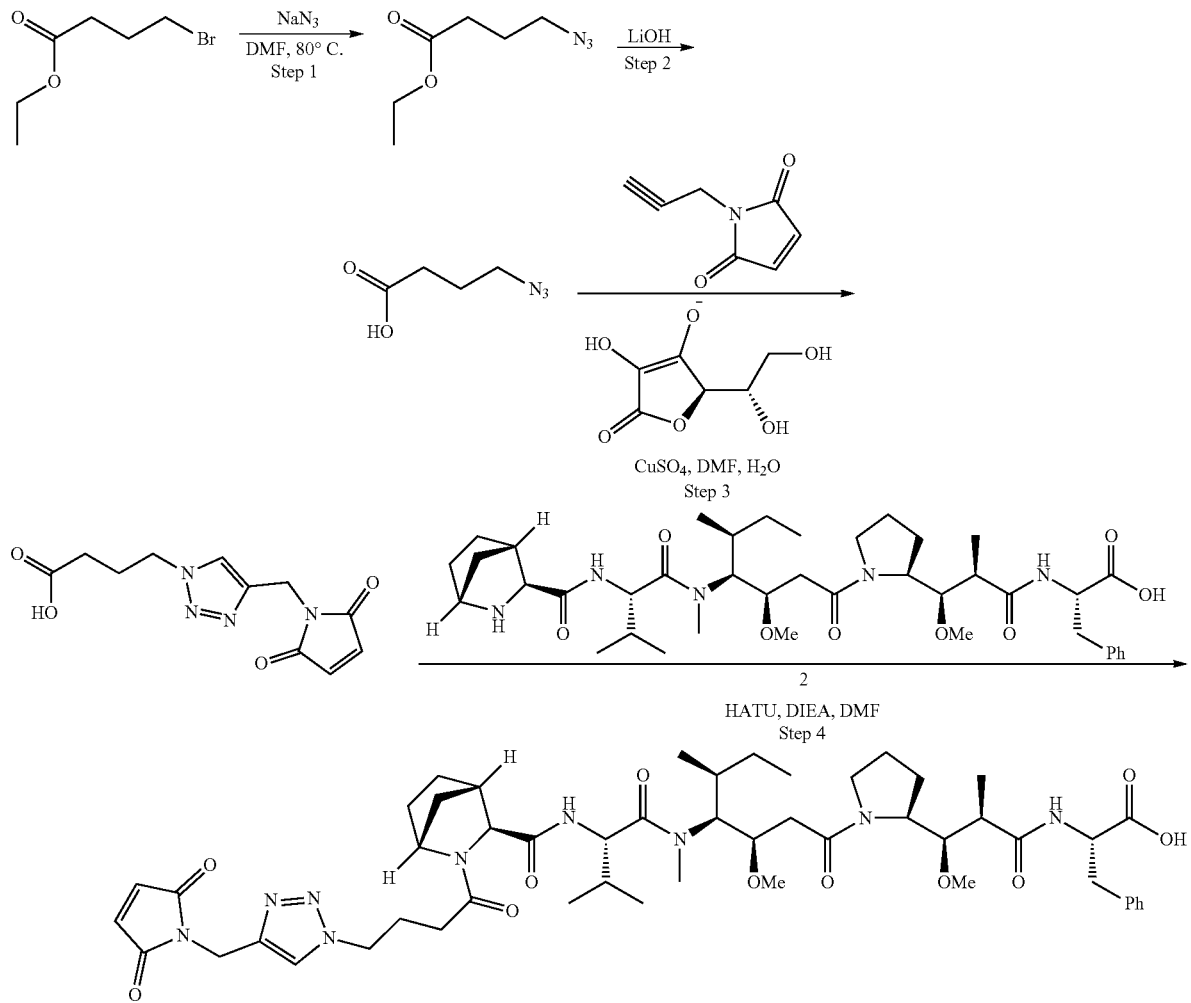

Step 1: To a solution of ethyl 4-bromobutanoate (3.4 g, 0.0174 mol) in DMF (100 mL) was added sodium azide (1.7 g, 0.0262 mol). The mixture was heated to 80° C. and stirred overnight. The reaction mixture was diluted with water and extracted 3 times with ether. The organic phase was washed with water 3 times, dried over MgSO₄, filtered and concentrated to give crude product which was used directly in next step without further purification.

Step 2: Ethyl 4-azidobutanoate (157 mg, 1.0 mmol) was dissolved in THF (4 mL), MeOH (0.5 mL) and water (0.5 mL). Then LiOH.H₂O (168 mg, 4.0 mmol) was added and the reaction mixture was stirred for 2 hours at room temperature. LCMS indicated the completion of the reaction. The reaction was stopped, the pH was adjusted to 2-3 by using 1N HCl and the reaction mixture was extracted with EtOAc. The combined organic phase was dried over MgSO4, concentrated to give crude product which was used directly in next step without further purification. ¹H NMR (400 MHz, CD₃OD): δ 3.36 (t, J=6.8 Hz, 2H), 2.39 (t, J=7.2 Hz, 2H), 1.89-1.82 (m, 2H).

Step 3: A solution of 4-azidobutanoic acid (19 mg, 0.147 mmol), 1-(prop-2-yn-1-yl)-1H-pyrrole-2,5-dione (39.8 mg, 0.294 mmol) and CuSO4 (17.62 mg, 0.11 mmol) in DMF (3.0 mL) and H₂O (0.75 mL) was treated with L-Ascorbic acid sodium salt (72.9 mg, 0.368 mmol) and stirred at room temperature for 2 hours. The reaction mixture was purified by Prep-HPLC, C18 column, eluted with 20-70% acetonitrile-H₂O containing 0.05% TFA. The fractions containing the desired product were pooled and lyophilized to obtain a white solid. MS m/z 265.1 (M+1). Retention time 0.642 minutes. ¹H NMR (400 MHz, CD₃OD): δ 7.94 (s, 1H), 6.86 (s, 2H), 4.77 (s, 2H), 4.43 (t, J=7.0 Hz, 2H), 2.31 (t, J=7.2 Hz, 2H), 2.17-2.13 (m, 2H).

Step 4: 4-(4-((2,5-Dioxo-2,5-dihydro-1H-pyrrol-1-yl)methyl)-1H-1,2,3-triazol-1-yl)butanoic acid (4.5 mg, 0.017 mmol) was dissolved in DMF (1 mL). DIEA (9.9 uL, 0.057 mmol) and HATU (5.61 mg, 0.015 mmol) were added and the mixture was stirred for 10 minutes before the addition of 2 (9.72 mg, 0.011 mmol). The reaction mixture was then stirred for 1 hour at room temperature. LC/MS analysis indicated the completion of the reaction. The product was purified by Prep-HPLC, C18 column, eluted with 20-70% acetonitrile-H₂O containing 0.05% TFA. The fractions containing the desired product 24 were pooled and lyophilized to obtain a white solid. MS m/z 988.5.1 (M+1). Retention time 1.074 minutes.

EXAMPLE 48

(1R,3S,4S)-N-((S)-1-(((3R,4S,5S)-1-((S)-2-((1R,2R)-3-(((S)-N-1-(Methylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-(6-(2,5-dioxo-2,5-dihydro-1H-pyrrol-1-yl)hexanoyl)-2-azabicyclo[2.2.1]heptane-3-carboxamide (25)

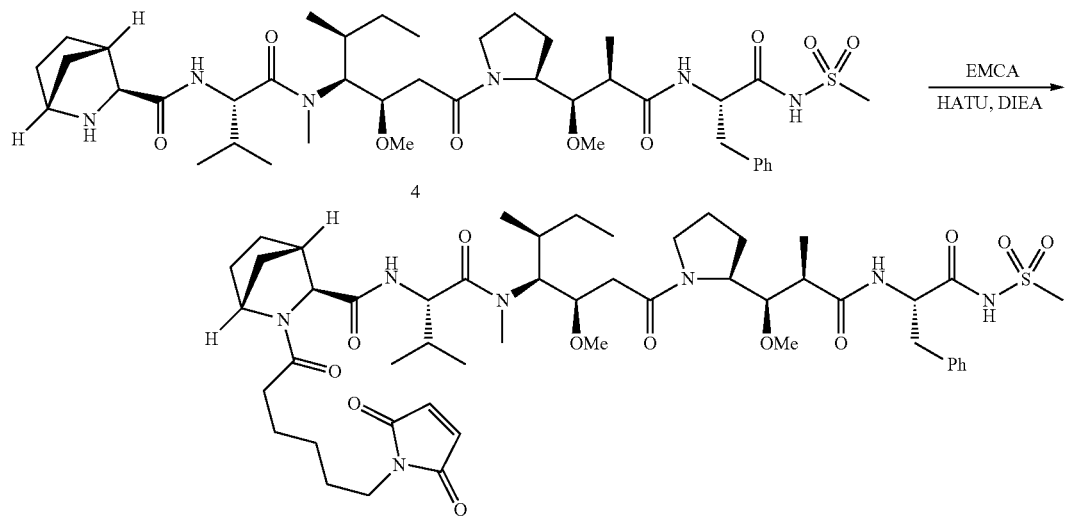

EMCA (4.1 mg, 0.019 mmol) was dissolved in DMF (2 mL). DIEA (8.31 mg, 0.064 mmol) and HATU (5.87 mg, 0.015 mmol) were added and after 10 minutes compound 4 (11 mg, 0.013 mmol) was added. The reaction mixture was stirred for 2 hours at room temperature. LC/MS analysis indicated the completion of the reaction. The product was purified by Prep-HPLC, C18 column, eluted with 30-50% acetonitrile-H₂O containing 0.05% TFA. The fractions containing the desired product were pooled and lyophilized to obtain desired product 25 as a white solid. MS m/z 1012.5 (M+1). Retention time 1.222 minutes.

EXAMPLE 49

(1R,3S,4S)-2-(6-(2,5-Dioxo-2,5-dihydro-1H-pyrrol-1-yl)hexanoyl)-N-((S)-1-(((3R,4S,5S)-3-methoxy-1-((S)-2-((1R,2R)-1-methoxy-2-methyl-3-oxo-3-(((S)-2-phenyl-1-(1H-tetrazol-5-yl)ethyl)amino)propyl)pyrrolidin-1-yl)-5-methyl-1-oxoheptan-4-yl)(methyl)amino)-3-methyl-1-oxobutan-2-yl)-2-azabicyclo[2.2.1]heptane-3-carboxamide (26)

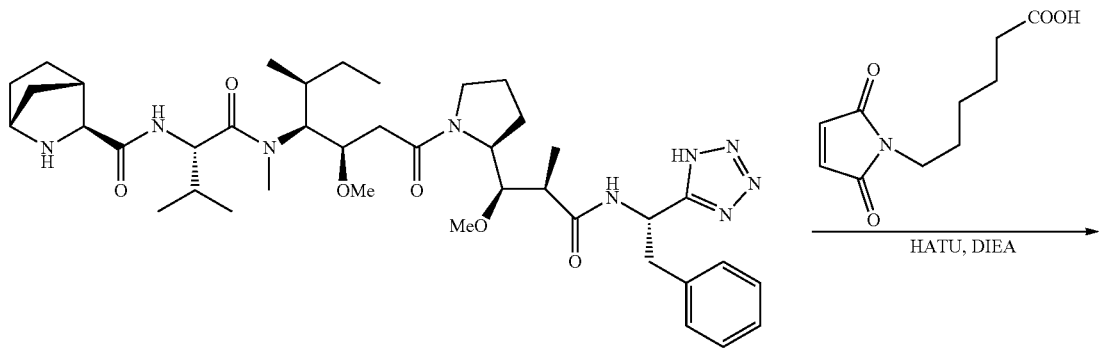

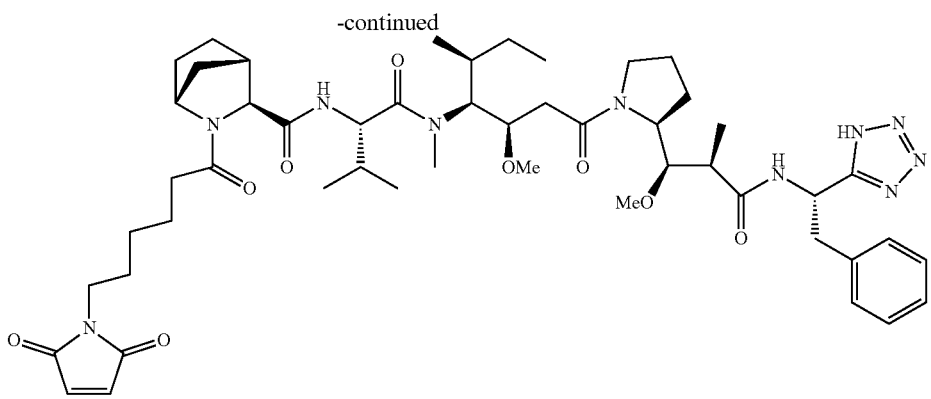

26

To a solution of EMCA (2.5 mg, 0.012 mmol) in DMF (1 ml) was added DIEA (6.2 ul, 0.035 mmol) and then HATU (4.5 mg, 0.012 mmol). The reaction mixture was stirred for 5 minutes and then added to (1R,3S,4S)-N-((S)-1-(((3R,4S,5S)-3-methoxy-1-((S)-2-((1R,2R)-1-methoxy-2-methyl-3-oxo-3-(((S)-2-phenyl-1-(1H-tetrazol-5-yl)ethyl)amino)propyl)pyrrolidin-1-yl)-5-methyl-1-oxoheptan-4-yl)(methyl)amino)-3-methyl-1-oxobutan-2-yl)-2-azabicyclo[2.2.1]heptane-3-carboxamide TFA salt (6.7 mg, 0.0076 mmol). The reaction mixture was kept at room temperature for 1 hour and the crude was purified by reverse phase HPLC, C18 column, eluted with 20-60% acetonitrile-H₂O, containing 0.05% TFA. The fractions containing desired product were concentrated to obtain compound 26 MS m/z 959.5 (M+1). Retention time 1.220 minutes.

EXAMPLE 50

((R)-1-((2R,3R)-3-((S)-1-((3R,4S,5S)-4-((S)-2-((1R,3S,4S)-2-(6-(2,5-Dioxo-2,5-dihydro-1H-pyrrol-1-yl)hexanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-2-phenylethyl)phosphonic acid (27)

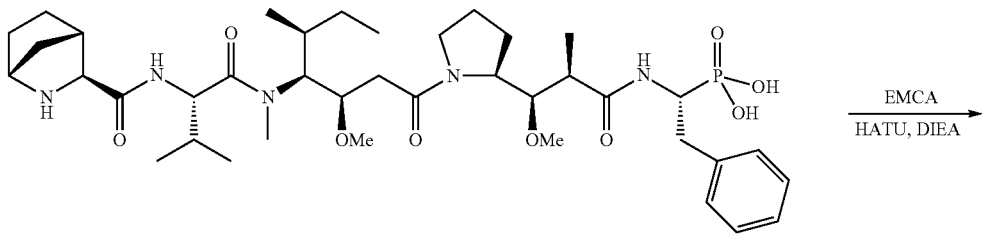

7

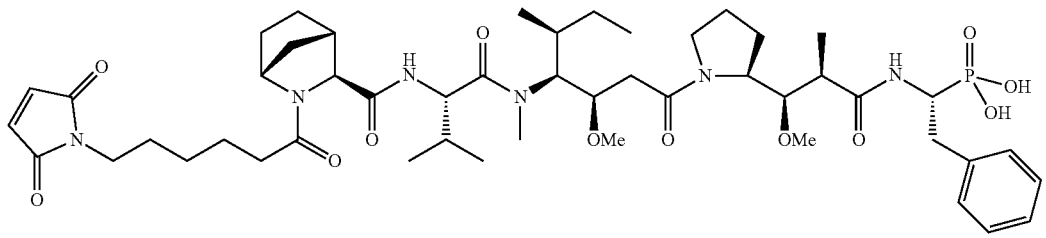

27

To a solution of EMCA (3.3 mg, 0.016 mmol) in DMF (1 ml) was added DIEA (2.7 ul, 0.016 mmol) and then HATU (5.93 mg, 0.016 mmol). The reaction mixture was stirred at room temperature for 10 minutes and then added to a solution of ((R)-1-((2R,3R)-3-((S)-1-((3R,4S,5S)-4-((S)-2-((1R,3S,4S)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-2-phenylethyl)phosphonic acid 7 (10 mg, 0.011 mmol) in DMF. The reaction mixture was stirred at room temperature for 1 hour. The crude was purified by reverse phase HPLC, C18 column, eluted with 30-60% acetonitrile-H$_2$O, containing 0.05% TFA. The fractions containing desired product were concentrated to ((R)-1-((2R,3R)-3-((S)-1-((3R,4S,5S)-4-((S)-2-((1R,3S,4S)-2-(6-(2,5-dioxo-2,5-dihydro-1H-pyrrol-1-yl)hexanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-2-phenylethyl)phosphonic acid 27. MS m/z 971.5 (M+1). Retention time 1.181 minutes.

EXAMPLE 51

((R)-1-((2R,3R)-3-((S)-1-((3R,4S,5S)-4-((S)-2-((1R,3S,4S)-2-(6-(2,5-Dioxo-2,5-dihydro-1H-pyrrol-1-yl)hexanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-2-phenylethyl)phosphinic acid (28)

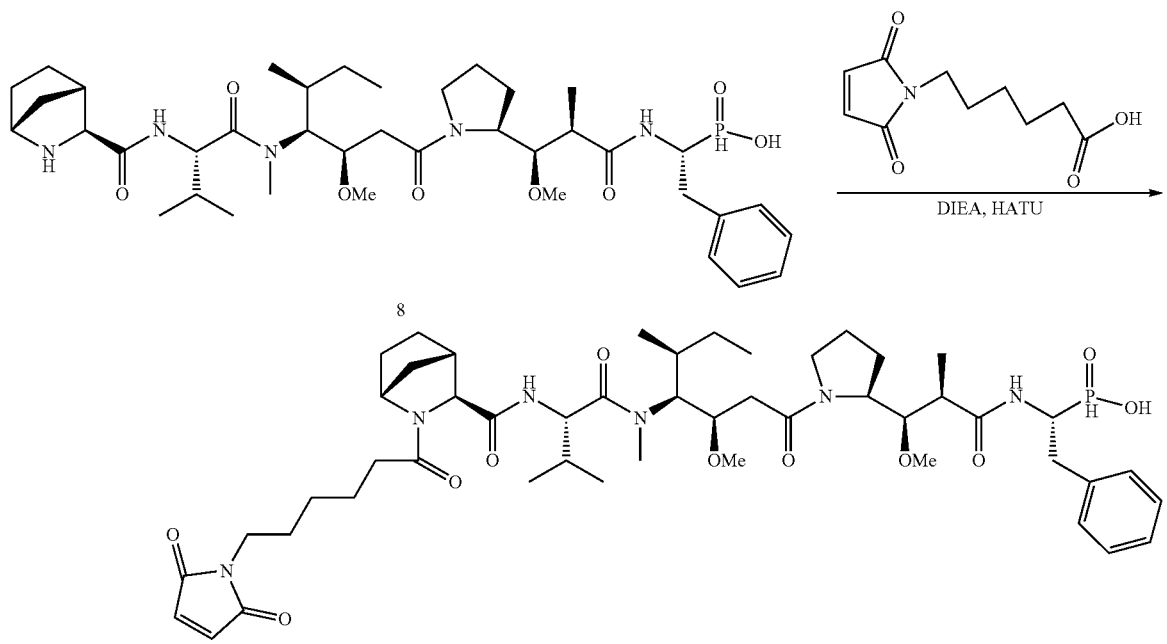

To a solution of EMCA (2.4 mg, 0.011 mmol) in DMF (1 ml) was added DIEA (6.6 ul, 0.038 mmol) and HATU (4.0 mg, 10.42 µmol). The reaction mixture was stirred for 5 minutes and then added to a solution of ((R)-1-((2R,3R)-3-((S)-1-((3R,4S,5S)-4-((S)-2-((1R,3S,4S)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-2-phenylethyl)phosphinic acid 8 (8.3 mg, 0.0095 mmol) in DMF (1 ml). The reaction mixture was complete in 10 minutes and the crude was purified by reverse phase HPLC, C18 column, eluted with 30-55% acetonitrile-H$_2$O, containing 0.05% TFA. The fractions containing desired product were concentrated to obtain ((R)-1-((2R,3R)-3-((S)-1-((3R,4S,5S)-4-((S)-2-((1R,3S,4S)-2-(6-(2,5-dioxo-2,5-dihydro-1H-pyrrol-1-yl)hexanoyl)-2-azabicyclo[2.2.1]heptane-3-carboxamido)-N,3-dimethylbutanamido)-3-methoxy-5-methylhepatanoyl)pyrrolidin-2-yl)-3-methoxy-2-methylpropanamido)-2-phenylethyl)phosphinic acid 28. MS m/z 955.5 (M+1). Retention time 1.151 minutes.

EXAMPLE 52

Butyl hydrogen ((R)-1-((2R,3R)-3-((S)-1-((3R,4S,5S)-4-((S)-2-((1R,3S,4S)-2-(6-(2,5-dioxo-2,5-dihydro-1H-pyrrol-1-yl)hexanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-2-phenylethyl) phosphonate (29)

0.044 mmol). The reaction was monitored by LCMS until all of the phosphorous acid was converted to the ester. Then a freshly prepared iodine (11 mg, 0.044 mmol) solution in wet pyridine-water (10:1 1 ml) was added. The reaction was monitored by LCMS until completion. Pyridine was removed by vacuum and the crude was purified by reverse phase HPLC, C18 column, eluted with 30-55% acetonitrile-H₂O, containing 0.05% TFA. The fractions containing desired product were concentrated to obtain butyl hydrogen

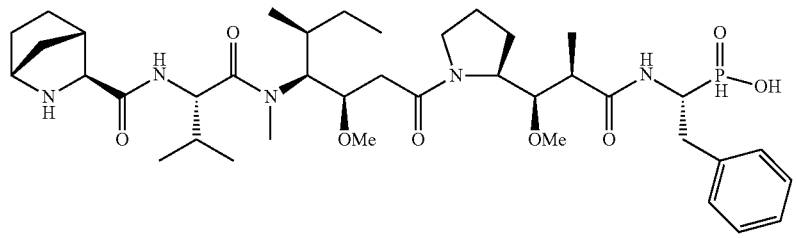
8

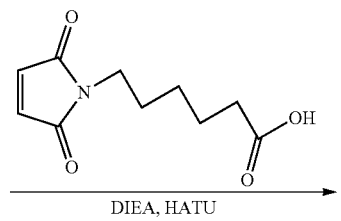

DIEA, HATU

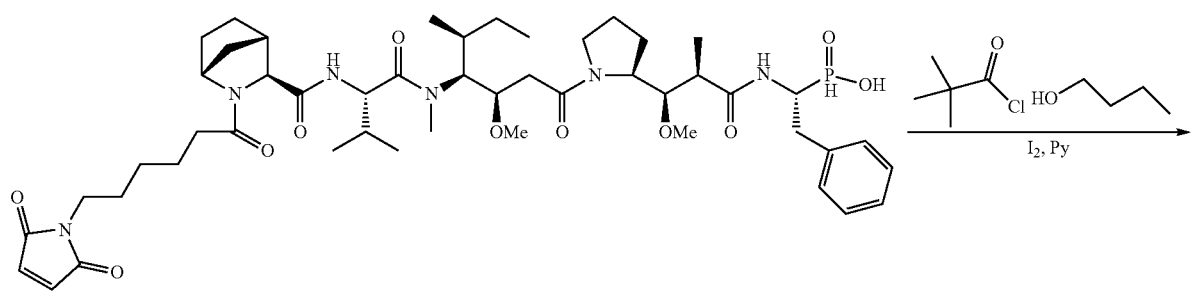

I₂, Py

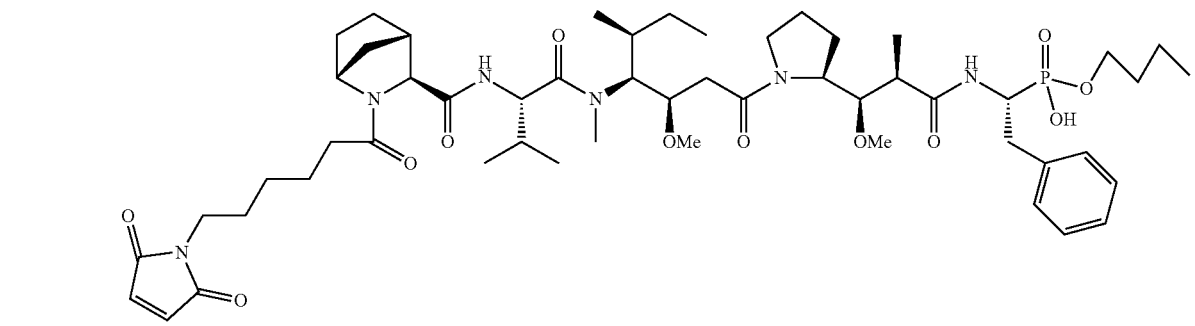
29

To a solution of ((R)-1-((2R,3R)-3-((S)-1-((3R,4S,5S)-4-((S)-2-((1R,3S,4S)-2-(6-(2,5-dioxo-2,5-dihydro-1H-pyrrol-1-yl)hexanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-2-phenylethyl)phosphinic acid 8 (4.2 mg, 0.0044 mmol) in pyridine (1 ml) was added n-BuOH (3.3 mg, 0.044 mmol) and then pivaloyl chloride (5.3 mg, ((R)-1-((2R,3R)-3-((S)-1-((3R,4S,5S)-4-((S)-2-((1R,3S,4S)-2-(6-(2,5-dioxo-2,5-dihydro-1H-pyrrol-1-yl)hexanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-2-phenylethyl) phosphonate 29. MS m/z 1027.5 (M+1). Retention time 1.300 minutes. The ester is prone to hydrolysis in acidic condition.

EXAMPLE 53

(S)-2-((2R,3R)-3-((S)-1-((3R,4S,5S)-4-((S)-2-((1R,3S,4S)-2-(6-((((1R,8S,9s)-Bicyclo[6.1.0]non-4-yn-9-ylmethoxy)carbonyl)amino)hexanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (75)

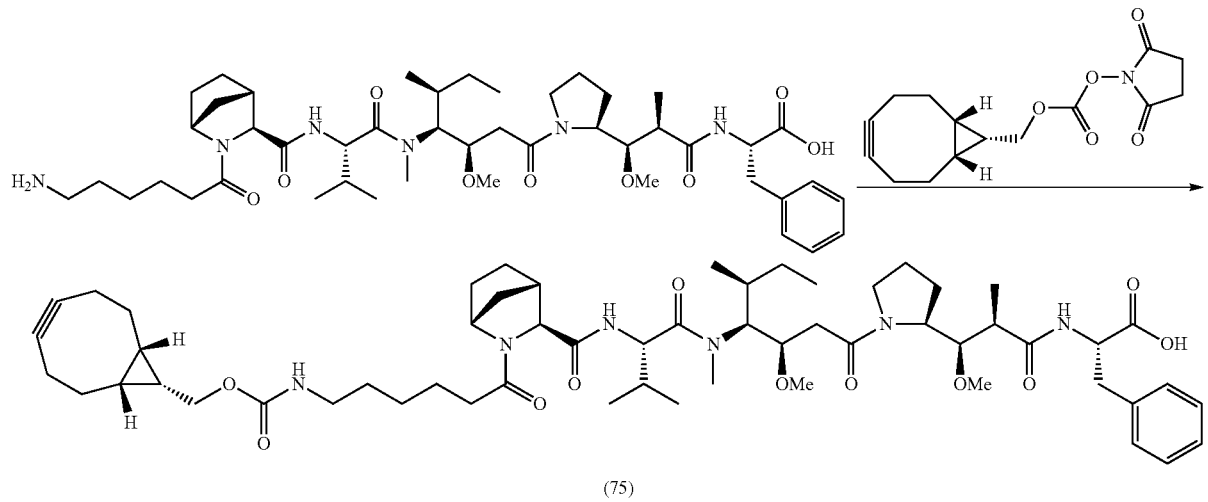

(75)

To (S)-2-((2R,3R)-3-((S)-1-((3R,4S,5S)-4-((S)-2-((1R,3S,4S)-2-(6-aminohexanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (Step 2, Example 44) (5 mg, 0.005 mmol) in DMF-THF (1:1, 2 ml) was added (1R,8S,9s)-bicyclo[6.1.0]non-4-yn-9-ylmethyl (2,5-dioxopyrrolidin-1-yl) carbonate (1.5 mg, 0.005 mmol) and DIEA (0.0025 ml, 0.014 mmol). The reaction mixture was stirred at rt for 30 min and then purified by preparative HPLC (40-65% acetonitrile-H$_2$O containing 0.05% TFA) to obtain compound (75). MS m/z 1031.6 (M+H). Retention time 1.337 min.

EXAMPLE 54

4-((S)-2-((S)-2-(6-(2,5-Dioxo-2,5-dihydro-1H-pyrrol-1-yl)hexanamido)-3-methylbutanamido)-5-ureidopentanamido)benzyl (1R,3S,4S)-3-(((S)-1-(((3R,4S,5S)-1-((S)-2-((1R,2R)-3-(((S)-1-Hydroxy-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)carbamoyl)-2-azabicyclo[2.2.1]heptane-2-carboxylate (76)

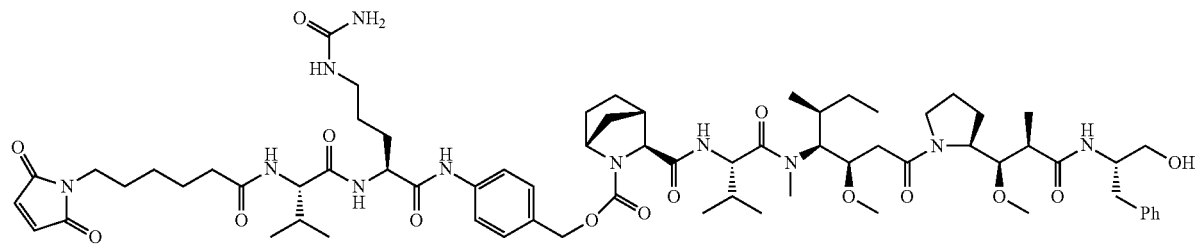 [SMILES: CC[C@H](C)[C@@H]([C@@H](CC(=O)N1CCC[C@H]1[C@H](OC)[C@@H](C)C(=O)N[C@H](CO)Cc1ccccc1)OC)N(C)C(=O)[C@@H](NC(=O)[C@@H]1[C@H]2CC[C@H](C2)N1C(=O)OCc1ccc(NC(=O)[C@H](CCCNC(N)=O)NC(=O)[C@@H](NC(=O)CCCCCN2C(=O)C=CC2=O)C(C)C)cc1)C(C)C]

To a solution of MC-Val-Cit-PAB-PNP (1.9 mg, 0.0026 mmol), compound (50) TFA salt (1.8 mg, 0.002 mmol) in DMF (1 ml) were added pyridine (0.25 ml), HOAT (0.29 mg, 0.002 mmol) and DIEA (0.0054 ml, 0.031 mmol). The reaction was stirred at 40° C. for 2 h and then at 30° C. for 18 h. The reaction mixture was concentrated and purified by preparative HPLC (20-60% acetonitrile-H$_2$O containing 0.05% TFA) to obtain compound (76). MS m/z 664.0 (M/2+H). Retention time 1.165 min.

EXAMPLE 55

(S)-2-((2R,3R)-3-((S)-1-((3R,4S,5S)-4-((S)-2-((1R,3S,4S)-2-(3-(2-(2,5-Dioxo-2,5-dihydro-1H-pyrrol-1-yl)ethoxy)propanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (77)

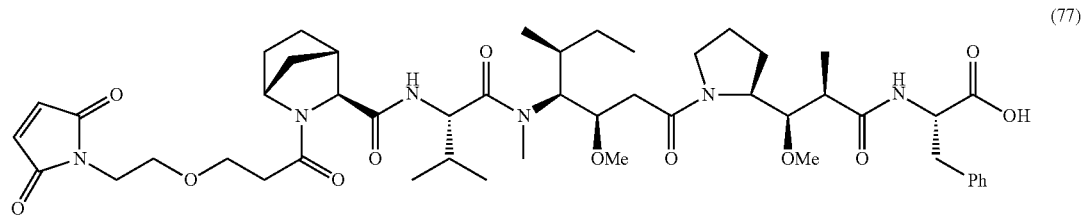 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@@H]1[C@H]2CC[C@H](C2)N1C(=O)CCOCCN1C(=O)C=CC1=O)C(C)C]

(77)

To a solution of 3-(2-(maleimido)ethoxy)propanoic acid (2.2 mg, 0.010 mmol) in DMF (1 ml) were added HATU (3.7 mg, 0.0098 mmol) and DIEA (3.6 mg, 0.028 mmol). The reaction was stirred for 5 min, and then (S)-2-((2R,3R)-3-((S)-1-((3R,4S,5S)-4-((S)-2-((1R,3S,4S)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (8 mg, 0.0093 mmol) in DMF (0.5 ml) was added. The reaction mixture was stirred at rt for 1 h and then concentrated. The crude was purified by preparative HPLC (10-60% acetonitrile-H$_2$O containing 0.05% TFA) to obtain compound (77). MS m/z 937.5 (M+H). Retention time 1.138 min.

EXAMPLE 56

(S)-2-((2R,3R)-3-((S)-1-((3R,4S,5S)-4-((S)-2-((1R,3S,4S)-2-(3-(2-(2-(2,5-Dioxo-2,5-dihydro-1H-pyrrol-1-yl)ethoxy)ethoxy)propanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (78)

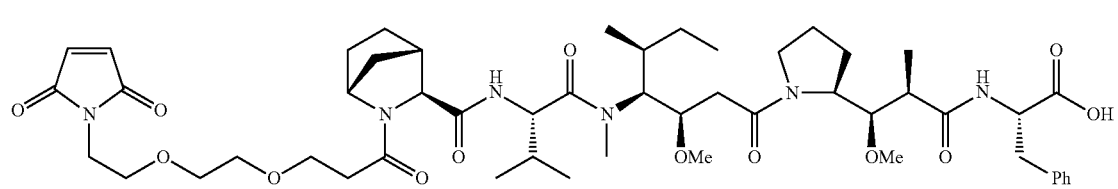

(78)

Compound (78) was prepared by the method described for compound (77) using 3-(2-(2-(maleimido)ethoxy)ethoxy)propanoic acid (2.6 mg, 0.010 mmol) in place of 3-(2-(maleimido)ethoxy)propanoic acid. MS m/z 981.5 (M+H). Retention time 1.140 min.

EXAMPLE 57

(S)-2-((2R,3R)-3-((S)-1-((3R,4S,5S)-4-((S)-2-((1R,3S,4S)-2-(3-(2-(2-(2-(2,5-Dioxo-2,5-dihydro-1H-pyrrol-1-yl)ethoxy)ethoxy)ethoxy)propanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (79)

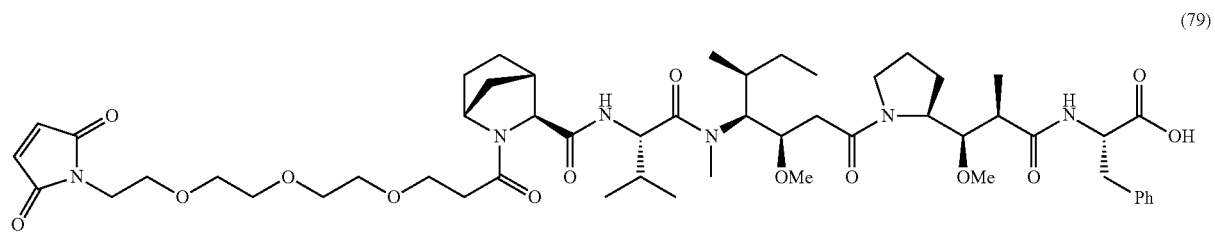 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@@H]1[C@H]2CC[C@H](C2)N1C(=O)CCOCCOCCOCCN1C(=O)C=CC1=O)C(C)C]

(79)

Compound (79) was prepared by the method described for compound (77) using 3-(2-(2-(2-(maleimido)ethoxy)ethoxy)ethoxy)propanoic acid (3.1 mg, 0.010 mmol) in place of 3-(2-(maleimido)ethoxy)propanoic acid. MS m/z 1025.5 (M+H). Retention time 1.143 min.

EXAMPLE 58

(S)-2-((2R,3R)-3-((S)-1-((3R,4S,5S)-4-((S)-2-((1R,3S,4S)-2-(1-(2,5-Dioxo-2,5-dihydro-1H-pyrrol-1-yl)-3,6,9,12-tetraoxapentadecan-15-oyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (80)

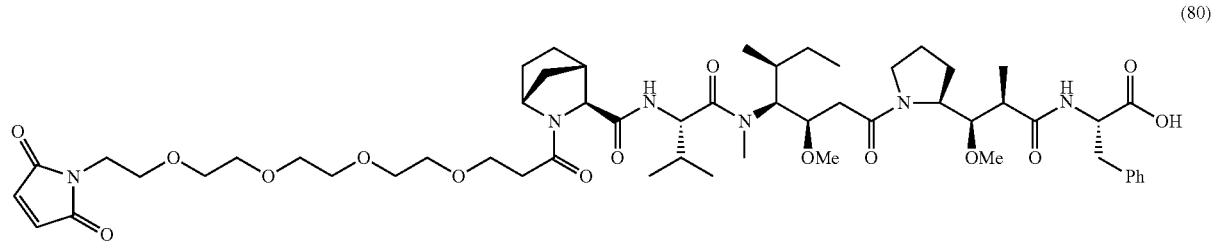 [SMILES: CC[C@H](C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@@H]1[C@H]2CC[C@H](C2)N1C(=O)CCOCCOCCOCCOCCN1C(=O)C=CC1=O)C(C)C]

(80)

Compound (80) was prepared by the method described for compound (77) using 1-(maleimido)-3,6,9,12-tetraoxapentadecan-15-oic acid (3.6 mg, 0.010 mmol) in place of 3-(2-(maleimido)ethoxy)propanoic acid. MS m/z 1069.5 (M+H). Retention time 1.144 min.

EXAMPLE 59

(S)-2-((2R,3R)-3-((S)-1-((3R,4S,5S)-4-((S)-N,3-Dimethyl-2-((1R,3S,4S)-2-(4-(1-(2-(2-(2-(2-(4-(5-(methylsulfonyl)-1,3,4-oxadiazol-2-yl)phenoxy)ethoxy)ethoxy)ethoxy)ethyl)-1H-1,2,3-triazol-4-yl)butanoyl)-2-azabicyclo[2.2.1]heptane-3-carboxamido)butanamido)-3-methoxy-5-methylheptanoyl)pyrrolidin-2-yl)-3-methoxy-2-methylpropanamido)-3-phenylpropanoic acid (81)

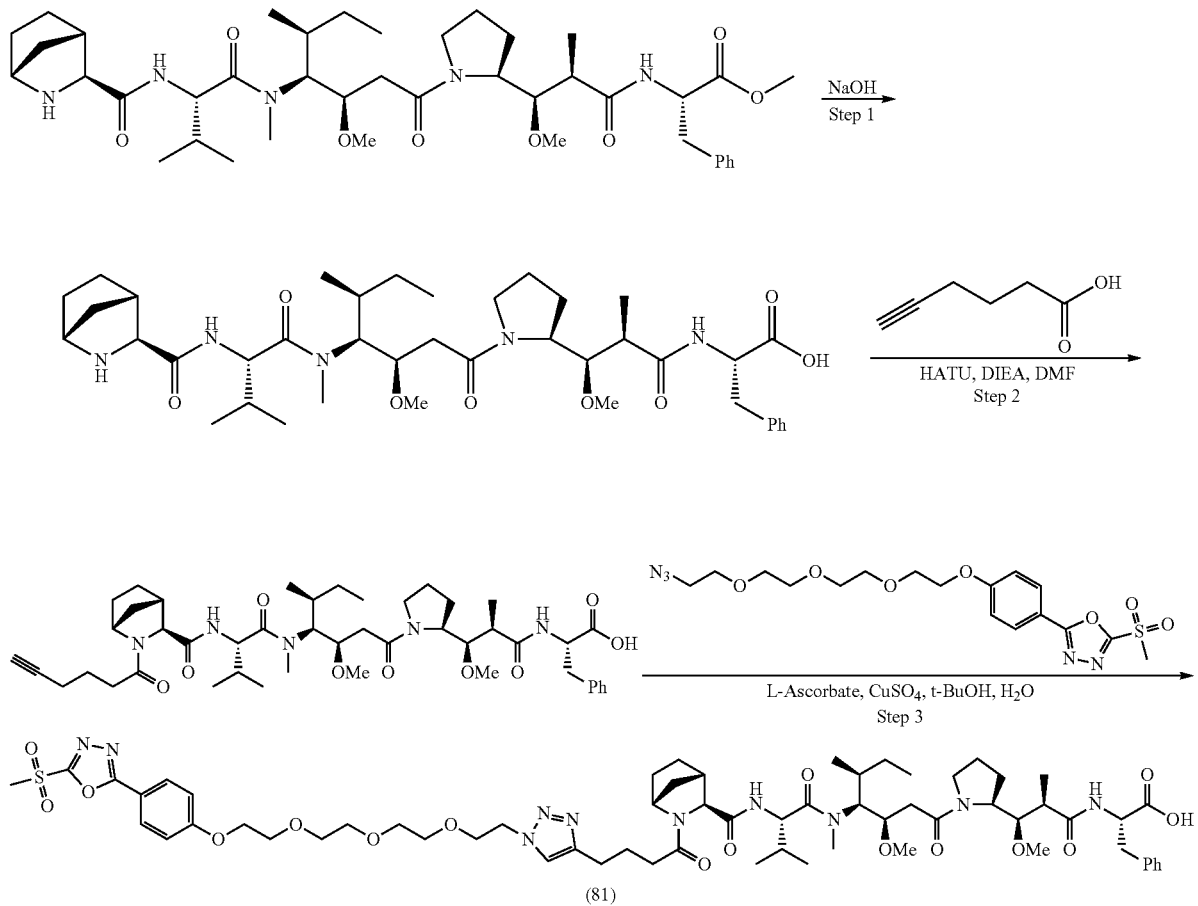

(81)

Step 1: (S)-Methyl 2-((2R,3R)-3-((S)-1-((3R,4S,5S)-4-((S)-2-((1R,3S,4S)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoate (1) (63 mg, 0.080 mmol) was dissolved in ACN (0.75 ml) and water (0.5 ml). NaOH (1M, 0.35 ml) was added. The reaction was stirred 2 h at rt. After neutralized with 1N HCl to approximately pH 5, the reaction mixture was diluted with water and lyophilized to give crude (S)-2-((2R,3R)-3-((S)-1-((3R,4S,5S)-4-((S)-2-((1R,3S,4S)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid. MS m/z 742.4 (M+1). Retention time 1.010 min. The product was used in the next step without further purification.

Step 2: To a solution of hex-5-ynoic acid (5.4 mg, 0.049 mmol) in DMF (2 ml) was added DIEA (26.1 mg, 0.35 mmol) and HATU (16.9 mg, 0.044 mmol). The reaction was stirred at rt for 15 min. Then the product obtained in step 1 (30 mg, 0.040 mmol) was added. The reaction was stirred at rt for 2 h. The crude was purified by preparative HPLC (10-90% acetonitrile-$H_2O$ containing 0.05% TFA) to obtain (S)-2-((2R,3R)-3-((S)-1-((3R,4S,5S)-4-((S)-2-((1R,3S,4S)-2-(hex-5-ynoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid. MS m/z 836.5 (M+1). Retention time 1.224 min.

Step 3: (S)-2-((2R,3R)-3-((S)-1-((3R,4S,5S)-4-((S)-2-((1R,3S,4S)-2-(Hex-5-ynoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (7 mg, 0.0084 mmol) and 2-(4-(2-(2-(2-(2-azidoethoxy)ethoxy)ethoxy)ethoxy)phenyl)-5-(methylsulfonyl)-1,3,4-oxadiazole (3.7 mg, 0.0084 mmol) were suspended in t-BuOH(1 ml) and water (1 ml). Sodium L-ascorbate (1.7 mg, 0.0084 mmol) in 0.3 ml $H_2O$ and $CuSO_4$ (0.3 mg, 0.0017 mmol) in 0.3 ml $H_2O$ were added sequentially using syringe and the reaction was stirred at rt for 3 h. The reaction mixture was purified by preparative (10-90% acetonitrile-$H_2O$ containing 0.05% TFA) to obtain compound (81) as white solid. MS m/z 639.4 (M/2+1). Retention time 1.196 min.

EXAMPLE 60

4-((S)-2-((S)-2-(6-(2,5-Dioxo-2,5-dihydro-1H-pyrrol-1-yl)hexanamido)-3-methylbutanamido)-5-ureidopentanamido)benzyl (1R,3S,4S)-3-(((S)-1-(((3R,4S,5S)-3-methoxy-1-((S)-2-((1R,2R)-1-methoxy-2-methyl-3-oxo-3-(((S)-1-phenyl-3-sulfamoylpropan-2-yl)amino)propyl)pyrrolidin-1-yl)-5-methyl-1-oxoheptan-4-yl)(methyl)amino)-3-methyl-1-oxobutan-2-yl)carbamoyl)-2-azabicyclo[2.2.1]heptane-2-carboxylate (82)

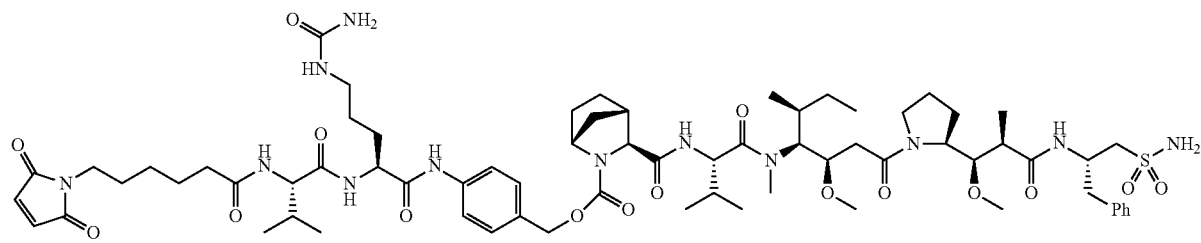

(82)

(1R,3S,4S)-N-((S)-1-(((3R,4S,5S)-3-Methoxy-1-((S)-2-((1R,2R)-1-methoxy-2-methyl-3-oxo-3-(((S)-1-phenyl-3-sulfamoylpropan-2-yl)amino)propyl)pyrrolidin-1-yl)-5-methyl-1-oxoheptan-4-yl)(methyl)amino)-3-methyl-1-oxobutan-2-yl)-2-azabicyclo[2.2.1]heptane-3-carboxamide ((56), 8.7 mg, 0.011 mmol), MC-Val-Cit-PABC-PNP (9.7 mg, 0.013 mmol), HOAT (1.7 mg, 0.011 mmol) and DIEA (0.013 ml, 0.077 mmol) were combined in pyridine (0.5 ml) and DMF (2 ml). The reaction was stirred for 4 h at rt. The reaction mixture was purified by preparative HPLC (10-60% acetonitrile-H$_2$O containing 0.05% TFA) to obtain compound (82) as white solid. MS m/z 695.5 (M/2+1). Retention time 1.139 min.

EXAMPLE 61

4-((S)-2-((S)-2-(6-(2,5-Dioxo-2,5-dihydro-1H-pyrrol-1-yl)hexanamido)-3-methylbutanamido)-5-ureidopentanamido)benzyl (1R,3S,4S)-3-(((S)-1-(((3R,4S,5S)-3-methoxy-1-((S)-2-((1R,2R)-1-methoxy-2-methyl-3-oxo-3-(((S)-2-phenyl-1-(4-phenyl-1H-imidazol-2-yl)ethyl)amino)propyl)pyrrolidin-1-yl)-5-methyl-1-oxoheptan-4-yl)(methyl)amino)-3-methyl-1-oxobutan-2-yl)carbamoyl)-2-azabicyclo[2.2.1]heptane-2-carboxylate (83)

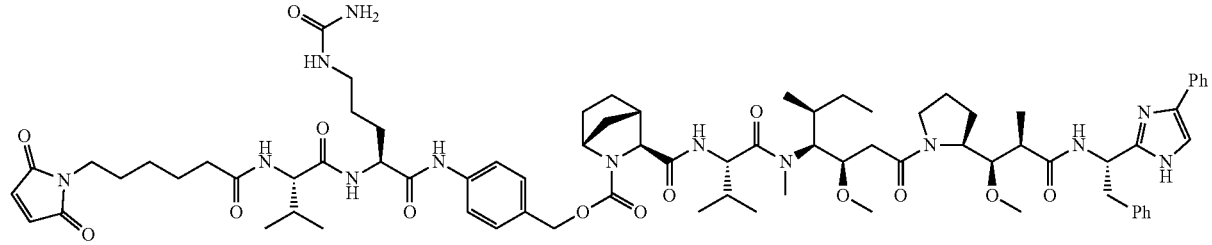

(83)

Compound (83) was prepared by the method described for compound (82) using (1R,3S,4S)-N-((S)-1-(((3R,4S,5S)-3-methoxy-1-((S)-2-((1R,2R)-1-methoxy-2-methyl-3-oxo-3-(((S)-2-phenyl-1-(5-phenyl-1H-imidazol-2-yl)ethyl)amino)propyl)pyrrolidin-1-yl)-5-methyl-1-oxoheptan-4-yl)(methyl)amino)-3-methyl-1-oxobutan-2-yl)-2-azabicyclo[2.2.1]heptane-3-carboxamide (57), in place of compound (56). MS m/z 720.0 (M/2+1). Retention time 1.169 min.

EXAMPLE 62

4-((S)-2-((S)-2-(6-(2,5-Dioxo-2,5-dihydro-1H-pyrrol-1-yl)hexanamido)-3-methylbutanamido)-5-ureidopentanamido)benzyl (1R,3S,4S)-3-(((S)-1-(((3R,4S,5S)-3-methoxy-1-((S)-2-((1R,2R)-1-methoxy-3-(((S)-1-methoxy-3-phenylpropan-2-yl)amino)-2-methyl-3-oxopropyl)pyrrolidin-1-yl)-5-methyl-1-oxoheptan-4-yl)(methyl)amino)-3-methyl-1-oxobutan-2-yl)carbamoyl)-2-azabicyclo[2.2.1]heptane-2-carboxylate (84)

(84)

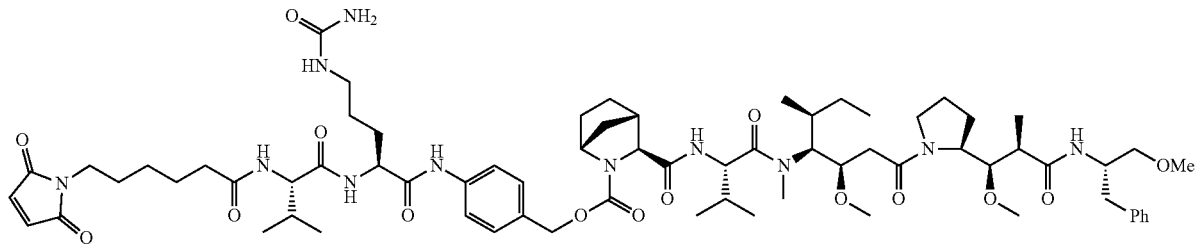

Compound (84) was prepared by the method described for compound (82) using (1R,3S,4S)-N-((S)-1-(((3R,4S,5S)-3-methoxy-1-((S)-2-((1R,2R)-1-methoxy-3-(((S)-1-methoxy-3-phenylpropan-2-yl)amino)-2-methyl-3-oxopropyl)pyrrolidin-1-yl)-5-methyl-1-oxoheptan-4-yl)(methyl)amino)-3-methyl-1-oxobutan-2-yl)-2-azabicyclo[2.2.1]heptane-3-carboxamide (58) in place of compound (56). MS m/z 671.0 (M/2+1). Retention time 1.236 min.

EXAMPLE 63

4-((S)-2-((S)-2-(6-(2,5-Dioxo-2,5-dihydro-1H-pyrrol-1-yl)hexanamido)-3-methylbutanamido)-5-ureidopentanamido)benzyl (1R,3S,4S)-3-(((S)-1-(((3R,4S,5S)-3-methoxy-1-((S)-2-((1R,2R)-1-methoxy-2-methyl-3-oxo-3-(((S)-2-phenyl-1-(1H-pyrazol-3-yl)ethyl)amino)propyl)pyrrolidin-1-yl)-5-methyl-1-oxoheptan-4-yl)(methyl)amino)-3-methyl-1-oxobutan-2-yl)carbamoyl)-2-azabicyclo[2.2.1]heptane-2-carboxylate (85)

(85)

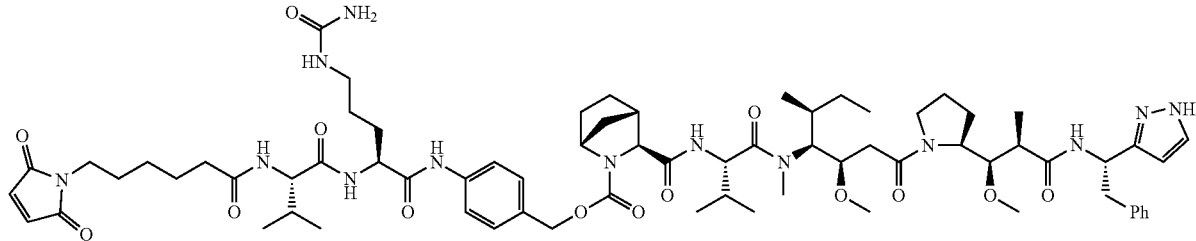

Compound (85) was prepared by the method described for compound (82) using (1R,3S,4S)-N-((S)-1-(((3R,4S,5S)-3-methoxy-1-((S)-2-((1R,2R)-1-methoxy-2-methyl-3-oxo-3-(((S)-2-phenyl-1-(1H-pyrazol-3-yl)ethyl)amino)propyl)pyrrolidin-1-yl)-5-methyl-1-oxoheptan-4-yl)(methyl)amino)-3-methyl-1-oxobutan-2-yl)-2-azabicyclo[2.2.1]heptane-3-carboxamide (59) in place of compound (56). MS m/z 682.1 (M/2+1). Retention time 1.172 min.

EXAMPLE 64

4-((S)-2-((S)-2-(6-(2,5-Dioxo-2,5-dihydro-1H-pyrrol-1-yl)hexanamido)-3-methylbutanamido)-5-ureidopentanamido)benzyl (1R,3S,4S)-3-(((S)-1-(((3R,4S,5S)-3-methoxy-1-((S)-2-((1R,2R)-1-methoxy-2-methyl-3-oxo-3-(((S)-2-phenyl-1-(5-phenyl-1,3,4-oxadiazol-2-yl)ethyl)amino)propyl)pyrrolidin-1-yl)-5-methyl-1-oxoheptan-4-yl)(methyl)amino)-3-methyl-1-oxobutan-2-yl)carbamoyl)-2-azabicyclo[2.2.1]heptane-2-carboxylate (86)

(86)

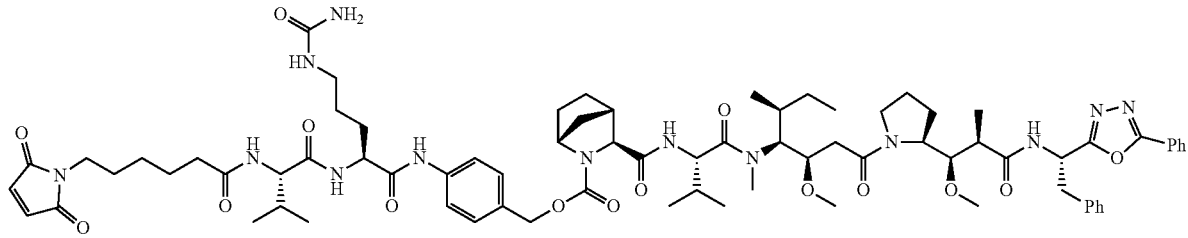

Compound (86) was prepared by the method described for compound (83) using (1R,3S,4S)-N-((S)-1-(((3R,4S,5S)-3-methoxy-1-((S)-2-((1R,2R)-1-methoxy-2-methyl-3-oxo-3-(((S)-2-phenyl-1-(5-phenyl-1,3,4-oxadiazol-2-yl)ethyl)amino)propyl)pyrrolidin-1-yl)-5-methyl-1-oxoheptan-4-yl)(methyl)amino)-3-methyl-1-oxobutan-2-yl)-2-azabicyclo[2.2.1]heptane-3-carboxamide (62) in place of compound (56). MS m/z 721.1 (M/2+1). Retention time 1.280 min.

EXAMPLE 65

4-((S)-2-((S)-2-(6-(2,5-Dioxo-2,5-dihydro-1H-pyrrol-1-yl)hexanamido)-3-methylbutanamido)-5-ureidopentanamido)benzyl (1R,3S,4S)-3-(((S)-1-(((3R,4S,5S)-3-methoxy-1-((S)-2-((1R,2R)-1-methoxy-2-methyl-3-oxo-3-(((S)-2-phenyl-1-(pyrimidin-2-yl)ethyl)amino)propyl)pyrrolidin-1-yl)-5-methyl-1-oxoheptan-4-yl)(methyl)amino)-3-methyl-1-oxobutan-2-yl)carbamoyl)-2-azabicyclo[2.2.1]heptane-2-carboxylate (87)

(87)

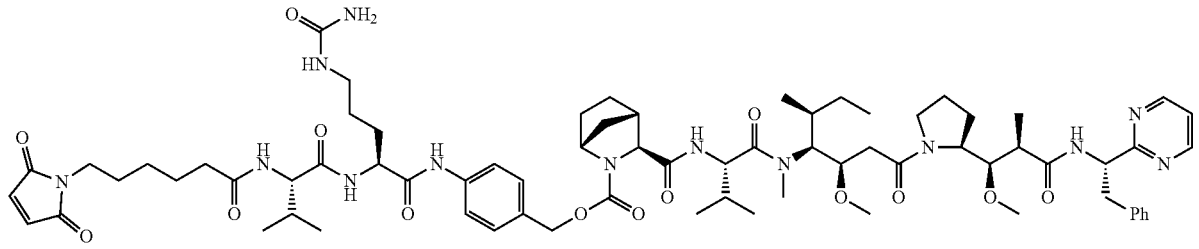

Compound (87) was prepared by the method described for compound (82) using (1R,3S,4S)-N-((S)-1-(((3R,4S,5S)-3-methoxy-1-((S)-2-((1R,2R)-1-methoxy-2-methyl-3-oxo-3-(((S)-2-phenyl-1-(pyrimidin-2-yl)ethyl)amino)propyl)pyrrolidin-1-yl)-5-methyl-1-oxoheptan-4-yl)(methyl)amino)-3-methyl-1-oxobutan-2-yl)-2-azabicyclo[2.2.1]heptane-3-carboxamide (60) in place of compound (56). Retention time 1.204 min.

EXAMPLE 66

4-((S)-2-((S)-2-(6-(2,5-Dioxo-2,5-dihydro-1H-pyrrol-1-yl)hexanamido)-3-methylbutanamido)-5-ureidopentanamido)benzyl (1R,3S,4S)-3-(((S)-1-(((3R,4S,5S)-3-methoxy-1-((S)-2-((1R,2R)-1-methoxy-2-methyl-3-oxo-3-(((R)-2-phenyl-1-(pyrimidin-2-yl)ethyl)amino)propyl)pyrrolidin-1-yl)-5-methyl-1-oxoheptan-4-yl)(methyl)amino)-3-methyl-1-oxobutan-2-yl)carbamoyl)-2-azabicyclo[2.2.1]heptane-2-carboxylate (88)

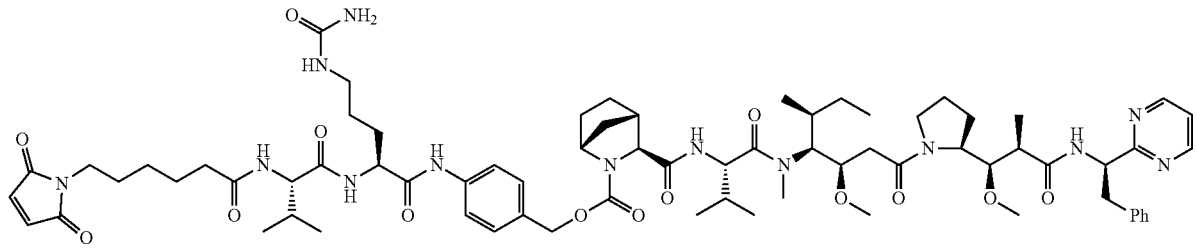

(88)

Compound (88) was prepared by the method described for compound (82) using (1R,3S,4S)-N-((S)-1-(((3R,4S,5S)-3-methoxy-1-((S)-2-((1R,2R)-1-methoxy-2-methyl-3-oxo-3-(((R)-2-phenyl-1-(pyrimidin-2-yl)ethyl)amino)propyl)pyrrolidin-1-yl)-5-methyl-1-oxoheptan-4-yl)(methyl)amino)-3-methyl-1-oxobutan-2-yl)-2-azabicyclo[2.2.1]heptane-3-carboxamide (61) in place of compound (56). MS m/z 688.0 (M/2+1). Retention time 1.221 min.

EXAMPLE 67

(S)-2-((2R,3R)-3-((S)-1-((3R,4S,5S)-4-((S)-2-((1R,3S,4S)-2-(6-(5-((2,5-Dioxopyrrolidin-1-yl)oxy)-5-oxopentanamido)hexanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (89)

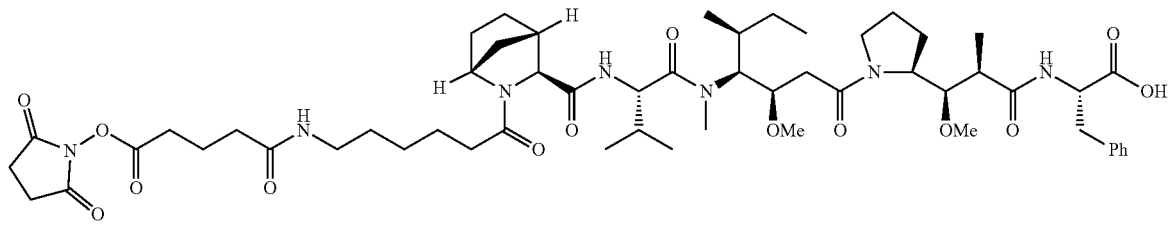

(89)

A solution of (S)-2-((2R,3R)-3-((S)-1-((3R,4S,5S)-4-((S)-2-((1R,3S,4S)-2-(6-aminohexanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid ((Step 2, Example 44) 20 mg, 0.021 mmol) and DIEA (0.018 ml, 0.10 mmol) in DMF (1 ml) was added to bis(2,5-dioxopyrrolidin-1-yl) glutarate (10.1 mg, 0.031 mmol) and DIEA (0.018 ml) in DMF (1 ml). The reaction was stirred for 2 h at rt. The crude was purified by preparative HPLC (20-70% acetonitrile-H$_2$O containing 0.05% TFA) to obtain (S)-2-((2R,3R)-3-((S)-1-((3R,4S,5S)-4-((S)-2-((1R,3S,4S)-2-(6-(5-((2,5-dioxopyrrolidin-1-yl)oxy)-5-oxopentanamido)hexanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (89). MS m/z 1066.5 (M+1). Retention time 1.103 min.

Synthetic Procedure for Example C-Terminal Linked Compounds of Formula (I)

EXAMPLE 68

(1R,3S,4S)-N-((S)-1-(((3R,4S,5S)-1-((S)-2-((1R,2R)-3-(((S)-1-((4-((6-(2,5-Dioxo-2,5-dihydro-1H-pyrrol-1-yl)hexanamido)methyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-azabicyclo[2.2.1]heptane-3-carboxamide (30)

Step 1: In a 15 mL round bottom flask were added (1R,3S,4S)-2-(tert-butoxycarbonyl)-2-azabicyclo[2.2.1]heptane-3-carboxylic acid (12 mg, 0.050 mmol) and DIEA (0.032 mL, 0.18 mmol) in DMF (2.0 mL), followed by HATU (19 mg, 0.050 mmol). The resulting solution was stirred for 5 minutes. Then N-(4-((S)-2-((2R,3R)-3-((S)-1-((3R,4S,5S)-4-((S)-2-amino-N,3-dimethylbutanamido)-3-methoxy-5-methylheptanoyl)pyrrolidin-2-yl)-3-methoxy-2-methylpropanamido)-3-phenylpropanamido)benzyl)-6-(2,5-dioxo-2,5-dihydro-1H-pyrrol-1-yl)hexanamide TFA salt (48.5 mg, 0.047 mmol) was added. The reaction mixture was stirred at room temperature for 1 hour. The crude was purified by reverse phase HPLC, C18 column, eluted with 10-70% acetonitrile-H$_2$O, containing 0.05% TFA. The fractions containing the desired product were pooled and concentrated to obtain (1R,3S,4S)-tert-butyl 3-(((S)-1-(((3R,4S,5S)-1-((S)-2-((1R,2R)-3-(((S)-1-((4-((6-(2,5-dioxo-2,5-dihydro-1H-pyrrol-1-yl)hexanamido)methyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)carbamoyl)-2-azabicyclo[2.2.1]heptane-2-carboxylate, MS m/z 1139.6 (M+1). Retention time 1.39 minutes.

Step 2: In a 15 mL round bottom flask were added the product obtained in step 1 (42.6 mg, 0.037 mmol), TFA (2.0 mL) and DCM (4.0 mL), resulting in a clear solution. The reaction mixture was stirred at room temperature for 1 hour at which time LCMS a analysis showed Boc was completely removed. The reaction mixture mixture was concentrated to obtain compound 30 as TFA salt, MS m/z 1039.6 (M+1). Retention time 1.06 minutes.

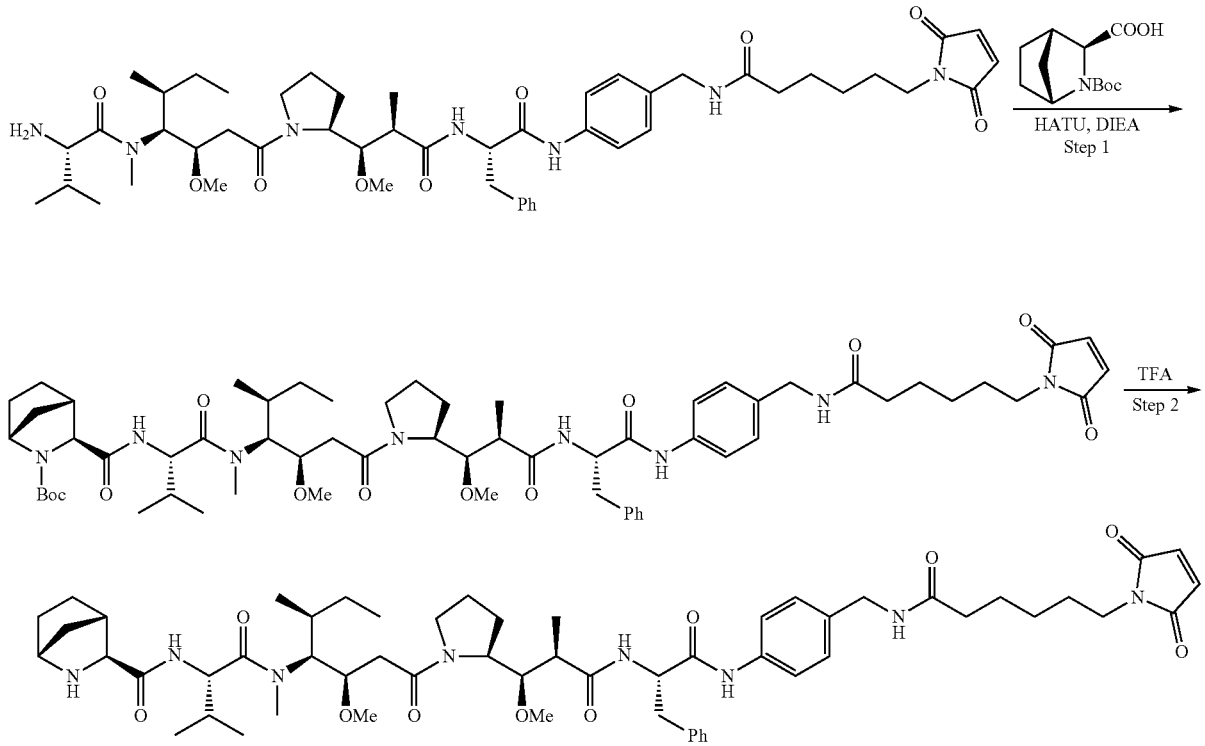

EXAMPLE 69

(1R,3S,4S)-N-((S)-1-(((3R,4S,5S)-1-((S)-2-((1R,2R)-3-(((S)-1-((4-((6-(2,5-Dioxo-2,5-dihydro-1H-pyrrol-1-yl)hexanamido)methyl)phenyl)amino)-1-oxo-3-phenylpropan-2-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (31)

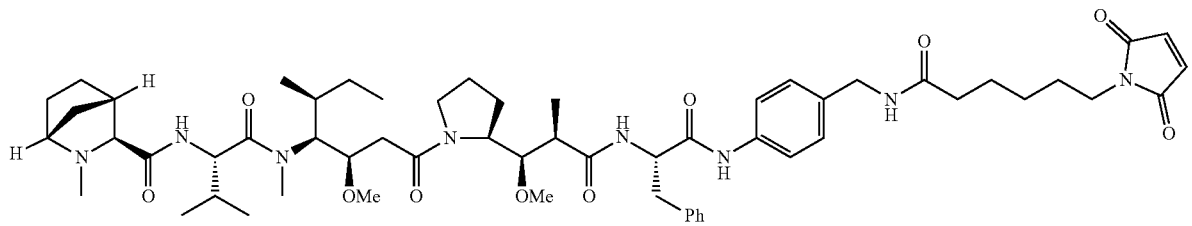

31

In a 15 mL round bottom flask were added (1R,3S,4S)-N-((S)-1-(((3R,4S,5S)-1-((S)-2-((1R,2R)-3-(((S)-1-((4-((6-(2,5-dioxo-2,5-dihydro-1H-pyrrol-1-yl)hexanamido)methyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-azabicyclo[2.2.1]heptane-3-carboxamide TFA salt (30) (20 mg, 0.017 mmol), paraformaldehyde (5.9 mg, 0.21 mmol), and acetic acid (0.0029 mL, 0.050 mmol) in MeOH (2.0 mL). To the resulting suspension was added NaCNBH$_3$ (6.6 mg, 0.11 mmol). The reaction mixture was stirred at room temperature for 18 hours. Additional formaldehyde and NaCNBH$_3$ were added and the reaction mixture was heated to 50° C. for 1 hour to complete the reaction. The crude was purified by reverse phase HPLC, C18 column, eluted with 10-50% acetonitrile-H$_2$O, containing 0.05% TFA. The fractions containing the desired product were pooled and concentrated to obtain compound 31 as TFA salt, MS m/z 1053.7 (M+1)). Retention time 1.07 minutes.

EXAMPLE 70

(1R,3S,4S)-2-Acetyl-N-((S)-1-(((3R,4S,5S)-1-((S)-2-((1R,2R)-3-(((S)-1-((4-((6-(2,5-Dioxo-2,5-dihydro-1H-pyrrol-1-yl)hexanamido)methyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-azabicyclo[2.2.1]heptane-3-carboxamide (32)

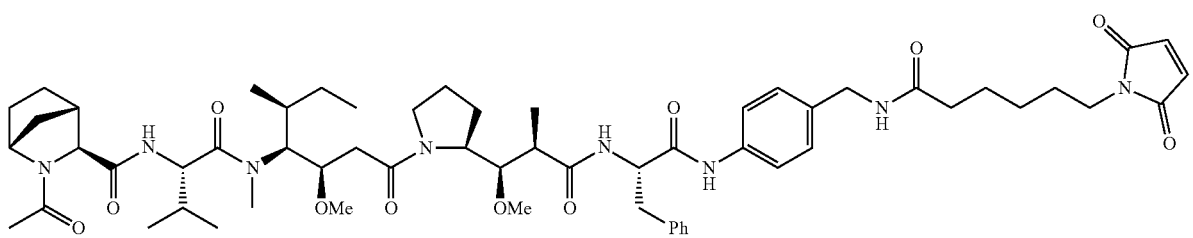

32

In a 15 mL round bottom flask were added acetic acid (0.79 mg, 0.013 mmol), DIEA (1.7 mg, 0.013 mmol) and DMF (1.0 mL), followed by HBTU (2.2 mg, 0.0058 mmol). The reaction mixture was stirred for 5 minutes before (2S,3S)-N-((S)-1-(((3R,4S,5S)-1-((S)-2-((1R,2R)-3-(((S)-1-((4-((6-(2,5-dioxo-2,5-dihydro-1H-pyrrol-1-yl)hexanamido)methyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-3-methylpyrrolidine-2-carboxamide TFA salt (30) (5.5 mg, 0.0048 mmol) was added. The reaction mixture was stirred at room temperature for 1 hour. The crude was purified by reverse phase HPLC, C18 column, eluted with 20-50% acetonitrile-H$_2$O, containing 0.05% TFA. The fractions containing the desired product were pooled and concentrated to obtain compound 32, MS m/z 1081.3 (M+1). Retention time 1.22 minutes.

EXAMPLE 71

(1R,3S,4S)-N-((S)-1-(((3R,4S,5S)-1-((S)-2-((1R,2R)-3-(((S)-1-((4-((6-(2,5-Dioxo-2,5-dihydro-1H-pyrrol-1-yl)hexanamido)methyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-(6-hydroxyhexyl)-2-azabicyclo[2.2.1]heptane-3-carboxamide (33)

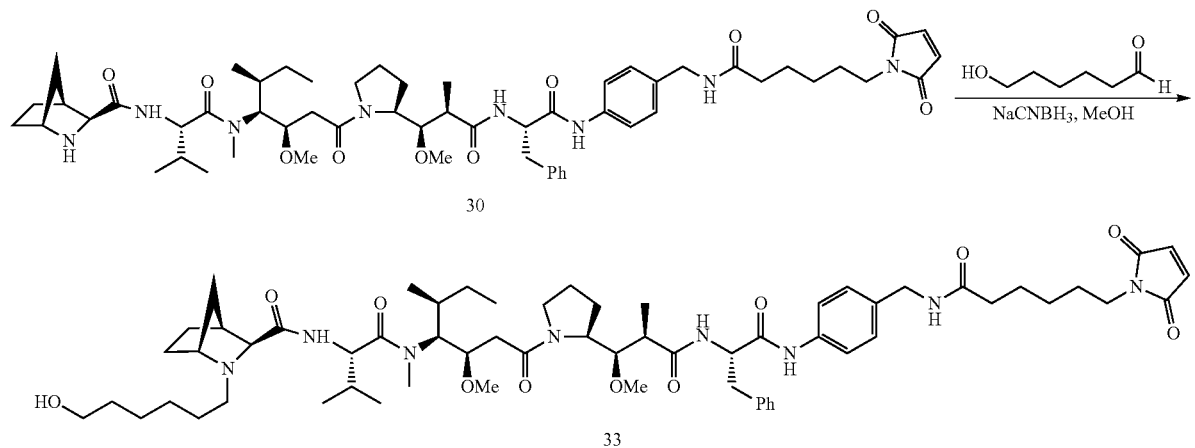

To compound 30 (3.0 mg, 0.0029 mmol) in MeOH (1.0 mL) was added 6-hydroxyhexanal (6.7 mg, 0.058 mmol), followed by NaBH$_3$CN (9.1 mg, 0.14 mmol). After 30 minutes, additional NaBH$_3$CN (9.1 mg, 0.14 mmol) was added. After another 30 minutes, LCMS analysis indicated the completion of the reaction. The reaction mixture mixture was purified by reverse phase HPLC using C18 column, eluted with 10-90% acetonitrile-H$_2$O containing 0.05% TFA. The fractions containing the desired product were pooled and lyophilized to obtain (1R,3S,4S)-N-((S)-1-(((3R,4S,5S)-1-((S)-2-((1R,2R)-3-(((S)-1-((4-((6-(2,5-dioxo-2,5-dihydro-1H-pyrrol-1-yl)hexanamido)methyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-(6-hydroxyhexyl)-2-azabicyclo[2.2.1]heptane-3-carboxamide 33, MS m/z 1139.6 (M+1). Retention time 1.10 minutes.

EXAMPLE 72

(1R,3S,4S)-N-((S)-1-(((3R,4S,5S)-1-((S)-2-((1R,2R)-3-(((S)-1-((4-((6-(2,5-Dioxo-2,5-dihydro-1H-pyrrol-1-yl)hexanamido)methyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-(6-hydroxyhexanoyl)-2-azabicyclo[2.2.1]heptane-3-carboxamide (34)

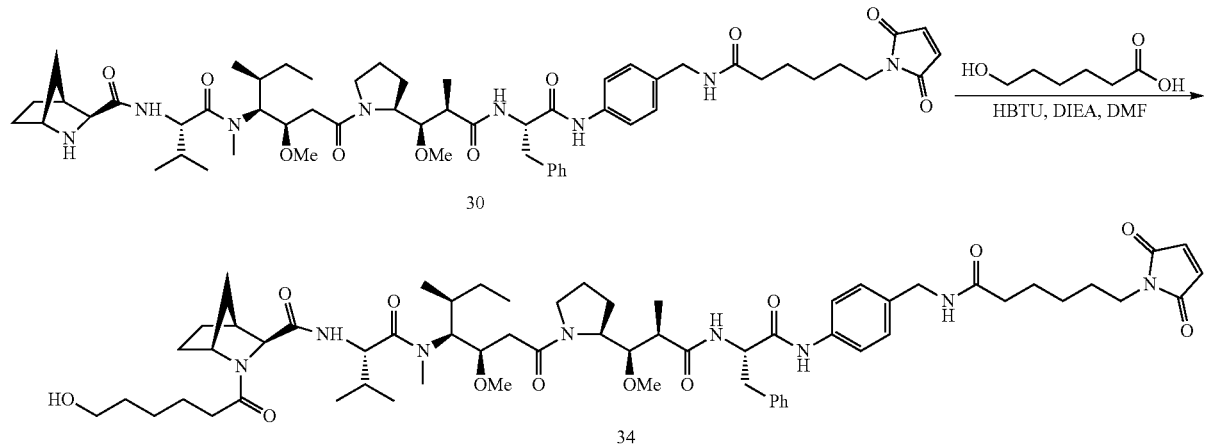

To 6-hydroxyhexanoic acid (3.8 mg, 0.029 mmol) in DMF (1 mL) were added DIEA (7.5 mg, 0.058 mmol) and HBTU (9.1 mg, 0.024 mmol). After 10 minutes, compound 30 (10 mg, 0.0096 mmol) was added. The reaction mixture was stirred for 1 hour, at which time LCMS analysis indicated the completion of the reaction. The reaction mixture was purified by reverse phase HPLC using C18 column, eluted with 10-90% acetonitrile-H$_2$O containing 0.05% TFA. The fractions containing the desired product were pooled and lyophilized to obtain compound 34, MS m/z 1153.5 (M+1). Retention time 1.20 minutes.

EXAMPLE 73

(2S)-N-((S)-1-(((3R,4S,5S)-1-((S)-2-((1R,2R)-3-(((S)-1-((4-((6-(2,5-Dioxo-2,5-dihydro-1H-pyrrol-1-yl)hexanamido)methyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-3-azabicyclo[3.1.0]hexane-2-carboxamide (35)

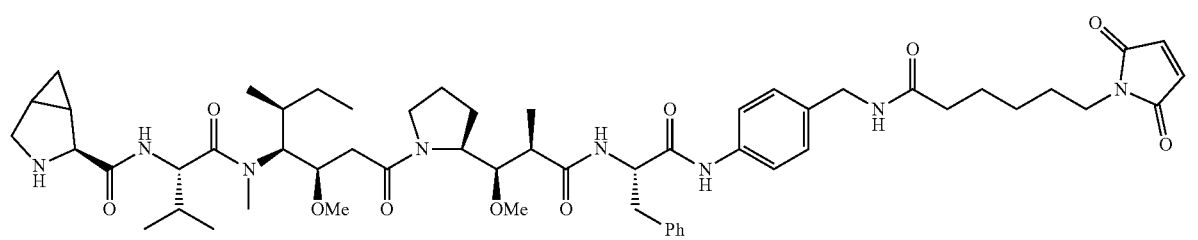

This compound was synthesized using the same method as described for compound 30 using 3-(tert-Butoxycarbonyl)-3-azabicyclo[3.1.0]hexane-2-carboxylic acid (12.5 mg, 0.055 mmol), DIEA (28.5 mg, 0.22 mmol), HATU (21 mg, 0.055 mmol) and N-(4-((S)-2-((2R,3R)-3-((S)-1-((3R,4S,5S)-4-((S)-2-amino-N,3-dimethylbutanamido)-3-methoxy-5-methylheptanoyl)pyrrolidin-2-yl)-3-methoxy-2-methylpropanamido)-3-phenylpropanamido)benzyl)-6-(2,5-dioxo-2,5-dihydro-1H-pyrrol-1-yl)hexanamide TFA salt (11 mg, 0.011 mmol). After purification, the Boc-protected intermediate was obtained, MS m/z 1125.5 (M+1). Retention time 1.34 minutes. The product thus obtained (10 mg, 0.0089 mmol) was treated with TFA (2.0 mL) in DCM (4.0 mL). The reaction mixture was stirred at room temperature for 1 hour and LCMS analysis showed Boc was completely removed. The solution was concentrated to obtain compound 35 as TFA salt, MS m/z 1025.5 (M+1). Retention time 1.06 minutes.

EXAMPLE 74

(2S)-N-((S)-1-(((3R,4S,5S)-1-((S)-2-((1R,2R)-3-(((S)-1-((4-((6-(2,5-Dioxo-2,5-dihydro-1H-pyrrol-1-yl)hexanamido)methyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-3-methyl-3-azabicyclo[3.1.0]hexane-2-carboxamide (36)

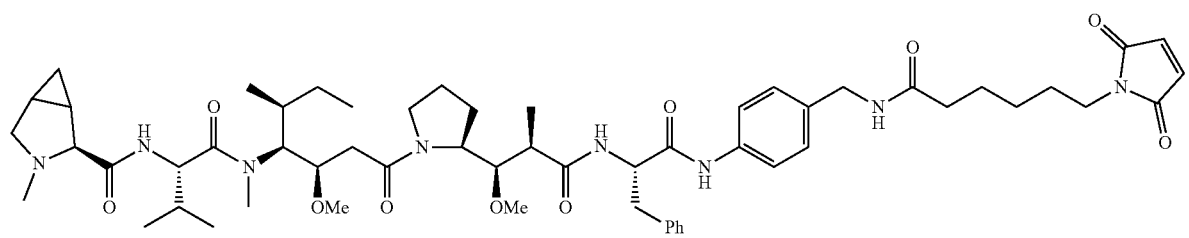

36

To (2S)-N-((S)-1-(((3R,4S,5S)-1-((S)-2-((1R,2R)-3-(((S)-1-((4-((6-(2,5-dioxo-2,5-dihydro-1H-pyrrol-1-yl)hexanamido)methyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-3-azabicyclo[3.1.0]hexane-2-carboxamide TFA salt (35) (7.9 mg, 0.0062 mmol) and paraformaldehyde (2.7 mg, 0.089 mmol) in MeOH (2.0 mL) was added NaCNBH₃ (11 mg, 0.018 mmol). The reaction mixture was stirred at 50° C. for 2 hours. The crude was purified by reverse phase HPLC, C18 column, eluted with 20-50% acetonitrile-H₂O, containing 0.05% TFA. The fractions containing the desired product were pooled and concentrated to obtain compound 36 as TFA salt, MS m/z 1039.5 (M+1). Retention time 1.07 minutes.

EXAMPLE 75

(1R,3S,4S)-N-((S)-1-(((3R,4S,5S)-1-((S)-2-((1R,2R)-3-(((S)-1-((4-((6-(2,5-Dioxo-2,5-dihydro-1H-pyrrol-1-yl)hexanamido)methyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-(2,5,8,11,14,17,20,23,26,29,32,35-dodecaoxaoctatriacontan-38-oyl)-2-azabicyclo[2.2.1]heptane-3-carboxamide (37)

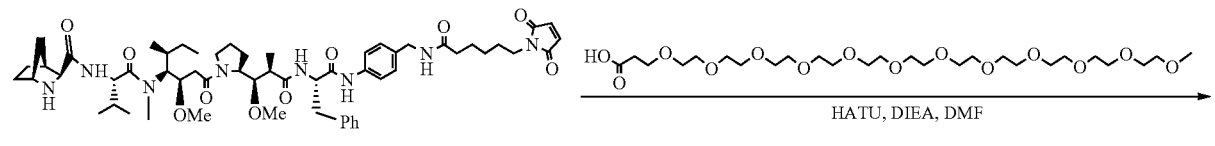

30

HATU, DIEA, DMF

-continued

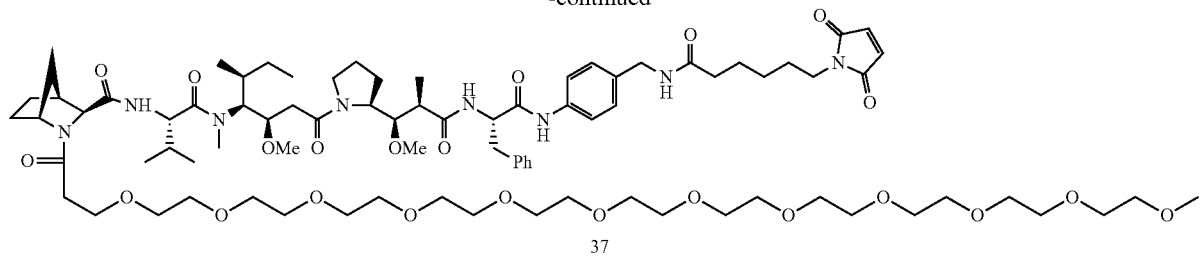
37

To 2,5,8,11,14,17,20,23,26,29,32,35-dodecaoxaoctatriacontan-38-oic acid (17.0 mg, 0.029 mmol) in DMF (1.5 mL) were added DIEA (7.5 mg, 0.058 mmol) and HATU (9.2 mg, 0.024 mmol). After 10 minutes, compound 30 (10.0 mg, 0.0096 mmol) was added. The reaction mixture was stirred for 2 hours at room temperature. The reaction mixture was purified by reverse phase HPLC using C18 column, eluted with 10-90% acetonitrile-$H_2O$ containing 0.05% TFA. The fractions containing the desire product were pooled and lyophilized to obtain compound 37, MS m/z 805.6 ((M+2)/2). Retention time 1.25 minutes.

EXAMPLE 76

(1R,3S,4S)-N-((S)-1-(((3R,4S,5S)-1-((S)-2-((1R,2R)-3-(((S)-1-((4-((6-(2,5-Dioxo-2,5-dihydro-1H-pyrrol-1-yl)hexanamido)methyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-(2,5,8,11,14,17,20,23-octaoxahexacosan-26-oyl)-2-azabicyclo[2.2.1]heptane-3-carboxamide (38)

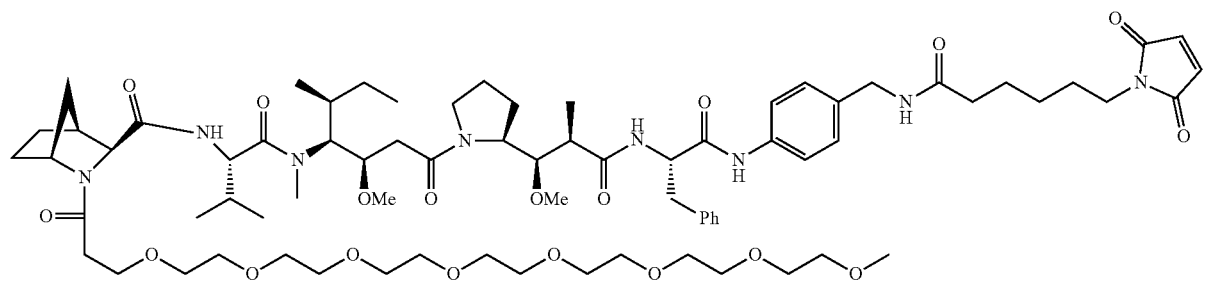
38

Compound 38 was synthesized by the same method as described for compound 37 using compound 30 (10 mg, 0.0096 mmol) and 2,5,8,11,14,17,20,23-octaoxahexacosan-26-oic acid (11.91 mg, 0.029 mmol), MS m/z 717.5 ((M+2)/2). Retention time 1.25 minutes.

EXAMPLE 77

(1R,3S,4S)-N-((S)-1-(((3R,4S,5S)-1-((S)-2-((1R,2R)-3-(((S)-1-((4-((6-(2,5-Dioxo-2,5-dihydro-1H-pyrrol-1-yl)hexanamido)methyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-(1-hydroxy-3,6,9,12-tetraoxapentadecan-15-oyl)-2-azabicyclo[2.2.1]heptane-3-carboxamide (39)

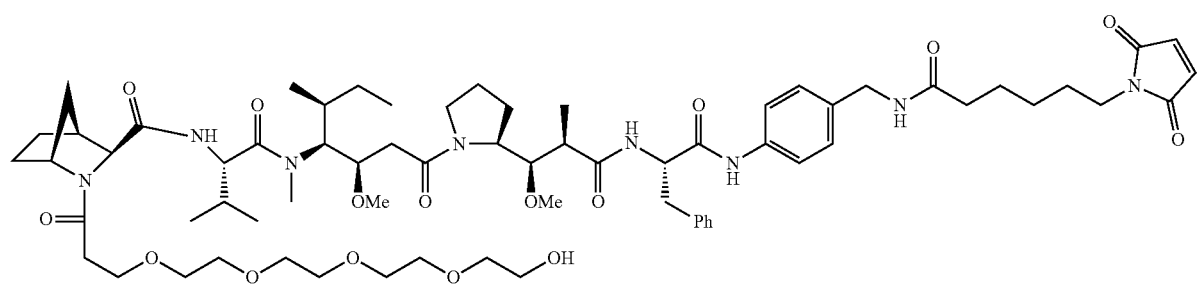

31

Compound 39 was synthesized by the same method as described for compound 37 using using 30 (10 mg, 0.0096 mmol), 1-hydroxy-3,6,9,12-tetraoxapentadecan-15-oic acid (7.7 mg, 0.029 mmol), DIEA (7.46 mg, 0.058 mmol) and HBTU (9.12 mg, 0.024 mmol) in DMF (1.5 mL), MS m/z 1287.6 (M+1)). Retention time 1.18 minutes.

EXAMPLE 78

(1R,3S,4S)-N-((S)-1-(((3R,4S,5S)-1-((S)-2-((1R,2R)-3-(((S)-1-((4-((4-((2,5-Dioxo-2,5-dihydro-1H-pyrrol-1-yl)methyl)cyclohexanecarboxamido)methyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (40)

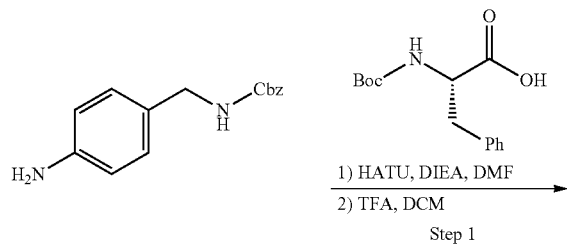

Step 1

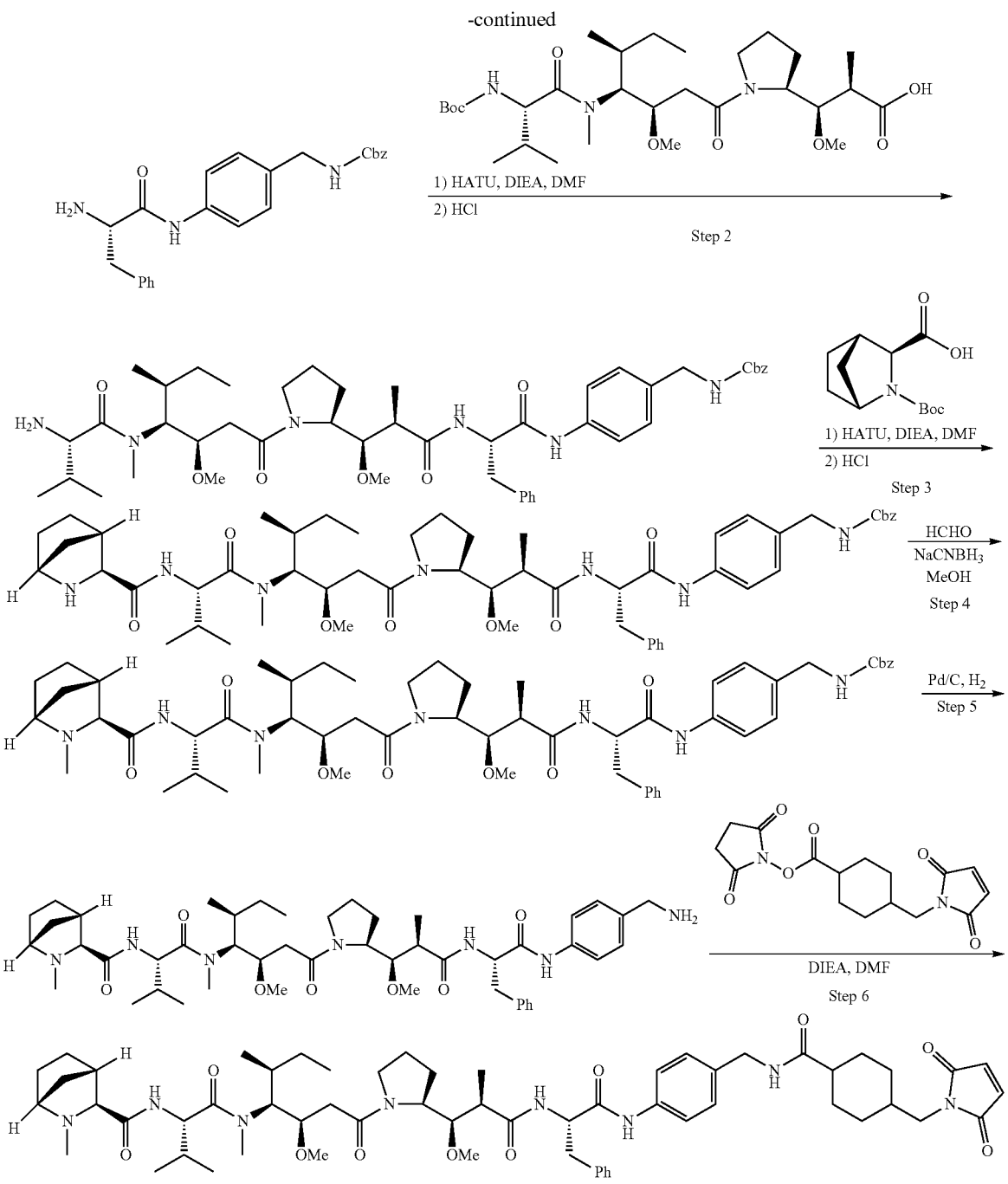

Step 1: (S)-2-((tert-Butoxycarbonyl)amino)-3-phenylpropanoic acid (964 mg, 3.63 mmol) was dissolved in DMF (10 mL). DIEA (1.27 g, 9.84 mmol) and HATU (1.13 g, 3.03 mmol) were added. After 10 minutes, benzyl 4-aminobenzylcarbamate (388 mg, 1.51 mmol) was added. The reaction mixture was stirred for 2 hours at room temperature at which time LCMS analysis indicated the completion of the reaction. EtOAc (60 mL) was added to the reaction. Then the reaction mixture was washed with saturated aqueous NaHCO$_3$. The aqueous layer was extracted with EtOAc (2×30 mL). The combined organic phases were washed with H$_2$O (5×10 mL), dried over MgSO$_4$, filtered and concentrated to afford the crude product. The crude product was dissolved in DCM (5.0 mL) and treated with TFA (5.0 mL). After 1 hour at room temperature, LCMS analysis indicated the completion of the reaction. Solvents were removed under reduced pressure. The residue was purified by ISCO using 0-8% MeOH with 2M ammonia in DCM to obtained (S)-benzyl 4-(2-amino-3-phenylpropanamido)benzylcarbamate as a white solid, MS m/z 404.2 (M+1)). $^1$H NMR (400 MHz, CD$_3$OD): δ 7.44-7.23 (m, 14H), 5.10 (s, 2H), 4.26 (s, 2H), 4.12 (d, J=7.4 Hz, 1H), 3.28-3.22 (m, 1H), 3.15-3.10 (m, 1H).

Step 2: (S)-Benzyl 4-(2-amino-3-phenylpropanamido)benzylcarbamate (201.7 mg, 0.50 mmol) and (2R,3R)-3-((S)-1-((3R,4S,5S)-4-((S)-2-((tert-butoxycarbonyl)amino)-N,3-dimethylbutanamido)-3-methoxy-5-methylheptanoyl)pyrrolidin-2-yl)-3-methoxy-2-methylpropanoic acid (429 mg, 0.75 mmol) were dissolved in DMF (6 mL). Then DIEA (323 mg, 2.50 mmol) and HATU (342 mg, 0.90 mmol) were added. The reaction mixture was stirred for 1 hour at room temperature. The reaction mixture was purified by reverse phase HPLC to afford benzyl 4-((S)-2-((2R,3R)-3-((S)-1-((3R,4S,5S)-4-((S)-2-amino-N,3-dimethylbutanamido)-3-methoxy-5-methylheptanoyl)pyrrolidin-2-yl)-3-methoxy-2-methylpropanamido)-3-phenylpropanamido)benzylcarbamate, MS m/z 957.5 (M+1), Retention time 1.54 minutes. The Boc protected product (393 mg, 0.41 mmol) was dissolved in methanolic HCl (3 M, 15 mL). The solvent was slowly evaporated under reduced pressure. LCMS analysis indicated the completion of the deprotection reaction. Acetonitrile and water were added and the resulting solution was lyophilized to obtain benzyl 4-((S)-2-((2R,3R)-3-((S)-1-((3R,4S,5S)-4-((S)-2-amino-N,3-dimethylbutanamido)-3-methoxy-5-methylheptanoyl)pyrrolidin-2-yl)-3-methoxy-2-methylpropanamido)-3-phenylpropanamido)benzylcarbamate as a HCl salt, MS m/z 857.5 (M+1). Retention time 1.16 minutes.

Step 3: (1R,3S,4S)-2-(tert-Butoxycarbonyl)-2-azabicyclo[2.2.1]heptane-3-carboxylic acid (190 mg, 0.788 mmol) was dissolved in DMF (5.0 mL). DIEA (254 mg, 1.97 mmol) and HATU (270 mg, 1.71 mmol) were added. The reaction mixture was stirred for 15 minutes, and benzyl 4-((S)-2-((2R,3R)-3-((S)-1-((3R,4S,5S)-4-((S)-2-amino-N,3-dimethylbutanamido)-3-methoxy-5-methylheptanoyl)pyrrolidin-2-yl)-3-methoxy-2-methylpropanamido)-3-phenylpropanamido)benzylcarbamate (336 mg, 0.394 mmol) was added. The reaction mixture was stirred for 2 hours at room temperature at which time LCMS analysis indicated the completion of the reaction. The reaction mixture was purified by reverse phase HPLC using C18 column, eluted with 10-90% acetonitrile-H$_2$O containing 0.05% TFA. The fractions containing the desired product were pooled and lyophilized to obtain (1R,3S,4S)-tert-butyl 3-(((S)-1-(((3R,4S,5S)-1-((S)-2-((1R,2R)-3-(((S)-1-((4-(((((benzyloxy)carbonyl)amino)methyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)carbamoyl)-2azabicyclo[2.2.1]heptane-2-carboxylate, MS m/z 1080.5 (M+1), Retention time 1.56 minutes.

The Boc protected product (88 mg, 0.081 mmol) was dissolved in methanolic HCl (3 M, 6.0 mL). The solvent was slowly evaporated under reduced pressure. LCMS analysis indicated the completion of the deprotection reaction. Acetonitrile and water were added and the resulting solution was lyophilized to obtain benzyl 4-((S)-2-((2R,3R)-3-((S)-1-((3R,4S,5S)-4-((S)-2-((1R,3S,4S)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanamido)benzylcarbamate as a HCl salt, MS m/z 980.5 (M+1).

Step 4: Benzyl 4-((S)-2-((2R,3R)-3-((S)-1-((3R,4S,5S)-4-((S)-2-((1R,3S,4S)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanamido)benzylcarbamate (65.8 mg, 0.067 mmol) was dissolved in MeOH (4 mL). Paraformaldehyde (22.8 mg, 0.76 mmol) and acetic acid (0.023 mL, 0.40 mmol) were added, followed by sodium cyanoborohydride (47.7 mg, 0.76 mmol). The reaction mixture was heated to 50° C. with stirring for 1 hour. LCMS analysis indicated the completion of the reaction. The crude was purified by reverse phase HPLC using C18 column, eluted with 10-90% acetonitrile-H$_2$O containing 0.05% TFA. The fractions containing the desired product were pooled and lyophilized to obtain benzyl 4-((S)-2-((2R,3R)-3-((S)-1-((3R,4S,5S)-4-((S)-N,3-dimethyl-2-((1R,3S,4S)-2-methyl-2-azabicyclo[2.2.1]heptane-3-carboxamido)butanamido)-3-methoxy-5-methylheptanoyl)pyrrolidin-2-yl)-3-methoxy-2-methylpropanamido)-3-phenylpropanamido)benzylcarbamate, MS m/z 994.5 (M+1). Retention time 1.21 minutes.

Step 5: Benzyl 4-((S)-2-((2R,3R)-3-((S)-1-((3R,4S,5S)-4-((S)-N,3-dimethyl-2-((1R,3S,4S)-2-methyl-2-azabicyclo[2.2.1]heptane-3-carboxamido)butanamido)-3-methoxy-5-methylheptanoyl)pyrrolidin-2-yl)-3-methoxy-2-methylpropanamido)-3-phenylpropanamido)benzylcarbamate (48 mg, 0.048 mmol) was dissolved in MeOH (5.0 mL), and flashed under N$_2$. Pd/C (20.5 mg, 10% Pd) was added. The reaction vessel was evacuated and backfilled with H$_2$. This operation was repeated five times to replace the reaction atmosphere with H$_2$. The reaction mixture was stirred for 2 hours at room temperature under H$_2$. LCMS analysis indicated the completion of the reaction. The reaction mixture was filtered, and concentrated to obtained (1R,3S,4S)-N-((S)-1-(((3R,4S,5S)-1-((S)-2-((1R,2R)-3-(((S)-1-((4-(aminomethyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide, MS m/z 860.5 (M+1). Retention time 0.86 minutes. The product thus obtained was used is the next step without further purification.

Step 6: (1R,3S,4S)-N-((S)-1-(((3R,4S,5S)-1-((S)-2-((1R,2R)-3-(((S)-1-((4-(Aminomethyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (12 mg, 0.014 mmol) and 2,5-dioxopyrrolidin-1-yl 4-((2,5-dioxo-2,5-dihydro-1H-pyrrol-1-yl)methyl)cyclohexanecarboxylate (5.6 mg, 0.017 mmol) were dissolved in DMF (1 mL), and DIEA (10.8 mg, 0.084 mmol) was added. The reaction mixture was stirred for 1 hour at room temperature. LCMS analysis indicated the completion of the reaction. The crude was purified by reverse phase HPLC using C18 column, eluted with 10-90% acetonitrile-H$_2$O containing 0.05% TFA. The fractions containing the desired product were pooled and lyophilized to obtain compound 40, MS m/z 1079.5 (M+1). Retention time 1.12 minutes.

EXAMPLE 79

(1R,3S,4S)-N-((S)-1-(((3R,4S,5S)-1-((S)-2-((1R,2R)-3-(((S)-1-((4-((3-(2-(2-(2,5-Dioxo-2,5-dihydro-1H-pyrrol-1-yl)ethoxy)ethoxy)propanamido)methyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (41)

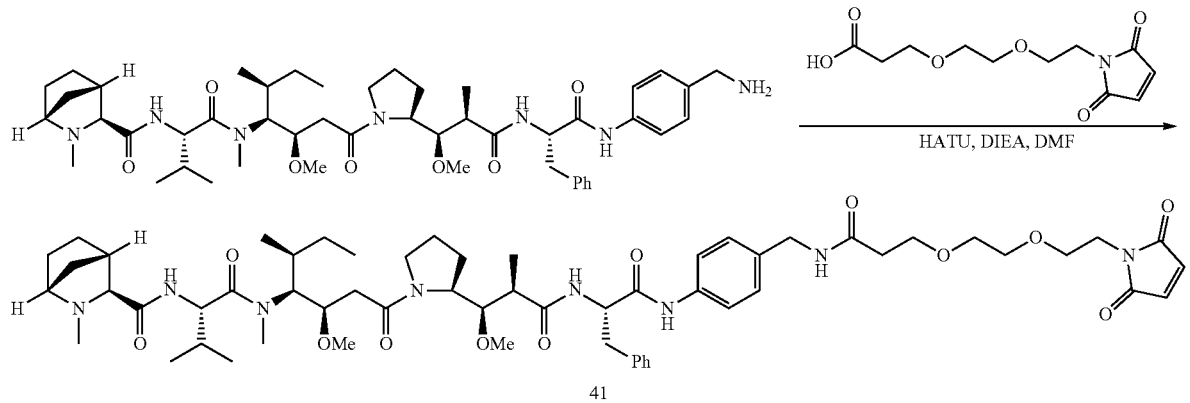

41

To 3-(2-(2-(2,5-dioxo-2,5-dihydro-1H-pyrrol-1-yl)ethoxy)ethoxy)propanoic acid (7.2 mg, 0.028 mmol) in DMF (1.5 ml) were added DIEA (10.8 mg, 0.084 mmol) and HATU (8.0 mg, 0.021 mmol). After 10 minutes, (1R,3S,4S)-N-((S)-1-(((3R,4S,5S)-1-((S)-2-((1R,2R)-3-(((S)-1-((4-(aminomethyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (12 mg, 0.014 mmol) was added. The reaction mixture was stirred for 2 hours at room temperature. The crude was purified by reverse phase HPLC using C18 column, eluted with 10-90% acetonitrile-H$_2$O containing 0.05% TFA. The fractions containing the desired product were pooled and lyophilized to obtain compound 41, MS m/z 1099.5 (M+1). Retention time 1.07 minutes.

EXAMPLE 80

(1R,3S,4S)-N-((S)-1-(((3R,4S,5S)-1-((S)-2-((1R,2R)-3-(((S)-1-((4-((2,5-Dioxo-2,5-dihydro-1H-pyrrol-1-yl)methyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (42)

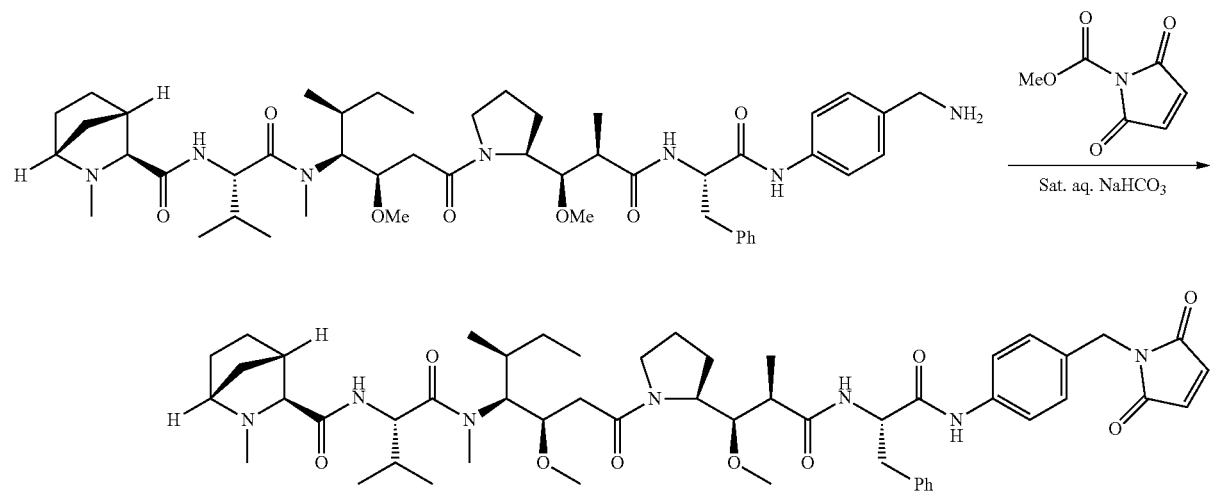

42

To saturated aqueous NaHCO₃ (3.0 mL) was added (1R, 3S,4S)-N-((S)-1-(((3R,4S,5S)-1-((S)-2-((1R,2R)-3-(((S)-1-((4-(Aminomethyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (20.0 mg, 0.023 mmol). The resulting suspension was cooled to 0° C., and methyl 2,5-dioxo-2,5-dihydro-1H-pyrrole-1-carboxylate (14.4 mg, 0.093 mmol) was added. The reaction mixture was stirred at 0° C. for 1.5 hours. The crude was purified by reverse phase HPLC using C18 column, eluted with 10-90% acetonitrile-H₂O containing 0.05% TFA. The fractions containing the desired product were pooled and lyophilized to obtain compound 42, MS m/z 940.5 (M+1). Retention time 1.13 minutes.

EXAMPLE 81

(1R,3S,4S)-N-((S)-1-(((3R,4S,5S)-1-((S)-2-((1R,2R)-3-(((S)-1-((4-((3-(6-(2,5-Dioxo-2,5-dihydro-1H-pyrrol-1-yl)hexyl)ureido)methyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (43)

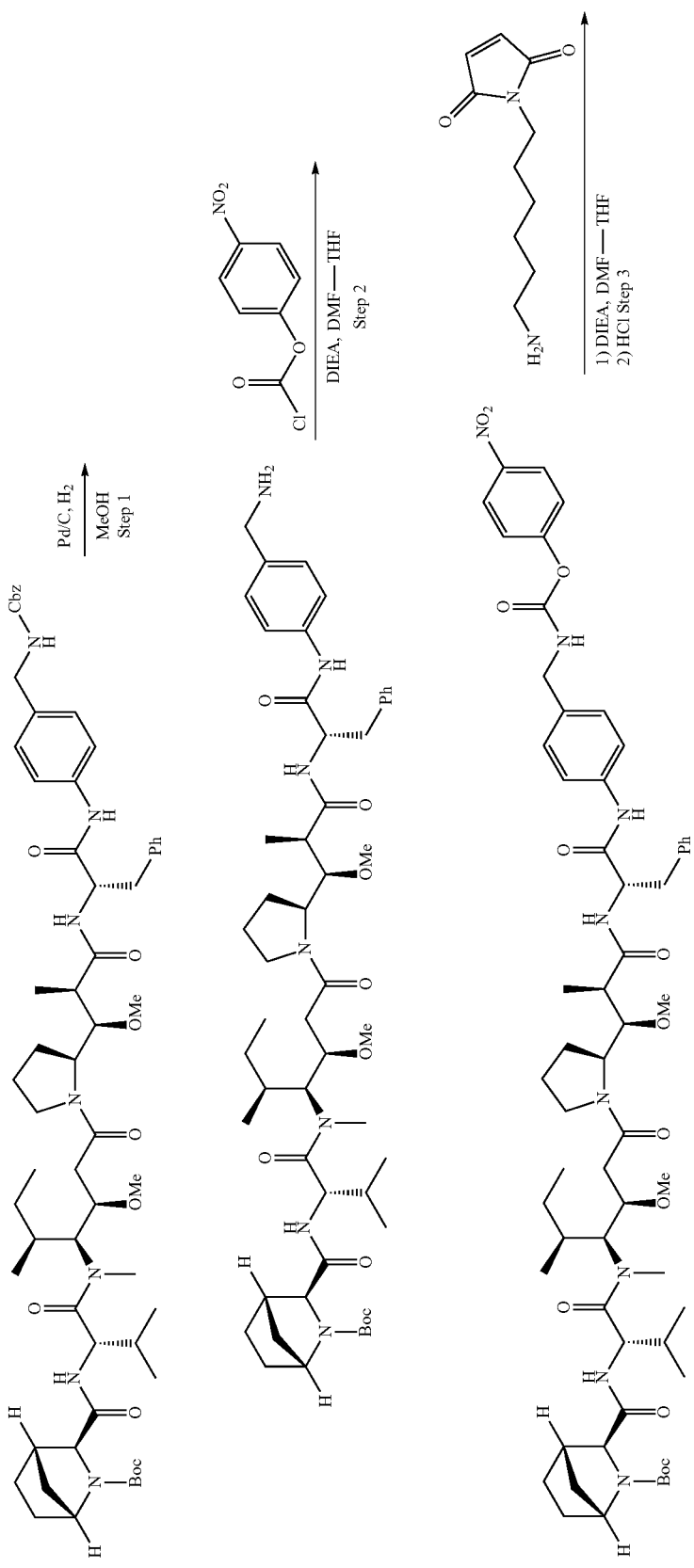

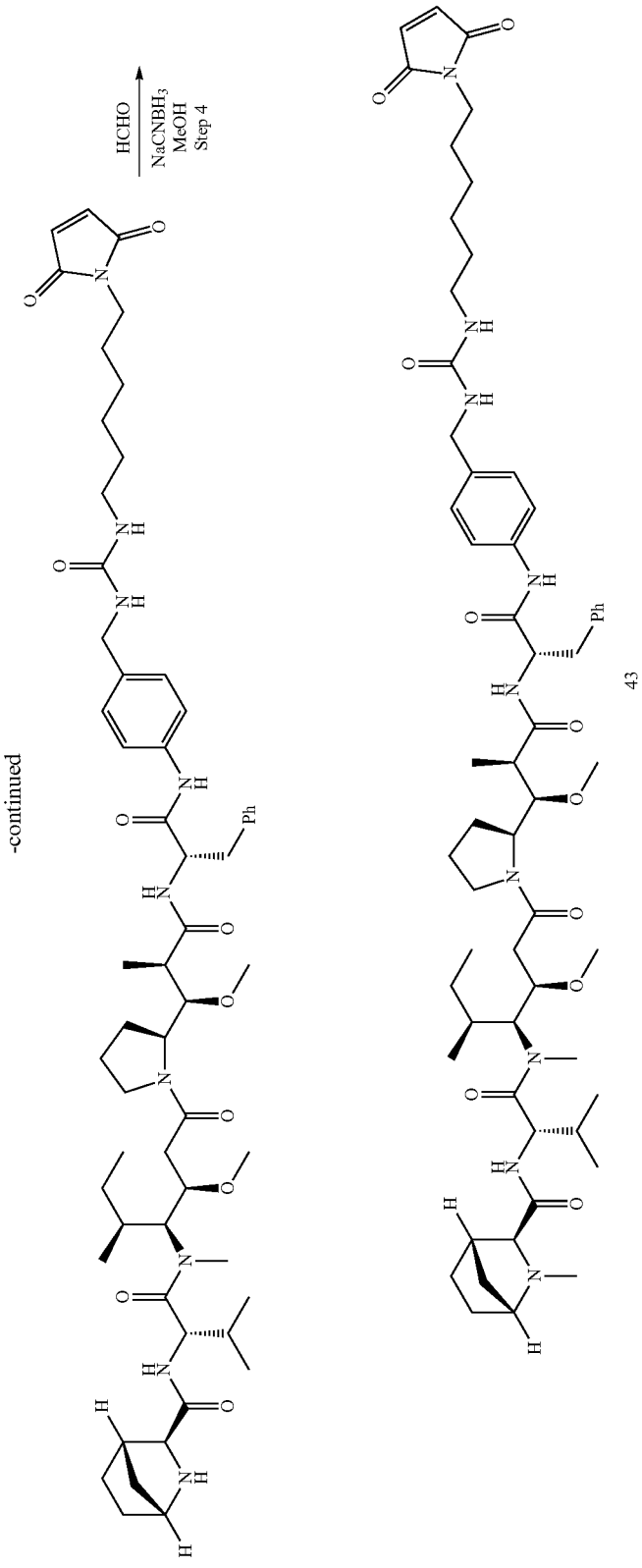

Step 1: (1R,3S,4S)-tert-Butyl 3-(((S)-1-(((3R,4S,5S)-1-((S)-2-((1R,2R)-3-(((S)-1-((4-(((Benzyloxy)carbonyl)amino)methyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)carbamoyl)-2-azabicyclo[2.2.1]heptane-2-carboxylate (211 mg, 0.195 mmol) was dissolved in MeOH (10 mL). Pd/C (41.6 mg, 10% Pd) was added. The reaction vessel was evacuated and backfilled with $H_2$. This operation was repeated five times to replace the reaction atmosphere with $H_2$. The reaction mixture was stirred for 2 hours at room temperature under $H_2$. LCMS analysis indicated the completion of the reaction. The reaction mixture was filtered and concentrated to afford (1R,3S,4S)-tert-butyl 3-(((S)-1-(((3R,4S,5S)-1-((S)-2-((1R,2R)-3-(((S)-1-((4-(aminomethyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)carbamoyl)-2-azabicyclo[2.2.1]heptane-2-carboxylate, MS m/z 946.6 (M+1)), which was used in the next step without purification.

Step 2: (1R,3S,4S)-tert-Butyl 3-(((S)-1-(((3R,4S,5S)-1-((S)-2-((1R,2R)-3-(((S)-1-((4-(aminomethyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)carbamoyl)-2-azabicyclo[2.2.1]heptane-2-carboxylate (30 mg, 0.032 mmol) was dissolved in DMF (3 ml) and THF (3 ml). Then DIEA (20.5 mg, 0.16 mmol) and 4-nitrophenyl carbonochloridate (12.8 mg, 0.063 mmol) were added. The reaction mixture was stirred for 2 hours at room temperature. LC/MS analysis indicated the completion of the reaction. The crude was purified by reverse phase HPLC using C18 column, eluted with 10-90% acetonitrile-$H_2O$ containing 0.05% TFA. The fractions containing the desired product were pooled and lyophilized to obtain (1R,3S,4S)-tert-butyl 3-(((S)-1-(((3R,4S,5S)-3-methoxy-1-((S)-2-((1R,2R)-1-methoxy-2-methyl-3-(((S)-1-((4-((((4-nitrophenoxy)carbonyl)amino)methyl)phenyl)amino)-1-oxo-3-phenylpropan-2-yl)amino)-3-oxopropyl)pyrrolidin-1-yl)-5-methyl-1-oxoheptan-4-yl)(methyl)amino)-3-methyl-1-oxobutan-2-yl)carbamoyl)-2-azabicyclo[2.2.1]heptane-2-carboxylate, MS m/z 1111.5 (M+1). Retention time 1.54 minutes.

Step 3: To (1R,3S,4S)-tert-Butyl 3-(((S)-1-(((3R,4S,5S)-3-methoxy-1-((S)-2-((1R,2R)-1methoxy-2-methyl-3-(((S)-1-((4-(((((4-nitrophenoxy)carbonyl)amino)methyl)phenyl)amino)-1-oxo-3-phenylpropan-2-yl)amino)-3-oxopropyl)pyrrolidin-1-yl)-5-methyl-1-oxoheptan-4-yl)(methyl)amino)-3-methyl-1-oxobutan-2-yl)carbamoyl)-2-azabicyclo[2.2.1]heptane-2-carboxylate (13.7 mg, 0.012 mmol) dissolved in DMF (1.0 mL) and THF (1.0 mL) were added 1-(6-aminohexyl)-1H-pyrrole-2,5-dione (14.5 mg, 0.074 mmol) and DIEA (31.9 mg, 0.25 mmol). The reaction mixture was stirred for 4 hours at room temperature. The LCMS analysis indicated the completion of the reaction. The crude was purified by reverse phase HPLC using C18 column, eluted with 10-90% acetonitrile-$H_2O$ containing 0.05% TFA. The fractions containing the desired product were pooled and lyophilized to obtain (1R,3S,4S)-tert-butyl 3-(((S)-1-(((3R,4S,5S)-1-((S)-2-((1R,2R)-3-(((S)-1-((4-((3-(6-(2,5-dioxo-2,5-dihydro-1H-pyrrol-1-yl)hexyl)ureido)methyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)carbamoyl)-2-azabicyclo[2.2.1]heptane-2-carboxylate, MS m/z 1168.6 (M+1). The Boc protected product thus obtained was dissolved in methanolic HCl (3 M, 2.0 mL). The solvent was removed slowly under reduced pressure. LCMS analysis indicated the completion of the reaction. The residue was dissolved in Acetonitrile and water and lyophilized to afford (1R,3S,4S)-N-((S)-1-(((3R,4S,5S)-1-((S)-2-((1R,2R)-3-(((S)-1-((4-((3-(6-(2,5-dioxo-2,5-dihydro-1H-pyrrol-1-yl)hexyl)ureido)methyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-azabicyclo[2.2.1]heptane-3-carboxamide as a HCl salt, MS m/z 1068.6 (M+1). Retention time 1.09 minutes Step 4: (1R,3S,4S)-N-((S)-1-(((3R,4S,5S)-1-((S)-2-((1R,2R)-3-(((S)-1-((4-((3-(6-(2,5-Dioxo-2,5-dihydro-1H-pyrrol-1-yl)hexyl)ureido)methyl)phenyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-azabicyclo[2.2.1]heptane-3-carboxamide (8.4 mg, 0.0079 mmol) was dissolved in MeOH(1.5 mL). Paraformaldehyde (2.7 mg, 0.089 mmol) and acetic acid (0.0027 mL, 0.046 mmol) were added, followed by sodium cyanoborohydride (5.6 mg, 0.089 mmol). The reaction mixture was heated to 50° C. for 1 hour with stirring. The crude was purified by reverse phase HPLC using C18 column, eluted with 10-90% acetonitrile-$H_2O$ containing 0.05% TFA. The fractions containing the desired product were pooled and lyophilized to obtain compound 43, MS m/z 1082.6 (M+1). Retention time 1.11 minutes.

EXAMPLE 82

(1R,3S,4S)-N-((S)-1-(((3R,4S,5S)-1-((S)-2-((1R,2R)-3-(((S)-1-((4-((6-(2,5-Dioxo-2,5-dihydro-1H-pyrrol-1-yl)hexanamido)methyl)phenyl)(methyl)amino)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (44)

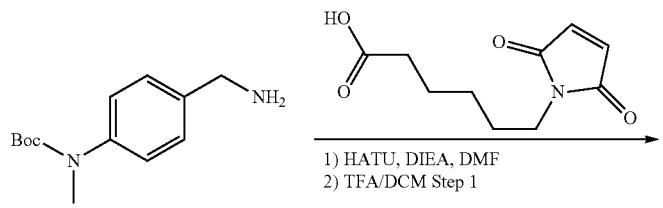

1) HATU, DIEA, DMF
2) TFA/DCM Step 1

251
252
-continued
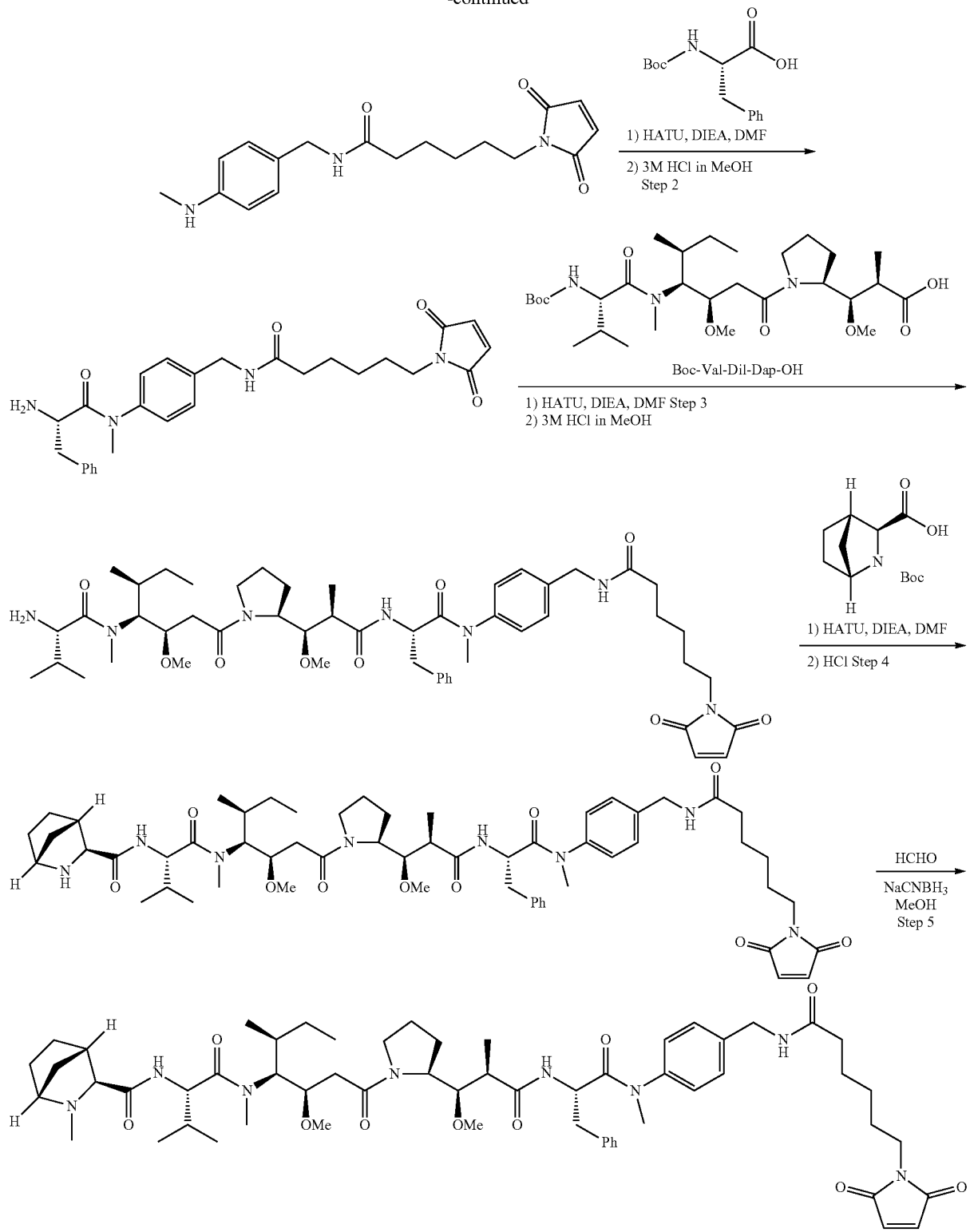
Step 1: 6-(2,5-Dioxo-2,5-dihydro-1H-pyrrol-1-yl) hexanoic acid (349 mg, 1.65 mmol) were dissolved in DMF (10 mL). Then DIEA (820 mg, 6.35 mmol) and HATU (579 mg, 1.52 mmol) were added and the reaction mixture was stirred at room temperature for 10 minutes. tert-Butyl (4-(aminomethyl)phenyl)(methyl)carbamate (300 mg, 1.27 mmol) was then added. The reaction mixture was stirred for 1 hour at room temperature. EtOAc (30 mL) was added to the reaction. Then the reaction mixture was washed with saturated aqueous NaHCO$_3$. The aqueous layer was extracted with EtOAc (2×30 mL). The combined organic phase was washed with H$_2$O (5×10 mL), dried with MgSO$_4$, concentrated and purified by ISCO (EtOAc/Hexane 0-80%). The desired product, MS m/z 374.2 (M+1-tBu), retention time 1.156 minutes, was obtained as a yellow oil. The product was dissolved in DCM (3 mL) and treated with TFA (1 mL). After 1 hour at room temperature, solvents were removed under reduced pressure. The residue was taken up in acetonitrile and H$_2$O and lyophilized to obtained 6-(2,5-dioxo-2,5-dihydro-1H-pyrrol-1-yl)-N-(4-(methylamino)benzyl)hexanamide as a yellow solid (MS m/z 330.2 (M+1), Retention time 0.61 minutes).

Step 2: To (S)-2-((tert-butoxycarbonyl)amino)-3-phenylpropanoic acid (219 mg, 0.827 mmol) dissolved in DMF (5 mL) were added DIEA (356 mg, 2.76 mmol) and HATU (288 mg, 0.758 mmol). After stirred for 10 minutes at room temperature, 6-(2,5-dioxo-2,5-dihydro-1H-pyrrol-1-yl)-N-(4-(methylamino)benzyl)hexanamide (227 mg, 0.689 mmol) was added. The reaction mixture was stirred for 2 hours at room temperature. EtOAc (20 mL) was added to the reaction. Then the reaction mixture was washed with saturated aqueous NaHCO$_3$. The aqueous layer was extracted with EtOAc (2×20 mL). The combined organic phase was washed with H$_2$O (5×10 mL), dried over anhydrous MgSO$_4$, concentrated and purified by ISCO (EtOAc/Hexane, 0-75%), affording the desired product. MS m/z 577.3 (M+1). Retention time 1.19 minutes. $^1$H NMR (400 MHz, DMSO-d$_6$): δ 10.00 (s, 1H), 8.24 (t, J=6.0 Hz, 1h), 7.52 (d, j=8.4 Hz, 2H), 7.32-7.09 (m, 7H), 7.01 (s, 2H), 4.31 (m, 1H), 4.19 (d, J=6.0 Hz, 2H), 3.38 (t, J=7.0 Hz, 2H), 3.17 (d, J=7.2 Hz, 2H), 3.00 (m, 1H), 2.85 (m, 1H), 2.10 (t, J=7.4 Hz, 2H), 1.54-1.44 (m, 4H), 1.31 (s, 9H), 1.22-1.15 (m, 4H). The product was dissolved in 3M HCl in MeOH (5 mL). Solvents were removed slowly under reduced pressure. The residue was taken up in acetonitrile and H$_2$O and lyophilized to obtained (S)-N-(4-(2-amino-N-methyl-3-phenylpropanamido)benzyl)-6-(2,5-dioxo-2,5-dihydro-1H-pyrrol-1-yl)hexanamide as HCl salt. MS m/z 477.2 (M+1). Retention time 0.83 minutes.

Step 3; To Boc-Val-Dil-Dap-OH (347 mg, 0.607 mmol) dissolved in DMF (4 mL) were added DIEA (261 mg, 2.02 mmol) and HATU (282 mg, 0.49 mmol) were. After stirred for 15 minutes at room temperature (S)-N-(4-(2-amino-N-methyl-3-phenylpropanamido)benzyl-6-(2,5-dioxo-2,5-dihydro-1H-pyrrol-1-yl)hexanamide (193 mg, 0.404 mmol) was added. The reaction mixture was stirred for 2 hours at room temperature. The reaction mixture was purified by reverse-phase HPLC to afford the desired product, N-(4-((S)-2-((2R,3R)-3-((S)-1-((3R,4S,5S)-4-((S)-2-amino-N,3-dimethylbutanamido)-3-methoxy-5-methylheptanoyl)pyrrolidin-2-yl)-3-methoxy-2-methylpropanamido)-N-methyl-3-phenylpropanamido)benzyl)-6-(2,5-dioxo-2,5-dihydro-1H-pyrrol-1-yl)hexanamide. MS m/z 1030.5 (M+1). Retention time 1.430 minutes. The product was dissolved in 3M methanolic HCl (3 mL). Solvents were removed under reduced pressure. The residue was taken up in acetonitrile and H$_2$O and lyophilized to obtained the desired product N-(4-((S)-2-((2R,3R)-3-((S)-1-((3R,4S,5S)-4-((S)-2-amino-N,3-dimethylbutanamido)-3-methoxy-5-methylheptanoyl)pyrrolidin-2-yl)-3-methoxy-2-methylpropanamido)-N-methyl-3-phenylpropanamido)benzyl)-6-(2,5-dioxo-2,5-dihydro-1H-pyrrol-1-yl)hexanamide as HCl salt. MS m/z 930.5 (M+1). Retention time 1.07 minutes.

Step 4-5: Following the same procedure as described for preparation of compound 30 and compound 31, compound 44 was obtained. MS m/z 1067.6 (M+1). Retention time 1.10 minutes.

EXAMPLE 83

(1R,3S,4S)-N-((S)-1-(((3R,4S,5S)-1-((S)-2-((1R,2R)-3-(((S)-N-1-(3-Azidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-azabicyclo[2.2.1]heptane-3-carboxamide (45)

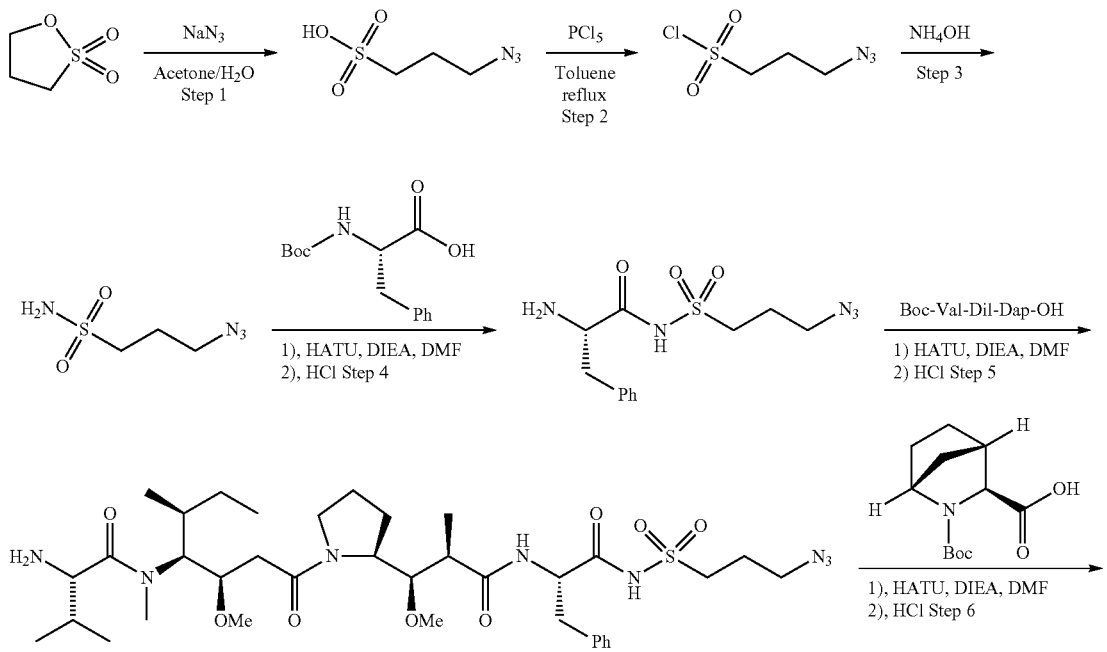

-continued

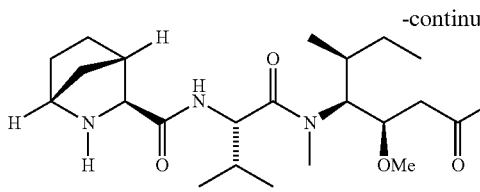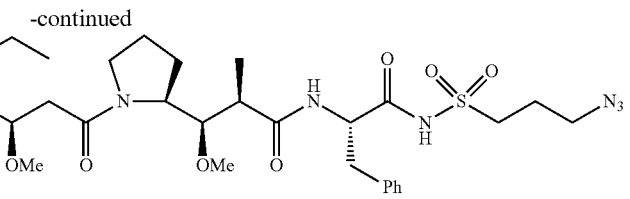

45

Step 1: To a stirred solution of sodium azide (3.50 g, 53.8 mmol) in water (25 mL) was added a solution of 1,3-propane sulfone (6.10 g, 50.0 mmol) in acetone (25 mL). The reaction mixture was stirred at room temperature for 24 hours and concentrated to dryness. The resulting solid was suspended in diethyl ether (100 mL) and stirred at reflux for 1 hour. The suspension was cooled to room temperature and the solid was collected by filtration, washed with acetone and diethyl ether, and dried under vacuum, affording 3-azido-1-propanesulfonic acid. MS m/z 188.1 (M+1). $^1$H NMR (400 MHz, CD$_3$OD): δ 3.47 (t, J=6.8 Hz, 2H), 2.87 (t, J=7.6 Hz, 2H), 2.07-2.00 (m, 2H).

Step 2: 3-Azido-1-propanesulfonic acid (2.07 g, 13.0 mmol) was suspended in toluene. PCl$_5$ (2.61 g, 13.0 mmol) was added. The mixture was heated at reflux for 3 hours. The reaction mixture was cooled to room temperature, and filtered to remove insolubles. The filter cake was washed with DCM. The combined filtrates were concentrated to give 3-azidopropane-1-sulfonyl chloride as a dark yellow oil, which was used in the next step without further purification.

Step 3: To NH$_4$OH (5 mlL) cooled at 0° C. was added 3-azidopropane-1-sulfonyl chloride (1.75 g, 9.53 mmol). After 10 minutes, The reaction mixture was warmed to room temperature and stirred at the same temperature for 3 hours. The oily mixture became clear. The reaction mixture was extracted with EtOAc three times. The organic phase was washed with brine, dried over anhydrous MgSO$_4$, and concentrated. The residual solvent was further removed under high vacuum for 18 hours to give 3-azidopropane-1-sulfonamide. MS m/z 187.1 (M+1). $^1$H NMR (400 MHz, CDCl$_3$): δ 4.83 (s, 2H), 3.51 (t, J=6.4 Hz, 2H), 3.23 (t, J=7.6 Hz, 2H), 2.17-2.10 (m, 2H).

Step 4: (S)-2-((tert-Butoxycarbonyl)amino)-3-phenylpropanoic acid (100 mg, 0.38 mmol) was dissolved in DMF (4 mL), followed by addition of DIEA (0.395 mL, 2.26 mmol) and HATU (358 mg, 0.940 mmol). After 15 minutes, 3-azidopropane-1-sulfonamide (186 mg, 1.13 mmol) was added. The reaction mixture was stirred for 2 hours at which time LCMS analysis indicated the completion of the reaction. The crude was purified by reverse phase HPLC using C18 column, eluted with 10-90% acetonitrile-H$_2$O containing 0.05% TFA. The fractions containing the desired roduct were pooled and lyophilized to obtain (S)-tert-butyl (1-(3-azidopropylsulfonamido)-1-oxo-3-phenylpropan-2-yl)carbamate. MS m/z 312.1 (M+1-Boc). Retention time 1.15 minutes. The product thus obtained (72.4 mg. 0.176 mmol) was dissolved in 3M methanolic HCl (5 mL). The solvent was removed under reduced pressure. The residue was taken up in acetonitrile and H$_2$O and lyophilized to give (S)-2-amino-N-((3-azidopropyl)sulfonyl)-3-phenylpropanamide as a pinkish yellowish solid. MS m/z 312.1 (M+1). $^1$H NMR (400 MHz, CD$_3$OD): δ 7.42-7.31 (m, 5H), 4.16-4.13 (m, 1H), 3.51-3.47 (m, 4H), 3.32-3.26 (m, 1H), 3.13-3.08 (m, 1H), 2.00-1.94 (m, 2H).

Step 5: To Boc-Val-Dil-Dap-OH (195 mg, 0.34 mmol) dissolved in DMF (4 mL) were added DIEA (132 mg, 1.02 mmol) and HATU (108 mg, 0.28 mmol). The reaction mixture was stirred for 15 minutes at room temperature before (S)-2-amino-N-((3-azidopropyl)sulfonyl)-3-phenylpropanamide (59.2 mg, 0.17 mmol) was added. The reaction mixture was stirred for additional 2 hours at room temperature. The crude was purified by reverse-phase HPLC to afford the desired product (95 mg, 65% yield, MS m/z 865.4 (M+1), Retention time 1.43 minutes). The product was dissolved in 3M HCl in MeOH (3 mL). Solvents were removed under vacuum. Then acetonitrile and H$_2$O were added to the residue and the solution was lyophilized to obtained the desired product, (S)-1-(((3R,4S,5S)-1-((S)-2-((1R,2R)-3-(((S)-N-1-(3-azidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-2-amino-3-methyl-1-oxobutane. MS m/z 765.4 (M+1). Retention time 1.04 minutes.

Step 6: To (1R,3S,4S)-2-(tert-butoxycarbonyl)-2-azabicyclo[2.2.1]heptane-3-carboxylic acid (16.5 mg, 0.068 mmol) in DMF (2.0 mL) were added DIEA (17.6 mg, 0.137 mmol) and HATU (21.6 mg, 0.057 mmol). The reaction mixture was stirred at room temperature for 10 minutes before (S)-1-(((3R,4S,5S)-1-((S)-2-((1R,2R)-3-(((S)-N-1-(3-azidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-2-amino-3-methyl-1-oxobutane (20 mg, TFA salt, 0.023 mmol) was added. The reaction mixture was stirred for 2 hours at room temperature at which time LCMS analysis indicated the completion of the reaction. The crude was purified by reverse phase HPLC using C18 column, eluted with 10-90% ACN-H$_2$O containing 0.05% TFA. The fractions containing the desired product were pooled and lyophilized to obtain (1R,3S,4S)-N-((S)-1-(((3R,4S,5S)-1-((S)-2-((1R,2R)-3-(((S)-N-1-(3-azidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-(tert-butoxycarbonyl)-2-azabicyclo[2.2.1]heptane-3-carboxamide. MS m/z 988.5 (M+1). Retention time 1.51 minutes. The product thus obtained (9.4 mg. 0.0095 mmol) was dissolved in methanolic HCl (3M, 2.0 mL). The solvent was removed slowly under reduced pressure. The residue was dissolved in acetonitrile and H$_2$O and lyophilized to give compound 45 as a HCl salt. MS m/z 888.5 (M+1). Retention time 1.10 minutes.

EXAMPLE 84

(1R,3S,4S)-N-((S)-1-(((3R,4S,5S)-1-((S)-2-((1R,2R)-3-(((S)-N-1-(3-Azidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (46)

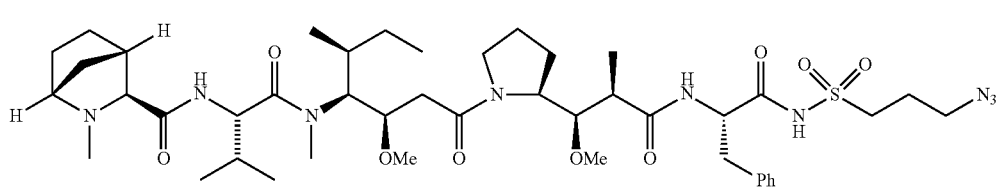

(1R,3S,4S)-N-((S)-1-(((3R,4S,5S)-1-((S)-2-((1R,2R)-3-(((S)-N-1-(3-Azidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl) amino)-3-methyl-1-oxobutan-2-yl)-2-azabicyclo[2.2.1] heptane-3-carboxamide (45) (8.8 mg, 0.0099 mmol) was dissolved in MeOH (2.0 mL). Paraformaldehyde (10.1 mg, 0.337 mmol) and acetic acid (0.0102 mL) were added, followed by sodium cyanoborohydride (21.2 mg, 0.337 mmol). The reaction mixture was heated at 50° C. with stirring for 1 hour. Additional paraformaldehyde (10.1 mg, 0.337 mmol), acetic acid (0.0102 mL) and sodium cyanoborohydride (21.2 mg, 0.337 mmol) were added. After 1 hour at 50° C., LCMS analysis indicated the completion of the reaction. The crude was purified by reverse phase HPLC using C18 column, eluted with 10-90% ACN—$H_2O$ containing 0.05% TFA. The fractions containing the desired product were pooled and lyophilized to obtain compound 46. MS m/z 902.5 (M+1). Retention time 1.12 minutes.

EXAMPLE 85

(1R,3S,4S)-N-((S)-1-(((3R,4S,5S)-1-((S)-2-((1R,2R)-3-(((S)-N-1-(3-(4-((2,5-Dioxo-2,5-dihydro-1H-pyrrol-1-yl)methyl)-1H-1,2,3-triazol-1-yl)propylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl) amino)-3-methyl-1-oxobutan-2-yl)-2-methyl-2-azabicyclo[2.2.1]heptane-3-carboxamide (47)

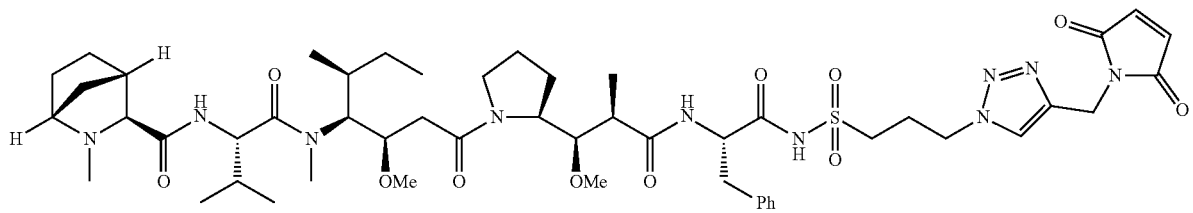

A solution of (1R,3S,4S)-N-((S)-1-(((3R,4S,5S)-1-((S)-2-((1R,2R)-3-(((S)-N-1-(3-azidopropylsulfonamido)-1-oxo-3-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (46) (5.2 mg, 0.0058 mmol), 1-(prop-2-yn-1-yl)-1H-pyrrole-2,5-dione (1.56 mg, 0.012 mmol) and CuSO₄ (0.7 mg, 0.004 mmol) in DMF (2.0 mL) and H₂O (0.5 mL) was treated with L-ascorbic acid sodium salt (2.5 mg, 0.014 mmol) and stirred at room temperature for 2 hours. Additional CuSO₄ (0.7 mg, 0.004 mmol) and L-ascorbic acid sodium salt (2.5 mg, 0.014 mmol) were added. After additional 2 hours at room temperature, LCMS analysis indicated the completion of the reaction. The crude was purified by reverse phase HPLC using C18 column, eluted with 10-90% acetonitrile-H₂O containing 0.05% TFA. The fractions containing the desired product were pooled and lyophilized to obtain compound 47. MS m/z 1037.4 (M+1). Retention time 1.00 minutes.

EXAMPLE 86

6-(2,5-Dioxo-2,5-dihydro-1H-pyrrol-1-yl)hexyl hydrogen ((R)-1-((2R,3R)-3-((S)-1-((3R,4S,5S)-4-((S)-N,3-dimethyl-2-((1R,3S,4S)-2-methyl-2-azabicyclo[2.2.1]heptane-3-carboxamido)butanamido)-3-methoxy-5-methylheptanoyl)pyrrolidin-2-yl)-3-methoxy-2-methylpropanamido)-2-phenylethyl) phosphonate (48)

To ((R)-1-((2R,3R)-3-((S)-1-((3R,4S,5S)-4-((S)-N,3-dimethyl-2-((1R,3S,4S)-2-methyl-2-azabicyclo[2.2.1]heptane-3-carboxamido)butanamido)-3-methoxy-5-methylheptanoyl)pyrrolidin-2-yl)-3-methoxy-2-methylpropanamido)-2-phenylethyl)phosphinic acid 9 (10.2 mg, 0.011 mmol) in pyridine (2 ml) was added 1-(6-hydroxyhexyl)-1H-pyrrole-2,5-dione (13.5 mg, 0.068 mmol) and then pivaloyl chloride (40 mg, 0.332 mmol). The reaction mixture was stirred at room temperature for 0.5 hour and the reaction was monitored by LCMS until 90% of the phosphinic acid disappeared. Then a freshly prepared I₂ solution in 5% H₂O in pyridine was added. Once the oxidation step was complete, pyridine was removed by high vacuum. The crude was dissolved in acetonitrile and the crude was purified by reverse phase HPLC, C18 column, eluted with 10-60% acetonitrile-H₂O, containing 0.05% TFA. The fractions containing desired product were concentrated to obtain compound 48. MS m/z 971.5 (M+1). Retention time 1.038 minutes.

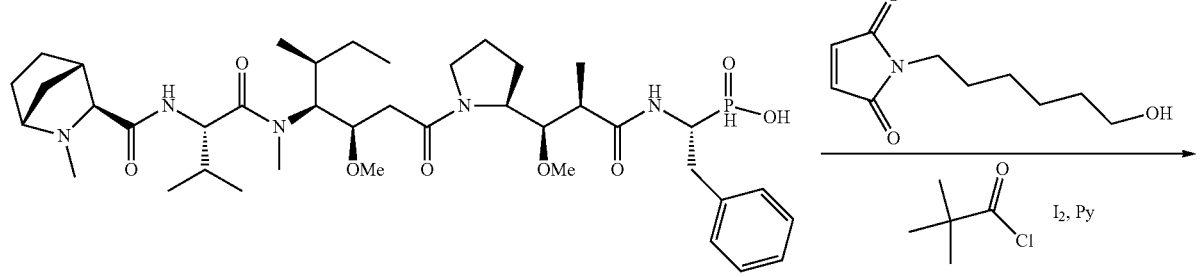

9

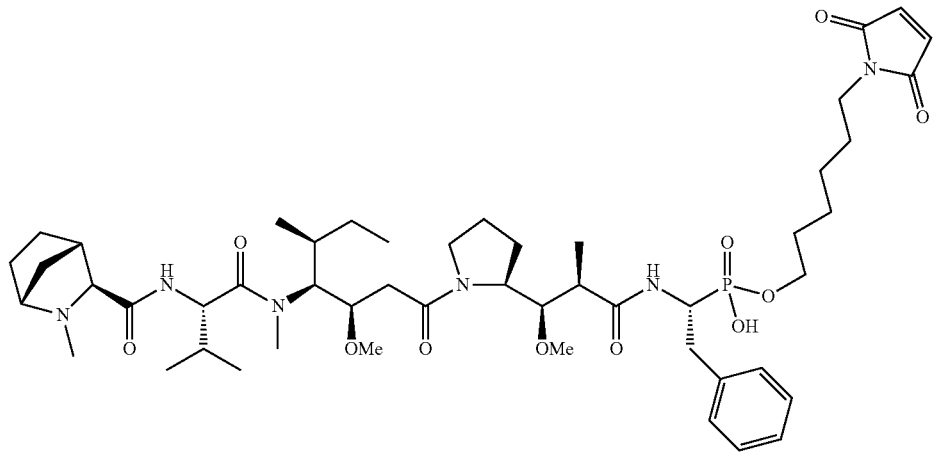

48

EXAMPLE 87

(1R,3S,4S)-N-((S)-1-(((3R,4S,5S)-1-((S)-2-((1R,2R)-3-(((S)-1-(3-(6-(2,5-Dioxo-2,5-dihydro-1H-pyrrol-1-yl)hexanamido)phenyl)-3-hydroxypropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (90)

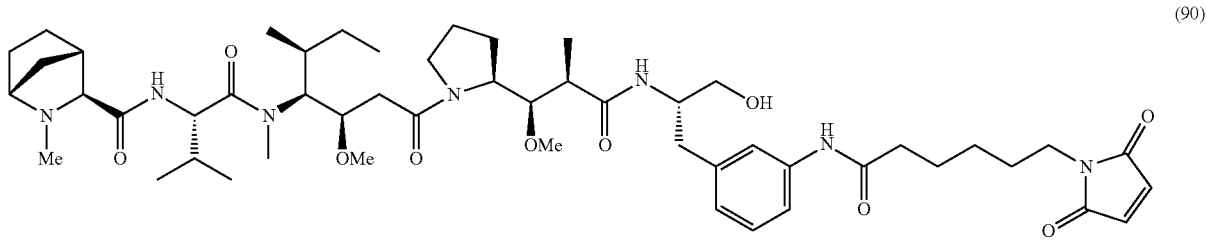 [SMILES: CC[C@H](C)[C@@H]([C@@H](CC(=O)N1CCC[C@H]1[C@H](OC)[C@@H](C)C(=O)N[C@H](CO)Cc1cccc(NC(=O)CCCCCN2C(=O)C=CC2=O)c1)OC)N(C)C(=O)[C@@H](NC(=O)[C@@H]1[C@H]2CC[C@H](C2)N1C)C(C)C]

(90)

EMCA (1.3 mg, 0.006 mmol) in DMF (0.5 ml) was treated with DIEA (0.006 ml, 0.03 mmol) and HATU (2.3 mg, 0.006 mmol) at rt for 10 min, and then compound (52) TFA salt (6 mg, 0.006 mmol) in DMF (0.5 ml) was added. The reaction was stirred at rt for 16 h. The crude was purified by preparative HPLC (10-45% acetonitrile-H$_2$O containing 0.05% TFA) to obtain compound (90) as TFA salt. MS m/z 950.6 (M+H). Retention time 0.934 min.

EXAMPLE 88

4-((S)-2-((S)-2-(6-(2,5-Dioxo-2,5-dihydro-1H-pyrrol-1-yl)hexanamido)-3-methylbutanamido)-5-ureidopentanamido)benzyl (3-((S)-2-((2R,3R)-3-((S)-1-((3R,4S,5S)-4-((S)-N,3-dimethyl-2-((1R,3S,4S)-2-methyl-2-azabicyclo[2.2.1]heptane-3-carboxamido)butanamido)-3-methoxy-5-methylheptanoyl)pyrrolidin-2-yl)-3-methoxy-2-methylpropanamido)-3-hydroxypropyl)phenyl)carbamate (91)

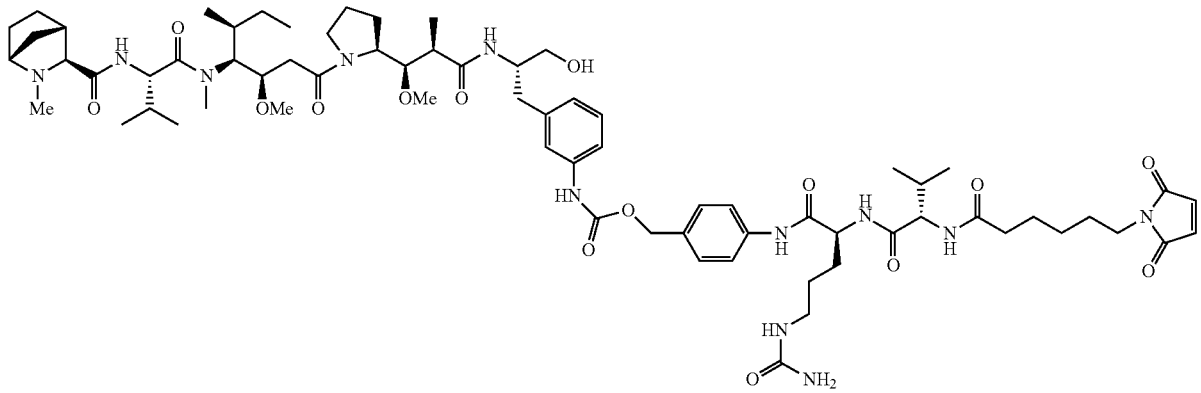

(91)

Pyridine (0.25 ml) was added to (52) TFA salt (6 mg, 0.006 mmol), MC-Val-Cit-PAB-PNP (13 mg, 0.018 mmol) in DMF (1 ml), followed by HOAT (0.8 mg, 0.006 mmol) and DIEA (13 mg, 0.098 mmol).The reaction was stirred at 40° C. for 48 h. The crude was purified by preparative HPLC (25-40% acetonitrile-H$_2$O containing 0.05% TFA) to obtain compound (91) as TFA salt. MS m/z 678.6 (M/2+H). Retention time 0.959 min.

EXAMPLE 89

(1R,3S,4S)-N-((S)-1-(((3R,4S,5S)-3-Methoxy-1-((S)-2-((1R,2R)-1-methoxy-2-methyl-3-oxo-3-(((S)-1-phenyl-3-(N-(6-(2,5-dioxo-2,5-dihydro-1H-pyrrol-1-yl)hexanoyl)-sulfamoylpropan)-2-yl)amino) propyl)pyrrolidin-1-yl)-5-methyl-1-oxoheptan-4-yl) (methyl)amino-3-methyl-1-oxobutan-2-yl)-2-methyl-2-azabicyclo[2.2.1]heptane-3-carboxamide (92)

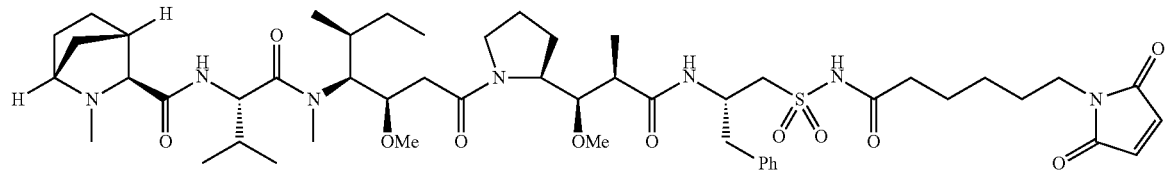

(92)

EMCA (12.1 mg, 0.057 mmol) was dissolved in DMF (1 ml). DIEA (0.0024 ml) and HATU (19.7 mg, 0.052 mmol) were added. Then (1R,3S,4S)-N-((S)-1-(((3R,4S,5S)-3-methoxy-1-((S)-2-((1R,2R)-1-methoxy-2-methyl-3-oxo-3-(((S)-1-phenyl-3-sulfamoylpropan-2-yl)amino)propyl)pyrrolidin-1-yl)-5-methyl-1-oxoheptan-4-yl)(methyl)amino)-3-methyl-1-oxobutan-2-yl)-2-methyl-2-azabicyclo[2.2.1] heptane-3-carboxamide ((55), 26.4 mg, 0.029 mmol) in DMF (2 ml) was added. The reaction was stirred at rt for 2 h. Then additional EMCA (12.1 mg, 0.057 mmol), DIEA (0.0024 ml) and HATU (19.7 mg, 0.052 mmol) were added. After 2 h, EMCA (12.1 mg, 0.057 mmol), DIEA (0.0024 ml) and HATU (19.7 mg, 0.052 mmol) were added again. Then the reaction was heated at 50° C. for 2 h. The reaction was cooled down, and additional EMCA (12.1 mg, 0.057 mmol), DIEA (0.0024 ml) and HATU (19.7 mg, 0.052 mmol) were added. The reaction was stirred for 16 h at rt. LCMS indicated approximately 20% of (55) was converted to the product. The reaction mixture was purified by preparative HPLC (30-50% acetonitrile-$H_2O$ containing 0.05% TFA) to obtain (1R,3S,4S)-N-((S)-1-(((3R,4S,5S)-3-methoxy-1-((S)-2-((1R,2R)-1-methoxy-2-methyl-3-oxo-3-(((S)-1-phenyl-3-(N-(6-(2,5-dioxo-2,5-dihydro-1H-pyrrol-1-yl) hexanoyl)-sulfamoylpropan)-2-yl)amino)propyl)pyrrolidin-1-yl)-5-methyl-1-oxoheptan-4-yl)(methyl)amino)-3-methyl-1-oxobutan-2-yl)-2-methyl-2-azabicyclo[2.2.1] heptane-3-carboxamide (92). MS m/z 998.5 (M+1). Retention time 1.041 min.

EXAMPLE 90

(1R,4S)-N-((S)-1-(((3R,4S,5S)-1-((S)-2-((3R,4R,7S)-7-Benzyl-20-(4-((2,5-dioxo-2,5-dihydro-1H-pyrrol-1-yl)methyl)-1H-1,2,3-triazol-1-yl)-4-methyl-5,8-dioxo-2,12,15,18-tetraoxa-6,9-diazaicosan-3-yl) pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (93)

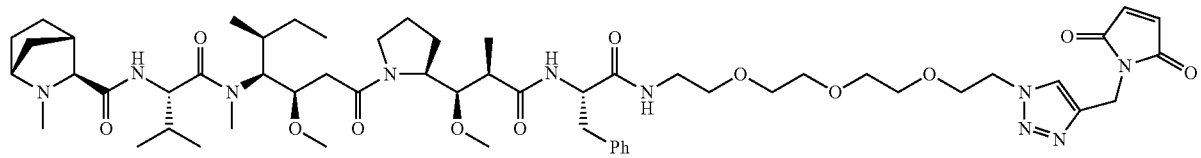

(93)

Step 1: (S)-2-((t-Butoxycarbonyl)amino)-3-phenylpropanoic acid (175 mg, 0.66 mmol) in DMF (4 ml) was treated with DIEA (0.48 ml, 2.75 mmol) and HATU (230 mg, 0.605 mmol) for 15 min, followed by addition of 2-(2-(2-(2-azidoethoxy)ethoxy)ethoxy)ethanamine (120 mg, 0.55 mmol). The reaction was stirred overnight. The crude was purified by preparative HPLC (20-70% acetonitrile-$H_2O$ containing 0.05% TFA) to obtain (S)-t-butyl (1-azido-13-oxo-15-phenyl-3,6,9-trioxa-12-azapentadecan-14-yl)carbamate. MS m/z 466.3 (M+1). Retention time 1.170 min.

Step 2: (S)-t-Butyl (1-azido-13-oxo-15-phenyl-3,6,9-trioxa-12-azapentadecan-14-yl)carbamate (117 mg, 0.251 mmol) was dissolved in methanolic HCl (3M, 5 ml). The solvent was slowly removed by evaporation, resulting in complete removal of the Boc group. The residual solvent was further removed under reduced pressure overnight to obtain (S)-2-amino-N-(2-(2-(2-(2-azidoethoxy)ethoxy)ethoxy)ethyl)-3-phenylpropanamide as HCl salt. MS m/z 366.1 (M+1). Retention time 0.858 min.

Step 3: (2R,3R)-3-((S)-1-((3R,4S,5S)-4-((S)-N,3-Dimethyl-2-((1R,3S,4S)-2-methyl-2-azabicyclo[2.2.1]heptane-3-carboxamido)butanamido)-3-methoxy-5-methylheptanoyl)pyrrolidin-2-yl)-3-methoxy-2-methylpropanoic acid (Step 2, Example 12, 8 mg, 0.01 mmol) was in DMF (1 ml) was treated with DIEA (0.011 ml, 0.066 mmol) and HATU (4.63 mg, 0.012 mmol) for 15 min, followed by addition of (S)-2-amino-N-(2-(2-(2-(2-azidoethoxy)ethoxy)ethoxy)ethyl)-3-phenylpropanamide (5.3 mg, 0.013 mmol) in DMF (1 ml). The reaction was stirred for 2 h at rt. The crude was purified by preparative HPLC (20-70% acetonitrile-H$_2$O containing 0.05% TFA) to obtain (1R,4S)-N-((S)-1-(((3R,4S,5S)-1-((S)-2-((3R,4R,7S)-20-azido-7-benzyl-4-methyl-5,8-dioxo-2,12,15,18-tetraoxa-6,9-diazaicosan-3-yl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide. MS m/z 956.5 (M+1). Retention time 1.051 min.

Step 4: To the product obtained in step 3 (6.2 mg, 0.0058 mmol) and 1-(prop-2-yn-1-yl)-1H-pyrrole-2,5-dione (1.6 mg, 0.012 mmol) in t-BuOH (1 ml) and water (1 ml) were added sodium L-ascorbate (1.1 mg, 0.0058 mmol) in 0.2 ml H$_2$O and CuSO$_4$ (0.2 mg, 0.001 mmol) in 0.1 ml water were added. The reaction mixture was stirred at rt for 4 h, and then purified by preparative HPLC (20-70% acetonitrile-H$_2$O containing 0.05% TFA) to obtain compound (93). MS m/z 1091.6 (M+1). Retention time 0.980 min.

EXAMPLE 91

(1R,4S)-N-((S)-1-(((3R,4S,5S)-1-((S)-2-((3R,4R,7S)-7-Benzyl-17-(2,5-dioxo-2,5-dihydro-1H-pyrrol-1-yl)-4-methyl-5,8-dioxo-2,12,15-trioxa-6,9-diazaheptadecan-3-yl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (94)

Step 1: t-Butyl (2-(2-(2-aminoethoxy)ethoxy)ethyl)carbamate (250 mg, 1.0 mmol) and methyl 2,5-dioxo-2,5-dihydro-1H-pyrrole-1-carboxylate (156 mg, 1.0 mmol) were combined in saturated aqueous NaHCO$_3$ (10 ml) and stirred for 1.5 h at 0° C. The reaction mixture was acidified to pH 2 with hydrochloric acid (2 M) and extracted with EtOAc. The organic phase was washed with brine, dried with MgSO$_4$, and concentrated. The crude was purified by ISCO using 0-4% MeOH/DCM to give t-butyl (2-(2-(2-(2,5-dioxo-2,5-dihydro-1H-pyrrol-1-yl)ethoxy)ethoxy)ethyl)carbamate as a colorless oil. MS m/z 229.2 (M+1-Boc). Retention time 0.963 min. $^1$H NMR (400 MHz, Chloroform-d) δ 6.71 (s, 2H), 5.04 (bs, 1H), 3.74 (t, J=5.4 Hz, 2H), 3.64 (t, J=5.4 Hz, 2H), 3.61-3.59 (m, 2H), 3.56-3.54 (m, 2H), 3.50 (t, J=5.2 Hz, 2H), 3.31-3.26 (m, 2H), 1.44 (s, 9H).

Step 2: t-Butyl (2-(2-(2-(2,5-dioxo-2,5-dihydro-1H-pyrrol-1-yl)ethoxy)ethoxy)ethyl)carbamate (184 mg, 0.56 mmol) in DCM (2 ml) was treated with TFA (0.4 ml) at 0° C. for 30 min and then at rt for 2 h. The reaction mixture was concentrated to give 1-(2-(2-(2-aminoethoxy)ethoxy)ethyl)-1H-pyrrole-2,5-as TFA salt. MS m/z 229.2 (M+1). Retention time 0.353 min.

Step 3: Boc-L-Phe-OH (30 mg, 0.113 mmol) in DMF (1 ml) was activated with DIEA (88 mg) and HATU (43 mg, 0.113 mmol) for 15 min, and 1-(2-(2-(2-aminoethoxy)ethoxy)ethyl)-1H-pyrrole-2,5-dione TFA salt (46.4 mg) in DMF (1 ml) was added. The reaction mixture was stirred at rt for 2 h and then purified by preparative HPLC (20-70% acetonitrile-H$_2$O containing 0.05% TFA) to obtain (S)-t-butyl (1-((2-(2-(2-(2,5-dioxo-2,5-dihydro-1H-pyrrol-1-yl)ethoxy)ethoxy)ethyl)amino)-1-oxo-3-phenylpropan-2-yl)carbamate. MS m/z 476.2 (M+1). Retention time 1.091 min. This product (31 mg, 0.065 mmol) in DCM (2 ml) was treated with TFA (0.2 ml) at 0° C. for 30 min and then at rt for 2 h. The reaction mixture was concentrated to give (S)-2-amino-N-(2-(2-(2-(2,5-dioxo-2,5-dihydro-1H-pyrrol-1-yl)ethoxy)ethoxy)ethyl)-3-phenylpropanamide as TFA salt. MS m/z 376.2 (M+1). Retention time 0.649 min.

Step 4: To (2R,3R)-3-((S)-1-((3R,4S,5S)-4-((S)-N,3-dimethyl-2-((1R,3S,4S)-2-methyl-2-azabicyclo[2.2.1]heptane-3-carboxamido)butanamido)-3-methoxy-5-methylheptanoyl)pyrrolidin-2-yl)-3-methoxy-2-methylpropanoic acid TFA salt (Step 2, Example 12) (7.2 mg, 0.010 mmol) in DMF (1 ml) were added DIEA (7.7 mg) and HATU (4.18 mg, 0.011 mmol). The reaction was stirred for 15 min, and (S)-2-amino-N-(2-(2-(2-(2,5-dioxo-2,5-dihydro-1H-pyrrol-1-yl)ethoxy)ethoxy)ethyl)-3-phenylpropanamide TFA salt (6.3 mg, 0.013 mmol) in DMF (1 ml) was added. The reaction mixture was stirred at rt for 2 h and purified by preparative HPLC (20-70% acetonitrile-H$_2$O containing 0.05% TFA) to obtain compound (93) as TFA salt. MS m/z 966.5 (M+1). Retention time 1.016 min.

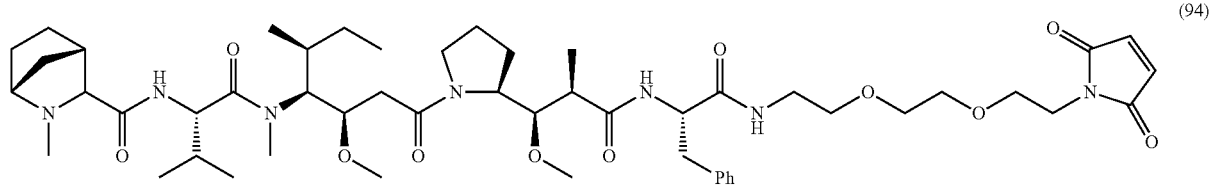 [SMILES: CC[C@H](C)[C@@H]([C@@H](CC(=O)N1CCC[C@H]1[C@H](OC)[C@@H](C)C(=O)N[C@@H](Cc1ccccc1)C(=O)NCCOCCOCCN1C(=O)C=CC1=O)OC)N(C)C(=O)[C@@H](NC(=O)C1[C@H]2CC[C@H](C2)N1C)C(C)C]

(94)

EXAMPLE 92

(1R,3S,4S)-N-((S)-1-(((3R,4S,5S)-1-((S)-2-((3R,4R,7S)-7-Benzyl-14-(2,5-dioxo-2,5-dihydro-1H-pyrrol-1-yl)-4-methyl-5,8-dioxo-2,12-dioxa-6,9-diazatetradecan-3-yl)pyrrolidin-1-yl)-3-methoxy-5-methyl-1-oxoheptan-4-yl)(methyl)amino)-3-methyl-1-oxobutan-2-yl)-2-methyl-2-azabicyclo[2.2.1]heptane-3-carboxamide (95)

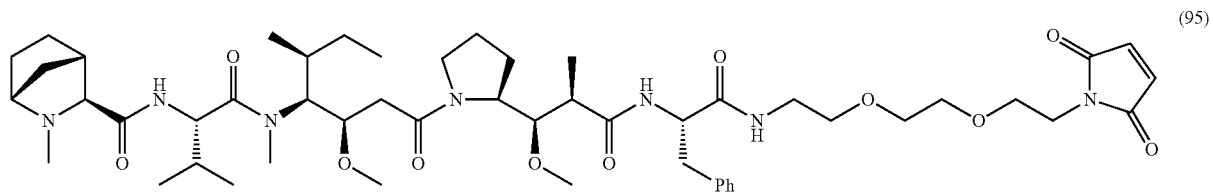 [SMILES: CC[C@H](C)[C@@H]([C@@H](CC(=O)N1CCC[C@H]1[C@H](OC)[C@@H](C)C(=O)N[C@@H](Cc1ccccc1)C(=O)NCCOCCOCCN1C(=O)C=CC1=O)OC)N(C)C(=O)[C@@H](NC(=O)[C@@H]1[C@H]2CC[C@H](C2)N1C)C(C)C]

Compound (95) was prepared by the method described for compound (94) using t-butyl (2-(2-aminoethoxy)ethyl)carbamate in place of t-butyl (2-(2-(2-aminoethoxy)ethoxy)ethyl)carbamate. MS m/z 922.5 (M+1). Retention time 1.044 min.

Synthetic Procedure for Coenzyme A Analogues

EXAMPLE 93

3-Buten-2-one adduct of Coenzyme A (49)

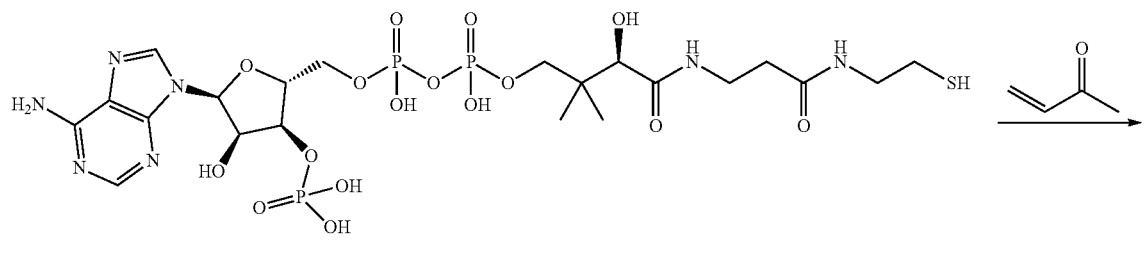

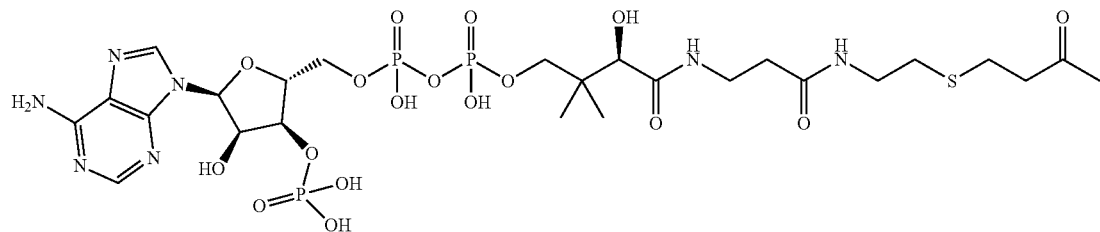

49

Coenzyme A trilithium salt (259 mg, Sigma, assay >93%) was dissolved in 2.0 mL of phosphate buffer with EDTA (100 mM phosphate, 5 mM EDTA, pH 7.5). To the reaction mixture was added 3-buten-2-one (29.04, Aldrich, 99%), and the reaction mixture was let stand at 20° C. for 75 minutes. The whole reaction mixture was loaded onto an ISCO C18Aq Gold 15.5 g column which was pre-equilibrated with 100% $H_2O$. The desired product was eluted at 100% $H_2O$. The fractions containing the pure desired product were combined and lyophilized, affording compound 49 as crystalline solid. MS (ESI+) m/z 838.2 (M+1). H-NMR (400 MHz, $D_2O$) δ 8.525 (s, 1H), 8.235 (s, 1H), 6.140 (d, 1H, J=7.2 Hz), 4.746 (m, 1H), 4.546 (bs, 1H), 4.195 (bs, 1H), 3.979 (s, 1H), 3.786 (dd, 1H, J=4.8, 9.6 Hz), 3.510 (dd, 1H, J=4.8, 9.6 Hz), 3.429 (t, 2H, J=6.6 Hz), 3.294S (t, 2H, J=6.6 Hz), 2.812 (t, 2H, J=6.8 Hz), 2.676 (t, 2H, J=6.8 Hz), 2.604 (t, 2H, J=6.8 Hz), 2.420 (t, 2H, J=6.6 Hz), 2.168 (s, 3H), 0.842 (s, 3H), 0.711 (s, 3H) (note: some peaks which overlap with $D_2O$ are not reported).

EXAMPLE 94

Ketone-Coenzyme A Analogue (CoA-(i-10))

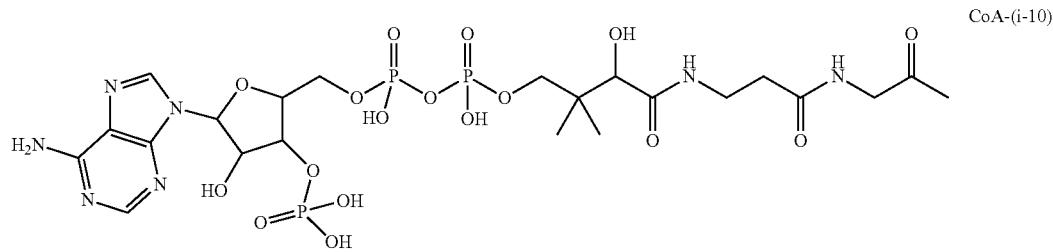 [SMILES: CC(=O)CNC(=O)CCNC(=O)C(O)C(C)(C)COP(=O)(O)OP(=O)(O)OCC1OC(n2cnc3c(N)ncnc32)C(O)C1OP(=O)(O)O]

Compound (i-10) was converted into the ketone-functionalized CoA analogue CoA-(i-10) by reacting 5 mM of compound (i-10) with 25 mM of ATP in the presence of 10 µM *Staphylococcus aureus* CoAA, 25 µM *Escherichia coli* CoAD, and 20 µM *Escherichia coli* CoAE for about 14 h at 37° C. in 50 mM HEPES buffer (pH 8.0) containing 20 MgCl$_2$. Soluble enzyme was separated by ultrafiltration through an Amicon Ultra centrifugal filter with 10 kDa cutoff. Enzymatic conversion of compound (i-10) into the CoA analogue CoA-(i-10) was verified by formation of the anti-Her2-HC-ins388-ybbR-(i-10)-22 ADC (see Table 9 and Table 10).

EXAMPLE 95

Azide-Coenzyme A Analogue (CoA-(i-11))

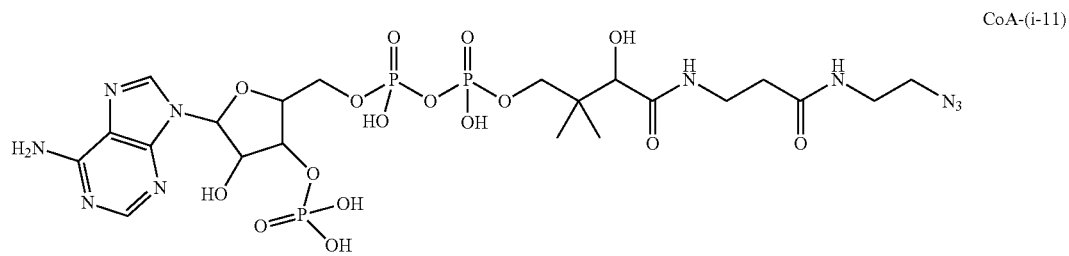 [SMILES: CC(C)(COP(=O)(O)OP(=O)(O)OCC1OC(n2cnc3c(N)ncnc32)C(O)C1OP(=O)(O)O)C(O)C(=O)NCCC(=O)NCCN=[N+]=[N-]]

Compound (i-11) was converted into the azide-functionalized CoA analogue CoA-(i-11) by reacting 5 mM of compound (i-11) with 25 mM of ATP in the presence of 10 µM *Staphylococcus aureus* CoAA, 25 µM *Escherichia coli* CoAD, and 20 µM *Escherichia coli* CoAE for about 14 h at 37° C. in 50 mM HEPES buffer (pH 8.0) containing 20 MgCl$_2$. Soluble enzyme was separated by ultrafiltration through an Amicon Ultra centrifugal filter with 10 kDa cutoff. Enzymatic conversion of compound (i-11) into the CoA analogue CoA-(i-11) was verified by LC-MS analysis after reaction of a small fraction of the ultrafiltrate with five-fold molar excess of compound (75). The copper-free click chemistry reaction was carried out for 3 h at 23° C. in 50% (v/v) DMSO/H$_2$O, and the reaction mixture was separated on a reverse-phase Acquity UPLC HSS T3 column (100 Å, 2.1 mm×50 mm, Waters) using a 1.35 min-gradient elution from 10 to 100% acetonitrile in water containing 0.05% TFA at a flow rate of 0.9 mL/min. Mass spectral analysis revealed the presence of the desired adduct thereby confirming conversion of compound (i-11) by all three CoA biosynthetic enzymes into CoA analogue CoA-(i-11). MS m/z 904.6 ((M+2)/2). Retention time 0.94 minutes.

EXAMPLE 96

Ketone-Coenzyme A Analogue (CoA-(i-12))

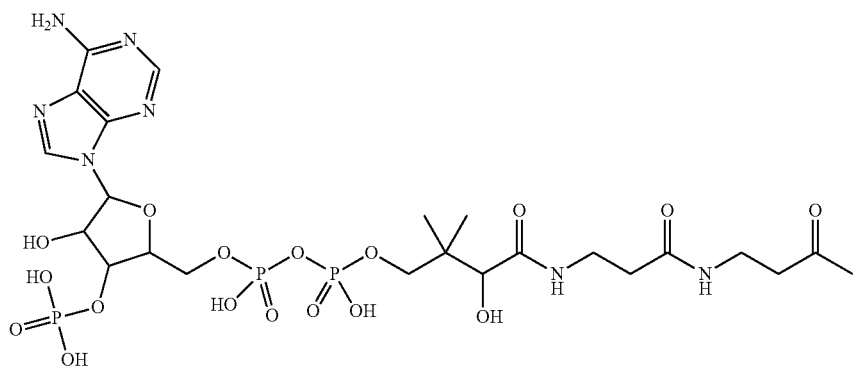

CoA-(i-12)

Compound (i-12) was converted into the ketone-functionalized CoA analogue CoA-(i-12) by reacting 5 mM of compound (i-12) with 25 mM of ATP in the presence of 10 µM *Staphylococcus aureus* CoAA, 25 µM *Escherichia coli* CoAD, and 20 µM *Escherichia coli* CoAE for about 16 h at 37° C. in 50 mM HEPES buffer (pH 8.0) containing 20 mM $MgCl_2$. After centrifugation of the reaction mixture at 20817×g for 2 min, soluble enzyme was separated by ultrafiltration through an Amicon Ultra centrifugal filter with 10 kDa cutoff (15 min; 14000×g). Enzymatic conversion of compound (i-12) into the CoA analogue CoA-(i-12) was verified by formation of the anti-Her2-HC-ins388-ybbR-(i-12)-22 ADC (see Table 10).

EXAMPLE 97

Ketone-Coenzyme A Analogue (CoA-(i-13))

CoA-(i-13)

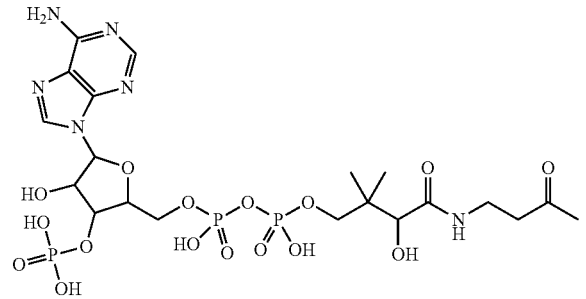

Compound (i-13) was converted into the ketone-functionalized CoA analogue CoA-(i-13) by reacting 10 mM of compound (i-13) with 25 mM of ATP in the presence of 10 µM *Staphylococcus aureus* CoAA, 25 µM *Escherichia coli* CoAD, and 20 µM *Escherichia coli* CoAE for about 48 h at 37° C. in 50 mM HEPES buffer (pH 8.0) containing 20 mM $MgCl_2$. After centrifugation of the reaction mixture at 20817×g for 2 min, soluble enzyme was separated by ultrafiltration through an Amicon Ultra centrifugal filter with 10 kDa cutoff (15 min; 14000×g).

Synthetic Procedure Comparative Peptide

Synthesis of (S)-2-((2R,3R)-3-((S)-1-((3R,4S,5S)-4-((S)-2-((S)-2-(6-(2,5-dioxo-2,5-dihydro-1H-pyrrol-1-yl)-N-methylhexanamido)-3-methylbutanamido)-N,3-dimethylbutanamido)-3-methoxy-5-methylheptanoyl)pyrrolidin-2-yl)-3-methoxy-2-methylpropanamido)-3-phenylpropanoic acid (MC-MMAF)

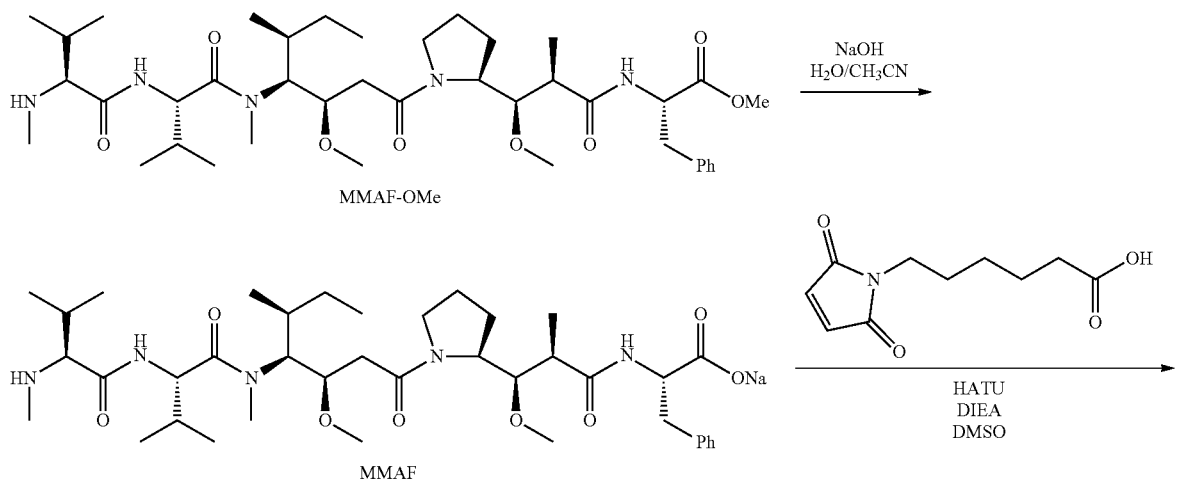

-continued

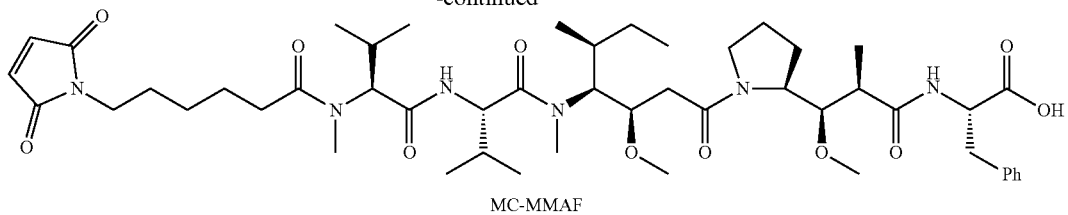

MC-MMAF

MMAF-OMe (135 mg, Concortis Biosystems) was dissolved in CH3CN (10 mL). To the resulting clear solution was added 5 mL water, followed by 0.375 mL of 1N aqueous sodium hydroxide (certified, Fisher Scientific). The reaction mixture was stirred magnetically at 21° C. for 18 hours, at which time LCMS analysis indicated a complete reaction. The reaction mixture mixture was frozen and lyophilized, affording MMAF sodium salt. LCMS retention time 0.911 minutes. MS (ESI+) m/z 732.5 (M+1). The whole MMAF sodium salt thus obtained in previous reaction was dissoved in 10 mL DMSO. In a separate reaction vessel, 6-(2,5-dioxo-2,5-dihydro-1H-pyrrol-1-yl)hexanoic acid (95 mg) was treated with HATU (165 mg) and DIEA (0.126 mL) in 3.0 mL DMSO at at 21° C. for 25min. The whole reaction mixture of the activated ester was added to the solution of MMAF sodium salt, and The reaction mixture was stirred at the same temperature for 3 hours. The reaction mixture mixture was partitioned between 40 mL of EtOAc and 20 mL of 5% aqueous citric acid. The organic layer was separated, and the aqueous layer was extracted with 20 mL of EtOAc. The combined organic layers were washed with 10 mL saturated aqueous NaCl, dryed over anhydrous MgSO4, filtered and concentrated under reduced pressure. The residue was purified on an ISCO CombiFlash instrument using an ISCO C18gold 15.5 g column. The desired material was eluted with 50% $CH_3CN$ in $H_2O$. The fractions containing the desired product was combined and lyophilized, affording compound as white solid. LCMS retention time 1.392 minutes. MS (ESI+) m/z 925.6 (M+1).

EXAMPLE 98

In Vitro Cell Killing Assay of Payloads

For evaluation of the cell killing potency of the cytotoxic peptides of Formula (I) in vitro, cell proliferation assays were performed in parallel with 8 cell lines: MDA-MB231 clone 16, clone 40, JimT1, HCC1954, H526, KU812, CMK11-5 cells and Jurkat cells. In addition, in vitro, cell proliferation assays were performed using 3 other cell lines: A375, SKBR3 and NCI-N87. All the cell lines are described in more detail in Example 106 and were also used to assess the in vitro potency of immunoconjugates of the invention. The cell proliferation assays were conducted with Cell-Titer-Glo™ (Promega) five days after cells were incubated with various concentrations of ADCs (Riss et al., (2004) Assay Drug Dev Technol. 2:51-62). In some studies, the cell based assays are high throughput and conducted on an automated system (Melnick et al., (2006) Proc Natl Acad Sci USA. 103:3153-3158). The in vitro cell killing potency obtained for certain examples of cytotoxic peptides of Formula (I) are given in Table 2a and Table 2b.

TABLE 2a

In vitro cell killing ($IC_{50}$ (nM)) of certain cytotoxic peptides of Formula (I)

| Cmpd No. | CMK-11-5 | HCC1954 | JimT1 | JURKAT | KU812 | MDA-MB-231 clone 16 | MDA-MB-231 clone 40 | NCI-H526 |
|---|---|---|---|---|---|---|---|---|
| 1 | 1.23 | 0.131 | 0.675 | 0.151 | 0.281 | 1.24 | 2.49 | 1.08 |
| 2 | 182 | 46.2 | 202 | 162 | 279 | 735 | 442 | 218 |
| 3 | 14.7 | 10.8 | 42.1 | 3.01 | 6.78 | 12.7 | 23.9 | 22 |
| 5 | 74.8 | 47 | 44.7 | 49.9 | 106 | 83.5 | 139 | 204 |
| 46 | 10.4 | 2.3 | 14.2 | 6.1 | 8.4 | 8.1 | 11.7 | 29.5 |

TABLE 2b

In vitro cell killing ($IC_{50}$ (nM)) of certain cytotoxic peptides of Formula (I)

| Compound No. | A375 | HCC1954 | SKBR3 | JimT1 | NCI-N87 | NCI-H526 |
|---|---|---|---|---|---|---|
| 50 | 5.16 | n.d. | 5.66 | 57.6 | 10.2 | 52.4 |
| 51 | 0.154 | 0.028 | 0.035 | 0.081 | 0.053 | 0.184 |
| 52 | 0.923 | 0.019 | 0.046 | 0.184 | 0.068 | 0.184 |
| 53 | 0.0121 | 0.009 | 0.008 | 0.011 | n.d. | 0.121 |
| 54 | 27.4 | 7.18 | n.d. | 17.1 | 7.59 | 54.8 |
| 55 | 2.75 | 0.124 | 0.210 | 0.751 | 0.643 | 0.364 |
| 57 | 0.049 | n.d. | 0.034 | 0.307 | 0.019 | 1.11 |
| 58 | 0.304 | n.d. | 0.307 | 2.15 | 0.310 | 4.08 |
| 59 | 3.55 | n.d. | 3.12 | 37.5 | 4.78 | 19.5 |
| 60 | 0.450 | n.d. | 0.591 | 4.82 | 0.801 | 8.35 |
| 61 | 5.43 | n.d. | 6.10 | 66.0 | 13.5 | 60.6 |
| 63 | 14.3 | 1.64 | n.d. | 5.08 | 2.09 | 6.49 |
| 64 | 25.6 | 1.09 | n.d. | 4.15 | 1.21 | 5.74 |
| 65 | 31.3 | 0.93 | n.d. | 6.88 | 3.67 | 3.82 |
| 66 | 0.050 | 0.023 | 0.031 | 0.052 | n.d. | 0.126 |
| 67 | 0.244 | 0.239 | n.d. | 0.369 | 0..596 | 0.614 |
| 68 | 0.596 | 0.127 | n.d. | 0.251 | 0.200 | 0.428 |
| 69 | 0.092 | 0.065 | n.d. | 0.091 | 0.142 | 0.189 |
| 70 | 2.16 | 1.38 | n.d. | 2.36 | 3.81 | 4.73 |
| 71 | 0.119 | 0.075 | n.d. | 0.124 | 0.091 | 0.352 |
| 72 | 0.189 | 0.079 | 0.085 | 0.224 | n.d. | 0.287 |
| 73 | 11.3 | 1.59 | 1.44 | 5.11 | n.d. | 3.66 |
| 74 | 0.571 | 0.270 | 0.351 | 0.587 | n.d. | 0.962 | n.d., not determined

Antigen-Binding Moieties

The antigen-binding moiety in Formula (II) or (III) can be any moiety that selectively binds to a cell-surface marker found on a targeted cell type. In some aspects, Ab is an antibody or antibody fragment (e.g. antigen binding fragment of an antibody) that specifically binds to an antigen predominantly or preferentially found on the surface of cancer cells, e.g., a tumor-associated antigen. In some aspects, Ab is an antibody or antibody fragment (e.g., antigen binding fragment) that specifically binds to a cell surface receptor protein or other cell surface molecules, a cell survival regulatory factor, a cell proliferation regulatory factor, a molecules associated with (for e.g., known or suspected to contribute functionally to) tissue development or differentiation, a lymphokine, a cytokine, a molecule involved in cell cycle regulation, a molecule involved in vasculogenesis or a molecule associated with (for e.g., known or suspected to contribute functionally to) angiogenesis. A tumor-associated antigen may be a cluster differentiation factor (i.e., a CD protein). In some aspects of the invention, the antigen binding moiety of the invention specifically binds to one antigen. In some aspects of the invention, the antigen binding moiety of the invention specifically binds to two or more antigens described herein, for example, the antigen binding moiety of the invention is a bispecific or multispecific antibody or antigen binding fragment thereof.

Exemplary antibodies or antigen binding fragments include but are not limited to anti-estrogen receptor antibody, anti-progesterone receptor antibody, anti-p53 antibody, anti-HER-2 antibody, anti-EGFR antibody, anti-cathepsin D antibody, anti-Bcl-2 antibody, anti-E-cadherin antibody, anti-CA125 antibody, anti-CA15-3 antibody, anti-CA19-9 antibody, anti-c-erbB-2 antibody, anti-P-glycoprotein antibody, anti-CEA antibody, anti-retinoblastoma protein antibody, anti-ras oncoprotein antibody, anti-Lewis X antibody, anti-Ki-67 antibody, anti-PCNA antibody, anti-CD3 antibody, anti-CD4 antibody, anti-CD5 antibody, anti-CD7 antibody, anti-CD8 antibody, anti-CD9/p24 antibody, anti-CD1-antibody, anti-CD11c antibody, anti-CD13 antibody, anti-CD14 antibody, anti-CD15 antibody, anti-CD19 antibody, anti-CD20 antibody, anti-CD22 antibody, anti-CD23 antibody, anti-CD30 antibody, anti-CD31 antibody, anti-CD33 antibody, anti-CD34 antibody, anti-CD35 antibody, anti-CD38 antibody, anti-CD39 antibody, anti-CD41 antibody, anti-LCA/CD45 antibody, anti-CD45RO antibody, anti-CD45RA antibody, anti-CD71 antibody, anti-CD95/Fas antibody, anti-CD99 antibody, anti-CD100 antibody, anti-S-100 antibody, anti-CD106 antibody, anti-ubiquitin antibody, anti-c-myc antibody, anti-cytokeratin antibody, anti-lambda light chains antibody, anti-melanosomes antibody, anti-prostate specific antigen antibody, anti-tau antigen antibody, anti-fibrin antibody, anti-keratins antibody, and anti-Tn-antigen antibody.

In one embodiment, the antigen binding moiety of the antibody-drug conjugates (ADC) of Formula (II) or (III) specifically binds to a receptor encoded by an ErbB gene. The antigen binding moiety may bind specifically to an ErbB receptor selected from EGFR, HER2, HER3 and HER4. The antigen binding moiety may be an antibody that will specifically bind to the extracellular domain (ECD) of the HER2 receptor and inhibit the growth of tumor cells which overexpress HER2 receptor. The antibody may be a monoclonal antibody, e.g. a murine monoclonal antibody, a chimeric antibody, or a humanized antibody. A humanized antibody may be huMAb4D5-1, huMAb4D5-2, huMAb4D5-3, huMAb4D5-4, huMAb4D5-5, huMAb4D5-6, huMAb4D5-7 or huMAb4D5-8 (trastuzumab). The antibody may be an antibody fragment, e.g. a Fab fragment.

Antigen-binding moieties in Formula (II) or (III) include, but are not limited to, antibodies or antibody fragments (e.g., antigen binding fragments) against cell surface receptors and tumor-associated antigens. Such tumor-associated antigens are known in the art, and can be prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Antibodies and antibody fragments (e.g., antigen binding fragment) useful for the immunoconjugates of the invention include modified or engineered antibodies, such as an antibody modified to introduce a cysteine residue (Junutula J R, Raab H, Clark S, Bhakta S, Leipold D D, Weir S, Chen Y, Simpson M, Tsai S P, Dennis M S, Lu Y et al.: Nat Biotechnol 2008, 26:925-932), or other reactive amino acid, including Pcl, pyrrolysine, peptide tags (such as S6, A1 and ybbR tags), and non-natural amino acids, in place of at least one amino acid of the native sequence, thus providing a reactive site on the antibody or antigen binding fragment for conjugation to a cytotoxic peptide of Formula (I) or subformulae thereof. For example, the antibodies or antibody fragments can be modified to incorporate Pcl or pyrrolysine (W. Ou et al. (2011) PNAS 108 (26), 10437-10442) or unnatural amino acids (J. Y. Axup, K. M. Bajjuri, M. Ritland, B. M. Hutchins, C. H. Kim, S. A. Kazane, R. Halder, J. S. Forsyth, A. F. Santidrian, K. Stafin, Y. Lu et al. Proc Natl Acad Sci USA, 109 (2012), pp. 16101-16106; for review, see C. C. Liu and P. G. Schultz (2010) Annu Rev Biochem 79, 413-444; C. H. Kim, J. Y. Axup, P. G. Schultz (2013) Curr Opin Chem Biol. 17, 412-419) as sites for conjugation to a drug. Similarly, peptide tags for enzymatic conjugation methods can be introduced into an antibody (Strop P. et al. Chem Biol, 2013, 20(2):161-7; Rabuka D., Curr Opin Chem Biol, 2010 December; 14(6):790-6; Rabuka D, et al., Nat Protoc. 2012, 7(6):1052-67). One other example is the use of 4'-phosphopantetheinyl transferases (PPTase) for the conjugation of Co-enzyme A analogs (WO2013184514). Methods for conjugating such modified or engineered antibodies with payloads or linker-payload combinations are known in the art.

Antigen-binding moieties (e.g., antibodies and antigen binding fragments) useful in the invention may also have other modifications or be conjugated to other moieties, such as but not limited to polyethylene glycol tags, albumin, and other fusion polypeptide.

The antibodies used in the examples herein have the heavy chain and light chain sequences listed in Table 3. These antibodies were engineered to contain cysteine residues or PPTase enzyme tags for site-specific conjugation with cytotoxic peptides of the invention. The examples herein illustrate that these engineered antibodies are suitable antibody for use in the immunoconjugates of Formula (II) or (III). In addition, non-engineered antibodies can also be used for the preparation of the immunoconjugates of Formula (II) or (III) through traditional methods (*Carter P J, Senter P D,* Antibody-drug conjugates for cancer therapy, *Cancer J.* 2008, 14(3):154-69; J. E. Stefano, M. Busch, L. Hou, A. Park, and D. A. Gianolio, p. 145-171, and M.-P. Brun and L. Gauzy-Lazo, p. 173-187 in Antibody-Drug Conjugate, Methods in Molecular Biology, Vol. 1045, Editor L. Ducry, Humana Press (2013).

TABLE 3

Amino acid sequences of example antibodies

SEQ ID NO: 1 (anti-Her2 heavy chain wild type)
EVQLVESGGGLVQPGGSLRLSCAAS<u>GFNIKDTYIH</u>WVRQAPGKGLEWVA<u>RIYPTNG
YTRYADSVKG</u>RFTISADTSKNTAYLQMNSLRAEDTAVYYCSRW<u>GGDGFYAMDY</u>WG
QGTLVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKKVEPKSCD
KTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIE
KTISKAKGQPREPQVYTLPPSREEMTKNQVSLTCLVKGFYPSDIAVEWESNGQPEN
NYKTTPPVLDSDGSFFLYSKLTVDKSRWQQGNVFSCSVMHEALHNHYTQKSLSLSP
GK SEQ ID NO: 2 (anti-Her2 light chain wild type)
DIQMTQSPSSLSASVGDRVTITC<u>RASQDVNTAVA</u>WYQQKPGKAPKLLIY<u>SASFLYSG</u>
VPSRFSGSRSGTDFTLTISSLQPEDFATYYC<u>QQHYTTPPT</u>FGQGTKVEIKRTVAAPS
VFIFPPSDEQLKSGTASVVCLLNNFYPREAKVQWKVDNALQSGNSQESVTEQDSKD
STYSLSSTLTLSKADYEKHKVYACEVTHQGLSSPVTKSFNRGEC SEQ ID NO: 3 (constant region of the mutant light chain of
anti-Her2 LC-S159C and antibody 20507 LC-S159C)
KRTVAAPSVFIFPPSDEQLKSGTASVVCLLNNFYPREAKVQWKVDNALQSGN<u>C</u>QES
VTEQDSKDSTYSLSSTLTLSKADYEKHKVYACEVTHQGLSSPVTKSFNRGEC SEQ ID NO: 4 (constant region of the mutant heavy chain of
antibody 20507 HC-E152C)
SASTKGPSVFPLAPSSKSTSGGTAALGCLVKDYFP<u>C</u>PVTVSWNSGALTSGVHTFPA
VLQSSGLYSLSSVVTVPSSSLGTQTYICNVNHKPSNTKVDKKVEPKSCDKTHTCPPC
PAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPGK SEQ ID NO: 5 (constant region of the mutant heavy chain of
antibody 20507 HC-S375C)
SASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCPPC
PAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQ
PREPQVYTLPPSREEMTKNQVSLTCLVKGFYP<u>C</u>DIAVEWESNGQPENNYKTTPPVL
DSDGSFFLYSKLTVDKSRWQQGNVFSCSVMHEALHNHYTQKSLSLSPGK SEQ ID NO: 6 (constant region of the mutant light chain of anti-
Her2-HC-E152C-S375C and antibody 20507-HC-E152C-S375C)
SASTKGPSVFPLAPSSKSTSGGTAALGCLVKDYFPCPVTVSWNSGALTSGVHTFPA
VLQSSGLYSLSSVVTVPSSSLGTQTYICNVNHKPSNTKVDKKVEPKSCDKTHTCPPC
PAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQ
PREPQVYTLPPSREEMTKNQVSLTCLVKGFYP<u>C</u>DIAVEWESNGQPENNYKTTPPVL
DSDGSFFLYSKLTVDKSRWQQGNVFSCSVMHEALHNHYTQKSLSLSPGK SEQ ID NO: 7 (constant region of the mutant light chain of antibody
20507 LC-K107C)
<u>C</u>RTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC SEQ ID NO: 8 (constant region of the heavy chain of anti-Her2 HC-
ins388-ybbR)
SASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCPPC
PAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPE**DSLEFIASKL
A**NNYKTTPPVLDSDGSFFLYSKLTVDKSRWQQGNVFSCSVMHEALHNHYTQKSLS
LSPGK SEQ ID NO: 9 (constant region of the mutant heavy chain HC-ins388-A1
in anti-Her2 and antibody 20507)
SASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCPPC
PAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPEGDSLDMLEW

TABLE 3-continued

Amino acid sequences of example antibodies

SLMNNYKTTPPVLDSDGSFFLYSKLTVDKSRWQQGNVFSCSVMHEALHNHYTQKS
LSLSPGK

SEQ ID NO: 10 (constant region of the heavy chain wild type of
antibody 20507)
SASTKGPSVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCPPC
PAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYKTTPPVL
DSDGSFFLYSKLTVDKSRWQQGNVFSCSVMHEALHNHYTQKSLSLSPGK SEQ ID NO: 11 (constant region of the light chain wild type of
antibody 20507)
KRTVAAPSVFIFPPSDEQLKSGTASVVCLLNNFYPREAKVQWKVDNALQSGNSQES
VTEQDSKDSTYSLSSTLTLSKADYEKHKVYACEVTHQGLSSPVTKSFNRGEC SEQ ID NO:1 and SEQ ID NO:2 are the full length amino acid sequence of wild-type anti-Her2 antibody heavy chain (HC) and light chain (LC), respectively. CDR regions are underlined. SEQ ID NO:3 is the amino acid sequence of the LC constant region of anti-Her2 LC-S159C and of antibody 20507-LC-S159C mutant antibody. SEQ ID NO:4, SEQ ID NO:5 and SEQ ID NO:6 are the amino acid sequences of the constant regions for the heavy chain HC-E152C and HC-S375C, and HC-E152C-S375C mutant antibodies, respectively. SEQ ID NO:7 is the light chain LC-K107C mutants of antibody 20507. SEQ ID NO:8 is the amino acid sequence of the constant region of the mutant heavy chain for anti-Her2 HC-ins388-ybbR wherein the ybbR tag is inserted after HC residue Glu388. SEQ ID NO:9 is the amino acid sequence of the constant region of the mutant heavy chain for both anti-Her2 and antibody 20507 HC-ins388-A1 antibodies wherein the A1 tag is inserted after HC residue Glu388. Mutant Cys residue and the inserted sequence tags of ybbR and A1 are shown in bold and are underlined in the sequences of corresponding mutant chains. SEQ ID NO:10 and SEQ ID NO:11 are the amino acid sequences of the constant regions of wild-type antibody 20507 heavy chain and light chain, respectively.

Production of the Antibody

The antibodies and antibody fragments (e.g., antigen binding fragments) of the invention can be produced by any means known in the art, including but not limited to, recombinant expression, chemical synthesis, and enzymatic digestion of antibody tetramers, whereas full-length monoclonal antibodies can be obtained by, e.g., hybridoma or recombinant production. Recombinant expression can be from any appropriate host cells known in the art, for example, mammalian host cells, bacterial host cells, yeast host cells, insect host cells, etc.

The invention further provides polynucleotides encoding the antibodies described herein, e.g., polynucleotides encoding heavy or light chain variable regions or segments comprising the complementary determining regions as described herein.

The polynucleotide sequences can be produced by de novo solid-phase DNA synthesis or by PCR mutagenesis of an existing sequence (e.g., sequences as described in the examples below) encoding an antibody or its binding fragment. Direct chemical synthesis of nucleic acids can be accomplished by methods known in the art, such as the phosphotriester method of Narang et al., Meth. Enzymol. 68:90, 1979; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR PROTOCOLS: A GUIDE TO METHODS AND APPLICATIONS, Innis et al. (Ed.), Academic Press, San Diego, Calif., 1990; Mattila et al., Nucleic Acids Res. 19:967, 1991; and Eckert et al., PCR Methods and Applications 1:17, 1991.

Also provided in the invention are expression vectors and host cells for producing the antibodies or antibody fragments described above. Various expression vectors can be employed to express the polynucleotides encoding the antibody chains or binding fragments of the invention. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet 15:345, 1997). For example, nonviral vectors useful for expression of the polynucleotides and polypeptides in mammalian (e.g., human) cells include pThioHis A, B & C, pcDNA3.1/His, pEBVHis A, B & C (Invitrogen, San Diego, Calif.), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an antibody chain or fragment of the invention. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of an antibody chain or fragment of the invention. These elements typically include an ATG initiation codon and adjacent ribosome binding site or other sequences. In addition, the efficiency of expression may be enhanced by the inclusion of enhancers appropriate to the cell system in use (see, e.g., Scharf et al., *Results Probl. Cell Differ.* 20:125, 1994; and Bittner et al., *Meth. Enzymol.*, 153:516, 1987). For example, the SV40 enhancer or CMV enhancer may be used to increase expression in mammalian host cells.

The expression vectors may also provide a secretion signal sequence position to form a fusion protein with polypeptides encoded by inserted antibody sequences. More often, the inserted antibody sequences are linked to a signal sequences before inclusion in the vector. Vectors to be used to receive sequences encoding antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human.

The host cells for harboring and expressing the antibody chains of the invention can be either prokaryotic or eukaryotic. *Escherichia coli* is one prokaryotic host useful for cloning and expressing the polynucleotides of the present invention. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters may be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express the antibodies or antibody fragments of the invention. Insect cells in combination with baculovirus vectors can also be used.

In one aspect, mammalian host cells are used to express and produce the antibodies and antibody fragments of the present invention. For example, they can be either a hybridoma cell line expressing endogenous immunoglobulin genes or a mammalian cell line harboring an exogenous expression vector. These include any normal mortal or normal or abnormal immortal animal or human cell. For example, a number of suitable host cell lines capable of secreting intact immunoglobulins have been developed, including the CHO cell lines, various Cos cell lines, HeLa cells, myeloma cell lines, transformed B-cells and hybridomas. The use of mammalian tissue cell culture to express polypeptides is discussed generally in, e.g., Winnacker, FROM GENES TO CLONES, VCH Publishers, N.Y., N.Y., 1987. Expression vectors for mammalian host cells can include expression control sequences, such as an origin of replication, a promoter, and an enhancer (see, e.g., Queen et al., *Immunol. Rev.* 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts (see generally Sambrook et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, *Cell* 88:223, 1997), agent-enhanced uptake of DNA, and ex vivo transduction. For long-term, high-yield production of recombinant proteins, stable expression will often be desired. For example, cell lines which stably express antibody chains or binding fragments can be prepared using expression vectors of the invention which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

EXAMPLE 99

Cloning of Anti-Her2 and Antibody 20507 Cys and A1/ybbR Tag Mutant Antibodies for Conjugation Studies DNA oligonucleotides encoding variable regions of heavy and light chains of an anti-Her2 antibody (Carter P, Presta L, Gorman C M, Ridgway J B, Henner D, Wong W L, Rowland A M, Kotts C, Carver M E, Shepard H M. (1992) Proc. Natl. Acad. Sci. USA, 89, 4285-4289. Humanization of an anti-p185her2 antibody for human Cancer therapy) were chemically synthesized and cloned into two mammalian expression vectors, pOG-HC and pOG-LC that contain the constant regions of human IgG1 and human kappa light chain, resulting in two wild-type constructs, pOG-anti-Her2 antibody HC and pOG-anti-Her2 antibody LC, respectively. In these vectors, the expression of antibody heavy and light chain in mammalian cells is driven by a CMV promoter. The vectors encode a synthetic 24 amino acid signal sequence, MKTFILLLWVLLLWVIFLLPGATA (SEQ ID NO:12), at the N-terminal of heavy chain and light chain to guide their secretion from mammalian cells. The signal sequence has been validated to be efficient in directing protein secretion in hundreds of mammalian proteins in 293 Freestyle™ cells (Gonzalez R, Jennings L L, Knuth M, Orth A P, Klock H E, Ou W, Feuerhelm J, Hull M V, Koesema E, Wang Y, Zhang J, Wu C, Cho C Y, Su Al, Batalov S, Chen H, Johnson K, Laffitte B, Nguyen D G, Snyder E Y, Schultz P G, Harris J L, Lesley S A. (2010) Proc Natl Acad Sci USA. 107:3552-7). Oligonucleotide directed mutagenesis was employed to prepare the LC-S159C mutant of the anti-Her2 antibody. The sense and anti-sense primers (Table 4) that correspond to the LC-S159C mutation site in the constant regions of human kappa light chain were chemically synthesized. PCR reactions were performed using PfuUltra II Fusion HS DNA Polymerase (Stratagene) with pOG-anti-Her2 antibody HC and pOG-anti-Her2 antibody LC as the templates. The PCR products were confirmed on agarose gels, and treated with DPN I followed by transformation in DH5a cells (Klock et al., (2009) *Methods Mol Biol.* 498:91-103).

The sequence of the LC-S159C mutant construct was confirmed by DNA sequencing. The full length amino acid sequence of wild-type anti-Her2 antibody heavy chain is shown as SEQ ID NO:1 and that of light chain shown as SEQ ID NO:2. The amino acid sequence of LC-S159C mutant antibody is shown in Table 3 with C159 in bold and underlined. Amino acid residues in human IgG1 heavy chain and human kappa light chain are numbered according to the Eu numbering system (Edelman et al, (1969) *Proc Natl Aced Sci USA,* 63:78-85). The anti-Her2- LC-S159C antibody was further cloned into vectors containing antibiotic selection markers for selection of stably transfected cell clones in media containing corresponding antibiotics.

Similarly, a double Cys mutant, HC-E152C-S375C, of the anti-Her2 antibody and four Cys mutants (HC-E152C, HC-S375C, LC-K107C, HC-E152C-S375C) of a second antibody, antibody 20507 were cloned using DNA primers listed in Table 4 and the above procedures. Antibody vector pOG-anti-Her2 antibody HC served as PCR template to obtain the corresponding HC-ins388-ybbR and HC-ins388-A1 insertion mutants. Table 4 lists the sense and anti-sense primers that were used for the cloning of these constructs. The vector encoding the antibody 20507-HC-ins388-A1 insertion mutant was prepared by amplifying the variable region of antibody 20507 heavy chain. The amplified DNA fragment was then moved into the existing vector encoding the anti-Her2-HC-ins388-A1 insertion mutant. All resulting expression vectors encoding peptide-tagged heavy chains were confirmed by DNA sequencing. The anti-Her2 antibodies containing HC-ins388-ybbR and HC-ins388-A1 insertions were further cloned into vectors with antibiotic selection markers, thereby allowing subsequent isolation of clones stably expressing the respective peptide-tagged constructs. The amino acid sequences of the constant regions of the A1/ybbR insertion mutants of the anti-Her2 antibody and the antibody 20507 are shown in Table 3. The inserted peptide tag is shown in bold and is underlined.

The anti-Her2 and antibody 20507 Cys and A1 tag mutant antibodies were prepared as described in Example 100, and conjugated with an exemplary cytotoxic peptide of formula (I) as described in Examples 101, 102, 103, 104 and 105.

TABLE 4

DNA sequences of mutation primers used to clone mutant antibodies

| | | | |
|---|---|---|---|
| LC-S159C | Sense | AGCGGCAACTGTCAGGAGAGCGTCACCGAGCAGGACAGCAA | SEQ ID NO: 13 |
| | Anti-sense | CTCTCCTGACAGTTGCCGCTCTGCAGGGCGTTGTCCACCT | SEQ ID NO: 14 |
| HC-E152C | Sense | TACTTCCCCTGTCCCGTGACCGTGTCCTGGAACAGCGGA | SEQ ID NO: 15 |
| | Anti-sense | GGTCACGGGACAGGGGAAGTAGTCCTTCACCAGGCAGC | SEQ ID NO: 16 |
| HC-S375C | Sense | TTCTACCCCTGCGACATCGCCGTGGAGTGGGAGAGCAACG | SEQ ID NO: 17 |
| | Anti-sense | GGCGATGTCGCAGGGGTAGAAGCCCTTCACCAGACAGGTCA | SEQ ID NO: 18 |
| LC-K107C | Sense | GTGGAGATCTGTCGAACGGTGGCCGCTCCCAGCGTGTTCA | SEQ ID NO: 19 |
| | Anti-sense | ACCGTTCGACAGATCTCCACCTTGGTACCCTGTCCGAAC | SEQ ID NO: 20 |
| HC-ins388-ybbR | Sense | CTGGAGTTCATCGCCAGCAAGCTGGCCAACAACTACAAGACCACACCTCCAG | SEQ ID NO: 21 |
| | Anti-sense | CTTGCTGGCGATGAACTCCAGGCTGTCCTCGGGCTGGCCGTTGCTC | SEQ ID NO: 22 |
| HC-ins388-A1 | Sense | CTGGACATGCTGGAGTGGAGCCTGATGAACAACTACAAGACCACACCTCCAG | SEQ ID NO: 23 |
| | Anti-sense | CCACTCCAGCATGTCCAGGCTGTCGCCCTCGGGCTGGCCGTTGCTC | SEQ ID NO: 24 |

20507 contains a human IgG1 heavy chain and a human kappa light chain. The constant parts of heavy and light chain of antibody 20507 are identical in amino acid sequence to those in anti-Her2 antibody. The amino acid sequences of the constant regions of the Cys mutants of the anti-Her2 antibody and of antibody 20507 are shown in Table 3 with the mutated Cys in bold and underlined.

Insertion of the ybbR and A1 peptide sequences into the constant region of the anti-Her2 antibody heavy chain was accomplished by standard molecular biology methods. The

EXAMPLE 100

Preparation of Anti-Her2 and Antibody 20507 Cys and A1/ybbR Tag Mutant Antibodies Anti-Her2 and antibody 20507 Cys, A1 tag and ybbR tag mutant expressed in 293 Freestyle™ cells by co-transfecting heavy chain and light chain plasmids using transient transfection method as described previously (Meissner, et al., *Biotechnol Bioeng.* 75:197-203 (2001)). The DNA plasmids used in co-transfection were prepared using Qiagen plasmid preparation kit according to manufacturer's protocol. 293 Freestyle™ cells were cultured in suspension in Freestyle™ expression media (Invitrogen) at 37° C. under 5% $CO_2$. On the day before transfection, cells were split to $0.7 \times 10^6$ cells/ml into fresh media. On the day of transfection, the cell density typically reached $1.5 \times 10^6$ cells/ml. The cells were transfected with a mixture of heavy chain and light chain plasmids at the ratio of 1:1 using the PEI method (Meissner et al., 2001 supra). The transfected cells were further cultured for five days. The media from the culture was harvested by centrifugation of the culture at 2000×g for 20 min and filtered through 0.2 micrometer filters. The expressed antibodies were purified from the filtered media using Protein A-Sepharose™ (GE Healthcare Life Sciences). Antibody IgGs were eluted from the Protein A-Sepharose™ column using a pH 3.0 elution buffer. Eluted IgG solutions were immediately neutralized with 1 M Tris-HCl (pH 8.0) followed by a buffer exchange to PBS.

Expression constructs for anti-Her2-LC-S159C, anti-Her2-HC-ins388-ybbR, and anti-Her2-HC-ins388-A1 antibodies were also transfected into CHO cells. Following standard protocols, cells stably expressing these antibodies were then selected using antibiotics. All anti-Her2 antibody constructs expressed in the selected CHO cell clones were purified by Protein A-Sepharose chromatography as described above.

In a separate study, the anti-Her2-LC-S159C antibody was stably expressed in CHO cell followed by selection by antibiotics selection. Anti-Her2-LC-S159C antibody expressed in established CHO cell clone was purified by Protein A-Sepharose column procedures as described above.

Immunoconjugates

Immunoconjugates of the invention that comprise such cytotoxic peptides as a payload (drug) include conjugates of Formula (II):

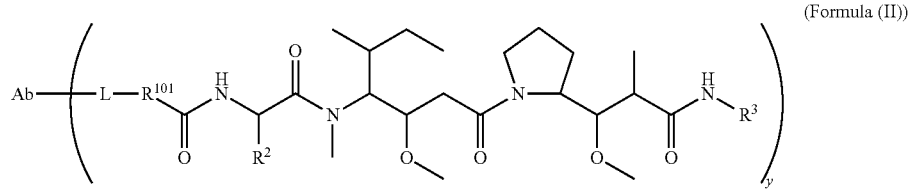
(Formula (II))

wherein:
Ab represents an antigen binding moiety;
L is a linker selected from $-L_1L_2L_3L_4L_5L_6-$, $-L_6L_5L_4L_3L_2L_1-$, $-L_1L_2L_3L_4L_5-$, $-L_5L_4L_3L_2L_1-$,- $L_1L_2L_3L_4-$, $-L_4L_3L_2L_1-$,-$L_1L_2L_3-$, $-L_3L_2L_1-$,-$L_1L_2-$, $-L_2L_1-$ and $-L_1$, wherein $-L_1$, $L_2$, $L_3$, $L_4$, $L_5$, and $L_6$ are as defined herein;
y is an integer from 1 to 16;
$R^{101}$ is a 6 membered heterocycloalkyl divalent radical containing 1-2 N heteroatoms and a $C_1$-$C_2$alkylene bridge, wherein the 6 membered heterocycloalkyl divalent radical is C-linked to the

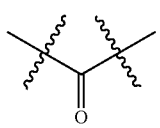 [SMILES: *C(*)=O]

group and is N-linked to $L_1$ or is C-linked to $L_1$, and the 6 membered heterocycloalkyl divalent radical is unsubstituted or substituted with 1 to 3 substituents independently selected from $R^5$ and $R^6$;
or $R^{101}$ is a 5-8 membered fused bicyclic heterocycloalkyl divalent radical containing 1-2 N heteroatoms, wherein the 5-8 membered fused bicyclic heterocycloalkyl divalent radical is C-linked to the

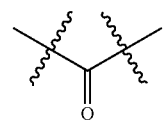 [SMILES: *C(*)=O]

group and is N-linked to $L_1$ or is C-linked to $L_1$, and the 5-8 membered fused bicyclic heterocycloalkyl divalent radical is unsubstituted or substituted with 1 to 3 substituents independently selected from $R^5$ and $R^6$;
$R^2$ is —$C_1$-$C_6$alkyl;
$R^3$ is

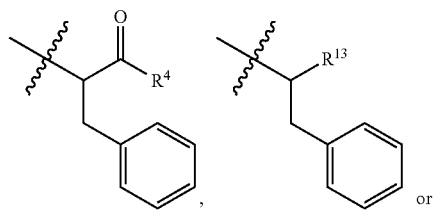

-continued
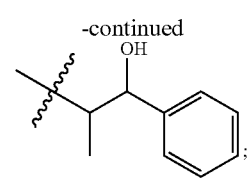

$R^4$ is —OH, $C_1$-$C_6$alkoxy, —$N(R^{14})_2$, —$R^{16}$, —$NR^{12}$ $(CH_2)_m N(R^{14})_2$, or —$NR^{12}(CH_2)_m R^{16}$, —$NHS(O)_2 R^{11}$ or

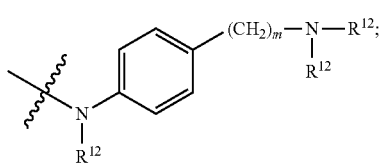

$R^5$ is $C_1$-$C_6$alkyl, $C_1$-$C_6$alkyl which is optionally substituted with 1 to 5 hydroxyl, —C(=O)$R^{11}$, —(CH$_2$)$_m$OH, —C(=O)(CH$_2$)$_m$OH, —C(=O)((CH$_2$)$_m$O)$_n$$R^{12}$, or —((CH$_2$)$_m$O)$_n$$R^{12}$;

$R^6$ is halo, oxo, OH, $C_1$-$C_6$alkyl, —N($R^{14}$)$_2$, —$R^{16}$ and —$NR^{12}$C(=O)$R^{11}$;

$R^{11}$ is $C_1$-$C_6$alkyl or $C_1$-$C_6$alkyl which is optionally substituted with 1 to 5 hydroxyl;

each $R^{12}$ is independently selected from H and $C_1$-$C_6$alkyl;

$R^{13}$ is tetrazolyl,

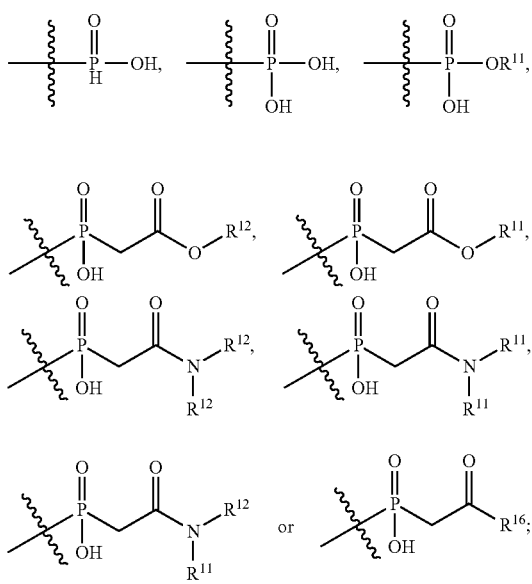

each $R^{14}$ is independently selected from H and $C_1$-$C_6$alkyl;

$R^{16}$ is an N-linked 4-8 membered heterocycloalkyl containing 1-2 heteroatoms independently selected from N and O;

each m is independently selected from 1, 2, 3, 4, 5, 6, 7, 8, 9 and 10, and each n is independently selected from 1, 2, 3, 4, 5, 6, 7, 8, 9, 10, 11, 12, 13, 14, 15, 16, 17 and 18.

Other Immunoconjugates of the invention that comprise such cytotoxic peptides as a payload (drug) include conjugates of Formula (III):

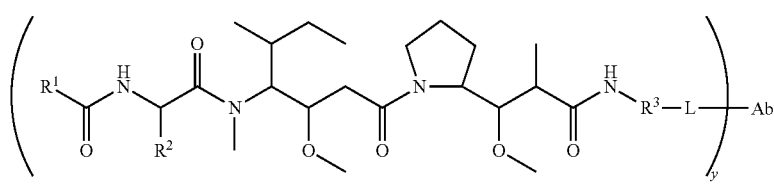

(Formula (III))

wherein:
Ab represents an antigen binding moiety;

L is selected from -L$_1$L$_2$L$_3$L$_4$L$_5$L$_6$-, -L$_6$L$_5$L$_4$L$_3$L$_2$L$_1$-, -L$_1$L$_2$L$_3$L$_4$L$_5$-, -L$_5$L$_4$L$_3$L$_2$L$_1$-, -L$_1$L$_2$L$_3$L$_4$-, -L$_4$L$_3$L$_2$L$_1$-, -L$_1$L$_2$L$_3$-, -L$_3$L$_2$L$_1$-, -L$_1$L$_2$-, -L$_2$L$_1$- and -L$_1$, wherein -L$_1$, L$_2$, L$_3$, L$_4$, L$_5$, and L$_6$ are as defined herein;

y is an integer from 1 to 16;

$R^1$ is a 6 membered heterocycloalkyl containing 1-2 N heteroatoms and a $C_1$-$C_2$alkylene bridge, wherein the 6 membered heterocycloalkyl is unsubstituted or substituted with 1 to 3 substituents independently selected from $R^5$ and $R^6$;

or $R^1$ is a 5-8 membered fused bicyclic heterocycloalkyl containing 1-2 N heteroatoms, wherein the 5-8 membered fused bicyclic heterocycloalkyl is unsubstituted or substituted with 1 to 3 substituents independently selected from $R^5$ and $R^6$;

$R^2$ is —$C_1$-$C_6$alkyl;

$R^3$ is

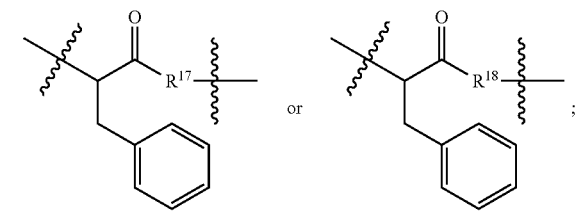

$R^5$ is $C_1$-$C_6$alkyl, $C_1$-$C_6$alkyl which is optionally substituted with 1 to 5 hydroxyl, —C(=O)$R^{11}$, —(CH$_2$)$_m$OH, —C(=O)(CH$_2$)$_m$OH, —C(=O)((CH$_2$)$_m$O)$_n$$R^{12}$, or —((CH$_2$)$_m$O)$_n$$R^{12}$;

$R^6$ is halo, oxo, OH, $C_1$-$C_6$alkyl, —N($R^{14}$)$_2$, —$R^{16}$ and —$NR^{12}$C(=O)$R^{11}$;

$R^{11}$ is $C_1$-$C_6$alkyl or $C_1$-$C_6$alkyl which is optionally substituted with 1 to 5 hydroxyl;

each $R^{12}$ is independently selected from H and $C_1$-$C_6$alkyl;

each $R^{14}$ is independently selected from H and $C_1$-$C_6$alkyl;

$R^{16}$ is an N-linked 4-8 membered heterocycloalkyl containing 1-2 heteroatoms independently selected from N and O;

$R^{17}$ is a bond, —NH—, —NHS(=O)$_2$—,

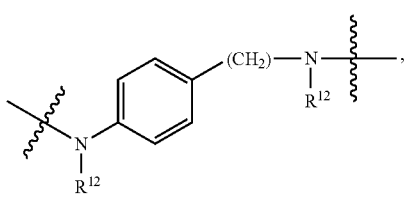

-continued

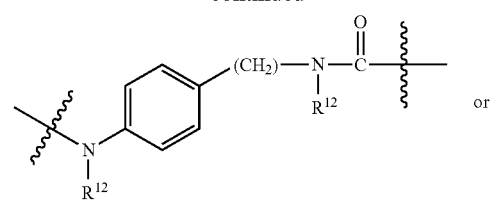

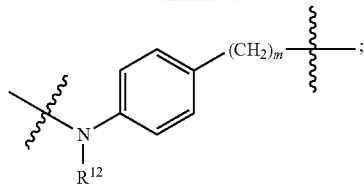

$R^{18}$ is a bond

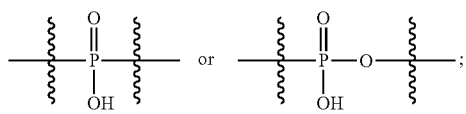 [SMILES: *P(*)(=O)O ; *OP(*)(=O)O]

each m is independently selected from 1, 2, 3, 4, 5, 6, 7, 8, 9 and 10, and each n is independently selected from 1, 2, 3, 4, 5, 6, 7, 8, 9, 10, 11, 12, 13, 14, 15, 16, 17 and 18.

Other immunoconjugates of Formula (II) and Formula (III) of the invention are provided in the enumerated embodiments below.

The invention provides immunoconjugates comprising one or more anti-mitotic cytotoxic peptides linked to an antigen-binding moiety, such as an antibody or antibody fragment. Preferred immunoconjugates of the invention are those of Formula (II) or (III) as described herein. Methods for making such immunoconjugates are well known in the art. Preferred immunoconjugates include, but are not limited to, those disclosed in Table 5, and variations thereof having another antigen binding moiety instead of anti-Her2 antibody, particularly such conjugates where anti-Her2 antibody is replaced by an antibody selected from the following list: anti-estrogen receptor antibody, anti-progesterone receptor antibody, anti-p53 antibody, anti-EGFR antibody, anti-cathepsin D antibody, anti-Bcl-2 antibody, anti-E-cadherin antibody, anti-CA125 antibody, anti-CA15-3 antibody, anti-CA19-9 antibody, anti-c-erbB-2 antibody, anti-P-glycoprotein antibody, anti-CEA antibody, anti-retinoblastoma protein antibody, anti-ras oncoprotein antibody, anti-Lewis X antibody, anti-Ki-67 antibody, anti-PCNA antibody, anti-CD3 antibody, anti-CD4 antibody, anti-CD5 antibody, anti-CD7 antibody, anti-CD8 antibody, anti-CD9/p24 antibody, anti-CD1-antibody, anti-CD11c antibody, anti-CD13 antibody, anti-CD14 antibody, anti-CD15 antibody, anti-CD19 antibody, anti-CD20 antibody, anti-CD22 antibody, anti-CD23 antibody, anti-CD30 antibody, anti-CD31 antibody, anti-CD33 antibody, anti-CD34 antibody, anti-CD35 antibody, anti-CD38 antibody, anti-CD39 antibody, anti-CD41 antibody, anti-LCA/CD45 antibody, anti-CD45RO antibody, anti-CD45RA antibody, anti-CD71 antibody, anti-CD95/Fas antibody, anti-CD99 antibody, anti-CD100 antibody, anti-S-100 antibody, anti-CD106 antibody, anti-ubiquitin antibody, anti-c-myc antibody, anti-cytokeratin antibody, anti-lambda light chains antibody, anti-melanosomes antibody, anti-prostate specific antigen antibody, anti-tau antigen antibody, anti-fibrin antibody, anti-keratins antibody, and anti-Tn-antigen antibody.

In some embodiments, an immunoconjugate of Formula (II) or Formula (III), or subformulae thereof, comprises an antibody or antibody fragment Ab having antigen-binding activity, where the linker L is attached to Ab at a cysteine sulfur atom of Ab. Typical reactive groups used for reaction with a cysteine sulfur group and the resulting group formed are given in Table 1. Non-limiting examples of linker components formed by reaction with a cysteine residue of the antigen binding moiety include, but are not limited to,

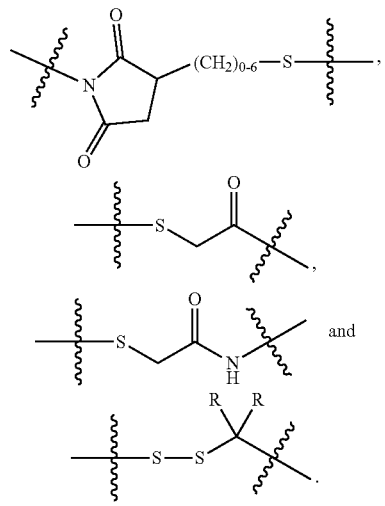

In other embodiments, an immunoconjugate of Formula (II) or Formula (III) comprise Ab, an antibody or antibody fragment having antigen-binding activity, where the linker is attached to Ab via a bridged disulfide in Ab. In such embodiments a

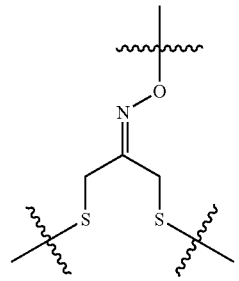 [SMILES: *ON=C(CS*)CS*]

moiety h is formed upon reaction of

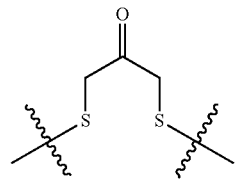 [SMILES: *SCC(=O)CS*]

and a compound of Formula (I) which contains a hydroxylamine.

In some embodiments, an immunoconjugate of Formula (II) or Formula (III), or subformulae thereof, comprises an antibody or antibody fragment Ab having antigen-binding activity, where the linker L is attached to Ab at a free —NH$_2$ of lysine. The Linker components formed by reaction with the —NH$_2$ of a lysine residue of the antigen binding moiety, where each p is 1-10, and each R is independently H or $C_{1-4}$ alkyl (preferably methyl) include, but are not limited to,

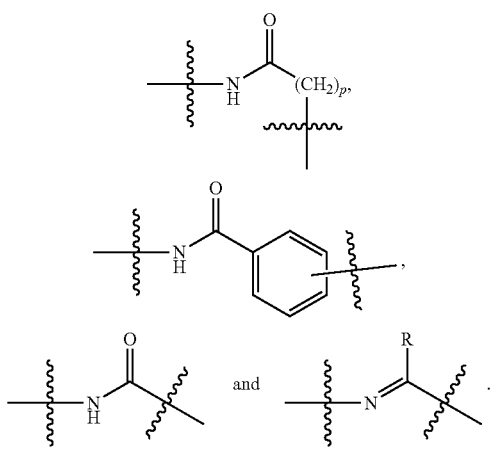

In some embodiments, an immunoconjugate of Formula (II) or Formula (III), or subformulae thereof, comprises an antibody or antibody fragment Ab having antigen-binding activity, where the linker L is attached to Ab at a Pcl or Pyl group engineered into an antibody. See e.g., Ou, et al., *PNAS* 108(26), 10437-42 (2011). Linker components formed by reaction with a Pcl or Pyl group include, but are not limited to,

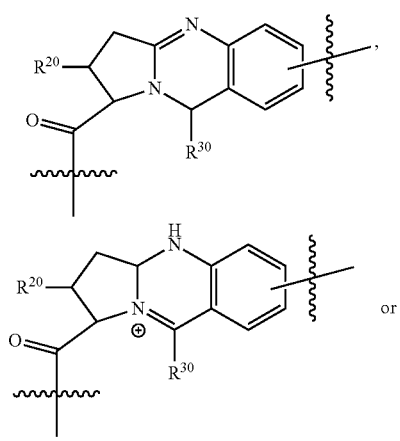

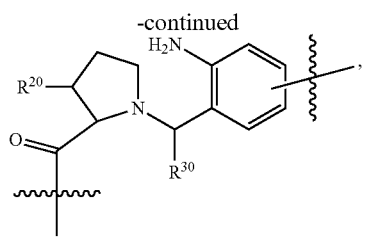

wherein $R^{20}$ is H or Me, and $R^{30}$ is H, Me or Phenyl, for linking, where the acyl group shown attaches to the lysine portion of a Pcl or Pyl in an engineered antibody.

In some embodiments, an immunoconjugate of Formula (II) or Formula (III), or subformulae thereof, comprises an antibody or antibody fragment Ab having antigen-binding activity, where the linker L is attached to Ab at serine residue in an S6, ybbR or A1 peptide engineered into an antibody. Linker components formed by reaction with such serine residues include, but are not limited to,

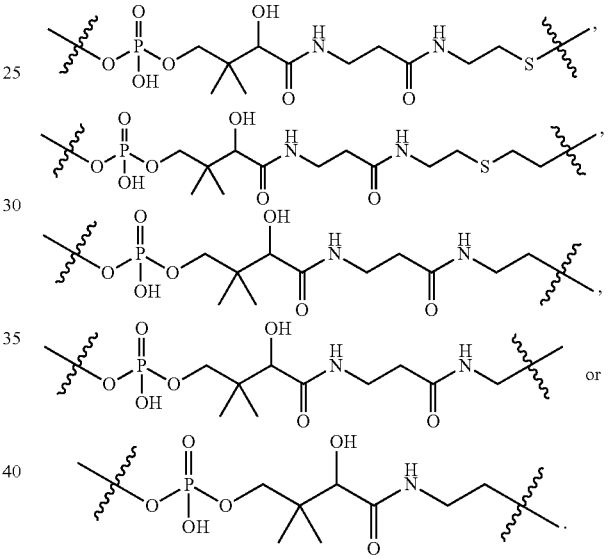

By way of example, one general reaction scheme for the formation of immunoconjugates of Formula (II) is shown in Scheme 13 below:

Scheme 13

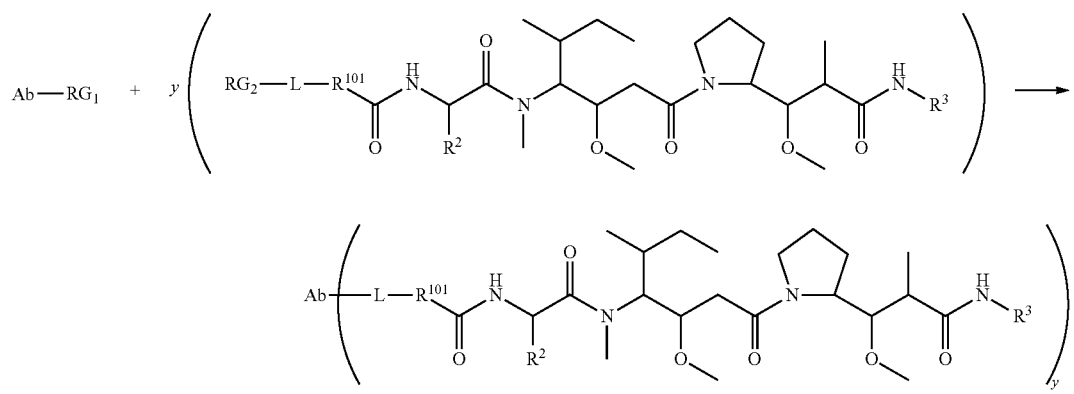

where RG₁ is a reactive group 1 from Table 1 and RG₂ is a reactive group 1 from Table 1 and the reaction product of the respective groups (as seen in Table 1) is a linker component of linker L. $R^{101}$, $R^2$, $R^3$, L and Ab are as defined herein.

Another general reaction scheme for the formation of immunoconjugates of Formula (II) is shown in Scheme 14 below:

Scheme 14

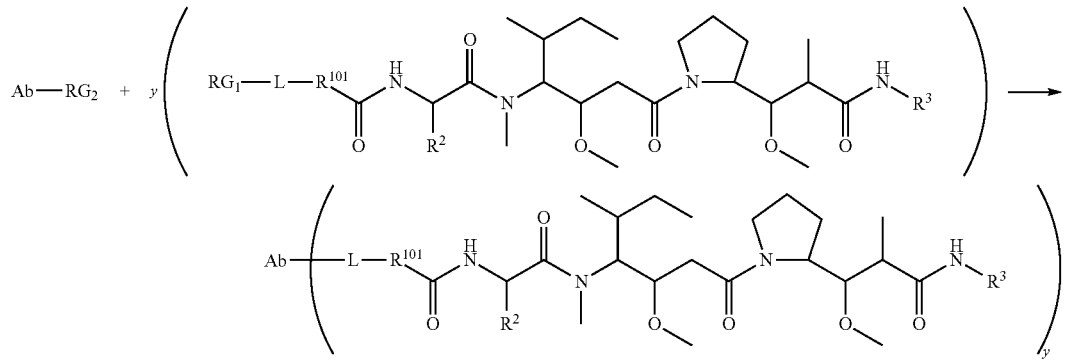

where RG₁ is a reactive group 1 from Table 1 and RG₂ is a reactive group 1 from Table 1 and the reaction product of the respective groups (as seen in Table 1) is a linker component of linker L. $R^{101}$, $R^2$, $R^3$, L and Ab are as defined herein.

By way of example, one general reaction scheme for the formation of immunoconjugates of Formula (III) is shown in Scheme 15 below:

Scheme 15

where RG₁ is a reactive group 1 from Table 1 and RG₂ is a reactive group 1 from Table 1 and the reaction product of the respective groups (as seen in Table 1) is a linker component of linker L. $R^1$, $R^2$, $R^3$, L and Ab are as defined herein.

Another general reaction scheme for the formation of immunoconjugates of Formula (II) is shown in Scheme 16 below:

Scheme 16

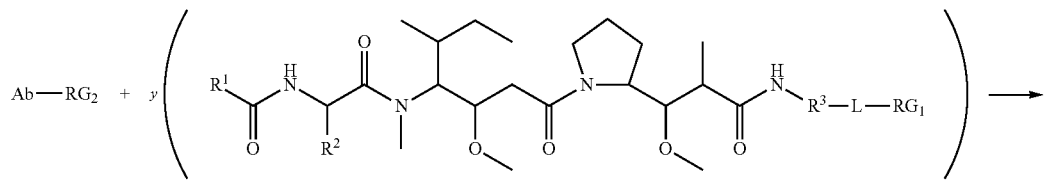

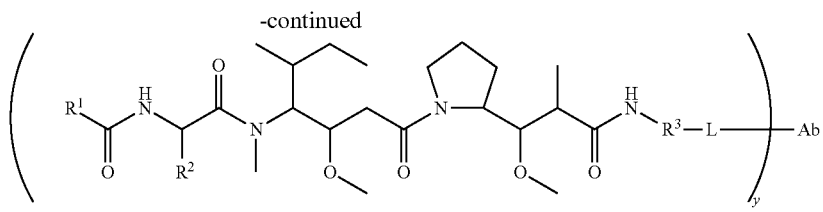

where $RG_1$ is a reactive group 1 from Table 1 and $RG_2$ is a reactive group 1 from Table 1 and the reaction product of the respective groups (as seen in Table 1) is a linker component of linker L. $R^1$, $R^2$, $R^3$, L and Ab are as defined herein.

In another aspect, the present invention provides a pharmaceutical composition comprising an immunoconjugate of Formula (II) or Formula (III) of the present invention, or subformulae thereof, and at least one pharmaceutically acceptable carrier. The pharmaceutical composition can be formulated for particular routes of administration such as intravenous administration, parenteral administration, and the like.

The immunoconjugates of the invention are typically formulated as solutions or suspensions in aqueous buffer and/or isotonic aqueous solution. They are typically administered parenterally, either by injection or by infusion. Methods for their formulation and administration are similar to those for formulation and administration of other biologic-based pharmaceuticals such as antibody therapeutics, and are known to those of skill in the art.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

The in vitro cell killing potency given in Table 2 obtained for certain cytotoxic peptides of Formula (I) shows that such compounds of formula (I) exhibit valuable pharmacological activities, and as such these compounds can be used as the payload of an ADC. The immunoconjugates comprising a compound of formula (I), as demonstrated herein, exhibit substantial activity on targeted cells in vitro and on tumors in vivo, as demonstrated by potent growth inhibition of xenograft tumors representing different human cancers. Thus the immunoconjugates of Formula (II) or (III) of the invention, comprising a payload of Formula (I), and subformulae thereof, linked to an antigen binding moiety such as an antibody, are also useful to treat cancers, such as gastric, myeloid, colon, nasopharyngeal, esophageal, and prostate tumors, glioma, neuroblastoma, breast cancer, lung cancer, ovarian cancer, colorectal cancer, thyroid cancer, leukemia (e.g., myelogenous leukemia, lymphocytic leukemia, acute myelogenous leukemia (AML), chronic myeloid leukemia (CML), acute lymphoblastic leukemia (ALL), T-lineage acute lymphoblastic leukemia or T-ALL chronic lymphocytic leukemia (CLL), myelodysplastic syndrome (MDS), hairy cell leukemia), lymphoma (Hodgkin's lymphoma (HL), non-Hodgkin's lymphoma (NHL)), multiple myeloma, bladder, renal, gastric (e.g., gastrointestinal stromal tumors (GIST)), liver, melanoma and pancreatic cancer, and sarcoma.

An embodiment of the invention provides conjugation of a compound of formula (I), and subformulae thereof, to an antigen binding moiety and thereby forming an immunoconjugate of Formula (II) or Formula (III), as described herein.

The immunoconjugates of the invention comprising a compound of Formula (I), or subformulae thereof, are particularly useful for treating cancers known in the art to be inhibited by anti-mitotic toxins, and those tumor types demonstrated herein to be susceptible to inhibition by the compounds and conjugates of the invention. Suitable indications for treatment include, but are not limited to, gastric, myeloid, colon, nasopharyngeal, esophageal, and prostate tumors, glioma, neuroblastoma, breast cancer, lung cancer, ovarian cancer, colorectal cancer, thyroid cancer, leukemia (e.g., myelogenous leukemia, lymphocytic leukemia, acute myelogenous leukemia (AML), chronic myeloid leukemia (CML), acute lymphoblastic leukemia (ALL), T-lineage acute lymphoblastic leukemia or T-ALL chronic lymphocytic leukemia (CLL), myelodysplastic syndrome (MDS), hairy cell leukemia), lymphoma (Hodgkin's lymphoma (HL), non-Hodgkin's lymphoma (NHL)), multiple myeloma, bladder, renal, gastric (e.g., gastrointestinal stromal tumors (GIST)), liver, melanoma and pancreatic cancer, and sarcoma. The immunoconjugates of the invention comprising a compound of Formula (I), or subformulae thereof, are particularly useful in therapy. In a further embodiment, the therapy is for a disease which may be treated by anti-mitotic toxins. In another embodiment, the compounds of the invention are useful to treat cancers, including but not limited to gastric, myeloid, colon, nasopharyngeal, esophageal, and prostate tumors, glioma, neuroblastoma, breast cancer, lung cancer, ovarian cancer, colorectal cancer, thyroid cancer, leukemia (e.g., myelogenous leukemia, lymphocytic leukemia, acute myelogenous leukemia (AML), chronic myeloid leukemia (CML), acute lymphoblastic leukemia (ALL), T-lineage acute lymphoblastic leukemia or T-ALL chronic lymphocytic leukemia (CLL), myelodysplastic syndrome (MDS), hairy cell leukemia), lymphoma (Hodgkin's lymphoma (HL), non-Hodgkin's lymphoma (NHL)), multiple myeloma, bladder, renal, gastric (e.g., gastrointestinal stromal tumors (GIST)), liver, melanoma and pancreatic cancer, and sarcoma.

The methods typically comprise administering an effective amount of an immunoconjugate of the invention as described herein or a pharmaceutical composition comprising such immunoconjugates to a subject in need of such treatment. The immunoconjugate may be administered by any suitable method such as those described herein, and the administration may be repeated at intervals selected by a treating physician.

Thus, as a further embodiment, the present invention provides the use of a immunoconjugate of formula (II) or (III), or any of the embodiments of such compounds described herein, for the manufacture of a medicament. In a further embodiment, the medicament is for treatment of a disease which may be treated by anti-mitotic toxins. In another embodiment, the disease is selected from gastric, myeloid, colon, nasopharyngeal, esophageal, and prostate tumors, glioma, neuroblastoma, breast cancer, lung cancer, ovarian cancer, colorectal cancer, thyroid cancer, leukemia (e.g., myelogenous leukemia, lymphocytic leukemia, acute myelogenous leukemia (AML), chronic myeloid leukemia (CML), acute lymphoblastic leukemia (ALL), T-lineage acute lymphoblastic leukemia or T-ALL chronic lymphocytic leukemia (CLL), myelodysplastic syndrome (MDS), hairy cell leukemia), lymphoma (Hodgkin's lymphoma (HL), non-Hodgkin's lymphoma (NHL)), multiple myeloma, bladder, renal, gastric (e.g., gastrointestinal stromal tumors (GIST)), liver, melanoma and pancreatic cancer, and sarcoma.

The pharmaceutical composition or combination of the present invention can be in unit dosage of about 1-1000 mg of active ingredient(s) for a subject of about 50-100 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-12}$ molar concentrations. A therapeutically effective amount in vivo may range depending on the route of administration, between about 0.1-500 mg/kg, or between about 1-100 mg/kg.

An immunoconjugate of Formula (II) or Formula (III), or subformulae thereof, of the present invention may be administered either simultaneously with, or before or after, one or more therapeutic co-agent(s). An immunoconjugate of Formula (II) or Formula (III), or subformulae thereof, of the present invention may be administered separately, by the same or different route of administration, or together in the same pharmaceutical composition as the co-agent(s).

In one embodiment, the invention provides a product comprising a compound of formula (I), or subformulae thereof, and at least one other therapeutic co-agent as a combined preparation for simultaneous, separate or sequential use in therapy. In one embodiment, the therapy is the treatment of a disease or condition such as cancer with an anti-mitotic toxin. Products provided as a combined preparation include a composition comprising an immunoconjugate of Formula (II) or Formula (III), or subformulae thereof, and the other therapeutic co-agent(s) together in the same pharmaceutical composition, or the immunoconjugate of Formula (II) or Formula (III), or subformulae thereof, and the other therapeutic co-agent(s) in separate form, e.g. in the form of a kit.

In one embodiment, the invention provides a pharmaceutical composition comprising an immunoconjugate of Formula (II) or Formula (III), or subformulae thereof, and another therapeutic co-agent(s). Optionally, the pharmaceutical composition may comprise a pharmaceutically acceptable carrier, as described above.

Suitable co-agents for use with the compounds and conjugates of the invention include other anti-cancer agents, anti-allergic agents, anti-nausea agents (or anti-emetics), pain relievers, anti-inflammatory agents, cytoprotective agents, and combinations thereof.

Specific co-agents considered for use in combination with the compounds and conjugates disclosed herein include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxol®), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

In one embodiment, the invention provides a kit comprising two or more separate pharmaceutical compositions, at least one of which contains a Formula (II) or Formula (III), or subformulae thereof. In one embodiment, the kit comprises means for separately retaining said compositions, such as a container, divided bottle, or divided foil packet In the combination therapies of the invention, the immunoconjugate of Formula (II) or Formula (III), or subformulae thereof, of the invention and the other therapeutic co-agent may be manufactured and/or formulated by the same or different manufacturers. Moreover, the immunoconjugate of Formula (II) or Formula (III), or subformulae thereof, of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

The invention also provides an immunoconjugate of Formula (II) or Formula (III), or subformulae thereof, for use in a method of treating a disease or condition with a cytotoxic peptide. The invention also provides an immunoconjugate of Formula (II) or Formula (III), or subformulae thereof, for use in a method of treating a disease or condition with a cytotoxic peptide, wherein the immunoconjugate of Formula (II) or Formula (III), or subformulae thereof, is prepared for administration with another therapeutic agent. The invention also provides another therapeutic co-agent for use in a method of treating a disease or condition with an a cytotoxic peptide, wherein the other therapeutic co-agent is prepared for administration with an immunoconjugate of Formula (II) or Formula (III), or subformulae thereof. The invention also provides an immunoconjugate of Formula (II) or Formula (III), or subformulae thereof, for use in a method of treating a disease or condition with an anti-mitotic toxin wherein the immunoconjugate of Formula (II) or Formula (III), or subformulae thereof, is administered with another therapeutic co-agent. The invention also provides another therapeutic co-agent for use in a method of treating a disease or condition with an anti-mitotic toxin, wherein the other therapeutic co-agent is administered with an immunoconjugate of Formula (II) or Formula (III), or subformulae thereof.

The invention also provides the use of an immunoconjugate of Formula (II) or Formula (III), or subformulae thereof, for treating a disease or condition with a cytotoxic peptide, wherein the patient has previously (e.g. within 24 hours) been treated with another therapeutic agent. The invention also provides the use of another therapeutic agent for treating a disease or condition with an anti-mitotic toxin, wherein the patient has previously (e.g. within 24 hours) been treated with an immunoconjugate of Formula (II) or Formula (III), or subformulae thereof.

The invention also provides an immunoconjugate of Formula (II) or Formula (III), or subformulae thereof, for use in a method of treating a disease or condition with an anti-mitotic toxin. The invention also provides an immunoconjugate of Formula (II) or Formula (III), or subformulae thereof, for use in a method of treating a disease or condition with an anti-mitotic toxin, wherein the immunoconjugate of Formula (II) or Formula (III), or subformulae thereof, is prepared for administration with another therapeutic agent. The invention also provides another therapeutic co-agent for use in a method of treating a disease or condition with an anti-mitotic toxin, wherein the other therapeutic co-agent is prepared for administration with an immunoconjugate of Formula (II) or Formula (III), or subformulae thereof. The invention also provides an immunoconjugate of Formula (II) or Formula (III), or subformulae thereof, for use in a method of treating a disease or condition with an anti-mitotic toxin wherein the immunoconjugate of Formula (II) or Formula (III), or subformulae thereof, is administered with another therapeutic co-agent. The invention also provides another therapeutic co-agent for use in a method of treating a disease or condition with an anti-mitotic toxin, wherein the other therapeutic co-agent is administered with an immunoconjugate of Formula (II) or Formula (III), or subformulae thereof.

The invention also provides the use of an immunoconjugate of Formula (II) or Formula (III), or subformulae thereof, for treating a disease or condition with an anti-mitotic toxin, wherein the patient has previously (e.g. within 24 hours) been treated with another therapeutic agent. The invention also provides the use of another therapeutic agent for treating a disease or condition with an anti-mitotic toxin, wherein the patient has previously (e.g. within 24 hours) been treated with an immunoconjugate of Formula (II) or Formula (III), or subformulae thereof.

Conjugation of Linker-Payload (L-P) with an Antigen Binding Moiety

EXAMPLE 101

Antibody Drug Conjugates (ADC) Formed by Conjugation of Anti-Her2 and Antibody 20507 Cys Mutant Antibodies with Cytotoxic Peptides of Formula (I)

Numerous methods of conjugating linker-payloads to antigen binding moiety are known in the art (reviewed in for example: Antibody-Drug Conjugate, Methods in Molecular Biology, Vol. 1045, Editor L. Ducry, Humana Press (2013)). In this example, compounds of Formula (I) of the invention comprising a linker were conjugated to cysteine residues engineered into an antibody using methods described in Junutula J R, Raab H, Clark S, Bhakta S, Leipold D D, Weir S, Chen Y, Simpson M, Tsai S P, Dennis M S, Lu Y, Meng Y G, Ng C, Yang J, Lee C C, Duenas E, Gorrell J, Katta V, Kim A, McDorman K, Flagella K, Venook R, Ross S, Spencer S D, Lee Wong W, Lowman H B, Vandlen R, Sliwkowski M X, Scheller R H, Polakis P, Mallet W. (2008) Nature Biotechnology 26:925-932. Conjugation of the cytoxic peptides of Formula (I) of the invention is herein illustrated using a small set of Cys antibody mutants but it is anticipated that the cytoxic peptides can be conjugated to most if not all possible Cys antibody mutants. Further more, it is expected that the cytoxic peptides can be conjugated to Cys mutants of numerous, if not all antibodies.

Because engineered Cys in antibodies expressed in mammalian cells are modified by adducts (disulfides) such as glutathione (GSH) and/or cysteine during their biosynthesis (Chen et al. 2009), the modified Cys in the product as initially expressed is unreactive to thiol reactive reagents such as maleimido or bromo-or iodo-acetamide groups. To conjugate the engineered cysteine after expression, the glutathione or cysteine adducts need to be removed by reducing these disulfides, which generally entails reducing all of the disulfides in the expressed protein. This can be accomplished by first exposing the antibody to a reducing agent such as dithiothreitol (DTT) followed by a procedure that allows for the re-oxidation of all native disulfide bonds of the antibody to restore and/or stabilize the functional antibody structure. Accordingly, in order to reduce all native disulfide bonds and the disulfide bound between the cysteine or GSH adducts of the engineered cysteine residue, freshly prepared DTT was added to purified anti-Her2 or antibody 20507 Cys mutant constructs, to a final concentration of 20 mM. After incubation with DTT at 37° C. for 1 hour, the mixtures were dialyzed at 4° C. against PBS for three days with daily buffer exchange to remove DTT and re-oxidize the native disulfide bonds. An alternative method is to remove the reducing reagents through a desalting column such as Sephadex G-25. Once the protein is fully reduced, 1 mM oxidized ascorbate (dehydro-ascorbic acid) is added to the desalted samples and the re-oxidation incubations are carried out for 20 hours. Both methods produce similar results. However, attempts to follow the re-oxidation protocols previously described in the literature using $CuSO_4$ resulted in protein precipitation (Junutula J R, Raab H, Clark S, Bhakta S, Leipold D D, Weir S, Chen Y, Simpson M, Tsai S P, Dennis M S, Lu Y, Meng Y G, Ng C, Yang J, Lee C C, Duenas E, Gorrell J, Katta V, Kim A, McDorman K, Flagella K, Venook R, Ross S, Spencer S D, Lee Wong W, Lowman H B, Vandlen R, Sliwkowski M X, Scheller R H, Polakis P, Mallet W. (2008) Nature Biotechnology 26:925). All examples herein use the dialysis protocol described above. Reoxidation restores intra-chain disulfides, while dialysis removes cysteines and glutathiones initially connected to the engineered cysteine(s) of the antibody.

After re-oxidation, the antibody was conjugated to a cytotoxic peptide of Formula (I), where the cytotoxic peptide of Formula (I) comprises a linker and a reactive moiety. By way of example, cytotoxic peptides of Formula (I) having a linked maleimide moiety (10 molar equivalents relative to the antibody) were added to re-oxidized anti-Her2 or antibody 20507 Cys mutant antibodies in PBS buffer (pH 7.2). The incubations were carried out for 1 hour. The conjugation process was monitored by reverse-phase HPLC, which is able to separate conjugated antibodies from non-conjugated ones. The conjugation reaction mixtures were analyzed on a PRLP-S column (4000 Å, 50 mm×2.1 mm, Agilent) heated to 80° C. and elution of the column was carried out by a linear gradient of 30-60% acetonitrile in water containing 0.1% TFA at a flow rate of 1.5 ml/min. The elution of proteins from the column was monitored at 280 nm, 254 nm and 215 nm.

Conjugation efficiency of various cytotoxic peptides having a linked maleimide to anti-Her2 or antibody 20507 Cys mutant antibody varied depending on the solubility of the cytotoxic peptides used but most reactions resulted in more than 90% conjugate (Tables 5 and 6). To evaluate the aggregation state, the resulting conjugates were analyzed in a size exclusion chromatography column (GE, Superdex200, 3.2/30) at a flow rate of 0.1 ml/min in PBS. All conjugates were mainly monomeric. The majority of the conjugates contain less than 3% dimeric and oligomeric material (Tables 5 and 6), indicating that conjugation of such cytotoxic peptides having a linked maleimide to anti-Her2 or antibody 20507 Cys mutant antibody did not cause aggregation. Similarly, enzymatic conjugation through A1 or ybbR tags (Examples 104 and 105) also proceeds with conjugation efficiencies of greater than 90% (Table 7 and 9) and results in conjugates that are monomeric with less than 3% detectable aggregates (Tables 7 and 9).

The conjugates were also characterized in terms of average loading of a cytotoxic peptide to the antibody binding moiety, generally referred to as drug to antibody ratio (DAR). The DAR value is extrapolated from LC-MS data for reduced and deglycosylated samples. LC/MS allows quantitation of the average number of molecules of payload (drug) attached to an antibody in an ADC. HPLC separates the antibody into light and heavy chains, and separates the heavy chain (HC) and light chain (LC) according to the number of Linker-Payload groups per chain. Mass spectral data enables identification of the component species in the mixture, e.g., LC, LC+1, LC+2, HC, HC+1, HC+2, etc. From the average loading on the LC and HC chains, the average DAR can be calculated for an ADC. The DAR for a given conjugate sample represents the average number of drug (payload) molecules attached to a tetrameric antibody containing two light chains and two heavy chains. Table 5 and 6 give the DAR values obtained for the conjugates obtained with anti-Her2 or antibody 20507 antibodies and certain cytotoxic peptides having a linked maleimide.

As comparators, antibody 20507-LC-S159C mutant antibody was conjugated with maleimidocaproyl mono-methyl auristatin F (MC-MMAF; Doronina S O, Mendelsohn B A, Bovee T D, Cerveny C G, Alley S C, Meyer D L, Oflazoglu E, Toki B E, Sanderson R J, Zabinski R F, Wahl A F, Senter P D. Bioconjug. Chem. 2006 January-February; 17(1):114-24.) following the same protocols. The properties of the comparator antibody 20507-LC-S159C-MMAF ADC are listed in Table 6.

EXAMPLE 102

Preparation of Antibody Drug Conjugates Through Partial Reduction of Native Disulfide Bonds of Non-Engineered Antibodies Cytotoxic drugs of the invention can also be conjugated to native cysteine residues of non-engineered antibodies using a procedure that involves partial reduction of the antibodies (Doronina, S. O., Toki, B. E., Torgov, M. Y., Mendelsohn, B. A., Cerveny, C. G., Chace, D. F., DeBlanc, R. L., Gearing, R. P., Bovee, T. D., Siegall, C. B., Francisco, J. A., Wahl, A. F., Meyer, D. L., and Senter, P. D. (2003) Development of potent monoclonal antibody auristatin conjugates for cancer therapy. Nat. Biotechnol. 21, 778-784). In this example, inter- and intra-chain disulfides bonds of anti-Her2 and antibody 20507 antibodies at a concentration of 5 to 10 mg/ml were first partially reduced in PBS containing 2 mM EDTA by adding solid mercaptoethylamine to a final concentration of 50 mM and incubating the mixture at 37° C. for 1 hour. After desalting and addition of 1% w/v PS-20 detergent, the partially reduced antibodies (1-2 mg/ml) were reacted overnight at 4° C. with 0.5 to 1 mg payload compound 10 per 10 mg antibody. The resulting ADCs, anti-Her2-10 and antibody 20507-10, were purified by Protein A chromatography. After base-line washing with PBS, the conjugates were eluted with 50 mM citrate, pH 2.7, 140 mM NaCl, neutralized and sterile filtered. The average DAR of the resulting two ADCs, anti-Her2-10 and antibody 20507-10 was determined by hydrophobic interaction chromatography and MS to be 4.1 and 4.6, respectively. Selected biochemical properties of the two ADCs were shown in Tables 5 and 6. In addition to anti-Her2 antibody and antibody 20507, it is expected that the cytoxic peptides of the invention can be conjugated the native cysteine residues of numerous, if not all antibodies using the above method (Example 102).

TABLE 5

Properties of various anti-Her2 Cys mutant ADCs

| Name of ADC[a] | Immuno-conjugate Formula | Conjugation efficiency[b] (%) | DAR[c] | Aggregation[d] (%) |
|---|---|---|---|---|
| anti-Her2-LC-S159C-17 | II | 95 | 1.9 | 2.6 |
| anti-Her2-LC-S159C-41 | III | 100 | 2.0 | 2.3 |
| anti-Her2-LC-S159C-34 | III | 95 | 1.9 | 1.7 |
| anti-Her2-LC-S159C-33 | III | 95 | 1.9 | 1.2 |
| anti-Her2-LC-S159C-36 | III | 83 | 1.7 | 2.9 |
| anti-Her2-LC-S159C-35 | III | 95 | 1.9 | 2.0 |
| anti-Her2-LC-S159C-47 | III | 80 | 1.6 | Below detection limit |
| anti-Her2-LC-S159C-43 | III | 90 | 1.8 | 1.7 |
| anti-Her2-LC-S159C-10 | II | 90 | 1.8 | 0 |
| anti-Her2-LC-S159C-11 | II | 95 | 1.9 | 5.0 |
| anti-Her2-LC-S159C-44 | III | 100 | 2.0 | 1.8 |
| anti-Her2-LC-S159C-42 | III | 35 | 0.7 | 2.0 |
| anti-Her2-LC-S159C-12 | II | 95 | 1.9 | 5.0 |
| anti-Her2-LC-S159C-32 | III | 95 | 1.9 | 2.2 |
| anti-Her2-LC-S159C-14 | II | 95 | 1.9 | 2.3 |
| anti-Her2-LC-S159C-38 | III | 95 | 1.9 | 2.4 |
| anti-Her2-LC-S159C-40 | III | 94 | 1.9 | 2.9 |
| anti-Her2-LC-S159C-31 | III | 100 | 2.0 | 2.0 |
| anti-Her2-LC-S159C-37 | III | 83 | 1.7 | 2.9 |
| anti-Her2-LC-S159C-30 | III | 95 | 1.9 | 5.0 |
| anti-Her2-LC-S159C-39 | III | 90 | 1.8 | 2.4 |
| anti-Her2-HC-E152C-S375C-10 | II | 95 | 3.8 | 0.3 |

TABLE 5-continued

Properties of various anti-Her2 Cys mutant ADCs

| Name of ADC[a] | Immuno-conjugate Formula | Conjugation efficiency[b] (%) | DAR[c] | Aggregation[d] (%) |
|---|---|---|---|---|
| Anti-Her2-10 | II | Not determined | 4.1 | 2.3 |

[a]Name consists of a description of the mutated antibody and the last number which corresponds to the compound used in the chemical conjugation step.
[b]Conjugation efficiency was measured by reverse-phase HPLC and describes the percentage of antibody converted to ADC.
[c]Drug-to-antibody ratio according to reverse-phase HPLC.
[d]Aggregation was measured analytical size exclusion chromatography and includes dimeric and oligomeric species.

TABLE 6

Properties of various antibody 20507 Cys mutant ADCs

| Name of ADC[a] | Immuno-conjugate Formula | Conjugation efficiency[b] (%) | DAR[c] | Aggregation[d] (%) |
|---|---|---|---|---|
| antibody 20507-HC-E152C-31 | III | 100 | 2 | 0.8 |
| antibody 20507-HC-E152-10 | II | 95 | 1.9 | 0.8 |
| antibody 20507-HC-S376C-47 | III | 95 | 1.9 | 0.5 |
| antibody 20507-LC-K107C-47 | III | 95 | 1.9 | 0.1 |
| antibody 20507-LC-S159C-43 | III | 80 | 1.6 | 1.8 |
| antibody 20507-LC-S159C-44 | III | 100 | 2 | 0.1 |
| antibody 20507-LC-S159C-40 | III | 35 | 0.7 | 2.4 |
| antibody 20507-LC-S159C-MMAF | Not applicable | 95 | 1.9 | 0.2 |
| antibody 20507-HC-E152C-S375C-10 | II | 98 | 3.9 | 0.6 |
| antibody 20507-10 | II | Not determined | 4.6 | 2.9 |

[a]Name consists of a description of the mutated antibody and the last number which corresponds to the compound used in the chemical conjugation step.
[b]Conjugation efficiency was measured by reverse-phase HPLC and describes the percentage of antibody converted to ADC.
[c]Drug-to-antibody ratio according to reverse-phase HPLC.
[d]Aggregation was measured analytical size exclusion chromatography and includes dimeric and oligomeric species.

EXAMPLE 103

Preparation of Antibody Drug Conjugates Using 1,3-dichloropropan-2-one to Reconnect Native Disulfide Bonds of Non-Engineered Antibodies Conjugation to native cysteine residues of non-engineered antibodies using the procedure in Example 102 has the disadvantage that some native disulfide bonds that naturally stabilize the antibody are broken and remain so after drug conjugation. In an alternative method that overcomes this disadvantage, inter- and intra-chain disulfides bonds of the antibody are first reduced and then chemically reconnected through a reaction with 1,3-dichloropropan-2-one. In the process, the four native interchain disulfide bonds in an antibody are replaced by a three carbon "ketone bridge" (Scheme 17). The ketone group can then specifically be conjugated with a cytotoxic drug in the second step. The resulting ADC has up to four drugs attached specifically at the location of the four native, interchain disulfide bonds of an antibody. In contrast to traditional conjugation to partially reduced native disulfides (Example 102), ADCs prepared in the example are more stable. In one example, non-engineered, recombinant anti-Her2 was prepared by standard methods and as described above. After purification, modified anti-Her2 was conjugated to a cytotoxic drug in two steps following Scheme 17.

Scheme 17

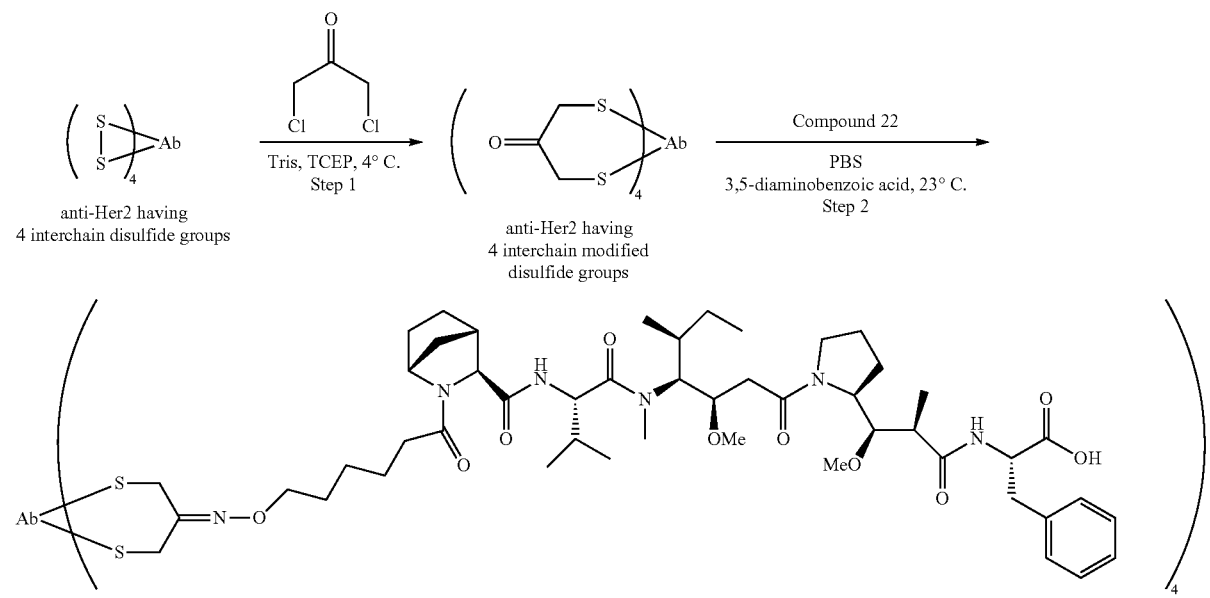

Step 1: Reduction of native disulfide bridges and re-bridging using 1,3-dichloropropan-2-one: TCEP.HCl (47.2 µg, 0.165 µmol) was added to a solution of anti-Her2 IgG (2036 µg, 0.014 µmol) and 1,3-dichloropropan-2-one (220 µg, 1.648 µmol) in Tris buffer (pH 7.4, 0.25 M, 177 µL) at 4° C. The resulting mixture was kept at 4° C. for 4 h. The reaction mixture was then desalted using a Zeba spin column 7K MWCO with PBS (pH 7.4) as the eluting buffer. The resulting solution was concentrated by 10K Amicon filter to give the the modified anti-Her2). ESI (Eluent A: water+0.1% Formic acid, Eluent B: Acetonitrile+0.04% Formic acid. Gradient: from 3 to 80% B in 2 min—Flow 1.0 ml/min. Column: Proswift Monolith 4.6*50 mm 40° C.); 145399 Da (after deglycosylation by PNGase F (New England biolab)).

Step 2: Conjugation of the cytotoxic drug: A solution of (S)-2-((2R,3R)-3-((S)-1-((3R,4S,5S)-4-((S)-2-((1R,3S,4S)-2-(6-(Aminooxy)hexanoyl)-2-azabicyclo[2.2.1]heptane-3-carboxamido)-N,3-dimethylbutanamido)-3-methoxy-5-methylheptanoyl)pyrrolidin-2-yl)-3-methoxy-2-methylpropanamido)-3-phenylpropanoic acid (22) (77 µg, 0.078 µmol, 0.77 µL in DMSO) and 3,5-diaminobenzoic acid (355 µg, 2.334 µmol, 1.42 µL in DMSO) were added to a solution of the modified anti-Her2 (577.5 µg, 0.0039 µmol, 35 µL in PBS, pH 7.4) at 23° C. The resulting mixture was kept at 23° C. for 21 h. The reaction mixture was then desalted using a Zeba spin column 7K MWCO with PBS (pH 7.4) as the eluting buffer for twice to give the modified anti-Her2 conjugated with compound (22). ESI-MS (Eluent A: water+0.1% Formic acid, Eluent B: Acetonitrile+0.04% Formic acid. Gradient: from 3 to 80% B in 2 min—Flow 1.0 ml/min. Column: Proswift Monolith 4.6*50 mm 40° C.); 147955 Da (DAR 3), 148807 Da (DAR 4) (after deglycosylation by the treatment with PNGase F (New England biolab)). The overall DAR was calculated as DAR 3.7.

Although only shown here for an anti-Her2 antibody, the conjugation approach in this example is expected to be applicable to numerous if not all other antibodies.

EXAMPLE 104

Conjugation of Anti-Her2 and Antibody 20507 A1/ybbR Tag Mutant Antibodies with Cytotoxic Peptides of Formula (I)

Post-translational 4'-phosphopantetheinylation is a versatile method for the site-specific labeling of recombinant proteins with structurally diverse small molecules (Yin J, Straight P D, McLoughlin S M, Zhou Z, Lin A J, Golan D E, Kelleher N L, Kolter R, Walsh C T (2005) Proc. Natl. Acad. Sci. U.S.A. 102:15815-15820) (Zhou Z, Cironi P, Lin A J, Xu Y, Hrvatin S, Golan D E, Silver P A, Walsh C T, Yin J (2007) ACS Chem. Biol. 2:337-346). This enzymatic approach, which is based on the catalytic action of promiscuous 4'-phosphopantetheinyl transferases (PPTases), was adopted for the preparation of highly homogeneous ADCs (WO2013184514). Enzymatic labeling is accomplished by incorporating 11 or 12-mer S6, ybbR, and A1 peptide sequences at various sites of the constant region of an IgG1 antibody. Although the following example describes PPTase-mediated ADC formation for only one site, the approach is expected to be applicable to numerous insertion sites within the antibody scaffold and is expected to be applicable to numerous antibodies.

Previous work by Burkart and co-workers revealed PPTases as versatile enzymes that accept a variety of CoA-reporter analogues as substrates (La Clair J J, Foley T L, Schegg T R, Regan C M, Burkart M D (2004) Chem. Biol. 11:195-201). Hence, in order to convert a drug payload into a substrate suitable for PPTase catalysis, the maleimide containing cytotoxic peptide of Formula (I) was conjugated to the terminal thiol group of CoA via a Michael addition (see Example 43). Having covalently linked the cytotoxic peptide to an enzymatic recognition element, the resulting cytotoxic CoA-peptide analogue (Compound 20) was enzymatically conjugated to the embedded peptide sequence of the respective antibody. By way of example, 2.5 µM of anti-Her2-HC-ins388-ybbR antibody or antibody 20507-HC-ins388-A1 were conjugated with 30 µM of cytotoxic CoA-peptide analogue (Compound 20) (12 molar equivalents relative to the antibody) in the presence of 1 µM of Sfp PPTase from *Bacillus subtilis*. The enzymatic conjugation reactions were carried out at room temperature for approximately 16 hours in 75 mM Tris-HCl buffer (pH 8.0) supplemented with 20 mM NaCl and 12.5 mM $MgCl_2$. In order to ensure near-complete labeling of antibody 20507-HC-ins388-A1 with the cytotoxic payload, the incubation time was extended by another three days and the concentrations of the CoA-peptide analogue of (Compound 20) and Sfp PPTase were increased to 35 µM (14 molar equivalents relative to the antibody) and 2 µM, respectively. Following conjugation, Sfp PPTase and excess reagent were removed by Protein A affinity chromatography (Protein A-Sepharose™, GE Healthcare Life Sciences). Elution of the column was carried out with 0.1 M of sodium acetate buffer (pH 3.0) followed by immediate neutralization with 1 M Tris-HCl buffer (pH 8.0). The peptide-tagged ADCs were finally buffer-exchanged into PBS using PD-10 desalting columns (GE Healthcare).

The extent of payload conjugation was determined by analytical HPLC on a PLRP-S column (4000 Å, 5 µM, 50×4.6 mm, Agilent Technologies) with a 6-min linear gradient of 25-50% acetonitrile in water containing 0.1% trifluoroacetic acid. Reverse-phase separation of conjugated and non-conjugated antibody was monitored at a wavelength of 280 nm. To this end, HPLC peak integration indicated near-complete labeling of anti-Her2-HC-ins388-ybbR and 20507-HC-ins388-A1 antibodies with the CoA-peptide analogue (Compound 20). The identity of the enzymatically labeled ADCs was further confirmed by obtaining deconvoluted ESI-MS spectra of the corresponding reduced and deglycosylated samples. As shown in Table 8, the observed masses are in agreement with the calculated molecular weights of the drug-labeled heavy chains of the anti-Her2-HC-ins388-ybbR and 20507-HC-ins388-A1 antibodies. Finally, the enzymatically labeled ADCs were analyzed by analytical size-exclusion chromatography (AnSEC) on a Shodex PROTEIN KW-803 column. Both antibody conjugates eluted at retention times that corresponded to the apparent molecular weight of monomeric ADC (see Table 7). No other species were detected indicating that conjugation of the hydrophilic CoA-peptide analogue did not promote antibody aggregation.

TABLE 7

Properties of anti-Her2 and antibody 20507 A1/ybbR tag ADCs

| Name of ADC[a] | Immuno-conjugate Formula | Conjugation efficiency[b] (%) | DAR[c] | Aggregation[d] (%) |
|---|---|---|---|---|
| anti-Her2-HC-ins388-ybbR-20 | II | 96 | 1.9 | Below detection limit |

TABLE 7-continued

Properties of anti-Her2 and antibody 20507 A1/ybbR tag ADCs

| Name of ADC[a] | Immuno-conjugate Formula | Conjugation efficiency[b] (%) | DAR[c] | Aggregation[d] (%) |
|---|---|---|---|---|
| antibody 20507-HC-ins388-A1-20 | II | 96 | 1.9 | Below detection limit |

[a]HC-ins388 refers to the insertion of the A1 or ybbR peptide tag after residue Glu388 in the heavy chain. The last number corresponds to the compound used in the chemical conjugation step.
[b]Conjugation efficiency was measured by reverse-phase HPLC and describes the percentage of antibody converted to ADC.
[c]Drug-to-antibody ratio according to reverse-phase HPLC.
[d]Aggregation was measured analytical size exclusion chromatography and includes dimeric and oligomeric species.

TABLE 8

Properties of anti-Her2 and antibody 20507 A1/ybbR tag ADCs

| Name of ADC[a] | Immuno-conjugate Formula | Observed mass (Da)[b] | Expected mass conjugate heavy chain (Da)[c] | Expected mass unmodified heavy chain (Da)[d] |
|---|---|---|---|---|
| anti-Her2-HC-ins388-ybbR-20 | II | 51605.02 | 51607.3 | 50331.8 |
| antibody 20507-HC-ins388-A1-20 | II | 51286.32 | 51289.9 | 50014.4 |

[a]HC-ins388 refers to the insertion of the A1 or ybbR peptide tag after residue Glu388 in the heavy chain. The last number corresponds to the compound used in the chemical conjugation step.
[b]Mass in Dalton as detected on an Agilent 6520 Q-TOF instrument (Agilent Technologies).
[c]Mass in Dalton as predicted for the conjugated heavy chain.
[d]Mass in Dalton as predicted for the uncoupled heavy chain.

EXAMPLE 105

Two-Step Conjugation of A1/ybbR-Tagged Anti-Her2 and Antibody 20507 Mutant Antibodies with a Cytotoxic Peptide of Formula (I)

The two-step method is an alternative strategy to prepare site-specific ADCs by post-translational 4'-phosphopantetheinylation (WO2013184514). The first step of this approach is based on the PPTase-catalyzed labeling of a peptide-tagged antibody with a CoA analogue containing a bioorthogonal group, such as an azido, alkene, alkyne, ketone, or aldehyde moiety. Following affinity purification of the bioorthogonally labeled antibody, the second step of the two-step method involves the conjugation of a cytotoxic payload comprising a moiety reactive with the bioorthogonal group. As way of example, the following section describes the two-step method for antibody 20507 and anti-Her2 mutant antibodies containing an A1 or ybbR tag insertion at a specific site within the constant region of the heavy chain. In addition, the following section describes the two-step method for antibody 20507 and anti-Her2 mutant antibodies containing an A1 or ybbR tag insertion at a specific site within the constant region of the heavy chain. However, it is anticipated that this strategy is broadly applicable to numerous insertion sites within the constant regions of a wide variety of antibodies. In addition, although the two-step method is exemplified for oxime ligation and copper-free click chemistry, it is conceivable that this strategy could be extended to other bioorthogonal chemistries, such as Staudinger ligation, isonitrile-based click chemistry, and tetrazine ligation.

Oxime ligation and copper-free click chemistry have been used by several research groups as an efficient, bioorthogonal method for the preparation of site-specific protein conjugates (Axup J Y, Bajjuri K M, Ritland M, Hutchins B M, Kim C H, Kazane S A, Halder R, Forsyth J S, Santidrian A F, Stafin K, Lu Y, Tran H, Seller A J, Biroc S L, Szydlik A, Pinkstaff J K, Tian F, Sinha S C, Felding-Habermann B, Smider V V, Schultz P G (2012) Proc Natl Acad Sci USA. 109:16101-16106) (Rabuka D, Rush J S, deHart G W, Wu P, Bertozzi C R (2012) Nat Protoc. 7:1052-1067) (Plass T, Milles S, Koehler C, Schultz C, Lemke E A (2011) Angew Chem Int Ed Engl. 50:3878-3881) (Kaya E, Vrabel M, Deiml C, Prill S, Fluxa V S, Carell T (2012) Angew Chem Int Ed Engl. 51:4466-4469). In order to combine post-translational 4'-phosphopantetheinylation with oxime ligation, a ketone group was covalently attached to CoA by reacting the latter with methyl vinyl ketone (see Example 93). Next, PPTase catalysis was used to enzymatically conjugate the bioorthogonal ketone group site-specifically onto the embedded A1 tag of an anti-Her2 antibody. Specifically, 2.5 µM of anti-Her2-HC-ins388-A1 antibody was conjugated with 30 µM of the resulting ketone-CoA analogue (Compound 49) (12 molar equivalents relative to the antibody) in the presence of 1 µM of Sfp PPTase from Bacillus subtilis. This first step of the two-step method was carried out for about 16 hours at room temperature in 75 mM Tris-HCl buffer (pH 8.0), supplemented with 12.5 mM $MgCl_2$ and 20 mM NaCl. Near complete labeling of the anti-Her2-HC-ins388-A1 antibody with the ketone-CoA analogue (Compound 49; see Example 93) was verified by obtaining deconvoluted ESI-MS spectra of the reduced and deglycosylated sample. Similar reaction conditions also resulted in near quantitative ketone functionalization of antibody 20507-HC-ins388-A1. As shown in Table 10, the observed masses are in agreement with the calculated molecular weights of the corresponding ketone-functionalized heavy chains. After removing Sfp PPTase and excess ketone-CoA analogue by Protein A affinity chromatography (Protein A-Sepharose™, GE Healthcare Life Sciences), the ketone-activated antibodies, anti-Her2-HC-ins388-A1-49 and antibody 20507-HC-ins388-A1-49, were eluted with 0.1 M of sodium acetate buffer (pH 3) followed by immediate neutralization with 1 M Tris-HCl buffer (pH 8). The neutralized antibody solutions were buffer-exchanged into water and passed through filters with 0.22 µm pore size.

In another aspect of this two step labeling approach, modified CoA analogues were prepared chemoenzymatically using the CoA biosynthetic enzymes CoAA, CoAD, and CoAE (Worthington A S, Burkart M D (2006) Org Biomol Chem. 4:44-46) (Kosa N M, Haushalter R W, Smith A R, Burkart M D (2012) Nat Methods 9:981-984). Adopting this approach, ketone-functionalized CoA analogues were prepared from the corresponding pantothenate precursor molecules (i-10), (i-12) and (i-13) (see Examples 94, 96 and 97). Likewise, an azide-functionalized CoA analogue was chemoenzymatically synthesized from the respective pantothenate derivative (i-11) (see Example 95). In this approach, the ultrafiltrates from Examples 94-97 were used without further purification, and the CoA analogues CoA-(i-10), CoA-(i-11), CoA-(i-12) and CoA-(i-13) were used for conjugation to anti-Her2-HC-ins388-ybbR (2.5 µM), at a final concentration of approximately 30 µM. Antibody labeling was performed in the presence of 1.5 µM B. subtilis Sfp PPTase for 16 to 72 hours at 23° C. in 75 mM Tris-HCl buffer (pH 8.0), supplemented with 12.5 mM $MgCl_2$ and 20 mM NaCl. Similarly, CoA-(i-13) was conjugated at a final concentration of approximately 25 µM in the presence of 2 µM Sfp enzyme.

Affinity chromatography (MabSelect SuRe™, GE Healthcare Life Sciences) of the bioorthogonally labeled antibodies was conducted in the exact same manner as described above for keto-CoA analogue 49. Following purification, the neutralized antibody solutions were buffer-exchanged into PBS. Covalent attachment of the ketone and azide moieties to the ybbR-tagged antibody was confirmed by mass spectrometric analysis following sample treatment with PNGase F and TCEP (Table 10).

Site-specific attachment of a ketone group enabled subsequent oxime ligation of a cytotoxic payload to ketone-activated anti-Her2-HC-ins388-A1-49, antibody 20507-HC-ins388-A1-49, anti-Her2-HC-ins388-ybbR-(i-10), and anti-Her2-HC-ins388-ybbR-(i-12) as the second step of the two-step method. 25 to 67 µM of ketone-functionalized antibody was reacted with 7.5 to 40-fold molar excess (0.5-1 mM) of the aminooxy-peptide analogue (Compound 22) in 50 or 100 mM sodium acetate buffer (pH 4-5) containing 2.5 to 5% (v/v) DMSO. After 16 to 36 hours of incubation at 23 or 37° C., excess aminooxy reagent was removed by preparative size-exclusion chromatography on a HiLoad 26/600 Superdex 200 prep grade column (GE Healthcare). The drug-to-antibody ratio (DAR) was determined by analytical HPLC on a PLRP-S column (4000 Å, 5 µM, 50×4.6 mm, Agilent Technologies) with a 5-min linear gradient of 30 to 60% acetonitrile in water containing 0.1% trifluoroacetic acid. The HPLC trace was monitored at a wavelength of 280 nm followed by peak integration of conjugated and non-conjugated antibody. As shown in Table 9, the two-step method afforded near quantitative labeling of ketone-activated anti-Her2-HC-ins388-A1-49 and antibody 20507-HC-ins388-A1-49 with the aminooxy-peptide analogue (Compound 22). In contrast, site-specific conjugation of compound 22 to ketone-activated anti-Her2-HC-ins388-ybbR-(i-10) antibody was less efficient, resulting in an ADC with a DAR of 1.3. ADC formation through oxime ligation was further confirmed by ESI-MS after reduction and deglycosylation of the immunoconjugates (Table 10). Finally, analytical size-exclusion chromatography (AnSEC) on Superdex 200 10/300 GL (GE Healthcare) and Protein KW-803 5 µm 300×8 mm (Shodex) columns revealed only small amounts of aggregated ADC, suggesting that little aggregation is induced during the two-step conjugation process.

Site-specific attachment of an azide moiety to an engineered antibody allows subsequent payload conjugation via copper-free click chemistry. In this example, the bioorthogonal reaction is promoted by the ring strain of the bicyclo[6.1.0]nonyne (BCN) group, which is covalently attached to the drug-linker. Strain-promoted alkyne-azide cycloaddition was carried out with the azide-activated anti-Her2-HC-ins388-ybbR-(i-11) antibody in the presence of the BCN-functionalized payload Compound 75. This second step of the two-step method was carried out with 127 µM of anti-Her2-HC-ins388-ybbR-(i-11) antibody and 1270 µM of the BCN-linked peptide analogue (Compound 75) in 100 mM sodium phosphate buffer (pH 7.5) supplemented with 1 M NaCl and 6% (v/v) DMSO. After approximately 16 hours of incubation at 23° C., excess BCN reagent was removed by standard Protein A affinity chromatography using MabSelect SuRe™ (GE Healthcare Life Sciences). Elution was carried out with IgG Elution Buffer (Thermo Scientific), followed by neutralization with 1 M Tris-HCl buffer (pH 8) and buffer exchange into PBS. As shown in Table 10, payload conjugation through copper-free click chemistry was confirmed by ESI-MS after reduction and deglycosylation of the ADC sample. The same method was used to calculate the average DAR of the immunoconjugate. In this process, 10 µg of ADC was supplemented with 10 µL of 50% slurry of IgG Sepharose 6 Fast Flow (GE Healthcare). Resin binding was performed under mild agitation for 1 h at 23° C. After washing the resin with PBS, the affinity-bound ADC was deglycosylated by addition of 5 µg of PNGase F and subsequent incubation at 37° C. for 3 hours. PNGase F enzyme was removed by washing the affinity resin with PBS. Next, the deglycosylated sample was eluted using 1% formic acid followed by immediate neutralization with 10 M ammonium acetate (pH 5). To effectively reduce the antibody construct to heavy and light chains, 20 µL of eluate was supplemented with 10 µL of 100 mM sodium formate buffer (pH 4.0) containing 6 M guanidine hydrochloride and 5 µL of 0.66 M TCEP in 10 M ammonium acetate (pH 5). After incubation for at least 30 min at 23° C., the reduced and deglycosylated sample was injected onto a 6550 iFunnel Q-TOF LC/MS system (Agilent Technologies). MassHunter Qualitative Analysis Software (Agilent Technologies) was used for processing of the spectral record and spectral deconvolution. The average DAR was calculated as the DAR state weighted average of the relative peak heights across a distribution. As shown in Table 9, the anti-Her2-HC-ins388-ybbR-(i-11)-75 ADC has an average DAR of 2.0, suggesting that both conjugation steps were nearly quantitative. Finally, the ADC was examined by analytical size-exclusion chromatography (AnSEC) on a Bio SEC-3 column (Agilent Technologies) and found to be 95% monomeric suggesting that little aggregation is induced in the conjugation process.

TABLE 9

Properties of A1- and ybbR-tagged antibodies/ADCs labeled through two-step conjugation process

| Name of Conjugate[a] | Immuno-conjugate Formula | Conjugation efficiency (%) | DAR | Aggregation[f] (%) |
|---|---|---|---|---|
| anti-Her2-HC-ins388-A1-49 | not applicable | not determined | not applicable | not determined |
| antibody 20507-HC-ins388-A1-49 | not applicable | not determined | not applicable | not determined |
| anti-Her2-HC-ins388-A1-49-22 | II | 91[b] | 1.8[d] | 3 |
| antibody 20507-HC-ins388-A1-49-22 | II | 93[b] | 1.9[d] | <1 |
| anti-Her2-HC-ins388-ybbR-(i-10) | not applicable | not determined | not applicable | not determined |
| anti-Her2-HC-ins388- | not | not | not | not |

TABLE 9-continued

Properties of A1- and ybbR-tagged antibodies/ADCs labeled through two-step conjugation process

| Name of Conjugate[a] | Immuno-conjugate Formula | Conjugation efficiency (%) | DAR | Aggregation[f] (%) |
|---|---|---|---|---|
| ybbR-(i-11) | applicable | determined | applicable | determined |
| anti-Her2-HC-ins388-ybbR-(i-10)-22 | II | 65[b] | 1.3[d] | <1 |
| anti-Her2-HC-ins388-ybbR-(i-11)-75 | II | 100[c] | 2.0[e] | 5 |

[a]HC-ins388 refers to the insertion of the A1 or ybbR peptide tag after residue Glu388 in the heavy chain. The last number corresponds to the compound used in the conjugation step. For example, anti-Her2-HC-ins388-A1-49-22 and antibody 20507-HC-ins388-A1-49-22 were first enzymatically conjugated with compound 49 followed by chemical conjugation with compound 22.
[b]Conjugation efficiency was measured by reverse-phase HPLC and describes the percentage of antibody converted to ADC.
[c]Conjugation efficiency was determined by mass spectrometry and describes the percentage of antibody converted to ADC.
[d]Drug-to-antibody ratio according to reverse-phase HPLC.
[e]Drug-to-antibody ratio according to mass spectrometry.
[f]Aggregation was measured by analytical size exclusion chromatography and includes dimeric and oligomeric species.

TABLE 10

Properties of A1- and ybbR-tagged antibodies/ADCs labeled through two-step conjugation process

| Name of Conjugate[a] | Immuno-conjugate Formula | Observed mass (Da)[b] | Expected mass conjugate heavy chain (Da)[c] | Expected mass unmodified heavy chain (Da)[d] |
|---|---|---|---|---|
| anti-Her2-HC-ins388-A1-49 | not applicable | 50940.08<br>50880.99[e] | 50945.4 | 50535.0 |
| antibody 20507-HC-ins388-A1-49 | not applicable | 50422.23 | 50424.8 | 50014.4 |
| anti-Her2-HC-ins388-A1-49-22 | II | 51793.38 | 51798.5 | 50535.0<br>50945.4[f] |
| antibody 20507-HC-ins388-A1-49-22 | II | 51274.91 | 51277.9 | 50014.4<br>50424.8[f] |
| anti-Her2-HC-ins388-ybbR-(i-10) | not applicable | 50665.06<br>50607.66[e] | 50668.1 | 50331.8 |
| anti-Her2-HC-ins388-ybbR-(i-12) | not applicable | 50679.05 | 50682.1 | 50331.8 |
| anti-Her2-HC-ins388-ybbR-(i-13) | not applicable | 50604.80 | 50611.0 | 50331.8 |
| anti-Her2-HC-ins388-ybbR-(i-11) | not applicable | 50679.55 | 50681.1 | 50331.8 |
| anti-Her2-HC-ins388-ybbR-(i-10)-22 | II | 51523.04<br>50668.67 | 51521.2 | 50331.8<br>50668.1[f] |
| anti-Her2-HC-ins388-ybbR-(i-12)-22 | II | 51529.21 | 51535.2 | 50331.8<br>50682.1[f] |
| anti-Her2-HC-ins388-ybbR-(i-11)-75 | II | 51713.37 | 51712.4 | 50331.8<br>50681.1[f] |

[a]HC-ins388 refers to the insertion of the A1 or ybbR peptide tag after residue Glu388 in the heavy chain. The last number corresponds to the compound used in the conjugation step. For example, anti-Her2-HC-ins388-A1-49-22 and antibody 20507-HC-ins388-A1-49-22 were first enzymatically conjugated with compound 49 followed by chemical conjugation with compound 22.
[b]Mass in Dalton as detected on an Agilent 6520 Q-TOF instrument (Agilent Technologies).
[c]Mass in Dalton as predicted for the conjugated heavy chain.
[d]Mass in Dalton as predicted for the uncoupled heavy chain.
[e]Minor peak of unknown identity.
[f]Unmodified heavy chain refers to both non-phosphopantetheinylated and ketone/azide-functionalized species.

While the immunoconjugates of Formula (II) and Formula (III) disclosed in Table 5 and 6 were obtained by conjugated anti-Her2 and antibody 20507 Cys antibodies and certain cytotoxic peptides of Formula (I) having a linked maleimide moiety, other linker-payload combinations of the invention have also been used. The immunoconjugates disclosed in Tables 7 to 10 are such examples. Conjugation to non-engineered antibodies is another example. This can be achieved by conjugation to partially reduced disulfide bonds as described in Examples 102 and 103. Non-engineered antibodies can also be conjugated lysines using, for example, compound 89, or a variety of other methods known in the art.

EXAMPLE 106

Cell Proliferation Assays to Measure In Vitro Cell Killing Potency of Anti-Her2 and Antibody 20507 Cys and A1/ybbR Tag ADCs Cells that naturally express target antigens or cell lines engineered to express target antigens are frequently used to assay the activity and potency of ADCs. For evaluation of the cell killing potency of anti-Her2 antibody ADCs in vitro, two engineered cell lines, MDA-MB231 clone 16 and clone 40, and four endogenous cell lines, JimT1, HCC1954, NCI-N87 and SKBR3 cells were employed (Clinchy B, Gazdar A, Rabinovsky R, Yefenof E, Gordon B, Vitetta E S. Breast Cancer Res Treat. (2000) 61:217-228). MDA-MB231 clone 16 cells stably express high copy numbers (~$5\times10^5$ copies/cell) of recombinant human Her2 while clone 40 expresses low copy numbers (~$5\times10^3$ copies/cell) of human Her2. High levels of Her2 are endogenously expressed in HCC1954 (~$5\times10^5$ copies/cell), SKBR-3 ($5.4\times10^5$ copies/cell) and NCI-N87 ($2.7\times10^5$ copies/cell) cell lines while JimT-1 cells express human Her2 at a medium level (~$8\times10^4$ copies/cell). As a negative control, the Her2 negative A375 cell line was used. An antigen dependent cytotoxic effect should only kill cells that express sufficient antigen in the cell surface and not cells lacking the antigen. The cell proliferation assays were conducted with Cell-Titer-Glo™ (Promega) five days after cells were incubated with various concentrations of ADCs (Riss et al., (2004) Assay Drug Dev Technol. 2:51-62). In some studies, the cell based assays are high throughput and conducted on an automated system (Melnick et al., (2006) Proc Natl Acad Sci USA. 103:3153-3158).

All anti-Her2 ADCs except one (anti-Her2-LC-S159C-44) specifically killed cell lines with high levels of Her2 expression, namely MDA-MB231 clone 16, HCC1954, NCI-N87, SKBR3, but did not show cytotoxic potency towards MDA-MB231 clone 40 cells, which express a low level of Her2, and also not toward Her2 negative A375 cells (FIG. 1; Table 11, Table 13). $IC_{50}$ of the anti-Her2 ADCs in the four cell lines expressing high levels of Her2 ranges from 20 pM to 700 pM (Table 11, Table 13). In JimT-1 cells which express medium level of Her2, the cell killing activities by the anti-Her2-ADCs varied widely. Some ADCs were active in cells expressing high levels of Her2 but not in JimT-1 cells. Many ADCs killed JimT-1 cell as effectively as cell lines expressing high levels of Her2 (Table 11, Table 13). The results suggest that the anti-Her2 ADCs killed Her2+ cells in a Her2-dependent manner and the ADCs are active towards multiple cell types. Similarly, anti-Her2 ADCs prepared by partial reduction method of wild type antibodies (Example 102) and by enzymatic methods through an A1 or ybbR tag (Examples 104 and 105) and by ketone bridge methodology (Example 103) also killed Her2+ cells in a Her2-dependent manner (Table 11), demonstrating that the cytotoxic peptides disclosed in the invention retain their potency when conjugated to antibodies through a different conjugation method and chemistry.

To verify whether cytotoxic peptides of Formula (I) are also active when conjugated to other antibodies, several cytotoxic peptides of Formula (I) were conjugated to antibody 20507, whose target antigen is expressed in H526, KU812 and CMK11-5 cells but not in Jurkat cells. As shown in FIG. 2 and Table 12, payload linker combinations that show cell killing activities in Her2+ cells are also active when conjugated to antibody 20507, killing cells that express the target antigen. The results indicate that the cytotoxic peptides of Formula (I) described herein show cytotoxicity towards a broad range of cell types.

TABLE 11

ADC potency in in vitro cell killing assay: $IC_{50}$ of anti-Her2 ADCs in MDA-MB231 clone 40, MDA-MB231 clone 16, HCC1954 and JimT-1 cell proliferation assays.

| | $IC_{50}$ (μM)[b] | | | |
|---|---|---|---|---|
| Name of ADC[a] | MDA-MB-231 clone 40 | HCC1954 | JimT1 | MDA-MB-231 clone 16 |
| anti-Her2-LC-S159C-17 | 5.28E−02 | 2.19E−04 | 5.28E−02 | 7.43E−05 |
| anti-Her2-LC-S159C-41 | 6.67E−02 | 5.78E−05 | 1.12E−04 | 2.81E−05 |
| anti-Her2-LC-S159C-34 | 6.67E−02 | 9.25E−05 | 4.26E−04 | 4.79E−05 |
| anti-Her2-LC-S159C-33 | 6.67E−02 | 1.89E−04 | 6.67E−02 | 7.97E−05 |
| anti-Her2-LC-S159C-36 | 6.67E−02 | 5.16E−05 | 1.07E−04 | 2.83E−05 |
| anti-Her2-LC-S159C-35 | 6.67E−02 | 6.71E−05 | 3.71E−04 | 4.65E−05 |
| anti-Her2-LC-S159C-47 | 6.67E−02 | 5.51E−05 | 7.74E−05 | 5.47E−05 |
| anti-Her2-LC-S159C-43 | 6.67E−02 | 7.32E−05 | 1.65E−04 | 4.55E−05 |
| anti-Her2-LC-S159C-10 | 6.67E−02 | 6.17E−05 | 1.17E−04 | 5.38E−05 |
| anti-Her2-LC-S159C-11 | 2.33E−02 | 4.85E−04 | 2.33E−02 | 7.40E−04 |
| anti-Her2-LC-S159C-44 | 6.67E−02 | 6.67E−02 | 6.67E−02 | 6.67E−02 |
| anti-Her2-LC-S159C-42 | 6.67E−02 | 7.27E−05 | 1.38E−03 | 6.67E−05 |
| anti-Her2-LCS159C-12 | 2.33E−02 | 5.09E−04 | 2.33E−02 | 3.70E−04 |
| anti-Her2-LC-S159C-32 | 6.67E−02 | 5.45E−05 | 9.83E−05 | 5.32E−05 |
| anti-Her2-LC-S159C-14 | 6.67E−02 | 7.51E−05 | 6.67E−02 | 6.74E−05 |
| anti-Her2-LC-S159C-38 | 6.67E−02 | 2.94E−04 | 6.67E−02 | 7.90E−05 |
| anti-Her2-LC-S159C-40 | 6.67E−02 | 7.33E−05 | 1.78E−04 | 3.44E−05 |
| anti-Her2-LC-S159C-31 | 4.70E−02 | 3.04E−05 | 4.82E−05 | 1.84E−05 |
| anti-Her2-LC-S159C-37 | 6.67E−02 | 1.56E−05 | 1.14E−04 | 1.58E−04 |
| anti-Her2-LC-S159C-30 | 1.87E−02 | 4.05E−04 | 1.87E−02 | 3.56E−04 |
| anti-Her2-LC-S159C-39 | 6.67E−02 | 6.00E−05 | 2.11E−04 | 3.75E−05 |
| anti-Her2-HC-E152C-S375C-10 | 6.67E−02 | 1.56E−04 | 1.70E−04 | 1.84E−04 |
| anti-Her2-10 | 6.67E−02 | 2.18E−04 | 1.29E−03 | 2.25E−04 |
| anti-Her2-HC-ins388-ybbR-20 | 6.02E−02[c] | 7.98E−05 | 2.47E−04 | 5.08E−05 |
| anti-Her2-HC-ins388-A1-49-22 | 5.73E−02[c] | 1.37E−04 | 1.53E−04 | 1.31E−04 |
| anti-Her2-HC-ins388-ybbR-(i-10)-22 | 6.53E−02[c] | 4.14E−05 | 1.01E−03 | 5.98E−04 |
| anti-Her2-HC-ins388-ybbR-(i-11)-75 | 6.00E−02[c] | 9.88E−05 | 6.53E−04 | 1.59E−04 |
| Anti-Her2-22 | 6.67E−02 | 6.52E−05 | 2.01E−04 | 2.96E−05 |

[a]Name consists of a description of the mutated antibody and the last number which corresponds to the compound used in the chemical conjugation step. HC-ins388 refers to the insertion of the A1 or ybbR peptide tag after residue Glu388 in the heavy chain.
[b]The highest concentration used in the assay was 6.67E−02 μM. $IC_{50}$ values of 6.67E−02 μM therefore refer to inactivity of the ADC in the assay.
[c]The value is equal to the highest concentration used in the assay, therefore indicating inactivity of the ADC.

TABLE 12

ADC potency in in vitro cell killing assay: $IC_{50}$ of antibody 20507 ADCs in Jurkat, H526, KU812 and CMK11-5 cell proliferation assays.

| | $IC_{50}$ (μM)[b] | | | |
|---|---|---|---|---|
| Name of ADC[a] | JURKAT | H526 | KU812 | CMK11-5 |
| antibody 20507-HC-E152C-10 | 6.67E−02 | 1.28E−04 | 7.82E−05 | 1.60E−04 |
| antibody 20507-LC-K107C-47 | 6.67E−02 | 5.40E−05 | 6.54E−05 | 6.24E−05 |
| antibody 20507-HC-S375C-47 | 6.67E−02 | 5.05E−05 | 5.35E−05 | 5.45E−05 |
| antibody 20507-LC-S159C-42 | 6.67E−02 | 7.30E−05 | 2.17E−04 | 5.77E−05 |
| antibody 20507-LC-S159C-43 | 6.67E−02 | 5.11E−05 | 5.01E−05 | 4.89E−05 |
| antibody 20507-LC-S159C-44 | 6.67E−02 | 6.67E−02 | 6.67E−02 | 6.67E−02 |
| antibody 20507-HC-E152C-S375C-10 | 6.67E−02 | 1.77E−05 | 2.07E−05 | 1.93E−05 |

TABLE 12-continued

ADC potency in in vitro cell killing assay: $IC_{50}$ of antibody 20507 ADCs in Jurkat, H526, KU812 and CMK11-5 cell proliferation assays.

| Name of ADC[a] | $IC_{50}$ (μM)[b] | | | |
|---|---|---|---|---|
| | JURKAT | H526 | KU812 | CMK11-5 |
| antibody 20507-10 | 6.67E−02 | 2.47E−05 | 2.09E−05 | 7.34E−06 |
| antibody 20507-HC-ins388-A1-20 | 4.50E−02 | 2.62E−04 | 1.86E−04 | 3.35E−04 |
| antibody 20507-HC-ins388-A1-49-22 | 6.67E−02 | 1.67E−04 | 2.37E−03 | 9.68E−04 |

[a]Name consists of a description of the mutated antibody and the last number which corresponds to the compound used in the chemical conjugation step. HC-ins388 refers to the insertion of the A1 peptide tag after residue Glu388 in the heavy chain.
[b]The highest concentration used in the assay was 6.67E−02 μM. $IC_{50}$ values of 6.67E−02 μM therefore refer to inactivity of the ADC in the assay.

TABLE 13

ADC potency in in vitro cell killing assay: $IC_{50}$ of anti-Her2 ADCs in A375, HCC1954, JimT-1 NCI-N87 and SKBR3 cell proliferation assays.

| Name of ADCs | IC50 (μM)[b] | | | | |
|---|---|---|---|---|---|
| | A375 | HCC1954 | JimT1 | NCI-N87 | SKBR3 |
| anti-Her2-LC-S159C-77 | 6.67E−02 | 1.73E−04 | 3.58E−04 | 2.12E−04 | 1.61E−04 |
| anti-Her2-LC-S159C-80 | 6.67E−02 | 1.72E−04 | 4.94E−04 | 1.79E−04 | 1.60E−04 |
| anti-Her2-LC-S159C-79 | 6.67E−02 | 1.87E−04 | 6.34E−04 | 2.03E−04 | 1.61E−04 |
| anti-Her2-LC-S159C-78 | 6.67E−02 | 1.08E−04 | 3.27E−04 | 1.08E−04 | 1.67E−04 |
| anti-Her2-LC-S159C-91 | 6.67E−02 | 2.21E−05 | 6.67E−02 | 4.23E−05 | 6.12E−05 |
| anti-Her2-LC-S159C-76 | 6.67E−02 | 1.07E−04 | 6.67E−02 | 4.27E−04 | 3.38E−04 |
| anti-Her2-LC-S159C-82 | 6.67E−02 | 6.67E−02 | 6.67E−02 | 9.80E−04 | N.D.[c] |
| anti-Her2-LC-S159C-89 | 6.67E−02 | 2.16E−04 | 6.67E−02 | 2.20E−04 | N.D.[c] |
| anti-Her2-LC-S159C-90 | 6.67E−02 | N.D.[c] | 7.70E−04 | 1.64E−04 | 1.55E−04 |
| anti-Her2-LC-S159C-83 | 6.67E−02 | 6.67E−02 | 6.67E−02 | N.D.[c] | N.D.[c] |
| anti-Her2-LC-S159C-84 | 6.67E−02 | 6.67E−02 | 6.67E−02 | N.D.[c] | N.D.[c] |
| anti-Her2-LC-S159C-85 | 6.67E−02 | 6.67E−02 | 6.67E−02 | 6.67E−02 | N.D.[c] |
| anti-Her2-LC-S159C-86 | 6.67E−02 | 6.67E−02 | 6.67E−02 | 6.67E−02 | N.D.[c] |
| anti-Her2-LC-S159C-87 | 6.67E−02 | 6.67E−02 | 6.67E−02 | N.D.[c] | N.D.[c] |
| anti-Her2-LC-S159C-88 | 6.67E−02 | 6.67E−02 | 6.67E−02 | N.D.[c] | N.D.[c] |
| anti-Her2-LC-S159C-93 | 6.67E−02 | 1.38E−04 | 2.12E−04 | N.D.[c] | N.D.[c] |
| anti-Her2-LC-S159C-94 | 6.67E−02 | 1.67E−04 | 2.41E−04 | N.D.[c] | N.D.[c] |
| anti-Her2-LC-S159C-92 | 6.67E−02 | 1.91E−04 | 3.02E−04 | N.D.[c] | N.D.[c] |

[a]Name consists of a description of the mutated antibody and the last number which corresponds to the compound used in the chemical conjugation step.
[b]The highest concentration used in the assay was 6.67E−02 μM. $IC_{50}$ values of 6.67E−02 μM therefore refer to inactivity of the ADC in the assay.
[c]N.D.: not determined

EXAMPLE 107

Pharmacokinetic Study of Anti-Her2 and Antibody 20507 ADCs

It has been demonstrated that a long serum half-life is critical for high in vivo efficacy of ADCs (Hamblett, et al., "Effects of drug loading on the antitumor activity of a monoclonal antibody drug conjugate," *Clin Cancer Res.*, 10:7063-7070 (2004); Alley et al., *Bioconjug Chem.* 19:759-765 (2008)). Attaching a hydrophobic drug payload to an antibody could affect the properties of an antibody, and this may lead to a fast clearance of the ADCs in vivo (Hamblett et al., 2004) and poor in vivo efficacy. To evaluate the effects of conjugation of various cytotoxic peptides of the invention on clearance of the ADCs in vivo, pharmacokinetic studies in non-tumor bearing mice were carried out. To detect the cytotoxic peptide (i.e. drug part) of the immunoconjugates of the invention in murine plasma, an anti-MMAF antibody was generated that also recognizes various cytotoxic peptides of the invention. ELISAs for the detection of immunoconjugates were developed on a Gyros™ platform using an anti-hIgG antibody to capture human IgG molecules from the plasma and a second anti-human IgG antibody and the anti-MMAF antibody for signal detection in two separate assays. The anti-MMAF antibody recognizes the cytotoxic peptides of the invention and therefore can be used to detect ADCs with the cytotoxic peptides attached ("intact" ADC). Hence, the two ELISAs measure the serum concentration of the human antibody and the "intact" ADC respectively.

Examples of PK studies are shown in FIG. 3 and FIG. 4. Three mice per group were administered with a single dose of the following ADCs at 1 mg/kg: anti-Her2-LC-S159C-10 (FIG. 3A), anti-Her2-LC-S159C-47 (FIG. 3B), anti-Her2-LC-S159C-77 (FIG. 3C), anti-Her2-LC-S159C-80 (FIG. 3D), anti-Her2-LC-S159C-79 (FIG. 3E), anti-Her2-LC-S159C-78 (FIG. 3F), anti-Her2-LC-S159C-14 (FIG. 3G), anti-Her2-HC-E152C-S375C-10 (FIG. 3H), anti-Her2-10 (FIG. 3I), antibody 20507-HC-E152C-10 (FIG. 4A), antibody 20507-LC-K107C-47 (FIG. 4B), antibody 20507-HC-ins388-A1-20 (FIG. 4C) antibody 20507-HC-E152C-S375C-10 (FIG. 4D), antibody 20507-10 (FIG. 4E), anti-Her2-HC-ins388-ybbR-20 (FIG. 4G), antibody 20507-HC-ins388-A1-49-22 (FIG. 4H), anti-Her2-HC-ins388-A1-49-22 (FIG. 4I), and anti-Her2-HC-ins388-ybbR-(i-11)-75 (FIG. 4J) ADCs. Antibody 20507-HC-ins388-A1-20 (FIG. 4F) was administered with a single dose of 10 mg/kg. Plasma samples were collected over the course of three weeks and assayed by ELISAs using an anti-hIgG antibody to capture the IgG molecules including antibody 20507 and anti-Her2 ADCs, as well as the respective naked antibodies. The anti-MMAF and an anti-hIgG antibody were then used for detection in two separate assays. The anti-MMAF antibody assay measures the concentration of antibody conjugates only and the anti-hIgG quantitates both antibody conjugates and antibody that lacks payloads. Standard curves were generated for each ADC separately using the same material as injected into the mice. The assays with anti-MMAF and anti-hIgG should therefore yield identical concentration readouts if no changes to the drug loading of the antibody 20507 or anti-Her2 ADC occur after injection into mice. For ADC that lost some of the payload, the assay with the anti-MMAF antibody will measure a lower concentration than the anti-hIgG assay. A comparison of the two concentration readouts therefore allows to measure drug-release from antibody 20507 and anti-Her2 ADCs during in vivo incubation in the mouse.

As shown in FIG. 3 and FIG. 4, plasma concentrations obtained by both anti-hIgG and anti-MMAF assays match well with most ADCs with maleimide payloads conjugating to engineered Cys(s) in both anti-Her2 and antibody 20507 antibodies (FIG. 3A-I, FIG. 4D), suggesting that there is a minimal drug loss in these ADCs during the testing period for these ADCs. The two ADCs prepared by partial reduction of wild-type antibodies, anti-Her2-10 (FIG. 3I) and antibody 20507-10 (FIG. 4E), showed a strong separation between concentrations determined by anti-hIgG and anti-MMAF assays with former being higher than later, suggesting there is a significant drug loss during the testing period for the two ADCs. ADCs prepared by enzyme-mediated methods, antibody 20507-HC-ins388-A1-20, anti-Her2-HC-ins388-ybbR-20, antibody 20507-HC-ins388-A1-49-22, and anti-Her2-HC-ins388-A1-49-22 ADCs showed a good match between concentrations determined by anti-IgG and anti-MMAF assays (FIGS. 4F, G, H and I). In contrast, the anti-Her2-HC-ins388-ybbR-(i-11)-75 ADC (FIG. 4J) displayed a large separation between anti-hIgG and anti-MMAF assays, suggesting that the ADC undergoes significant drug deconjugation during the course of the PK study.

As shown in FIG. 4, plasma concentrations obtained by both anti-hIgG assay and anti-MMAF assay match well with antibody 20507-HC-E153C-10 ADC, antibody 20507-LC-K107C-47 ADC and antibody 20507-HC-ins388-A1-20 ADC, suggesting that there is a minimal drug loss in these ADCs during the testing period.

To determine the retention of drug payloads for ADCs after three weeks in mouse circulation in more detail, the ADCs were affinity-purified from mouse serum collected through terminal bleeding and the drug payloads attached to ADCs were analyzed by MS analysis. In a typical process, 200 µl of plasma was diluted with an equal amount of PBS containing 10 mM EDTA. To the dilution, 10 µl of affinity resin (IgG Select Sepharose 6 Fast flow; GE Healthcare 17-0969-01; 50% slurry) was added. Incubation of the resin with the diluted plasma samples was performed for 1 hr at room temperature by applying mild agitation to avoid resin settling. The resin was then filtered off and washed two times with 200 µl of PBS. To deglycosylate the antibody, 10 µl of PNGase F (1 mg/mL, 1/2× TBS pH 7.4, 2.5 mM EDTA, 50% Glycerol) diluted with 10 µl of PBS was added to the resin and the mixtures were incubated for 2-3 hrs at 37° C. After PNGase F was removed by washing the affinity resin twice with 200 µl PBS, the sample was eluted twice from the affinity resin by adding 20 µl of 1% formic acid and filtering off the resin. The combined eluates were diluted with 20 µl of 6 M guanidine hydrochloride and 5 µl of reduction buffer (0.66 M TCEP, 3.3 M ammonium acetate, pH 5). To effectively reduce the antibody, samples were incubated for at least 30 min at room temperature before analysis. LCMS was performed with an Agilent Technologies 6550-iFunnel QTOF MS/Agilent 1260 HPLC system. A standard reversed-phase chromatography was used for sample desalting with a PLRS column (8 µm, 2.1×50 mm, 1000 Å, Agilent) at a flow rate of 0.5 ml/min at 80° C. Elution was carried out using a linear gradient of 20%- to 60%-acetonitrile containing 0.1% formic acid in 6 min. Agilent Qualitative Analysis was used for processing of the spectral record and spectral deconvolution. For analysis the spectral record was summed over the time interval covering elution of all relevant species. Summed spectra were deconvoluted in charge state and images of the deconvoluted spectra were recorded. The values of peak intensity were extracted for assignable species. Assignments of DAR state and fragment species were made based on values of calculated mass from the sequence of the analyzed antibodies and the expected mass shifts of the conjugates with drug molecules. The average DAR was calculated using the relative peak heights of all DAR states across a distribution. Average antibody DAR was calculated as the sum of DARs from 2 average light chains and 2 average heavy chains.

The average DAR of purified ADCs after three weeks in mouse circulation, as measured by MS, was compared to the DAR in the original ADC preparations. "Payload retention" was calculated from the ratio of the two DARs (DAR of ADC isolated from mouse plasma divided by the DAR of original ADC preparation), and represent the percentage of payloads retained on the ADC after three weeks in mouse circulation. Payload retention of various ADCs as measured by MS are largely in agreement with results obtained by the aforementioned ELISA assay using anti-MMAF antibody (FIGS. 3 and 4).

As shown in Table 14, payload retention ranged widely from 5% to 96% depending on the compound, conjugation sites and conjugation method. For ADCs prepared by the PPTase enzymatic method, payload retention (by MS) for compounds 20 and 22 are greater than 50%, while for compound 75 the payload retention is only 5% (Table 14). In the latter case, mass spectrometric assessment of the ADC purified from terminal bleed serum revealed nearly quantitative cleavage of the carbamate moiety of the drug-linker, whereas the click chemistry linkage between antibody and cytotoxic payload remained stable in circulation.

For ADCs prepared with Cys reactive cytotoxic peptides featuring a maleimide group, payload retention ranged from 18% to 96% depending on the compound structure and conjugation sites (Table 14). The MS results for ADCs isolated from plasma samples confirm that deconjugation of payloads from ADCs occurred between the maleimide payloads and the thiol group of the conjugated Cys residues. No breaks in the linker structures were observed. Therefore payload retention for the maleimide linked payloads may be inversely related to deconjugation via the reverse Michael addition, as the observed mass of recovered unconjugated antibody is that of the unmodified antibody.

It is known that the reaction to form a thioether between a maleimide and a free thiol group is reversible (Bioconjugate Chem. 2011, 22, 1946-1953). The reverse reaction is believed to be responsible for the deconjugation of maleimide drug payloads from ADCs in vivo and in vitro. Subsequently the maleimide of the deconjugated payloads can react with free thiols in the form of amino acid, peptides or proteins. (Bioconjugate Chem. 2008, 19, 759-765; Nat. Biotechnol. 2012, 30, 184-189).

For certain cytotoxic peptides of the invention, payload deconjugation from ADCs in mouse blood circulation was found to be negligible (Table 14). After three weeks in mice circulation, 90% of the payloads were found to be retained for ADCs prepared with compounds 47, 14, 77, 80, 79, and 78 conjugating to engineered Cys of antibodies. MS analysis of these ADCs isolated from plasma samples revealed that the mass of the ADCs increased by 18 dalton for each conjugated drug payload suggesting that a hydrolysis reaction had taken place. The succinimide ring resulting from the reaction of a maleimide group with a cysteine is known to undergo spontaneous hydrolysis (Gregory, J. Am. Chem. Soc. 1955, 77, 3922; Knight, P. *Biochem. J.* 1979, 179, 191-197; Khan M. N. J Pharm Sci. 1984, 73:1767-1771). In fact, the group can purposely be hydrolyzed by exposing a conjugate to basic pH (for example, Biochem. J. 1979 179, 191-197; *Biochemistry* 1976, 15, 2863-8; Chem Commun. 2011; 47: 5452-5454). The hydrolytic ring opening of the succinimide group will produce a stable thioether linkage which will not be subjected to the aforementioned maleimide reverse reaction (Bioconjugate Chem. 2011, 22, 1946-1953; Nat. Biotechnol. 2012, 30, 184-189; Nat. Biotechnol. 2014, 32, 1059). Certain compounds of the invention, exemplified by compounds 47, 14, 77, 80, 79, and 78, have greater succinimide ring hydrolysis when conjugated to Cys residues in antibodies and thereby produce more stable antibody drug conjugates.

TABLE 14

Payload retention of selected ADCs after 3 weeks in naïve mice as determined by IP-MS

| ADC | Payload retention rate (%) |
|---|---|
| anti-Her2-LC-S159C-MMAF | 76% |
| anti-Her2-LC-S159C-10 | 69% |
| anti-Her2-LC-S159C-47 | 93% |
| anti-Her2-LC-S159C-14 | 88% |
| anti-Her2-LC-S159C-77 | 88% |
| anti-Her2-LC-S159C-80 | 96% |
| anti-Her2-LC-S159C-79 | 88% |
| anti-Her2-LC-S159C-78 | 92% |
| anti-Her2-HC-E152C-S375C-10 | 50% |
| antibody 20507-HC-E152C-S375C-10 | 56% |
| antibody 20507-LC-K107C-47 | 85% |
| antibody 20507-HC-E152C-10 | 68% |
| anti-Her2-MMAF | 30% |
| anti-Her2-10 | 18% |
| antibody 20507-10 | 20% |
| antibody 20507-HC-ins388-A1-20 | 69% |
| anti-Her2-HC-ins388-A1-49-22 | 75% |
| antibody 20507-HC-ins388-A1-49-22 | 54% |
| anti-Her2-HC-ins388-ybbR-(i-11)-75 | 5% |

EXAMPLE 108

In Vitro Stability of ADCs

Figure 5A:
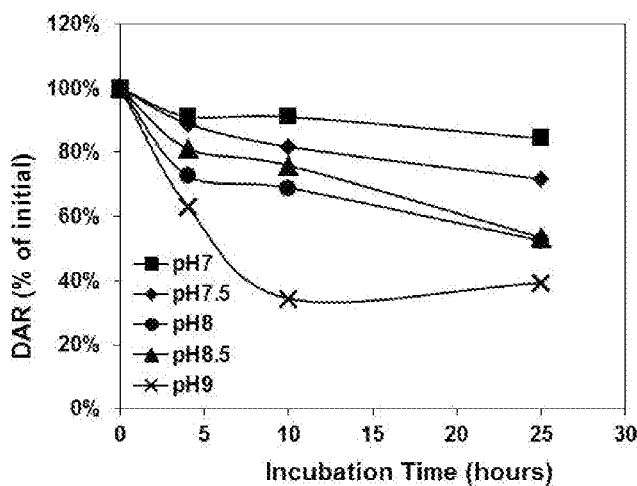
FIG. 5. In vitro stability studies of ADCs. Time course of payload retention of anti-Her2-LC-S159C-10 incubated in buffers with different pH at 37° C. (A), Time course of succinimide ring hydrolysis of anti-Her2-LC-S159C-10 incubated in buffers with different pH at 37° C. (B), Time course of payload retention of anti-Her2-LC-S159C-47 incubated in buffers with different pH at 37° C. (C), Time course of succinimide ring hydrolysis of anti-Her2-LC-S159C-47 incubated in buffers with different pH at 37° C. (D), Payload retention rate of anti-Her2-LC-S159C-10, anti-Her2-LC-S159C-77, anti- Her2-LC-S159C-80, anti- Her2-LC-S159C-79, anti-Her2-LC-S159C-78 and anti-Her2-LC-S159C-14 incubated in pH 8.5 buffers at 37° C. for 24 hours (E), Extent of succinimide ring hydrolysis of anti-Her2-LC-S159C-10, anti-Her2-LC-S159C-77, anti-Her2-LC-S159C-80, anti-Her2-LC-S159C-79, anti-Her2-LC-S159C-78 and anti-Her2-LC-S159C-14 incubated in pH 8.5 buffers at 37° C. for 24 hours (F).

The effects of succinimide ring hydrolysis on the stability of ADCs prepared with cytotoxic peptides of the invention were further studied in vitro. Mass changes resulting from payload deconjugation and the hydrolysis of the succinimide ring of maleimide payloads conjugated to antibodies were monitored by LC-MS. The hydrolysis of the succinimide ring has been reported to be stimulated by certain conditions such as high pH, high temperature, or high salts (J. Am. Chem. Soc. 1955, 77, 3922; Biochemistry, 1976, 1 5, 2836; *Biochem. J.* 1979, 179, 191-197; J Pharm Sci. 1984, 73:1767-1771, Bioorg. Med. Chem. Lett. 17 (2007) 6286-6289). To probe the in vitro stability of ADCs as a function of pH, Anti-Her2-LC-S159C-10 and anti-Her2-LC-S159C-47 were incubated at 37° C. in buffers ranging from pH 7.0 to pH 9.0 and the ADCs were analyzed at various time points by MS to determine the extent of the payload deconjugation and succinimide hydrolysis. The relative populations of deconjugated ADCs, ADCs with attached payload with hydrolyzed succinimide ring and ADCs with attached payload with intact succinimide ring, were calculated from the relative MS intensities of the corresponding ADC species. As shown in FIG. 5A, increasing the pH of the incubation buffer enhances deconjugation of anti-Her2-LC-S159C-10. In pH 7.0 buffer, anti-Her2-LC-S159C-10 was stable with approximately 10% payload loss after 10 hours. However, incubation in pH 8.0 and pH 9.0 buffer for 10 hours, increased the extent of payload deconjugation to approximately 30% and 60%, respectively (FIG. 5A). In contrast, incubation of anti-Her2-LC-S159C-47 in buffers with pH 7.0 to pH 9.0 at 37° C. for 25 hours did not result in more than 15% deconjugation (FIG. 5C).

Figure 5B:
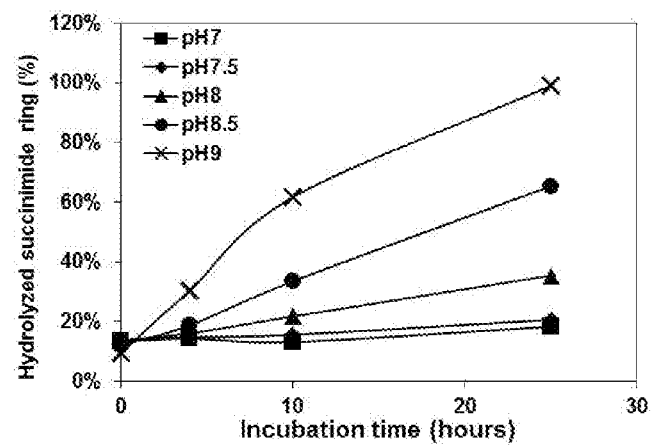
Figure 5C:
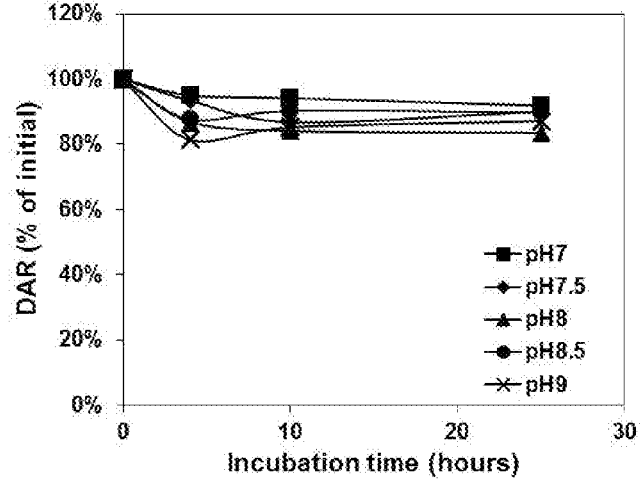
Figure 5D:
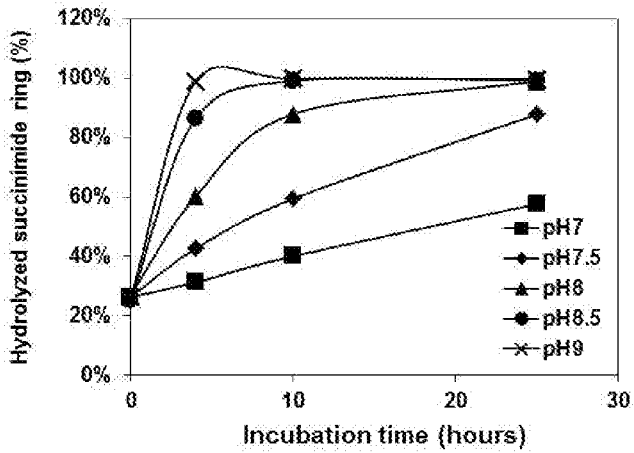
Figure 5E:
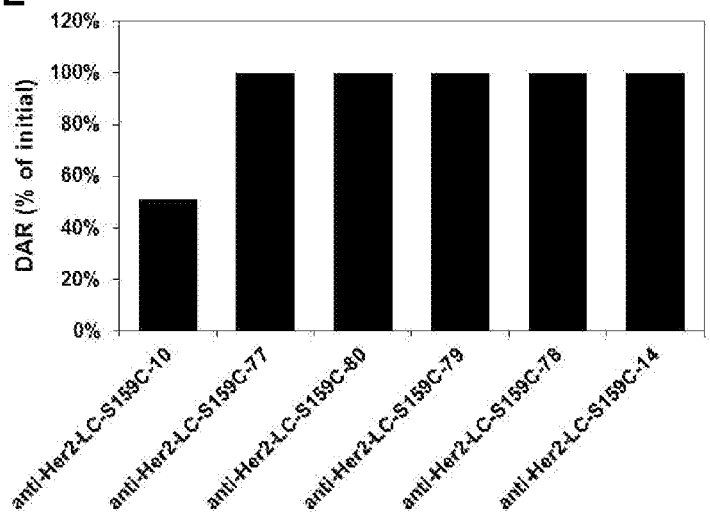
Figure 5F:
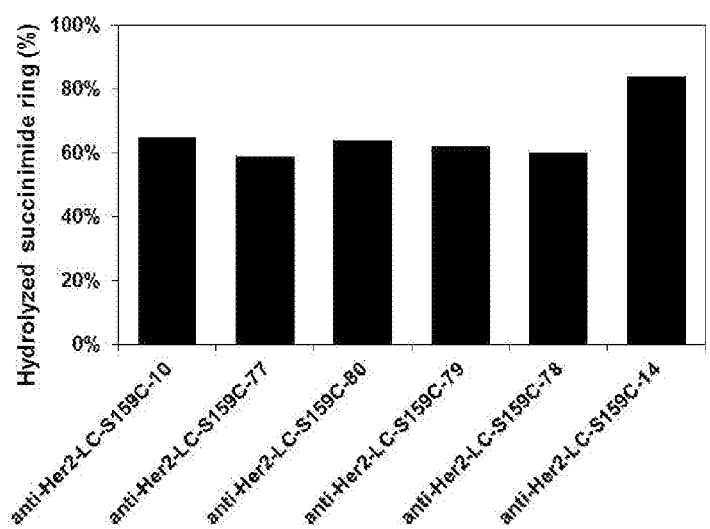

In parallel, the extent of the succinimide ring hydrolysis of the two ADCs was also determined at the various time points (FIG. 5B and FIG. 5D). For both ADCs, increasing the pH of the incubation buffer stimulated hydrolysis of the succinimide ring. For anti-Her2-LC-S159C-47 succinimide ring hydrolysis occurred significantly more rapidly than for anti-Her2-LC-S159C-10. Incubation of anti-Her2-LC-S159C-10 in pH 7.5 buffer for 25 hours led to deconjugation of 30% of the payload and 20% of the payload that was still attached to the antibody was hydrolyzed (FIG. 5A and FIG. 5B). Under the same incubation conditions, anti-Her2-LC-S159C-47 only lost approximately 10% of the payload while approximately 90% of the attached payload was hydrolyzed (FIG. 5C and FIG. 5D). As shown in FIGS. 5E, and F, in vitro payload conjugation and succinimide ring hydrolysis were analyzed for anti-Her2-LC-S159C-10, anti-Her2-LC-S159C-77, anti-Her2-LC-S159C-80, anti-Her2-LC-S159C-79, anti-Her2-LC-S159C-78 and anti-Her2-LC-S159C-14 ADCs incubated in pH 8.5 buffers for 24 hours at 37° C.: While deconjugation of the payloads was not detectable for anti-Her2-LC-S159C-77, anti-Her2-LC-S159C-80, anti-Her2-LC-S159C-79, anti-Her2-LC-S159C-78 and anti-Her2-LC-S159C-14 ADCs (FIG. 5E), a high degree of succinimide ring hydrolysis was observed for all ADCs (FIG. 5F). Thus, certain compounds of the invention, exemplified by compounds 47, 14, 77, 80, 79, and 78, exhibit improved ADC stability due to lower susceptibility to deconjugation through the reverse maleimide reaction and further stabilization through succinimide ring hydrolysis.

EXAMPLE 109

In Vivo Efficacy Studies with Antibody 20507 ADCs

Figure 6A:
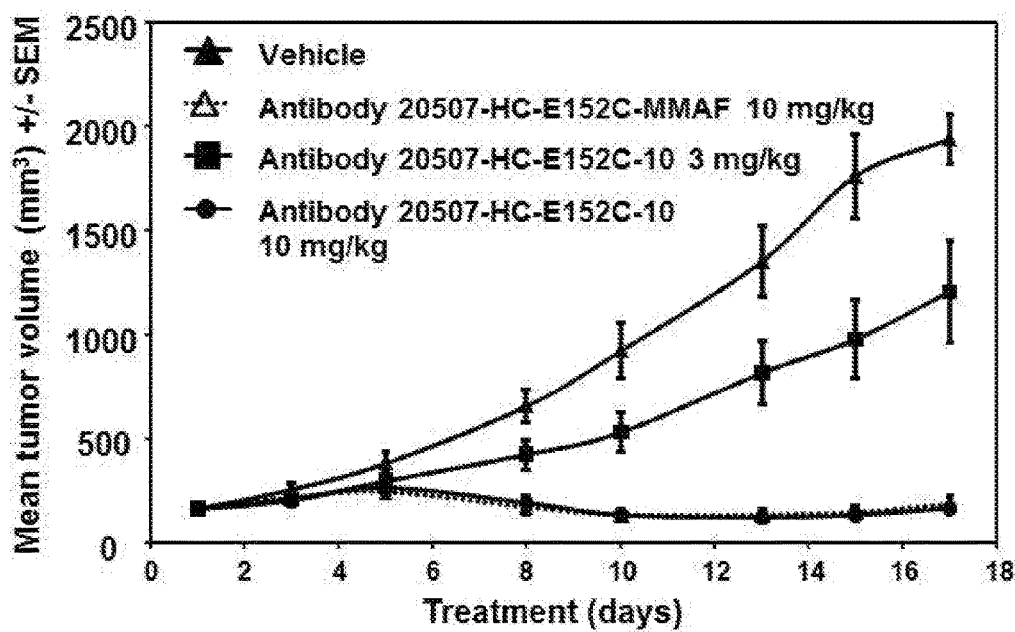
FIG. 6. In vivo efficacy study of antibody 20507 ADCs in H526 tumor model. (A) Antibody 20507-HC-E152C-10 and antibody 20507-HC-E152C-MMAF ADCs. (B) Antibody 20507-HC-E152C-10, antibody 20507-HC-ins388-A1-20 and antibody 20507-LC-S159C-MMAF ADCs. (C) Antibody 20507-HC-E152C-S375C-10 and antibody 20507-10. (D) Antibody 20507-HC-E152C-10, antibody 20507-HC-ins388-A1-49-22, and anti-Her2-HC-ins388-A1-49-22 ADCs.
Figure 6B:
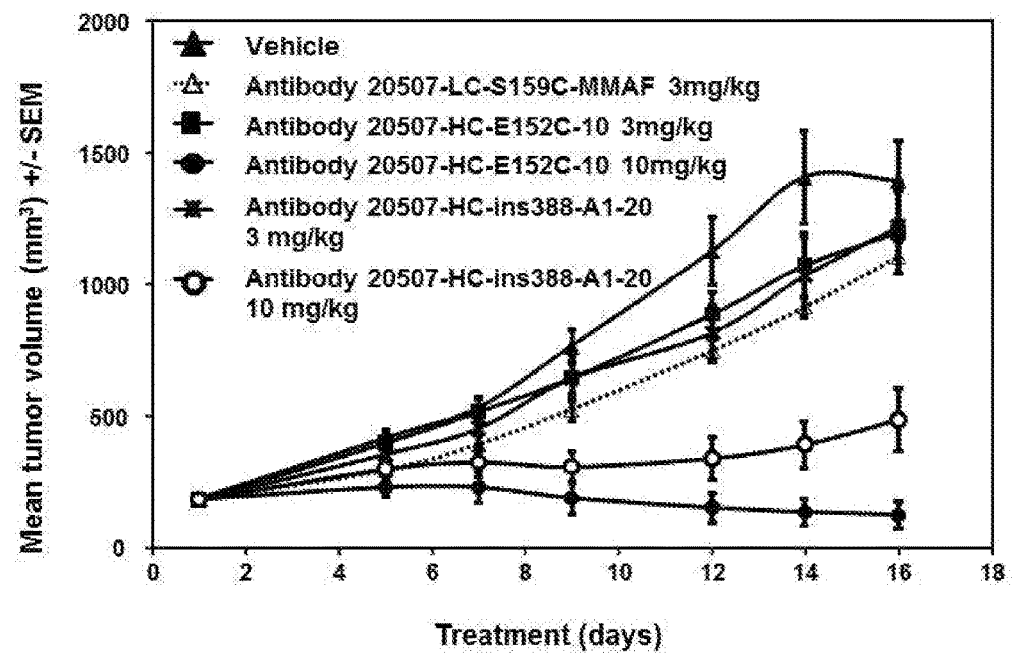

In vivo xenograft tumor models simulate biological activity observed in humans and consist of grafting relevant and well characterized human primary tumors or tumor cell lines into immune-deficient nude mice. Studies on treatment of tumor xenograft mice with anti-cancer reagents have provided valuable information regarding in vivo efficacy of the tested reagents (Sausville and Burger, (2006) Cancer Res. 66:3351-3354). Because H526 cells express the antigen of antibody 20507 on their surface and are selectively killed by antibody 20507 ADCs (FIG. 2, Table 12), the cell line was used to generate a xenograph model to evaluate the in vivo activity of antibody 20507 ADCs. All animal studies were conducted in accordance with the Guide for the Care and Use of Laboratory Animals (NIH publication; National Academy Press, $8^{th}$ edition, 2001). H526 cells were implanted in nu/nu mice subcutaneously (Morton and Houghton, Nat Protoc. 2007; 2:247-250). After the tumor size reached ~200 mm³, three antibody 20507 ADCs were administered into the mice by i.v. injection in a single dose at 3 mg/kg or 10 mg/kg. The tumor growth was measured periodically after ADC injection. Each treatment group included 7 mice. An example of such an in vivo efficacy study is shown in FIG. 6A. Treatment of mice with 3 mg/kg of antibody 20507-HC-E152C-10 ADC caused tumor growth inhibition while treatment with 10 mg/kg of antibody20507-HC-E152C-10 ADC led to tumor regression (FIG. 6A). The efficacy of antibody 20507-HC-E152C-10 ADC is equivalent to that of a positive control ADC, antibody 20507-HC-E152C-MMAF conjugated with the reference compound MC-MMAF. No weight loss was observed associated with the ADC treatment suggesting low systemic toxicity. The results confirmed that with a single dose treatment at 10 mg/kg, antibody 20507-HC-E152C-10 ADC effectively caused regression of H526 tumors without significant weight loss. In a second study, antibody 20507-HC-E152C-10 and antibody 20507-HC-ins388-A1-20 ADCs were administered in H526 tumor-bearing mice at doses of 3 mg/kg and 10 mg/kg (FIG. 6B). Both ADCs exhibited similar tumor inhibition activity at 3 mg/kg and tumor regression activity at 10 mg/kg. Antibody 20507-HC-E152C-10 ADC was slightly more efficacious than the 20507-HC-ins388-A1-20 ADC.

Figure 6C:
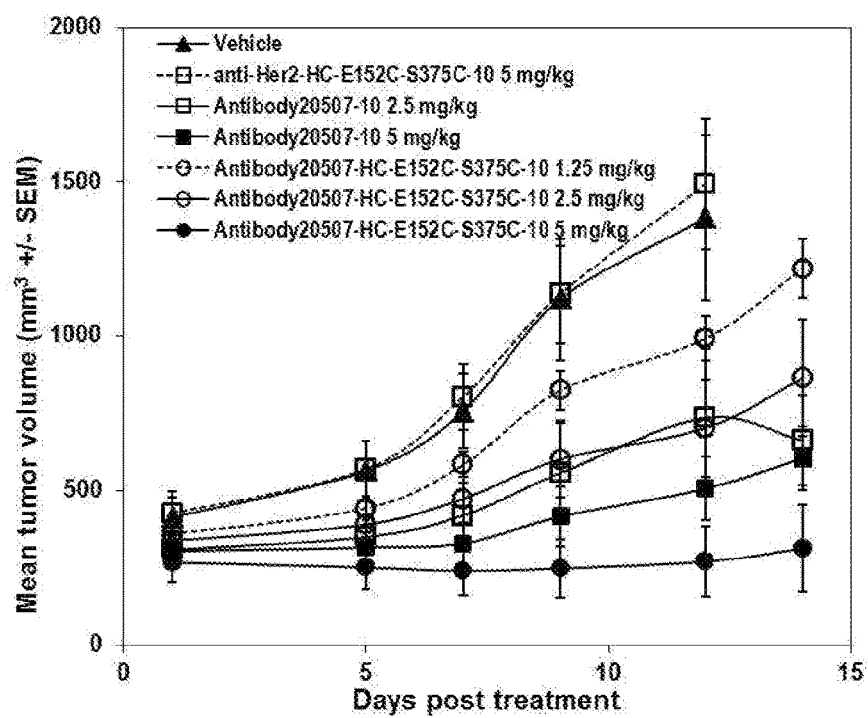

In another example, we compared the in vivo efficacy of two antibody 20507 ADCs antibody 20507-HC-E152C-S375C-10 and antibody 20507-10, in the H526 xenograft model (FIG. 6C). The two ADCs were prepared with the same payload, compound 10 conjugating to different Cys sites using two different methods. Antibody 20507-HC-E152C-S375C-10 was prepared with a Cys mutant antibody, as described in Example 101 with compound 10 conjugated to engineered Cys residues, HC-E152C and HC-S375C. Antibody 20507-10 was prepared by using the partial reduction method of wild type antibody 20507 as described in Example 102 with compound 10 conjugated to native Cys residues. Antibody 20507-10 has a slightly higher DAR (DAR 4.6) than antibody 20507-HC-E152C-S375C-10 (DAR 3.9) (Table 6). Pharmacokinetic studies showed that the two ADCs retained the same payload to a very different extent during three week of circulation in mouse (FIG. 4D, FIG. 4E, Table 14): Antibody 20507-HC-E152C-S375C-10 displaying a much better payload retention (56%) than antibody 20507-10 (20%).

In the H526 xenograft model, the same dosage of antibody 20507-HC-E152C-S375C-10 is more efficacious in inhibiting tumors than antibody 20507-10 (FIG. 6C). Anti-Her2-HC-E152C-S375C-10, whose antigen is not expressed in H526 cells, did not show any tumor inhibiting activity.

Figure 6D:
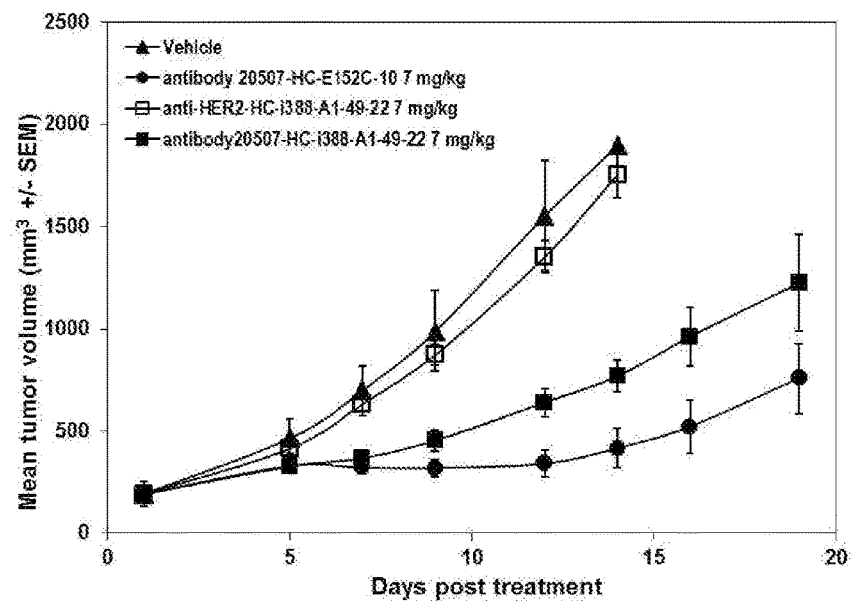

In a third study, antibody 20507-HC-E152C-10 and antibody 20507-HC-ins388-A1-49-22 ADCs were injected i.v. into H526 tumor-bearing mice at a single dose of 7 mg/kg (FIG. 6D). While antibody 20507-HC-ins388-A1-49-22 ADC displayed tumor inhibition, antibody 20507-HC-E152C-10 ADC exhibited tumor regression at the same dose level, indicative of higher efficacy of the latter ADC. No significant tumor inhibitory activity was observed for the isotype control ADC, anti-Her2-HC-ins388-A1-49-22, suggesting antigen specific tumor killing by the antibody 20507 ADCs. Together, all three studies confirm that cytotoxic peptides of the invention attached by a variety of methods to an antibody can cause regression of an antigen-expressing cancer in a mouse xenograft model.

EXAMPLE 110

Production of Sfp 4'-phosphopantetheinyl Transferase (PPTase)

The *Bacillus subtilis* Sfp PPTase was cloned into the pET22b expression vector using the PIPE method (see Klock et al., Proteins 71:982-994 (2008)). To allow cleavage of the C-terminal His$_6$ tag, a TEV (tobacco etch virus) protease recognition site was inserted downstream of the Sfp coding sequence. All primers used for cloning and the Sfp protein sequence are listed in Table 15.

TABLE 15

Primers used for cloning and Sfp protein sequence

| Sequence name | Sequence | SEQ ID NO |
|---|---|---|
| B. subtilis Sfp pET22b | GAAGGAGATATACATATGAAAATTTA TGGGATTTACATGGATCGC | SEQ ID NO: 25 |
| | GTGGTGGTGGTGGTGGTGCAGCAAT TCTTCATAGGAGACCATCG | SEQ ID NO: 26 |
| pET22b | CACCACCACCACCACCACTGAG | SEQ ID NO: 27 |
| | CATATGTATATCTCCTTCTTAAAGTTA AACAAAATTATTTC | SEQ ID NO: 28 |
| TEV into B. subtilis Sfp pET22b | GAGAACCTGTACTTCCAAGGCCACC ACCACCACCACCACTGAG | SEQ ID NO: 29 |
| | GCCTTGGAAGTACAGGTTCTCCAGC AATTCTTCATAGGAGACCATCG | SEQ ID NO: 30 |
| Bacillus subtilis Sfp PPTase with C-terminal TEV cleavage site and His6 tag | MKIYGIYMDRPLSQEENERFMSFISPE KREKCRRFYHKEDAHRTLLGDVLVRS VISRQYQLDKSDIRFSTQEYGKPCIPD LPDAHFNISHSGRWVICAFDSQPIGIDI EKTKPISLEIAKRFFSKTEYSDLLAKDK DEQTDYFYHLWSMKESFIKQEGKGLS LPLDSFSVRLHQDGQVSIELPDSHSP CYIKTYEVDPGYKMAVCAAHPDFPEDI TMVSYEELL<u>ENLYFQG</u>HHHHHH | SEQ ID NO: 31 |

Protein expression and purification were performed according to Yin et al. (see Nat. Protoc. 1:280-285 (2006)) with some modifications. Briefly, 1 L of TB medium was inoculated from saturated overnight cultures of *Escherichia coli* BL21 (DE3) cells harboring the pET22b/sfp expression plasmid. The culture was shaken at 250 rpm at 37° C. and induced by addition of 1 mM IPTG after reaching an optical density (600 nm) of 0.7. The temperature was lowered to 30° C. and the culture was shaken at 250 rpm for approximately 16 hours before the bacterial cells were harvested by centrifugation (20 min at 3400 rpm). Prior to use, the cell pellets were stored at −20° C. To initiate protein purification, the frozen pellets were thawed for approximately 15 minutes on ice and resuspended in a buffer containing 20 mM Tris/HCl (pH 8), 0.5 M NaCl, 5 mM imidazole, and 2 U/mL DNase I (3 mL of buffer per g wet weight of cells). Cell lysis was induced by sonication for a total time of 2 min using 1 sec sonication pulses with intermittent 1 sec delays. In order to remove insoluble cell debris, the resulting lysate was centrifuged at 40000×g for 25 min at 4° C. The $His_6$-tagged Sfp enzyme was then captured by adding 4 mL of 50% Ni-NTA agarose slurry (Qiagen) to the cleared lysate. After shaking for 1 hour at 4° C., the resin-lysate mixture was poured into a disposable column. The settled resin was washed with 50 column volumes of 50 mM Tris/HCl (pH 8), 300 mM NaCl, and 20 mM imidazole. Elution was performed with 6 column volumes of 50 mM Tris/HCl (pH 8), 300 mM NaCl, and 250 mM imidazole. The Sfp enzyme was exchanged into TEV cleavage buffer containing 50 mM Tris/HCl (pH 8) and 50 mM NaCl. $His_6$ tag removal was carried out by digestion with 7% (w/w) TEV protease at 23° C. for 1 hour and then at 4° C. for approximately 16 hours. The TEV-digested Sfp enzyme was then reloaded onto fresh Ni-NTA columns pre-equilibrated with PBS. The cleaved enzyme was collected from the column flowthrough and from a washing step involving 5 column volumes of 50 mM Tris/HCl (pH 8), 300 mM NaCl, and 20 mM imidazole. Purified Sfp enzyme was then dialyzed against 10 mM Tris/HCl (pH 7.4), 1 mM EDTA, and 10% glycerol using Slide-A-Lyzer Dialysis Cassettes (Pierce) with 3.5 kDa cut-off. After passing the dialysate through a 0.22 μm filter, the yield of Sfp enzyme was quantified by ultraviolet spectroscopy at 280 nm (ND-1000 UV-Vis Spectrophotometer, NanoDrop Technologies, Wilmington, Del.) using a molar extinction coefficient of 28620 $M^{-1}cm^{-1}$. 19 mg of TEV-cleaved Sfp enzyme was obtained per liter culture. Next, Sfp PPTase was concentrated to 151 μM using Amicon Ultra Centrifugal Filter Units (Millipore) with 10 kDa cut-off. The purity of the enzyme was assessed by SDS-PAGE, and $His_6$ tag removal was verified by LC-MS. According to analytical size-exclusion chromatography, TEV-cleaved Sfp PPTase is 90% monomeric. The concentrated enzyme was aliquoted, flash-frozen in liquid nitrogen, and stored at −80° C.

Other aspects and examples of the invention are provided in the following listing of enumerated embodiments. It will be recognized that features specified in each embodiment may be combined with other specified features to provide further embodiments of the present invention.

Embodiment 1. The compound or stereoisomer thereof having the structure of Formula (I)

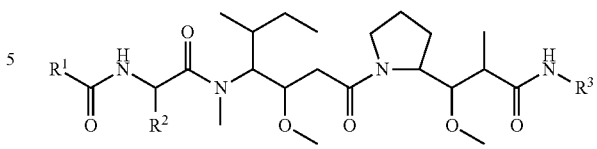

(Formula (I))

wherein:

$R^1$ is a C-linked 6 membered heterocycloalkyl containing 1-2 N heteroatoms and a $C_1$-$C_2$alkylene bridge, or $R^1$ is a C-linked 5-8 membered fused bicyclic heterocycloalkyl containing 1-2 N heteroatoms, wherein each is unsubstituted, or each is substituted with 1 to 3 substituents independently selected from $R^5$ and $R^6$;

$R^2$ is —$C_1$-$C_6$alkyl;

$R^3$ is

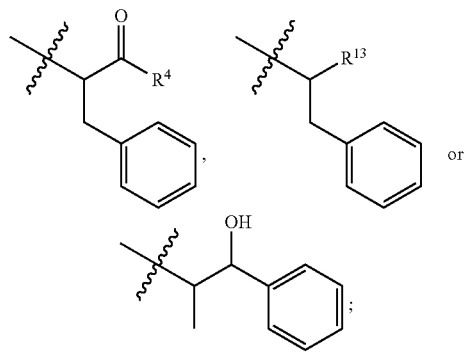

$R^4$ is —OH, $C_1$-$C_6$alkoxy, —$N(R^{14})_2$, —$R^{16}$, —$NR^{12}$ $(CH_2)_m$ $N(R^{14})_2$, —$NR^{12}(CH_2)_mR^{16}$, —$NHS(O)_2R_{11}$,

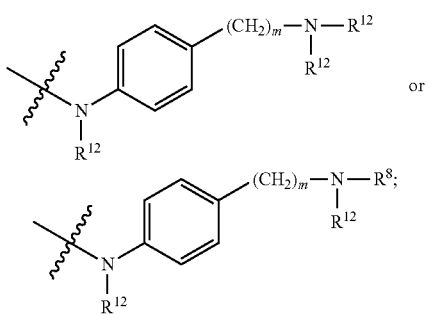

$R^5$ is $C_1$-$C_6$alkyl, $C_1$-$C_6$alkyl which is optionally substituted with 1 to 5 hydroxyl, —$C(=O)R^{11}$, —$(CH_2)_mOH$, —$C(=O)(CH_2)_mOH$, —$C(=O)((CH_2)_mO)_nR^{12}$, or —$((CH_2)_mO)_nR^{12}$;

$R^6$ is halo, oxo, OH, $C_1$-$C_6$alkyl, —$N(R^{14})_2$, —$R^{16}$ and —$NR^{12}C(=O)R^{11}$;

$R^8$ is H;

each $R^{11}$ is independently selected from $C_1$-$C_6$alkyl and $C_1$-$C_6$alkyl which is optionally substituted with 1 to 5 hydroxyl;

each $R^{12}$ is independently selected from H and $C_1$-$C_6$alkyl;

$R^{13}$ is tetrazolyl,

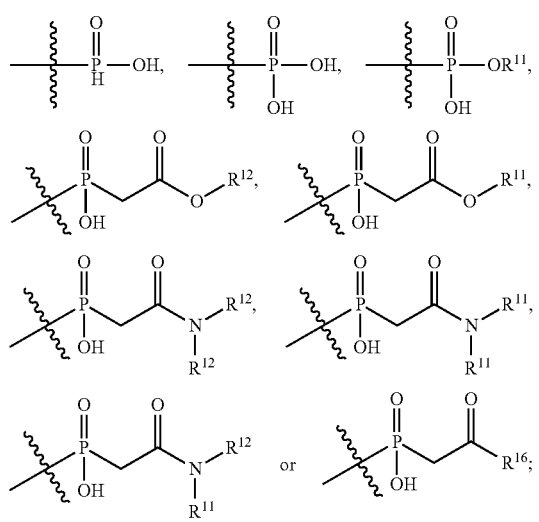

each $R^{14}$ is independently selected from H and $C_1$-$C_6$alkyl;

$R^{15}$ is 2-pyridyl or 4-pyridyl;

$R^{16}$ is an unsubstituted N-linked 4-8 membered heterocycloalkyl containing 1-2 heteroatoms independently selected from N and O;

each m is independently selected from 1, 2, 3, 4, 5, 6, 7, 8, 9 and 10, and each n is independently selected from 1, 2, 3, 4, 5, 6, 7, 8, 9, 10, 11, 12, 13, 14, 15, 16, 17 and 18.

Embodiment 2. The compound according to embodiment 1, wherein:

$R^1$ is a C-linked 6 membered heterocycloalkyl containing 1-2 N heteroatoms and a $C_1$-$C_2$alkylene bridge, wherein the C-linked 6 membered heterocycloalkyl is unsubstituted or is substituted with 1 to 3 substituents independently selected from $R^5$ and $R^6$.

Embodiment 3. The compound or stereoisomer thereof having the structure of Formula (I)

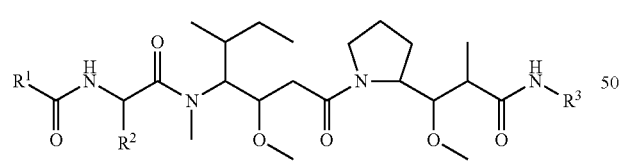

(Formula (I))

wherein:

$R^1$ is a C-linked 6 membered heterocycloalkyl containing 1-2 N heteroatoms and a $C_1$-$C_2$alkylene bridge or $R^1$ is a C-linked 5-8 membered fused bicyclic heterocycloalkyl containing 1-2 N heteroatoms, wherein each is unsubstituted, or each is substituted with an $R^7$ and 0 to 3 substituents independently selected from $R^5$ and $R^6$, or each is substituted with 1 to 3 substituents independently selected from $R^5$ and $R^6$;

$R^2$ is —$C_1$-$C_6$alkyl;

$R^3$ is

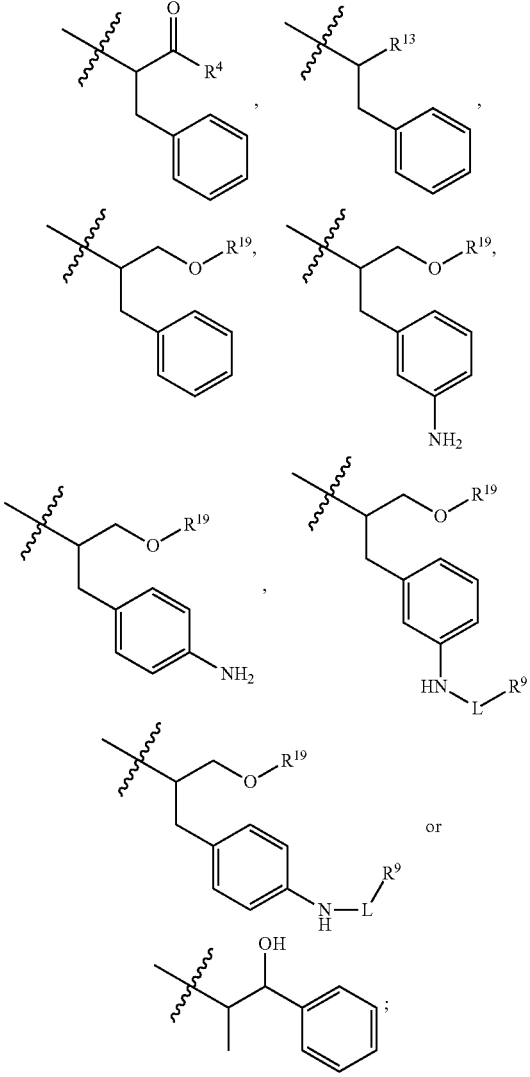

$R^4$ is —OH, $C_1$-$C_6$alkoxy, —N($R^{14}$)$_2$, —$R^{16}$, —$NR^{12}$(CH$_2$)$_m$ N($R^{14}$)$_2$, —$NR^{12}$(CH$_2$)$_m$$R^{16}$, -L$R^9$, —NHS(O)$_2$$R_{11}$, —NHS(O)$_2$(CH$_2$)$_m$N$_3$, —NHS(=O)$_2$L$R^9$,

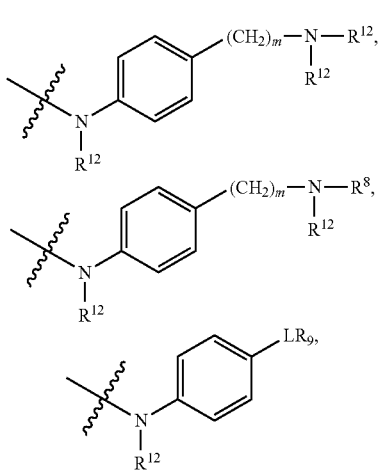

327

-continued

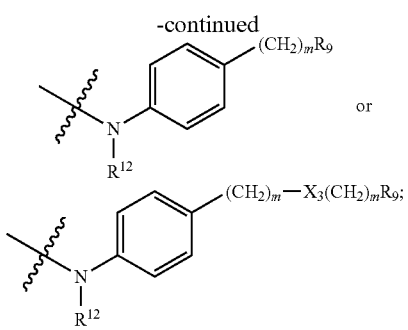

$R^5$ is $C_1$-$C_6$alkyl, —C(=O)$R^{11}$, —(CH$_2$)$_m$OH, —C(=O)(CH$_2$)$_m$OH, —C(=O)((CH$_2$)$_m$O)$_n$$R^{12}$, —((CH$_2$)$_m$O)$_n$$R^{12}$, or $C_1$-$C_6$alkyl which is optionally substituted with —CN, —C(=O)NH$_2$ or 1 to 5 hydroxyl;
$R^6$ is halo, oxo, OH, $C_1$-$C_6$alkyl, —N($R^{14}$)$_2$, —$R^{16}$ and —NR$^{12}$C(=O)$R^{11}$;
$R^7$ is L$R^9$;
$R^8$ is H or L$R^9$;
each L is independently selected from -$L_1L_2L_3L_4L_5L_6$-, -$L_6L_5L_4L_3L_2L_1$-, -$L_1L_2L_3L_4L_5$-, -$L_5L_4L_3L_2L_1$-, -$L_1L_2L_3L_4$-, -$L_4L_3L_2L_1$-, -$L_1L_2L_3$-, -$L_3L_2L_1$-, -$L_1L_2$-, -$L_2L_1$- and -$L_1$, wherein -$L_1$, $L_2$, $L_3$, $L_4$, $L_5$, and $L_6$ are as defined herein;
$R^9$ is

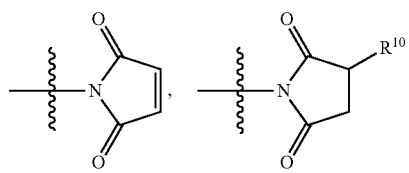

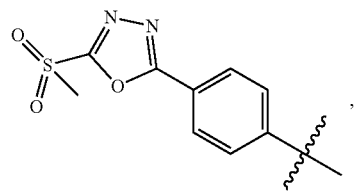

328

-continued

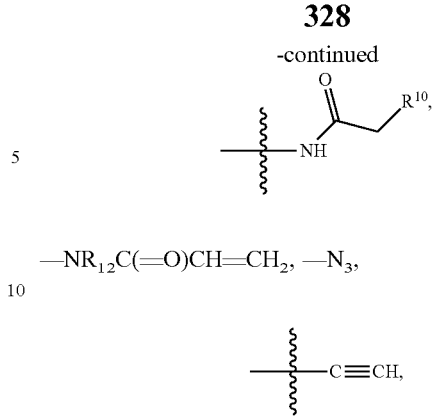

—NR$_{12}$C(=O)CH=CH$_2$, —N$_3$,

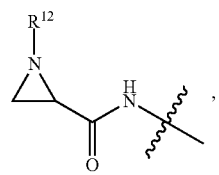

SH, —SSR$^{15}$, —S(=O)$_2$(CH=CH$_2$), —(CH$_2$)$_2$S(=O)$_2$(CH=CH$_2$), —NR$_{12}$S(=O)$_2$(CH=CH$_2$), —NR$_{12}$C(=O)CH$_2$R$^{10}$, —NR$_{12}$C(=O)CH$_2$Br, —NR$_{12}$C(=O)CH$_2$I, —NHC(=O)CH$_2$Br, —NHC(=O)CH$_2$I, —ONH$_2$, —C(O)NHNH$_2$,

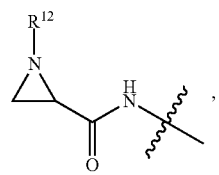

—CO$_2$H, —NH$_2$, —NCO, —NCS,

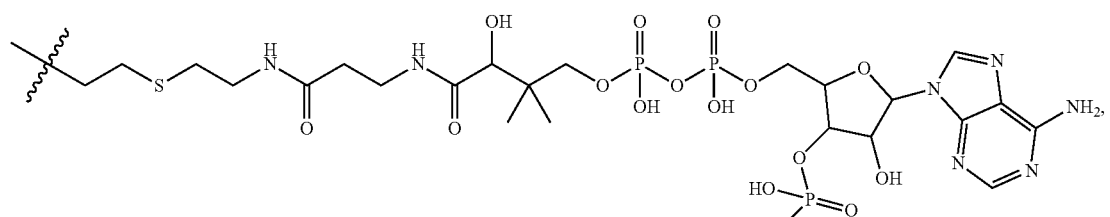

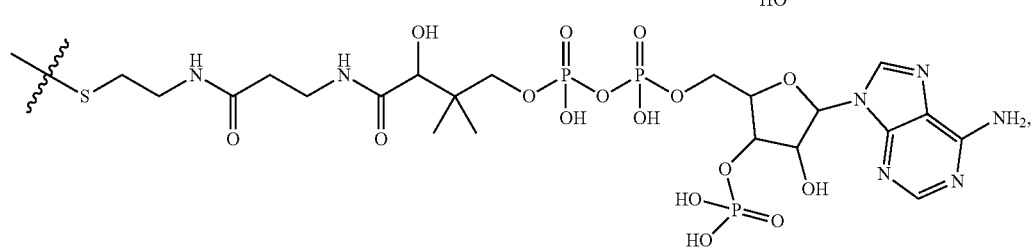

-continued
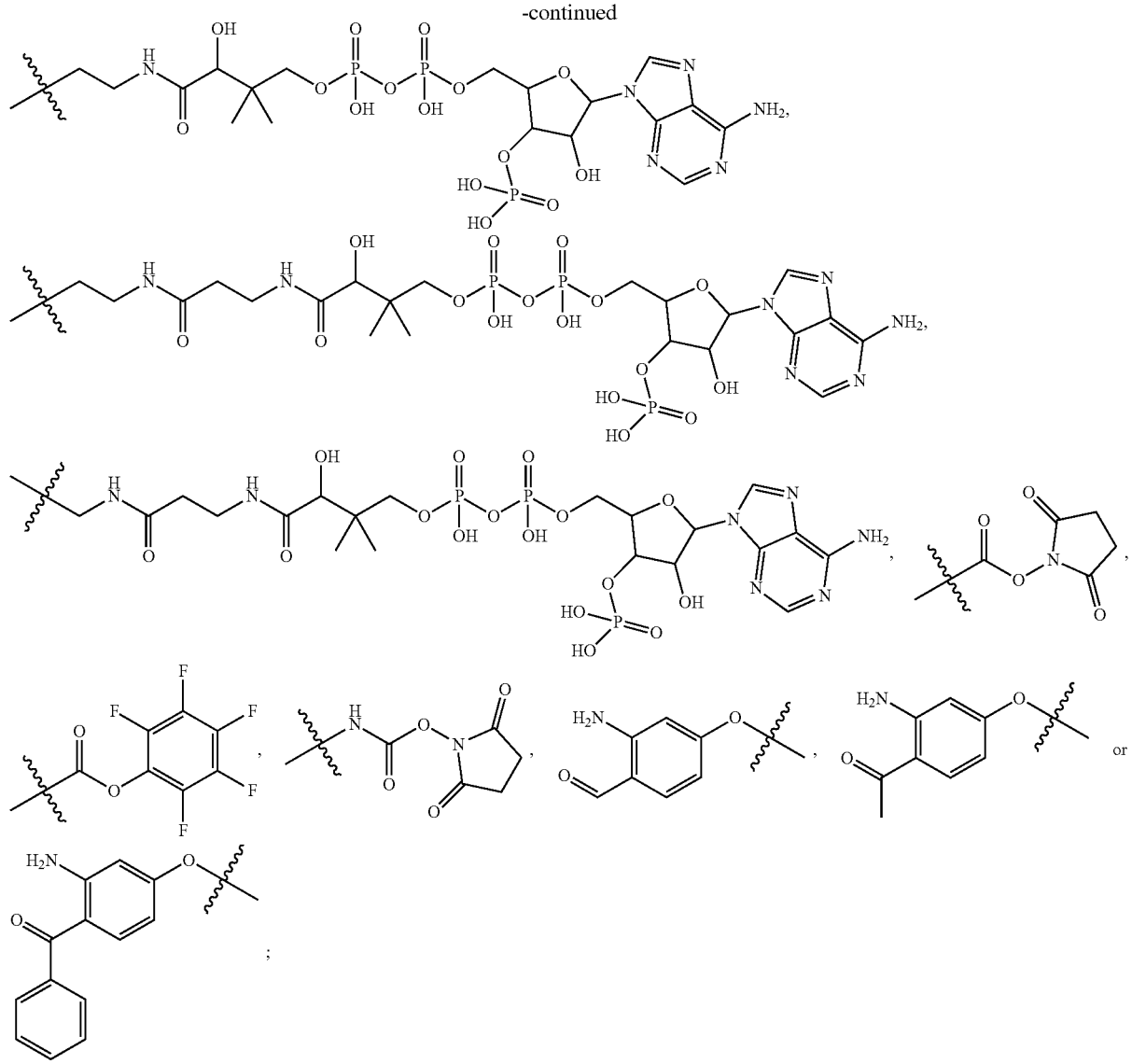
$R^{10}$ is
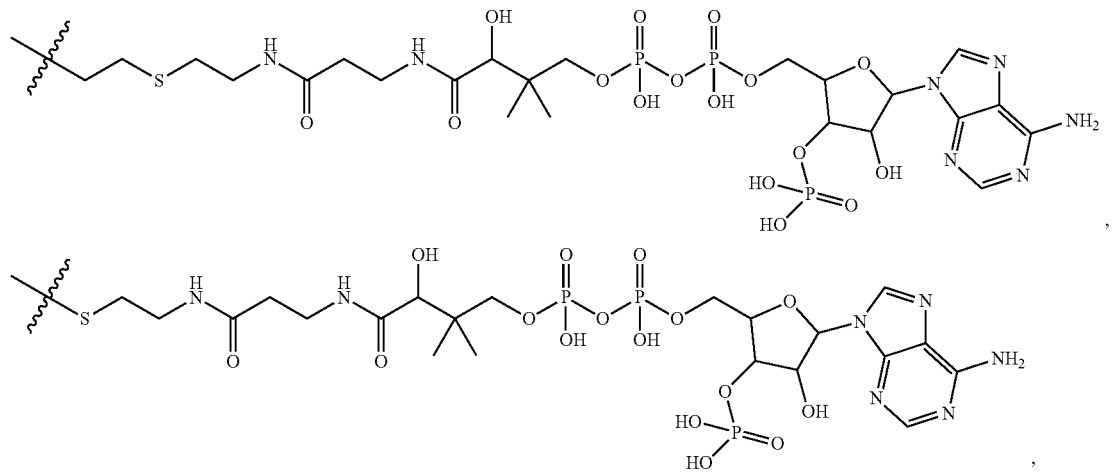

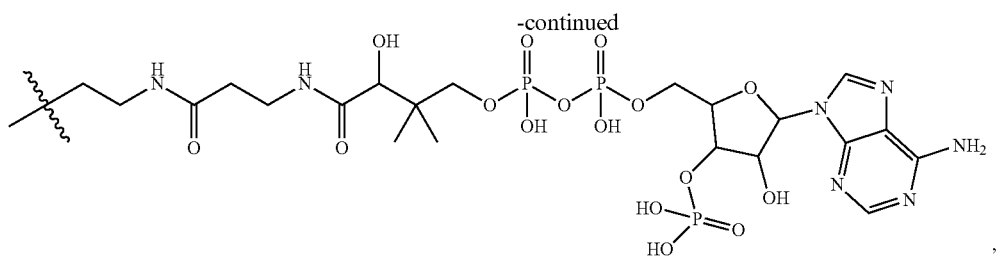

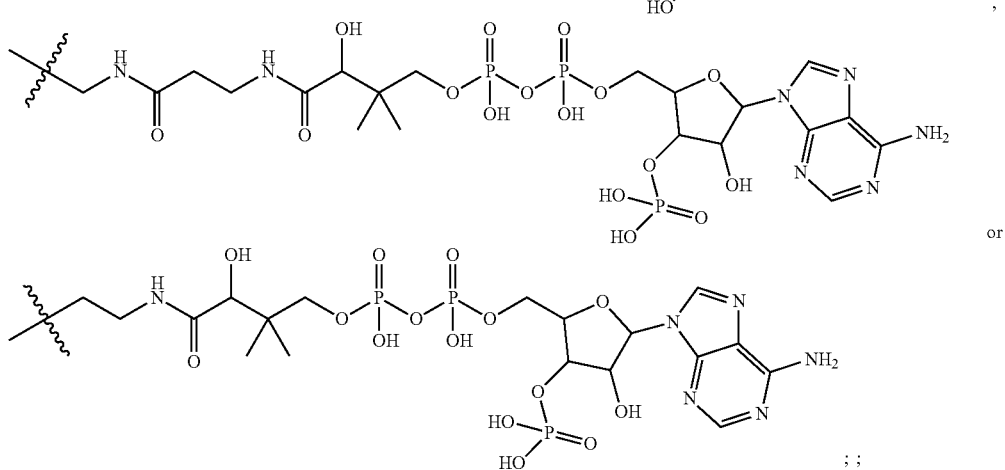

each R[11] is independently selected from $C_1$-$C_6$alkyl and $C_1$-$C_6$alkyl which is optionally substituted with 1 to 5 hydroxyl;

each R[12] is independently selected from H and $C_1$-$C_6$alkyl;

R[13] is tetrazolyl, imidazolyl substituted with phenyl, oxadiazolyl substituted with phenyl, pyrazolyl, pyrimidinyl,

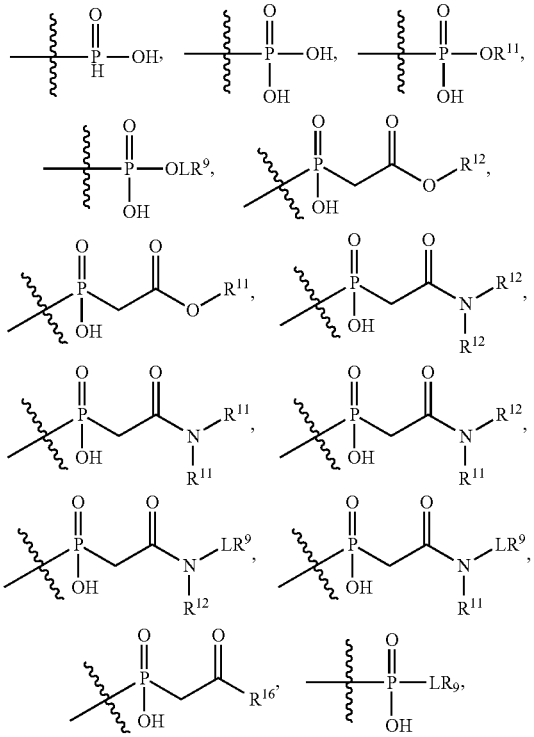

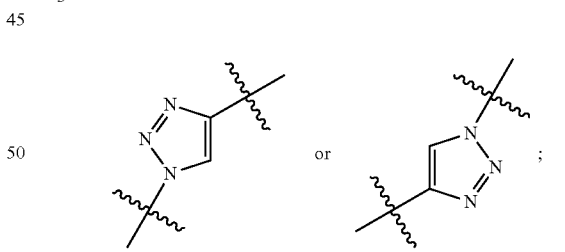

$CH_2S(=O)_2NH_2$, —$CH_2S(=O)_2NHLR^9$, -LR[9] or —$X_4LR^9$;

each R[14] is independently selected from H and $C_1$-$C_6$alkyl;

R[15] is 2-pyridyl or 4-pyridyl;

R[16] is an N-linked 4-8 membered heterocycloalkyl containing 1-2 heteroatoms independently selected from N and O, which is unsubstituted or substituted with -LR[9];

$X_3$ is

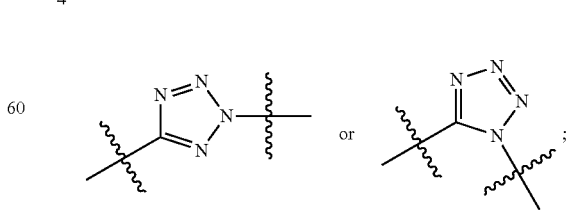

$X_4$ is each m is independently selected from 1, 2, 3, 4, 5, 6, 7, 8, 9 and 10;

each n is independently selected from 1, 2, 3, 4, 5, 6, 7, 8, 9, 10, 11, 12, 13, 14, 15, 16, 17 and 18, or a pharmaceutically acceptable salt thereof.

Embodiment 4. A compound or stereoisomer thereof having the structure of Formula (I) wherein:

(Formula (I))

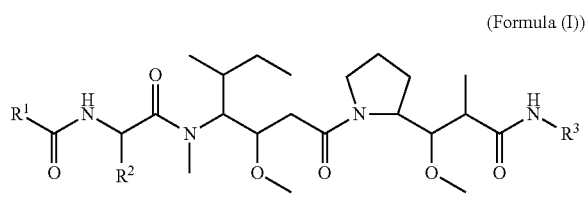

$R^1$ is a C-linked 6 membered heterocycloalkyl containing 1-2 N heteroatoms and a $C_1$-$C_2$alkylene bridge or $R^1$ is a C-linked 5-8 membered fused bicyclic heterocycloalkyl containing 1-2 N heteroatoms, wherein each is unsubstituted, or each is substituted with an $R^7$ and 0 to 3 substituents independently selected from $R^5$ and $R^6$, or each is substituted with 1 to 3 substituents independently selected from $R^5$ and $R^6$;

$R^2$ is —$C_1$-$C_6$alkyl;

$R^3$ is

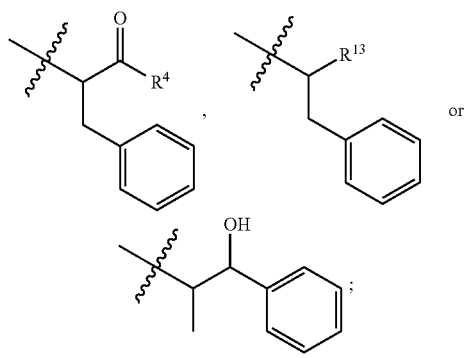

$R^4$ is —OH, $C_1$-$C_6$alkoxy, —$N(R^{14})_2$, —$R^{16}$, —$NR^{12}$ $(CH_2)_m N(R^{14})_2$, —$NR^{12}(CH_2)_m R^{16}$, -$LR^9$, —$NHS(O)_2$ $R_{11}$, —$NHS(O)_2(CH_2)_m N_3$, —$NHS(=O)_2 LR^9$,

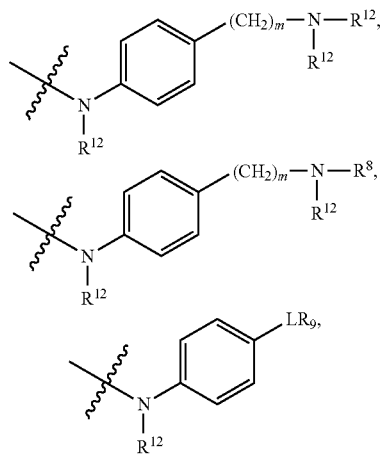

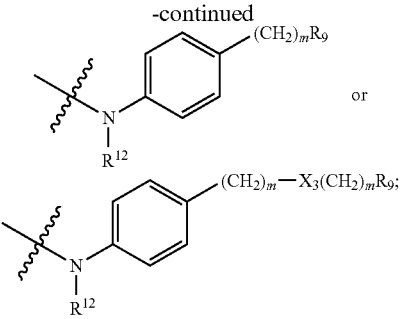

$R^5$ is $C_1$-$C_6$alkyl, $C_1$-$C_6$alkyl which is optionally substituted with 1 to 5 hydroxyl, —C(=O)$R^{11}$, —(CH$_2$)$_m$OH, —C(=O)(CH$_2$)$_m$OH, —C(=O)((CH$_2$)$_m$O)$_n$$R^{12}$, or —((CH$_2$)$_m$O)$_n$$R^{12}$;

$R^6$ is halo, oxo, OH, $C_1$-$C_6$alkyl, —$N(R^{14})_2$, —$R^{16}$ and —$NR^{12}C(=O)R^{11}$;

$R^7$ is $LR^9$;

$R^8$ is H or $LR^9$;

each L is independently selected from -$L_1L_2L_3L_4L_5L_6$-, -$L_6L_5L_4L_3L_2L_1$-, -$L_1L_2L_3L_4L_5$-, -$L_5L_4L_3L_2L_1$-,- $L_1L_2L_3L_4$-, -$L_4L_3L_2L_1$-,-$L_1L_2L_3$-, -$L_3L_2L_1$-,-$L_1L_2$-, -$L_2L_1$- and -$L_1$, wherein -$L_1$, $L_2$, $L_3$, $L_4$, $L_5$, and $L_6$ are as defined herein;

$R^9$ is

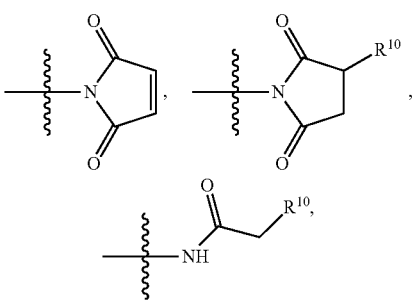

—$NR_{12}C(=O)CH=CH_2$, —$N_3$,

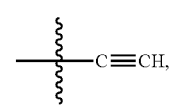

SH, —$SSR^{15}$, —$S(=O)_2(CH=CH_2)$, —$(CH_2)_2S(=O)_2$ (CH=CH$_2$), —$NR_{12}S(=O)_2(CH=CH_2)$, —$NR_{12}C(=O)$ CH$_2R^{10}$, —$NR_{12}C(=O)CH_2Br$, —$NR_{12}C(=O)CH_2I$, —$NHC(=O)CH_2Br$, —$NHC(=O)CH_2I$, —$ONH_2$, —$C(O)$ $NHNH_2$,

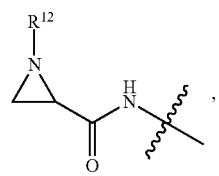

—$CO_2H$, —$NH_2$, —NCO, —NCS,

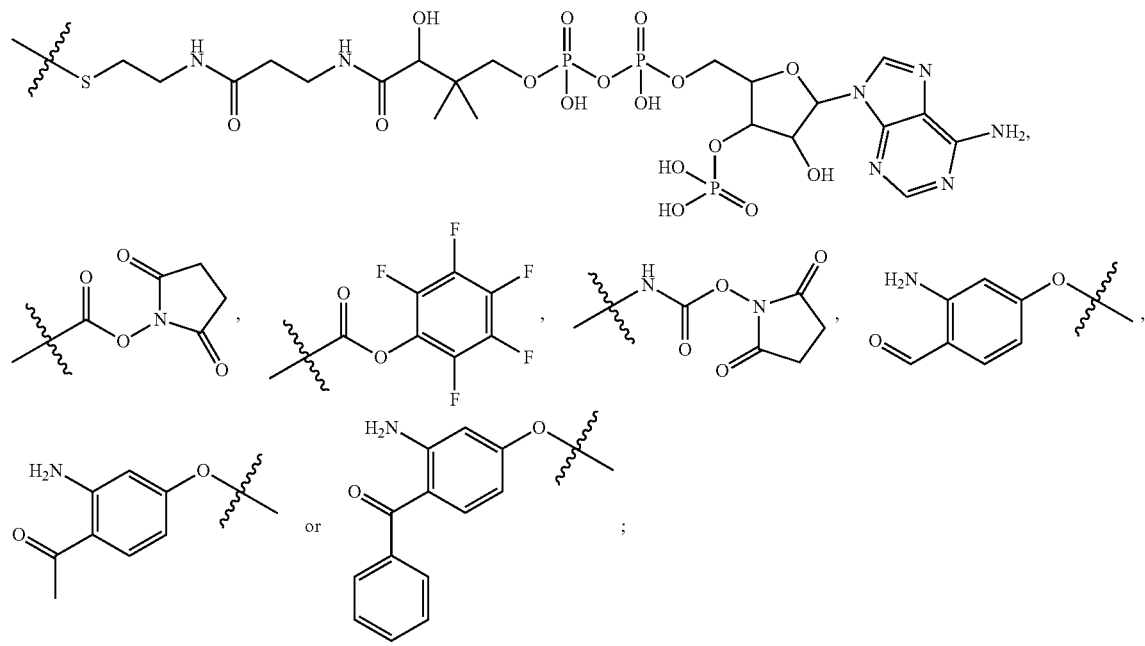

$R^{10}$ is

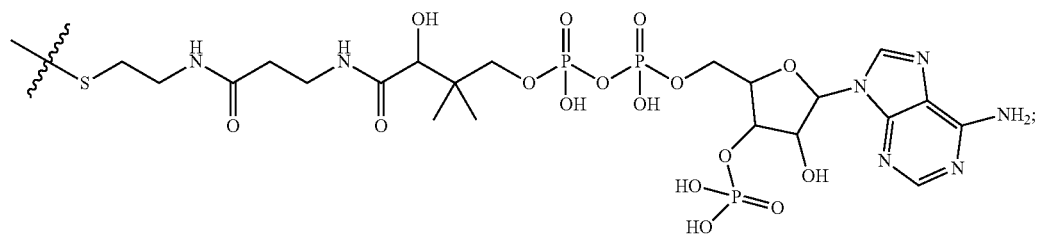 [SMILES: *SCCNC(=O)CCNC(=O)C(O)C(C)(C)COP(=O)(O)OP(=O)(O)OCC1OC(n2cnc3c(N)ncnc32)C(O)C1OP(=O)(O)O]

each $R^{11}$ is independently selected from $C_1$-$C_6$alkyl and $C_1$-$C_6$alkyl which is optionally substituted with 1 to 5 hydroxyl;
each $R^{12}$ is independently selected from H and $C_1$-$C_6$alkyl;
$R^{13}$ is tetrazolyl,

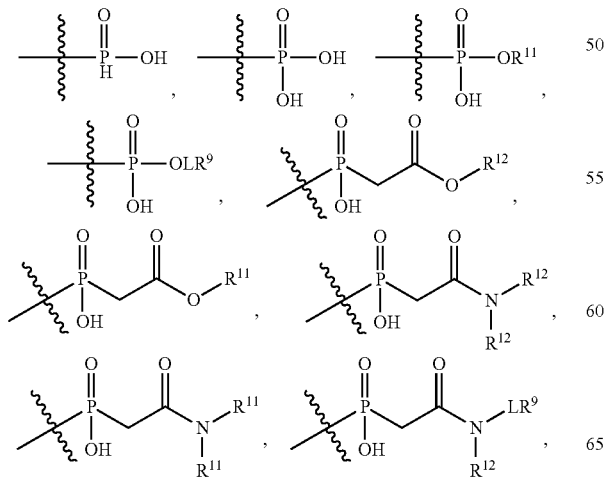

-continued

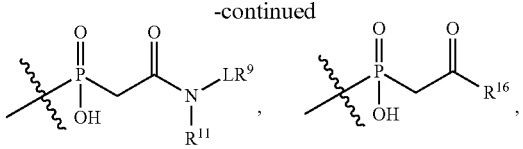

$LR^9$ or —$X_4LR^9$;
each $R^{14}$ is independently selected from H and $C_1$-$C_6$alkyl;
$R^{15}$ is 2-pyridyl or 4-pyridyl;
$R^{16}$ is an N-linked 4-8 membered heterocycloalkyl containing 1-2 heteroatoms independently selected from N and O, which is unsubstituted or substituted with -$LR^9$;

$X_3$ is

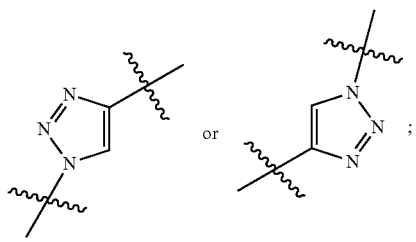 [SMILES: *c1cn(*)nn1 ; *c1cn(*)nn1]

or ;

$X_4$ is

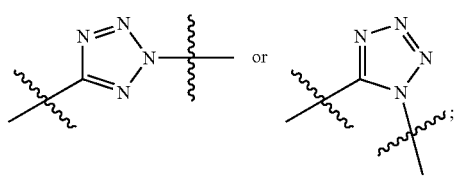 [SMILES: *c1nnn(*)n1 ; *c1nnnn1*]

or ;

each m is independently selected from 1, 2, 3, 4, 5, 6, 7, 8, 9 and 10;
each n is independently selected from 1, 2, 3, 4, 5, 6, 7, 8, 9, 10, 11, 12, 13, 14, 15, 16, 17 and 18,
or a pharmaceutically acceptable salt thereof.

Embodiment 5. The compound according to any one of embodiments 1 to 4, wherein the compound is a compound having the structure of Formula (Ia):

(Formula (Ia))

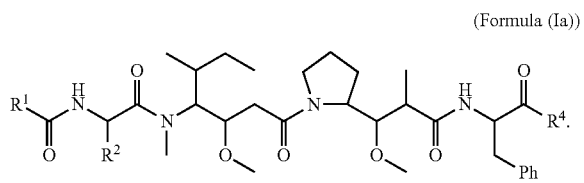

Embodiment 6. The compound according to any one of embodiments 1 to 5, wherein the compound is a compound having the structure of Formula (Ib):

(Formula (Ib))

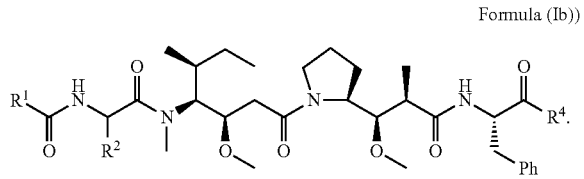

Embodiment 7. The compound according to any one of embodiments 1 to 4, wherein the compound is a compound having the structure of Formula (Ic):

(Formula (Ic))

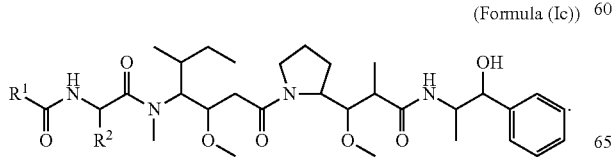

Embodiment 8. The compound according to any one of embodiments 1 to 4, and 7, wherein the compound is a compound having the structure of Formula (Id):

(Formula (Id))

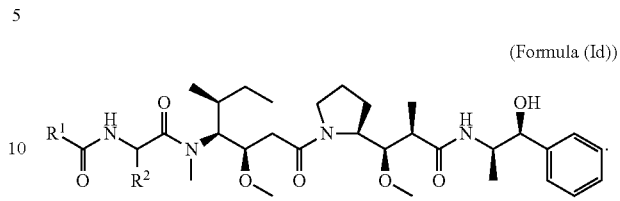

Embodiment 9. The compound according to any one of embodiments 1 to 4, wherein the compound is a compound having the structure of Formula (Ie):

(Formula (Ie))

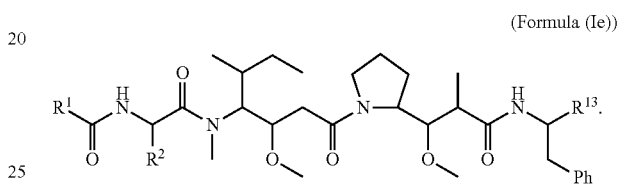

Embodiment 10. The compound according to any one of embodiments 1 to 4, and 9, wherein the compound is a compound having the structure of Formula (If):

(Formula (If))

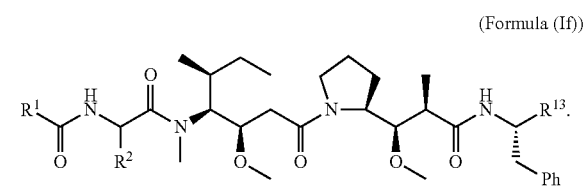

Embodiment 11. The compound according to any one of embodiments 1 to 4, wherein the compound is a compound having the structure of Formula (Ig):

(Formula (Ig))

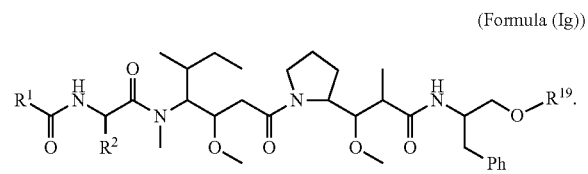

Embodiment 12. The compound according to any one of embodiments 1 to 4 or 11, wherein the compound is a compound having the structure of Formula (Ih):

(Formula (Ih))

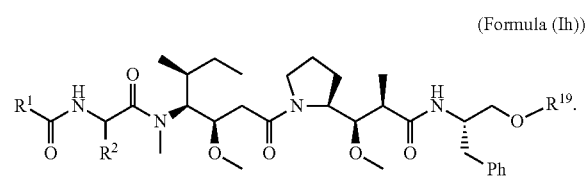

Embodiment 13. The compound according to any one of embodiments 1 to 4, wherein the compound is a compound having the structure of Formula (Ii) or Formula (Ij):

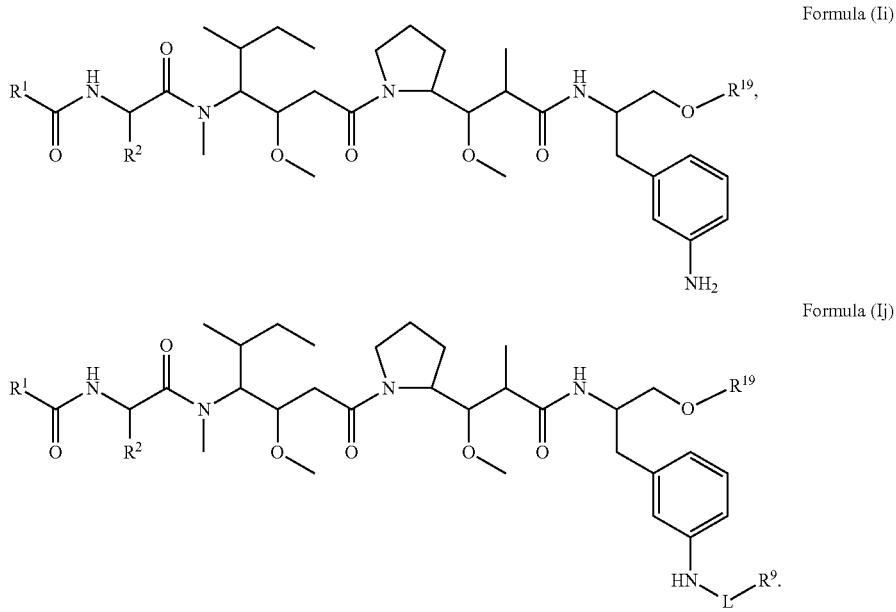

Formula (Ii)

Formula (Ij)

Embodiment 14. The compound according to any one of embodiments 1 to 4 or 13, wherein the compound is a compound having the structure of Formula (Ik) or Formula (Im):

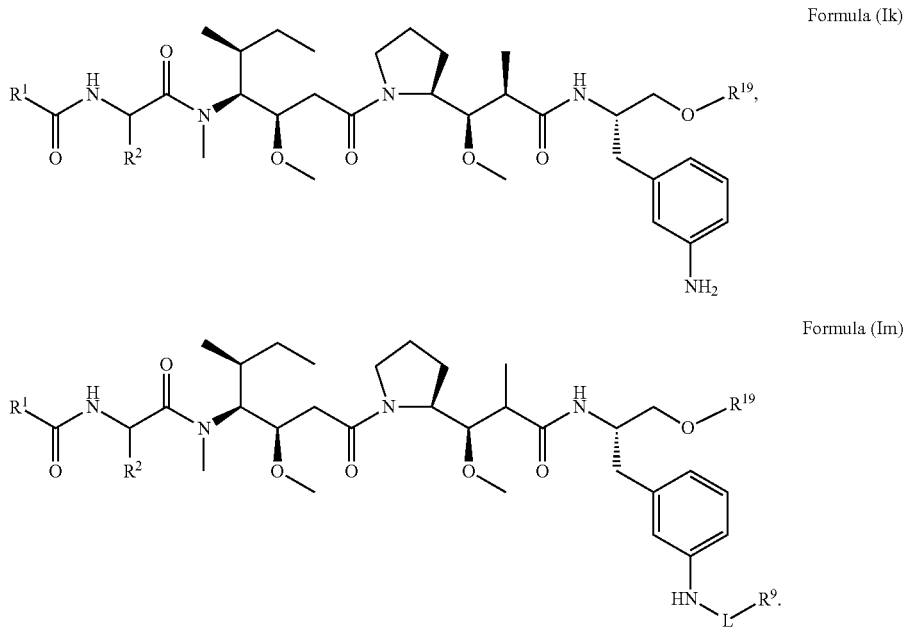

Formula (Ik)

Formula (Im)

Embodiment 15. The compound according to any one of embodiments 1 to 4, wherein the compound is a compound having the structure of Formula (In) or Formula (Io):

Formula (In)

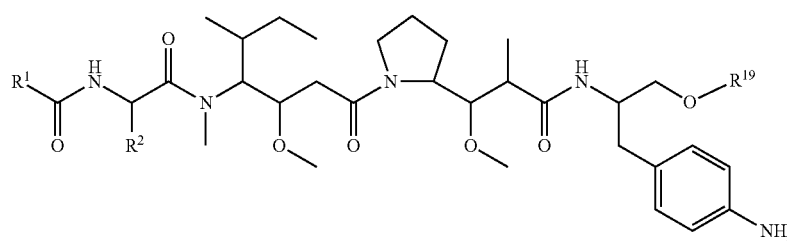

Formula (Io)

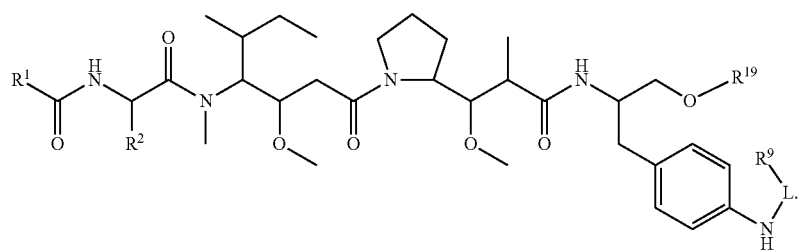

Embodiment 16. The compound of according to any one of embodiments 1 to 4 or 15, wherein the compound is a compound having the structure of Formula (Ip) or Formula (Iq):

Formula (Ip)

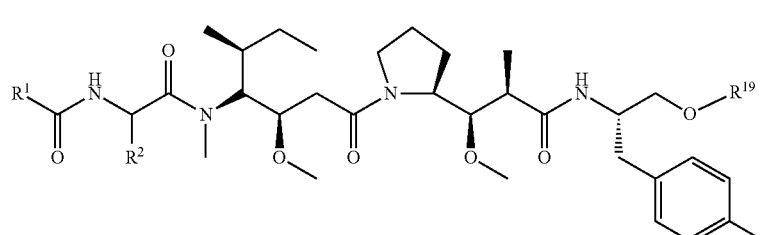

Formula (Iq)

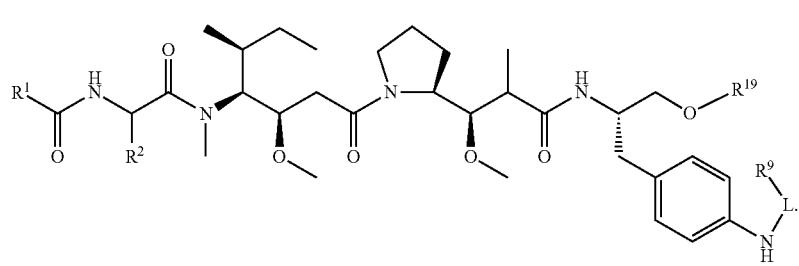

Embodiment 17. The compound of any one of embodiments 11 to 16, wherein $R^{19}$ is H.

Embodiment 18. The compound according to any one of embodiments 3 to 17, wherein each L is independently selected from $-L_1L_2L_3L_4L_5L_6-$ and $-L_6L_5L_4L_3L_2L_1-$, and wherein $-L_1$, $L_2$, $L_3$, $L_4$, $L_5$, and $L_6$ are as defined herein.

Embodiment 19. The compound according to any one of embodiments 3 to 18, wherein each L is independently selected from $-L_1L_2L_3L_4L_5-$, $-L_5L_4L_3L_2L_1-$, $-L_1L_2L_3L_4-$, $-L_4L_3L_2L_1-$, $-L_1L_2L_3-$ and $-L_3L_2L_1-$, wherein $-L_1$, $L_2$, $L_3$, $L_4$, $L_5$, and $L_6$ are as defined herein.

Embodiment 20. The compound according to any one of embodiments 3 to 19, wherein each L is independently selected from $-L_1L_2-$ and $-L_2L_1-$, and wherein $-L_1$ and $L_2$ are as defined herein.

Embodiment 21. The compound according to any one of embodiments 3 to 19, wherein L is $-L_1-$, wherein $-L_1$ is as defined herein.

Embodiment 22. The compound according to any one of embodiments 3 to 21, wherein:
$R^1$ is a C-linked 6 membered heterocycloalkyl containing 1-2 N heteroatoms and a $C_1$-$C_2$alkylene bridge, or $R^1$ is a C-linked 5-8 membered fused bicyclic heterocycloalkyl containing 1-2 N heteroatoms, wherein each is substituted with an $R^7$ and 0 to 3 substituents independently selected from $R^5$ and $R^6$.

Embodiment 23. The compound according to any one of embodiments 3 to 21, wherein:
$R^1$ is a C-linked 6 membered heterocycloalkyl containing 1-2 N heteroatoms and a $C_1$-$C_2$alkylene bridge, wherein the C-linked 6 membered heterocycloalkyl is substituted with an $R^7$ and 0 to 3 substituents independently selected from $R^5$ and $R^6$.

Embodiment 24. The compound according to any one of embodiments 3 to 6 and 18 to 21, wherein: $R^1$ is a C-linked 6 membered heterocycloalkyl containing 1-2 N heteroatoms and a $C_1$-$C_2$alkylene bridge, or $R^1$ is a C-linked 5-8 membered fused bicyclic heterocycloalkyl containing 1-2 N heteroatoms, wherein each is substituted with an $R^7$ and 0 to 3 substituents independently selected from $R^5$ and $R^6$, and $R^4$ is —OH, $C_1$-$C_6$alkoxy, —N($R^{14}$)$_2$, —$R^{16}$, —$NR^{12}$(CH$_2$)$_m$N($R^{14}$)$_2$, —NHS(O)$_2$(CH$_2$)$_m$N$_3$, —$NR^{12}$(CH$_2$)$_m$R$^{16}$, —NHS(O)$_2$R$_{11}$,

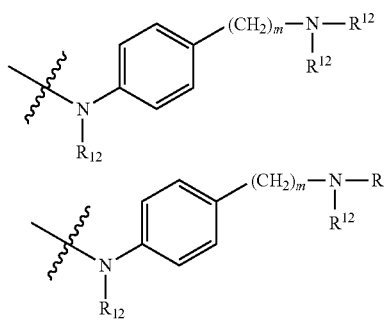

or

Embodiment 25. The compound according to any one of embodiments 3 to 6, 18 to 21 and 24, wherein: $R^1$ is a C-linked 6 membered heterocycloalkyl containing 1-2 N heteroatoms and a $C_1$-$C_2$alkylene bridge, wherein the C-linked 6 membered heterocycloalkyl is substituted with an $R^7$ and 0 to 3 substituents independently selected from $R^5$ and $R^6$, and $R^4$ is —OH, $C_1$-$C_6$alkoxy, —N($R^{14}$)$_2$, —$R^{16}$, —$NR^{12}$(CH$_2$)$_m$N($R^{14}$)$_2$, —NHS(O)$_2$(CH$_2$)$_m$N$_3$, —$NR^{12}$(CH$_2$)$_m$R$^{16}$, —NHS(O)$_2$R$_{11}$,

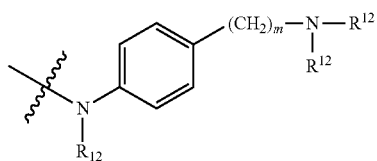

or

Embodiment 26. The compound according to any one of embodiments 3 to 25, wherein:
$R^2$ is —$C_1$-$C_6$alkyl;
$R^5$ is $C_1$-$C_6$alkyl, $C_1$-$C_6$alkyl which is optionally substituted with 1 to 5 hydroxyl, —C(=O)R$^{11}$, —(CH$_2$)$_m$OH, —C(=O)(CH$_2$)$_m$OH, —C(=O)((CH$_2$)$_m$O)$_n$R$^{12}$, or —((CH$_2$)$_m$O)$_n$R$^{12}$;
$R^6$ is halo, oxo, OH, $C_1$-$C_6$alkyl, —N($R^{14}$)$_2$, —$R^{16}$ and —$NR^{12}$C(=O)R$^{11}$;
$R^7$ is $L_1R^9$;
$R^8$ is H;
$R^9$ is

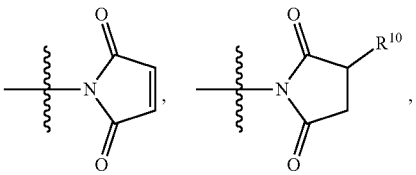

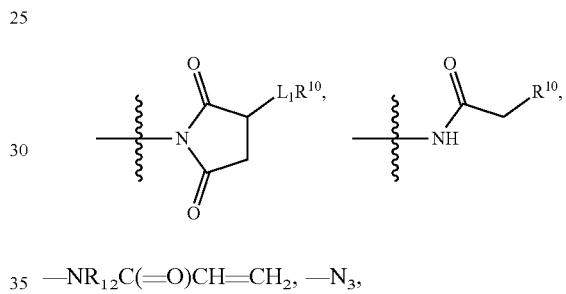

—NR$_{12}$C(=O)CH=CH$_2$, —N$_3$,

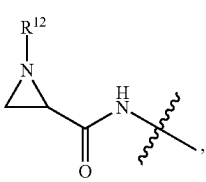

SH, —SSR$^{15}$, —S(=O)$_2$(CH=CH$_2$), —(CH$_2$)$_2$S(=O)$_2$(CH=CH$_2$), —NR$_{12}$S(=O)$_2$(CH=CH$_2$), —NR$_{12}$C(=O)CH$_2$Br, —NR$_{12}$C(=O)CH$_2$I, —NHC(=O)CH$_2$Br, —NHC(=O)CH$_2$I, —ONH$_2$, —C(O)NHNH$_2$,

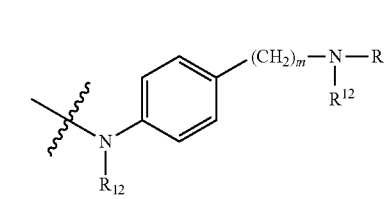

—CO$_2$H, —NH$_2$, —NCO, —NCS,

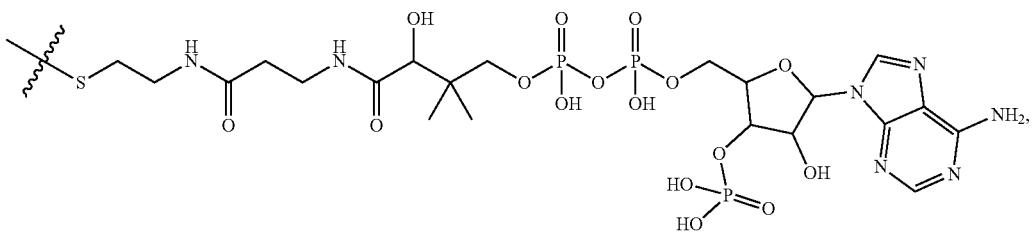 [SMILES: *SCCNC(=O)CCNC(=O)C(O)C(C)(C)COP(=O)(O)OP(=O)(O)OCC1OC(n2cnc3c(N)ncnc32)C(O)C1OP(=O)(O)O]

-continued

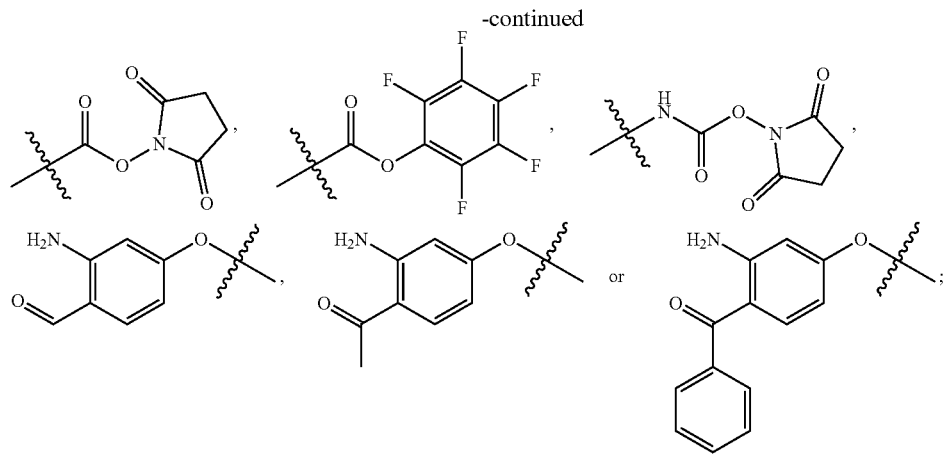

$R^{10}$ is

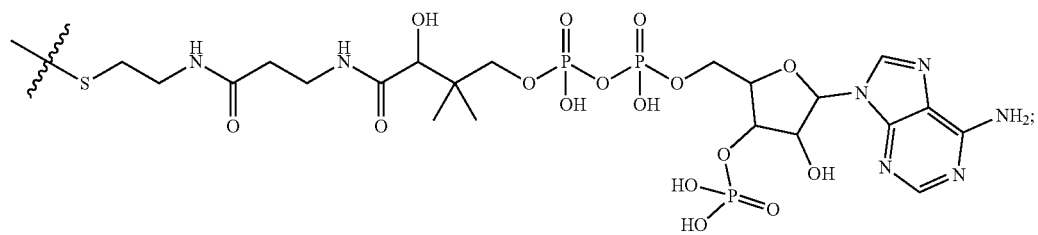

each $R^{11}$ is independently selected from $C_1$-$C_6$alkyl or $C_1$-$C_6$alkyl which is optionally substituted with 1 to 5 hydroxyl;
each $R^{12}$ is independently selected from H and $C_1$-$C_6$alkyl;
$R^{13}$ is tetrazolyl,

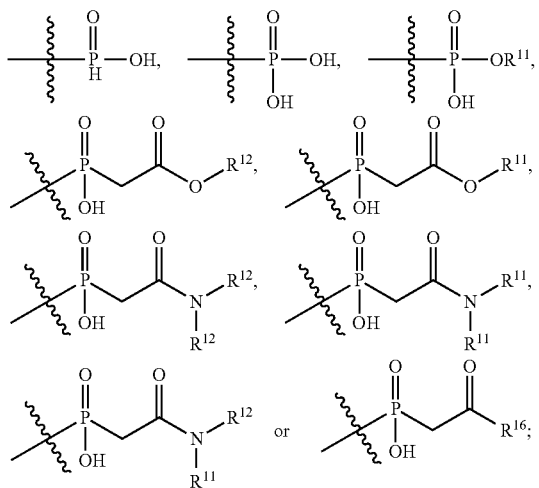

each $R^{14}$ is independently selected from H and $C_1$-$C_6$alkyl;
$R^{15}$ is 2-pyridyl or 4-pyridyl,
and
$R^{16}$ is an unsubstituted N-linked 4-8 membered heterocycloalkyl containing 1-2 heteroatoms independently selected from N and O.

Embodiment 27. The compound according to any one of embodiments 1 to 21, wherein:
$R^1$ is a C-linked 6 membered heterocycloalkyl containing 1-2 N heteroatoms and a $C_1$-$C_2$alkylene bridge, or $R^1$ is a C-linked 5-8 membered fused bicyclic heterocycloalkyl containing 1-2 N heteroatoms, wherein each is unsubstituted or each is substituted with 1 to 3 substituents independently selected from $R^5$ and $R^6$.

Embodiment 28. The compound according to any one of embodiments 1 to 21 and 27, wherein:
$R^1$ is a C-linked 6 membered heterocycloalkyl containing 1-2 N heteroatoms and a $C_1$-$C_2$alkylene bridge, wherein the C-linked 6 membered heterocycloalkyl is unsubstituted or is substituted with 1 to 3 substituents independently selected from $R^5$ and $R^6$.

Embodiment 29. The compound according to any one of embodiments 3 to 27, wherein:
$R^1$ is a C-linked 6 membered heterocycloalkyl containing 1-2 N heteroatoms and a $C_1$-$C_2$alkylene bridge, or $R^1$ is a C-linked 5-8 membered fused bicyclic heterocycloalkyl containing 1-2 N heteroatoms, wherein each is unsubstituted or each is substituted with 1 to 3 substituents independently selected from $R^5$ and $R^6$;
$R^3$ is

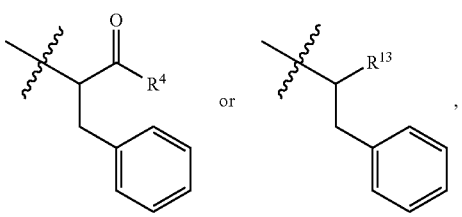

and
$R^4$ is -$L_1R^9$, —NHS(=O)$_2L_1R^9$,

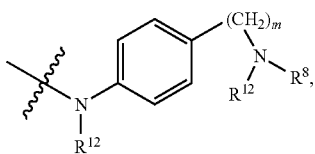

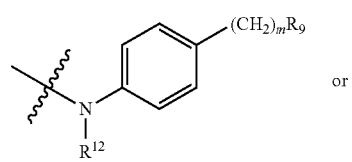

or

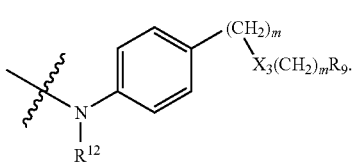

Embodiment 30. The compound according to any one of embodiments 3 to 20 and 29, wherein:
$R^1$ is a C-linked 6 membered heterocycloalkyl containing 1-2 N heteroatoms and a $C_1$-$C_2$alkylene bridge, wherein the C-linked 6 membered heterocycloalkyl is unsubstituted or is substituted with 1 to 3 substituents independently selected from $R^5$ and $R^6$;
$R^3$ is

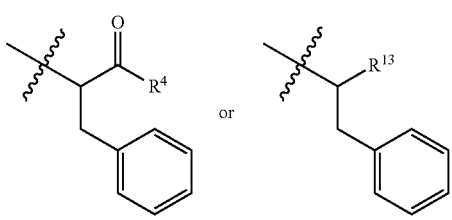

and
$R^4$ is -$L_1R^9$, —NHS(=O)$_2L_1R^9$,

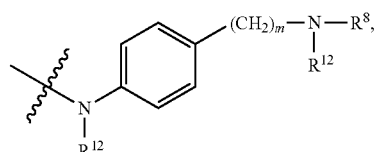

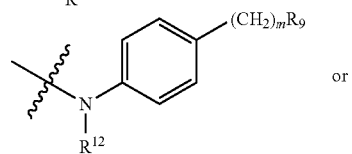

or

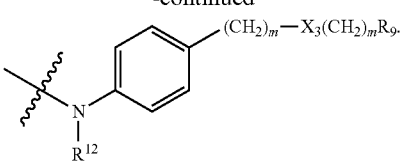

Embodiment 31. The compound according to any one of embodiments 3 to 21 and 27 to 30, wherein:

$R^2$ is —$C_1$-$C_6$alkyl;

$R^5$ is $C_1$-$C_6$alkyl, $C_1$-$C_6$alkyl which is optionally substituted with 1 to 5 hydroxyl, —C(=O)$R^{11}$, —(CH$_2$)$_m$OH, —C(=O)(CH$_2$)$_m$OH, —C(=O)((CH$_2$)$_m$O)$_n$$R^{12}$, or —((CH$_2$)$_m$O)$_n$$R^{12}$;

$R^6$ is halo, oxo, OH, $C_1$-$C_6$alkyl, —N($R^{14}$)$_2$ and —N$R^{12}$C(=O)$R^{11}$;

$R^8$ is $L_1R^9$;

$R^9$ is

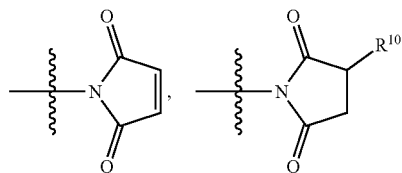

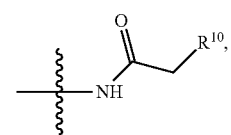

—N$R_{12}$C(=O)CH=CH$_2$, —N$_3$,

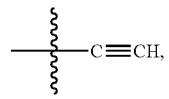 [SMILES: *C#C]

SH, —S(=O)$_2$(CH=CH$_2$), —(CH$_2$)$_2$S(=O)$_2$(CH=CH$_2$), —N$R_{12}$S(=O)$_2$(CH=CH$_2$), —N$R_{12}$C(=O)CH$_2R^{10}$, —N$R_{12}$C(=O)CH$_2$Br, —N$R_{12}$C(=O)CH$_2$I, —NHC(=O)CH$_2$Br, —NHC(=O)CH$_2$I, —ONH$_2$, —C(O)NHNH$_2$,

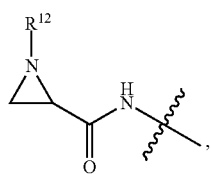

—CO$_2$H, —NH$_2$, —NCO, —NCS,

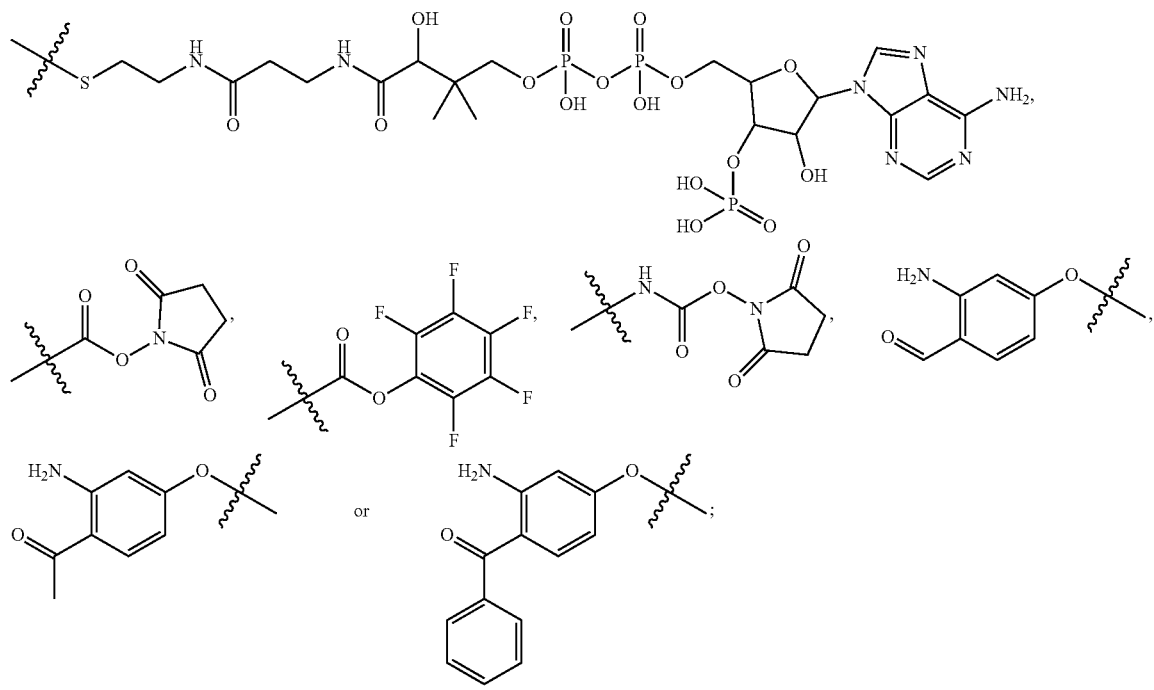

$R^{10}$ is

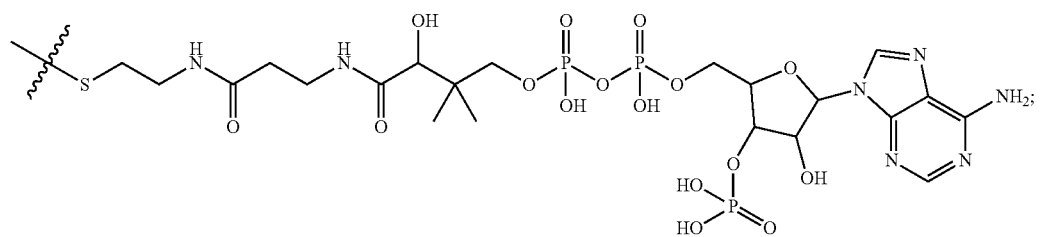 [SMILES: *SCCNC(=O)CCNC(=O)C(O)C(C)(C)COP(=O)(O)OP(=O)(O)OCC1OC(n2cnc3c(N)ncnc32)C(O)C1OP(=O)(O)O]

each $R^{11}$ is independently selected from $C_1$-$C_6$alkyl and $C_1$-$C_6$alkyl which is optionally substituted with 1 to 5 hydroxyl;

each $R^{12}$ is independently selected from H and $C_1$-$C_6$alkyl;

$R^{13}$ is

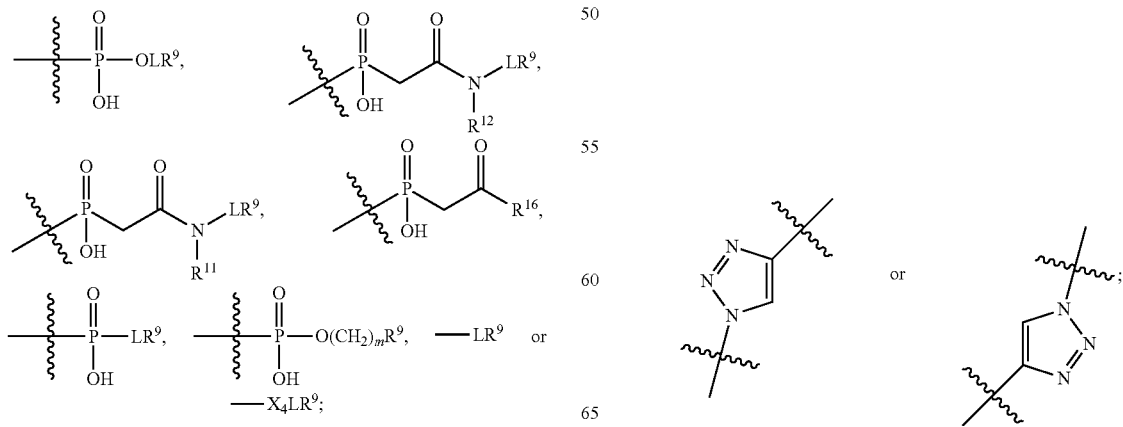

each $R^{14}$ is independently selected from H and $C_1$-$C_6$alkyl;

$R^{16}$ is an N-linked 4-8 membered heterocycloalkyl containing 1-2 heteroatoms independently selected from N and O, which is substituted with -$LR^9$;

$X_3$ is $X_4$ is

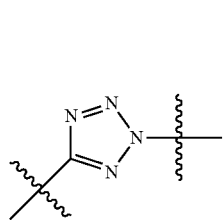 or 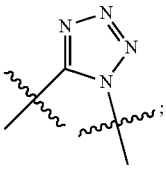 ;

each m is independently selected from 1, 2, 3, 4, 5, 6, 7, 8, 9 and 10, and each n is independently selected from 1, 2, 3, 4, 5, 6, 7, 8, 9, 10, 11, 12, 13, 14, 15, 16, 17 and 18.

Embodiment 32. The compound according to any one of embodiments 1 to 6 and 18 to 28, wherein $R^4$ is —OH, —OCH$_3$, —NHS(O)$_2$R$^{11}$ or

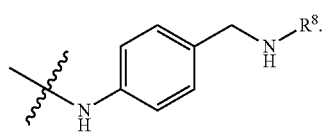

Embodiment 33. The compound according to any one of embodiments 3 to 6 and 18 to 28, wherein $R^4$ is —OH, —OCH$_3$, —NHS(O)$_2$R$^{11}$, —NHS(O)$_2$(CH$_2$)$_m$N$_3$ or

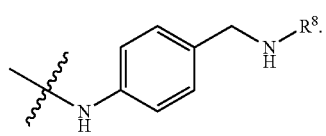

Embodiment 34. The compound according to any one of embodiments 3 to 6, 18 to 23 and 27 to 31, wherein $R^4$ is -L$_1$R$^9$, —NHS(=O)$_2$L$_1$R$^9$,

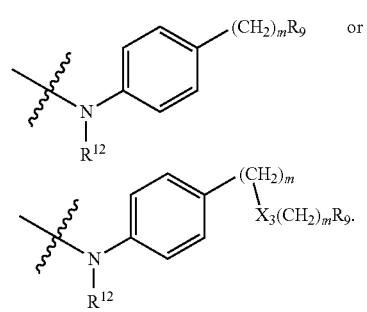

Embodiment 35. The compound according to any one of embodiments 1 to 4, 9, 10 and 18 to 30, wherein $R^{13}$ is

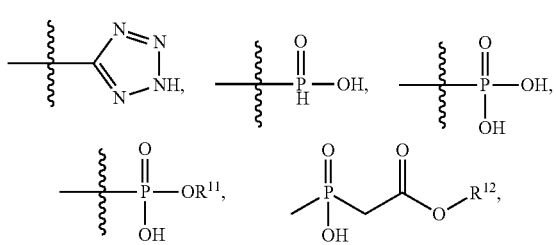

Embodiment 36. The compound according to any one of embodiments 1 to 4, 9, 10 and 18 to 30 and 35, wherein $R^{13}$ is

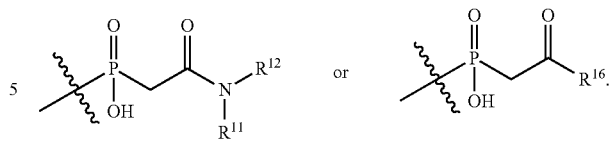

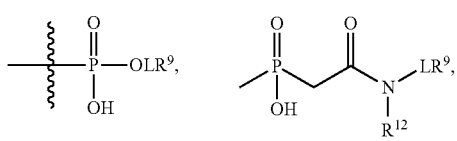

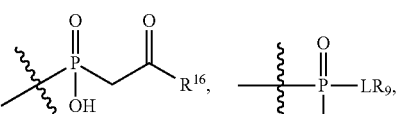

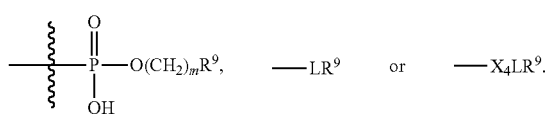

Embodiment 37. The compound according to any one of embodiments 1 to 21 and 26 to 36, wherein $R^1$ is

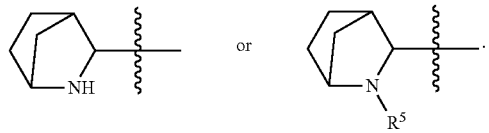

Embodiment 38. The compound according to any one of embodiments 1 to 21 and 26 to 37, wherein $R^1$ is

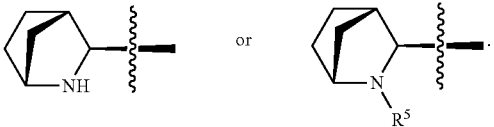

Embodiment 39. The compound according to any one of embodiments 1, 3 to 21, 26, 27, 29 and 31 to 36, wherein $R^1$ is

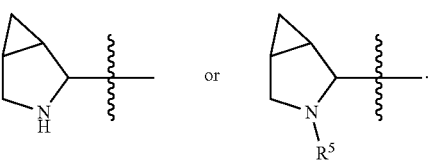

Embodiment 40. The compound according to any one of embodiments 1, 3 to 21, 26, 27, 29, 31 to 36 and 39, wherein $R^1$ is

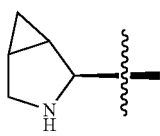 or 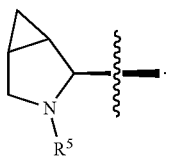

Embodiment 41. The compound according to any one of embodiments 3 to 26, and 32 to 36, wherein $R^1$ is

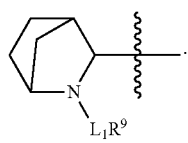

Embodiment 42. The compound according to any one of embodiments 3 to 26, 32 to 36 and 41, wherein $R^1$ is

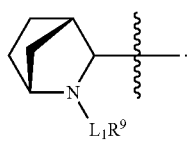

Embodiment 43. The compound according to any one of embodiments 3 to 22, 24 and 31 to 36, wherein $R^1$ is

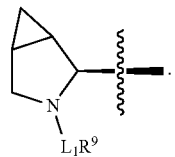

Embodiment 44. The compound according to any one of embodiments 3 to 22, 24, 31 to 36 and 43, wherein $R^1$ is Embodiment 44. The compound according to any one of embodiments 3 to 22, 24, 31 to 36 and 43, wherein $R^9$ is

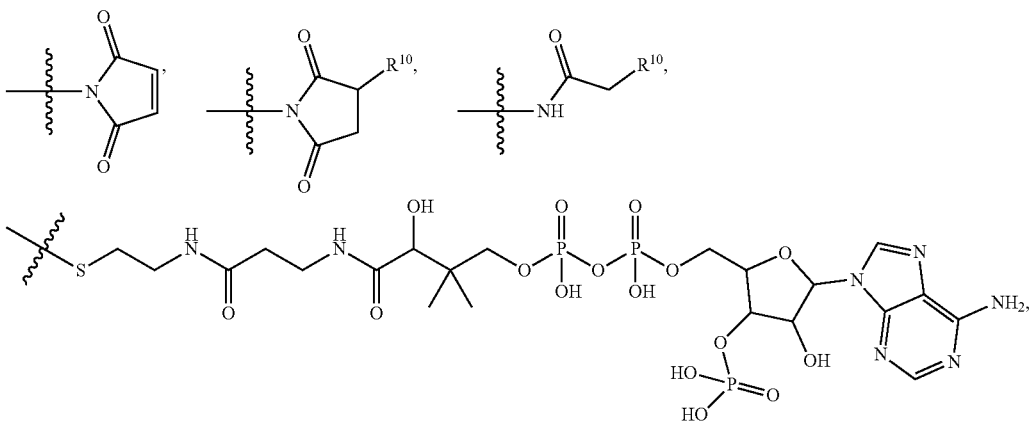

—S(=O)$_2$(CH=CH$_2$), —NHC(=O)CH$_2$Br, —NHC(=O)CH$_2$I, —ONH$_2$, N$_3$,

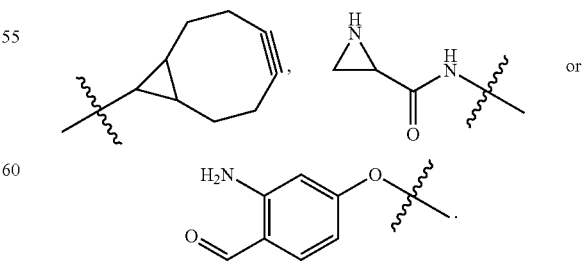

Embodiment 45. The compound according to any one of embodiments 3 to 44, wherein $R^9$ is

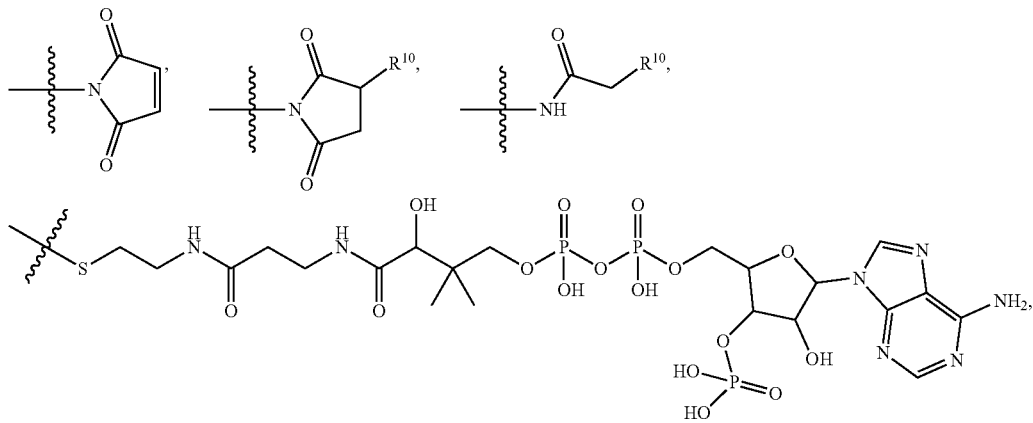

—S(=O)$_2$(CH=CH$_2$), —NHC(=O)CH$_2$Br, —NHC(=O)CH$_2$I, —ONH$_2$, N$_3$,

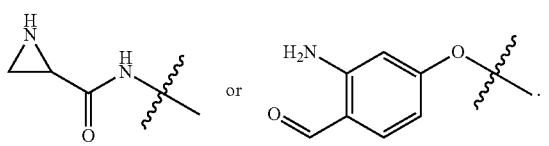 [SMILES: *NC(=O)C1CN1 ; *Oc1ccc(C=O)c(N)c1]

Embodiment 46. An immunoconjugate of Formula (II):

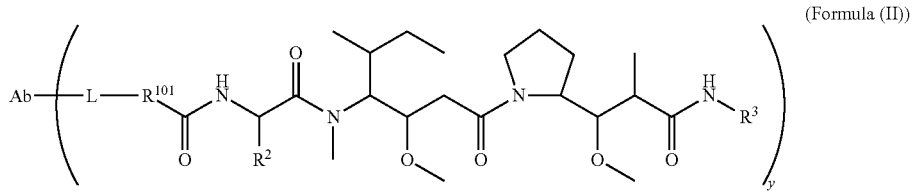

wherein:
Ab represents an antigen binding moiety;
L is selected from -L$_1$L$_2$L$_3$L$_4$L$_5$L$_6$-, -L$_6$L$_5$L$_4$L$_3$L$_2$L$_1$-, -L$_1$L$_2$L$_3$L$_4$L$_5$-, -L$_5$L$_4$L$_3$L$_2$L$_1$-,-L$_1$L$_2$L$_3$L$_4$-, -L$_4$L$_3$L$_2$L$_1$-,-L$_1$L$_2$L$_3$-, -L$_3$L$_2$L$_1$-,-L$_1$L$_2$-, -L$_2$L$_1$- and -L$_1$, wherein -L$_1$, L$_2$, L$_3$, L$_4$, L$_5$, and L$_6$ are as defined herein;
y is an integer from 1 to 16;
$R^{101}$ is a 6 membered heterocycloalkyl divalent radical containing 1-2 N heteroatoms and a C$_1$-C$_2$alkylene bridge, wherein the 6 membered heterocycloalkyl divalent radical is C-linked to the

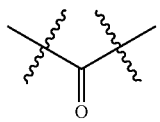

group and is N-linked to L$_1$ or is C-linked to L$_1$, and the 6 membered heterocycloalkyl divalent radical is unsubstituted or substituted with 1 to 3 substituents independently selected from R$^5$ and R$^6$;

or $R^{101}$ is a 5-8 membered fused bicyclic heterocycloalkyl divalent radical containing 1-2 N heteroatoms, wherein the 5-8 membered fused bicyclic heterocycloalkyl divalent radical is C-linked to the

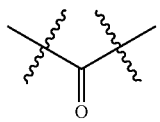

group and is N-linked to L$_1$ or is C-linked to L$_1$, and the 5-8 membered fused bicyclic heterocycloalkyl divalent radical is unsubstituted or substituted with 1 to 3 substituents independently selected from R$^5$ and R$^6$;
$R^2$ is —C$_1$-C$_6$alkyl;
$R^3$ is

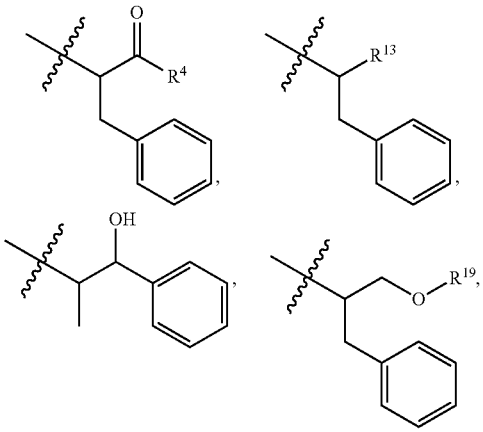

357

-continued

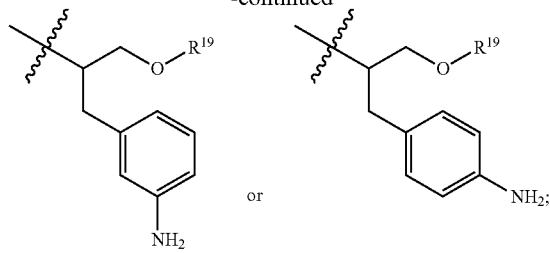

R⁴ is —OH, $C_1$-$C_6$alkoxy, —N($R^{14}$)$_2$, —$R^{16}$, —$NR^{12}$($CH_2$)$_m$ N($R^{14}$)$_2$, or —$NR^{12}$($CH_2$)$_m$$R^{16}$, —NHS(O)$_2$$R^{11}$ or

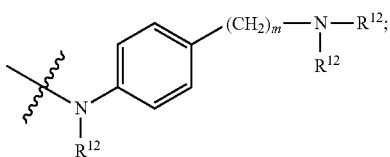

R⁵ is $C_1$-$C_6$alkyl, —C(=O)$R^{11}$, —($CH_2$)$_m$OH, —C(=O)($CH_2$)$_m$OH, —C(=O)(($CH_2$)$_m$O)$_n$$R^{12}$, —(($CH_2$)$_m$O)$_n$$R^{12}$, or $C_1$-$C_6$alkyl which is optionally substituted with —CN, —C(=O)NH$_2$ or 1 to 5 hydroxyl, R⁶ is halo, oxo, OH, $C_1$-$C_6$alkyl, —N($R^{14}$)$_2$, —$R^{16}$ and —$NR^{12}$C(=O)$R^{11}$;

R¹¹ is $C_1$-$C_6$alkyl or $C_1$-$C_6$alkyl which is optionally substituted with 1 to 5 hydroxyl;

each R¹² is independently selected from H and $C_1$-$C_6$alkyl;

R¹³ is tetrazolyl, imidazolyl substituted with phenyl, oxadiazolyl substituted with phenyl, pyrazolyl, pyrimidinyl,

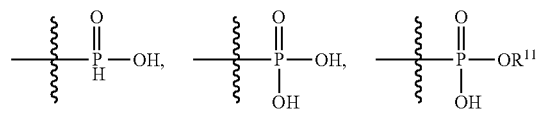

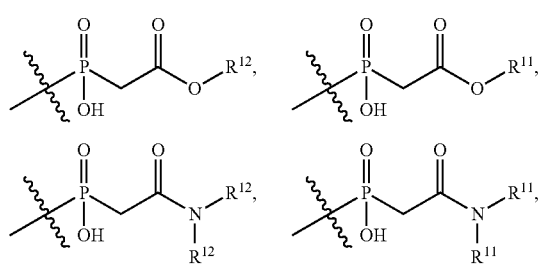

358

-continued

—CH$_2$S(=O)$_2$NH$_2$;

each R¹⁴ is independently selected from H and $C_1$-$C_6$alkyl;

R¹⁶ is an N-linked 4-8 membered heterocycloalkyl containing 1-2 heteroatoms independently selected from N and O;

R¹⁹ is H or $C_1$-$C_6$alkyl;

each m is independently selected from 1, 2, 3, 4, 5, 6, 7, 8, 9 and 10, and each n is independently selected from 1, 2, 3, 4, 5, 6, 7, 8, 9, 10, 11, 12, 13, 14, 15, 16, 17 and 18.

Embodiment 47. An immunoconjugate of Formula (II):

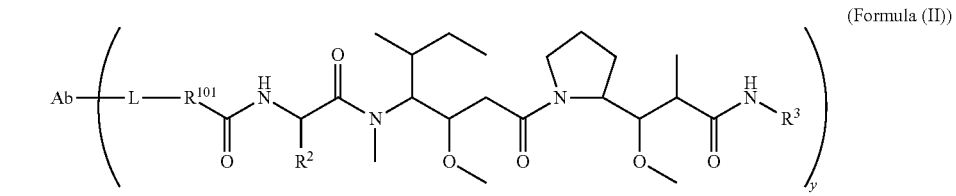

(Formula (II))

wherein:

Ab represents an antigen binding moiety;

L is selected from -$L_1L_2L_3L_4L_5L_6$-, -$L_6L_5L_4L_3L_2L_1$-, -$L_1L_2L_3L_4L_5$-, -$L_5L_4L_3L_2L_1$-, -$L_1L_2L_3L_4$-, -$L_4L_3L_2L_1$-, -$L_1L_2L_3$-, -$L_3L_2L_1$-, -$L_1L_2$-, -$L_2L_1$- and -$L_1$, wherein -$L_1$, $L_2$, $L_3$, $L_4$, $L_5$, and $L_6$ are as defined herein;

y is an integer from 1 to 16;

R¹⁰¹ is a 6 membered heterocycloalkyl divalent radical containing 1-2 N heteroatoms and a $C_1$-$C_2$alkylene bridge, wherein the 6 membered heterocycloalkyl divalent radical is C-linked to the

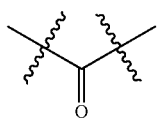 [SMILES: *C(*)=O]

group and is N-linked to $L_1$ or is C-linked to $L_1$, and the 6 membered heterocycloalkyl divalent radical is unsubstituted or substituted with 1 to 3 substituents independently selected from R⁵ and R⁶;

or R¹⁰¹ is a 5-8 membered fused bicyclic heterocycloalkyl divalent radical containing 1-2 N heteroatoms, wherein the 5-8 membered fused bicyclic heterocycloalkyl divalent radical is C-linked to the

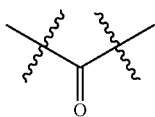

group and is N-linked to $L_1$ or is C-linked to $L_1$, and the 5-8 membered fused bicyclic heterocycloalkyl divalent radical is unsubstituted or substituted with 1 to 3 substituents independently selected from $R^5$ and $R^6$;

$R^2$ is —$C_1$-$C_6$alkyl;

$R^3$ is

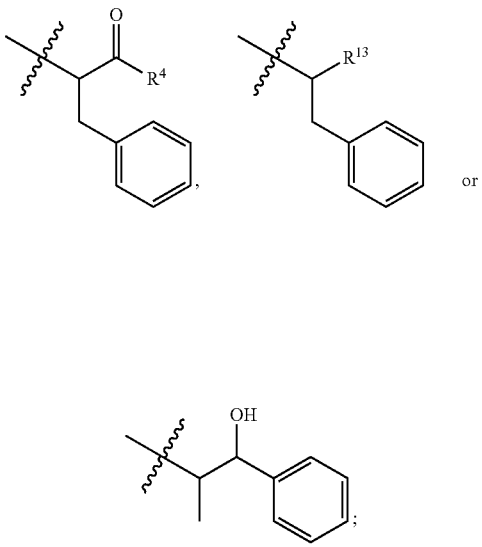

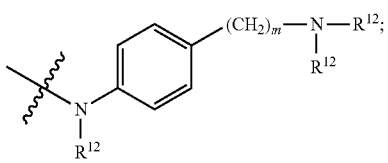

$R^4$ is —OH, $C_1$-$C_6$alkoxy, —$N(R^{14})_2$, —$R^{16}$, —$NR^{12}$$(CH_2)_m$ $N(R^{14})_2$, or —$NR^{12}(CH_2)_m R^{16}$, —$NHS(O)_2 R^{11}$ or

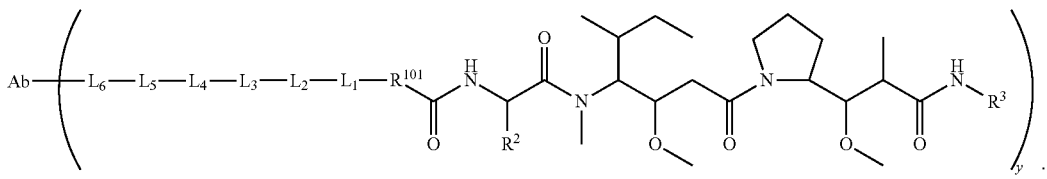

$R^5$ is $C_1$-$C_6$alkyl, $C_1$-$C_6$alkyl which is optionally substituted with 1 to 5 hydroxyl, —C(=O)$R^{11}$, —(CH$_2$)$_m$OH, —C(=O)(CH$_2$)$_m$OH, —C(=O)((CH$_2$)$_m$O)$_n R^{12}$, or —((CH$_2$)$_m$O)$_n R^{12}$;

$R^6$ is halo, oxo, OH, $C_1$-$C_6$alkyl, —$N(R^{14})_2$, —$R^{16}$ and —$NR^{12}$C(=O)$R^{11}$;

$R^{11}$ is $C_1$-$C_6$alkyl or $C_1$-$C_6$alkyl which is optionally substituted with 1 to 5 hydroxyl;

each $R^{12}$ is independently selected from H and $C_1$-$C_6$alkyl;

$R^{13}$ is tetrazolyl,

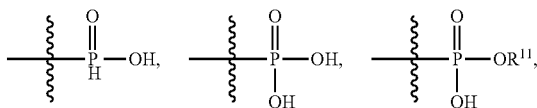

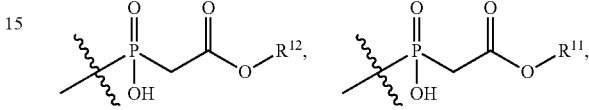

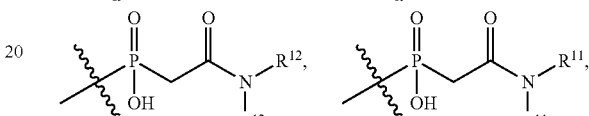

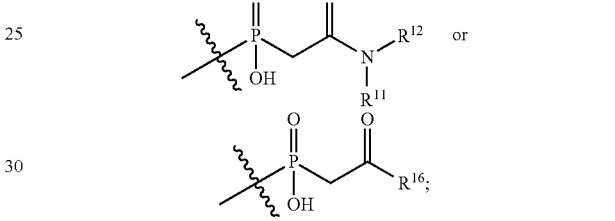

each $R^{14}$ is independently selected from H and $C_1$-$C_6$alkyl;

$R^{16}$ is an N-linked 4-8 membered heterocycloalkyl containing 1-2 heteroatoms independently selected from N and O;

each m is independently selected from 1, 2, 3, 4, 5, 6, 7, 8, 9 and 10, and each n is independently selected from 1, 2, 3, 4, 5, 6, 7, 8, 9, 10, 11, 12, 13, 14, 15, 16, 17 and 18.

Embodiment 48. The immunoconjugate according to embodiments 46 and 47, wherein L is -$L_1 L_2 L_3 L_4 L_5 L_6$- or -$L_6 L_5 L_4 L_3 L_2 L_1$-, and wherein -$L_1$, $L_2$, $L_3$, $L_4$, $L_5$, and $L_6$ are as defined herein.

Embodiment 49. The immunoconjugate according to embodiments 46 and 47, wherein L is selected from -$L_1 L_2 L_3 L_4 L_5$-, -$L_5 L_4 L_3 L_2 L_1$-,-$L_1 L_2 L_3 L_4$-, -$L_4 L_3 L_2 L_1$-, -$L_1 L_2 L_3$- and - $L_3 L_2 L_1$-, wherein -$L_1$, $L_2$, $L_3$, $L_4$, $L_5$, and $L_6$ are as defined herein.

Embodiment 50. The immunoconjugate according to any one of embodiments 47 and 49, wherein the immunoconjugate of Formula (II) is an immunoconjugate of Formula (IIa):

(Formula (IIa))

Embodiment 51. The immunoconjugate according to embodiments 46 and 47, wherein L is —L$_1$L$_2$- or -L$_2$L$_1$-, and wherein -L$_1$ and L$_2$ are as defined herein.

Embodiment 52. The immunoconjugate according to any one of embodiments 46, 47 and 51, wherein the immunoconjugate of Formula (II) is an immunoconjugate of Formula (IIb):

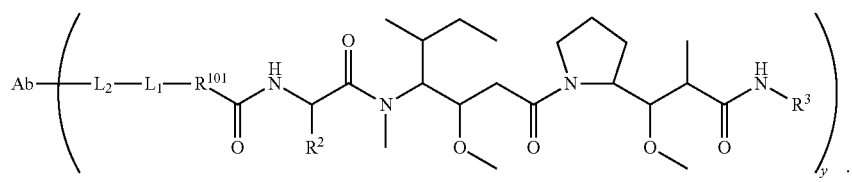

(Formula (IIb))

Embodiment 53. The immunoconjugate according to any one of embodiments 46, 47, 51 and 52, wherein the immunoconjugate of Formula (II), Formula (IIa) or Formula (IIb) is an immunoconjugate having the structure of Formula (IIc):

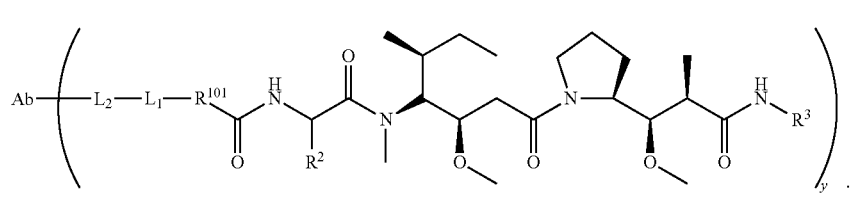

(Formula (IIc))

Embodiment 54. The immunoconjugate according to any one of embodiments 46 to 53, wherein:

R$^{101}$ is a 6 membered heterocycloalkyl divalent radical containing 1-2 N heteroatoms and a C$_1$-C$_2$alkylene bridge, wherein the 6 membered heterocycloalkyl divalent radical is C-linked to the

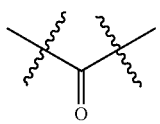 [SMILES: *C(*)=O]

group and is N-linked to L$_1$, and the 6 membered heterocycloalkyl divalent radical is unsubstituted or substituted with 1 to 3 substituents independently selected from R$^5$ and R$^6$;

or

R$^{101}$ is a 5-8 membered fused bicyclic heterocycloalkyl divalent radical containing 1-2 N heteroatoms, wherein the 5-8 membered fused bicyclic heterocycloalkyl divalent radical is C-linked to the

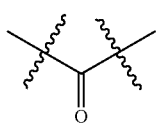

group and is N-linked to L$_1$, and the 5-8 membered fused bicyclic heterocycloalkyl divalent radical is unsubstituted or substituted with 1 to 3 substituents independently selected from R$^5$ and R$^6$.

Embodiment 55. The immunoconjugate according to any one of embodiments 46 to 54, wherein:

R$^{101}$ is a 6 membered heterocycloalkyl divalent radical containing 1-2 N heteroatoms and a C$_1$-C$_2$alkylene bridge, wherein the 6 membered heterocycloalkyl divalent radical is C-linked to the

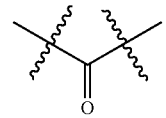

group and is N-linked to L$_1$, and the 6 membered heterocycloalkyl divalent radical is unsubstituted or substituted with 1 to 3 substituents independently selected from R$^5$ and R$^6$.

Embodiment 56. The immunoconjugate according to any one of embodiments 46 to 55, wherein:

R$^{101}$ is a 6 membered heterocycloalkyl divalent radical containing 1-2 N heteroatoms and a C$_1$-C$_2$alkylene bridge, wherein the 6 membered heterocycloalkyl divalent radical is C-linked to the

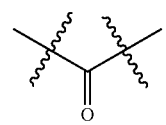 [SMILES: *C(*)=O]

group and is N-linked to L$_1$ and the 6 membered heterocycloalkyl divalent radical is unsubstituted.

Embodiment 57. The immunoconjugate according to any one of embodiments 46-56, wherein R$^{101}$ is Embodiment 58. The immunoconjugate according to any one of embodiments 46-57, wherein $R^{101}$ is

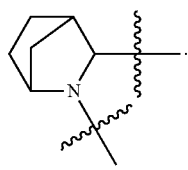

Embodiment 59. The immunoconjugate according to any one of embodiments 46-58, wherein $R^3$ is

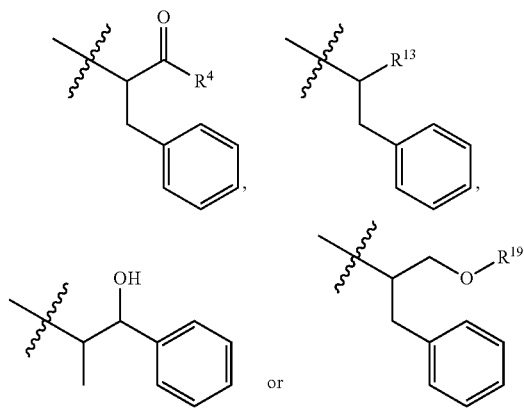

and $R^{19}$ is H.

Embodiment 60. The immunoconjugate according to any one of embodiments 46 to 59, wherein
$R^4$ is —OH, $C_1$-$C_6$alkoxy, —N($R^{14}$)$_2$, —$R^{16}$, —$NR^{12}$(CH$_2$)$_m$ N($R^{14}$)$_2$, —NHS(O)$_2R_{11}$, or —$NR^{12}$(CH$_2$)$_m$$R^{16}$; and
$R^{13}$ is tetrazolyl,

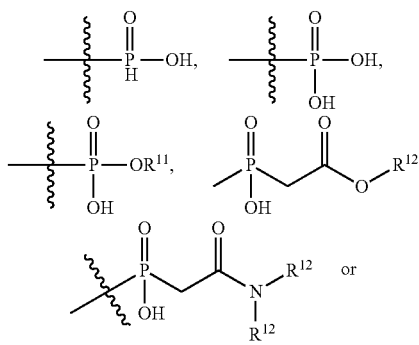

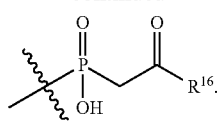

Embodiment 61. The immunoconjugate according to any one of embodiments 46 to 60, wherein:
$R^4$ is —OH, $C_1$-$C_6$alkoxy, —N($R^{14}$)$_2$, —$R^{16}$, —$NR^{12}$(CH$_2$)$_m$ N($R^{14}$)$_2$, or —$NR^{12}$(CH$_2$)$_m$$R^{16}$.

Embodiment 62. The immunoconjugate according to any one of embodiments 46 to 61, wherein:
$R^{13}$ is tetrazolyl,

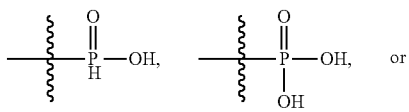

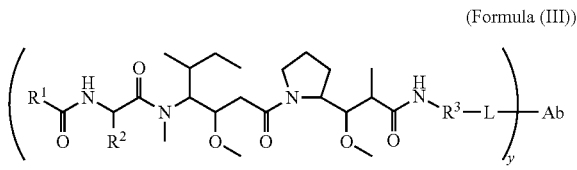

Embodiment 63. The immunoconjugate according to any one of embodiments 46 to 62, wherein $R^4$ is —OH or $C_1$-$C_6$alkoxy.

Embodiment 64. An immunoconjugate of Formula (III):

(Formula (III))

$$\left( R^1 \underset{O}{\overset{H}{N}} \underset{R^2}{\overset{O}{\prod}} \underset{|}{\overset{}{N}} \underset{O}{\overset{}{\prod}} \underset{O \diagdown}{\overset{N}{\prod}} \underset{O \diagdown}{\overset{}{\prod}} \underset{O}{\overset{H}{N}} R^3 - L \right)_y - Ab$$

wherein:

Ab represents an antigen binding moiety;

L is selected from -$L_1L_2L_3L_4L_5L_6$-, -$L_6L_5L_4L_3L_2L_1$-, -$L_1L_2L_3L_4L_5$-, -$L_5L_4L_3L_2L_1$-,-$L_1L_2L_3L_4$-, -$L_4L_3L_2L_1$-,-$L_1L_2L_3$-, -$L_3L_2L_1$-,-$L_1L_2$-, -$L_2L_1$- and -$L_1$, wherein -$L_1$, $L_2$, $L_3$, $L_4$, $L_5$, and $L_6$ are as defined herein;

y is an integer from 1 to 16;

$R^1$ is a 6 membered heterocycloalkyl containing 1-2 N heteroatoms and a $C_1$-$C_2$alkylene bridge, wherein the 6 membered heterocycloalkyl is unsubstituted or substituted with 1 to 3 substituents independently selected from $R^5$ and $R^6$;

or $R^1$ is a 5-8 membered fused bicyclic heterocycloalkyl containing 1-2 N heteroatoms, wherein the 5-8 membered fused bicyclic heterocycloalkyl is unsubstituted or substituted with 1 to 3 substituents independently selected from $R^5$ and $R^6$;

$R^2$ is —$C_1$-$C_6$alkyl;

$R^3$ is

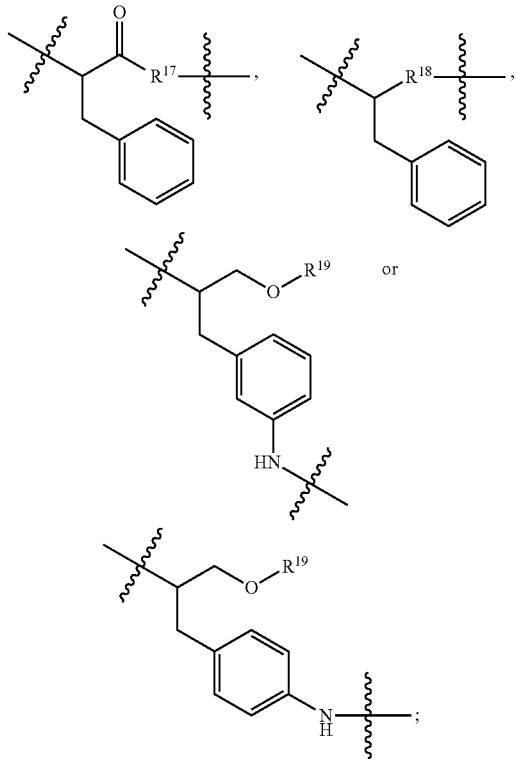

$R^5$ is $C_1$-$C_6$alkyl, $C_1$-$C_6$alkyl which is optionally substituted with 1 to 5 hydroxyl, —C(=O)$R^{11}$, —(CH$_2$)$_m$OH, —C(=O)(CH$_2$)$_m$OH, —C(=O)((CH$_2$)$_m$O)$_n$$R^{12}$, or —((CH$_2$)$_m$O)$_n$$R^{12}$;

$R^6$ is halo, oxo, OH, $C_1$-$C_6$alkyl, —N($R^{14}$)$_2$, —$R^{16}$ and —$NR^{12}$C(=O)$R^{11}$;

$R^{11}$ is $C_1$-$C_6$alkyl or $C_1$-$C_6$alkyl which is optionally substituted with 1 to 5 hydroxyl;

each $R^{12}$ is independently selected from H and $C_1$-$C_6$alkyl;

each $R^{14}$ is independently selected from H and $C_1$-$C_6$alkyl;

$R^{16}$ is an N-linked 4-8 membered heterocycloalkyl containing 1-2 heteroatoms independently selected from N and O;

$R^{17}$ is a bond, —NH—, —NHS(=O)$_2$—,

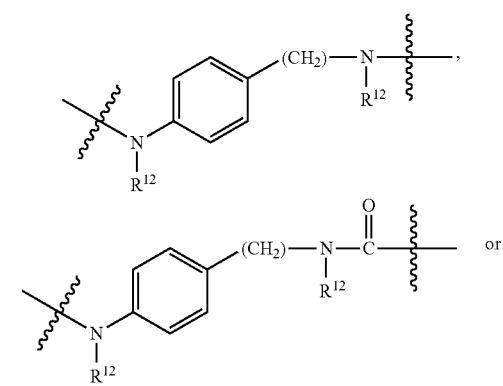

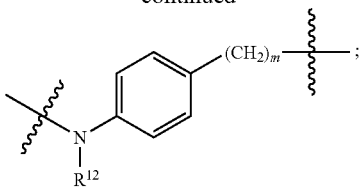

$R^{18}$ is a bond,

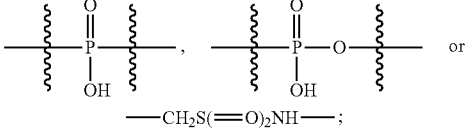

—CH$_2$S(=O)$_2$NH—;

$R^{19}$ is H or $C_1$-$C_6$alkyl;
each m is independently selected from 1, 2, 3, 4, 5, 6, 7, 8, 9 and 10, and
each n is independently selected from 1, 2, 3, 4, 5, 6, 7, 8, 9, 10, 11, 12, 13, 14, 15, 16, 17 and 18.

Embodiment 65. An immunoconjugate of Formula (III), (Formula (III))

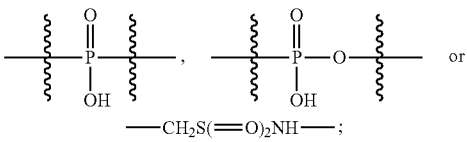

wherein:
Ab represents an antigen binding moiety;
L is selected from -$L_1L_2L_3L_4L_5L_6$-, -$L_6L_5L_4L_3L_2L_1$-, -$L_1L_2L_3L_4L_5$-, -$L_5L_4L_3L_2L_1$-,-$L_1L_2L_3L_4$-, -$L_4L_3L_2L_1$-,-$L_1L_2L_3$-, -$L_3L_2L_1$-,-$L_1L_2$-, -$L_2L_1$- and -$L_1$, wherein -$L_1$, $L_2$, $L_3$, $L_4$, $L_5$, and $L_6$ are as defined herein;
y is an integer from 1 to 16;
$R^1$ is a 6 membered heterocycloalkyl containing 1-2 N heteroatoms and a $C_1$-$C_2$alkylene bridge, wherein the 6 membered heterocycloalkyl is unsubstituted or substituted with 1 to 3 substituents independently selected from $R^5$ and $R^6$;
or $R^1$ is a 5-8 membered fused bicyclic heterocycloalkyl containing 1-2 N heteroatoms, wherein the 5-8 membered fused bicyclic heterocycloalkyl is unsubstituted or substituted with 1 to 3 substituents independently selected from $R^5$ and $R^6$;
$R^2$ is —$C_1$-$C_6$alkyl;
$R^3$ is

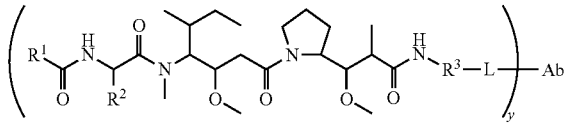

$R^5$ is $C_1$-$C_6$alkyl, $C_1$-$C_6$alkyl which is optionally substituted with 1 to 5 hydroxyl, —C(=O)$R^{11}$, —(CH$_2$)$_m$OH, —C(=O)(CH$_2$)$_m$OH, —C(=O)((CH$_2$)$_m$O)$_n$$R^{12}$, or —((CH$_2$)$_m$O)$_n$$R^{12}$;

$R^6$ is halo, oxo, OH, $C_1$-$C_6$alkyl, —N($R^{14}$)$_2$, —$R^{16}$ and —$NR^{12}$C(=O)$R^{11}$;

$R^{11}$ is $C_1$-$C_6$alkyl or $C_1$-$C_6$alkyl which is optionally substituted with 1 to 5 hydroxyl;

each $R^{12}$ is independently selected from H and $C_1$-$C_6$alkyl;

each $R^{14}$ is independently selected from H and $C_1$-$C_6$alkyl;

$R^{16}$ is an N-linked 4-8 membered heterocycloalkyl containing 1-2 heteroatoms independently selected from N and O;

$R^{17}$ is a bond, —NH—, —NHS(=O)$_2$—,

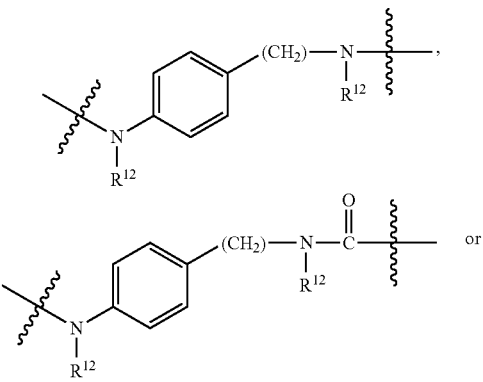

or

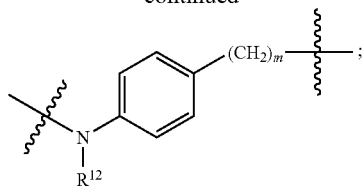

$R^{18}$ is a bond,

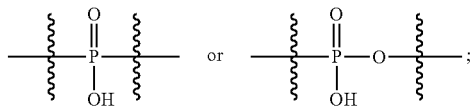 [SMILES: *P(*)(=O)O ; *OP(*)(=O)O]

each m is independently selected from 1, 2, 3, 4, 5, 6, 7, 8, 9 and 10, and each n is independently selected from 1, 2, 3, 4, 5, 6, 7, 8, 9, 10, 11, 12, 13, 14, 15, 16, 17 and 18.

Embodiment 66. The immunoconjugate according to any one of embodiment 64 and 65, wherein L is —L$_1$L$_2$L$_3$L$_4$L$_5$L$_6$- or -L$_6$L$_5$L$_4$L$_3$L$_2$L$_1$-, and wherein -L$_1$, L$_2$, L$_3$, L$_4$, L$_5$, and L$_6$ are as defined herein.

Embodiment 67. The immunoconjugate according to any one of embodiment 64 and 65, wherein L is selected from -L$_1$L$_2$L$_3$L$_4$L$_5$-, -L$_5$L$_4$L$_3$L$_2$L$_1$-,-L$_1$L$_2$L$_3$L$_4$-, -L$_4$L$_3$L$_2$L$_1$-, -L$_1$L$_2$L$_3$- and -L$_3$L$_2$L$_1$-, wherein -L$_1$, L$_2$, L$_3$, L$_4$, L$_5$, and L$_6$ are as defined herein.

Embodiment 68. The immunoconjugate according to any one of embodiments 64, 65 and to 66, wherein the immunoconjugate of Formula (III) is an immunoconjugate of Formula (IIIa):

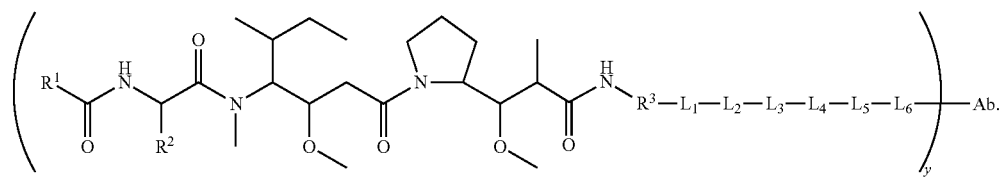

(Formula (IIIa))

Embodiment 69. The immunoconjugate according to any one of embodiment 64 and 65, wherein L is —L$_1$L$_2$- or L$_2$L$_1$-, and wherein -L$_1$ and L$_2$ are as defined herein.

Embodiment 70. The immunoconjugate according to any one of embodiments 64, 65 and 69, wherein the immunoconjugate of Formula (III) is an immunoconjugate of Formula (IIIb):

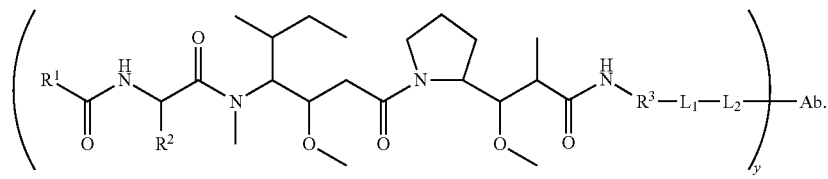

(Formula (IIIb))

Embodiment 71. The immunoconjugate according to any one of embodiments 64, 65, 69 and 70, wherein the immunoconjugate of Formula (III), Formula (IIIa) or Formula (IIIb) is an immunoconjugate of Formula (IIIc):

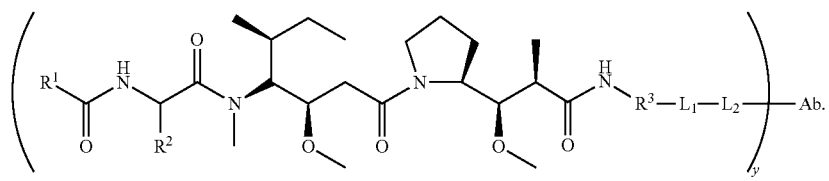

(Formula (IIIc))

Embodiment 72. The immunoconjugate according to any one of embodiments 64 to 71, wherein:

$R^1$ is a 6 membered heterocycloalkyl containing 1-2 N heteroatoms and a $C_1$-$C_2$alkylene bridge, wherein the 6 membered heterocycloalkyl is unsubstituted or substituted with 1 to 3 substituents independently selected from $R^5$ and $R^6$.

Embodiment 73. The immunoconjugate according to any one of embodiments 64 to 72, wherein:

$R^1$ is a 6 membered heterocycloalkyl containing 1-2 N heteroatoms and a $C_1$-$C_2$alkylene bridge, wherein the 6 membered heterocycloalkyl is unsubstituted or substituted with 1 to 3 substituents independently selected from $R^5$.

Embodiment 74. The immunoconjugate according to any one of embodiments 64 to 73, wherein $R^1$ is

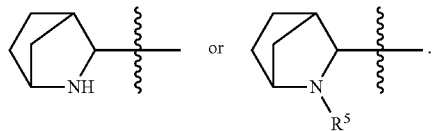

Embodiment 75. The immunoconjugate according to any one of embodiments 64 to 74, wherein $R^1$ is

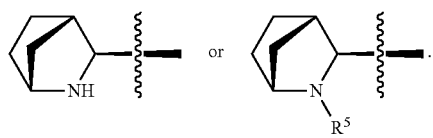

Embodiment 76. The immunoconjugate according to any one of embodiments 64 to 71, wherein $R^1$ is

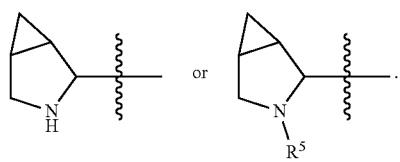

Embodiment 77. The immunoconjugate according to any one of embodiments 64 to 71, wherein $R^1$ is Embodiment 78. The compound according to any one of embodiments 1 to 45, or the immunoconjugate of any one of embodiments 46 to 77, wherein $R^5$ is —$CH_3$ or —C(=O)$CH_3$.

Embodiment 79. The compound according to any one of embodiments 1 to 45 and 78, or the immunoconjugate of any one of embodiments 46 to 78, wherein $R^{12}$ is H, —$CH_3$ or —$CH_2CH_3$.

Embodiment 80. The compound according to any one of embodiments 1 to 45, 78 and 79, or the immunoconjugate of any one of embodiments 46 to 79, wherein $R^2$ is methyl, ethyl, isopropyl or sec-butyl.

Embodiment 81. The compound of any one of embodiments 3 to 45 and 78 to 80, and the immunoconjugate according to any one of embodiments 46 to 80, wherein $L_1$ is selected from —$(CH_2)_m$—, —C(=O)$(CH_2)_m$—, —C(=O)$X_1X_2$C(=O)$(CH_2)_m$—, —C(=O)$X_1X_2$C(=O)$(CH_2)_m$$NR^{12}$C(=O)$(CH_2)_m$—, —C(=O)$X_1X_2$C(=O)$(CH_2)_m$$X_3$$(CH_2)_m$—, —C(=O)$X_1X_2$C(=O)$((CH_2)_mO)_n(CH_2)_m$—, —C(=O)$X_1X_2$C(=O)$((CH_2)_mO)_n(CH_2)_m$$NR^{12}$C(=O)$(CH_2)_m$—, —C(=O)$X_1X_2$C(=O)$((CH_2)_mO)_n(CH_2)_m$$NR^{12}$C(=O)$(CH_2)_m$$X_3$$(CH_2)_m$—, —C(=O)$X_1X_2$C(=O)$((CH_2)_mO)_n(CH_2)_m$$X_3$$(CH_2)_m$—, —C(=O)$X_1X_2$C(=O)$(CH_2)_m$$NR^{12}$C(=O)$((CH_2)_mO)_n(CH_2)_m$—, —C(=O)$X_1X_2$C(=O)$(CH_2)_m$$NR^{12}$C(=O)$((CH_2)_mO)_n(CH_2)_m$$X_3$$(CH_2)_m$—, —C(=O)$X_1X_2$$(CH_2)_m$$X_3$$(CH_2)_m$—, —C(=O)$X_1X_2$$((CH_2)_mO)_n(CH_2)_m$—, —C(=O)$X_1X_2$$((CH_2)_mO)_n$$(CH_2)_m$$NR^{12}$C(=O)$(CH_2)_m$—, —C(=O)$X_1X_2$$((CH_2)_mO)_n(CH_2)_m$$NR^{12}$C(=O)$(CH_2)_m$$X_3$$(CH_2)_m$—, —C(=O)$X_1X_2$$((CH_2)_mO)_n(CH_2)_m$$X_3$$(CH_2)_m$—, —C(=O)$X_1X_2$$(CH_2)_m$$NR^{12}$$((CH_2)_mO)_n(CH_2)_m$—, —C(=O)$X_1X_2$C(=O)$(CH_2)_m$$NR^{12}$$((CH_2)_mO)_n(CH_2)_m$$X_3$$(CH_2)_m$—, —$(CH_2)_m$$NR^{12}$C(=O)$(CH_2)_m$—, —C(=O)$((CH_2)_mO)_n(CH_2)_m$—, —$(CH_2)_mS(=O)_2$$((CH_2)_mO)_n(CH_2)_m$—, —C(=O)$(CH_2)_m$$NR^{12}$$(CH_2)_m$—, —C(=O)$NR^{12}$$(CH_2)_m$—, —C(=O)$NR^{12}$$(CH_2)_m$$X_3$$(CH_2)_m$—, —C(=O)NH$(CH_2)_m$$NR^{12}$C(=O)$X_1X_2$C(=O)$(CH_2)_m$—, —C(=O)$(CH_2)_m$$X_3$$((CH_2)_mO)_n$—, —C(=O)$X_1$C(=O)$NR^{12}$$(CH_2)_m$$NR^{12}$C(=O)$(CH_2)_m$—, —C(=O)$X_1$C(=O)$NR^{12}$$(CH_2)_m$$X_3$$(CH_2)_m$—, —C(=O)$NR^{12}$$(CH_2)_m$$NR^{12}$C(=O)$(CH_2)_m$—, —C(=O)$NR^{12}$$(CH_2)_m$$NR^{12}$C(=O)$(CH_2)_m$$X_3$$(CH_2)_m$—,

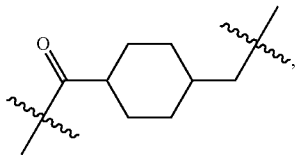

—(CH$_2$)$_m$C(=O)NR$^{12}$(CH$_2$)$_m$NR$^{12}$C(=O)(CH$_2$)$_m$—, —(CH$_2$)$_m$C(=O)—, —(CH$_2$)$_m$C(=O)X$_2$X$_1$C(=O)—, —(CH$_2$)$_m$X$_3$(CH$_2$)$_m$C(=O)X$_2$X$_1$C(=O)—, —(CH$_2$)$_m$C(=O)NR$^{12}$(CH$_2$)$_m$—, —(CH$_2$)$_m$X$_3$(CH$_2$)$_m$C(=O)NR$^{12}$(CH$_2$)$_m$—, —(CH$_2$)$_m$NR$^{12}$C(=O)(CH$_2$)$_m$X$_3$(CH$_2$)$_m$—, —(CH$_2$)$_m$(O(CH$_2$)$_m$)$_n$C(=O)—, —(CH$_2$)$_m$(O(CH$_2$)$_m$)$_n$S(=O)$_2$(CH$_2$)$_m$—, —(CH$_2$)$_m$NR$^{12}$(CH$_2$)$_m$C(=O)—, —(CH$_2$)$_m$NR$^{12}$C(=O)—, —(CH$_2$)$_m$C(=O)X$_2$X$_1$C(=O)NR$^{12}$(CH$_2$)$_m$NHC(=O)—, —(CH$_2$)$_m$C(=O)NR$^{12}$(CH$_2$)$_m$NR$^{12}$C(=O)X$_1$—, —(CH$_2$)$_m$C(=O)NR$^{12}$(CH$_2$)$_m$NR$^{12}$C(=O)—,

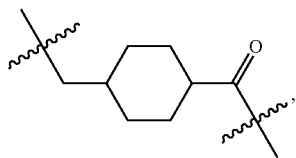

—((CH$_2$)$_m$O)$_n$(CH$_2$)$_m$—, —(CH$_2$)$_m$(O(CH$_2$)$_m$)$_n$—, —(CH$_2$)$_m$(O(CH$_2$)$_m$)$_n$X$_3$(CH$_2$)$_m$—, —(CH$_2$)$_m$X$_3$((CH$_2$)$_m$O)$_n$(CH$_2$)$_m$—, —(CH$_2$)$_m$X$_3$(CH$_2$)$_m$C(=O)—, —C(=O)(CH$_2$)$_m$X$_3$(CH$_2$)$_m$—, —(CH$_2$)$_m$X$_3$(CH$_2$)$_m$(O(CH$_2$)$_m$)$_n$C(=O)—, —C(=O)((CH$_2$)$_m$O)$_n$(CH$_2$)$_m$X$_3$(CH$_2$)$_m$—, —(CH$_2$)$_m$C(=O)NR$^{12}$(CH$_2$)$_m$C(=O)—, —C(=O)(CH$_2$)$_m$NR$^{12}$C(=O)O(CH$_2$)$_m$—, —(CH$_2$)$_m$OC(=O)NR$^{12}$(CH$_2$)$_m$C(=O)—, —S(=O)$_2$(CH$_2$)$_m$NR$^{12}$C(=O)O(CH$_2$)$_m$—, —(CH$_2$)$_m$OC(=O)NR$^{12}$(CH$_2$)$_m$S(=O)$_2$—, —(CH$_2$)$_m$C(=O)NR$^{12}$(CH$_2$)$_m$(O(CH$_2$)$_m$)$_n$C(=O)—, —C(=O)((CH$_2$)$_m$O)$_n$(CH$_2$)$_m$NR$^{12}$C(=O)(CH$_2$)$_m$—, —(CH$_2$)$_m$C(=O)NR$^{12}$(CH$_2$)$_m$C(=O)NR$^{12}$(CH$_2$)$_m$—, —(CH$_2$)$_m$NR$^{12}$C(=O)(CH$_2$)$_m$NR$^{12}$C(=O)(CH$_2$)$_m$—, —C(=O)NR$^{12}$(CH$_2$)$_m$S(=O)$_2$C(=O)—, —(CH$_2$)$_m$S(=O)$_2$—, —NR$^{12}$C(=O)(CH$_2$)$_m$—, —NR$^{12}$C(=O)(CH$_2$)$_m$X$_3$(CH$_2$)$_m$—, —(CH$_2$)$_m$X$_3$(CH$_2$)$_m$C(=O)NR$^{12}$—, —(CH$_2$)$_m$C(=O)NR$^{12}$—, —(CH$_2$)$_m$NR$^{12}$(CH$_2$)$_m$—, —(CH$_2$)$_m$X$_3$(CH$_2$)$_m$—, —((CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$—, —NR$^{12}$(CH$_2$)$_m$—, —NR$^{12}$C(R$^{12}$)$_2$(CH$_2$)$_m$—, —(CH$_2$)$_m$C(R$^{12}$)$_2$NR$^{12}$—, —(CH$_2$)$_m$C(=O)NR$^{12}$(CH$_2$)$_m$NR$^{12}$—, —NR$^{12}$(CH$_2$)$_m$NR$^{12}$C(=O)(CH$_2$)$_m$—, —NR$^{12}$C(R$^{12}$)$_2$(CH$_2$)$_m$NR$^{12}$C(=O)(CH$_2$)$_m$—, —(CH$_2$)$_m$C(=O)NR$^{12}$(CH$_2$)$_m$C(R$^{12}$)$_2$NR$^{12}$—, —NR$^{12}$(CH$_2$)$_m$X$_3$(CH$_2$)$_m$—, —NR$^{12}$C(R$^{12}$)$_2$(CH$_2$)$_m$X$_3$(CH$_2$)$_m$—, —(CH$_2$)$_m$X$_3$(CH$_2$)$_m$C(R$^{12}$)$_2$NR$^{12}$—, —NR$^{12}$C(R$^{12}$)$_2$(CH$_2$)$_m$OC(=O)NR$^{12}$(CH$_2$)$_m$—, —(CH$_2$)$_m$NR$^{12}$C(=O)O(CH$_2$)$_m$C(R$^{12}$)$_2$NR$^{12}$—, —NR$^{12}$C(R$^{12}$)$_2$(CH$_2$)$_m$OC(=O)NR$^{12}$(CH$_2$)$_m$X$_3$(CH$_2$)$_m$—, —NR$^{12}$(CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NR$^{12}$—, —NR$^{12}$(CH$_2$)$_m$O)$_n$(CH$_2$)$_m$—, —(CH$_2$)$_m$(O(CH$_2$)$_m$)$_n$NR$^{12}$—, —(CH$_2$)$_m$X$_3$(CH$_2$)$_m$NR$^{12}$C(=O)O(CH$_2$)$_m$C(R$^{12}$)$_2$NR$^{12}$—, —NR$^{12}$C(R$^{12}$)$_2$(CH$_2$)$_m$OC(=O)NR$^{12}$((CH$_2$)$_m$O)$_n$(CH$_2$)$_m$—, —(CH$_2$)$_m$(O(CH$_2$)$_m$)$_n$NR$^{12}$C(=O)O(CH$_2$)$_m$C(R$^{12}$)$_2$NR$^{12}$—, —NR$^{12}$C(R$^{12}$)$_2$(CH$_2$)$_m$OC(=O)NR$^{12}$((CH$_2$)$_m$O)$_n$(CH$_2$)$_m$X$_3$(CH$_2$)$_m$—, —(CH$_2$)$_m$X$_3$(CH$_2$)$_m$O(CH$_2$)$_m$)$_n$NR$^{12}$C(=O)O(CH$_2$)$_m$C(R$^{12}$)$_2$NR$^{12}$—, —(CH$_2$)$_m$X$_3$(CH$_2$)$_m$NR$^{12}$—, —NR$^{12}$((CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NR$^{12}$—, —(CH$_2$)$_m$NR$^{12}$—, —NR$^{12}$((CH$_2$)$_m$O)$_n$(CH$_2$)$_m$—, —NR$^{12}$((CH$_2$)$_m$O)$_n$(CH$_2$)$_m$NR$^{12}$—, —NR$^{12}$((CH$_2$)$_m$O)$_n$(CH$_2$)$_m$NR$^{12}$C(=O)(CH$_2$)$_m$—, —(CH$_2$)$_m$C(=O)NR$^{12}$(CH$_2$)$_m$O(CH$_2$)$_m$)$_n$NR$^{12}$—, —(CH$_2$)$_m$(O(CH$_2$)$_m$)$_n$NR$^{12}$—, —(C(R$_{12}$)$_m$)$_m$—, —(CH$_2$CH$_2$O)$_n$—, —(OCH$_2$CH$_2$)$_n$—, —(CH$_2$)$_m$O(CH$_2$)$_m$—, —S(=O)$_2$(CH$_2$)$_m$—, —(CH$_2$)$_m$S(=O)$_2$—, —S(=O)$_2$(CH$_2$)$_m$NR$^{12}$C(=O)(CH$_2$)$_m$—, —(CH$_2$)$_m$C(=O)NR$^{12}$(CH$_2$)$_m$S(=O)$_2$—, —S(=O)$_2$(CH$_2$)$_m$X$_3$(CH$_2$)$_m$—, —(CH$_2$)$_m$X$_3$(CH$_2$)$_m$S(=O)$_2$—, —(CH$_2$)$_m$X$_2$X$_1$C(=O)—, —C(=O)X$_1$X$_2$(CH$_2$)$_m$—, —(CH$_2$)$_m$(O(CH$_2$)$_m$)$_n$C(=O)X$_2$X$_1$C(=O)—, —C(=O)X$_1$X$_2$C(=O)((CH$_2$)$_m$O)$_n$(CH$_2$)$_m$—, —(CH$_2$)$_m$(O(CH$_2$)$_m$)$_n$X$_2$X$_1$C(=O)—, —(CH$_2$)$_m$X$_3$(CH$_2$)$_m$X$_2$X$_1$C(=O)—, —C(=O)X$_1$X$_2$(CH$_2$)$_m$X$_3$(CH$_2$)$_m$—, —(CH$_2$)$_m$X$_3$(CH$_2$)$_m$(O(CH$_2$)$_m$)$_n$X$_2$X$_1$C(=O)—, —(CH$_2$)$_m$X$_3$(CH$_2$)$_m$C(=O)NR$^{12}$(CH$_2$)$_m$NR$^{12}$C(=O)—, —(CH$_2$)$_m$X$_3$(CH$_2$)$_m$C(=O)NR$^{12}$(CH$_2$)$_m$C(=O)—, —C(=O)(CH$_2$)$_m$NR$^{12}$C(=O)(CH$_2$)$_m$X$_3$(CH$_2$)$_m$—, —(CH$_2$)$_m$X$_3$(CH$_2$)$_m$C(=O)NR$^{12}$(CH$_2$)$_m$(O(CH$_2$)$_m$)$_n$C(=O)—, —C(=O)((CH$_2$)$_m$O)$_n$(CH$_2$)$_m$NR$^{12}$C(=O)(CH$_2$)$_m$X$_3$(CH$_2$)$_m$—, —(CH$_2$)$_m$NR$^{12}$C(=O)X$_1$X$_2$C(=O)(CH$_2$)$_m$—, —(CH$_2$)$_m$C(=O)X$_2$X$_1$C(=O)NR$^{12}$(CH$_2$)$_m$—, —X$_4$X$_1$X$_2$C(=O)(CH$_2$)$_m$—, —(CH$_2$)$_m$C(=O)X$_2$X$_1$X$_4$—, —X$_1$C(=O)(CH$_2$)$_m$NHC(=O)(CH$_2$)$_m$—, —(CH$_2$)$_m$C(=O)NH(CH$_2$)$_m$C(=O)X$_1$—, —C(=O)CHR$^{aa}$NR$^{12}$—, —CHR$^{aa}$C(=O)—, —C(=O)NR$^{12}$—, —C(=O)O—, —S—, —SCH$_2$C(=O)NR$^{12}$—, —NR$^{12}$C(=O)CH$_2$S—, —S(=O)$_2$CH$_2$CH$_2$S—, —SCH$_2$CH$_2$S(=O)$_2$—, —(CH$_2$)$_2$S(=O)$_2$CH$_2$CH$_2$S—, —SCH$_2$CH$_2$S(=O)$_2$CH$_2$CH$_2$—, —NR$^{12}$C(=S)—, —(CH$_2$)$_m$X$_3$(O(CH$_2$)$_m$)$_n$C(=O)—, —C(=O)((CH$_2$)$_m$O)$_n$X$_3$(CH$_2$)$_m$—, —(CH$_2$)$_m$NR$^{12}$C(=O)((CH$_2$)$_m$O)$_n$(CH$_2$)$_m$—, —(CH$_2$)$_m$(O(CH$_2$)$_m$)$_n$C(=O)NR$^{12}$(CH$_2$)$_m$—, —(CH$_2$)$_m$NR$^{12}$C(=O)NR$^{12}$(CH$_2$)$_m$—, —(CH$_2$)$_m$X$_3$(CH$_2$)$_m$NR$^{12}$C(=O)—, —C(=O)NR$^{12}$(CH$_2$)$_m$X$_3$(CH$_2$)$_m$—, —NR$_{12}$S(=O)$_2$(CH$_2$)$_m$X$_3$(CH$_2$)$_m$—, —(CH$_2$)$_m$X$_3$(CH$_2$)$_m$S(=O)$_2$NR$_{12}$—,

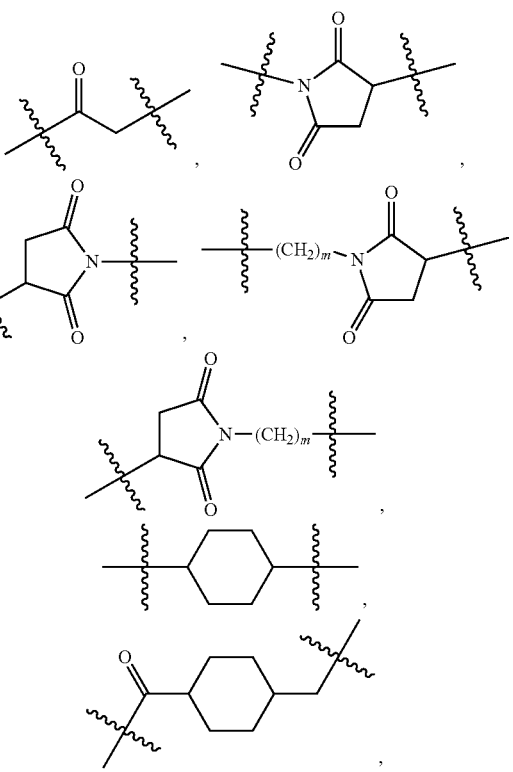

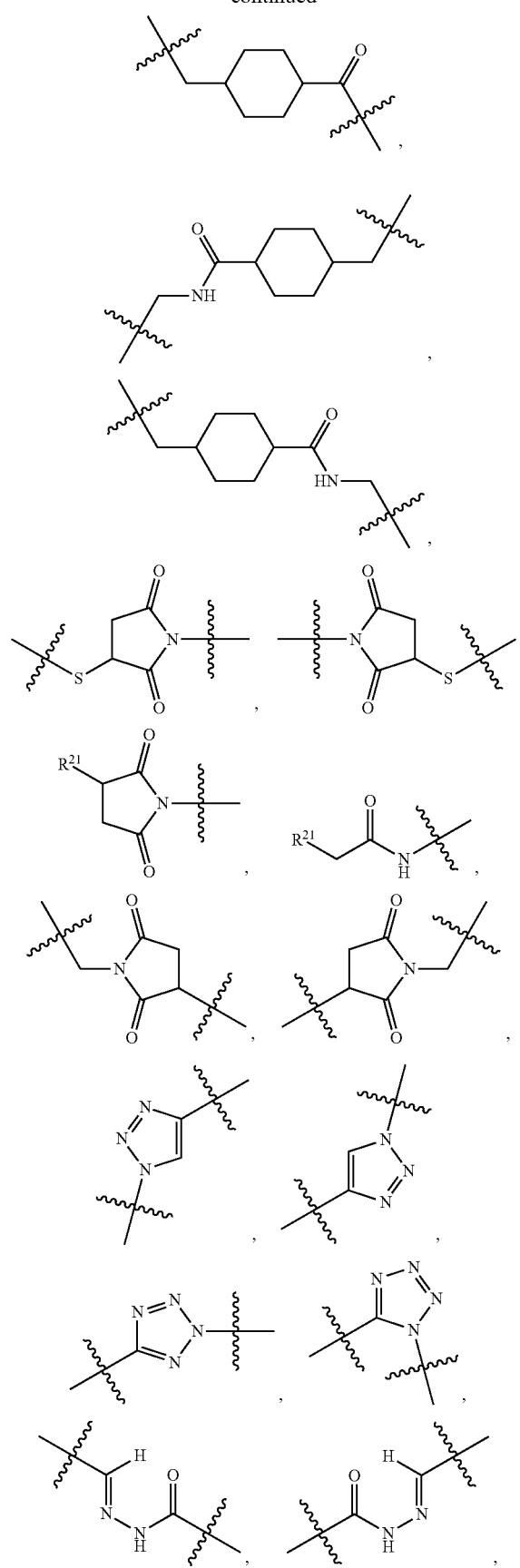
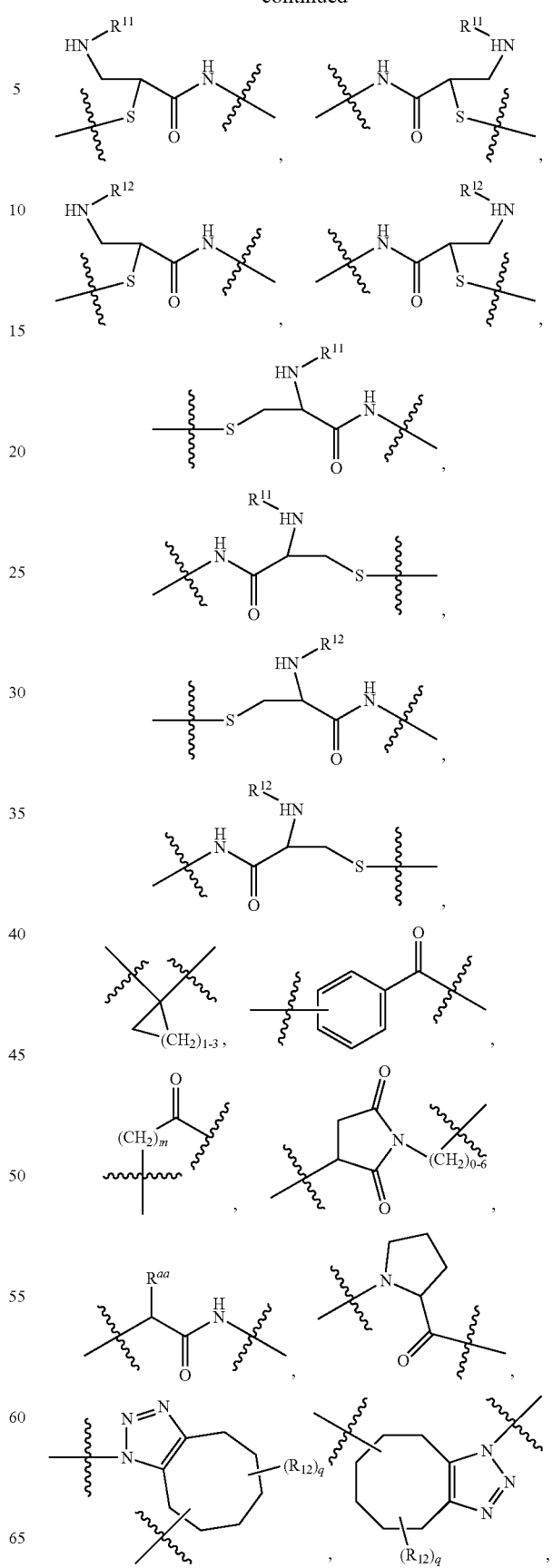

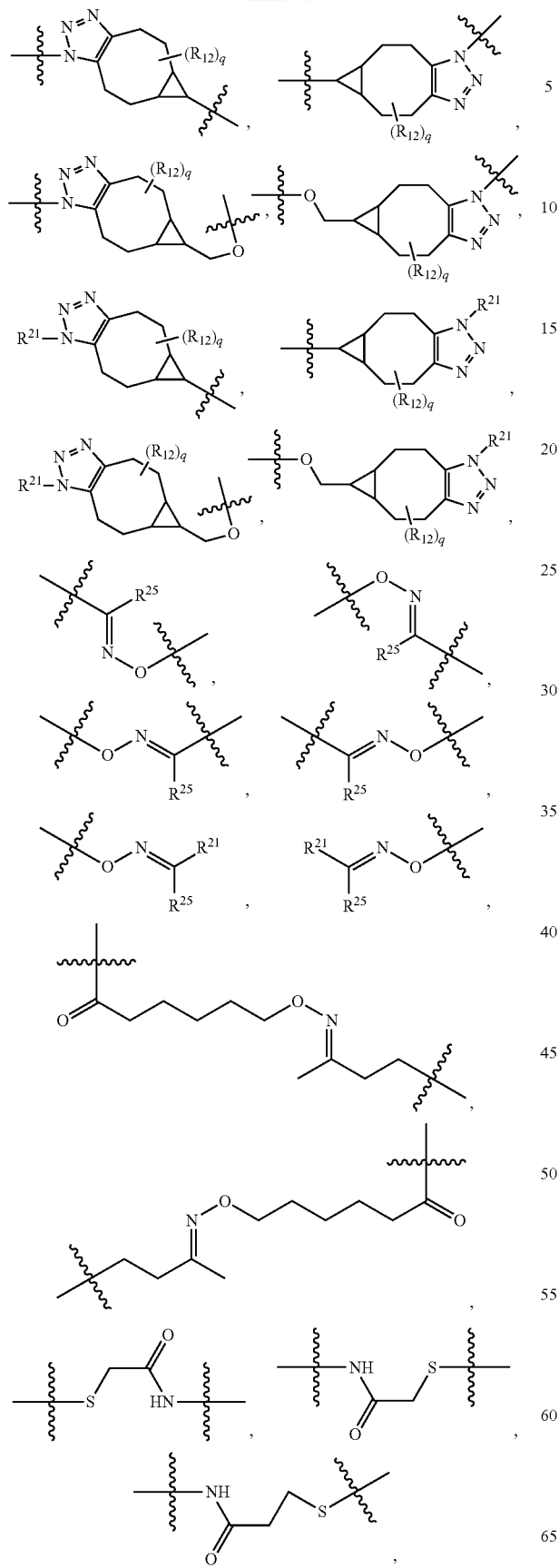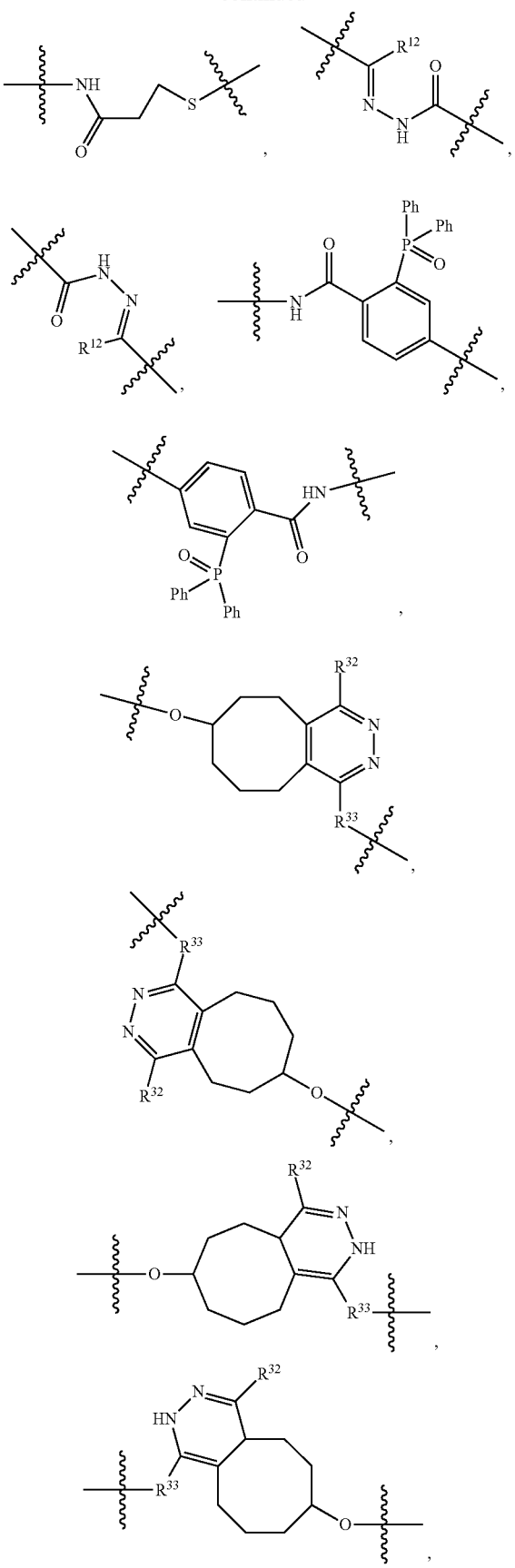

377
-continued
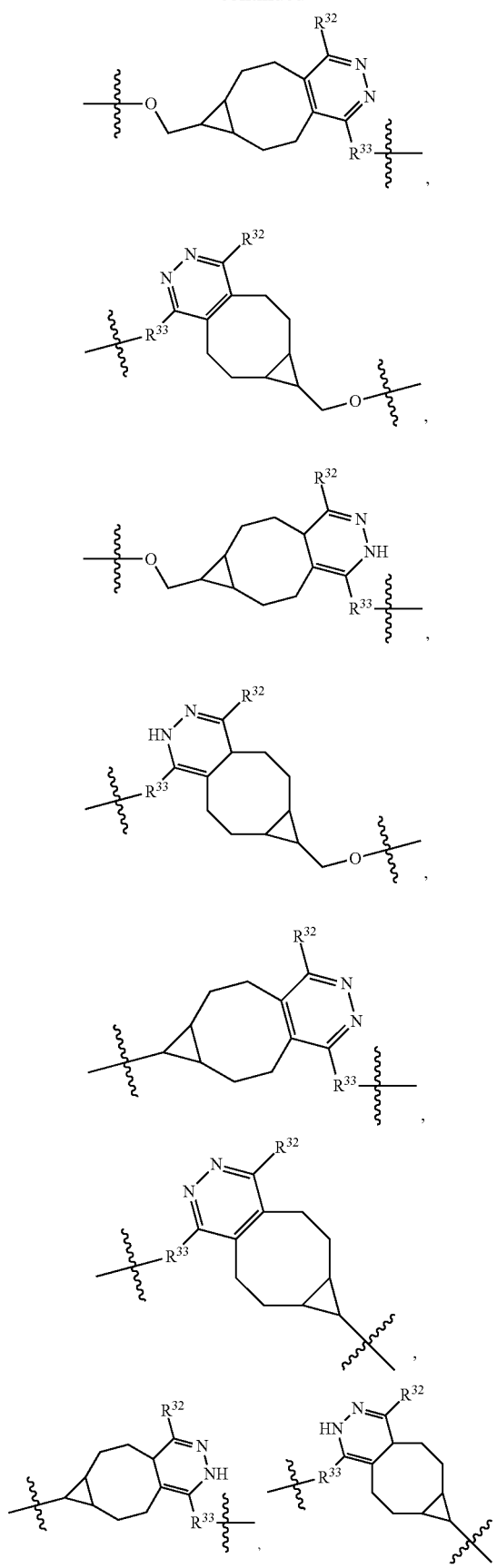
378
-continued
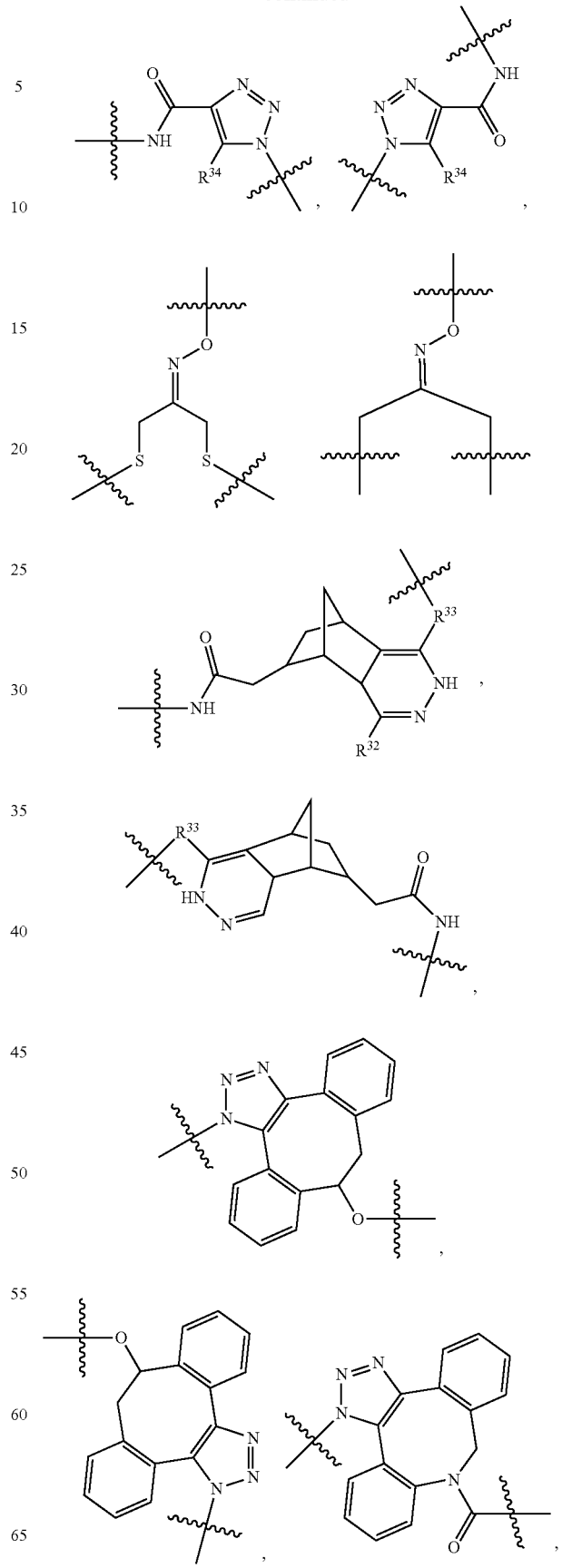

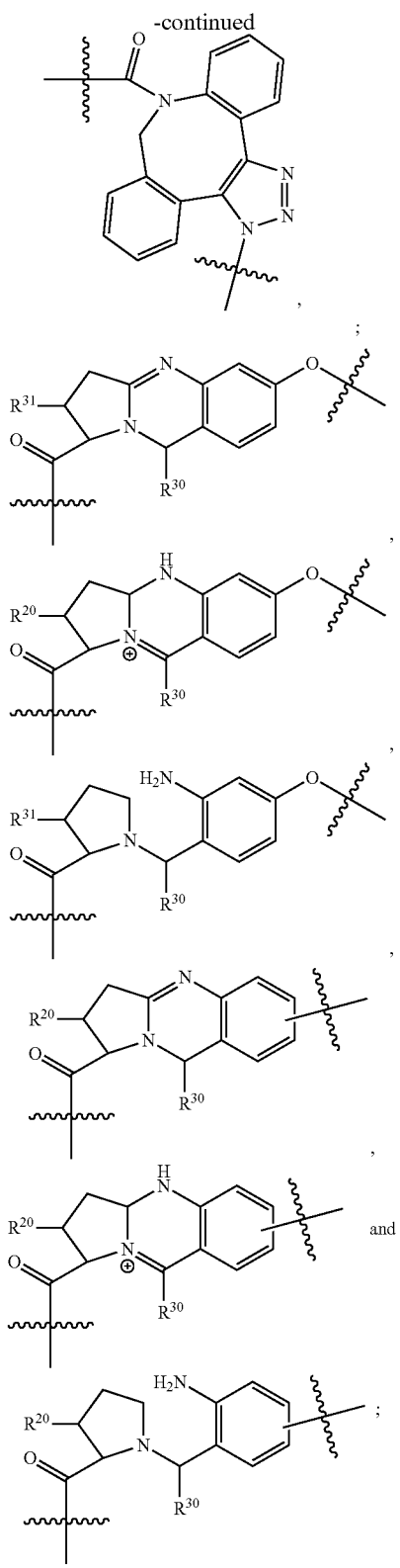

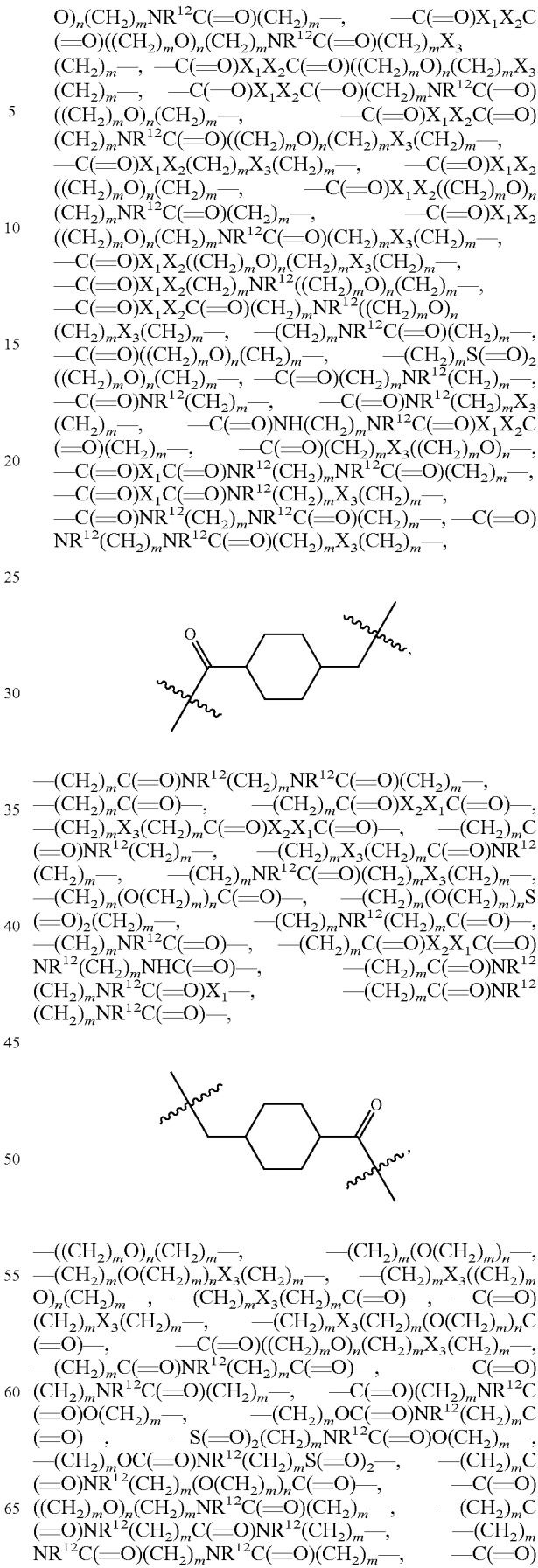

$L_2$, $L_3$, $L_4$, $L_5$, and $L_6$ are each independently selected from a bond, —$(CH_2)_m$—, —$C(=O)(CH_2)_m$—, —$C(=O)X_1X_2C(=O)(CH_2)_m$—, —$C(=O)X_1X_2C(=O)(CH_2)_mNR^{12}C(=O)(CH_2)_m$—, —$C(=O)X_1X_2C(=O)(CH_2)_mX_3(CH_2)_m$—, —$C(=O)X_1X_2C(=O)((CH_2)_mO)_n(CH_2)_m$—, —$C(=O)X_1X_2C(=O)((CH_2)_mO)_n(CH_2)_mNR^{12}C(=O)(CH_2)_m$—, —$C(=O)X_1X_2C(=O)((CH_2)_mO)_n(CH_2)_mNR^{12}C(=O)(CH_2)_mX_3(CH_2)_m$—, —$C(=O)X_1X_2C(=O)(CH_2)_mX_3(CH_2)_m$—, —$C(=O)X_1X_2C(=O)(CH_2)_mNR^{12}C(=O)((CH_2)_mO)_n(CH_2)_m$—, —$C(=O)X_1X_2C(=O)(CH_2)_mNR^{12}C(=O)((CH_2)_mO)_n(CH_2)_mX_3(CH_2)_m$—, —$C(=O)X_1X_2(CH_2)_mX_3(CH_2)_m$—, —$C(=O)X_1X_2((CH_2)_mO)_n(CH_2)_m$—, —$C(=O)X_1X_2((CH_2)_mO)_n(CH_2)_mNR^{12}C(=O)(CH_2)_m$—, —$C(=O)X_1X_2((CH_2)_mO)_n(CH_2)_mNR^{12}C(=O)(CH_2)_mX_3(CH_2)_m$—, —$C(=O)X_1X_2((CH_2)_mO)_n(CH_2)_mX_3(CH_2)_m$—, —$C(=O)X_1X_2(CH_2)_mNR^{12}((CH_2)_mO)_n(CH_2)_m$—, —$C(=O)X_1X_2C(=O)(CH_2)_mNR^{12}((CH_2)_mO)_n(CH_2)_mX_3(CH_2)_m$—, —$(CH_2)_mNR^{12}C(=O)(CH_2)_m$—, —$C(=O)((CH_2)_mO)_n(CH_2)_m$—, —$(CH_2)_mS(=O)_2((CH_2)_mO)_n(CH_2)_m$—, —$C(=O)(CH_2)_mNR^{12}(CH_2)_m$—, —$C(=O)NR^{12}(CH_2)_m$—, —$C(=O)NR^{12}(CH_2)_mX_3(CH_2)_m$—, —$C(=O)NH(CH_2)_mNR^{12}C(=O)X_1X_2C(=O)(CH_2)_m$—, —$C(=O)(CH_2)_mX_3((CH_2)_mO)_n$—, —$C(=O)X_1C(=O)NR^{12}(CH_2)_mNR^{12}C(=O)(CH_2)_m$—, —$C(=O)X_1C(=O)NR^{12}(CH_2)_mX_3(CH_2)_m$—, —$C(=O)NR^{12}(CH_2)_mNR^{12}C(=O)(CH_2)_m$—, —$C(=O)NR^{12}(CH_2)_mNR^{12}C(=O)(CH_2)_mX_3(CH_2)_m$—, —$(CH_2)_mC(=O)NR^{12}(CH_2)_mNR^{12}C(=O)(CH_2)_m$—, —$(CH_2)_mC(=O)$—, —$(CH_2)_mC(=O)X_2X_1C(=O)$—, —$(CH_2)_mX_3(CH_2)_mC(=O)X_2X_1C(=O)$—, —$(CH_2)_mC(=O)NR^{12}(CH_2)_m$—, —$(CH_2)_mX_3(CH_2)_mC(=O)NR^{12}(CH_2)_m$—, —$(CH_2)_mNR^{12}C(=O)(CH_2)_mX_3(CH_2)_m$—, —$(CH_2)_m(O(CH_2)_m)_nC(=O)$—, —$(CH_2)_m(O(CH_2)_m)_nS(=O)_2(CH_2)_m$—, —$(CH_2)_mNR^{12}(CH_2)_mC(=O)$—, —$(CH_2)_mNR^{12}C(=O)$—, —$(CH_2)_mC(=O)X_2X_1C(=O)NR^{12}(CH_2)_mNHC(=O)$—, —$(CH_2)_mC(=O)NR^{12}(CH_2)_mNR^{12}C(=O)X_1$—, —$(CH_2)_mC(=O)NR^{12}(CH_2)_mNR^{12}C(=O)$—, —$((CH_2)_mO)_n(CH_2)_m$—, —$(CH_2)_m(O(CH_2)_m)_n$—, —$(CH_2)_m(O(CH_2)_m)_nX_3(CH_2)_m$—, —$(CH_2)_mX_3((CH_2)_mO)_n(CH_2)_m$—, —$(CH_2)_mX_3(CH_2)_mC(=O)$—, —$C(=O)(CH_2)_mX_3(CH_2)_m$—, —$(CH_2)_mX_3(CH_2)_m(O(CH_2)_m)_nC(=O)$—, —$C(=O)((CH_2)_mO)_n(CH_2)_mX_3(CH_2)_m$—, —$(CH_2)_mC(=O)NR^{12}(CH_2)_mC(=O)$—, —$C(=O)(CH_2)_mNR^{12}C(=O)(CH_2)_m$—, —$C(=O)(CH_2)_mNR^{12}C(=O)O(CH_2)_m$—, —$(CH_2)_mOC(=O)NR^{12}(CH_2)_mC(=O)$—, —$S(=O)_2(CH_2)_mNR^{12}C(=O)O(CH_2)_m$—, —$(CH_2)_mOC(=O)NR^{12}(CH_2)_mS(=O)_2$—, —$(CH_2)_mC(=O)NR^{12}(CH_2)_m(O(CH_2)_m)_nC(=O)$—, —$C(=O)((CH_2)_mO)_n(CH_2)_mNR^{12}C(=O)NR^{12}(CH_2)_m$—, —$(CH_2)_mC(=O)NR^{12}(CH_2)_mC(=O)NR^{12}(CH_2)_m$—, —$(CH_2)_mNR^{12}C(=O)(CH_2)_mNR^{12}C(=O)(CH_2)_m$—, —$C(=O)

$-NR^{12}(CH_2)_m NR^{12}C(=O)-$, $-(CH_2)_m S(CH_2)_m-$, $-NR^{12}C(=O)(CH_2)_m-$, $-NR^{12}C(=O)(CH_2)_m X_3(CH_2)_m-$, $-(CH_2)_m X_3(CH_2)_m C(=O)NR^{12}-$, $-(CH_2)_m C(=O)NR^{12}-$, $-(CH_2)_m NR^{12}(CH_2)_m-$, $-(CH_2)_m X_3(CH_2)_m-$, $-((CH_2)_m O)_n (CH_2)_m X_3 (CH_2)_m-$, $-(CH_2)_m X_3 (CH_2)_m (O(CH_2)_m)_n-$, $-NR^{12}(CH_2)_m-$, $-NR^{12}C(R^{12})_2(CH_2)_m-$, $-(CH_2)_m C(R^{12})_2 NR^{12}-$, $-(CH_2)_m C(=O)NR^{12}(CH_2)_m NR^{12}-$, $-NR^{12}(CH_2)_m NR^{12}C(=O)(CH_2)_m-$, $-NR^{12}C(R^{12})_2(CH_2)_m NR^{12}C(=O)(CH_2)_m-$, $-(CH_2)_m C(=O)NR^{12}(CH_2)_m C(R^{12})_2 NR^{12}-$, $-NR^{12}(CH_2)_m X_3(CH_2)_m-$, $-NR^{12}C(R^{12})_2(CH_2)_m X_3(CH_2)_m-$, $-(CH_2)_m X_3(CH_2)_m C(R^{12})_2 NR^{12}-$, $-NR^{12}C(R^{12})_2 (CH_2)_m OC(=O)NR^{12}(CH_2)_m-$, $-(CH_2)_m C(=O)O(CH_2)_m C(R^{12})_2 NR^{12}-$, $-NR^{12}C(R^{12})_2(CH_2)_m OC(=O)NR^{12}(CH_2)_m X_3(CH_2)_m-$, $-(CH_2)_m X_3(CH_2)_m (O(CH_2)_m)_n NR^{12}-$, $-NR^{12}(CH_2)_m O)_n(CH_2)_m-$, $-(CH_2)_m (O(CH_2)_m)_n NR^{12}-$, $-(CH_2)_m X_3(CH_2)_m NR^{12}C(=O)O(CH_2)_m C(R^{12})_2 NR^{12}-$, $-NR^{12}C(R^{12})_2(CH_2)_m OC(=O)NR^{12}((CH_2)_m O)_n(CH_2)_m-$, $-(CH_2)_m (O(CH_2)_m)_n NR^{12}C(=O)O(CH_2)_m C(R^{12})_2 NR^{12}-$, $-NR^{12}C(R^{12})_2(CH_2)_m OC(=O)NR^{12}((CH_2)_m O)_n(CH_2)_m X_3(CH_2)_m-$, $-(CH_2)_m X_3(CH_2)_m (O(CH_2)_m)_n NR^{12}C(=O)O(CH_2)_m C(R^{12})_2 NR^{12}-$, $-(CH_2)_m X_3(CH_2)_m NR^{12}-$, $-(CH_2)_m X_3(CH_2)_m (O(CH_2)_m)_n NR^{12}-$, $-(CH_2)_m NR^{12}-$, $-NR^{12}((CH_2)_m O)_n(CH_2)_m-$, $-NR^{12}((CH_2)_m O)_n(CH_2)_m NR^{12}C(=O)(CH_2)_m-$, $-(CH_2)_m C(=O)NR^{12}(CH_2)_m (O(CH_2)_m)_n NR^{12}-$, $-(CH_2)_m (O(CH_2)_m)_n NR^{12}-$, $-(C(R_{12})_2)_m-$, $-(CH_2CH_2O)_n-$, $-(OCH_2CH_2)_n-$, $-(CH_2)_m O(CH_2)_m-$, $-S(=O)_2(CH_2)_m-$, $-(CH_2)_m S(=O)_2-$, $-S(=O)_2(CH_2)_m NR^{12}C(=O)(CH_2)_m-$, $-(CH_2)_m C(=O)NR^{12}(CH_2)_m S(=O)_2-$, $-S(=O)_2(CH_2)_m X_3(CH_2)_m-$, $-(CH_2)_m X_3(CH_2)_m S(=O)_2-$, $-(CH_2)_m X_2 X_1 C(=O)-$, $-(CH_2)_m X_2 X_1 C(=O)(CH_2)_m-$, $-(CH_2)_m (O(CH_2)_m)_n C(=O)X_2 X_1 C(=O)-$, $-C(=O)X_1 X_2 C(=O)((CH_2)_m O)_n(CH_2)_m-$, $-(CH_2)_m (O(CH_2)_m)_n X_2 X_1 C(=O)-$, $-(CH_2)_m X_3(CH_2)_m X_2 X_1 C(=O)-$, $-C(=O)X_1 X_2 (CH_2)_m X_3(CH_2)_m-$, $-(CH_2)_m X_3 (CH_2)_m (O(CH_2)_m)_n X_2 X_1 C(=O)-$, $-(CH_2)_m X_3 (CH_2)_m C(=O)NR^{12}(CH_2)_m NR^{12}C(=O)-$, $-(CH_2)_m X_3 (CH_2)_m C(=O)NR^{12}(CH_2)_m C(=O)-$, $-C(=O)(CH_2)_m NR^{12}C(=O(CH_2)_m X_3(CH_2)_m-$, $-(CH_2)_m X_3(CH_2)_m C(=O)NR^{12}(CH_2)_m (O(CH_2)_m)_n C(=O)-$, $-C(=O)((CH_2)_m O)_n (CH_2)_m NR^{12}C(=O)(CH_2)_m X_3(CH_2)_m-$, $-(CH_2)_m NR^{12}C(=O)X_1 X_2 C(=O)(CH_2)_m-$, $-(CH_2)_m C(=O)X_2 X_1 C(=O)NR^{12}(CH_2)_m-$, $-X_4 X_1 X_2 C(=O)(CH_2)_m-$, $-(CH_2)_m C(=O)X_2 X_1 X_4-$, $-X_1 C(=O)(CH_2)_m NHC(=O)(CH_2)_m-$, $-(CH_2)_m C(=O)NH(CH_2)_m C(=O)X_1-$, $-C(=O)CHR^{aa}NR^{12}-$, $-CHR^{aa}C(=O)-$, $-C(=O)NR^{12}-$, $-C(=O)O-$, $-S-$, $-SCH_2C(=O)NR^{12}-$, $-NR^{12}C(=O)CH_2S-$, $-S(=O)_2CH_2CH_2S-$, $-SCH_2C(=O)_2-$, $-(CH_2)_2S(=O)_2CH_2CH_2S-$, $-SCH_2CH_2S(=O)_2CH_2CH_2-$, $-NR^{12}C(=S)-$, $-(CH_2)_m X_3(O(CH_2)_n C(=O)-$, $-C(=O)((CH_2)_m O)_n X_3(CH_2)_m-$, $-(CH_2)_m NR^{12}C(=O)((CH_2)_m O)_n(CH_2)_m-$, $-(CH_2)_m (O(CH_2)_m)_n C(=O)NR^{12}(CH_2)_m-$, $-(CH_2)_m NR^{12}C(=O)NR^{12}(CH_2)_m-$, $-(CH_2)_m X_3(CH_2)_m NR^{12}C(=O)-$, $-C(=O)NR^{12}(CH_2)_m X_3(CH_2)_m-$, $-NR_{12}S(=O)_2(CH_2)_m X_3(CH_2)_m-$, $-(CH_2)_m X_3(CH_2)_m S(=O)_2 NR_{12}-$,

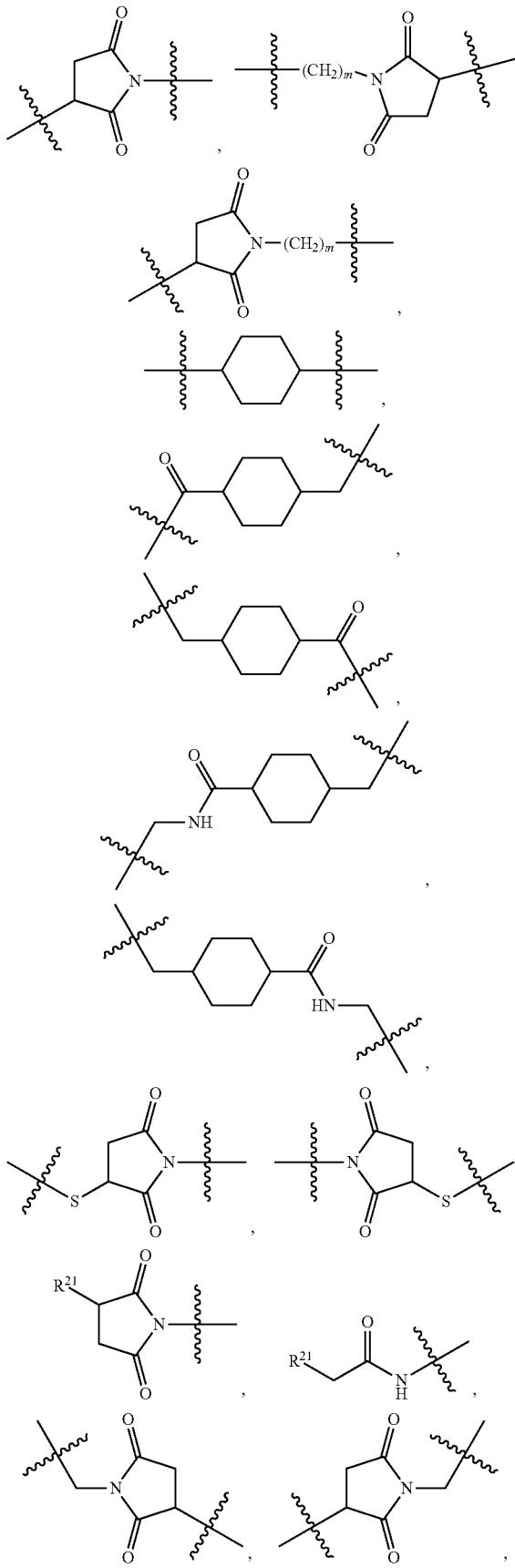

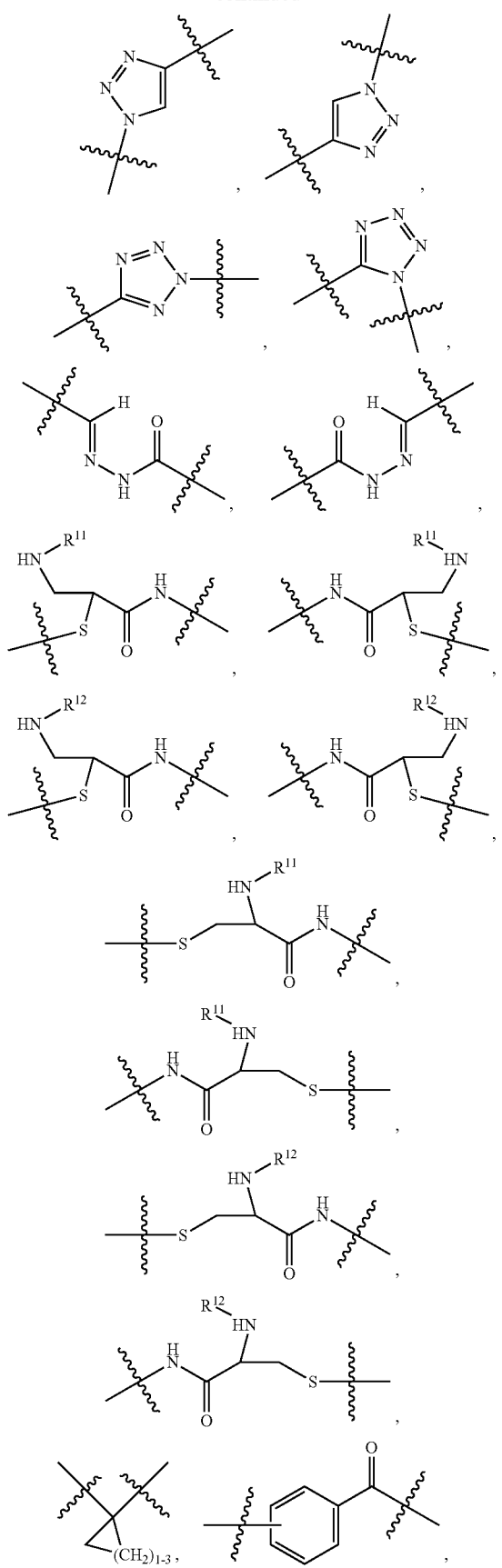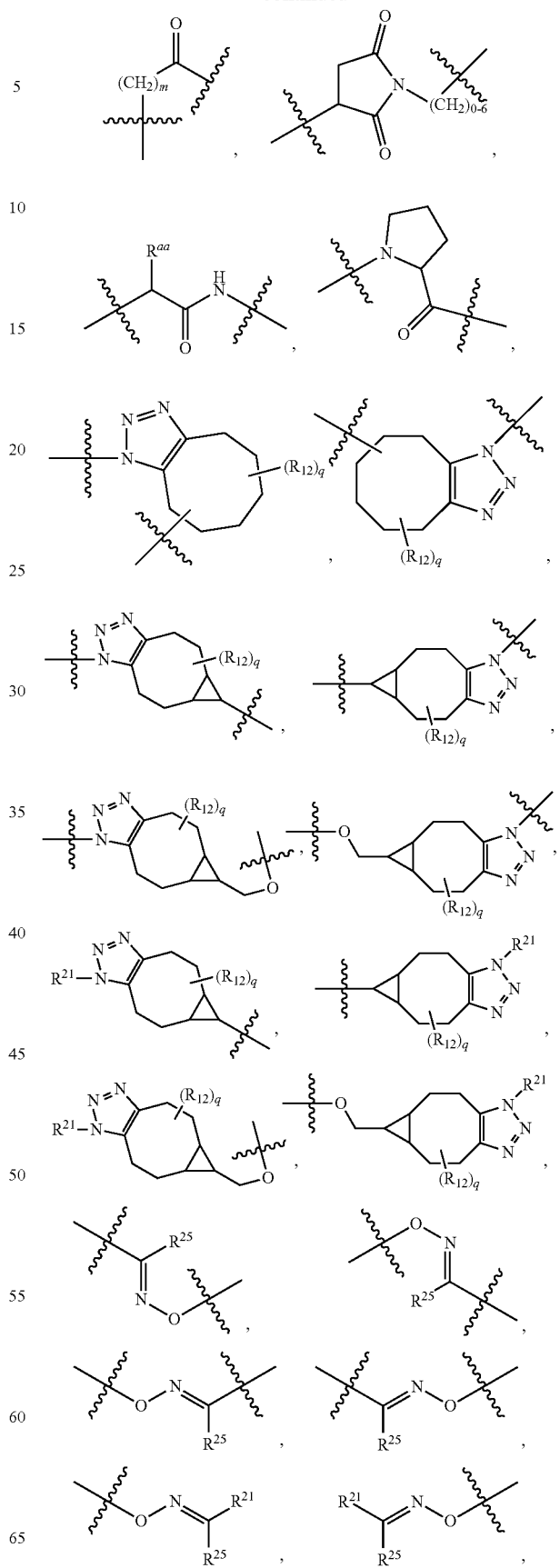

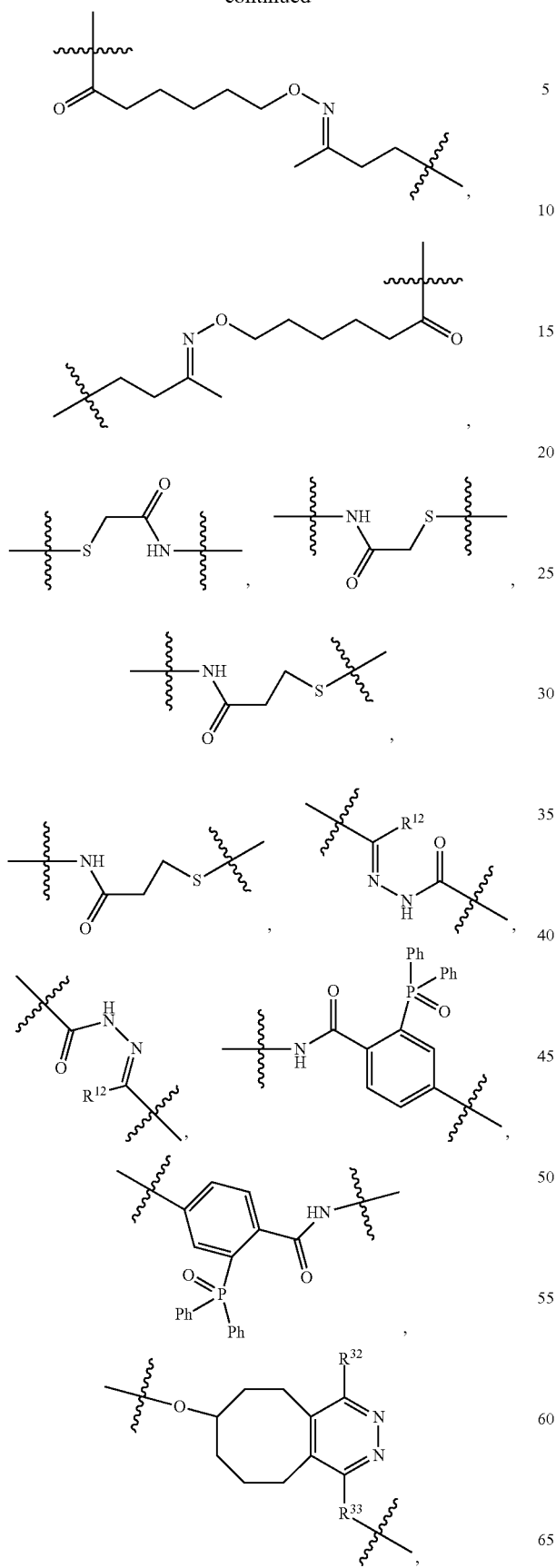
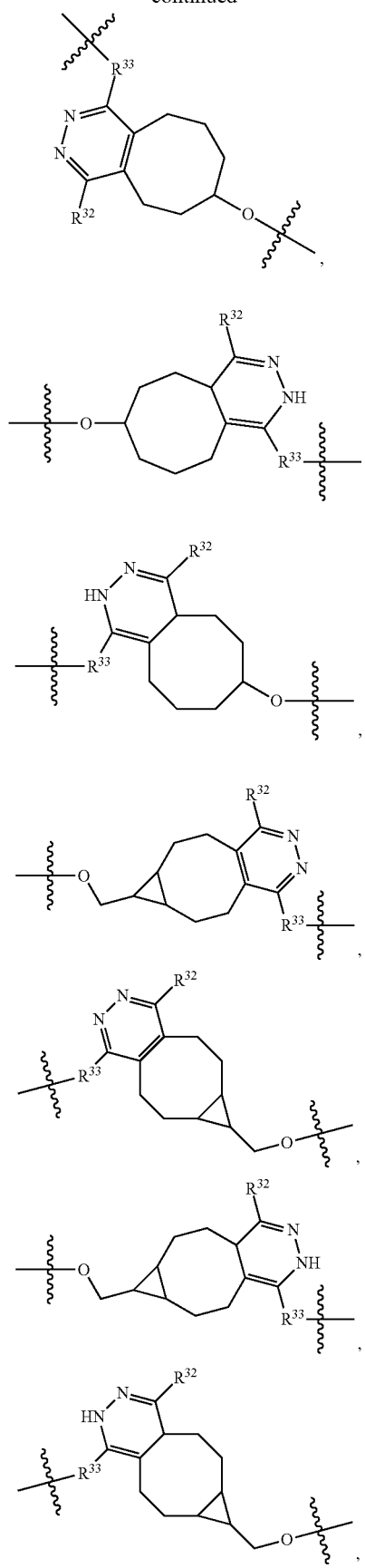

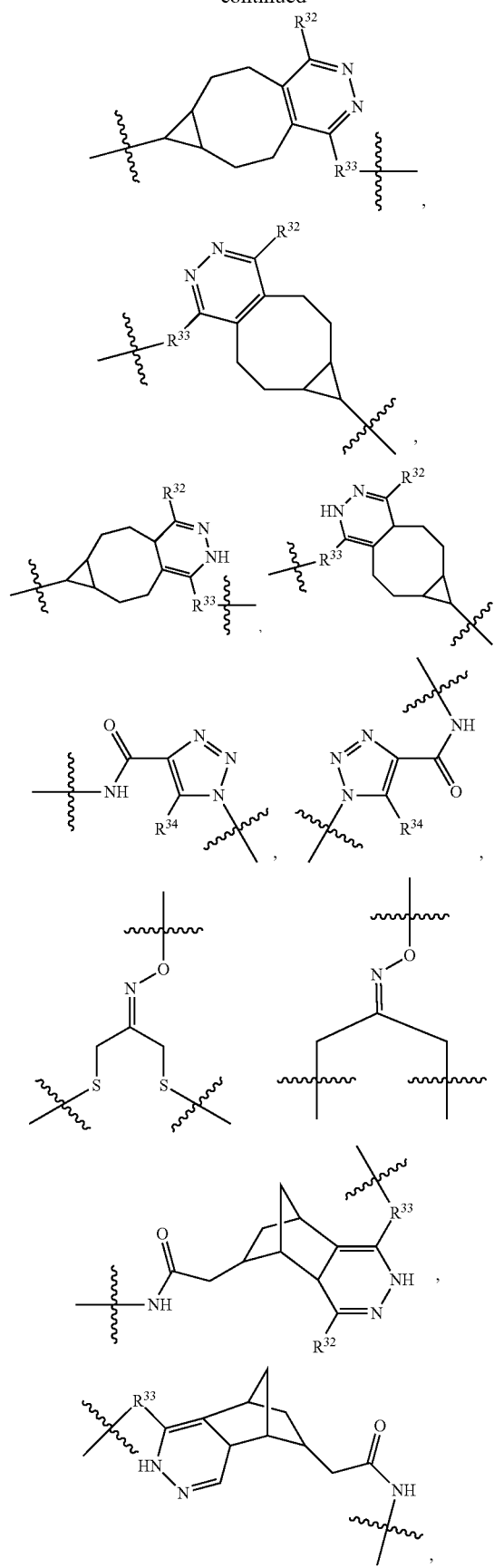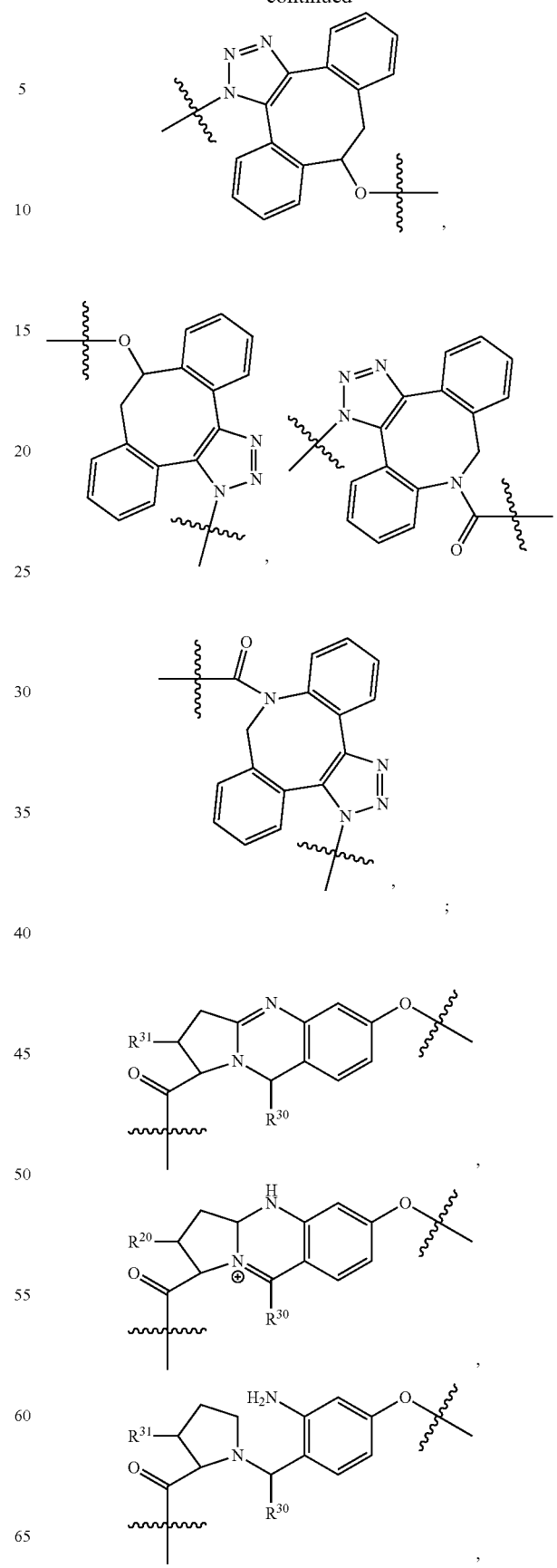

389
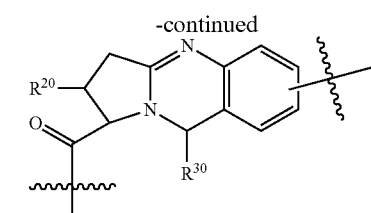
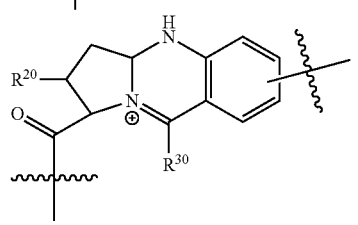
390
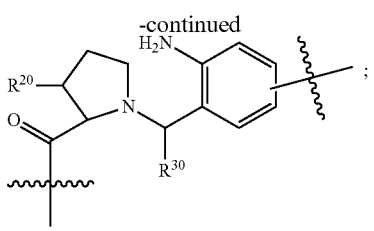
wherein:
R²⁰ is H or Me, and R³⁰ is H, —CH₃ or phenyl;
R²¹ is
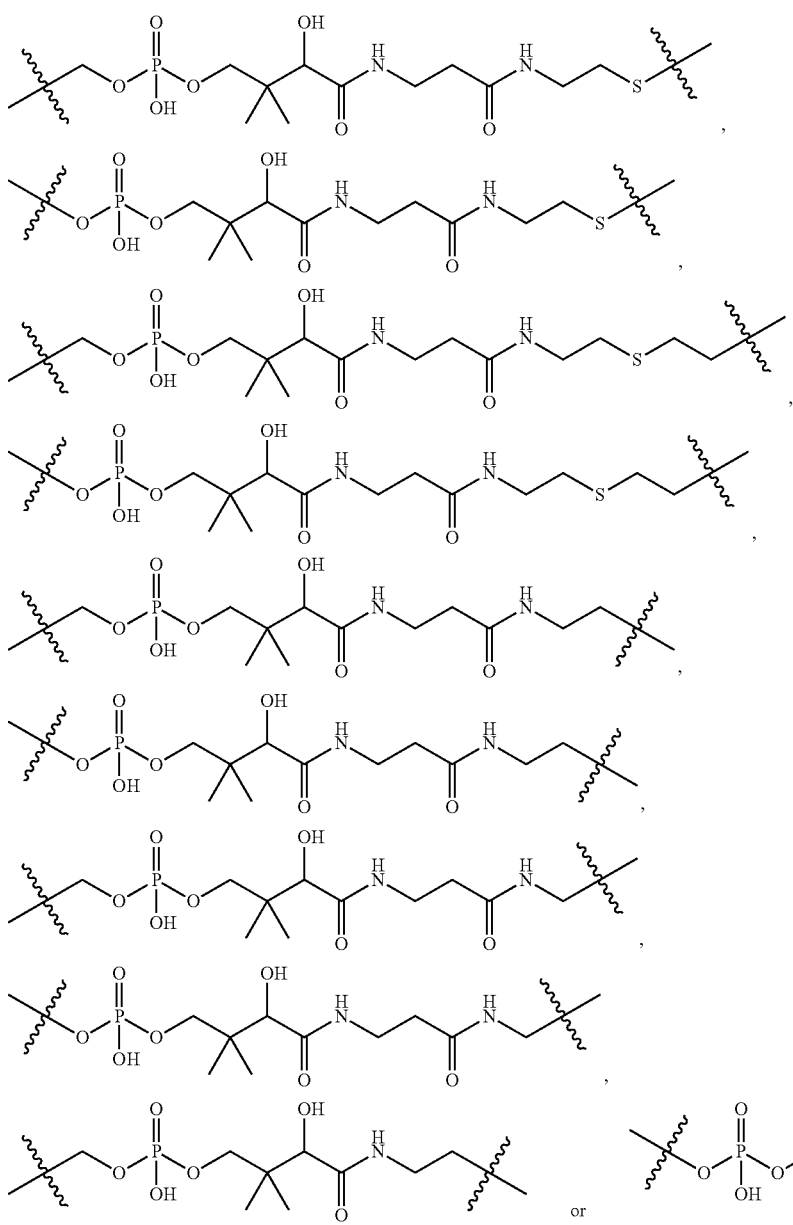

each $R^{25}$ is independently selected from H or $C_{1-4}$ alkyl;

$R^{aa}$ is a side chain of an amino acid selected from glycine, alanine, tryptophan, tyrosine, phenylalanine, leucine, isoleucine, valine, asparagine, glutamic acid, glutamine, aspatic acid, histidine, arginine, lysine, cysteine, methionine, serine, threonine, phenylglycine and t-butylglycine;

$R^{32}$ is independently selected from H, $C_{1-4}$ alkyl, phenyl, pyrimidine and pyridine;

$R^{33}$ is independently selected from

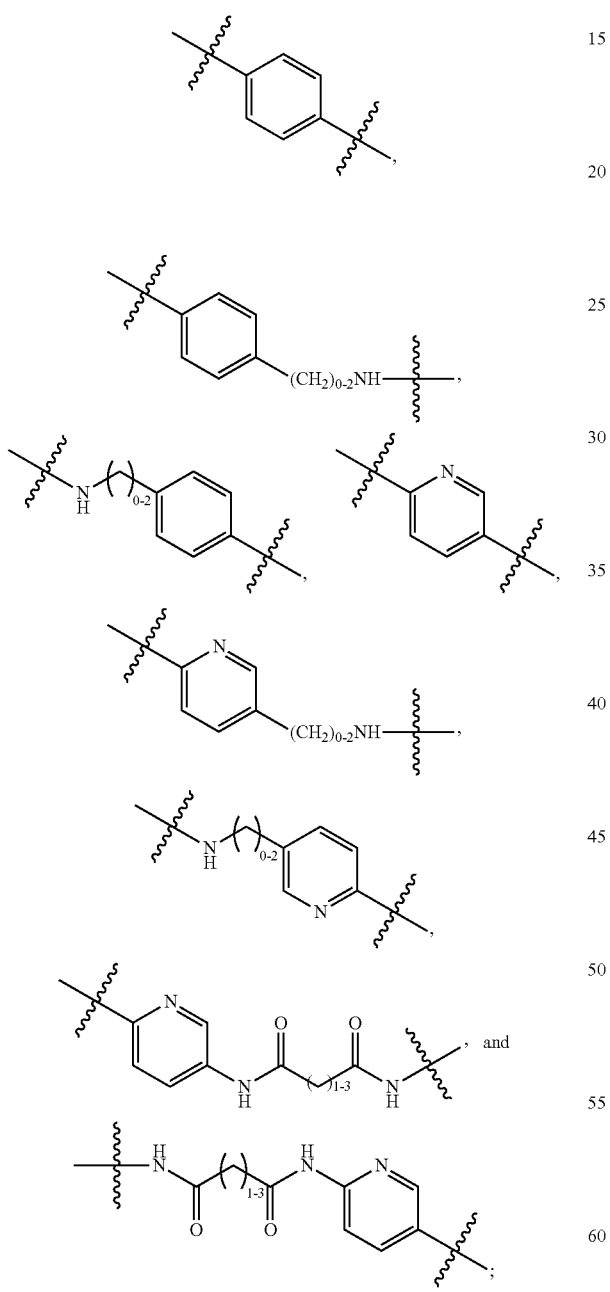

and $R^{34}$ is independently selected from H, $C_{1-4}$ alkyl, and $C_{1-6}$ haloalkyl;

$X_1$ is self immolative spacer selected from

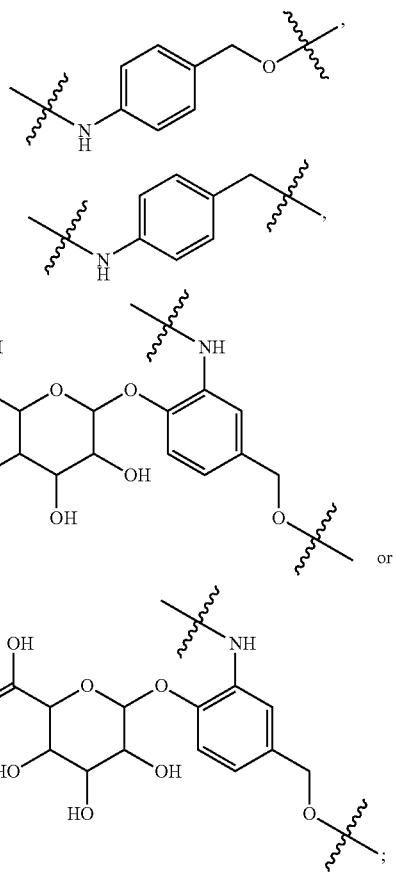

$X_2$ is dipeptide selected from

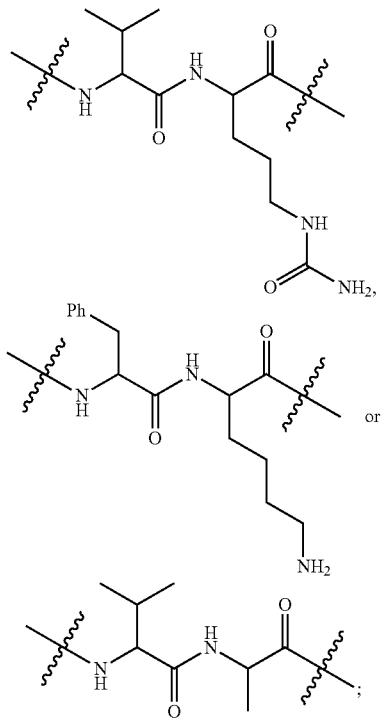

$X_3$ is

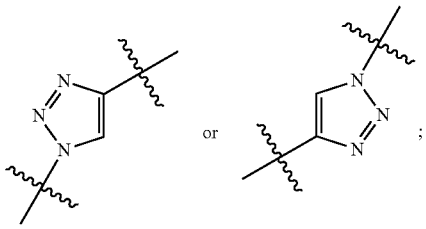 [SMILES: *c1cn(*)nn1 ; *c1cn(*)nn1]

or and $X_4$ is

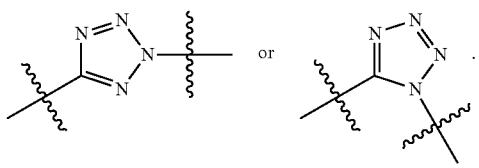 [SMILES: *c1nnn(*)n1 ; *c1nnnn1*]

or .

Embodiment 82. The compound of any one of embodiments 3 to 45 and 78 to 80, and the immunoconjugate according to any one of embodiments 46 to 80, wherein
$L_1$ is selected from —$(CH_2)_m$—, —$C(=O)(CH_2)_m$—, —$C(=O)X_1X_2C(=O)(CH_2)_m$—, —$C(=O)X_1X_2C(=O)(CH_2)_mNR^{12}C(=O)(CH_2)_m$—, —$C(=O)X_1X_2C(=O)(CH_2)_mX_3(CH_2)_m$—, —$C(=O)X_1X_2C(=O)((CH_2)_mO)_n(CH_2)_m$—, —$C(=O)X_1X_2C(=O)((CH_2)_mO)_n(CH_2)_mNR^{12}C(=O)(CH_2)_m$—, —$C(=O)X_1X_2C(=O)((CH_2)_mO)_n(CH_2)_mNR^{12}C(=O)(CH_2)_mX_3(CH_2)_m$—, —$C(=O)X_1X_2C(=O)((CH_2)_mO)_n(CH_2)_mX_3(CH_2)_m$—, —$C(=O)X_1X_2C(=O)(CH_2)_mNR^{12}C(=O)((CH_2)_mO)_n(CH_2)_m$—, —$C(=O)X_1X_2C(=O)((CH_2)_mO)_n(CH_2)_mNR^{12}C(=O)((CH_2)_mO)_n(CH_2)_mX_3(CH_2)_m$—, —$C(=O)X_1X_2(CH_2)_mX_3(CH_2)_m$—, —$C(=O)X_1X_2((CH_2)_mO)_n(CH_2)_m$—, —$C(=O)X_1X_2((CH_2)_mO)_n(CH_2)_mNR^{12}C(=O)(CH_2)_m$—, —$C(=O)X_1X_2((CH_2)_mO)_n(CH_2)_mNR^{12}C(=O)(CH_2)_mX_3(CH_2)_m$—, —$C(=O)X_1X_2((CH_2)_mO)_n(CH_2)_mX_3(CH_2)_m$—, —$C(=O)X_1X_2(CH_2)_mNR^{12}((CH_2)_mO)_n(CH_2)_m$—, —$C(=O)X_1X_2C(=O)(CH_2)_mNR^{12}((CH_2)_mO)_n(CH_2)_mX_3(CH_2)_m$—, —$(CH_2)_mNR^{12}C(=O)(CH_2)_m$—, —$C(=O)((CH_2)_mO)_n(CH_2)_m$—, —$(CH_2)_mS(=O)_2((CH_2)_mO)_n(CH_2)_m$—, —$C(=O)(CH_2)_mNR^{12}(CH_2)_m$—, —$C(=O)NR^{12}(CH_2)_m$—, —$C(=O)NR^{12}(CH_2)_mX_3(CH_2)_m$—, —$C(=O)NH(CH_2)_mNR^{12}C(=O)X_1X_2C(=O)(CH_2)_m$—, —$C(=O)X_1C(=O)NR^{12}(CH_2)_mNR^{12}C(=O)(CH_2)_m$—, —$C(=O)X_1C(=O)NR^{12}(CH_2)_mX_3(CH_2)_m$—, —$C(=O)NR^{12}(CH_2)_mNR^{12}C(=O)(CH_2)_m$—, —$C(=O)NR^{12}(CH_2)_mNR^{12}C(=O)(CH_2)_mX_3(CH_2)_m$—,

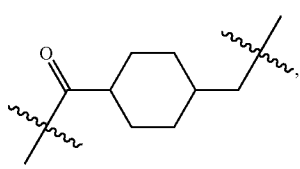

—$(CH_2)_mC(=O)NR^{12}(CH_2)_mNR^{12}C(=O)(CH_2)_m$—, —$(CH_2)_mC(=O)$—, —$(CH_2)_mC(=O)X_2X_1C(=O)$—, —$(CH_2)_mX_3(CH_2)_mC(=O)X_2X_1C(=O)$—, —$(CH_2)_mC(=O)NR^{12}(CH_2)_m$—, —$(CH_2)_mX_3(CH_2)_mC(=O)NR^{12}(CH_2)_m$—, —$(CH_2)_mNR^{12}C(=O)(CH_2)_mX_3(CH_2)_m$—, —$(CH_2)_m(O(CH_2)_m)_nC(=O)$—, —$(CH_2)_m(O(CH_2)_m)_nS(=O)_2(CH_2)_m$—, —$(CH_2)_mNR^{12}(CH_2)_mC(=O)$—, —$(CH_2)_mNR^{12}C(=O)$—, —$(CH_2)_mC(=O)X_2X_1C(=O)NR^{12}(CH_2)_mNHC(=O)$—, —$(CH_2)_mC(=O)NR^{12}(CH_2)_mNR^{12}C(=O)X_1$—, —$(CH_2)_mC(=O)NR^{12}(CH_2)_mNR^{12}C(=O)$—,

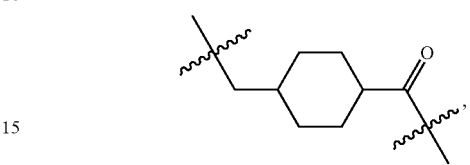

—$((CH_2)_mO)_n(CH_2)_m$—, —$(CH_2)_m(O(CH_2)_m)_n$—, —$(CH_2)_m(O(CH_2)_m)_nX_3(CH_2)_m$—, —$(CH_2)_mX_3((CH_2)_mO)_n(CH_2)_m$—, —$(CH_2)_mX_3(CH_2)_mC(=O)$—, —$C(=O)(CH_2)_mX_3(CH_2)_m$—, —$(CH_2)_mX_3(CH_2)_m(O(CH_2)_m)_nC(=O)$—, —$C(=O)((CH_2)_mO)_n(CH_2)_mX_3(CH_2)_m$—, —$(CH_2)_mC(=O)NR^{12}(CH_2)_mC(=O)$—, —$C(=O)(CH_2)_mNR^{12}C(=O)(CH_2)_m$—, —$(CH_2)_mC(=O)NR^{12}(CH_2)_m(O(CH_2)_m)_nC(=O)$—, —$C(=O)((CH_2)_mO)_n(CH_2)_mNR^{12}C(=O)(CH_2)_m$—, —$(CH_2)_mC(=O)NR^{12}(CH_2)_mC(=O)NR^{12}(CH_2)_m$—, —$(CH_2)_mNR^{12}C(=O)(CH_2)_mNR^{12}C(=O)(CH_2)_m$—, —$C(=O)NR^{12}(CH_2)_mNR^{12}C(=O)$—, —$(CH_2)_mS(CH_2)_m$—, —$NR^{12}C(=O)(CH_2)_m$—, —$NR^{12}C(=O)(CH_2)_mX_3(CH_2)_m$—, —$(CH_2)_mX_3(CH_2)_mC(=O)NR^{12}$—, —$(CH_2)_mC(=O)NR^{12}$—, —$(CH_2)_mNR^{12}(CH_2)_m$—, —$(CH_2)_mX_3(CH_2)_m$—, —$((CH_2)_mO)_n(CH_2)_mX_3(CH_2)_m$—, —$(CH_2)_mX_3(CH_2)_m(O(CH_2)_m)_n$—, —$NR^{12}(CH_2)_m$—, —$NR^{12}C(R^{12})_2(CH_2)_m$—, —$(CH_2)_mC(R^{12})_2NR^{12}$—, —$(CH_2)_mC(=O)NR^{12}(CH_2)_mNR^{12}$—, —$NR^{12}(CH_2)_mNR^{12}C(=O)(CH_2)_m$—, —$NR^{12}C(R^{12})_2(CH_2)_mNR^{12}C(=O)(CH_2)_m$—, —$(CH_2)_mC(=O)NR^{12}(CH_2)_mC(R^{12})_2NR^{12}$—, —$NR^{12}(CH_2)_mX_3(CH_2)_m$—, —$NR^{12}C(R^{12})_2(CH_2)_mX_3(CH_2)_m$—, —$(CH_2)_mX_3(CH_2)_mC(R^{12})_2NR^{12}$—, —$NR^{12}C(R^{12})_2(CH_2)_mOC(=O)NR^{12}(CH_2)_m$—, —$(CH_2)_mNR^{12}C(=O)O(CH_2)_mC(R^{12})_2NR^{12}$—, —$NR^{12}C(R^{12})_2(CH_2)_mOC(=O)NR^{12}(CH_2)_mX_3(CH_2)_m$—, —$(CH_2)_mX_3(CH_2)_mNR^{12}C(=O)O(CH_2)_mC(R^{12})_2NR^{12}$—, —$NR^{12}C(R^{12})_2(CH_2)_mOC(=O)NR^{12}((CH_2)_mO)_n(CH_2)_m$—, —$(CH_2)_m(O(CH_2)_m)_nNR^{12}C(=O)O(CH_2)_mC(R^{12})_2NR^{12}$—, —$NR^{12}C(R^{12})_2(CH_2)_mOC(=O)NR^{12}((CH_2)_mO)_n(CH_2)_mX_3(CH_2)_m$—, —$(CH_2)_mX_3(CH_2)_m(O(CH_2)_m)_nNR^{12}C(=O)O(CH_2)_mC(R^{12})_2NR^{12}$—, —$(CH_2)_mX_3(CH_2)_mNR^{12}$—, —$NR^{12}((CH_2)_mO)_n(CH_2)_mX_3(CH_2)_m$—, —$(CH_2)_mX_3(CH_2)_m(O(CH_2)_m)_nNR^{12}$—, —$(CH_2)_mNR^{12}$—, —$NR^{12}((CH_2)_mO)_n(CH_2)_m$—, —$NR^{12}((CH_2)_mO)_n(CH_2)_mNR^{12}C(=O)(CH_2)_m$—, —$(CH_2)_mC(=O)NR^{12}(CH_2)_m(O(CH_2)_m)_nNR^{12}$—, —$(CH_2)_m(O(CH_2)_m)_nNR^{12}$—, —$(CR_{12})_2)_m$—, —$(CH_2CH_2O)_n$—, —$(OCH_2CH_2)_n$—, —$(CH_2)_mO(CH_2)_m$—, —$S(=O)_2(CH_2)_m$—, —$(CH_2)_mS(=O)_2$—, —$S(=O)_2(CH_2)_mNR^{12}C(=O)(CH_2)_m$—, —$(CH_2)_mC(=O)NR^{12}(CH_2)_mS(=O)_2$—, —$S(=O)_2(CH_2)_mX_3(CH_2)_m$—, —$(CH_2)_mX_3(CH_2)_mS(=O)_2$—, —$(CH_2)_mX_2X_1C(=O)$—, —$C(=O)X_1X_2(CH_2)_m$—, —$(CH_2)_m(O(CH_2)_m)_nC(=O)X_2X_1C(=O)$—, —$C(=O)X_1X_2C(=O)((CH_2)_mO)_n(CH_2)_m$—, —$(CH_2)_m(O(CH_2)_m)_nX_2X_1C(=O)$—, —$(CH_2)_mX_3(CH_2)_mX_2X_1C(=O)$—, —$C(=O)X_1X_2(CH_2)_mX_3(CH_2)_m$—, —$(CH_2)_mX_3(CH_2)_m(O(CH_2)_m)_nX_2X_1C(=O)$—, —$(CH_2)_mX_3(CH_2)_mC(=O)NR^{12}(CH_2)_mNR^{12}C(=O)$—, —$(CH_2)_mX_3(CH_2)_mC(=O)

NR$^{12}$(CH$_2$)$_m$C(=O)—, —C(=O)(CH$_2$)$_m$NR$^{12}$C(=O)(CH$_2$)$_m$X$_3$(CH$_2$)$_m$—, —(CH$_2$)$_m$X$_3$(CH$_2$)$_m$C(=O)NR$^{12}$(CH$_2$)$_m$(O(CH$_2$)$_m$)$_n$C(=O)—, —C(=O)((CH$_2$)$_m$O)$_n$(CH$_2$)$_m$NR$^{12}$C(=O)(CH$_2$)$_m$X$_3$(CH$_2$)$_m$—, —(CH$_2$)$_m$NR$^{12}$C(=O)X$_1$X$_2$C(=O)(CH$_2$)$_m$—, —(CH$_2$)$_m$C(=O)X$_2$X$_1$C(=O)NR$^{12}$(CH$_2$)$_m$—, —X$_4$X$_1$X$_2$C(=O)(CH$_2$)$_m$—, —(CH$_2$)$_m$C(=O)X$_2$X$_1$X$_4$—, —X$_1$C(=O)(CH$_2$)$_m$NHC(=O)(CH$_2$)$_m$—, —(CH$_2$)$_m$C(=O)NH(CH$_2$)$_m$C(=O)X$_1$—, —C(=O)CHR$^{aa}$NR$^{12}$—, —CHR$^{aa}$C(=O)—, —C(=O)NR$^{12}$—, —C(=O)O—, —S—, —SCH$_2$(C=O)NR$^{12}$—, —NR$^{12}$C(=O)CH$_2$S—, —S(=O)$_2$CH$_2$CH$_2$S—, —SCH$_2$CH$_2$S(=O)$_2$—, —(CH$_2$)$_2$S(=O)$_2$CH$_2$CH$_2$S—, —SCH$_2$CH$_2$S(=O)$_2$CH$_2$CH$_2$—, —NR$^{12}$C(=S)—, —(CH$_2$)$_m$X$_3$(O(CH$_2$)$_n$)$_n$C(=O)—, —C(=O)((CH$_2$)$_m$O)$_n$X$_3$(CH$_2$)$_m$—, —(CH$_2$)$_m$NR$^{12}$C(=O)((CH$_2$)$_m$O)$_n$(CH$_2$)$_m$—, —(CH$_2$)$_m$(O(CH$_2$)$_m$)$_n$C(=O)NR$^{12}$(CH$_2$)$_m$—, —(CH$_2$)$_m$NR$^{12}$C(=O)NR$^{12}$(CH$_2$)$_m$—, —(CH$_2$)$_m$X$_3$(CH$_2$)$_m$NR$^{12}$C(=O)—, —C(=O)NR$^{12}$(CH$_2$)$_m$X$_3$(CH$_2$)$_m$—, —NR$_{12}$S(=O)$_2$(CH$_2$)$_m$X$_3$(CH$_2$)$_m$—, —(CH$_2$)$_m$X$_3$(CH$_2$)$_m$S(=O)$_2$NR$_{12}$—,

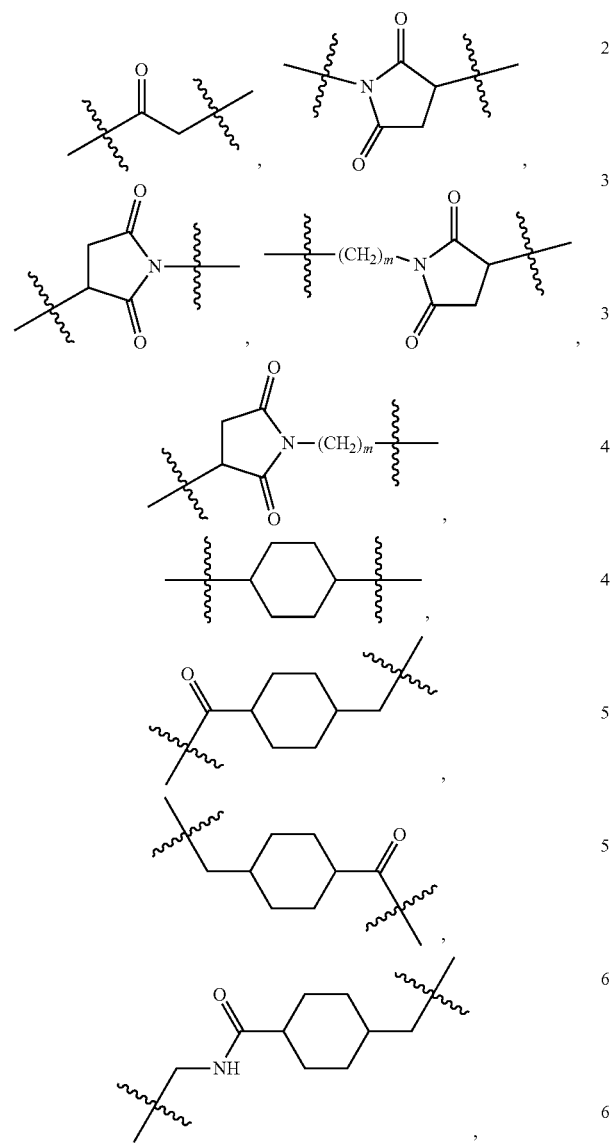

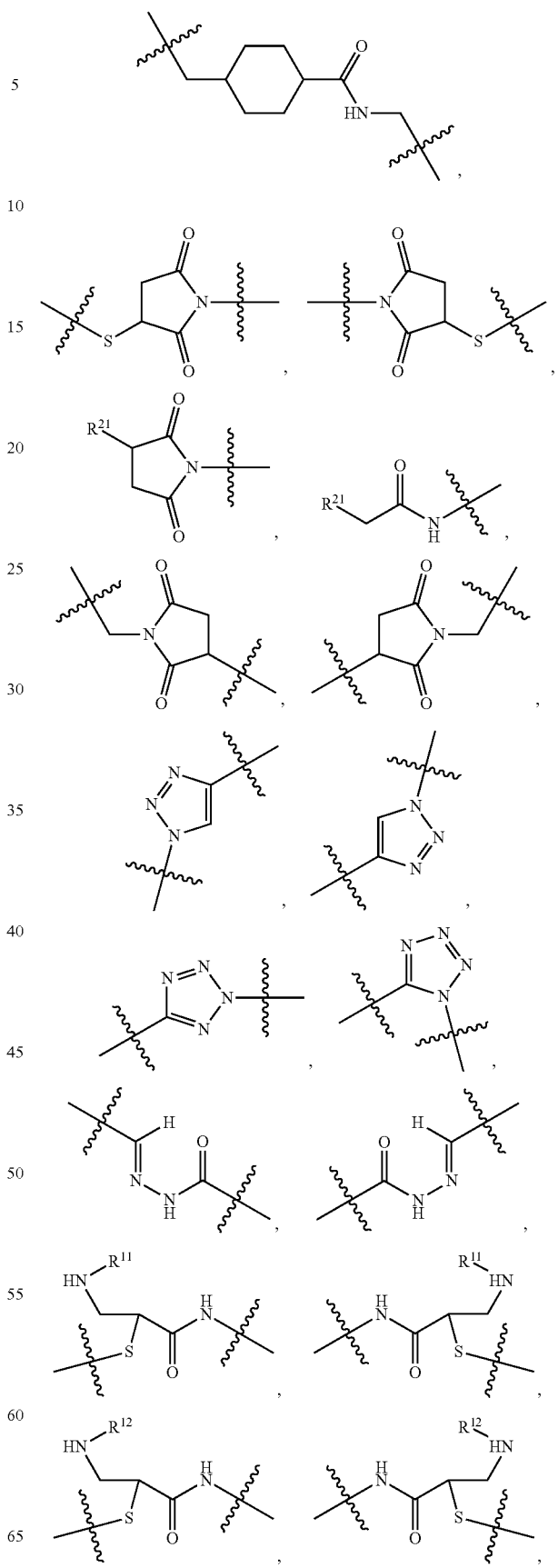

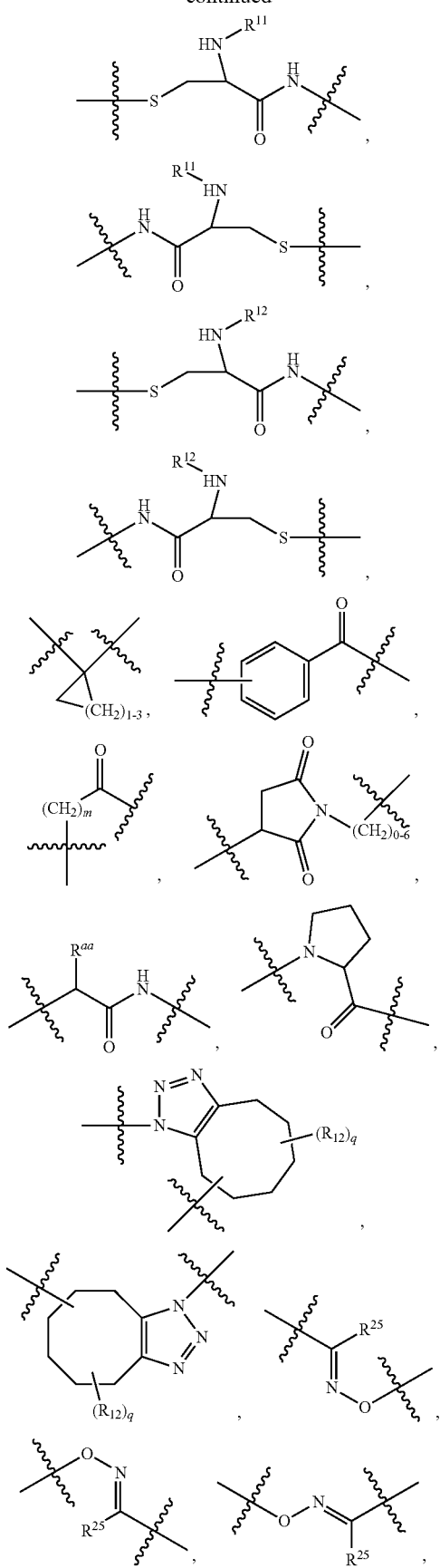
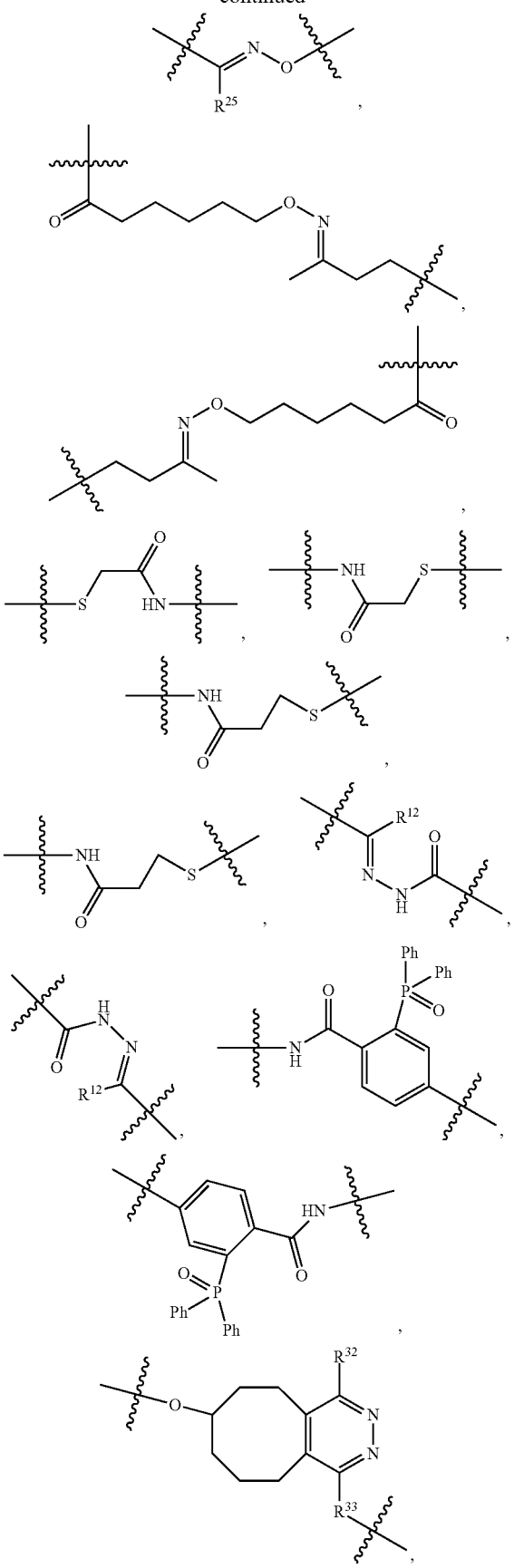

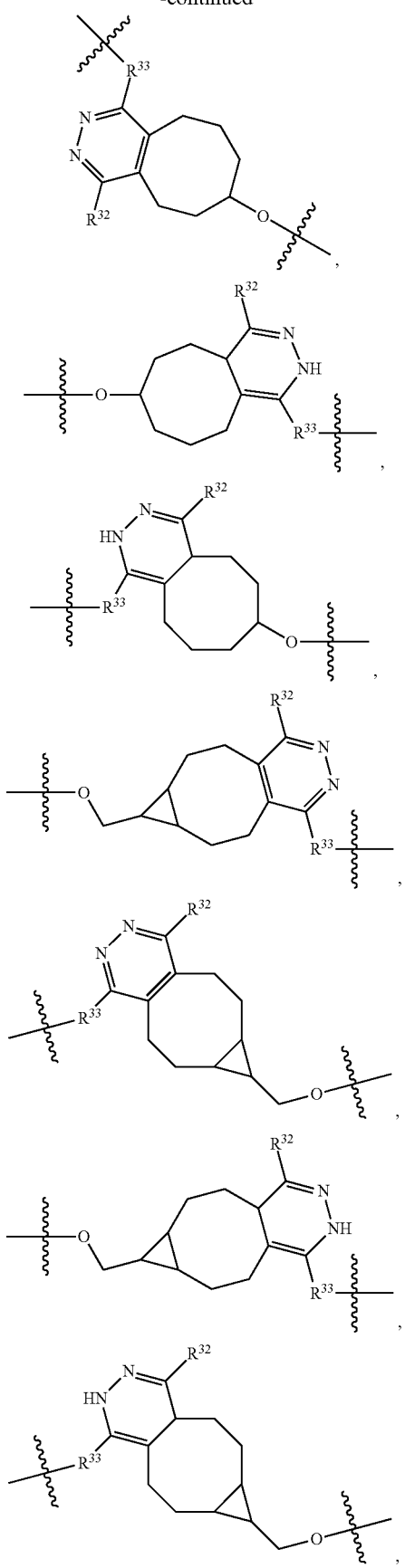
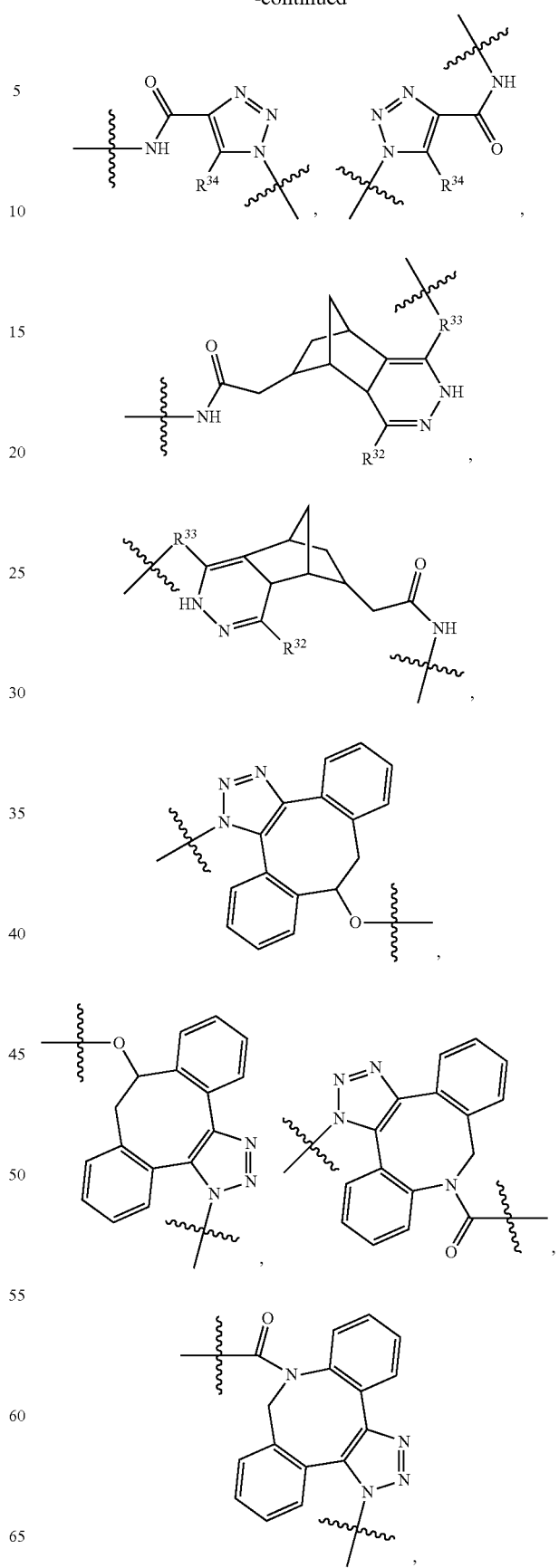

-continued

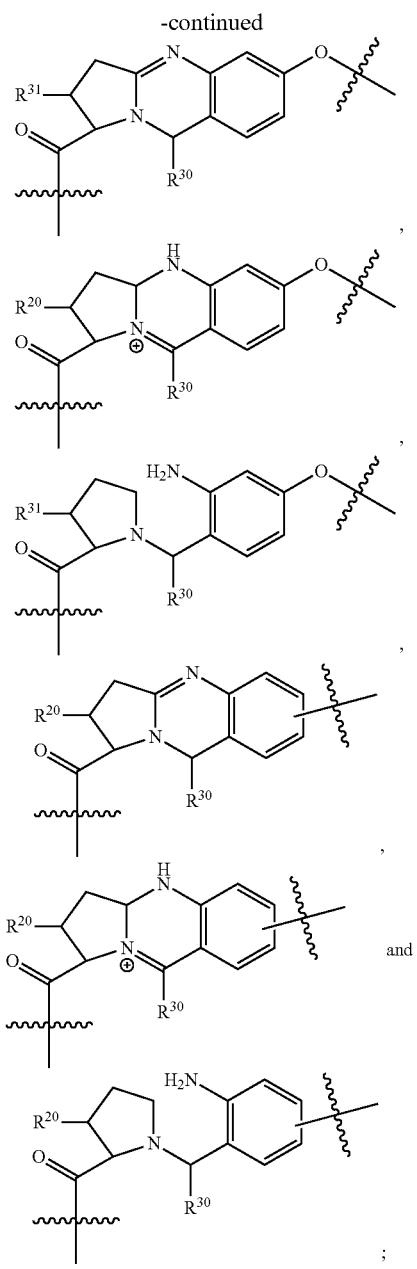

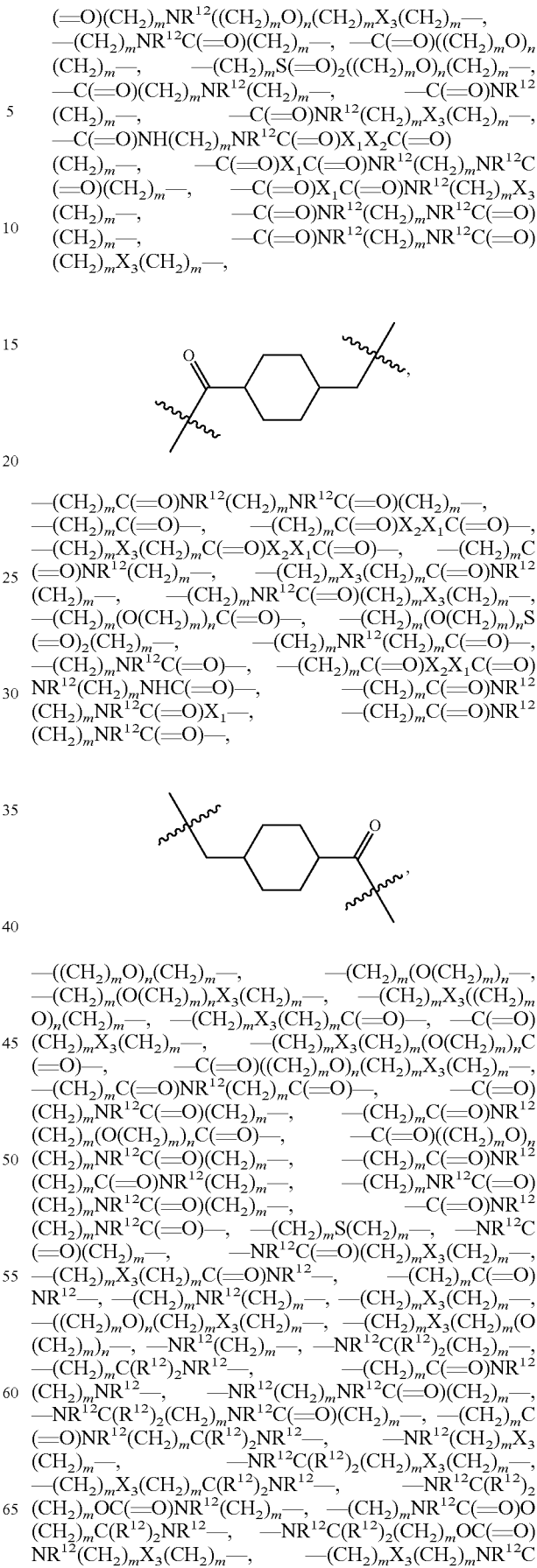

$L_2$, $L_3$, $L_4$, $L_5$, and $L_6$ are each independently selected from a bond, —$(CH_2)_m$—, —$C(=O)(CH_2)_m$—, —$C(=O)X_1X_2C(=O)(CH_2)_m$—, —$C(=O)X_1X_2C(=O)(CH_2)_mNR^{12}C(=O)(CH_2)_m$—, —$C(=O)X_1X_2C(=O)(CH_2)_mX_3(CH_2)_m$—, —$C(=O)X_1X_2C(=O)((CH_2)_mO)_n(CH_2)_m$—, —$C(=O)X_1X_2C(=O)((CH_2)_mO)_n(CH_2)_mNR^{12}C(=O)(CH_2)_m$—, —$C(=O)X_1X_2C(=O)((CH_2)_mO)_n(CH_2)_mNR^{12}C(=O)(CH_2)_mX_3(CH_2)_m$—, —$C(=O)X_1X_2C(=O)((CH_2)_mO)_n(CH_2)_mX_3(CH_2)_m$—, —$C(=O)X_1X_2C(=O)(CH_2)_mNR^{12}C(=O)((CH_2)_mO)_n(CH_2)_m$—, —$C(=O)X_1X_2C(=O)(CH_2)_mNR^{12}C(=O)((CH_2)_mO)_n(CH_2)_mX_3(CH_2)_m$—, —$C(=O)X_1X_2$ $(CH_2)_mX_3(CH_2)_m$—, —$C(=O)X_1X_2((CH_2)_mO)_n$ $(CH_2)_m$—, —$C(=O)X_1X_2((CH_2)_mO)_n(CH_2)_mNR^{12}C$ $(=O)(CH_2)_m$—, —$C(=O)X_1X_2((CH_2)_mO)_n$ $(CH_2)_mNR^{12}C(=O)(CH_2)_mX_3(CH_2)_m$—, —$C(=O)$ $X_1X_2((CH_2)_mO)_n(CH_2)_mX_3(CH_2)_m$—, —$C(=O)X_1X_2$ $(CH_2)_mNR^{12}((CH_2)_mO)_n(CH_2)_m$—, —$C(=O)X_1X_2C$ $(=O)(CH_2)_mNR^{12}((CH_2)_mO)_n(CH_2)_mX_3(CH_2)_m$—, —$(CH_2)_mNR^{12}C(=O)(CH_2)_m$—, —$C(=O)((CH_2)_mO)_n$ $(CH_2)_m$—, —$(CH_2)_mS(=O)_2((CH_2)_mO)_n(CH_2)_m$—, —$C(=O)(CH_2)_mNR^{12}(CH_2)_m$—, —$C(=O)NR^{12}$ $(CH_2)_m$—, —$C(=O)NR^{12}(CH_2)_mX_3(CH_2)_m$—, —$C(=O)NH(CH_2)_mNR^{12}C(=O)X_1X_2C(=O)$ $(CH_2)_m$—, —$C(=O)X_1C(=O)NR^{12}(CH_2)_mNR^{12}C$ $(=O)(CH_2)_m$—, —$C(=O)X_1C(=O)NR^{12}(CH_2)_mX_3$ $(CH_2)_m$—, —$C(=O)NR^{12}(CH_2)_mNR^{12}C(=O)$ $(CH_2)_m$—, —$C(=O)NR^{12}(CH_2)_mNR^{12}C(=O)$ $(CH_2)_mX_3(CH_2)_m$—, —$(CH_2)_mC(=O)NR^{12}(CH_2)_mNR^{12}C(=O)(CH_2)_m$—, —$(CH_2)_mC(=O)$—, —$(CH_2)_mC(=O)X_2X_1C(=O)$—, —$(CH_2)_mX_3(CH_2)_mC(=O)X_2X_1C(=O)$—, —$(CH_2)_mC(=O)NR^{12}(CH_2)_m$—, —$(CH_2)_mX_3(CH_2)_mC(=O)NR^{12}$ $(CH_2)_m$—, —$(CH_2)_mNR^{12}C(=O)(CH_2)_mX_3(CH_2)_m$—, —$(CH_2)_m(O(CH_2)_m)_nC(=O)$—, —$(CH_2)_m(O(CH_2)_m)_nS$ $(=O)_2(CH_2)_m$—, —$(CH_2)_mNR^{12}(CH_2)_mC(=O)$—, —$(CH_2)_mNR^{12}C(=O)$—, —$(CH_2)_mC(=O)X_2X_1C(=O)$ $NR^{12}(CH_2)_mNHC(=O)$—, —$(CH_2)_mC(=O)NR^{12}$ $(CH_2)_mNR^{12}C(=O)X_1$—, —$(CH_2)_mC(=O)NR^{12}$ $(CH_2)_mNR^{12}C(=O)$—, —$((CH_2)_mO)_n(CH_2)_m$—, —$(CH_2)_m(O(CH_2)_m)_n$—, —$(CH_2)_m(O(CH_2)_m)_nX_3(CH_2)_m$—, —$(CH_2)_mX_3((CH_2)_mO)_n(CH_2)_m$—, —$(CH_2)_mX_3(CH_2)_mC(=O)$—, —$C(=O)(CH_2)_mX_3(CH_2)_m$—, —$(CH_2)_mX_3(CH_2)_m(O(CH_2)_m)_nC$ $(=O)$—, —$C(=O)((CH_2)_mO)_n(CH_2)_mX_3(CH_2)_m$—, —$(CH_2)_mC(=O)NR^{12}(CH_2)_mC(=O)$—, —$C(=O)$ $(CH_2)_mNR^{12}C(=O)(CH_2)_m$—, —$(CH_2)_mC(=O)NR^{12}$ $(CH_2)_m(O(CH_2)_m)_nC(=O)$—, —$C(=O)((CH_2)_mO)_n$ $(CH_2)_mNR^{12}C(=O)(CH_2)_m$—, —$(CH_2)_mC(=O)NR^{12}$ $(CH_2)_mC(=O)NR^{12}(CH_2)_m$—, —$(CH_2)_mNR^{12}C(=O)$ $(CH_2)_mNR^{12}C(=O)(CH_2)_m$—, —$C(=O)NR^{12}$ $(CH_2)_mNR^{12}C(=O)$—, —$(CH_2)_mS(CH_2)_m$—, —$NR^{12}C$ $(=O)(CH_2)_m$—, —$NR^{12}C(=O)(CH_2)_mX_3(CH_2)_m$—, —$(CH_2)_mX_3(CH_2)_mC(=O)NR^{12}$—, —$(CH_2)_mC(=O)$ $NR^{12}$—, —$(CH_2)_mNR^{12}(CH_2)_m$—, —$(CH_2)_mX_3(CH_2)_m$—, —$((CH_2)_mO)_n(CH_2)_mX_3(CH_2)_m$—, —$(CH_2)_mX_3(CH_2)_m(O(CH_2)_m)_n$—, —$NR^{12}(CH_2)_m$—, —$NR^{12}C(R^{12})_2(CH_2)_m$—, —$(CH_2)_mC(R^{12})_2NR^{12}$—, —$(CH_2)_mC(=O)NR^{12}$ $(CH_2)_mNR^{12}$—, —$NR^{12}(CH_2)_mNR^{12}C(=O)(CH_2)_m$—, —$NR^{12}C(R^{12})_2(CH_2)_mNR^{12}C(=O)(CH_2)_m$—, —$(CH_2)_mC$ $(=O)NR^{12}(CH_2)_mC(R^{12})_2NR^{12}$—, —$NR^{12}(CH_2)_mX_3$ $(CH_2)_m$—, —$NR^{12}C(R^{12})_2(CH_2)_mX_3(CH_2)_m$—, —$(CH_2)_mX_3(CH_2)_mC(R^{12})_2NR^{12}$—, —$NR^{12}C(R^{12})_2$ $(CH_2)_mOC(=O)NR^{12}(CH_2)_m$—, —$(CH_2)_mNR^{12}C(=O)O$ $(CH_2)_mC(R^{12})_2NR^{12}$—, —$NR^{12}C(R^{12})_2(CH_2)_mOC(=O)$ $NR^{12}(CH_2)_mX_3(CH_2)_m$—, —$(CH_2)_mX_3(CH_2)_mNR^{12}C$ $-$(=O)O(CH$_2$)$_m$C(R$^{12}$)$_2$NR$^{12}-$, $-$NR$^{12}$C(R$^{12}$)$_2$(CH$_2$)$_m$OC(=O)NR$^{12}$((CH$_2$)$_m$O)$_n$(CH$_2$)$_m-$, $-$(CH$_2$)$_m$(O(CH$_2$)$_m$)$_n$NR$^{12}$C(R$^{12}$)$_2$NR$^{12}-$, $-$NR$^{12}$C(R$^{12}$)$_2$(CH$_2$)$_m$OC(=O)NR$^{12}$((CH$_2$)$_m$O)$_n$(CH$_2$)$_m$X$_3$(CH$_2$)$_m-$, $-$(CH$_2$)$_m$X$_3$(CH$_2$)$_m$(O(CH$_2$)$_m$)$_n$NR$^{12}$C(=O)O(CH$_2$)$_m$C(R$^{12}$)$_2$NR$^{12}-$, $-$(CH$_2$)$_m$X$_3$(CH$_2$)$_m$NR$^{12}-$, $-$NR$^{12}$((CH$_2$)$_m$O)$_n$(CH$_2$)$_m$X$_3$(CH$_2$)$_m-$, $-$(CH$_2$)$_m$X$_3$(CH$_2$)$_m$(O(CH$_2$)$_m$)$_n$NR$^{12}-$, $-$(CH$_2$)$_m$NR$^{12}-$, $-$NR$^{12}$((CH$_2$)$_m$O)$_n$(CH$_2$)$_m-$, $-$NR$^{12}$((CH$_2$)$_m$O)$_n$(CH$_2$)$_m$NR$^{12}$C(=O)(CH$_2$)$_m-$, $-$(CH$_2$)$_m$C(=O)NR$^{12}$(CH$_2$)$_m$(O(CH$_2$)$_m$)$_n$NR$^{12}-$, $-$(CH$_2$)$_m$(O(CH$_2$)$_m$)$_n$NR$^{12}-$, $-$(C(R$_{12}$)$_2$)$_m-$, $-$(CH$_2$CH$_2$O)$_n-$, $-$(OCH$_2$CH$_2$)$_n-$, $-$(CH$_2$)$_m$O(CH$_2$)$_m-$, $-$(CH$_2$)$_m$S(=O)$_2-$, $-$S(=O)$_2$(CH$_2$)$_m$NR$^{12}$C(=O)(CH$_2$)$_m-$, $-$(CH$_2$)$_m$C(=O)NR$^{12}$(CH$_2$)$_m$S(=O)$_2-$, $-$S(=O)$_2$(CH$_2$)$_m$X$_3$(CH$_2$)$_m-$, $-$(CH$_2$)$_m$X$_3$(CH$_2$)$_m$S(=O)$_2-$, $-$(CH$_2$)$_m$X$_2$X$_1$C(=O)$-$, $-$C(=O)X$_1$X$_2$(CH$_2$)$_m-$, $-$(CH$_2$)$_m$(O(CH$_2$)$_m$)$_n$C(=O)X$_2$X$_1$C(=O)$-$, $-$C(=O)X$_1$X$_2$C(=O)((CH$_2$)$_m$O)$_n$(CH$_2$)$_m-$, $-$(CH$_2$)$_m$(O(CH$_2$)$_m$)$_n$X$_2$X$_1$C(=O)$-$, $-$(CH$_2$)$_m$X$_3$(CH$_2$)$_m$X$_2$X$_1$C(=O)$-$, $-$C(=O)X$_1$X$_2$(CH$_2$)$_m$X$_3$(CH$_2$)$_m-$, $-$(CH$_2$)$_m$X$_3$(CH$_2$)$_m$(O(CH$_2$)$_m$)$_n$X$_2$X$_1$C(=O)$-$, $-$(CH$_2$)$_m$X$_3$(CH$_2$)$_m$C(=O)NR$^{12}$(CH$_2$)$_m$NR$^{12}$C(=O)$-$, $-$(CH$_2$)$_m$X$_3$(CH$_2$)$_m$C(=O)NR$^{12}$(CH$_2$)$_m$C(=O)$-$, $-$C(=O)(CH$_2$)$_m$NR$^{12}$C(=O)(CH$_2$)$_m$X$_3$(CH$_2$)$_m-$, $-$(CH$_2$)$_m$X$_3$(CH$_2$)$_m$C(=O)NR$^{12}$(CH$_2$)$_m$(O(CH$_2$)$_m$)$_n$C(=O)$-$, $-$C(=O)((CH$_2$)$_m$O)$_n$(CH$_2$)$_m$NR$^{12}$C(=O)(CH$_2$)$_m$X$_3$(CH$_2$)$_m-$, $-$(CH$_2$)$_m$NR$^{12}$C(=O)X$_1$X$_2$C(=O)(CH$_2$)$_m-$, $-$(CH$_2$)$_m$C(=O)X$_2$X$_1$C(=O)NR$^{12}$(CH$_2$)$_m-$, $-$X$_4$X$_1$X$_2$C(=O)(CH$_2$)$_m-$, $-$(CH$_2$)$_m$C(=O)X$_2$X$_1$X$_4-$, $-$X$_1$C(=O)(CH$_2$)$_m$NHC(=O)(CH$_2$)$_m-$, $-$(CH$_2$)$_m$C(=O)NH(CH$_2$)$_m$C(=O)X$_1-$, $-$C(=O)CHR$^{aa}$NR$^{12}-$, $-$CHR$^{aa}$C(=O)$-$, $-$C(=O)NR$^{12}-$, $-$C(=O)O$-$, $-$S$-$, $-$SCH$_2$(C=O)NR$^{12}-$, $-$NR$^{12}$C(=O)CH$_2$S$-$, $-$S(=O)$_2$CH$_2$CH$_2-$, $-$SCH$_2$CH$_2$S(=O)$_2-$, $-$(CH$_2$)$_2$S(=O)$_2$CH$_2$CH$_2$S$-$, $-$SCH$_2$CH$_2$S(=O)$_2$CH$_2$CH$_2-$, $-$NR$^{12}$C(=S)$-$, $-$(CH$_2$)$_m$X$_3$(O(CH$_2$)$_m$)$_n$C(=O)$-$, $-$C(=O)((CH$_2$)$_m$O)$_n$X$_3$(CH$_2$)$_m-$, $-$(CH$_2$)$_m$NR$^{12}$C(=O)((CH$_2$)$_m$O)$_n$(CH$_2$)$_m-$, $-$(CH$_2$)$_m$(O(CH$_2$)$_m$)$_n$C(=O)NR$^{12}$(CH$_2$)$_m-$, $-$(CH$_2$)$_m$NR$^{12}$C(=O)NR$^{12}$(CH$_2$)$_m-$, $-$(CH$_2$)$_m$X$_3$(CH$_2$)$_m$NR$^{12}$C(=O)$-$, $-$C(=O)NR$^{12}$(CH$_2$)$_m$X$_3$(CH$_2$)$_m-$, $-$NR$_{12}$S(=O)$_2$(CH$_2$)$_m$X$_3$(CH$_2$)$_m-$, $-$(CH$_2$)$_m$X$_3$(CH$_2$)$_m$S(=O)$_2$NR$_{12}-$,

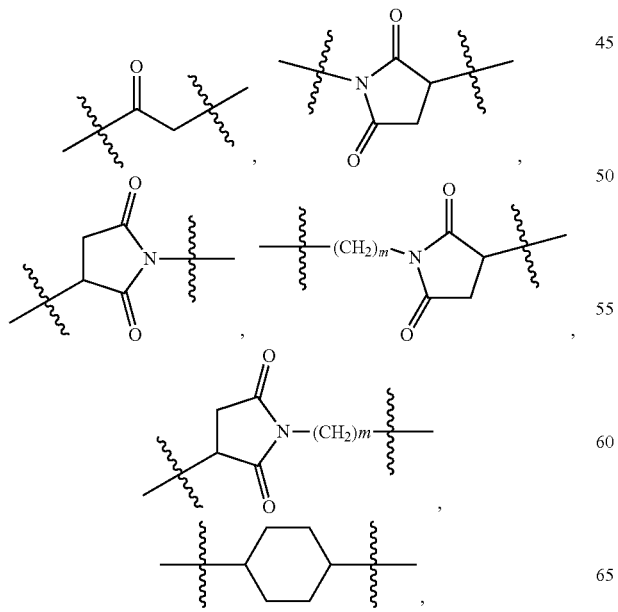

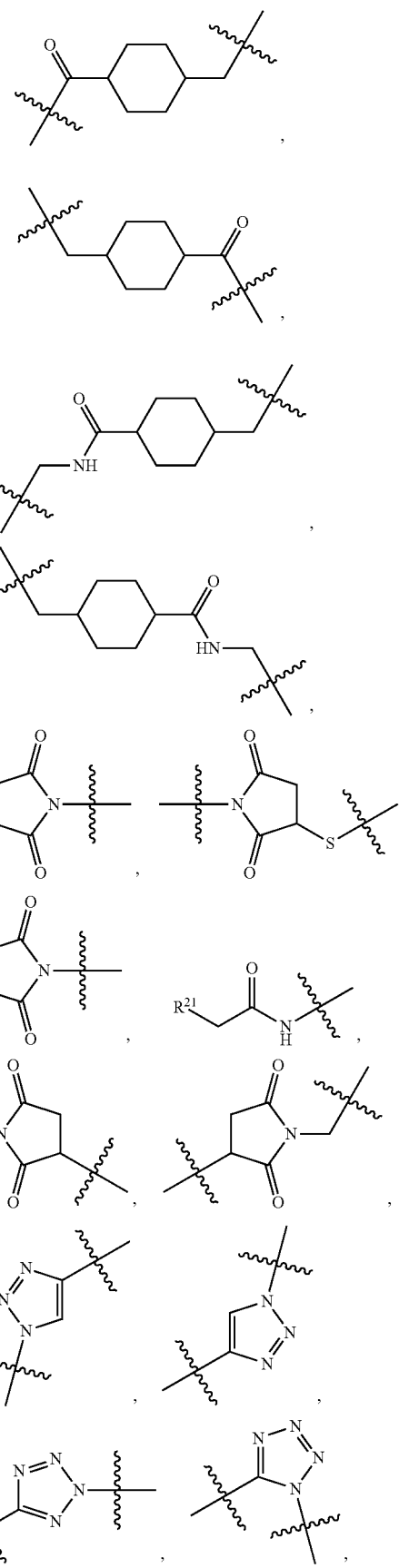

405
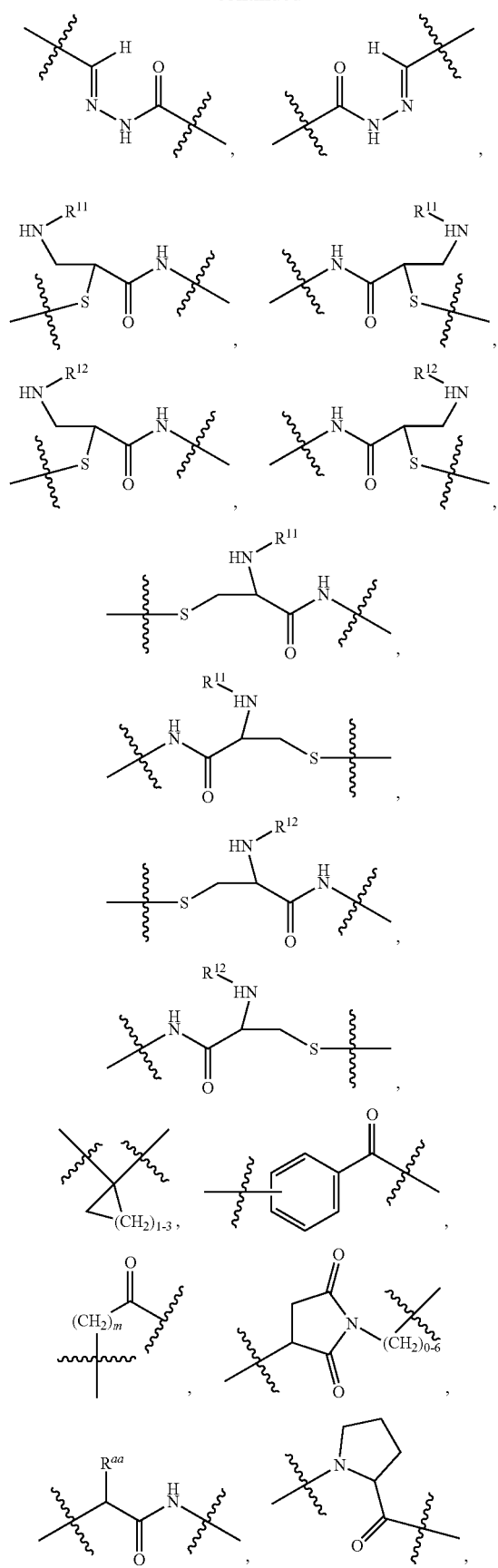
406
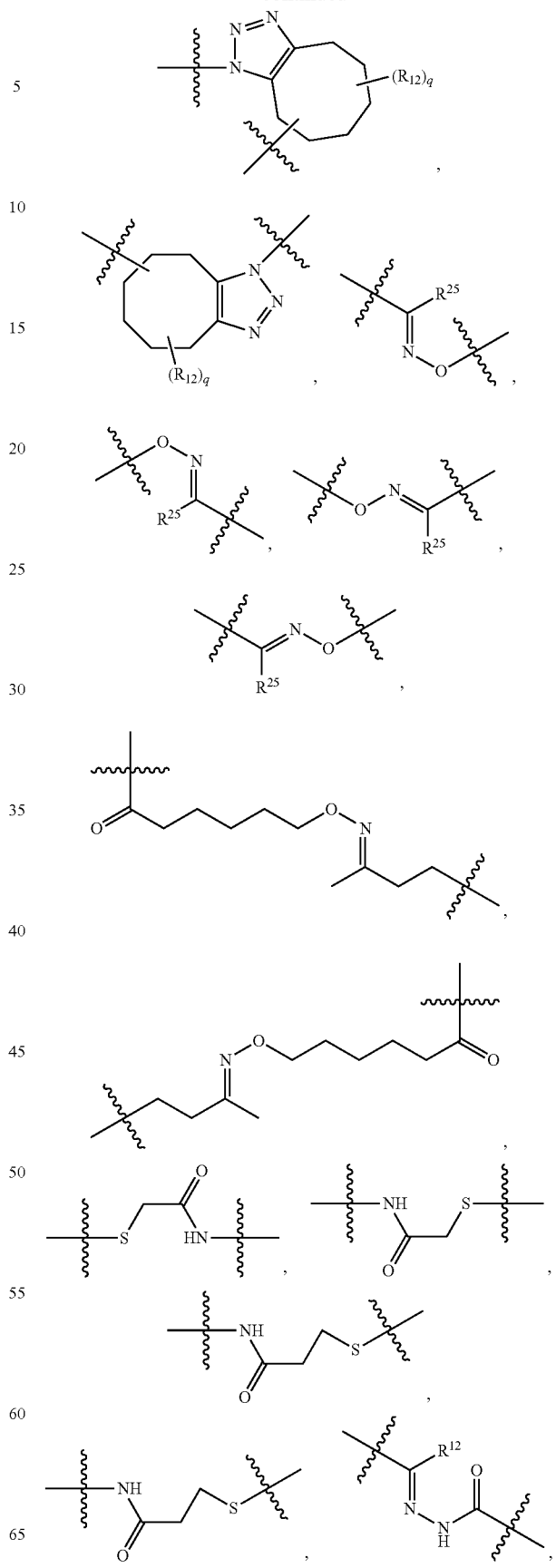

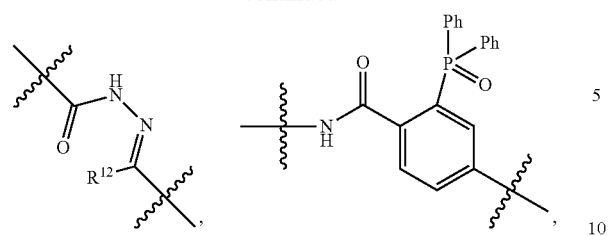
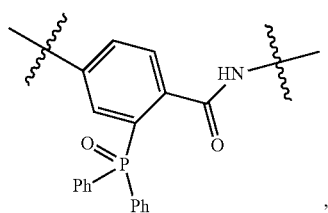
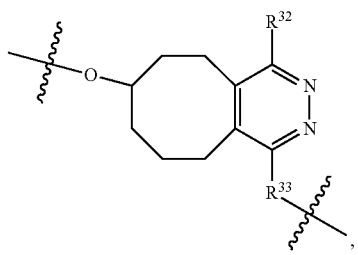
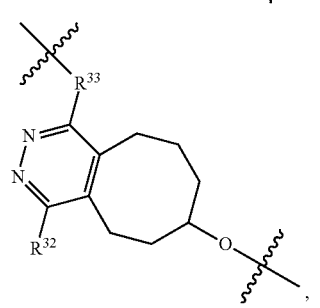
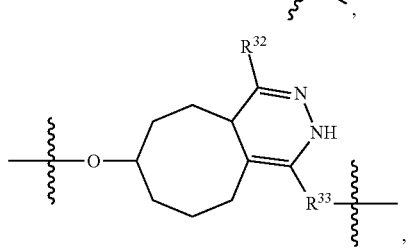
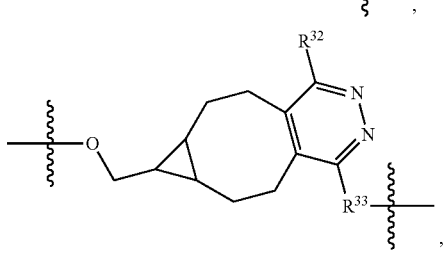
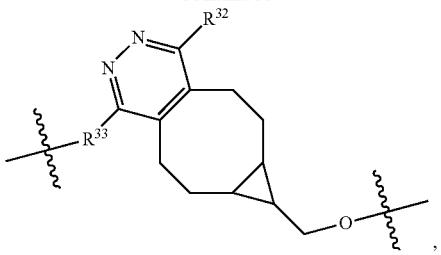
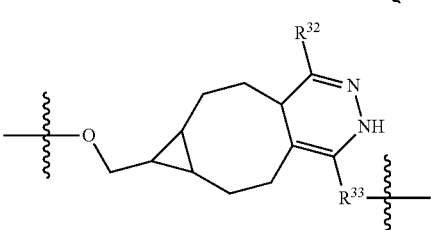
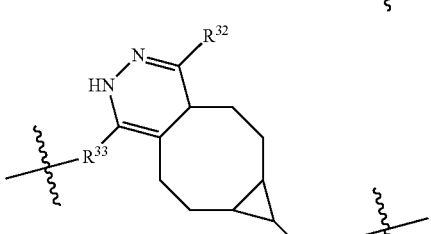
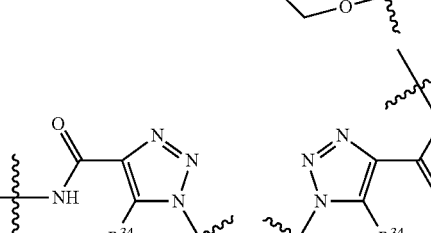
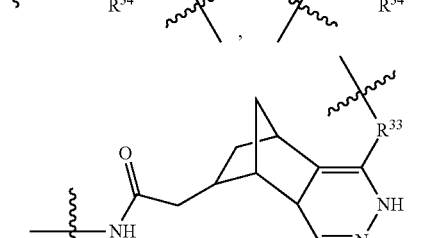
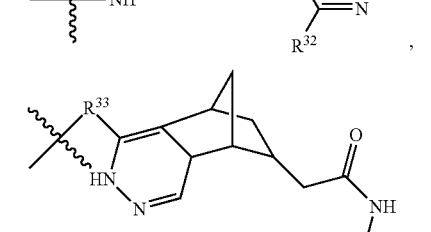
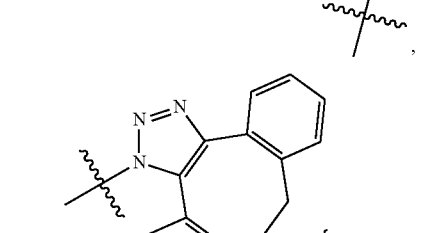

409
-continued

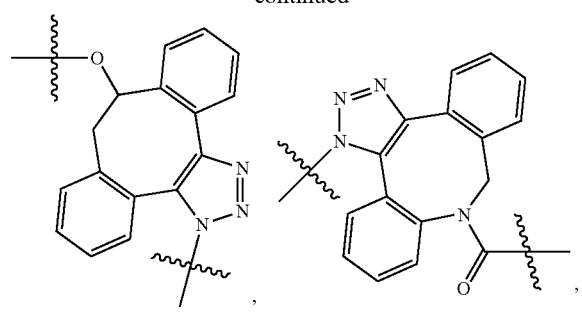,

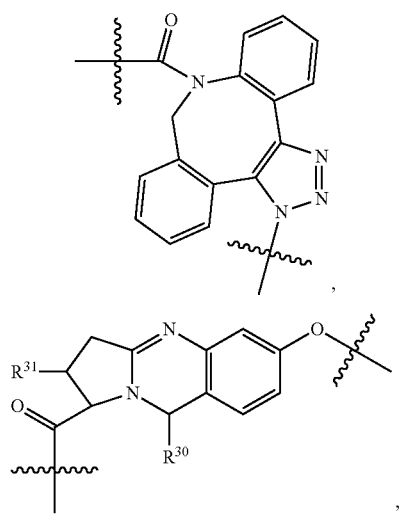,

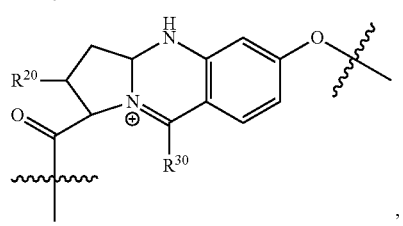,

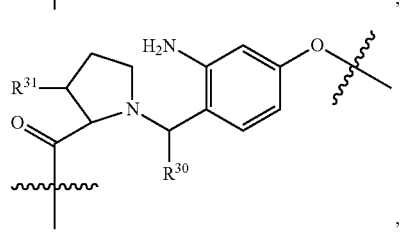,

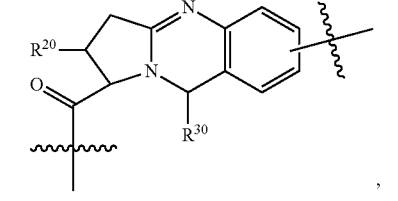,

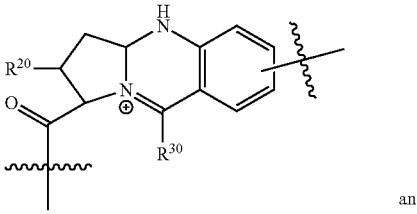

and

410
-continued

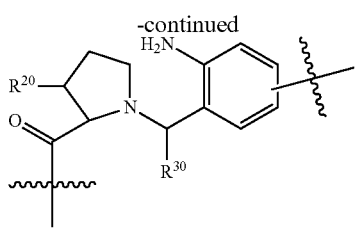;

wherein:
$R^{20}$ is H or Me, and $R^{30}$ is H, —CH₃ or phenyl;
$R^{21}$ is

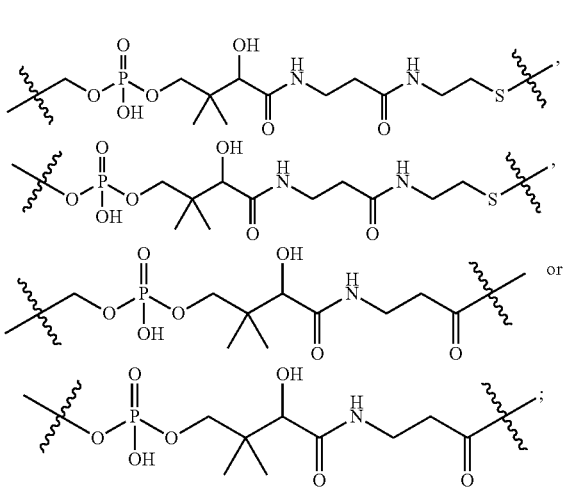;

each $R^{25}$ is independently selected from H or $C_{1-4}$ alkyl;
$R^{aa}$ is a side chain of an amino acid selected from glycine, alanine, tryptophan, tyrosine, phenylalanine, leucine, isoleucine, valine, asparagine, glutamic acid, glutamine, aspatic acid, histidine, arginine, lysine, cysteine, methionine, serine, threonine, phenylglycine and t-butylglycine;
$R^{32}$ is independently selected from H, $C_{1-4}$ alkyl, phenyl, pyrimidine and pyridine;
$R^{33}$ is independently selected from

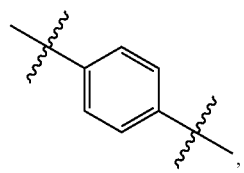,

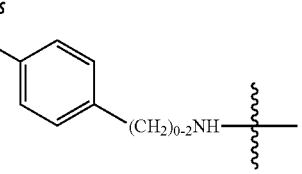,

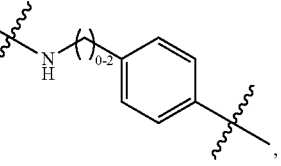,

411
-continued
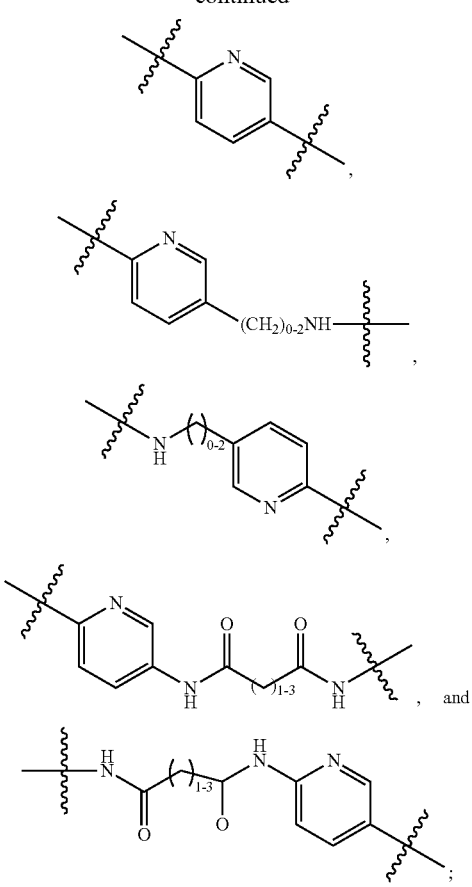
and
R³⁴ is independently selected from H, $C_{1-4}$ alkyl, and $C_{1-6}$ haloalkyl;
$X_1$ is self immolative spacer selected from
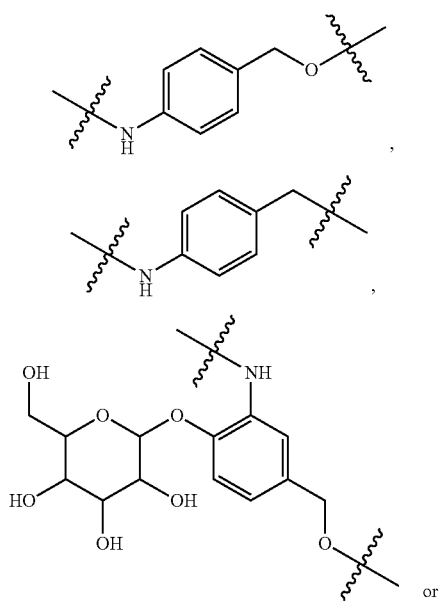
or
412
-continued
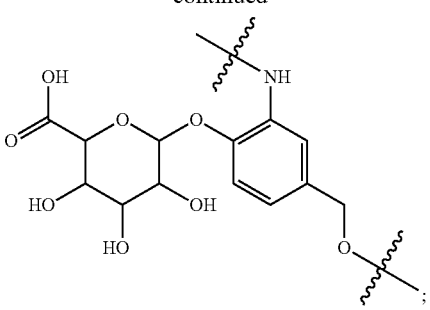
$X_2$ is dipeptide selected from
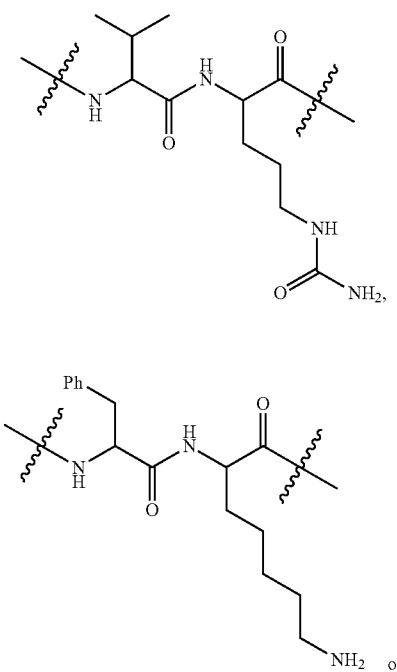
$X_3$ is
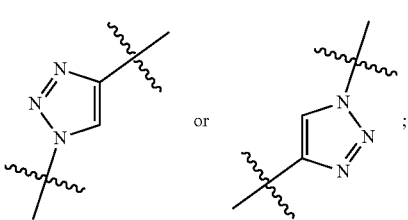 [SMILES: *c1cn(*)nn1 ; *c1cn(*)nn1]

and $X_4$ is

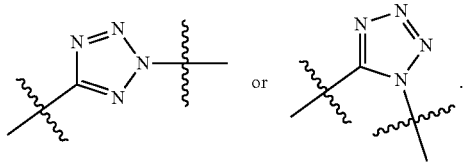 [SMILES: *c1nnn(*)n1 ; *c1nnnn1*]

Embodiment 83. The compound of any one of embodiments 3 to 45 and 78 to 80, and the immunoconjugate according to any one of embodiments 46 to 80, wherein $L_1$ is selected from —$(CH_2)_m$—, —$C(=O)(CH_2)_m$—, —$C(=O)X_1X_2C(=O)(CH_2)_m$—, —$C(=O)X_1X_2C(=O)(CH_2)_m NHC(=O)(CH_2)_m$—, —$C(=O)X_1X_2C(=O)(CH_2)_m X_3(CH_2)_m$—, —$C(=O)X_1X_2C(=O)((CH_2)_m O)_n(CH_2)_m$—, —$C(=O)X_1X_2C(=O)((CH_2)_m O)_n(CH_2)_m NHC(=O)(CH_2)_m$—, —$C(=O)X_1X_2C(=O)((CH_2)_m O)_n(CH_2)_m NHC(=O)(CH_2)_m X_3(CH_2)_m$—, —$C(=O)X_1X_2C(=O)((CH_2)_m O)_n(CH_2)_m X_3(CH_2)_m$—, —$C(=O)X_1X_2C(=O)(CH_2)_m NHC(=O)((CH_2)_m O)_n(CH_2)_m$—, —$C(=O)X_1X_2C(=O)(CH_2)_m NHC(=O)((CH_2)_m O)_n(CH_2)_m X_3(CH_2)_m$—, —$C(=O)X_1X_2(CH_2)_m X_3(CH_2)_m$—, —$C(=O)X_1X_2((CH_2)_m O)_n(CH_2)_m$—, —$C(=O)X_1X_2((CH_2)_m O)_n(CH_2)_m NHC(=O)(CH_2)_m$—, —$C(=O)X_1X_2((CH_2)_m O)_n(CH_2)_m NHC(=O)(CH_2)_m X_3(CH_2)_m$—, —$C(=O)X_1X_2((CH_2)_m O)_n(CH_2)_m X_3(CH_2)_m$—, —$C(=O)X_1X_2(CH_2)_m NH((CH_2)_m O)_n(CH_2)_m$—, —$C(=O)X_1X_2C(=O)(CH_2)_m NH((CH_2)_m O)_n(CH_2)_m X_3(CH_2)_m$—, —$(CH_2)_m NHC(=O)(CH_2)_m$—, —$C(=O)((CH_2)_m O)_n(CH_2)_m$—, —$(CH_2)_m S(=O)_2((CH_2)_m O)_n(CH_2)_m$—, —$C(=O)(CH_2)_m NH(CH_2)_m$—, —$C(=O)NH(CH_2)_m$—, —$C(=O)NH(CH_2)_m X_3(CH_2)_m$—, —$C(=O)NH(CH_2)_m NHC(=O)X_1X_2C(=O)(CH_2)_m$—, —$C(=O)X_1C(=O)NH(CH_2)_m NHC(=O)(CH_2)_m$—, —$C(=O)X_1C(=O)NH(CH_2)_m X_3(CH_2)_m$—, —$C(=O)NH(CH_2)_m NHC(=O)(CH_2)_m$—, —$C(=O)NH(CH_2)_m NHC(=O)(CH_2)_m X_3(CH_2)_m$—,

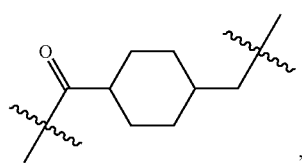 [SMILES: *CC1CCC(C(*)=O)CC1],

—$(CH_2)_m C(=O)NH(CH_2)_m NHC(=O)(CH_2)_m$—, —$(CH_2)_m C(=O)$—, —$(CH_2)_m C(=O)X_2X_1C(=O)$—, —$(CH_2)_m X_3(CH_2)_m C(=O)X_2X_1C(=O)$—, —$(CH_2)_m C(=O)NH(CH_2)_m$—, —$(CH_2)_m X_3(CH_2)_m C(=O)NH(CH_2)_m$—, —$(CH_2)_m NHC(=O)(CH_2)_m X_3(CH_2)_m$—, —$(CH_2)_m (O(CH_2)_m)_n C(=O)$—, —$(CH_2)_m (O(CH_2)_m)_n S(=O)_2(CH_2)_m$—, —$(CH_2)_m NH(CH_2)_m C(=O)$—, —$(CH_2)_m NHC(=O)$—, —$(CH_2)_m C(=O)X_2X_1C(=O)NH(CH_2)_m NHC(=O)$—, —$(CH_2)_m C(=O)NH(CH_2)_m NHC(=O)X_1$—, —$(CH_2)_m C(=O)NH(CH_2)_m NHC(=O)$—,

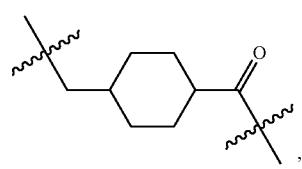 [SMILES: *CC1CCC(C(*)=O)CC1],

—$((CH_2)_m O)_n(CH_2)_m$—, —$(CH_2)_m (O(CH_2)_m)_n$—, —$(CH_2)_m (O(CH_2)_m)_n X_3(CH_2)_m$—, —$(CH_2)_m X_3((CH_2)_m O)_n(CH_2)_m$—, —$(CH_2)_m X_3(CH_2)_m C(=O)$—, —$C(=O)(CH_2)_m X_3(CH_2)_m$—, —$(CH_2)_m X_3(CH_2)_m (O(CH_2)_m)_n C(=O)$—, —$C(=O)((CH_2)_m O)_n(CH_2)_m X_3(CH_2)_m$—, —$(CH_2)_m C(=O)NH(CH_2)_m C(=O)$—, —$C(=O)(CH_2)_m NHC(=O)(CH_2)_m$—, —$(CH_2)_m C(=O)NH(CH_2)_m (O(CH_2)_m)_n C(=O)$—, —$C(=O)((CH_2)_m O)_n(CH_2)_m NHC(=O)(CH_2)_m$—, —$(CH_2)_m C(=O)NH(CH_2)_m C(=O)NH(CH_2)_m$—, —$(CH_2)_m NHC(=O)(CH_2)_m NHC(=O)(CH_2)_m$—, —$C(=O)NH(CH_2)_m NHC(=O)$—, —$(CH_2)_m S(CH_2)_m$—, —$NHC(=O)(CH_2)_m$—, —$NHC(=O)(CH_2)_m X_3(CH_2)_m$—, —$(CH_2)_m X_3(CH_2)_m C(=O)NH$—, —$(CH_2)_m C(=O)NH$—, —$(CH_2)_m NH(CH_2)_m$—, —$(CH_2)_m X_3(CH_2)_m$—, —$((CH_2)_m O)_n(CH_2)_m X_3(CH_2)_m$—, —$(CH_2)_m X_3(CH_2)_m (O(CH_2)_m)_n$—, —$NH(CH_2)_m$—, —$NHC(R^{12})_2(CH_2)_m$—, —$(CH_2)_m C(R^{12})_2NH$—, —$(CH_2)_m C(=O)NH(CH_2)_m NH$—, —$NH(CH_2)_m NHC(=O)(CH_2)_m$—, —$NHC(R^{12})_2(CH_2)_m NHC(=O)(CH_2)_m$—, —$(CH_2)_m C(=O)NH(CH_2)_m C(R^{12})_2NH$—, —$NH(CH_2)_m X_3(CH_2)_m$—, —$NHC(R^{12})_2(CH_2)_m X_3(CH_2)_m$—, —$(CH_2)_m X_3(CH_2)_m C(R^{12})_2NH$—, —$NHC(R^{12})_2(CH_2)_m OC(=O)NH(CH_2)_m$—, —$(CH_2)_m NHC(=O)OCH_2)_m C(R^{12})_2NH$—, —$NHC(R^{12})_2(CH_2)_m OC(=O)NH(CH_2)_m X_3(CH_2)_m$—, —$(CH_2)_m X_3(CH_2)_m NHC(=O)O(CH_2)_m C(R^{12})_2NH$—, —$NHC(R^{12})_2(CH_2)_m OC(=O)NH((CH_2)_m O)_n(CH_2)_m$—, —$(CH_2)_m (O(CH_2)_m)_n NHC(=O)O(CH_2)_m C(R^{12})_2NH$—, —$NHC(R^{12})_2(CH_2)_m OC(=O)NH((CH_2)_m O)_n(CH_2)_m X_3(CH_2)_m$—, —$(CH_2)_m X_3(CH_2)_m (OCH_2)_m)_n NHC(=O)OCH_2)_m C(R^{12})_2NH$—, —$(CH_2)_m X_3(CH_2)_m NH$—, —$NH((CH_2)_m O)_n(CH_2)_m X_3(CH_2)_m$—, —$(CH_2)_m X_3(CH_2)_m (O(CH_2)_m)_n NH$—, —$(CH_2)_m NH$—, —$NH((CH_2)_m O)_n(CH_2)_m$—, —$NH((CH_2)_m O)_n(CH_2)_m NHC(=O)(CH_2)_m$—, —$(CH_2)_m C(=O)NH(CH_2)_m (O(CH_2)_m)_n NH$—, —$(CH_2)_m (O(CH_2)_m)_n NH$—, —$(CH_2CH_2O)_n$—, —$(OCH_2CH_2)_n$—, —$(CH_2)_m O(CH_2)_m$—, —$S(=O)_2(CH_2)_m$—, —$(CH_2)_m S(=O)_2$—, —$S(=O)_2(CH_2)_m NHC(=O)(CH_2)_m$—, —$(CH_2)_m C(=O)NH(CH_2)_m S(=O)_2$—, —$S(=O)_2(CH_2)_m X_3(CH_2)_m$—, —$(CH_2)_m X_3(CH_2)_m S(=O)_2$—, —$(CH_2)_m X_2X_1C(=O)$—, —$C(=O)X_1X_2(CH_2)_m$—, —$(CH_2)_m (O(CH_2)_m)_n C(=O)X_2X_1C(=O)$—, —$C(=O)X_1X_2C(=O)((CH_2)_m O)_n(CH_2)_m$—, —$(CH_2)_m (O(CH_2)_m)_n X_2X_1C(=O)$—, —$(CH_2)_m X_3(CH_2)_m X_2X_1C(=O)$—, —$C(=O)X_1X_2(CH_2)_m X_3(CH_2)_m$—, —$(CH_2)_m X_3(CH_2)_m (O(CH_2)_m)_n X_2X_1C(=O)$—, —$(CH_2)_m X_3(CH_2)_m C(=O)NH(CH_2)_m NHC(=O)$—, —$(CH_2)_m X_3(CH_2)_m C(=O)NH(CH_2)_m C(=O)$—, —$C(=O)(CH_2)_m NHC(=O(CH_2)_m X_3(CH_2)_m$—, —$(CH_2)_m X_3(CH_2)_m C(=O)NH(CH_2)_m (O(CH_2)_m)_n C(=O)$—, —$C(=O)((CH_2)_m O)_n(CH_2)_m NHC(=O)(CH_2)_m X_3(CH_2)_m$—, —$(CH_2)_m NHC(=O)X_1X_2C(=O)(CH_2)_m$—, —$(CH_2)_m C(=O)X_2X_1C(=O)NH(CH_2)_m$—, —$X_4X_1X_2C(=O)(CH_2)_m$—, —$(CH_2)_m C(=O)X_2X_1X_4$—, —$X_1C(=O)(CH_2)_m NHC(=O)(CH_2)_m$—, —$(CH_2)_m C(=O)NH(CH_2)_m C(=O)X_1$—, —$C(=O)CHR^{aa}NH$—, —$CHR^{aa}C(=O)$—, —$C(=O)NH$—, —$C(=O)O$—, —$S$—, —$SCH_2C(=O)NH$—, —$NHC(=O)CH_2S$—, —$S(=O)_2CH_2CH_2S$—, —$SCH_2CH_2S(=O)_2$—, —$(CH_2)_2S(=O)_2CH_2CH_2S$—, —$SCH_2CH_2S(=O)_2CH_2CH_2$—, —$NHC(=S)$—, —$(CH_2)_m X_3(O(CH_2)_m)_n C(=O)$—, —$C(=O)((CH_2)_m O)_n X_3(CH_2)_m$—, —$(CH_2)_m NHC(=O)((CH_2)_m O)_n(CH_2)_m$—, —$(CH_2)_m (O(CH_2)_m)_n C(=O)NH(CH_2)_m$—, —$(CH_2)_m NHC(=O)NH(CH_2)_m$—, —$(CH_2)_m X_3(CH_2)_m NHC(=O)$—, —$C(=O)NH(CH_2)_m X_3(CH_2)_m$—, —$NHS(=O)_2(CH_2)_m X_3(CH_2)_m$—, —$(CH_2)_m X_3(CH_2)_m S(=O)_2NH$—,

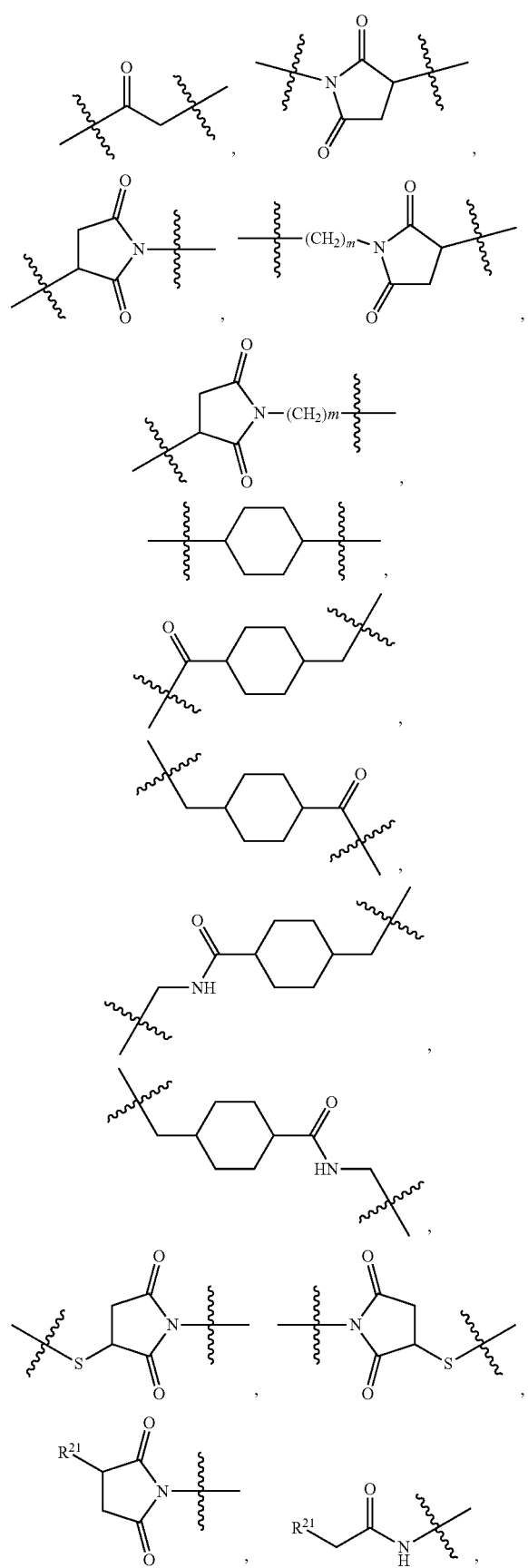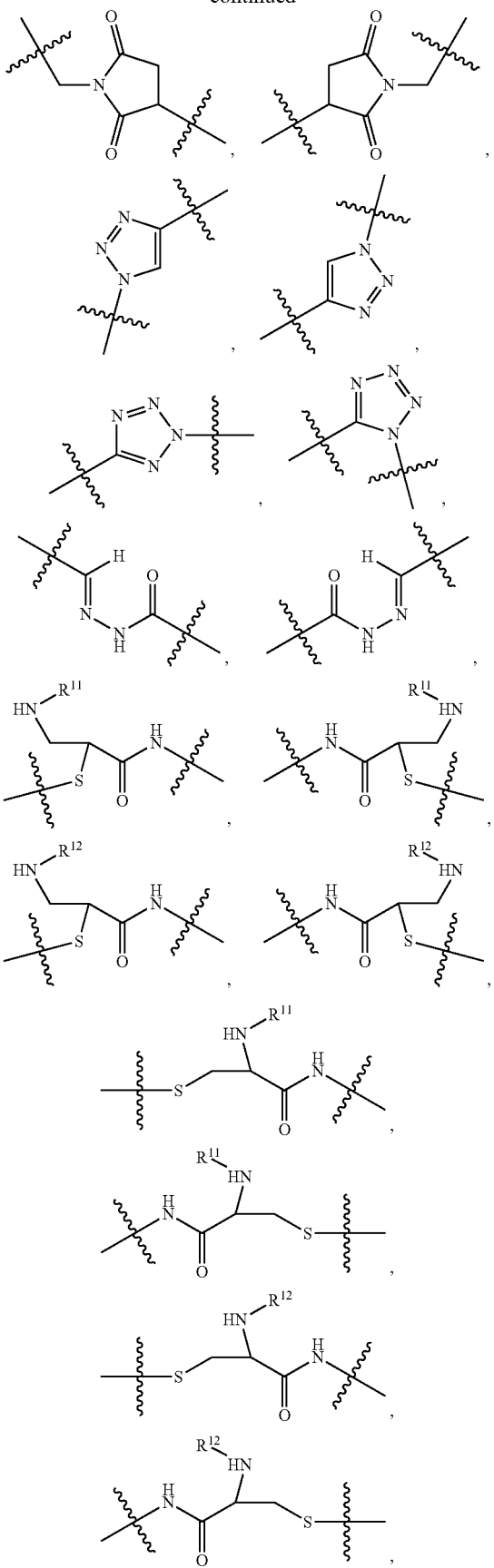

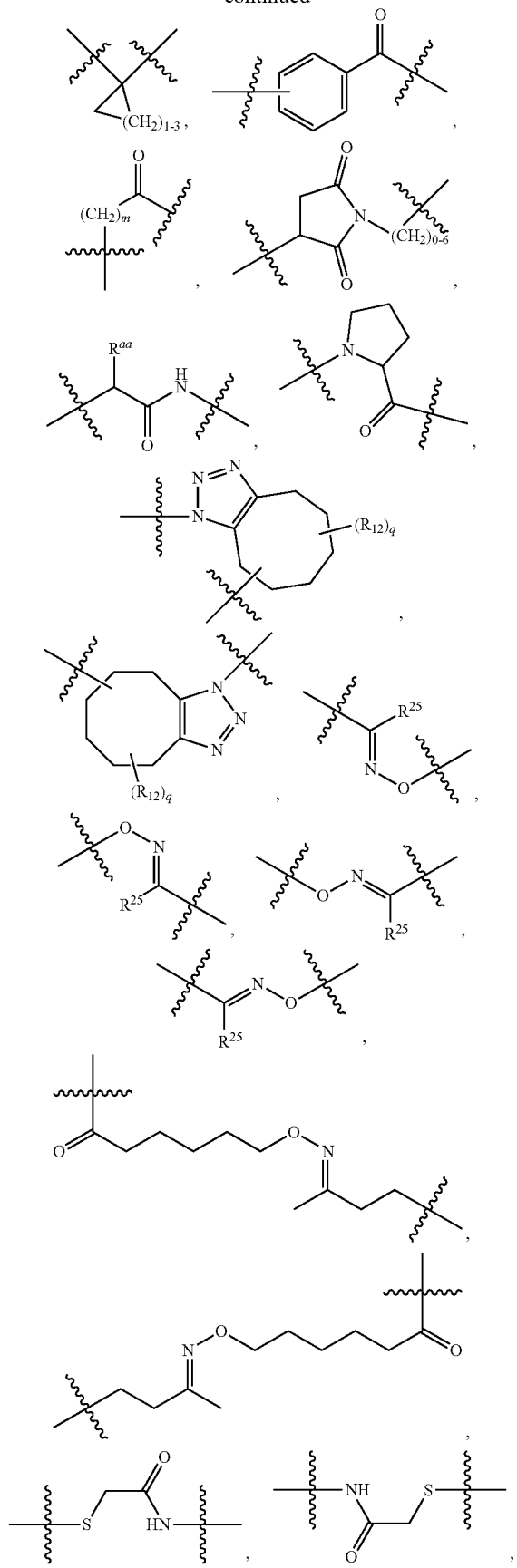
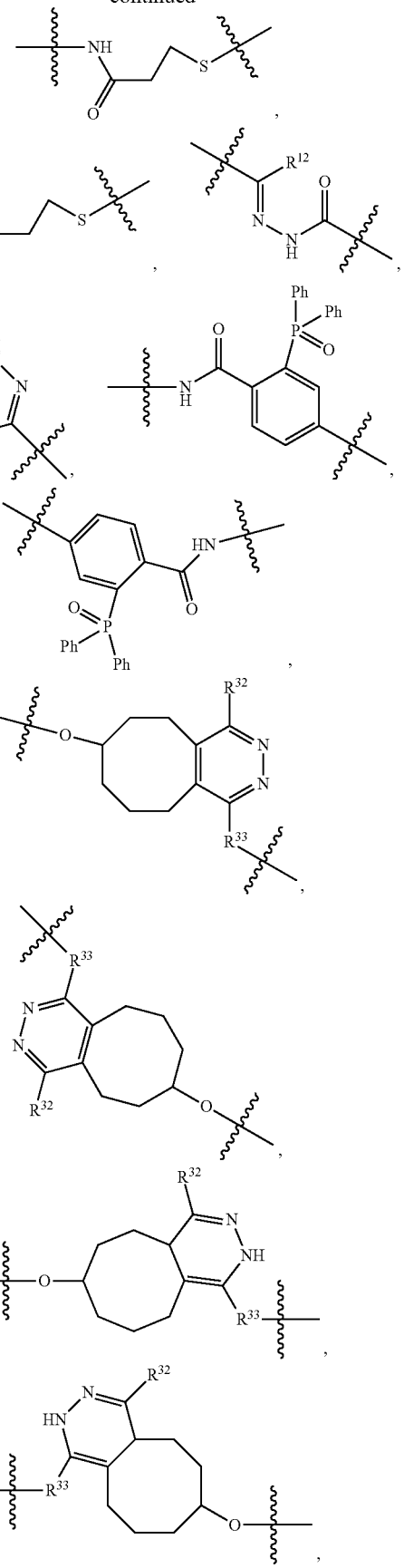

-continued
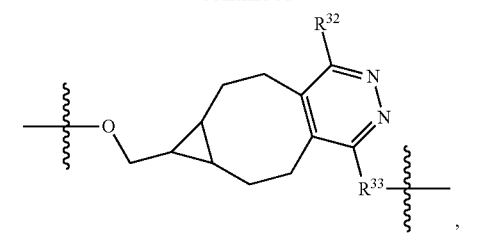,
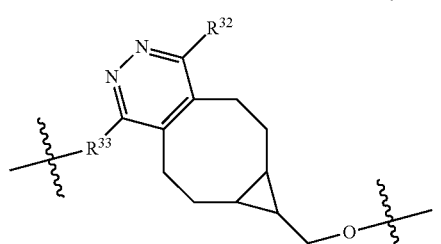,
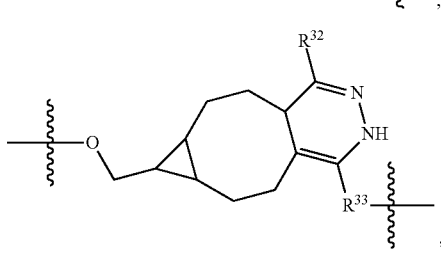,
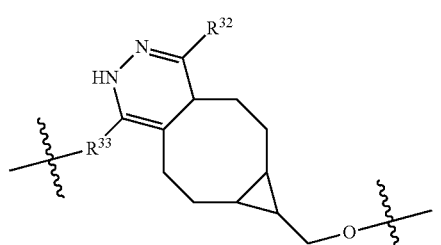,
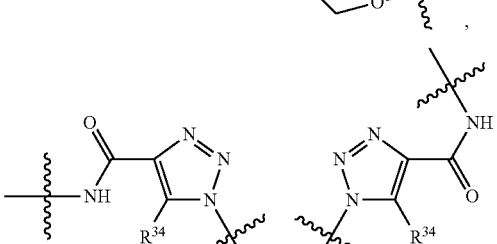,
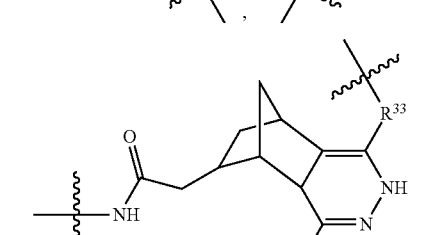,
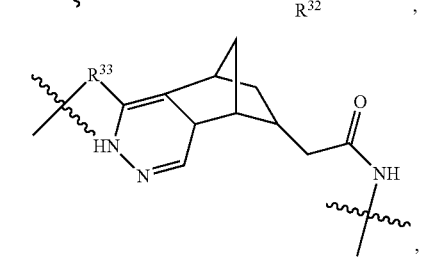,
-continued
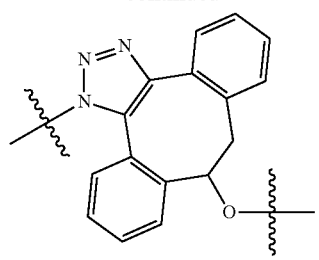,
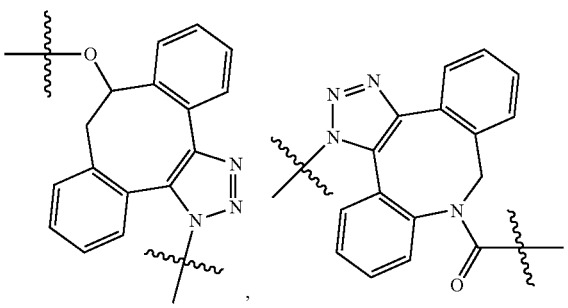,
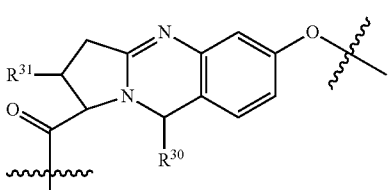,
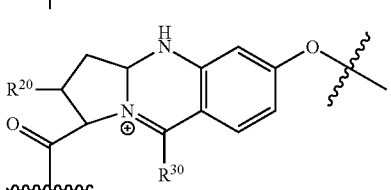,
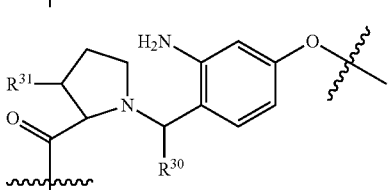,
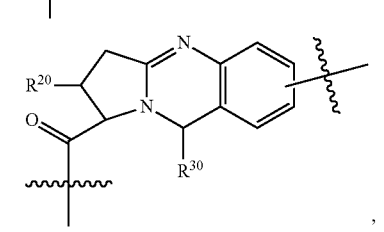,

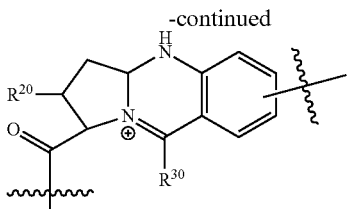

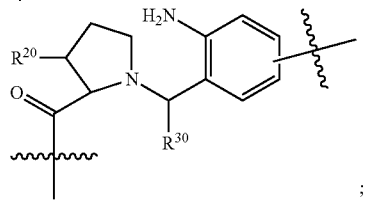

$L_2$, $L_3$, $L_4$, $L_5$, and $L_6$ are each independently selected from a bond, —(CH$_2$)$_m$—, —C(=O)(CH$_2$)$_m$—, —C(=O)X$_1$X$_2$C(=O)(CH$_2$)$_m$—, —C(=O)X$_1$X$_2$C(=O)(CH$_2$)$_m$NHC(=O)(CH$_2$)$_m$—, —C(=O)X$_1$X$_2$C(=O)(CH$_2$)$_m$X$_3$(CH$_2$)$_m$—, —C(=O)X$_1$X$_2$C(=O)((CH$_2$)$_m$O)$_n$(CH$_2$)$_m$—, —C(=O)X$_1$X$_2$C(=O)((CH$_2$)$_m$O)$_n$(CH$_2$)$_m$NHC(=O)(CH$_2$)$_m$—, —C(=O)X$_1$X$_2$C(=O)((CH$_2$)$_m$O)$_n$(CH$_2$)$_m$NHC(=O)(CH$_2$)$_m$X$_3$(CH$_2$)$_m$—, —C(=O)X$_1$X$_2$C(=O)((CH$_2$)$_m$O)$_n$(CH$_2$)$_m$X$_3$(CH$_2$)$_m$—, —C(=O)X$_1$X$_2$C(=O)(CH$_2$)$_m$NHC(=O)((CH$_2$)$_m$O)$_n$(CH$_2$)$_m$—, —C(=O)X$_1$X$_2$C(=O)(CH$_2$)$_m$NHC(=O)((CH$_2$)$_m$O)$_n$(CH$_2$)$_m$X$_3$(CH$_2$)$_m$—, —C(=O)X$_1$X$_2$(CH$_2$)$_m$X$_3$(CH$_2$)$_m$—, —C(=O)X$_1$X$_2$((CH$_2$)$_m$O)$_n$(CH$_2$)$_m$—, —C(=O)X$_1$X$_2$((CH$_2$)$_m$O)$_n$(CH$_2$)$_m$NHC(=O)(CH$_2$)$_m$—, —C(=O)X$_1$X$_2$((CH$_2$)$_m$O)$_n$(CH$_2$)$_m$NHC(=O)(CH$_2$)$_m$X$_3$(CH$_2$)$_m$—, —C(=O)X$_1$X$_2$((CH$_2$)$_m$O)$_n$(CH$_2$)$_m$X$_3$(CH$_2$)$_m$—, —C(=O)X$_1$X$_2$(CH$_2$)$_m$NH((CH$_2$)$_m$O)$_n$(CH$_2$)$_m$—, —C(=O)X$_1$X$_2$C(=O)(CH$_2$)$_m$NH((CH$_2$)$_m$O)$_n$(CH$_2$)$_m$X$_3$(CH$_2$)$_m$—, —(CH$_2$)$_m$NHC(=O)(CH$_2$)$_m$—, —C(=O)((CH$_2$)$_m$O)$_n$(CH$_2$)$_m$—, —(CH$_2$)$_m$S(=O)$_2$((CH$_2$)$_m$O)$_n$(CH$_2$)$_m$—, —C(=O)(CH$_2$)$_m$NH(CH$_2$)$_m$—, —C(=O)NH(CH$_2$)$_m$—, —C(=O)NH(CH$_2$)$_m$X$_3$(CH$_2$)$_m$—, —C(=O)NH(CH$_2$)$_m$NHC(=O)X$_1$X$_2$C(=O)(CH$_2$)$_m$—, —C(=O)X$_1$C(=O)NH(CH$_2$)$_m$NHC(=O)(CH$_2$)$_m$—, —C(=O)X$_1$C(=O)NH(CH$_2$)$_m$X$_3$(CH$_2$)$_m$—, —C(=O)NH(CH$_2$)$_m$NHC(=O)(CH$_2$)$_m$—, —C(=O)NH(CH$_2$)$_m$NHC(=O)(CH$_2$)$_m$X$_3$(CH$_2$)$_m$—,

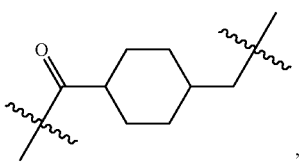 [SMILES: *CC1CCC(C(*)=O)CC1]

—(CH$_2$)$_m$C(=O)NH(CH$_2$)$_m$NHC(=O)(CH$_2$)$_m$—, —(CH$_2$)$_m$C(=O)—, —(CH$_2$)$_m$C(=O)X$_2$X$_1$C(=O)—, —(CH$_2$)$_m$X$_3$(CH$_2$)$_m$C(=O)X$_2$X$_1$C(=O)—, —(CH$_2$)$_m$C(=O)NH(CH$_2$)$_m$—, —(CH$_2$)$_m$X$_3$(CH$_2$)$_m$C(=O)NH(CH$_2$)$_m$—, —(CH$_2$)$_m$NHC(=O)(CH$_2$)$_m$X$_3$(CH$_2$)$_m$—, —(CH$_2$)$_m$(O(CH$_2$)$_m$)$_n$C(=O)—, —(CH$_2$)$_m$(O(CH$_2$)$_m$)$_n$S(=O)$_2$(CH$_2$)$_m$—, —(CH$_2$)$_m$NH(CH$_2$)$_m$C(=O)—, —(CH$_2$)$_m$NHC(=O)—, —(CH$_2$)$_m$C(=O)X$_2$X$_1$C(=O)NH(CH$_2$)$_m$NHC(=O)—, —(CH$_2$)$_m$C(=O)NH(CH$_2$)$_m$NHC(=O)X$_1$—, —(CH$_2$)$_m$C(=O)NH(CH$_2$)$_m$NHC(=O)—,

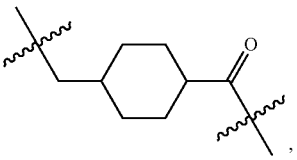 [SMILES: *CC1CCC(C(*)=O)CC1]

—((CH$_2$)$_m$O)$_n$(CH$_2$)$_m$—, —(CH$_2$)$_m$(O(CH$_2$)$_m$)$_n$—, —(CH$_2$)$_m$(O(CH$_2$)$_m$)$_n$X$_3$(CH$_2$)$_m$—, —(CH$_2$)$_m$X$_3$((CH$_2$)$_m$O)$_n$(CH$_2$)$_m$—, —(CH$_2$)$_m$X$_3$(CH$_2$)$_m$C(=O)—, —C(=O)(CH$_2$)$_m$X$_3$(CH$_2$)$_m$—, —(CH$_2$)$_m$X$_3$(CH$_2$)$_m$(O(CH$_2$)$_m$)$_n$C(=O)—, —C(=O)((CH$_2$)$_m$O)$_n$(CH$_2$)$_m$X$_3$(CH$_2$)$_m$—, —(CH$_2$)$_m$C(=O)NH(CH$_2$)$_m$C(=O)—, —C(=O)(CH$_2$)$_m$NHC(=O)(CH$_2$)$_m$—, —(CH$_2$)$_m$C(=O)NH(CH$_2$)$_m$(O(CH$_2$)$_m$)$_n$C(=O)—, —C(=O)((CH$_2$)$_m$O)$_n$(CH$_2$)$_m$NHC(=O)(CH$_2$)$_m$—, —(CH$_2$)$_m$C(=O)NH(CH$_2$)$_m$C(=O)NH(CH$_2$)$_m$—, —(CH$_2$)$_m$NHC(=O)(CH$_2$)$_m$NHC(=O)(CH$_2$)$_m$—, —C(=O)NH(CH$_2$)$_m$NHC(=O)—, —(CH$_2$)$_m$S(CH$_2$)$_m$—, —NHC(=O)(CH$_2$)$_m$—, —NHC(=O)(CH$_2$)$_m$X$_3$(CH$_2$)$_m$—, —(CH$_2$)$_m$X$_3$(CH$_2$)$_m$C(=O)NH—, —(CH$_2$)$_m$C(=O)NH—, —(CH$_2$)$_m$NH(CH$_2$)$_m$—, —(CH$_2$)$_m$X$_3$(CH$_2$)$_m$—, —((CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$—, —NH(CH$_2$)$_m$—, —(CH$_2$)$_m$C(R$^{12}$)$_2$(CH$_2$)$_m$—, —(CH$_2$)$_m$C(R$^{12}$)$_2$NH—, —(CH$_2$)$_m$C(=O)NH(CH$_2$)$_m$NH—, —NH(CH$_2$)$_m$NHC(=O)(CH$_2$)$_m$—, —NHC(R$^{12}$)$_2$(CH$_2$)$_m$NHC(=O)(CH$_2$)$_m$—, —(CH$_2$)$_m$C(=O)NH(CH$_2$)$_m$C(R$^{12}$)$_2$NH—, —NH(CH$_2$)$_m$X$_3$(CH$_2$)$_m$—, —NHC(R$^{12}$)$_2$(CH$_2$)$_m$X$_3$(CH$_2$)$_m$—, —(CH$_2$)$_m$X$_3$(CH$_2$)$_m$C(R$^{12}$)$_2$NH—, —NHC(R$^{12}$)$_2$(CH$_2$)$_m$OC(=O)NH(CH$_2$)$_m$—, —(CH$_2$)$_m$NHC(=O)O(CH$_2$)$_m$C(R$^{12}$)$_2$NH—, —NHC(R$^{12}$)$_2$(CH$_2$)$_m$OC(=O)NH(CH$_2$)$_m$X$_3$(CH$_2$)$_m$—, —(CH$_2$)$_m$X$_3$(CH$_2$)$_m$NHC(=O)O(CH$_2$)$_m$C(R$^{12}$)$_2$NH—, —NHC(R$^{12}$)$_2$(CH$_2$)$_m$OC(=O)NH((CH$_2$)$_m$O)$_n$(CH$_2$)$_m$—, —(CH$_2$)$_m$(O(CH$_2$)$_m$)$_n$NHC(=O)O(CH$_2$)$_m$C(R$^{12}$)$_2$NH—, —NHC(R$^{12}$)$_2$(CH$_2$)$_m$OC(=O)NH((CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NHC(=O)O(CH$_2$)$_m$C(R$^{12}$)$_2$NH—, —(CH$_2$)$_m$X$_3$(CH$_2$)$_m$NH—, —NH((CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NH—, —(CH$_2$)$_m$NH—, —NH((CH$_2$)$_m$O)$_n$(CH$_2$)$_m$—, —NH((CH$_2$)$_m$O)$_n$(CH$_2$)$_m$NHC(=O)(CH$_2$)$_m$—, —(CH$_2$)$_m$C(=O)NH(CH$_2$)$_m$(O(CH$_2$)$_m$)$_n$NH—, —(CH$_2$)$_m$(O(CH$_2$)$_m$)$_n$NH—, —(OCH$_2$CH$_2$)$_n$—, —(OCH$_2$CH$_2$)$_n$—, —(CH$_2$)$_m$O(CH$_2$)$_m$—, —S(=O)$_2$(CH$_2$)$_m$—, —(CH$_2$)$_m$S(=O)$_2$—, —S(=O)$_2$(CH$_2$)$_m$NHC(=O)(CH$_2$)$_m$—, —(CH$_2$)$_m$C(=O)NH(CH$_2$)$_m$S(=O)$_2$—, —S(=O)$_2$(CH$_2$)$_m$X$_3$(CH$_2$)$_m$—, —(CH$_2$)$_m$X$_3$(CH$_2$)$_m$S(=O)$_2$—, —(CH$_2$)$_m$X$_2$X$_1$C(=O)—, —C(=O)X$_1$X$_2$(CH$_2$)$_m$—, —(CH$_2$)$_m$(O(CH$_2$)$_m$)$_n$C(=O)X$_2$X$_1$C(=O)—, —C(=O)X$_1$X$_2$C(=O)((CH$_2$)$_m$O)$_n$(CH$_2$)$_m$—, —(CH$_2$)$_m$(O(CH$_2$)$_m$)$_n$X$_2$X$_1$C(=O)—, —(CH$_2$)$_m$X$_3$(CH$_2$)$_m$X$_2$X$_1$C(=O)—, —C(=O)X$_1$X$_2$(CH$_2$)$_m$X$_3$(CH$_2$)$_m$—, —(CH$_2$)$_m$X$_3$(CH$_2$)$_m$(O(CH$_2$)$_m$)$_n$X$_2$X$_1$C(=O)—, —(CH$_2$)$_m$X$_3$(CH$_2$)$_m$C(=O)NH(CH$_2$)$_m$NHC(=O)—, —(CH$_2$)$_m$X$_3$(CH$_2$)$_m$C(=O)NH(CH$_2$)$_m$C(=O)—, —C(=O)(CH$_2$)$_m$NHC(=O)(CH$_2$)$_m$X$_3$(CH$_2$)$_m$—, —(CH$_2$)$_m$NHC(=O)X$_1$X$_2$C(=O)(CH$_2$)$_m$—, —(CH$_2$)$_m$C(=O)X$_2$X$_1$C(=O)NH(CH$_2$)$_m$—, —X$_4$X$_1$X$_2$C(=O)(CH$_2$)$_m$—, —(CH$_2$)$_m$C(=O)X$_2$X$_1$X$_4$—, —X$_1$C(=O)(CH$_2$)$_m$NHC(=O)(CH$_2$)$_m$—, —(CH$_2$)$_m$C(=O)NH(CH$_2$)$_m$C(=O)X$_1$—, —C(=O)CHR$^{aa}$NH—, —CHR$^{aa}$C(=O)—, —C(=O)NH—, —C(=O)O—, —S—, —SCH$_2$C(=O)NH—, —NHC(=O)CH$_2$S—, —S(=O)$_2$CH$_2$CH$_2$S—, —SCH$_2$CH$_2$S(=O)$_2$—, —(CH$_2$)$_2$S(=O)$_2$CH$_2$CH$_2$S—, —SCH$_2$CH$_2$S(=O)$_2$CH$_2$CH$_2$—, —NHC(=S)—, —(CH$_2$)$_m$X$_3$(O(CH$_2$)$_m$)$_n$C(=O)—, —C(=O)

((CH$_2$)$_m$O)$_n$X$_3$(CH$_2$)$_m$—, —(CH$_2$)$_m$NHC(=O)((CH$_2$)$_m$O)$_n$(CH$_2$)$_m$—, —(CH$_2$)$_m$(O(CH$_2$)$_m$)$_n$C(=O)NH(CH$_2$)$_m$—, —(CH$_2$)$_m$NHC(=O)NH(CH$_2$)$_m$—, —(CH$_2$)$_m$X$_3$(CH$_2$)$_m$NHC(=O)—, —C(=O)NH(CH$_2$)$_m$X$_3$(CH$_2$)$_m$—, —NHS(=O)$_2$(CH$_2$)$_m$X$_3$(CH$_2$)$_m$—, —(CH$_2$)$_m$X$_3$(CH$_2$)$_m$S(=O)$_2$NH—,
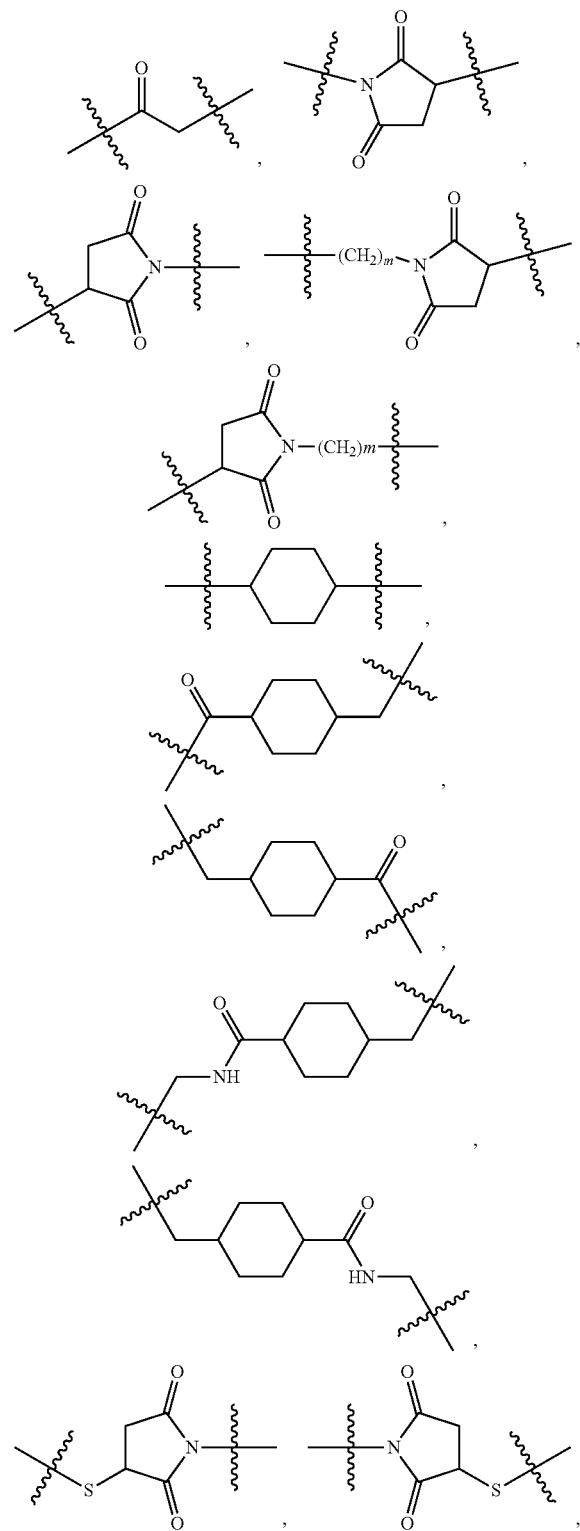
-continued
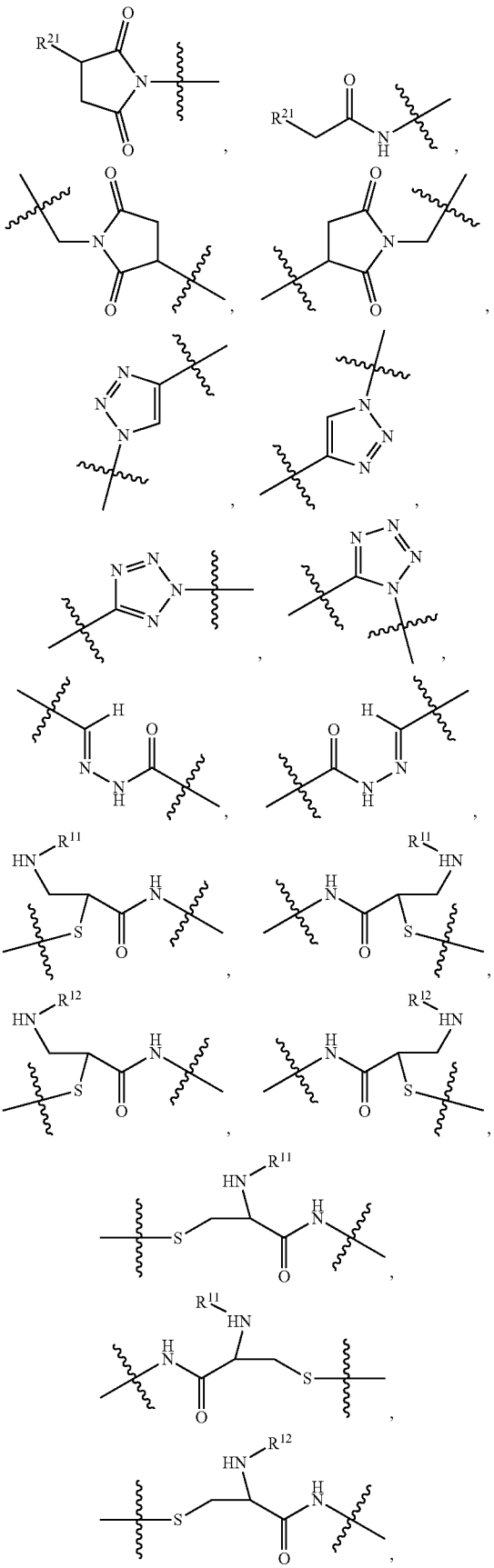

425
-continued
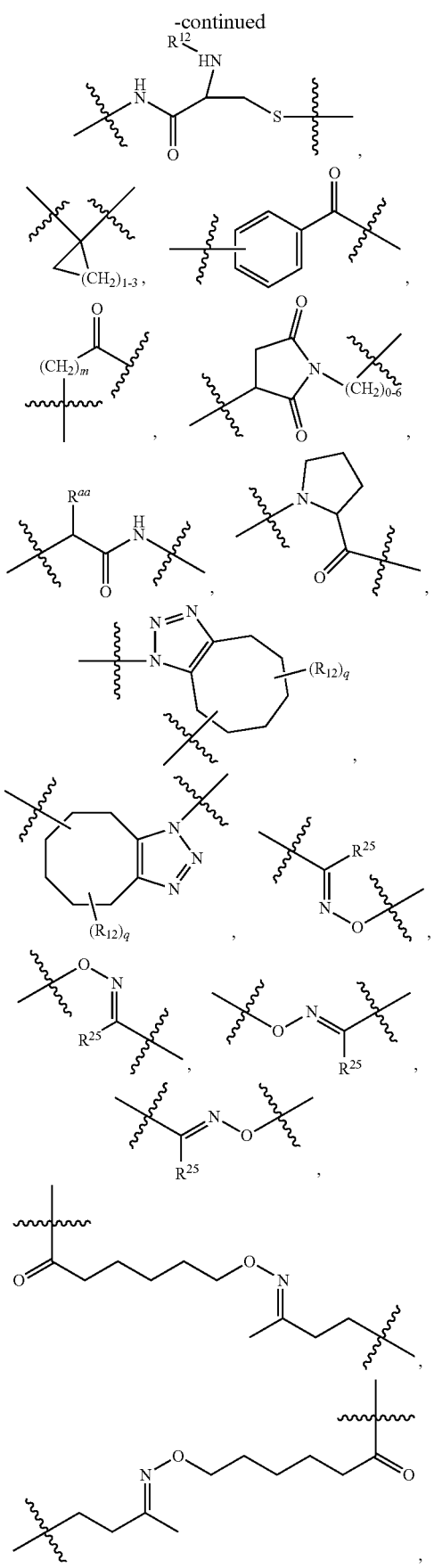
426
-continued
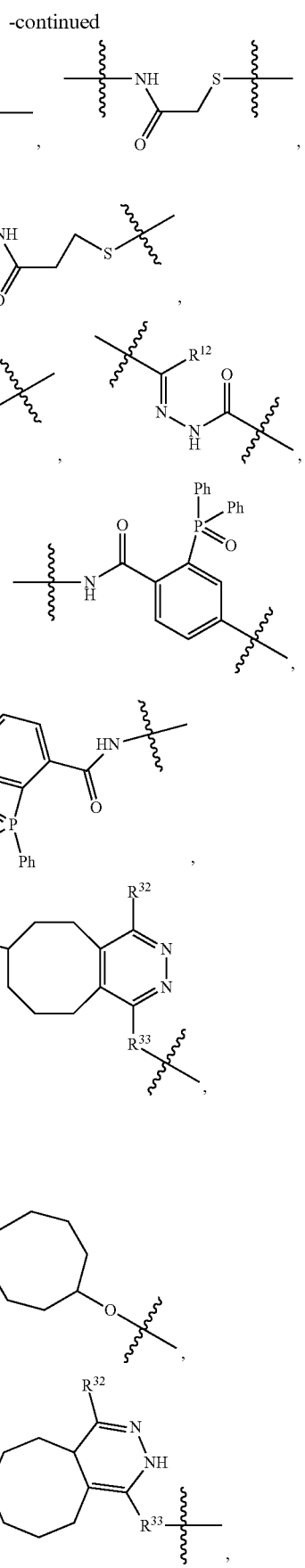

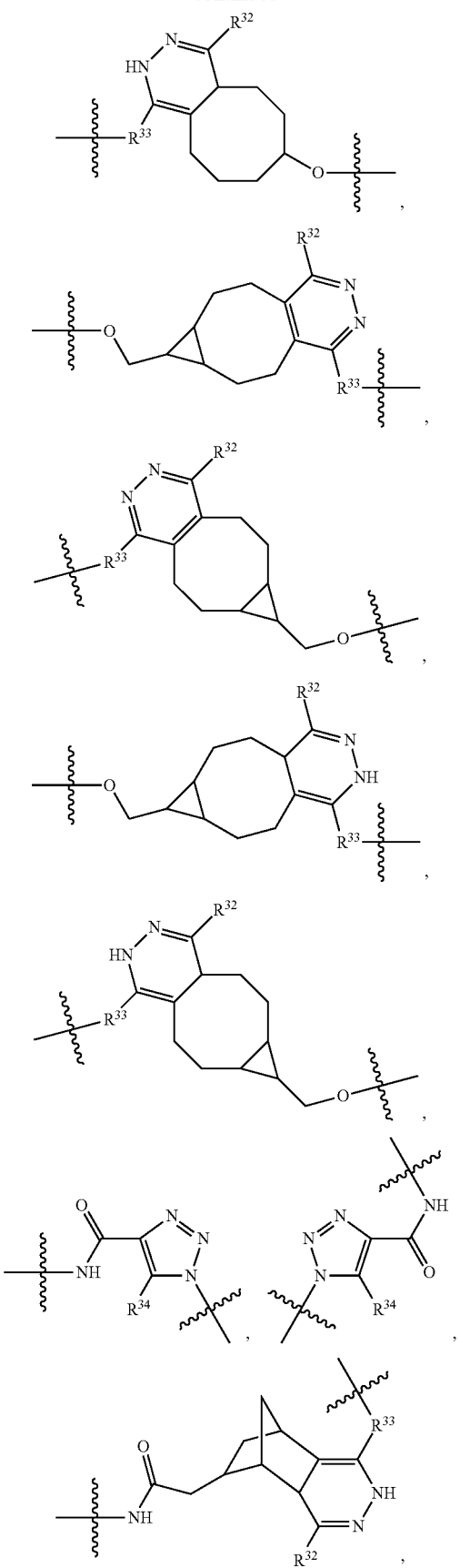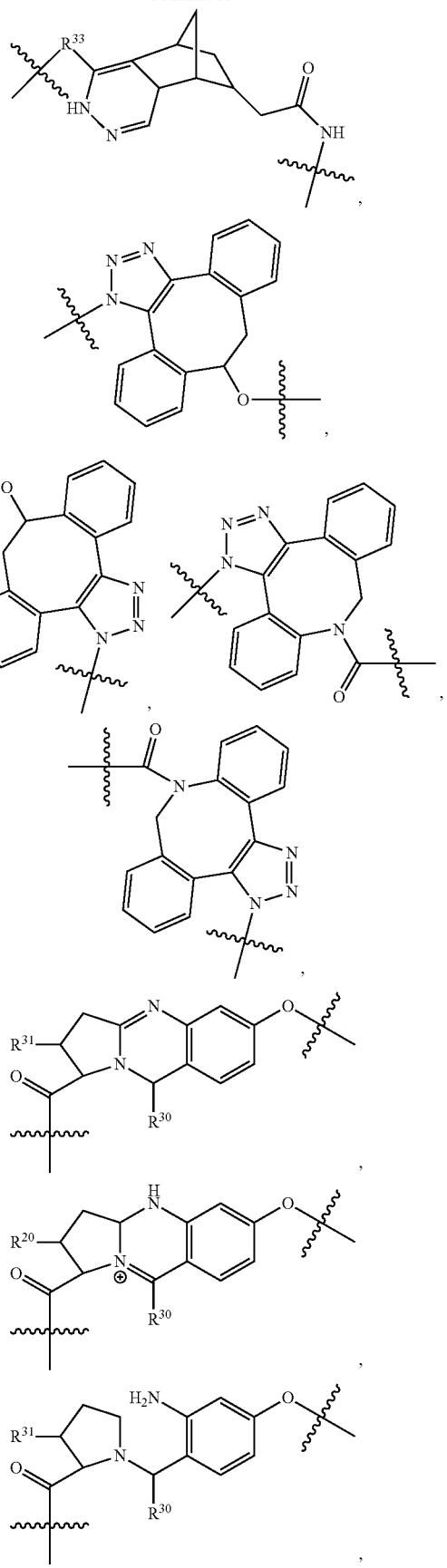

429
-continued

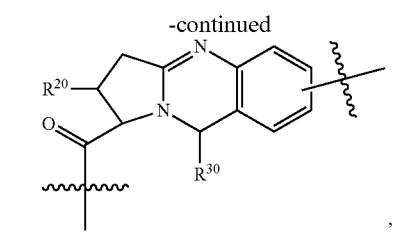

,

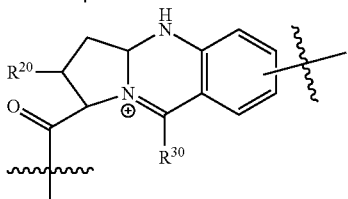

and

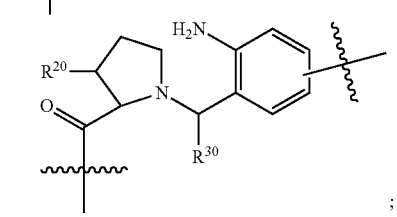

;

wherein:
R[20] is H or Me, and R[30] is H, —CH₃ or phenyl;
R[21] is

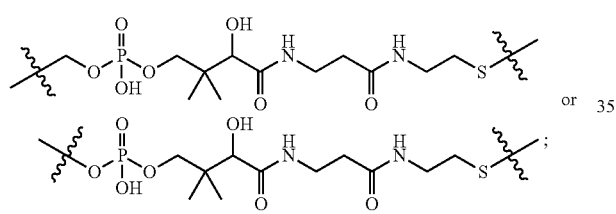

or each R[25] is independently selected from H or $C_{1-4}$ alkyl;
R[aa] is a side chain of an amino acid selected from glycine, alanine, tryptophan, tyrosine, phenylalanine, leucine, isoleucine, valine, asparagine, glutamic acid, glutamine, aspatic acid, histidine, arginine, lysine, cysteine, methionine, serine, threonine, phenylglycine and t-butylglycine;
R[32] is independently selected from H, $C_{1-4}$ alkyl, phenyl, pyrimidine and pyridine;
R[33] is independently selected from

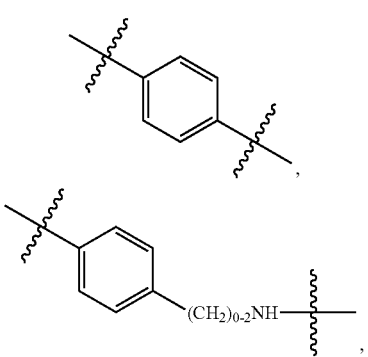

,

430
-continued

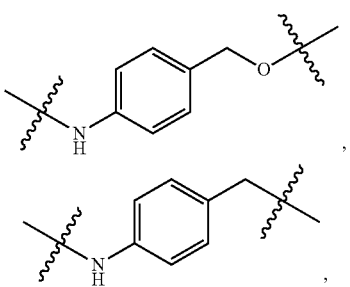

and
R[34] is independently selected from H, $C_{1-4}$ alkyl, and $C_{1-6}$ haloalkyl;
X₁ is self immolative spacer selected from -continued

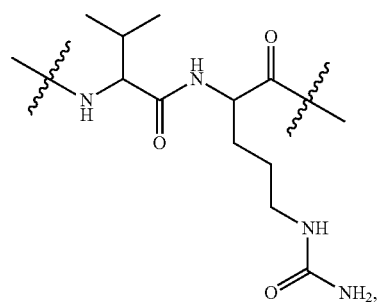

or

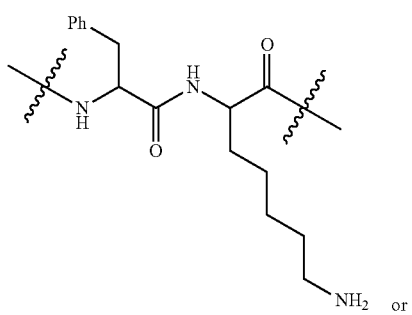

$X_2$ is dipeptide selected from

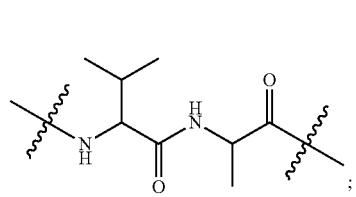

$X_3$ is

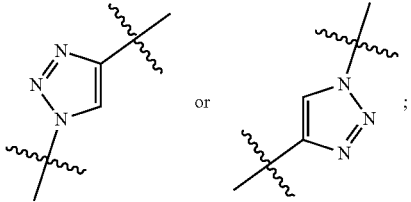 [SMILES: *c1cn(*)nn1 ; *c1cn(*)nn1]

and $X_4$ is

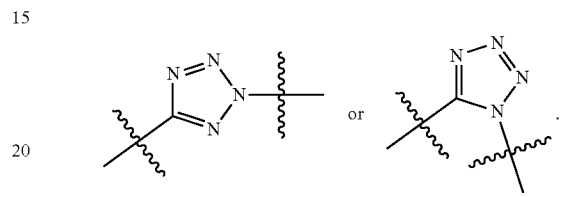

Embodiment 84. The compound of any one of embodiments 3 to 45 and 78 to 80, and the immunoconjugate according to any one of embodiments 46 to 80, wherein:
$L_2$, $L_3$, $L_4$, $L_5$ and $L_6$ are a bond, and
$L_1$ is selected from —(CH$_2$)$_m$—, —C(=O)(CH$_2$)$_m$—, —C(=O)X$_1$X$_2$C(=O)(CH$_2$)$_m$—, —C(=O)X$_1$X$_2$C(=O)(CH$_2$)$_m$NR$^{12}$C(=O)(CH$_2$)$_m$—, —C(=O)X$_1$X$_2$C(=O)(CH$_2$)$_m$X$_3$(CH$_2$)$_m$—, —C(=O)X$_1$X$_2$C(=O)((CH$_2$)$_m$O)$_n$(CH$_2$)$_m$—, —C(=O)X$_1$X$_2$C(=O)((CH$_2$)$_m$O)$_n$(CH$_2$)$_m$NR$^{12}$C(=O)(CH$_2$)$_m$—, —C(=O)X$_1$X$_2$C(=O)((CH$_2$)$_m$O)$_n$(CH$_2$)$_m$X$_3$(CH$_2$)$_m$—, —C(=O)X$_1$X$_2$C(=O)((CH$_2$)$_m$O)$_n$(CH$_2$)$_m$X$_3$(CH$_2$)$_m$—, —C(=O)X$_1$X$_2$C(=O)(CH$_2$)$_m$NR$^{12}$C(=O)((CH$_2$)$_m$O)$_n$(CH$_2$)$_m$—, —C(=O)X$_1$X$_2$C(=O)(CH$_2$)$_m$NR$^{12}$C(=O)((CH$_2$)$_m$O)$_n$(CH$_2$)$_m$X$_3$(CH$_2$)$_m$—, —C(=O)X$_1$X$_2$C(=O)(CH$_2$)$_m$X$_3$(CH$_2$)$_m$—, —C(=O)X$_1$X$_2$((CH$_2$)$_m$O)$_n$(CH$_2$)$_m$—, —C(=O)X$_1$X$_2$((CH$_2$)$_m$O)$_n$(CH$_2$)$_m$NR$^{12}$C(=O)(CH$_2$)$_m$—, —C(=O)X$_1$X$_2$((CH$_2$)$_m$O)$_n$(CH$_2$)$_m$NR$^{12}$C(=O)(CH$_2$)$_m$X$_3$(CH$_2$)$_m$—, —C(=O)X$_1$X$_2$((CH$_2$)$_m$O)$_n$(CH$_2$)$_m$X$_3$(CH$_2$)$_m$—, —C(=O)X$_1$X$_2$(CH$_2$)$_m$NR$^{12}$((CH$_2$)$_m$O)$_n$(CH$_2$)$_m$—, —C(=O)X$_1$X$_2$C(=O)(CH$_2$)$_m$NR$^{12}$((CH$_2$)$_m$O)$_n$(CH$_2$)$_m$X$_3$(CH$_2$)$_m$—, —(CH$_2$)$_m$NR$^{12}$C(=O)(CH$_2$)$_m$—, —C(=O)((CH$_2$)$_m$O)$_n$(CH$_2$)$_m$—, —(CH$_2$)$_m$S(=O)$_2$((CH$_2$)$_m$O)$_n$(CH$_2$)$_m$—, —C(=O)(CH$_2$)$_m$NR$^{12}$(CH$_2$)$_m$—, —C(=O)NR$^{12}$(CH$_2$)$_m$—, —C(=O)NR$^{12}$(CH$_2$)$_m$X$_3$(CH$_2$)$_m$—, —C(=O)NH(CH$_2$)$_m$NR$^{12}$C(=O)X$_1$X$_2$C(=O)(CH$_2$)$_m$—, —C(=O)X$_1$C(=O)NR$^{12}$(CH$_2$)$_m$NR$^{12}$C(=O)(CH$_2$)$_m$—, —C(=O)X$_1$C(=O)NR$^{12}$(CH$_2$)$_m$X$_3$(CH$_2$)$_m$—, —C(=O)NR$^{12}$(CH$_2$)$_m$NR$^{12}$C(=O)(CH$_2$)$_m$—, —C(=O)NR$^{12}$(CH$_2$)$_m$NR$^{12}$C(=O)(CH$_2$)$_m$X$_3$(CH$_2$)$_m$—,

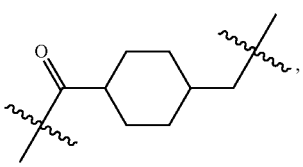 [SMILES: *CC1CCC(C(*)=O)CC1]

(CH$_2$)$_m$C(=O)NR$^{12}$(CH$_2$)$_m$NR$^{12}$C(=O)(CH$_2$)$_m$—, —(CH$_2$)$_m$C(=O)—, —(CH$_2$)$_m$C(=O)X$_2$X$_1$C(=O)—,

—(CH$_2$)$_m$X$_3$(CH$_2$)$_m$C(=O)X$_2$X$_1$C(=O)—, —(CH$_2$)$_m$C(=O)NR$^{12}$(CH$_2$)$_m$—, —(CH$_2$)$_m$X$_3$(CH$_2$)$_m$C(=O)NR$^{12}$(CH$_2$)$_m$—, —(CH$_2$)$_m$NR$^{12}$C(=O)(CH$_2$)$_m$X$_3$(CH$_2$)$_m$—, —(CH$_2$)$_m$(O(CH$_2$)$_m$)$_n$C(=O)—, —(CH$_2$)$_m$(O(CH$_2$)$_m$)$_n$S(=O)$_2$(CH$_2$)$_m$—, —(CH$_2$)$_m$NR$^{12}$(CH$_2$)$_m$C(=O)—, —(CH$_2$)$_m$NR$^{12}$C(=O)—, —(CH$_2$)$_m$C(=O)X$_2$X$_1$C(=O)NR$^{12}$(CH$_2$)$_m$NHC(=O)—, —(CH$_2$)$_m$C(=O)NR$^{12}$(CH$_2$)$_m$NR$^{12}$C(=O)X$_1$—, —(CH$_2$)$_m$C(=O)NR$^{12}$(CH$_2$)$_m$NR$^{12}$C(=O)—,

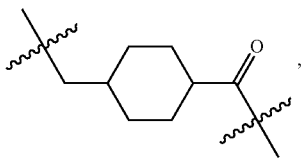

—((CH$_2$)$_m$O)$_n$(CH$_2$)$_m$—, —(CH$_2$)$_m$(O(CH$_2$)$_m$)$_n$—, —(CH$_2$)$_m$(O(CH$_2$)$_m$)$_n$X$_3$(CH$_2$)$_m$—, —(CH$_2$)$_m$X$_3$((CH$_2$)$_m$O)$_n$(CH$_2$)$_m$—, —(CH$_2$)$_m$X$_3$(CH$_2$)$_m$C(=O)—, —C(=O)(CH$_2$)$_m$X$_3$(CH$_2$)$_m$—, —(CH$_2$)$_m$X$_3$(CH$_2$)$_m$(O(CH$_2$)$_m$)$_n$C(=O)—, —C(=O)((CH$_2$)$_m$O)$_n$(CH$_2$)$_m$X$_3$(CH$_2$)$_m$—, —C(=O)(CH$_2$)$_m$C(=O)NR$^{12}$(CH$_2$)$_m$C(=O)—, —(CH$_2$)$_m$NR$^{12}$C(=O)(CH$_2$)$_m$C(=O)—, —(CH$_2$)$_m$C(=O)NR$^{12}$(CH$_2$)$_m$(O(CH$_2$)$_m$)$_n$C(=O)—, —C(=O)((CH$_2$)$_m$O)$_n$(CH$_2$)$_m$NR$^{12}$C(=O)(CH$_2$)$_m$—, —(CH$_2$)$_m$C(=O)NR$^{12}$(CH$_2$)$_m$C(=O)NR$^{12}$(CH$_2$)$_m$—, —(CH$_2$)$_m$NR$^{12}$C(=O)(CH$_2$)$_m$NR$^{12}$C(=O)(CH$_2$)$_m$—, —C(=O)NR$^{12}$(CH$_2$)$_m$NR$^{12}$C(=O)—, —(CH$_2$)$_m$S(CH$_2$)$_m$—, —NR$^{12}$C(=O)(CH$_2$)$_m$—, —NR$^{12}$C(=O)(CH$_2$)$_m$X$_3$(CH$_2$)$_m$—, —(CH$_2$)$_m$X$_3$(CH$_2$)$_m$C(=O)NR$^{12}$—, —(CH$_2$)$_m$C(=O)NR$^{12}$—, —(CH$_2$)$_m$NR$^{12}$(CH$_2$)$_m$—, —(CH$_2$)$_m$X$_3$(CH$_2$)$_m$—, —((CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$—, —NR$^{12}$(CH$_2$)$_m$—, —NR$^{12}$C(R$^{12}$)$_2$(CH$_2$)$_m$—, —(CH$_2$)$_m$C(R$^{12}$)$_2$NR$^{12}$—, —(CH$_2$)$_m$C(=O)NR$^{12}$(CH$_2$)$_m$NR$^{12}$—, —NR$^{12}$(CH$_2$)$_m$NR$^{12}$C(=O)(CH$_2$)$_m$—, —NR$^{12}$C(R$^{12}$)$_2$(CH$_2$)$_m$NR$^{12}$C(=O)(CH$_2$)$_m$—, —(CH$_2$)$_m$C(=O)NR$^{12}$(CH$_2$)$_m$C(R$^{12}$)$_2$NR$^{12}$—, —NR$^{12}$(CH$_2$)$_m$X$_3$(CH$_2$)$_m$—, —NR$^{12}$C(R$^{12}$)$_2$(CH$_2$)$_m$X$_3$(CH$_2$)$_m$—, —(CH$_2$)$_m$X$_3$(CH$_2$)$_m$C(R$^{12}$)$_2$NR$^{12}$—, —NR$^{12}$C(R$^{12}$)$_2$(CH$_2$)$_m$OC(=O)NR$^{12}$(CH$_2$)$_m$—, —(CH$_2$)$_m$NR$^{12}$C(=O)O(CH$_2$)$_m$C(R$^{12}$)$_2$NR$^{12}$—, —NR$^{12}$C(R$^{12}$)$_2$(CH$_2$)$_m$OC(=O)NR$^{12}$(CH$_2$)$_m$X$_3$(CH$_2$)$_m$—, —(CH$_2$)$_m$X$_3$(CH$_2$)$_m$NR$^{12}$C(=O)O(CH$_2$)$_m$C(R$^{12}$)$_2$NR$^{12}$—, —NR$^{12}$C(R$^{12}$)$_2$(CH$_2$)$_m$OC(=O)NR$^{12}$((CH$_2$)$_m$O)$_n$(CH$_2$)$_m$—, —(CH$_2$)$_m$(O(CH$_2$)$_m$)$_n$NR$^{12}$C(=O)O(CH$_2$)$_m$C(R$^{12}$)$_2$NR$^{12}$—, —NR$^{12}$C(R$^{12}$)$_2$(CH$_2$)$_m$OC(=O)NR$^{12}$((CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NR$^{12}$C(=O)O(CH$_2$)$_m$C(R$^{12}$)$_2$NR$^{12}$—, —(CH$_2$)$_m$X$_3$(CH$_2$)$_m$NR$^{12}$—, —NR$^{12}$((CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NR$^{12}$—, —(CH$_2$)$_m$NR$^{12}$—, —NR$^{12}$((CH$_2$)$_m$O)$_n$(CH$_2$)$_m$—, —NR$^{12}$((CH$_2$)$_m$O)$_n$(CH$_2$)$_m$NR$^{12}$C(=O)(CH$_2$)$_m$—, —(CH$_2$)$_m$C(=O)NR$^{12}$(CH$_2$)$_m$(O(CH$_2$)$_m$)$_n$NR$^{12}$—, —(CH$_2$)$_m$(O(CH$_2$)$_m$)$_n$NR$^{12}$—, —(C(R$_{12}$)$_2$)$_m$—, —(CH$_2$CH$_2$O)$_n$—, —(OCH$_2$CH$_2$)$_n$—, —(CH$_2$)$_m$O(CH$_2$)$_m$—, —S(=O)$_2$(CH$_2$)$_m$—, —(CH$_2$)$_m$S(=O)$_2$—, —S(=O)$_2$(CH$_2$)$_m$NR$^{12}$C(=O)(CH$_2$)$_m$—, —(CH$_2$)$_m$C(=O)NR$^{12}$(CH$_2$)$_m$S(=O)$_2$—, —S(=O)$_2$(CH$_2$)$_m$X$_3$(CH$_2$)$_m$—, —(CH$_2$)$_m$X$_3$(CH$_2$)$_m$S(=O)$_2$—, —(CH$_2$)$_m$X$_2$X$_1$C(=O)—, —C(=O)X$_1$X$_2$(CH$_2$)$_m$—, —(CH$_2$)$_m$(O(CH$_2$)$_m$)$_n$C(=O)X$_2$X$_1$C(=O)—, —C(=O)X$_1$X$_2$C(=O)((CH$_2$)$_m$O)$_n$(CH$_2$)$_m$—, —(CH$_2$)$_m$(O(CH$_2$)$_m$)$_n$X$_2$X$_1$C(=O)—, —(CH$_2$)$_m$X$_3$(CH$_2$)$_m$X$_2$X$_1$C(=O)—, —C(=O)X$_1$X$_2$(CH$_2$)$_m$X$_3$(CH$_2$)$_m$—, —(CH$_2$)$_m$X$_3$(CH$_2$)$_m$(O(CH$_2$)$_m$)$_n$X$_2$X$_1$C(=O)—, —(CH$_2$)$_m$X$_3$(CH$_2$)$_m$C(=O)NR$^{12}$(CH$_2$)$_m$NR$^{12}$C(=O)—, —(CH$_2$)$_m$X$_3$(CH$_2$)$_m$C(=O)NR$^{12}$(CH$_2$)$_m$C(=O)—, —C(=O)(CH$_2$)$_m$NR$^{12}$C(=O(CH$_2$)$_m$X$_3$(CH$_2$)$_m$—, —(CH$_2$)$_m$X$_3$(CH$_2$)$_m$C(=O)NR$^{12}$(CH$_2$)$_m$(O(CH$_2$)$_m$)$_n$C(=O)—, —C(=O)((CH$_2$)$_m$O)$_n$(CH$_2$)$_m$NR$^{12}$C(=O)(CH$_2$)$_m$X$_3$(CH$_2$)$_m$—, —(CH$_2$)$_m$NR$^{12}$C(=O)X$_1$X$_2$C(=O)(CH$_2$)$_m$—, —(CH$_2$)$_m$C(=O)X$_2$X$_1$C(=O)NR$^{12}$(CH$_2$)$_m$—, —X$_4$X$_1$X$_2$C(=O)(CH$_2$)$_m$—, —(CH$_2$)$_m$C(=O)X$_2$X$_1$X$_4$—, —X$_1$C(=O)(CH$_2$)$_m$NHC(=O)(CH$_2$)$_m$—, —(CH$_2$)$_m$C(=O)NH(CH$_2$)$_m$C(=O)X$_1$—, —C(=O)CHR$^{aa}$NR$^{12}$—, —CHR$^{aa}$C(=O)—, —C(=O)NR$^{12}$—, —C(=O)O—, —S—, —SCH$_2$(C=O)NR$^{12}$—, —NR$^{12}$C(=O)CH$_2$S—, —S(=O)$_2$CH$_2$CH$_2$S—, —SCH$_2$CH$_2$S(=O)$_2$—, —(CH$_2$)$_2$S(=O)$_2$CH$_2$CH$_2$S—, —SCH$_2$CH$_2$S(=O)$_2$CH$_2$CH$_2$—, —(CH$_2$)$_m$X$_3$(O(CH$_2$)$_m$)$_n$C(=O)—, —C(=O)((CH$_2$)$_m$O)$_n$X$_3$(CH$_2$)$_m$—, —(CH$_2$)$_m$NHC(=O)((CH$_2$)$_m$O)$_n$(CH$_2$)$_m$—, —(CH$_2$)$_m$(O(CH$_2$)$_m$)$_n$C(=O)NH(CH$_2$)$_m$—, —(CH$_2$)$_m$NHC(=O)NH(CH$_2$)$_m$—, —(CH$_2$)$_m$X$_3$(CH$_2$)$_m$NHC(=O)—, —C(=O)NH(CH$_2$)$_m$X$_3$(CH$_2$)$_m$—, —NR$^{12}$S(=O)$_2$(CH$_2$)$_m$X$_3$(CH$_2$)$_m$—, and —(CH$_2$)$_m$X$_3$(CH$_2$)$_m$S(=O)$_2$NR$^{12}$—;

X$_1$ is self immolative spacer selected from

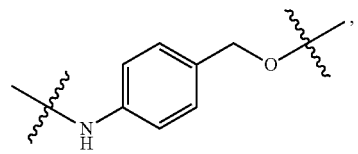

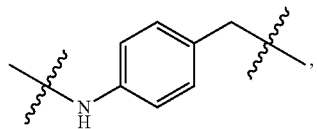

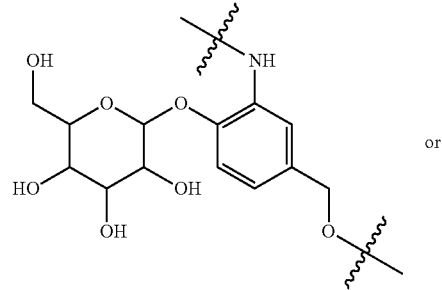

or

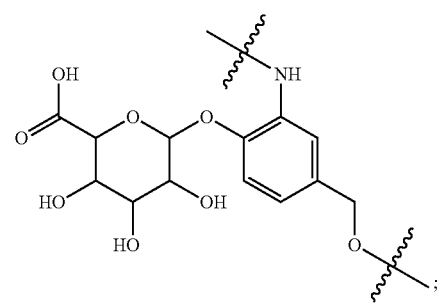

435

$X_2$ is dipeptide selected from

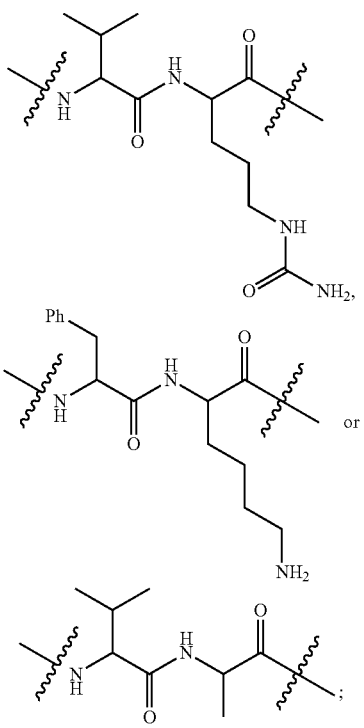

$X_3$ is

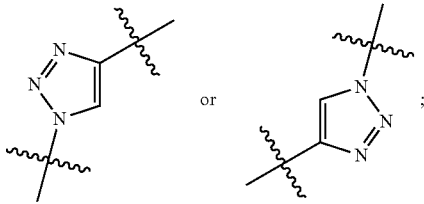 [SMILES: *c1cn(*)nn1 ; *c1cn(*)nn1]

and $X_4$ is

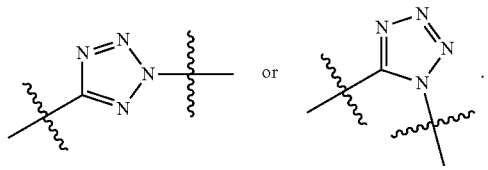 [SMILES: *c1nnn(*)n1 ; *c1nnnn1*]

Embodiment 85. The compound of any one of embodiments 3 to 45 and 78 to 80, and the immunoconjugate according to any one of embodiments 46 to 80, wherein:
$L_2$, $L_3$, $L_4$, $L_5$ and $L_6$ are a bond, and
$L_1$ is selected from $-(CH_2)_m-$, $-C(=O)(CH_2)_m-$, $-C(=O)X_1X_2C(=O)(CH_2)_m-$, $-C(=O)X_1X_2C(=O)(CH_2)_mNHC(=O)(CH_2)_m-$, $-C(=O)X_1X_2C(=O)(CH_2)_mX_3(CH_2)_m-$, $-C(=O)X_1X_2C(=O)((CH_2)_mO)_n(CH_2)_m-$, $-C(=O)X_1X_2C(=O)((CH_2)_mO)_n(CH_2)_mNHC(=O)(CH_2)_m-$, $-C(=O)X_1X_2C(=O)((CH_2)_mO)_n(CH_2)_mNHC(=O)(CH_2)_mX_3(CH_2)_m-$, $-C(=O)X_1X_2C(=O)X_1X_2C(=O)((CH_2)_mO)_n(CH_2)_mX_3(CH_2)_m-$, $-C(=O)X_1X_2C(=O)(CH_2)_mNHC(=O)((CH_2)_mO)_n(CH_2)_m-$,

436

$(CH_2)_mNHC(=O)((CH_2)_mO)_n(CH_2)_m-$, $-C(=O)X_1X_2C(=O)(CH_2)_mNHC(=O)((CH_2)_mO)_n(CH_2)_mX_3(CH_2)_m-$, $-C(=O)X_1X_2(CH_2)_mX_3(CH_2)_m-$, $-C(=O)X_1X_2((CH_2)_mO)_n(CH_2)_m-$, $-C(=O)X_1X_2((CH_2)_mO)_n(CH_2)_mNHC(=O)(CH_2)_m-$, $-C(=O)X_1X_2((CH_2)_mO)_n(CH_2)_mNHC(=O)(CH_2)_mX_3(CH_2)_m-$, $-C(=O)X_1X_2((CH_2)_mO)_n(CH_2)_mX_3(CH_2)_m-$, $-C(=O)X_1X_2(CH_2)_mNH((CH_2)_mO)_n(CH_2)_m-$, $-C(=O)X_1X_2C(=O)(CH_2)_mNH((CH_2)_mO)_n(CH_2)_mX_3(CH_2)_m-$, $-(CH_2)_mNHC(=O)(CH_2)_m-$, $-C(=O)((CH_2)_mO)_n(CH_2)_m-$, $-(CH_2)_mS(=O)_2((CH_2)_mO)_n(CH_2)_m-$, $-C(=O)(CH_2)_mNH(CH_2)_m-$, $-C(=O)NH(CH_2)_m-$, $-C(=O)NH(CH_2)_mX_3(CH_2)_m-$, $-C(=O)NH(CH_2)_mNHC(=O)X_1X_2C(=O)(CH_2)_m-$, $-C(=O)X_1C(=O)NH(CH_2)_mNHC(=O)(CH_2)_m-$, $-C(=O)X_1C(=O)NH(CH_2)_mX_3(CH_2)_m-$, $-C(=O)NH(CH_2)_mNHC(=O)(CH_2)_m-$, $-C(=O)NH(CH_2)_mNHC(=O)(CH_2)_mX_3(CH_2)_m-$,

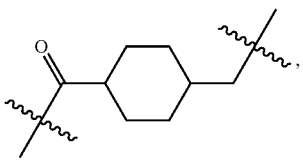 [SMILES: *CC1CCC(C(*)=O)CC1]

$-(CH_2)_mC(=O)NH(CH_2)_mNHC(=O)(CH_2)_m-$, $-(CH_2)_mC(=O)-$, $-(CH_2)_mC(=O)X_2X_1C(=O)-$, $-(CH_2)_mX_3(CH_2)_mC(=O)X_2X_1C(=O)-$, $-(CH_2)_mC(=O)NH(CH_2)_m-$, $-(CH_2)_mX_3(CH_2)_mC(=O)NH(CH_2)_m-$, $-(CH_2)_mNHC(=O)(CH_2)_mX_3(CH_2)_m-$, $-(CH_2)_m(O(CH_2)_m)_nC(=O)-$, $-(CH_2)_m(O(CH_2)_m)_nS(=O)_2(CH_2)_m-$, $-(CH_2)_mNH(CH_2)_mC(=O)-$, $-(CH_2)_mNHC(=O)-$, $-(CH_2)_mC(=O)X_2X_1C(=O)NH(CH_2)_mNHC(=O)-$, $-(CH_2)_mC(=O)NH(CH_2)_mNHC(=O)X_1-$, $-(CH_2)_mC(=O)NH(CH_2)_mNHC(=O)-$,

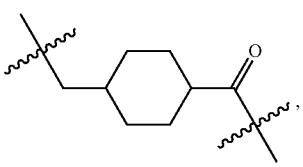 [SMILES: *CC1CCC(C(*)=O)CC1]

$-((CH_2)_mO)_n(CH_2)_m-$, $-(CH_2)_m(O(CH_2)_m)_n-$, $-(CH_2)_m(O(CH_2)_m)_nX_3(CH_2)_m-$, $-(CH_2)_mX_3(CH_2)_mC(=O)-$, $-C(=O)(CH_2)_mX_3(CH_2)_m-$, $-(CH_2)_mX_3(CH_2)_m(O(CH_2)_m)_nC(=O)-$, $-C(=O)((CH_2)_mO)_n(CH_2)_mX_3(CH_2)_m-$, $-(CH_2)_mC(=O)NH(CH_2)_mC(=O)-$, $-C(=O)(CH_2)_mNHC(=O)(CH_2)_m-$, $-(CH_2)_mC(=O)NH(CH_2)_m(O(CH_2)_m)_nC(=O)-$, $-C(=O)((CH_2)_mO)_n(CH_2)_mNHC(=O)(CH_2)_m-$, $-(CH_2)_mC(=O)NH(CH_2)_mC(=O)NH(CH_2)_m-$, $-(CH_2)_mNHC(=O)(CH_2)_mNHC(=O)(CH_2)_m-$, $-C(=O)NH(CH_2)_mNHC(=O)-$, $-(CH_2)_mS(CH_2)_m-$, $-NHC(=O)(CH_2)_m-$, $-NHC(=O)(CH_2)_mX_3(CH_2)_m-$, $-(CH_2)_mX_3(CH_2)_mC(=O)NH-$, $-(CH_2)_mC(=O)NH-$, $-(CH_2)_mNH(CH_2)_m-$, $-(CH_2)_mX_3(CH_2)_m-$, $-((CH_2)_mO)_n(CH_2)_mX_3(CH_2)_m-$, $-(CH_2)_mX_3(CH_2)_m(O(CH_2)_m)_n-$, $-NH(CH_2)_m-$, $-NHC(R^{12})_2(CH_2)_m-$, $-(CH_2)_mC(R^{12})_2NH-$, $-(CH_2)_mC(=O)NH(CH_2)_mNH-$, $-NH(CH_2)_mNHC(=O)(CH_2)_m-$, $-NHC(R^{12})_2(CH_2)_mNHC(=O)(CH_2)_m-$, $-(CH_2)_mC(=O)NH$ $(CH_2)_mC(R^{12})_2NH-$, $-NH(CH_2)_mX_3(CH_2)_m-$, $-NHC(R^{12})_2(CH_2)_mX_3(CH_2)_m-$, $-(CH_2)_mX_3(CH_2)_mC(R^{12})_2NH-$, $-NHC(R^{12})_2(CH_2)_mOC(=O)NH(CH_2)_m-$, $-(CH_2)_mNHC(=O)O(CH_2)_mC(R^{12})_2NH-$, $-NHC(R^{12})_2(CH_2)_mOC(=O)NH(CH_2)_mX_3(CH_2)_m-$, $-(CH_2)_mX_3(CH_2)_mNHC(=O)O(CH_2)_mC(R^{12})_2NH-$, $-NHC(R^{12})_2(CH_2)_mOC(=O)NH((CH_2)_mO)_n(CH_2)_m-$, $-(CH_2)_m(O(CH_2)_m)_nNHC(=O)O(CH_2)_mC(R^{12})_2NH-$, $-NHC(R^{12})_2(CH_2)_mOC(=O)NH((CH_2)_mO)_n(CH_2)_mX_3(CH_2)_m-$, $-(CH_2)_mX_3(CH_2)_m(O(CH_2)_m)_nNHC(=O)O(CH_2)_mC(R^{12})_2NH-$, $-(CH_2)_mX_3(CH_2)_mNH-$, $-NH((CH_2)_mO)_n(CH_2)_mX_3(CH_2)_m-$, $-(CH_2)_mX_3(CH_2)_m(O(CH_2)_m)_nNH-$, $-(CH_2)_mNH-$, $-NH((CH_2)_mO)_n(CH_2)_m-$, $-NH((CH_2)_mO)_n(CH_2)_mNHC(=O)(CH_2)_m-$, $-(CH_2)_mC(=O)NH(CH_2)_m(O(CH_2)_m)_nNH-$, $-(CH_2)_m(O(CH_2)_m)_nNH-$, $-(CH_2CH_2O)_n-$, $-(OCH_2CH_2)_n-$, $-(CH_2)_mO(CH_2)_m-$, $-S(=O)_2(CH_2)_m-$, $-(CH_2)_mS(=O)_2-$, $-S(=O)_2(CH_2)_mNHC(=O)(CH_2)_m-$, $-(CH_2)_mC(=O)NH(CH_2)_mS(=O)_2-$, $-S(=O)_2(CH_2)_mX_3(CH_2)_m-$, $-(CH_2)_mX_3(CH_2)_mS(=O)_2-$, $-(CH_2)_mX_2X_1C(=O)-$, $-C(=O)X_1X_2(CH_2)_m-$, $-(CH_2)_m(O(CH_2)_m)_nC(=O)X_2X_1C(=O)-$, $-C(=O)X_1X_2C(=O)((CH_2)_mO)_n(CH_2)_m-$, $-(CH_2)_m(O(CH_2)_m)_nX_2X_1C(=O)-$, $-(CH_2)_mX_3(CH_2)_mX_2X_1C(=O)-$, $-C(=O)X_1X_2(CH_2)_mX_3(CH_2)_m-$, $-(CH_2)_mX_3(CH_2)_m(O(CH_2)_m)_nX_2X_1C(=O)-$, $-(CH_2)_mX_3(CH_2)_mC(=O)NH(CH_2)_mNHC(=O)-$, $-(CH_2)_mX_3(CH_2)_mC(=O)NH(CH_2)_mC(=O)-$, $-C(=O)(CH_2)_mNHC(=O)(CH_2)_mX_3(CH_2)_m-$, $-(CH_2)_mX_3(CH_2)_mC(=O)NH(CH_2)_m(O(CH_2)_m)_nC(=O)-$, $-C(=O)((CH_2)_mO)_n(CH_2)_mNHC(=O)(CH_2)_mX_3(CH_2)_m-$, $-(CH_2)_mNHC(=O)X_1X_2C(=O)(CH_2)_m-$, $-(CH_2)_mC(=O)X_2X_1C(=O)NH(CH_2)_m-$, $-X_4X_1X_2C(=O)(CH_2)_m-$, $-(CH_2)_mC(=O)X_2X_1X_4-$, $-X_1C(=O)(CH_2)_mNHC(=O)(CH_2)_m-$, $-(CH_2)_mC(=O)NH(CH_2)_mC(=O)X_1-$, $-C(=O)CHR^{aa}NH-$, $-CHR^{aa}C(=O)-$, $-C(=O)NH-$, $-C(=O)O-$, $-S-$, $-SCH_2C(=O)NH-$, $-NHC(=O)CH_2S-$, $-S(=O)_2CH_2CH_2S-$, $-SCH_2CH_2S(=O)_2-$, $-(CH_2)_2S(=O)CH_2CH_2S-$ and $-SCH_2CH_2S(=O)_2CH_2CH_2-$, $-(CH_2)_mX_3(O(CH_2)_m)_nC(=O)-$, $-C(=O)((CH_2)_mO)_nX_3(CH_2)_m-$, $-(CH_2)_mNHC(=O)((CH_2)_mO)_n(CH_2)_m-$, $-(CH_2)_m(O(CH_2)_m)_nC(=O)NH(CH_2)_m-$, $-(CH_2)_mNHC(=O)NH(CH_2)_m-$, $-(CH_2)_mX_3(CH_2)_mNHC(=O)-$, $-C(=O)NH(CH_2)_mX_3(CH_2)_m-$, $-NHS(=O)_2(CH_2)_mX_3(CH_2)_m-$, and $-(CH_2)_mX_3(CH_2)_mS(=O)_2NH-$;

$X_1$ is self immolative spacer selected from

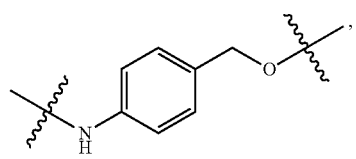

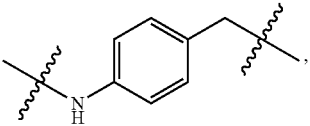

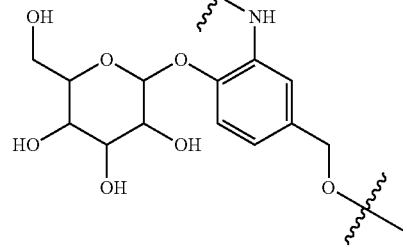

or

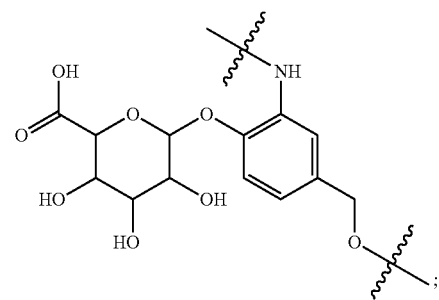

;

$X_2$ is dipeptide selected from

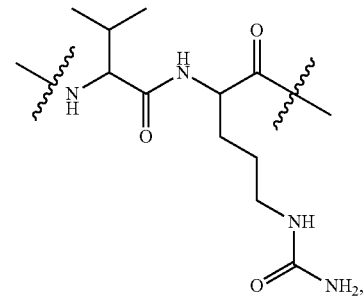

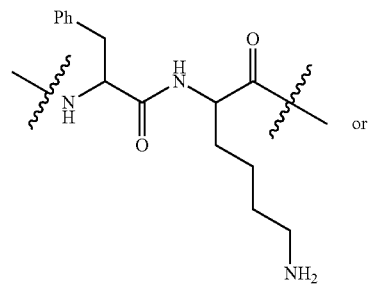

or

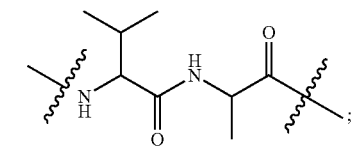

;

$X_3$ is

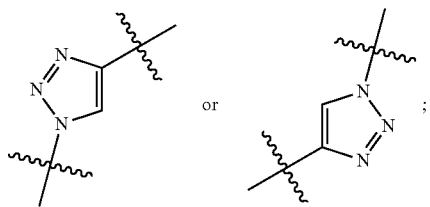 [SMILES: *c1cn(*)nn1 ; *c1cn(*)nn1]

and $X_4$ is

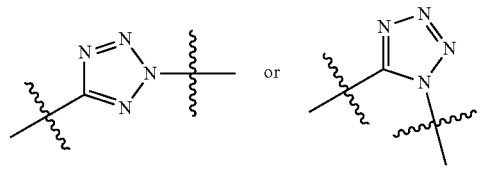

Embodiment 86. The compound of any one of embodiments 3 to 45 and 78 to 80, and the immunoconjugate according to any one of embodiments 45 to 80, wherein:

$L_2$, $L_3$, $L_4$, $L_5$ and $L_6$ are a bond, and $L_1$ is selected from —$(CH_2)_m$—, —$(CH_2)_mX_3(CH_2)_m$—, —$C(=O)(CH_2)_m$—, —$C(=O)(CH_2)_mX_3(CH_2)_m$—, —$C(=O)X_1X_2C(=O)(CH_2)_m$—, —$C(=O)X_1X_2C(=O)(CH_2)_mX_3(CH_2)_m$—, —$(CH_2)_mNHC(=O)(CH_2)_m$—, —$(CH_2)_mNHC(=O)(CH_2)_mX_3(CH_2)_m$—, —$C(=O)((CH_2)_mO)_n(CH_2)_m$—, —$C(=O)((CH_2)_mO)_n(CH_2)_mX_3(CH_2)_m$—, —$(CH_2)_mS(=O)_2((CH_2)_mO)_n(CH_2)_m$—, —$C(=O)(CH_2)_mNH(CH_2)_m$—, —$C(=O)NH(CH_2)_m$—, —$C(=O)NH(CH_2)_mX_3(CH_2)_m$—, —$C(=O)NH(CH_2)_mNHC(=O)X_1X_2C(=O)(CH_2)_m$—, —$C(=O)NH(CH_2)_mNHC(=O)(CH_2)_m$—, —$C(=O)X_1X_2((CH_2)_mO)_n(CH_2)_m$—,

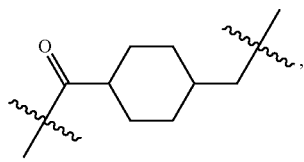 [SMILES: *CC1CCC(C(*)=O)CC1]

—$(CH_2)_mC(=O)NH(CH_2)_mNHC(=O)(CH_2)_m$—, —$(CH_2)_mC(=O)$—, —$(CH_2)_mX_3(CH_2)_mC(=O)$—, —$(CH_2)_mC(=O)X_2X_1C(=O)$—, —$(CH_2)_mX_3(CH_2)_mC(=O)X_2X_1C(=O)$—, —$(CH_2)_mC(=O)NH(CH_2)_m$—, —$(CH_2)_mX_3(CH_2)_mC(=O)NH(CH_2)_m$—, —$(CH_2)_m(O(CH_2)_m)_nC(=O)$—, —$(CH_2)_mX_3(CH_2)_m(O(CH_2)_m)_nC(=O)$—, —$NHC(R^{12})_2(CH_2)_m$—, —$NH(CH_2)_mX_3(CH_2)_m$—, —$NHCH_2(CH_2)_mOC(=O)NH((CH_2)_mO)_n(CH_2)_m$—, —$(CH_2)_m(O(CH_2)_m)_n$—, —$(CH_2)_m(O(CH_2)_m)_nX_3(CH_2)_m$—, —$(CH_2)_m(O(CH_2)_m)_nS(=O)_2(CH_2)_m$—, —$(CH_2)_mNH(CH_2)_mC(=O)$—, —$(CH_2)_mNHC(=O)$—, —$(CH_2)_mC(=O)X_2X_1C(=O)NH(CH_2)_mNHC(=O)$—, —$(CH_2)_mC(=O)NH(CH_2)_mNHC(=O)X_1$—, —$(CH_2)_mC(=O)NH(CH_2)_mNHC(=O)$—,

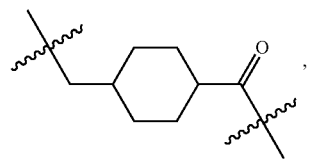 [SMILES: *CC1CCC(C(*)=O)CC1]

—$(CH_2)_mX_2X_1C(=O)$—, —$C(=O)X_1X_2(CH_2)_m$—, —$(CH_2)_m(O(CH_2)_m)_nX_2X_1C(=O)$—, —$(CH_2)_m(O(CH_2)_m)_nC(=O)X_2X_1C(=O)$—, —$(CH_2)_mX_3(CH_2)_mX_2X_1C(=O)$—, —$C(=O)X_1X_2(CH_2)_mX_3(CH_2)_m$—, —$(CH_2)_mX_3(CH_2)_m(O(CH_2)_m)_nX_2X_1C(=O)$—, —$C(=O)X1X2((CH2)mO)n(CH2)mX3(CH2)m$—, —$S(=O)_2(CH_2)_mX_3(CH_2)_m$—, —$(CH_2)_mX_3(O(CH_2)_m)_nC(=O)$—, —$C(=O)((CH_2)_mO)_nX_3(CH_2)_m$—, —$(CH_2)_mNHC(=O)((CH_2)_mO)_n(CH_2)_m$—, —$(CH_2)_m(O(CH_2)_m)_nC(=O)NH(CH_2)_m$—, —$(CH_2)_mNHC(=O)NH(CH_2)_m$—, —$(CH_2)_mX_3(CH_2)_mNHC(=O)$—, —$C(=O)NH(CH_2)_mX_3(CH_2)_m$—, —$NHS(=O)_2(CH_2)_mX_3(CH_2)_m$— and —$(CH_2)_mX_3(CH_2)_mS(=O)_2NH$—;

$X_1$ is self immolative spacer selected from

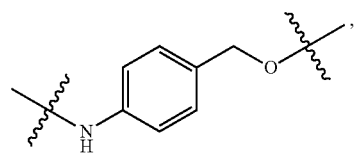

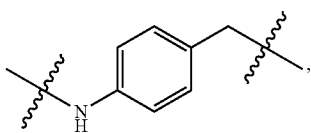

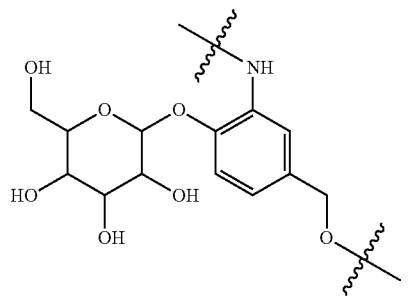

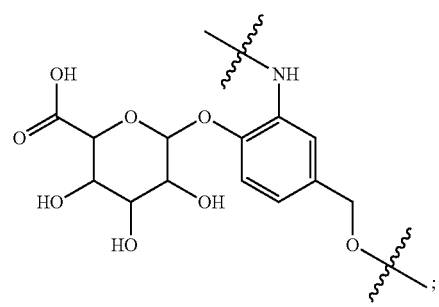

$X_2$ is dipeptide selected from

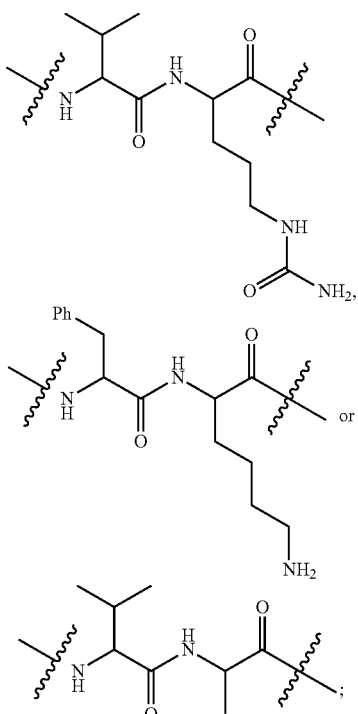

$X_3$ is

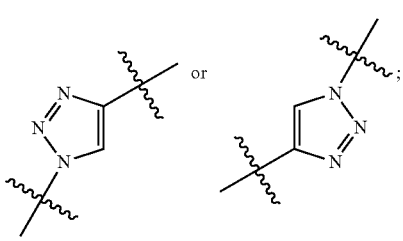 [SMILES: *c1cn(*)nn1 ; *c1cn(*)nn1]

and $X_4$ is

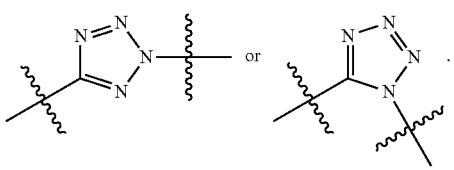 [SMILES: *c1nnn(*)n1 ; *c1nnnn1*]

Embodiment 87. The compound of any one of embodiments 3 to 45 and 78 to 80, and the immunoconjugate according to any one of embodiments 46 to 80, wherein:
$L_2$, $L_3$, $L_4$, $L_5$ and $L_6$ are a bond, and
$L_1$ is selected from —$(CH_2)_m$—, —$(CH_2)_mX_3(CH_2)_m$—, —$C(=O)(CH_2)_m$—, —$C(=O)(CH_2)_mX_3(CH_2)_m$—, —$C(=O)X_1X_2C(=O)(CH_2)_m$—, —$C(=O)X_1X_2C(=O)(CH_2)_mX_3(CH_2)_m$—, —$(CH_2)_mNHC(=O)(CH_2)_m$—, —$(CH_2)_mNHC(=O)(CH_2)_mX_3(CH_2)_m$—, —$C(=O)((CH_2)_mO)_n(CH_2)_m$—, —$C(=O)((CH_2)_mO)_n(CH_2)_mX_3(CH_2)_m$—, —$S(=O)_2(CH_2)_mX_3(CH_2)_m$—, —$(CH_2)_mC(=O)$—, —$(CH_2)_mX_3(CH_2)_mC(=O)$—, —$(CH_2)_mC(=O)X_2X_1C(=O)$—, —$(CH_2)_mX_3(CH_2)_mC(=O)X_2X_1C(=O)$—, —$(CH_2)_mC(=O)NH(CH_2)_m$—, —$(CH_2)_mX_3(CH_2)_mC(=O)NH(CH_2)_m$—, —$(CH_2)_m(O(CH_2)_m)_nC(=O)$—, —$(CH_2)_mX_3(CH_2)_m(O(CH_2)_m)_nC(=O)$—, —NHC$(R^{12})_2(CH_2)_m$—, —NH$(CH_2)_mX_3(CH_2)_m$—, —NHCH$_2(CH_2)_mOC(=O)NH((CH_2)_mO)_n(CH_2)_m$—, —$(CH_2)_mX_2X_1C(=O)$—, —$C(=O)X_1X_2(CH_2)_m$—, —$(CH_2)_m(O(CH_2)_m)_n$—, —$(CH_2)_m(O(CH_2)_m)_nC(=O)X_2X_1C(=O)$—, —$C(=O)X_1X_2((CH_2)_mO)_n(CH_2)_m$—, —$(CH_2)_m(O(CH_2)_m)_nX_2X_1C(=O)$—, —$(CH_2)_mX_3(CH_2)_mX_2X_1C(=O)$—, —$(CH_2)_mX_3(CH_2)_m(O(CH_2)_m)_nX_2X_1C(=O)$—, —$(CH_2)_m(O(CH_2)_m)_nX_3(CH_2)_m$— and —$(CH_2)_mX_3(O(CH_2)_m)_nC(=O)$—, —$C(=O)((CH_2)_mO)_nX_3(CH_2)_m$—, —$(CH_2)_mNHC(=O)((CH_2)_mO)_n(CH_2)_m$—, —$(CH_2)_m(O(CH_2)_m)_nC(=O)NH(CH_2)_m$—, —$(CH_2)_mNHC(=O)NH(CH_2)_m$—, —$(CH_2)_mX_3(CH_2)_mNHC(=O)$—, —$C(=O)NH(CH_2)_mX_3(CH_2)_m$—, —NHS$(=O)_2(CH_2)_mX_3(CH_2)_m$— and —$(CH_2)_mX_3(CH_2)_mS(=O)_2NH$—;

$X_1$ is self immolative spacer selected from

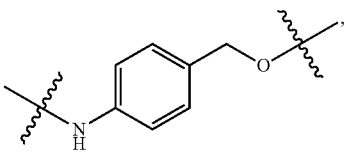

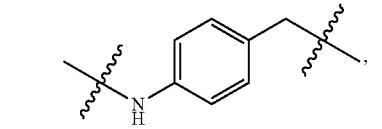

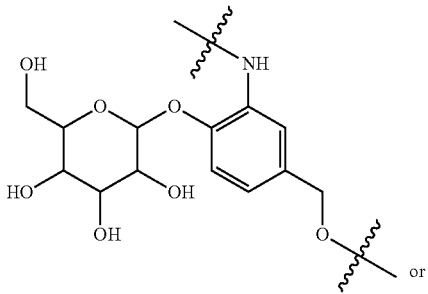

or

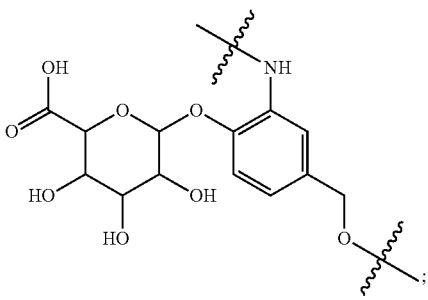

;

443

$X_2$ is dipeptide selected from

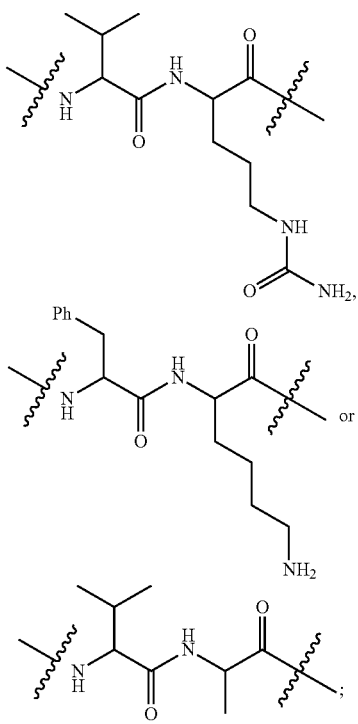

$X_3$ is

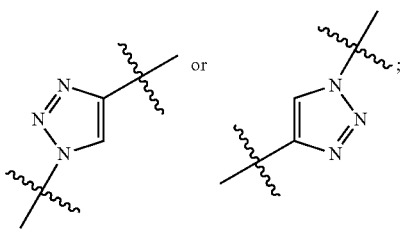 [SMILES: *c1cn(*)nn1 ; *c1cn(*)nn1]

and $X_4$ is

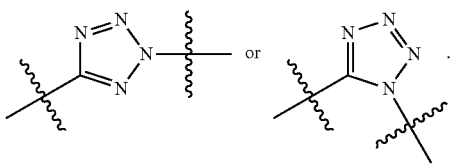 [SMILES: *c1nnn(*)n1 ; *c1nnnn1*]

Embodiment 88. The compound of any one of embodiments 3 to 45 and 78 to 80, and the immunoconjugate according to any one of embodiments 46 to 63 and 78 to 80, wherein:

$L_1$ is —$(CH_2)_mNHC(=O)(CH_2)_mX_3(CH_2)_m$*—, —*$C(=O)(CH_2)_mX_3((CH_2)_mO)_n$—, —$(CH_2)_mC(=O)$*—, —$(CH_2)_m$—, —$(CH_2)_mC(=O)X_2X_1C(=O)$*—, —$(CH_2)_mX_2X_1C(=O)$*—, —$(CH_2)_m(O(CH_2)_m)_nC(=O)$*—, —$(CH_2)_m(O(CH_2)_m)_nC(=O)X_2X_1C(=O)$*—, —$(CH_2)_m(O(CH_2)_m)_nX_2X_1C(=O)$*—, —$(CH_2)_m(O(CH_2)_m)_nS(=O)_2(CH_2)_m$*—, —$(CH_2)_mNH(CH_2)_mC(=O)$*—, —$(CH_2)_mNR^{12}$ $(CH_2)_mC(=O)$*—, —$((CH_2)_mO)_n(CH_2)_m$*—, —$(CH_2)_mX_3(CH_2)_mC(=O)$*—, —$(CH_2)_mX_3(CH_2)_m$—, —$(CH_2)_mX_3(CH_2)_mC(=O)X_2X_1C(=O)$*—, —$(CH_2)_mX_3(CH_2)_mX_2X_1C(=O)$*—, —$(CH_2)_mX_3(CH_2)_m(O(CH_2)_m)_nX_2X_1C(=O)$*—, —$(CH_2)_mNHC(=O)$*—, —$(CH_2)_mX_3(CH_2)_m(O(CH_2)_m)_nC(=O)$*—, —$(CH_2)_mX_3((CH_2)_mO)_n(CH_2)_m$*—, —$(CH_2)_mC(=O)NH(CH_2)_m$*—, —$(CH_2)_mX_3(CH_2)_mC(=O)NH(CH_2)_m$*—, —$(CH_2)_mC(=O)NH(CH_2)_mNHC(=O)$*—, —$(CH_2)_mX_3(CH_2)_mNHC(=O)$*—, —$(CH_2)_mC(=O)NH(CH_2)_mC(=O)$*—, —$(CH_2)_mX_3(CH_2)_mC(=O)NH(CH_2)_mNHC(=O)$*—, —$(CH_2)_mX_3(CH_2)_mC(=O)NH(CH_2)_mC(=O)$*—, —$(CH_2)_mC(=O)NH(CH_2)_m(O(CH_2)_m)_nC(=O)$*—, —$(CH_2)_mX_3(CH_2)_mC(=O)NH(CH_2)_m(O(CH_2)_m)_nC(=O)$*—, —$(CH_2)_mC(=O)NH(CH_2)_mNHC(=O)(CH_2)_m$*—, —$(CH_2)_mC(=O)NH(CH_2)_mC(=O)NH(CH_2)_m$*—, —$(CH_2)_mX_3(CH_2)_mC(=O)NH(CH_2)_m$*—, —$(CH_2)_mS(=O)_2$*—, —$(CH_2)_mX_3(CH_2)_mS(=O)_2$*—, —$(CH_2)_mOC(=O)NH(CH_2)_mC(=O)$*—, and —$(CH_2)_mOC(=O)NH(CH_2)_mS(=O)_2$*—, wherein in the immunoconjugate embodiments the * indicates the point of attachment to $R^{101}$ whereas in the compound embodiments the * indicates the point of attachment to $R^1$;

$L_2$ is a bond,

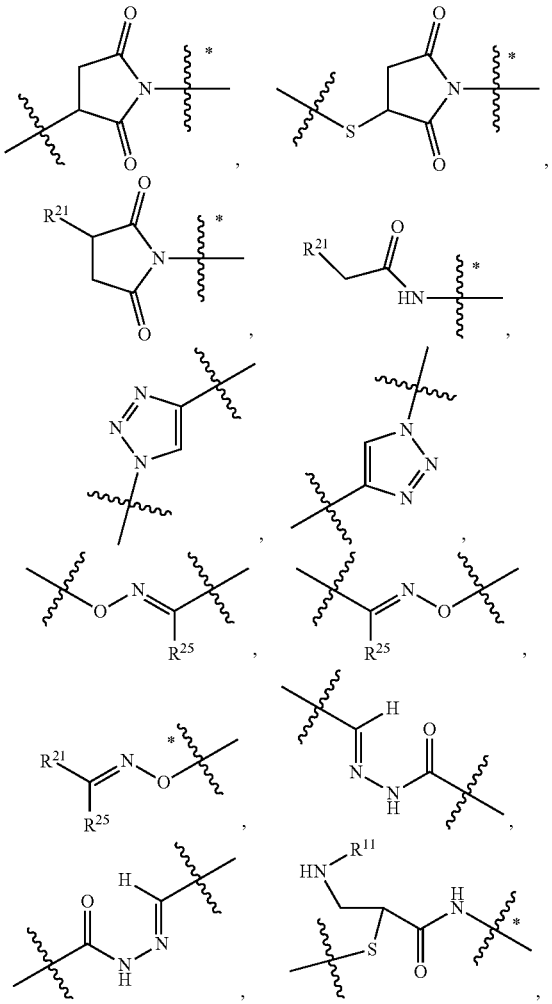

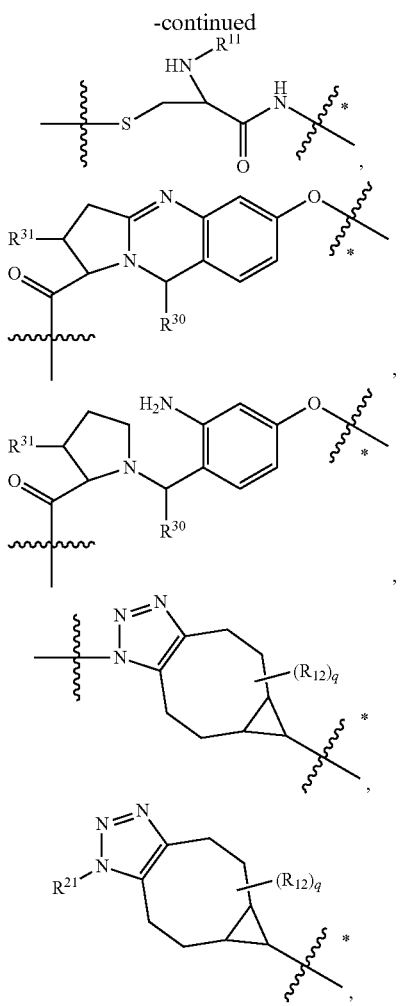

—S—, —SCH₂(C=O)NH—, —NHC(=O)CH₂S—, —SCH₂CH₂C(=O)NH—, —NHC(=O)CH₂CH₂S—, —SCH₂CH₂S(=O)₂—, —S(=O)₂CH₂CH₂S—, —SCH₂CH₂S(=O)₂NH— or —NHS(=O)₂CH₂CH₂S—, wherein the * indicates the point of attachment to $L_1$; and $L_3$, $L_4$, $L_5$ and $L_6$ are a bond.

Embodiment 89. The compound of any one of embodiments 3 to 45 and 78 to 80, and the immunoconjugate according to any one of embodiments 46 to 63 and 78 to 80, wherein:

$L_1$ is —(CH₂)$_m$NHC(=O)(CH₂)$_m$X₃(CH₂)$_m$*—, —(CH₂)$_m$C(=O)*—, —(CH₂)$_m$—, —(CH₂)$_m$C(=O)X₂X₁C(=O)*—, —(CH₂)$_m$X₂X₁C(=O)*—, —(CH₂)$_m$(O(CH₂)$_m$)$_n$C(=O)*—, —(CH₂)$_m$(O(CH₂)$_m$)$_n$C(=O)X₂X₁C(=O)*—, —(CH₂)$_m$(O(CH₂)$_m$)$_n$X₂X₁C(=O)*—, —(CH₂)$_m$(O(CH₂)$_m$)$_n$S(=O)₂(CH₂)$_m$*—, —(CH₂)$_m$NH(CH₂)$_m$C(=O)*—, —(CH₂)$_m$NR¹²(CH₂)$_m$C(=O)*—, —((CH₂)$_m$O)$_n$(CH₂)$_m$*—, —(CH₂)$_m$X₃(CH₂)$_m$C(=O)*—, —(CH₂)$_m$X₃(CH₂)$_m$—, —(CH₂)$_m$X₃(CH₂)$_m$C(=O)X₂X₁C(=O)*—, —(CH₂)$_m$X₃(CH₂)$_m$X₂X₁C(=O)*—, —(CH₂)$_m$X₃(CH₂)$_m$(O(CH₂)$_m$)$_n$X₂X₁C(=O)*—, —(CH₂)$_m$NHC(=O)*—, —(CH₂)$_m$X₃(CH₂)$_m$(O(CH₂)$_m$)$_n$C(=O)*—, —(CH₂)$_m$X₃((CH₂)$_m$O)$_n$(CH₂)$_m$*—, —(CH₂)$_m$C(=O)NH(CH₂)$_m$*—, —(CH₂)$_m$X₃(CH₂)$_m$C(=O)NH(CH₂)$_m$*—, —(CH₂)$_m$C(=O)NH(CH₂)$_m$NHC(=O)*—, —(CH₂)$_m$X₃(CH₂)$_m$NHC(=O)*—, —(CH₂)$_m$C(=O)NH(CH₂)$_m$C(=O)*—, —(CH₂)$_m$X₃(CH₂)$_m$C(=O)NH(CH₂)$_m$NHC(=O)*—, —(CH₂)$_m$X₃(CH₂)$_m$C(=O)NH(CH₂)$_m$C(=O)*—, —(CH₂)$_m$C(=O)NH(CH₂)$_m$(O(CH₂)$_m$)$_n$C(=O)*—, —(CH₂)$_m$X₃(CH₂)$_m$C(=O)NH(CH₂)$_m$(O(CH₂)$_m$)$_n$C(=O)*—, —(CH₂)$_m$C(=O)NH(CH₂)$_m$NHC(=O)(CH₂)$_m$*—, —(CH₂)$_m$C(=O)NH(CH₂)$_m$C(=O)NH(CH₂)$_m$*—, —(CH₂)$_m$X₃(CH₂)$_m$C(=O)NH(CH₂)$_m$*—, —(CH₂)$_m$S(=O)₂*— and —(CH₂)$_m$X₃(CH₂)$_m$S(=O)₂*—, wherein in the immunoconjugate embodiments the * indicates the point of attachment to $R^{101}$ whereas in the compound embodiments the * indicates the point of attachment to $R^1$;

$L_2$ is a bond,

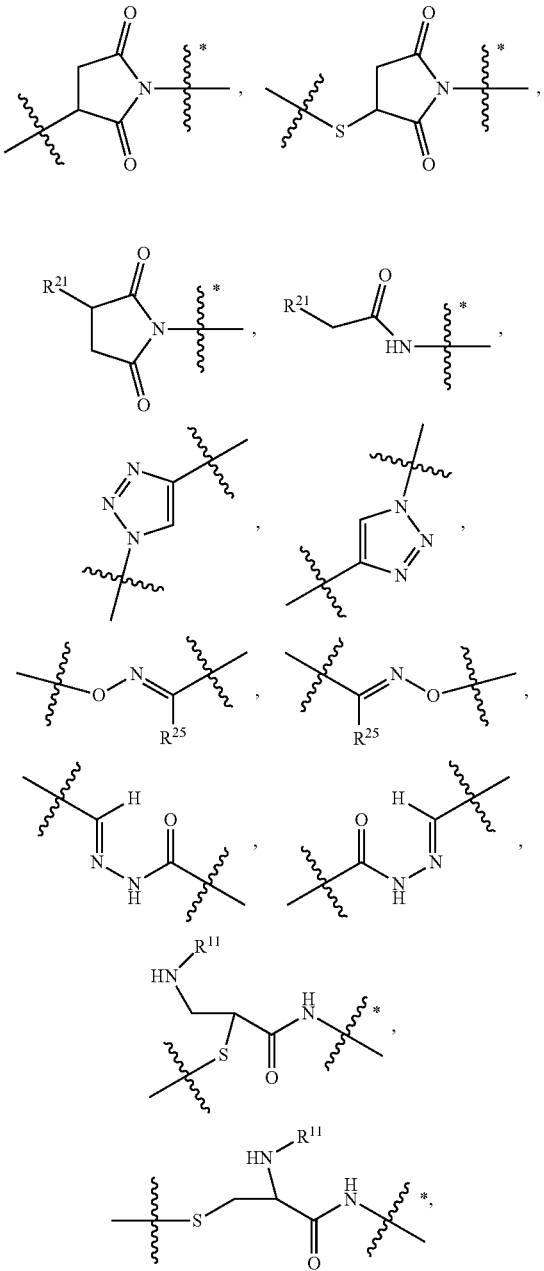

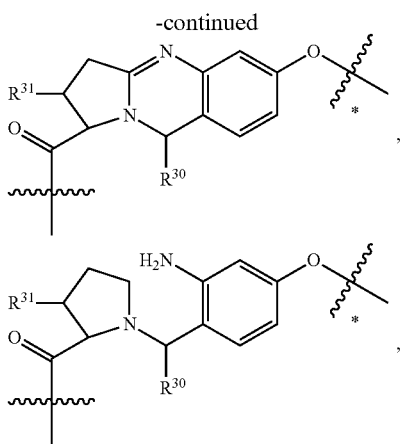

—S—, —SCH$_2$(C(=O)NH—, —NHC(=O)CH$_2$S—, —SCH$_2$CH$_2$C(=O)NH—, —NHC(=O)CH$_2$CH$_2$S—, —SCH$_2$CH$_2$S(=O)$_2$—, —S(=O)$_2$CH$_2$CH$_2$S—, —SCH$_2$CH$_2$S(=O)$_2$NH— or —NHS(=O)$_2$CH$_2$CH$_2$S—, wherein the * indicates the point of attachment to L$_1$; and L$_3$, L$_4$, L$_5$ and L$_6$ are a bond.

Embodiment 90. The compound of any one of embodiments 3 to 45 and 78 to 80, and the immunoconjugate according to any one of embodiments 46 to 63 and 78 to 80, wherein:

L$_1$ is selected from —(CH$_2$)$_m$C(=O)*—, —(CH$_2$)$_m$X$_3$(CH$_2$)$_m$C(=O)*—, —(CH$_2$)$_m$—, —(CH$_2$)$_m$X$_3$(CH$_2$)$_m$—, —(CH$_2$)$_m$C(=O)X$_2$X$_1$C(=O)*—, —(CH$_2$)$_m$X$_3$(CH$_2$)$_m$C(=O)X$_2$X$_1$C(=O)*—, —(CH$_2$)$_m$(O(CH$_2$)$_m$)$_n$C(=O)*—, —(CH$_2$)$_m$X$_3$(CH$_2$)$_m$(O(CH$_2$)$_m$)$_n$C(=O)*—, —(CH$_2$)$_m$(O(CH$_2$)$_m$)$_n$S(=O)$_2$(CH$_2$)$_m$*— and —(CH$_2$)$_m$NR$^{12}$(CH$_2$)$_m$C(=O)*—, wherein in the immunoconjugate embodiments the * indicates the point of attachment to R$^{101}$ whereas in the compound embodiments the * indicates the point of attachment to R$^1$;

L$_2$ is

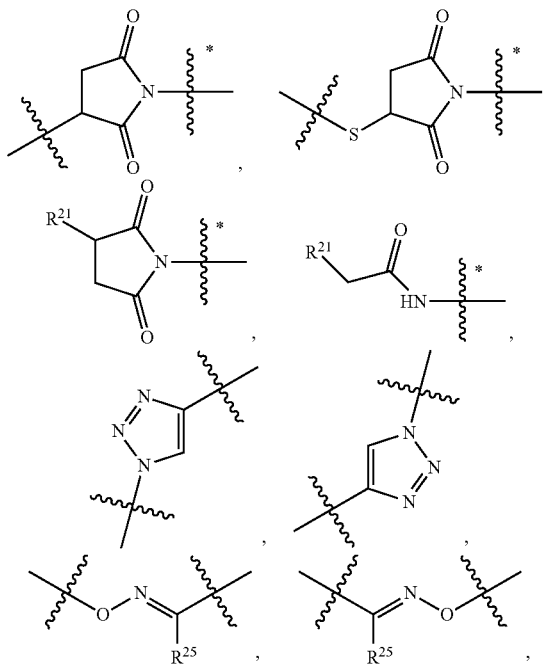

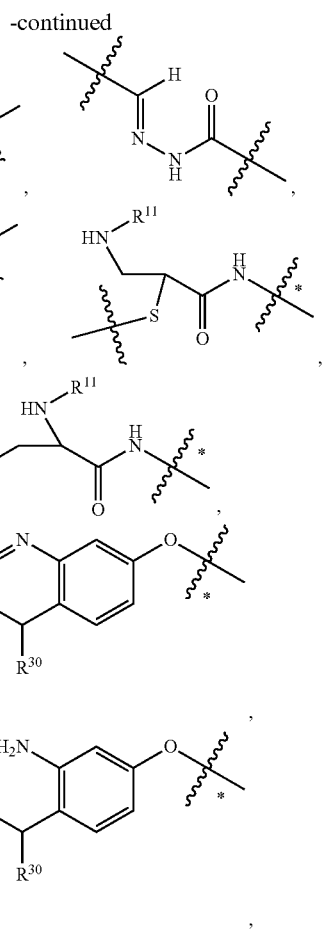

—S—, —SCH$_2$(C(=O)NH—, —NHC(=O)CH$_2$S—, —SCH$_2$CH$_2$C(=O)NH—, —NHC(=O)CH$_2$CH$_2$S—, —SCH$_2$CH$_2$S(=O)$_2$—, —S(=O)$_2$CH$_2$CH$_2$S—, —SCH$_2$CH$_2$S(=O)$_2$NH— or —NHS(=O)$_2$CH$_2$CH$_2$S—, wherein the * indicates the point of attachment to L$_1$, and L$_3$, L$_4$, L$_5$ and L$_6$ are a bond.

Embodiment 91. The compound of any one of embodiments 3 to 45 and 78 to 80, and the immunoconjugate according to any one of embodiments 46 to 63 and 78 to 80, wherein:

L$_1$ is selected from —(CH$_2$)$_m$C(=O)*—, —(CH$_2$)$_m$—, —(CH$_2$)$_m$C(=O)X$_2$X$_1$C(=O)*—, —(CH$_2$)$_m$X$_3$(CH$_2$)$_m$C(=O)*—, —(CH$_2$)$_m$X$_3$(CH$_2$)$_m$—, —(CH$_2$)$_m$X$_3$(CH$_2$)$_m$C(=O)X$_2$X$_1$C(=O)*—, —(CH$_2$)$_m$(O(CH$_2$)$_m$)$_n$C(=O)*—, —(CH$_2$)$_m$X$_3$(CH$_2$)$_m$(O(CH$_2$)$_m$)$_n$C(=O)*—, —(CH$_2$)$_m$(O(CH$_2$)$_m$)$_n$S(=O)$_2$(CH$_2$)$_m$*— and —(CH$_2$)$_m$NR$^{12}$(CH$_2$)$_m$C(=O)*—, wherein in the immunoconjugate embodiments the * indicates the point of attachment to R$^{101}$ whereas in the compound embodiments the * indicates the point of attachment to R$^1$;

L$_2$ is

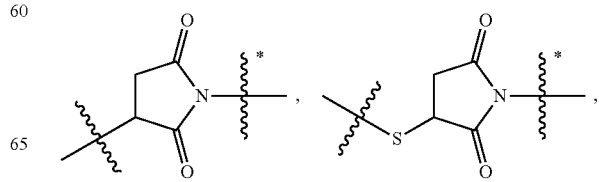

-continued

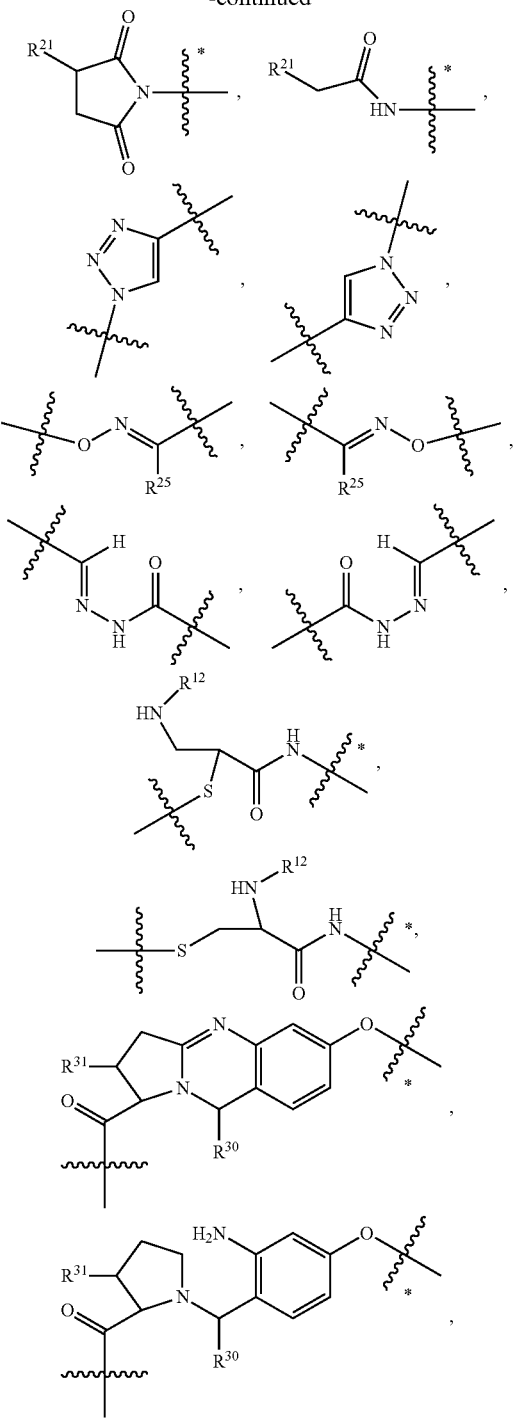

—S—, —SCH$_2$(C=O)NH—, —NHC(=O)CH$_2$S—,
—NH(=O)CH$_2$CH$_2$S—, —SCH$_2$CH$_2$C(=O)NH—,
—S(=O)$_2$CH$_2$CH$_2$S—, —SCH$_2$CH$_2$S(=O)$_2$—, —(CH$_2$)$_2$S(=O)$_2$CH$_2$CH$_2$S— or —SCH$_2$CH$_2$S(=O)$_2$CH$_2$CH$_2$—,
wherein the * indicates the point of attachment to L$_1$,
and L$_3$, L$_4$, L$_5$ and L$_6$ are a bond.

Embodiment 92. The compound of any one of embodiments 3 to 45 and 78 to 80, and the immunoconjugate according to any one of embodiments 46 to 63 and 78 to 80, wherein:

L$_1$ is selected from —(CH$_2$)$_m$C(=O)*—, —(CH$_2$)$_m$—, —(CH$_2$)$_m$X$_3$(CH$_2$)$_m$C(=O)*—, —(CH$_2$)$_m$C(=O)X$_2$X$_1$C(=O)*—, —(CH$_2$)$_m$X$_3$(CH$_2$)$_m$—, —(CH$_2$)$_m$X$_3$(CH$_2$)$_m$C(=O)X$_2$X$_1$C(=O)*—, —(CH$_2$)$_m$(O(CH$_2$)$_m$)$_n$C(=O)*—, —(CH$_2$)$_m$X$_3$(CH$_2$)$_m$(O(CH$_2$)$_m$)$_n$C(=O)*—, —(CH$_2$)$_m$(O(CH$_2$)$_m$)$_n$S(=O)$_2$(CH$_2$)$_m$*— and —(CH$_2$)$_m$NR$^{12}$(CH$_2$)$_m$C(=O)*—,
wherein in the immunoconjugate embodiments the * indicates the point of attachment to R$^{101}$ whereas in the compound embodiments the * indicates the point of attachment to R$^1$;

L$_2$ is

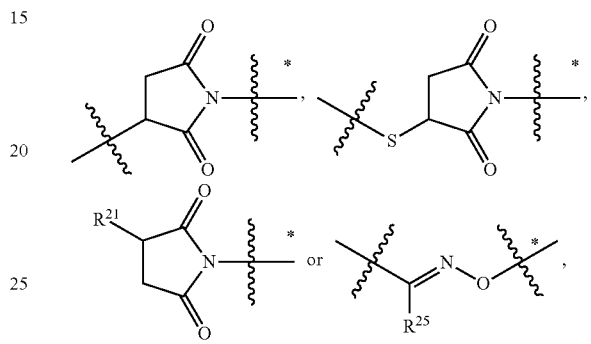

wherein the * indicates the point of attachment to L$_1$,
and L$_3$, L$_4$, L$_5$ and L$_6$ are a bond.

Embodiment 93. The compound of any one of embodiments 3 to 45 and 78 to 80, and the immunoconjugate according to any one of embodiments 46 to 63 and 78 to 80, wherein:

L$_1$ is selected from —(CH$_2$)$_m$C(=O)*—, —(CH$_2$)$_m$—, —(CH$_2$)$_m$C(=O)X$_2$X$_1$C(=O)*—, —(CH$_2$)$_m$(O(CH$_2$)$_m$)$_n$C(=O)*—, —(CH$_2$)$_m$(O(CH$_2$)$_m$)$_n$S(=O)$_2$(CH$_2$)$_m$*— and —(CH$_2$)$_m$NR$^{12}$(CH$_2$)$_m$C(=O)*—,
wherein in the immunoconjugate embodiments the * indicates the point of attachment to R$^{101}$ whereas in the compound embodiments the * indicates the point of attachment to R$^1$;

L$_2$ is

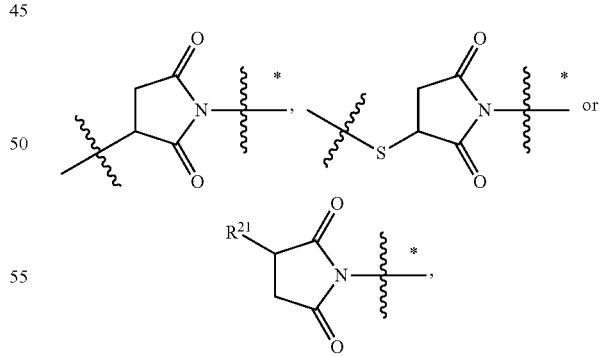

wherein the * indicates the point of attachment to L$_1$,
and L$_3$, L$_4$, L$_5$ and L$_6$ are a bond.

Embodiment 94. The compound of any one of embodiments 3 to 45 and 78 to 80, and the immunoconjugate according to any one of embodiments 46 to 63 and 78 to 80, wherein:

L$_1$ is selected from —(CH$_2$)$_m$C(=O)*—, —(CH$_2$)$_m$—, —(CH$_2$)$_m$C(=O)X$_2$X$_1$C(=O)*—, —(CH$_2$)$_m$(O —(CH$_2$)$_m$)$_n$C(=O)*—, —(CH$_2$)$_m$(O(CH$_2$)$_m$)$_n$S(=O)$_2$(CH$_2$)$_m$*— and —(CH$_2$)$_m$NR$^{12}$(CH$_2$)$_m$C(=O)*—, wherein in the immunoconjugate embodiments the * indicates the point of attachment to R$^{101}$ whereas in the compound embodiments the * indicates the point of attachment to R$^1$;

L$_2$ is

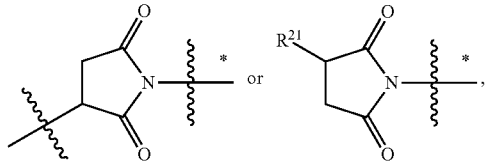

wherein the * indicates the point of attachment to L$_1$, and L$_3$, L$_4$, L$_5$ and L$_6$ are a bond.

Embodiment 95. The compound of any one of embodiments 3 to 21, 27 to 31, 34, 36 to 40, 45 and 78 to 80, and the immunoconjugate according to any one of embodiments 64 to 80, wherein:

L$_1$ is selected from —*C(=O)(CH$_2$)$_m$—, —(CH$_2$)$_m$—, —*(CH$_2$)$_m$NHC(=O)X$_1$X$_2$C(=O)(CH$_2$)$_m$—, —*X$_4$X$_1$X$_2$C(=O)(CH$_2$)$_m$—, —*X$_1$C(=O)(CH$_2$)$_m$NHC(=O)(CH$_2$)$_m$—, —*(CH$_2$)$_m$C(=O)NH(CH$_2$)$_m$NHC(=O)(CH$_2$)$_m$—, —*S(=O)$_2$(CH$_2$)mX$_3$(CH$_2$)$_m$—,

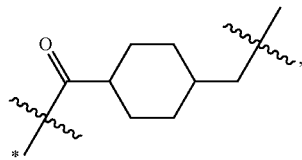 [SMILES: *CC1CCC(C(*)=O)CC1]

—*C(=O)((CH$_2$)$_m$O)$_n$(CH$_2$)$_m$)—, —*C(=O)NH(CH$_2$)$_m$—, —*C(=O)X$_1$X$_2$C(=O)(CH$_2$)$_m$—, —*C(=O)((CH$_2$)$_m$O)$_n$(CH$_2$)$_m$—, —*((CH$_2$)$_m$O)$_n$(CH$_2$)$_m$—, —*(CH$_2$)$_m$S(=O)$_2$((CH$_2$)$_m$O)$_n$(CH$_2$)$_m$—, —*C(=O)(CH$_2$)$_m$NR$^{12}$(CH$_2$)$_m$—, —*C(=O)(CH$_2$)$_m$NH(CH$_2$)$_m$—, —*(CH$_2$)$_m$(O(CH$_2$)$_m$)$_n$—, —*C(=O)(CH$_2$)$_m$X$_3$(CH$_2$)$_m$—, —*C(=O)NH(CH$_2$)$_m$—, —*C(=O)((CH$_2$)$_m$O)$_n$(CH$_2$)$_m$X$_3$(CH$_2$)$_m$—, —*(CH$_2$)$_m$NHC(=O)(CH$_2$)$_m$—, —*C(=O)NH(CH$_2$)$_m$NHC(=O)(CH$_2$)$_m$—, —*C(=O)(CH$_2$)$_m$NHC(=O)(CH$_2$)$_m$—, —*C(=O)((CH$_2$)$_m$O)$_n$(CH$_2$)$_m$NHC(=O)(CH$_2$)$_m$—, —*((CH$_2$)$_m$O)$_n$(CH$_2$)$_m$X$_3$(CH$_2$)$_m$—, —(CH$_2$)$_m$C(=O)NH(CH$_2$)$_m$NHC(=O)(CH$_2$)$_m$—, —*NH$_2$S(=O)$_2$(CH$_2$)$_m$X$_3$(CH$_2$)$_m$—, —*(CH$_2$)$_m$NHC(=O)(CH$_2$)$_m$NHC(=O)(CH$_2$)$_m$— and —C(=O)NH(CH$_2$)$_m$NHC(=O)—, wherein the * indicates the point of attachment to R$^3$;

L$_2$ is a bond,

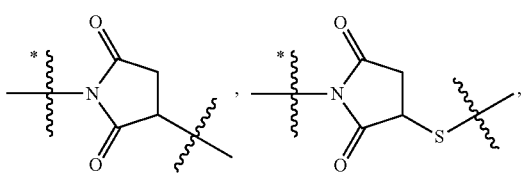

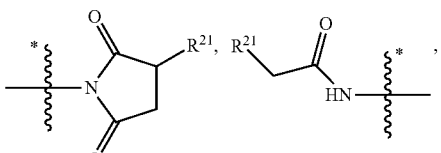

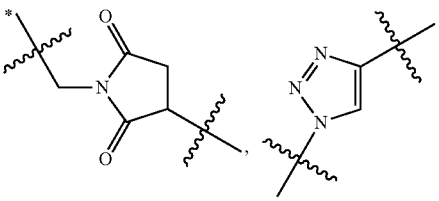

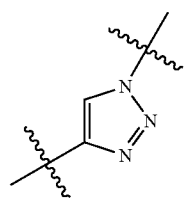

—S—, —SCH$_2$(C=O)NH—, —NHC(=O)CH$_2$S—,

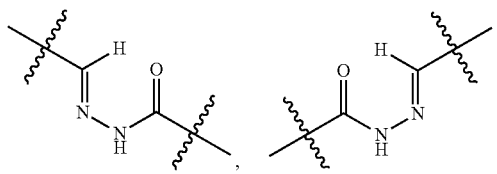

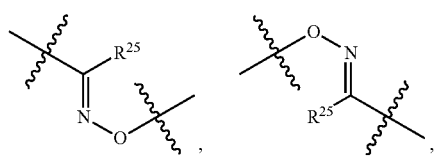

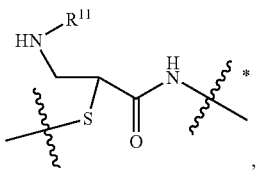

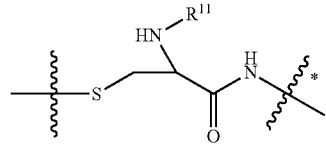

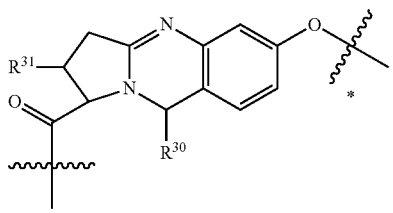

-continued

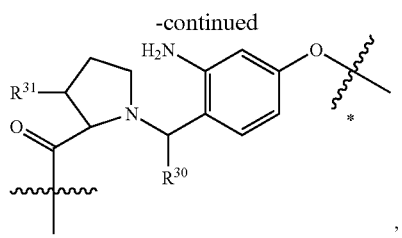

—S(=O)$_2$CH$_2$CH$_2$S—, —SCH$_2$CH$_2$S(=O)$_2$—, —(CH$_2$)$_2$S(=O)$_2$CH$_2$CH$_2$S— or —SCH$_2$CH$_2$S(=O)$_2$CH$_2$CH$_2$—, wherein the * indicates the point of attachment to L$_1$, and L$_3$, L$_4$, L$_5$ and L$_6$ are a bond.

Embodiment 96. The compound of any one of embodiments 3 to 21, 27 to 31, 34, 36 to 40, 45 and 78 to 80, and the immunoconjugate according to any one of embodiments 64 to 80, wherein:

L$_1$ is selected from —*C(=O)(CH$_2$)$_m$—, —(CH$_2$)$_m$—, —*(CH$_2$)$_m$NHC(=O)X$_1$X$_2$C(=O)(CH$_2$)$_m$—, —*X$_4$X$_1$X$_2$C(=O)(CH$_2$)$_m$—, —*X$_1$C(=O)(CH$_2$)$_m$NHC(=O)(CH$_2$)$_m$—, —*(CH$_2$)$_m$C(=O)NH(CH$_2$)$_m$NHC(=O)(CH$_2$)$_m$—, —*S(=O)$_2$(CH$_2$)mX$_3$(CH$_2$)$_m$—,

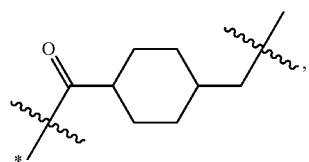 [SMILES: *CC1CCC(C(*)=O)CC1]

—*C(=O)((CH$_2$)$_m$O)$_n$(CH$_2$)$_m$)—, —*C(=O)NH(CH$_2$)$_m$)—, —*C(=O)X$_1$X$_2$C(=O)(CH$_2$)$_m$—, —*C(=O)((CH$_2$)$_m$O)$_n$(CH$_2$)$_m$—, —*(CH$_2$)$_m$S(=O)$_2$((CH$_2$)$_m$O)$_n$(CH$_2$)$_m$—, —*C(=O)(CH$_2$)$_m$NR$^{12}$(CH$_2$)$_m$—, —*C(=O)(CH$_2$)$_m$NH(CH$_2$)$_m$—, —*(CH$_2$)$_m$(O(CH$_2$)$_m$)$_n$—, —*C(=O)(CH$_2$)$_m$X$_3$(CH$_2$)$_m$—, —*C(=O)NH(CH$_2$)$_m$—, —*C(=O)((CH$_2$)$_m$O)$_n$(CH$_2$)$_m$X$_3$(CH$_2$)$_m$—, —*(CH$_2$)$_m$NHC(=O)(CH$_2$)$_m$—, —*C(=O)NH(CH$_2$)$_m$NHC(=O)(CH$_2$)$_m$—, —*C(=O)(CH$_2$)$_m$NHC(=O)(CH$_2$)$_m$—, —*C(=O)((CH$_2$)$_m$O)$_n$(CH$_2$)$_m$NHC(=O)(CH$_2$)$_m$—, —(CH$_2$)$_m$C(=O)NH(CH$_2$)$_m$NHC(=O)(CH$_2$)$_m$—, —*NH$_2$S(=O)$_2$(CH$_2$)$_m$X$_3$(CH$_2$)$_m$—, —*(CH$_2$)$_m$NHC(=O)(CH$_2$)$_m$NHC(=O)(CH$_2$)$_m$— and —C(=O)NH(CH$_2$)$_m$NHC(=O)—, wherein the * indicates the point of attachment to R$^3$;

L$_2$ is a bond,

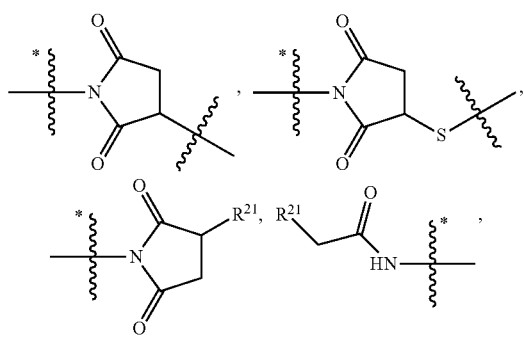

-continued

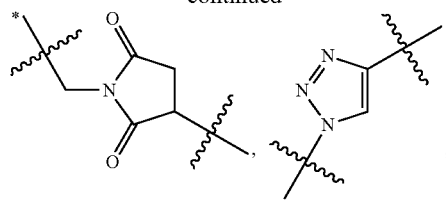

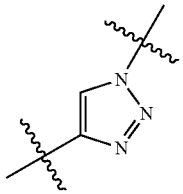

—S—, —SCH$_2$(C=O)NH—, —NHC(=O)CH$_2$S—,

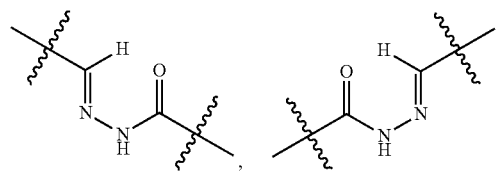

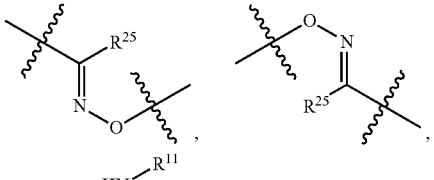

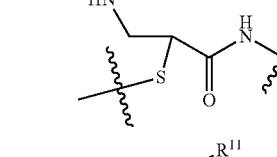

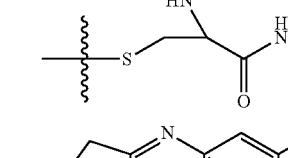

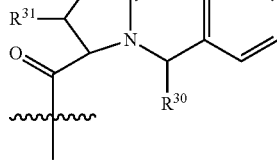

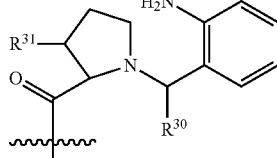

—S(=O)$_2$CH$_2$CH$_2$S—, —SCH$_2$CH$_2$S(=O)$_2$—, —(CH$_2$)$_2$S(=O)$_2$CH$_2$CH$_2$S— or —SCH$_2$CH$_2$S(=O)$_2$CH$_2$CH$_2$—, wherein the * indicates the point of attachment to L$_1$, and L$_3$, L$_4$, L$_5$ and L$_6$ are a bond.

Embodiment 97. The compound of any one of embodiments 3 to 21, 27 to 31, 34, 36 to 40, 45 and 78 to 80, and the immunoconjugate according to any one of embodiments 64 to 80, wherein:

$L_1$ is selected from —*C(=O)(CH$_2$)$_m$—, —(CH$_2$)$_m$—, —*(CH$_2$)$_m$NHC(=O)X$_1$X$_2$C(=O)(CH$_2$)$_m$—, —*X$_4$X$_1$X$_2$C(=O)(CH$_2$)$_m$—, —*X$_1$C(=O)(CH$_2$)$_m$NHC(=O)(CH$_2$)$_m$—, —*(CH$_2$)$_m$C(=O)NH(CH$_2$)$_m$NHC(=O)(CH$_2$)$_m$—, —*S(=O)$_2$(CH$_2$)mX$_3$(CH$_2$)$_m$—,

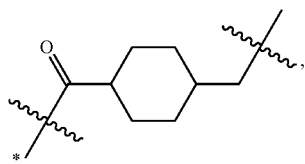 [SMILES: *CC1CCC(C(*)=O)CC1]

—*NH$_2$S(=O)$_2$(CH$_2$)$_m$X$_3$(CH$_2$)$_m$—, —*C(=O)((CH$_2$)$_m$O)$_n$(CH$_2$)$_m$)— and —*C(=O)NH(CH$_2$)$_m$)—, wherein the * indicates the point of attachment to R$^3$;

$L_2$ is

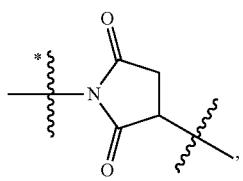 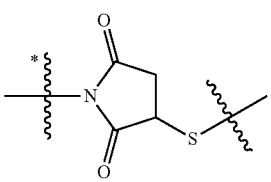

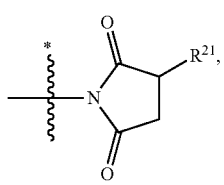 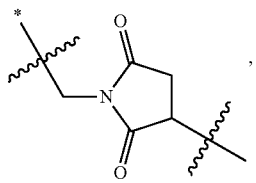

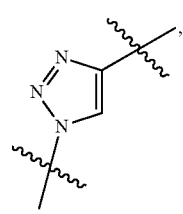 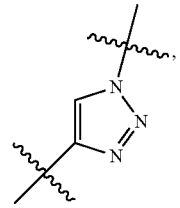

—S—, —SCH$_2$(C=O)NH—, —NHC(=O)CH$_2$S—,

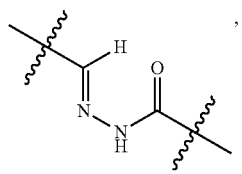 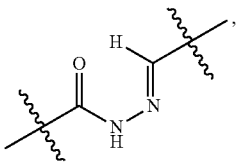

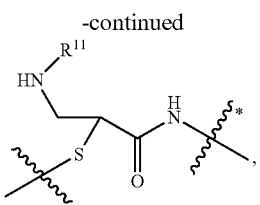

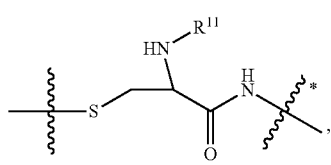

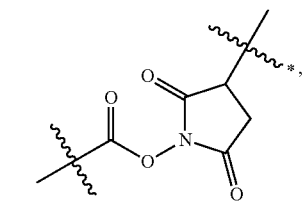

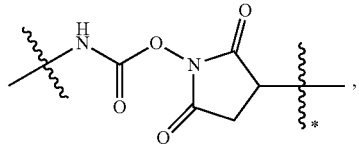

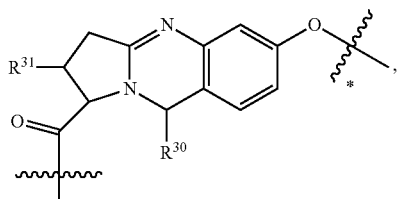

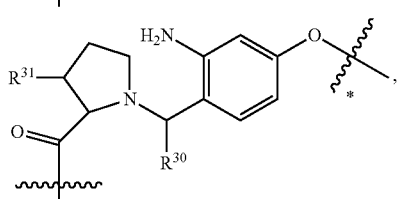

—S(=O)$_2$CH$_2$CH$_2$S—, —SCH$_2$CH$_2$S(=O)$_2$—, —(CH$_2$)$_2$S(=O)$_2$CH$_2$CH$_2$S— or —SCH$_2$CH$_2$S(=O)$_2$CH$_2$CH$_2$—, wherein the * indicates the point of attachment to $L_1$, and $L_3$, $L_4$, $L_5$ and $L_6$ are a bond.

Embodiment 98. The compound of any one of embodiments 3 to 21, 27 to 31, 34, 36 to 40, 45 and 78 to 80, and the immunoconjugate according to any one of embodiments 64 to 80, wherein:

$L_1$ is selected from —*C(=O)(CH$_2$)$_m$—, —(CH$_2$)$_m$—, —*(CH$_2$)$_m$NHC(=O)X$_1$X$_2$C(=O)(CH$_2$)$_m$—, —*X$_4$X$_1$X$_2$C(=O)(CH$_2$)$_m$—, —*X$_1$C(=O)(CH$_2$)$_m$NHC(=O)(CH$_2$)$_m$—, —*(CH$_2$)$_m$C(=O)NH(CH$_2$)$_m$NHC(=O)(CH$_2$)$_m$—, —*S(=O)$_2$(CH$_2$)mX$_3$(CH$_2$)$_m$—,

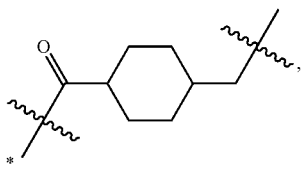 [SMILES: *CC1CCC(C(*)=O)CC1]

—*NH$_2$S(=O)$_2$(CH$_2$)$_m$X$_3$(CH$_2$)$_m$—, —*C(=O)((CH$_2$)$_m$O)$_n$(CH$_2$)$_m$)— and —*C(=O)NH(CH$_2$)$_m$)—, wherein the * indicates the point of attachment to R$^3$;

L$_2$

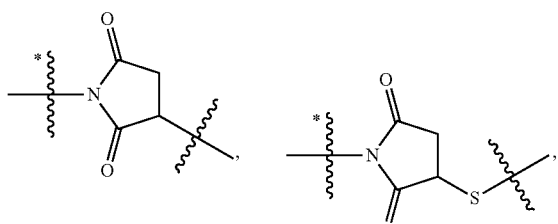

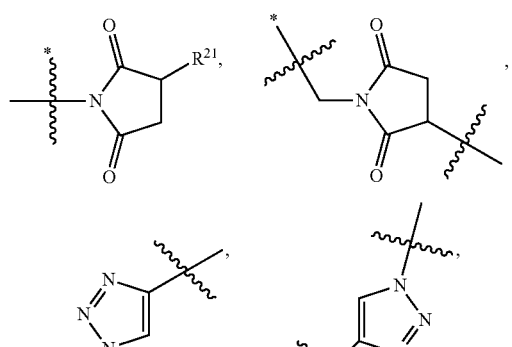

—S—, —SCH$_2$(C=O)NH—, —NHC(=O)CH$_2$S—,

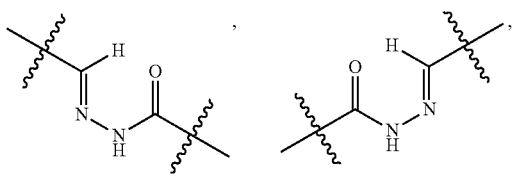

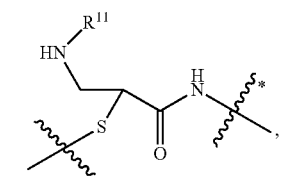

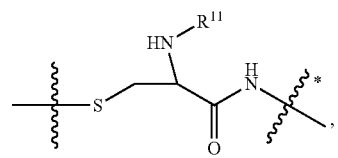

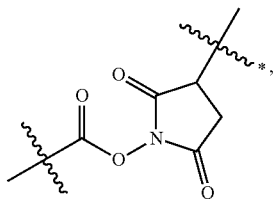

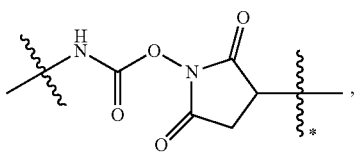

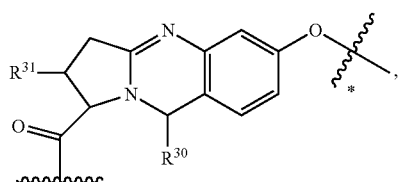

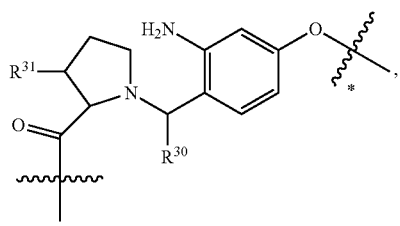

—S(=O)$_2$CH$_2$CH$_2$S—, —SCH$_2$CH$_2$S(=O)$_2$—, —(CH$_2$)$_2$S(=O)$_2$CH$_2$CH$_2$S— or —SCH$_2$CH$_2$S(=O)$_2$CH$_2$CH$_2$—, wherein the * indicates the point of attachment to L$_1$, and L$_3$, L$_4$, L$_5$ and L$_6$ are a bond.

Embodiment 99. The compound of any one of embodiments 3 to 21, 27 to 31, 34, 36 to 40, 45 and 78 to 80, and the immunoconjugate according to any one of embodiments 64 to 80, wherein:

L$_1$ is selected from —*C(=O)(CH$_2$)$_m$—, —(CH$_2$)$_m$—, —*(CH$_2$)$_m$NHC(=O)X$_1$X$_2$C(=O)(CH$_2$)$_m$—, —*X$_4$X$_1$X$_2$C(=O)(CH$_2$)$_m$—, —*X$_1$C(=O)(CH$_2$)$_m$NHC(=O)(CH$_2$)$_m$—, —*(CH$_2$)$_m$C(=O)NH(CH$_2$)$_m$NHC(=O)(CH$_2$)$_m$—, —*S(=O)$_2$(CH$_2$)mX$_3$(CH$_2$)$_m$—,

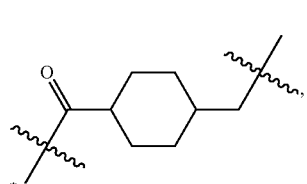

—*NH$_2$S(=O)$_2$(CH$_2$)$_m$X$_3$(CH$_2$)$_m$—, —*C(=O)((CH$_2$)$_m$O)$_n$(CH$_2$)$_m$)— and —*C(=O)NH(CH$_2$)$_m$)—, wherein the * indicates the point of attachment to R$^3$;

$L_2$ is

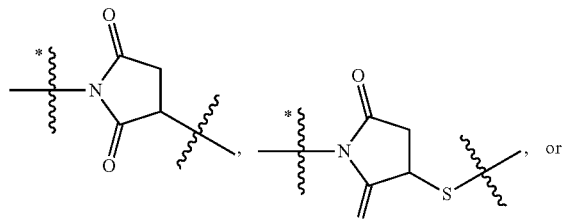

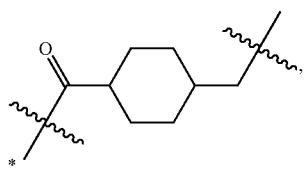 [SMILES: *CC1CCC(C(*)=O)CC1]

wherein the * indicates the point of attachment to $L_1$, and $L_3$, $L_4$, $L_5$ and $L_6$ are a bond.

Embodiment 100. The compound of any one of embodiments 3 to 21, 27 to 31, 34, 36 to 40, 45 and 78 to 80, and the immunoconjugate according to any one of embodiments 64 to 80, wherein:

$L_1$ is selected from —*C(=O)(CH$_2$)$_m$—, —(CH$_2$)$_m$—, —*(CH$_2$)$_m$NHC(=O)X$_1$X$_2$C(=O)(CH$_2$)$_m$—, —*X$_4$X$_1$X$_2$C(=O)(CH$_2$)$_m$—, —*X$_1$C(=O)(CH$_2$)$_m$NHC(=O)(CH$_2$)$_m$—, —*(CH$_2$)$_m$C(=O)NH(CH$_2$)$_m$NHC(=O)(CH$_2$)$_m$—, —*S(=O)$_2$(CH$_2$)mX$_3$(CH$_2$)$_m$—,

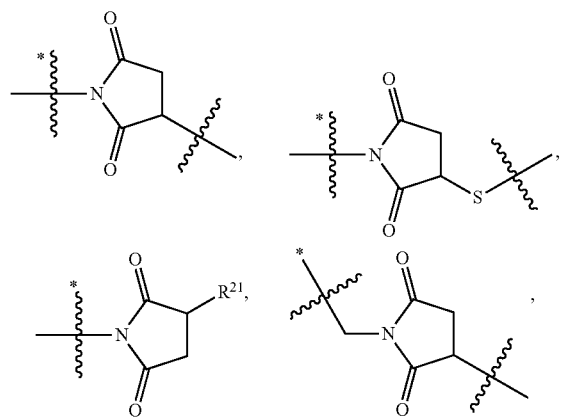

—*NH$_2$S(=O)$_2$(CH$_2$)$_m$X$_3$(CH$_2$)$_m$—, —*C(=O)((CH$_2$)$_m$O)$_n$(CH$_2$)$_m$)— and —*C(=O)NH(CH$_2$)$_m$)—, wherein the * indicates the point of attachment to $R^3$;

$L_2$ is

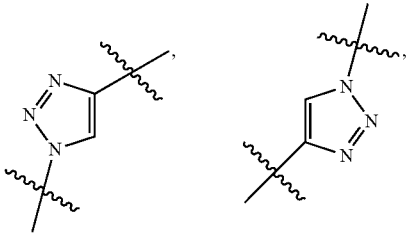

—S—, —SCH$_2$(C=O)NH—, —NHC(=O)CH$_2$S—,

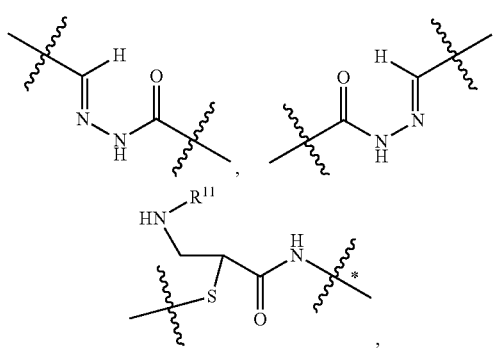

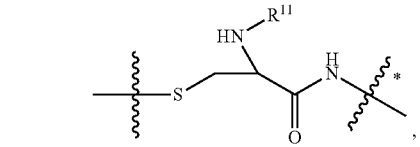

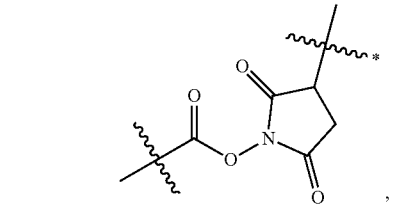

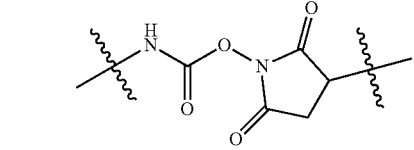

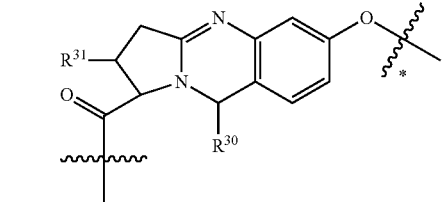

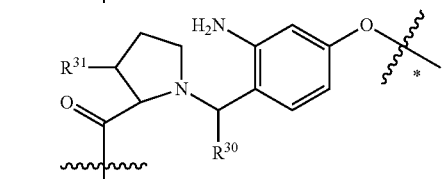

—S(=O)$_2$CH$_2$CH$_2$S—, —SCH$_2$CH$_2$S(=O)$_2$—, —(CH$_2$)$_2$S(=O)$_2$CH$_2$CH$_2$S— or —SCH$_2$CH$_2$S(=O)$_2$CH$_2$CH$_2$—, wherein the * indicates the point of attachment to $L_1$, and $L_3$, $L_4$, $L_5$ and $L_6$ are a bond.

Embodiment 101. The compound of any one of embodiments 3 to 21, 27 to 31, 34, 36 to 40, 45 and 78 to 80, and the immunoconjugate according to any one of embodiments 64 to 80, wherein:

$L_1$ is selected from —*C(=O)(CH$_2$)$_m$—, —(CH$_2$)$_m$—, —*(CH$_2$)$_m$NHC(=O)X$_1$X$_2$C(=O)(CH$_2$)$_m$—, —*X$_4$X$_1$X$_2$C(=O)(CH$_2$)$_m$—, —*X$_1$C(=O)(CH$_2$)$_m$NHC(=O)(CH$_2$)$_m$—, —*(CH$_2$)$_m$C(=O)NH(CH$_2$)$_m$NHC(=O)(CH$_2$)$_m$—, —*S(=O)$_2$(CH$_2$)mX$_3$(CH$_2$)$_m$—,

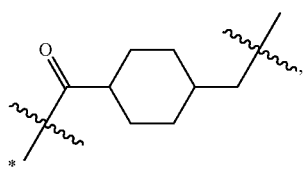 [SMILES: *CC1CCC(C(*)=O)CC1]

—*NH$_2$S(=O)$_2$(CH$_2$)$_m$X$_3$(CH$_2$)$_m$—, —*C(=O)((CH$_2$)$_m$O)$_n$(CH$_2$)$_m$)— and —*C(=O)NH(CH$_2$)$_m$)—, wherein the * indicates the point of attachment to R$^3$;

$L_2$ is

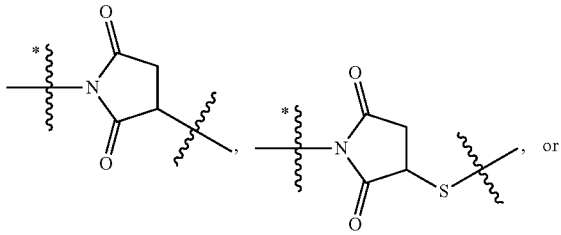

or

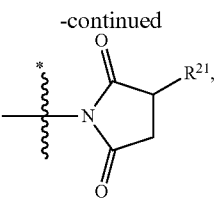

wherein the * indicates the point of attachment to $L_1$, and $L_3$, $L_4$, $L_5$ and $L_6$ are a bond.

Embodiment 102. The compound of any one of embodiments 3 to 21, 27 to 31, 34, 36 to 40, 45 and 78 to 80, and the immunoconjugate according to any one of embodiments 64 to 80, wherein:

$L_1$ is selected from —*C(=O)(CH$_2$)$_m$—, —(CH$_2$)$_m$—, —*(CH$_2$)$_m$NHC(=O)X$_1$X$_2$C(=O)(CH$_2$)$_m$—, —*X$_4$X$_1$X$_2$C(=O)(CH$_2$)$_m$—, —*X$_1$C(=O)(CH$_2$)$_m$NHC(=O)(CH$_2$)$_m$—, —*(CH$_2$)$_m$C(=O)NH(CH$_2$)$_m$NHC(=O)(CH$_2$)$_m$—, —*S(=O)$_2$(CH$_2$)mX$_3$(CH$_2$)$_m$—,

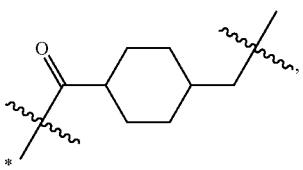 [SMILES: *CC1CCC(C(*)=O)CC1]

—*NH$_2$S(=O)$_2$(CH$_2$)$_m$X$_3$(CH$_2$)$_m$—, —*C(=O)((CH$_2$)$_m$O)$_n$(CH$_2$)$_m$)— and —*C(=O)NH(CH$_2$)$_m$)—, wherein the * indicates the point of attachment to R$^3$;

$L_2$ is

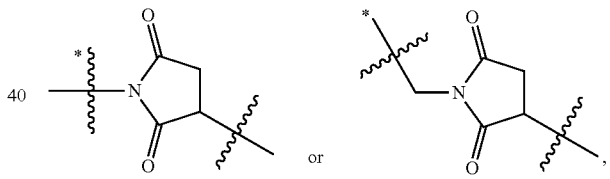

or wherein the * indicates the point of attachment to $L_1$, and $L_3$, $L_4$, $L_5$ and $L_6$ are a bond.

Embodiment 103. The compound of any one of embodiments 1 to 45, and 78 to 102, wherein the compound is selected from

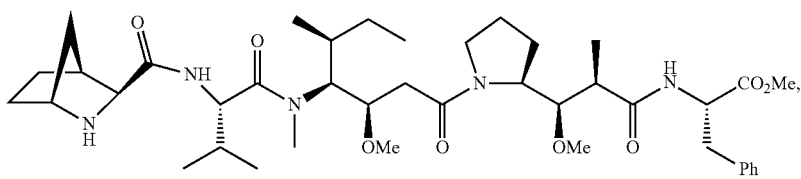

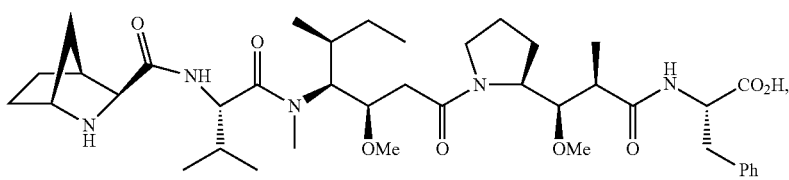

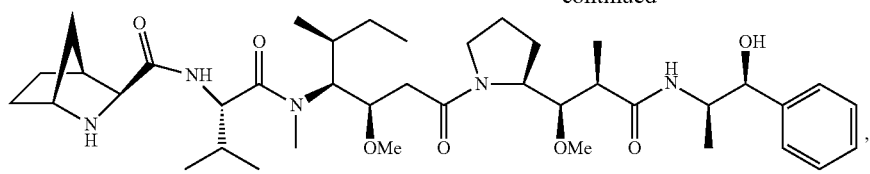
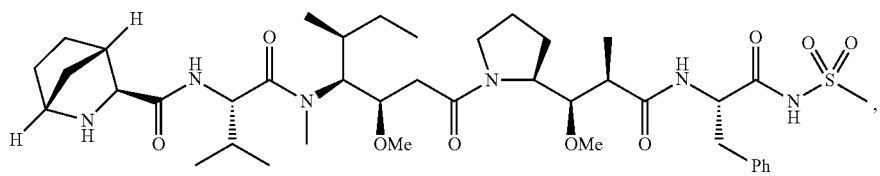
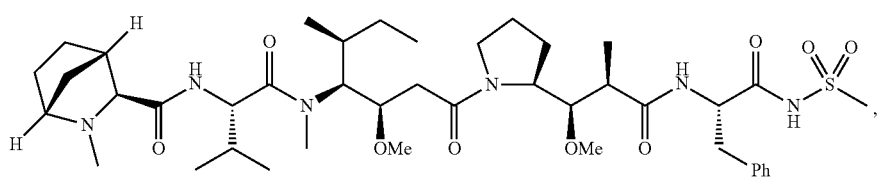
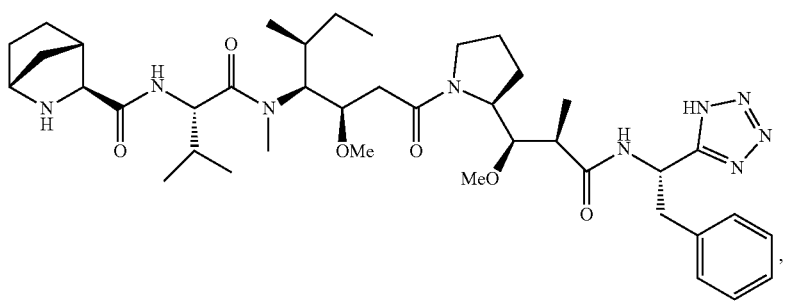
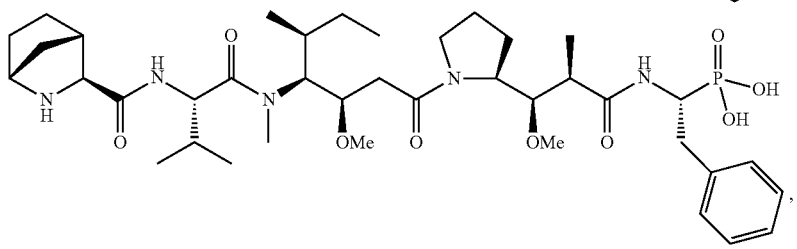
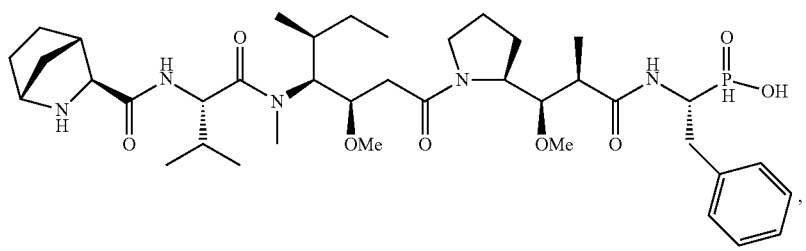
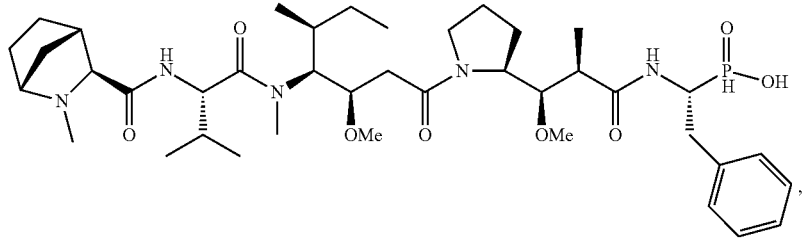

465
466
-continued
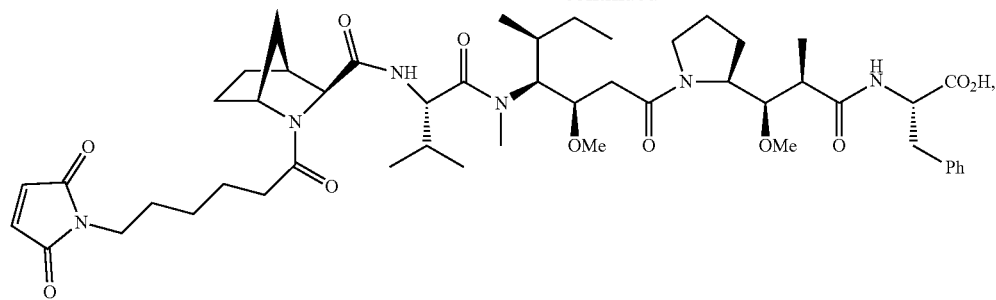
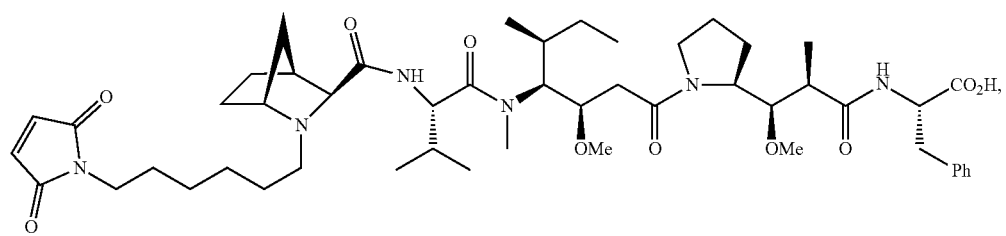
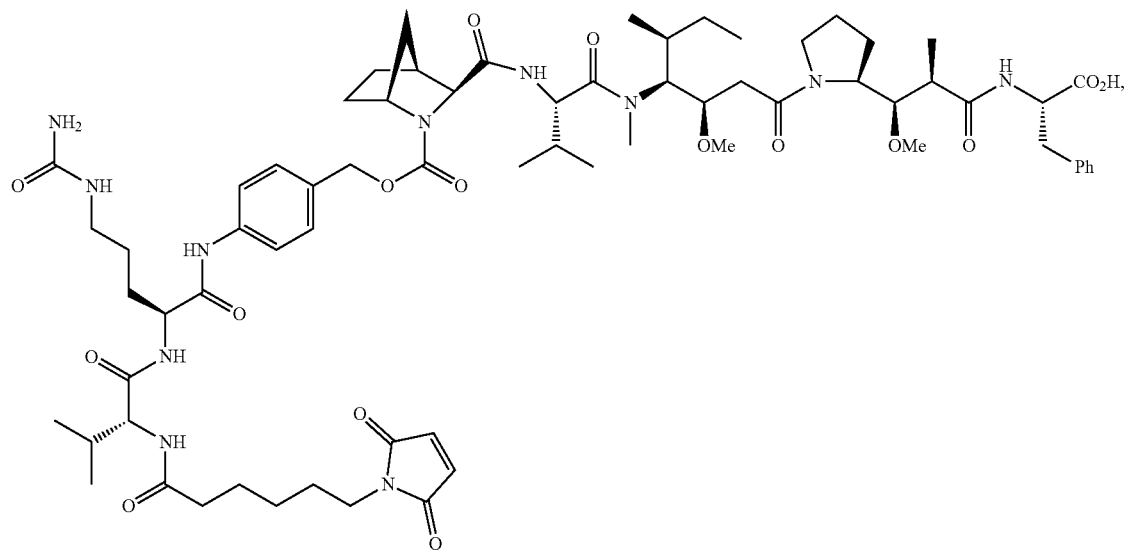
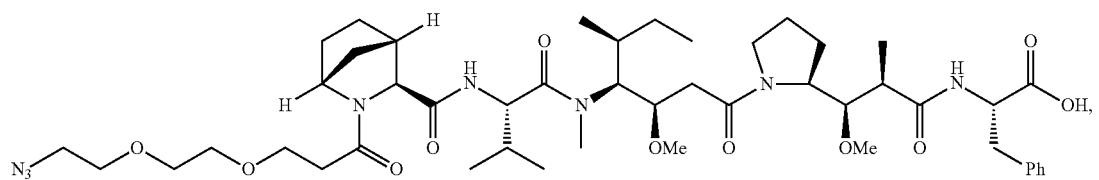
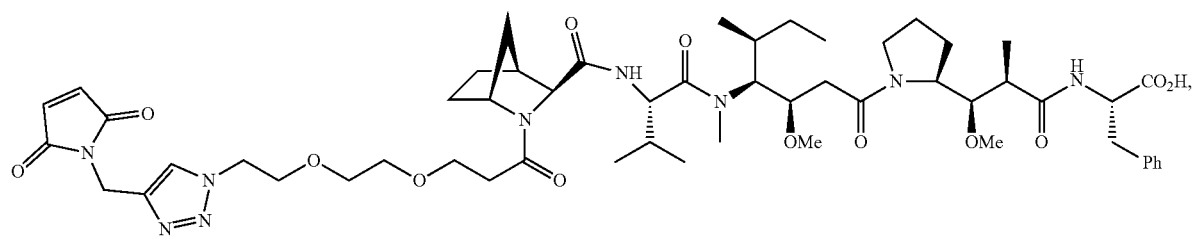

467
468
-continued
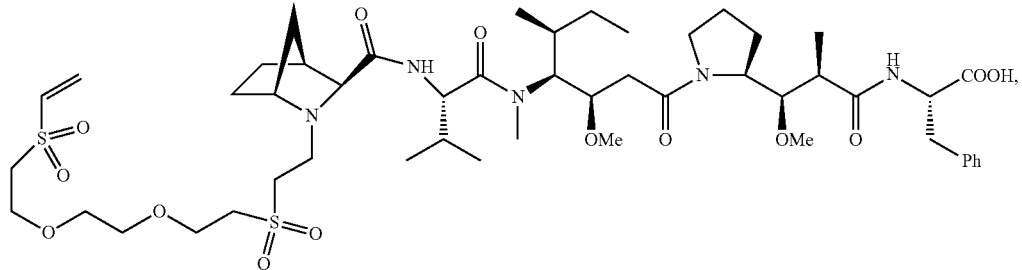
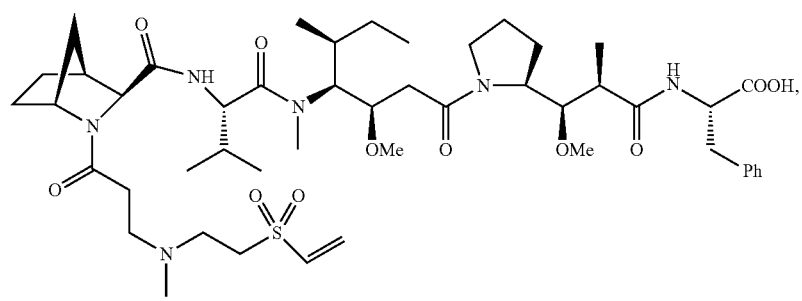
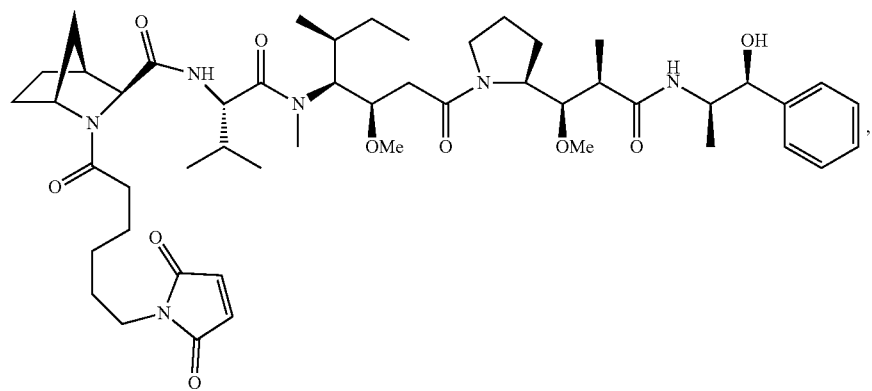
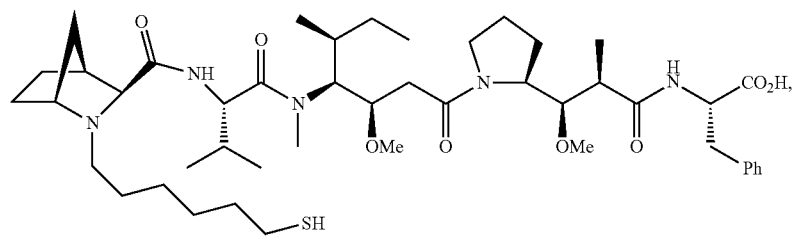
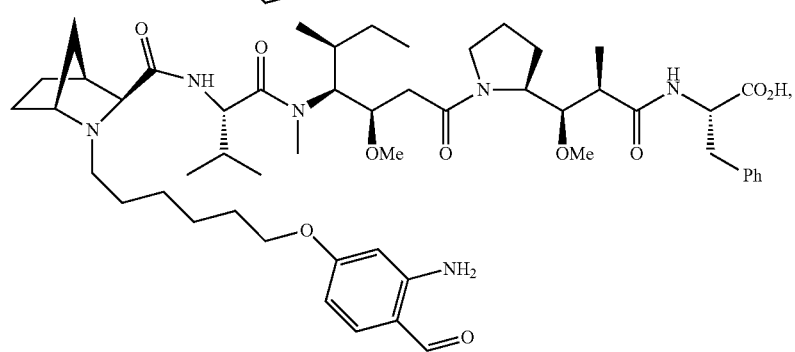

-continued
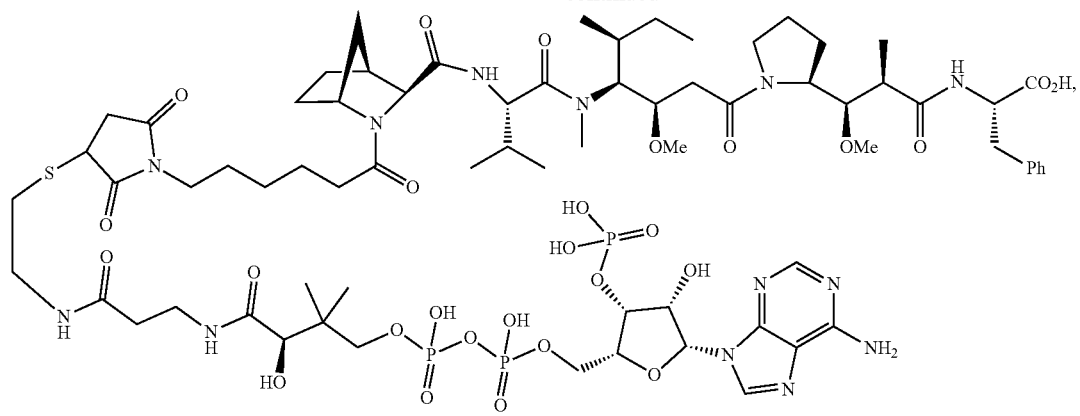
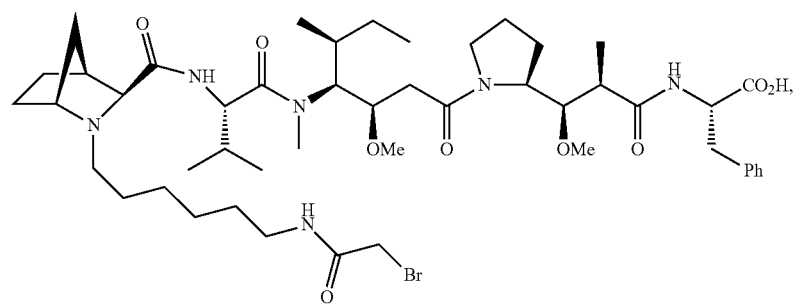
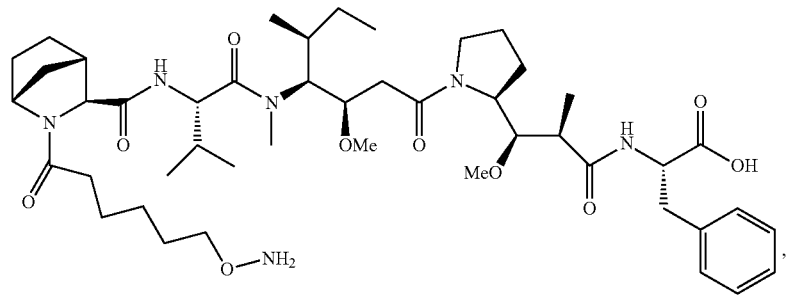
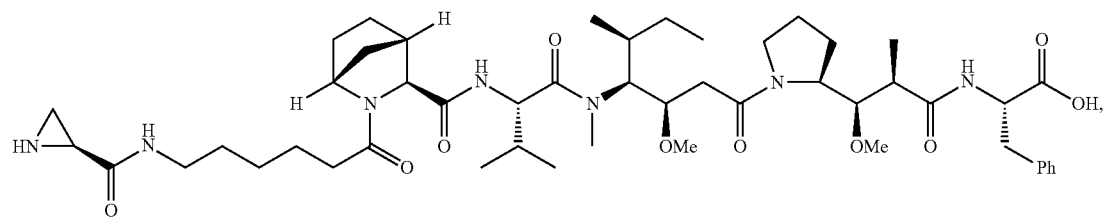
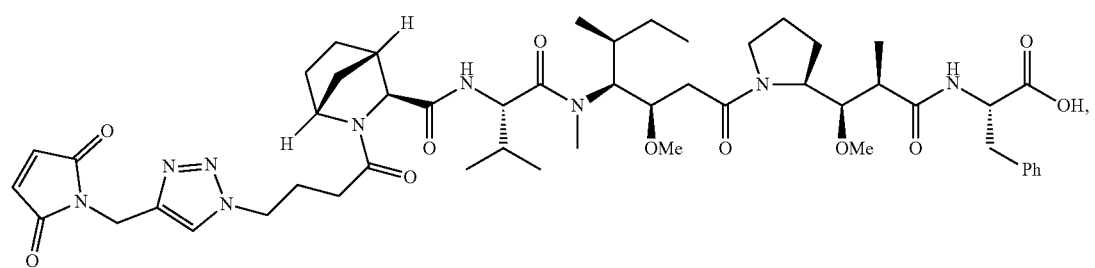

-continued
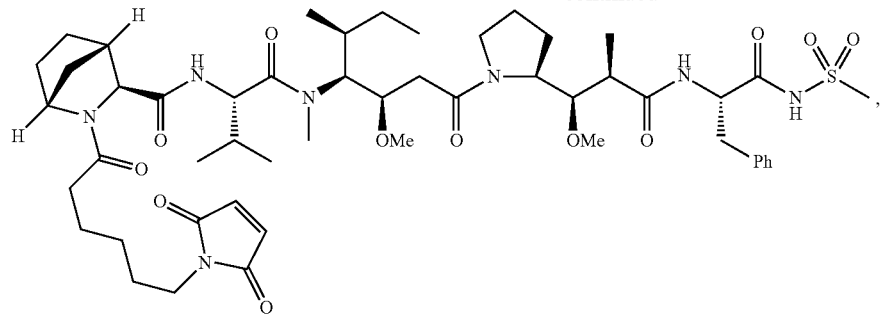
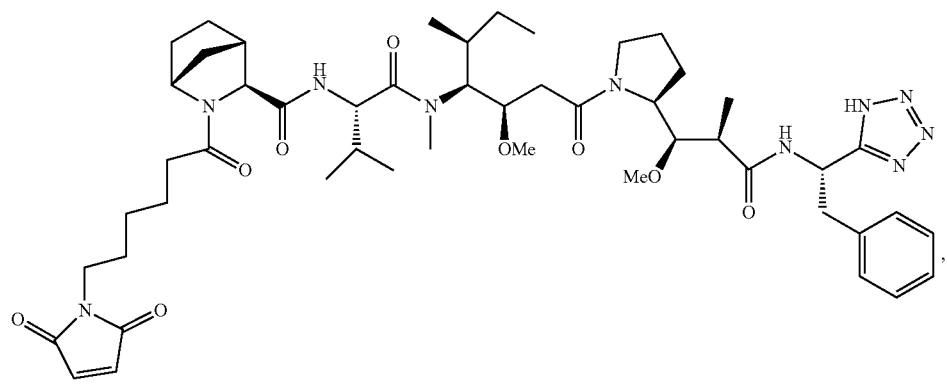
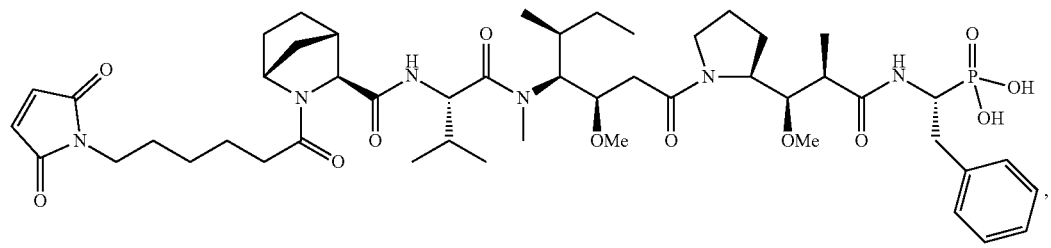
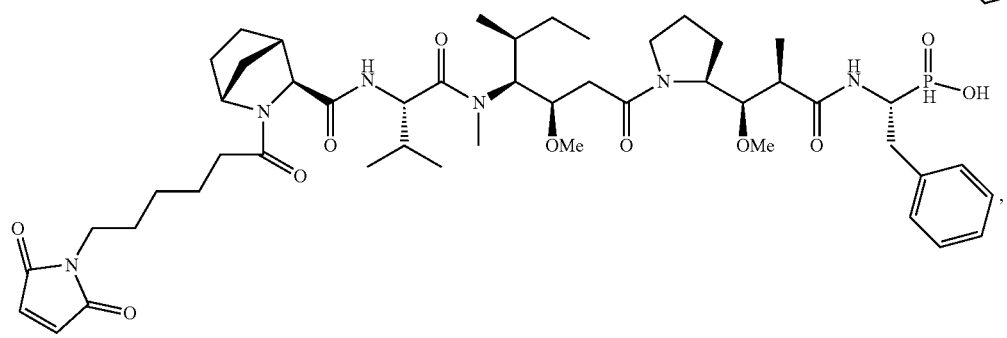
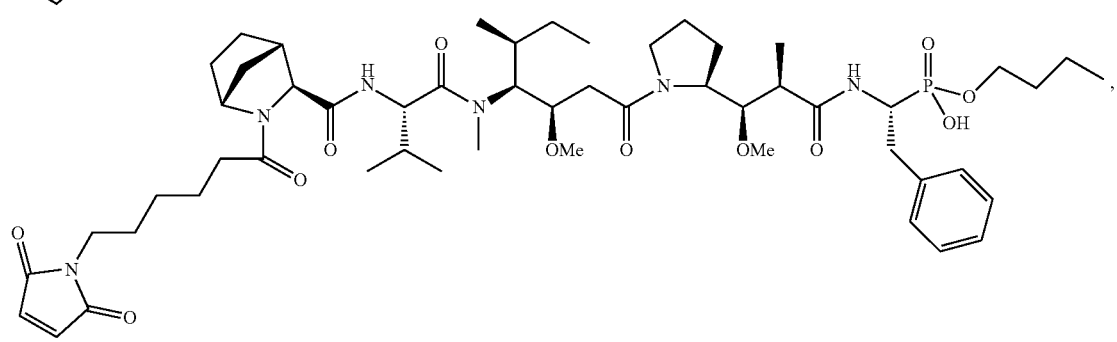

473 474
-continued
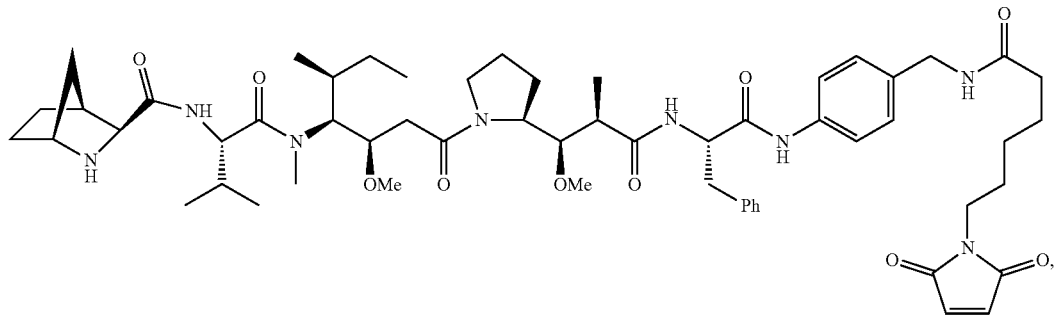
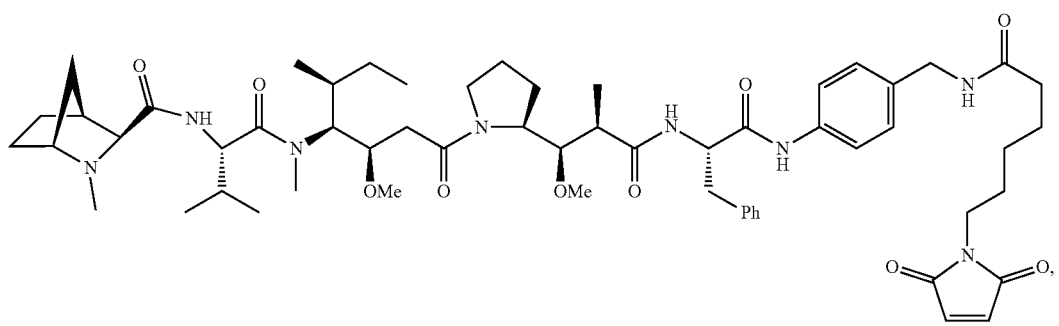
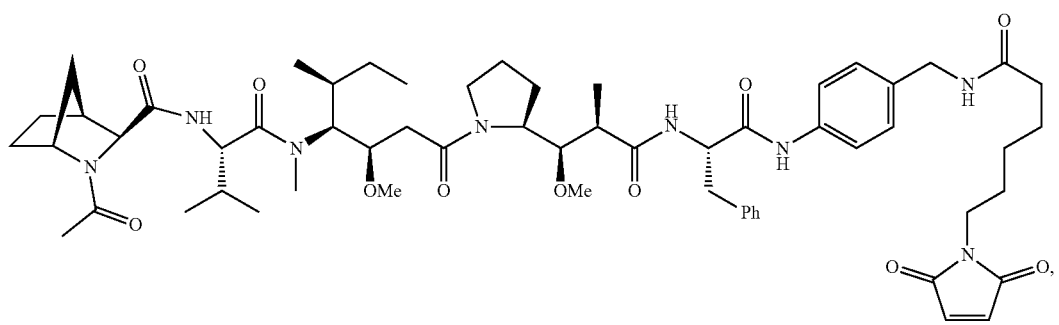
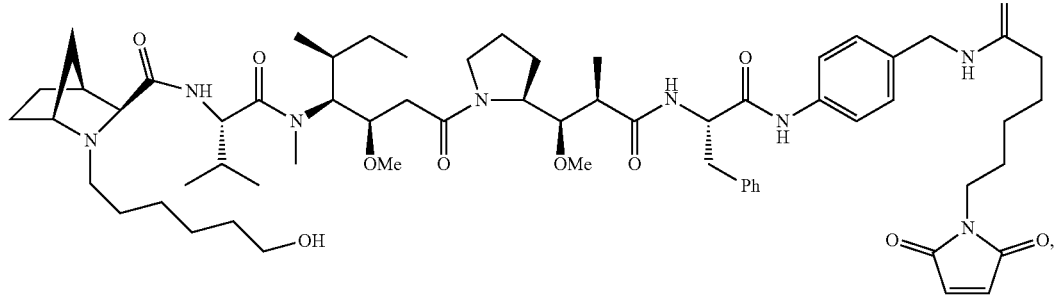
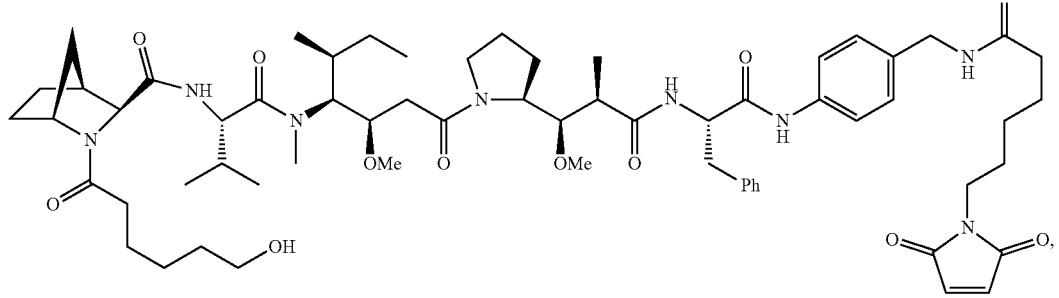

475                                                                 476
-continued
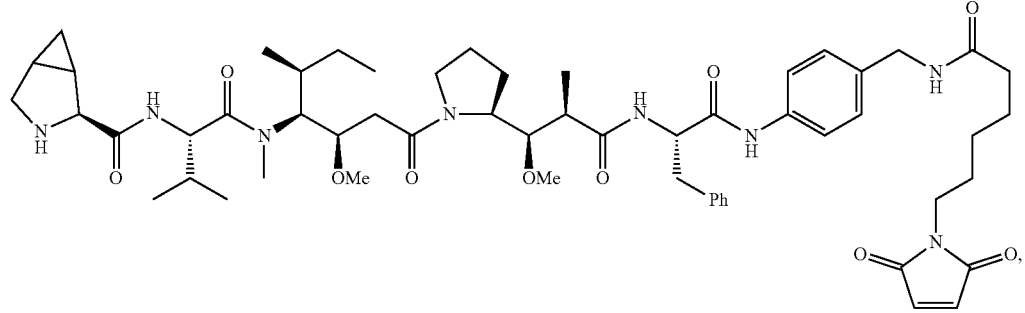
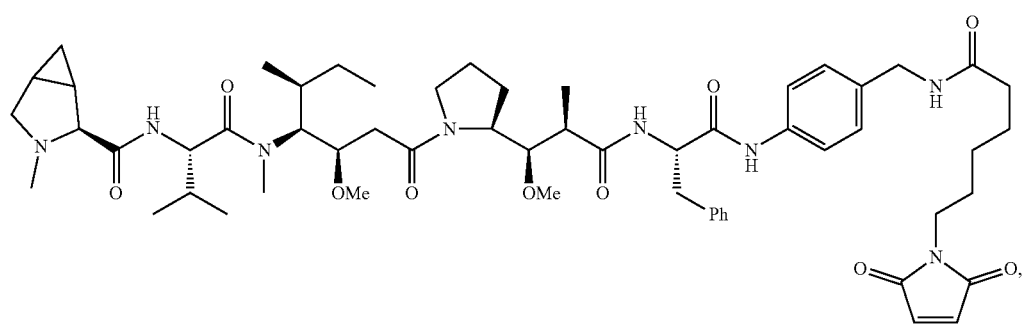
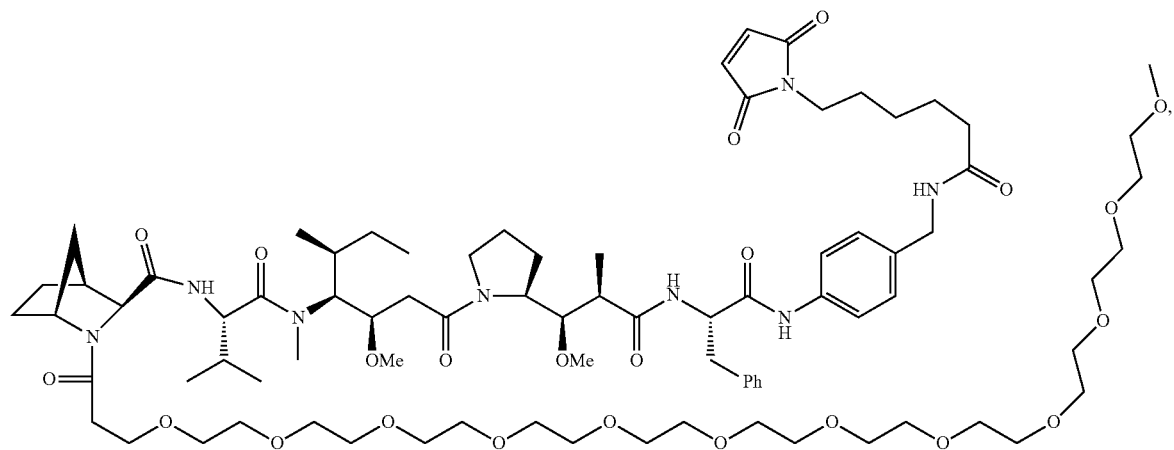
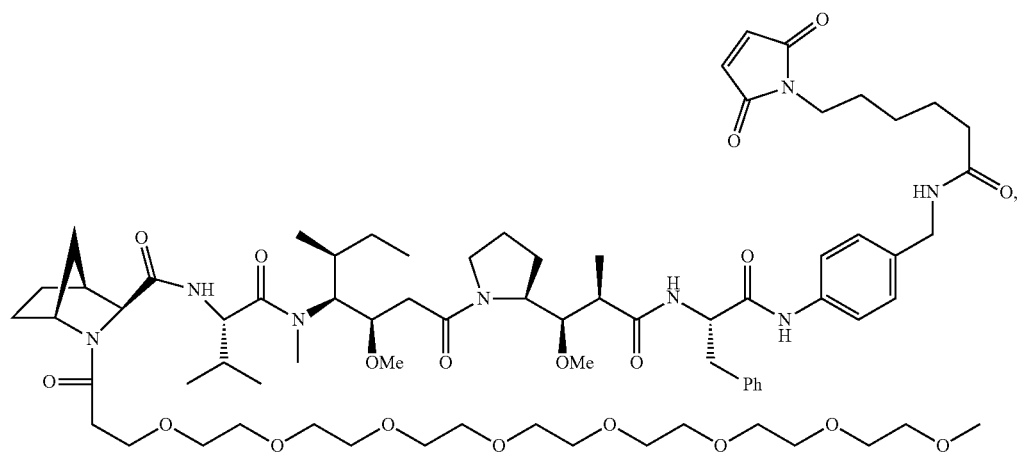

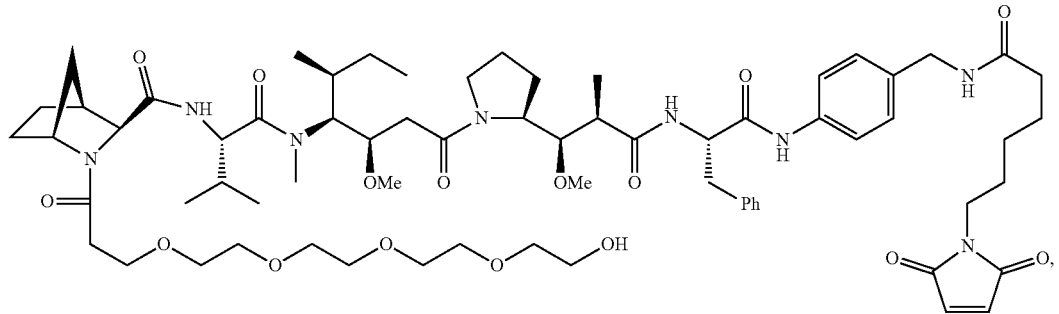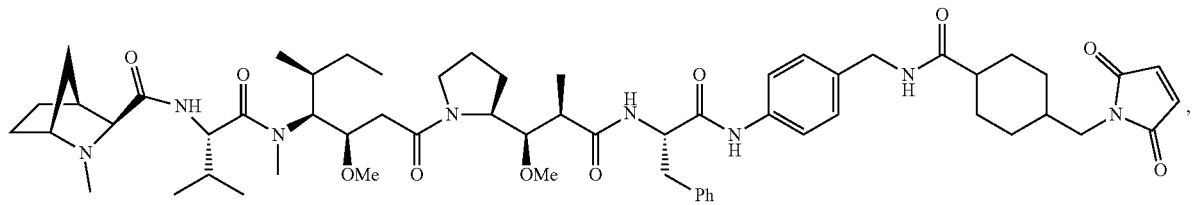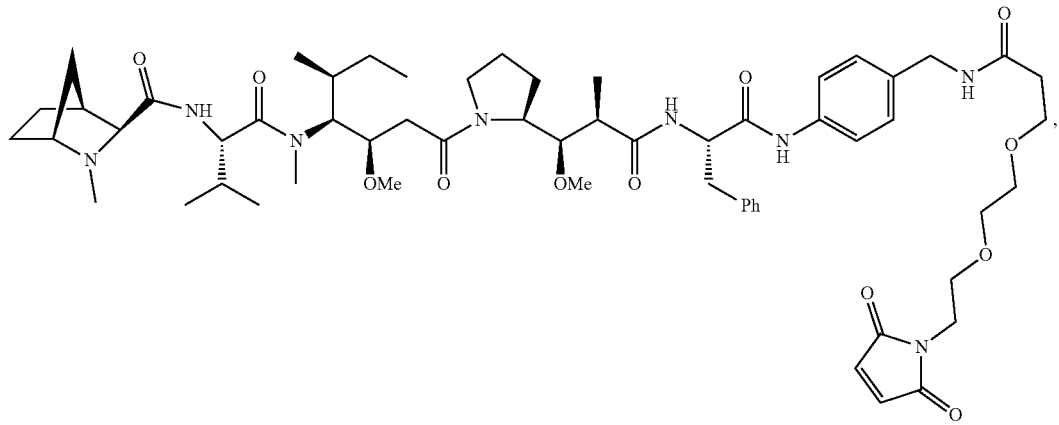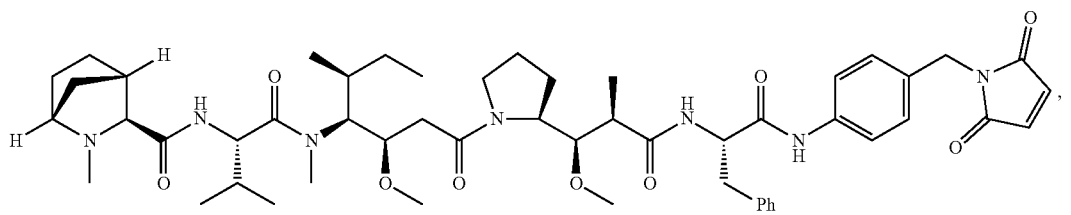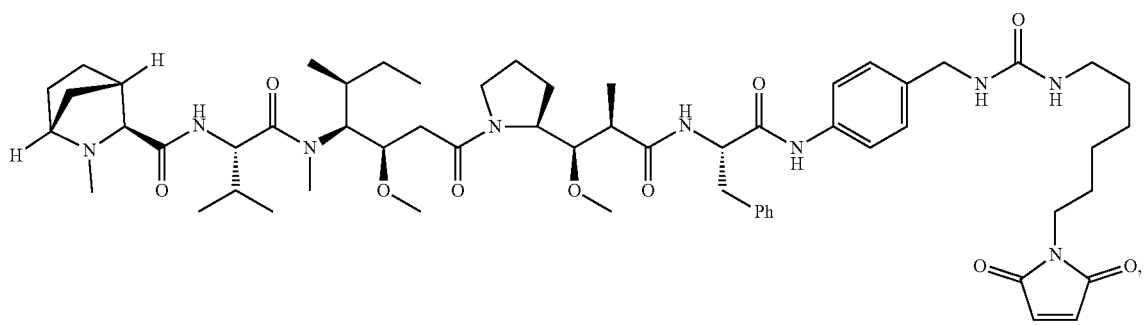

-continued
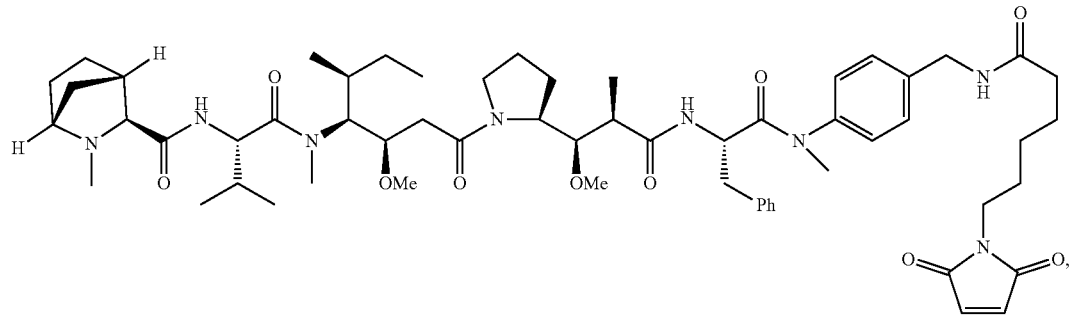
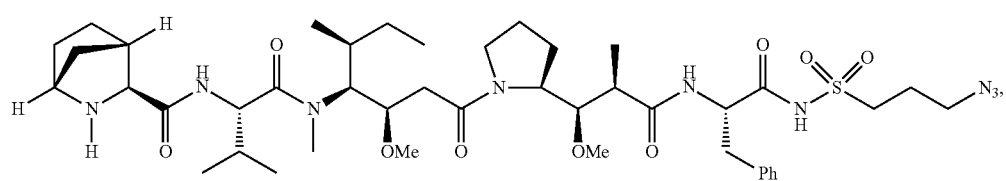
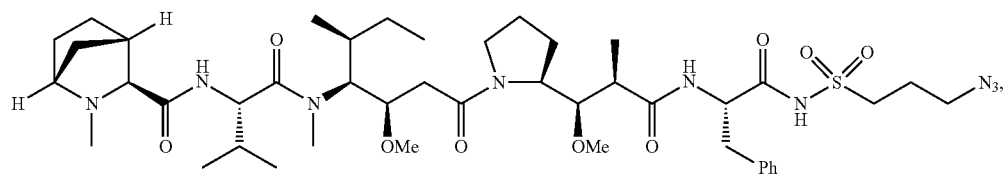
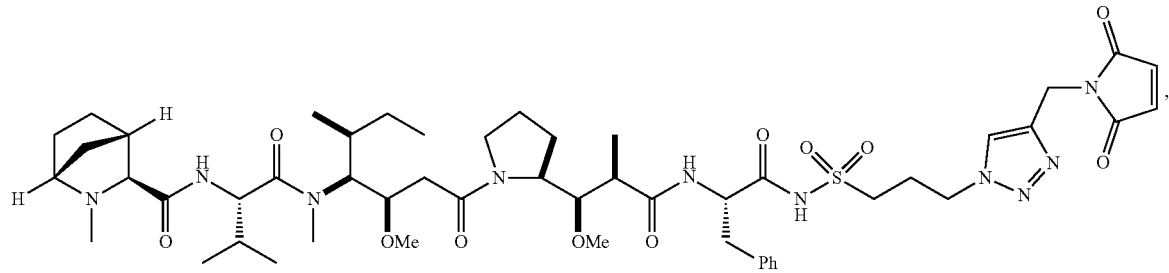
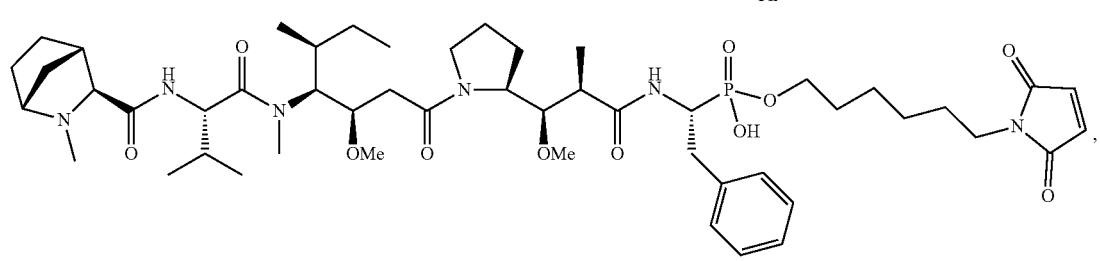
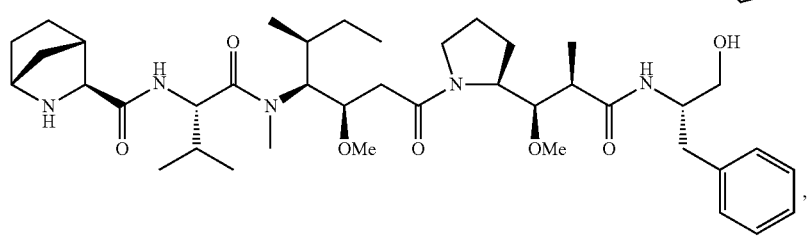
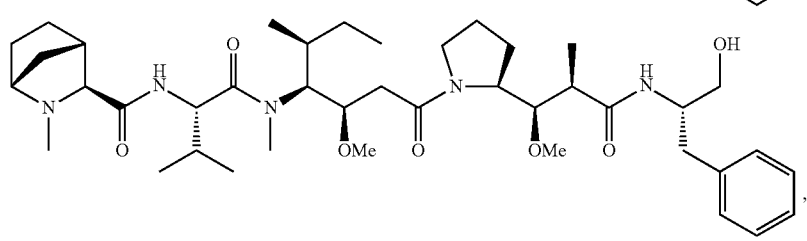

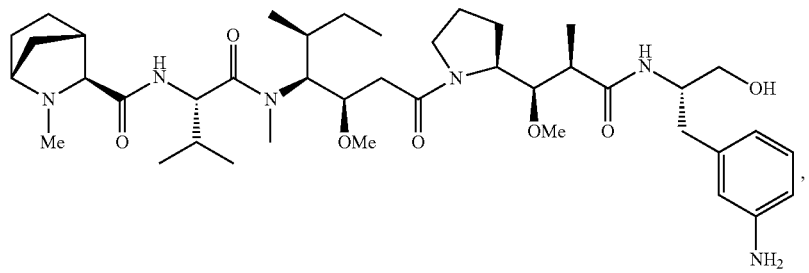
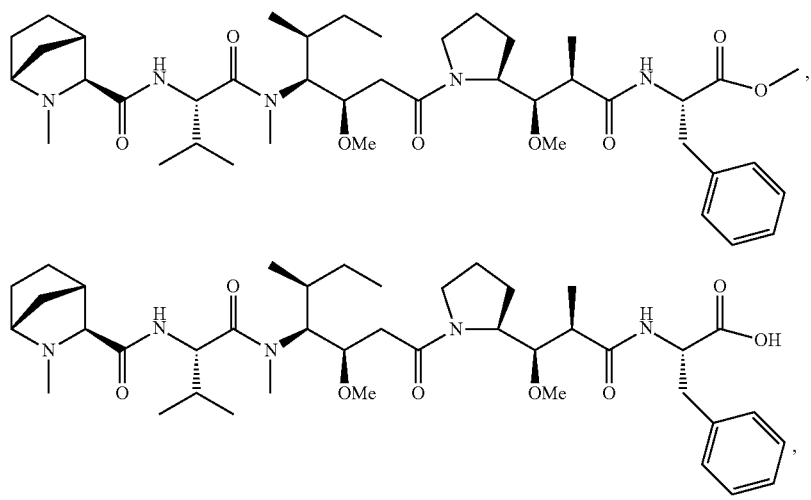
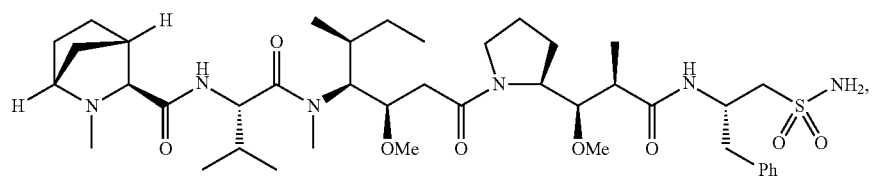
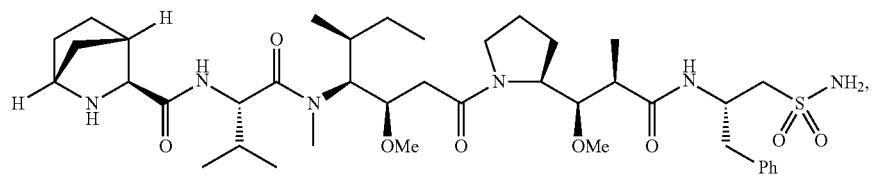
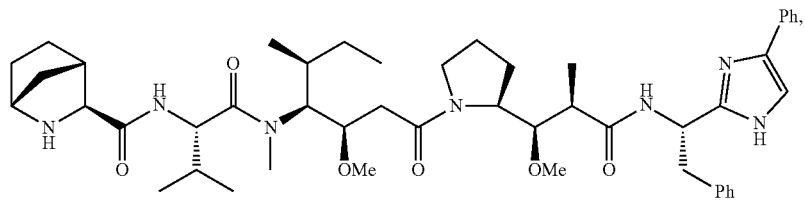
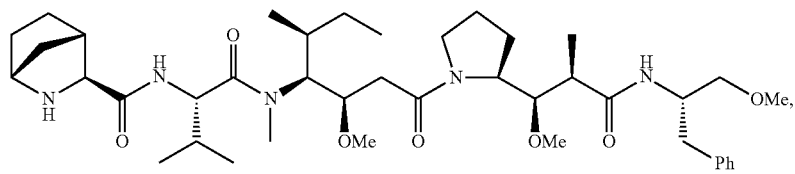
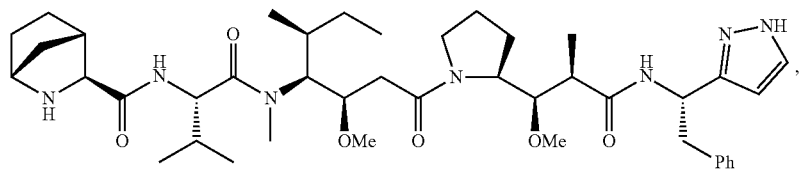

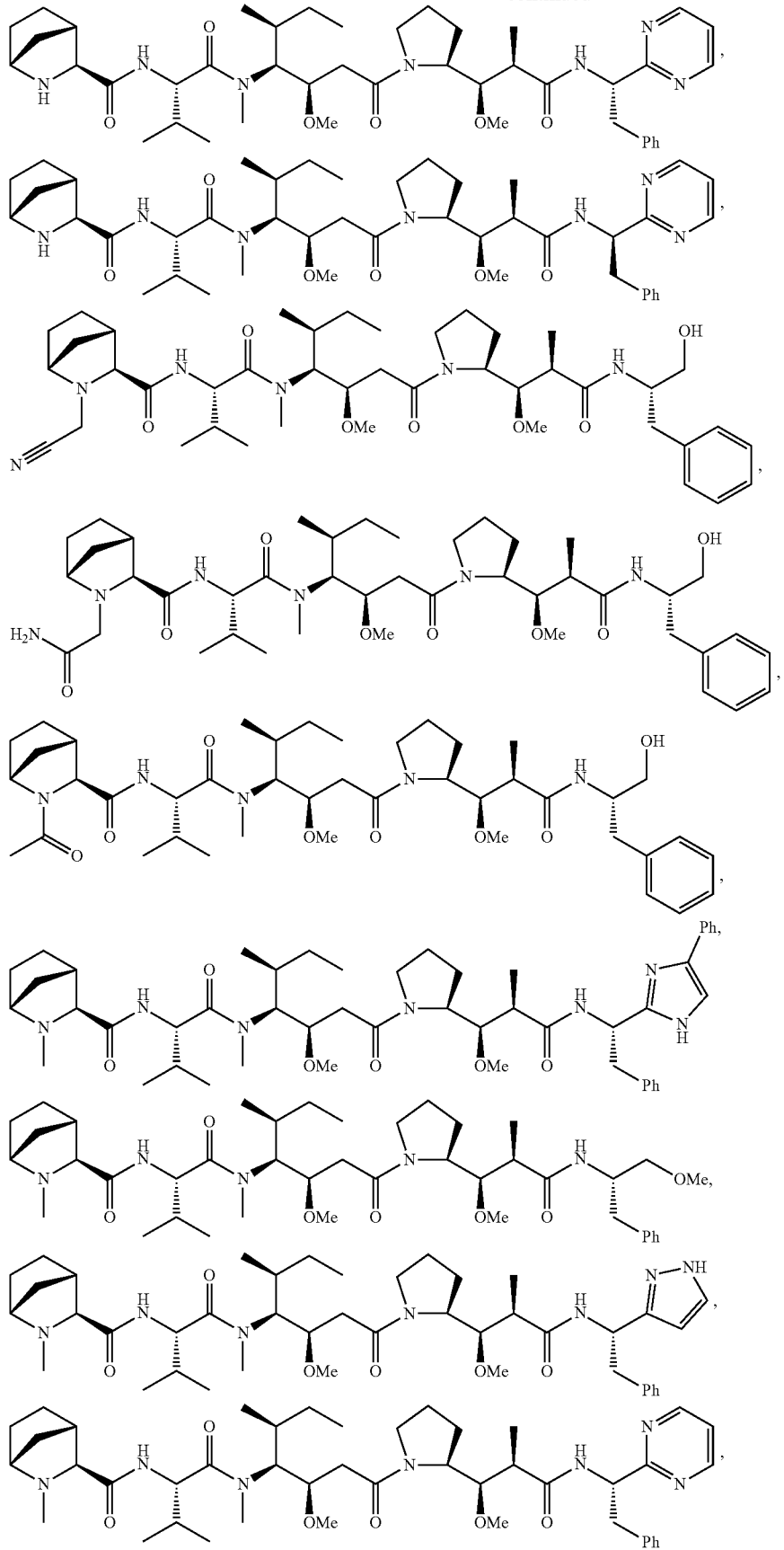

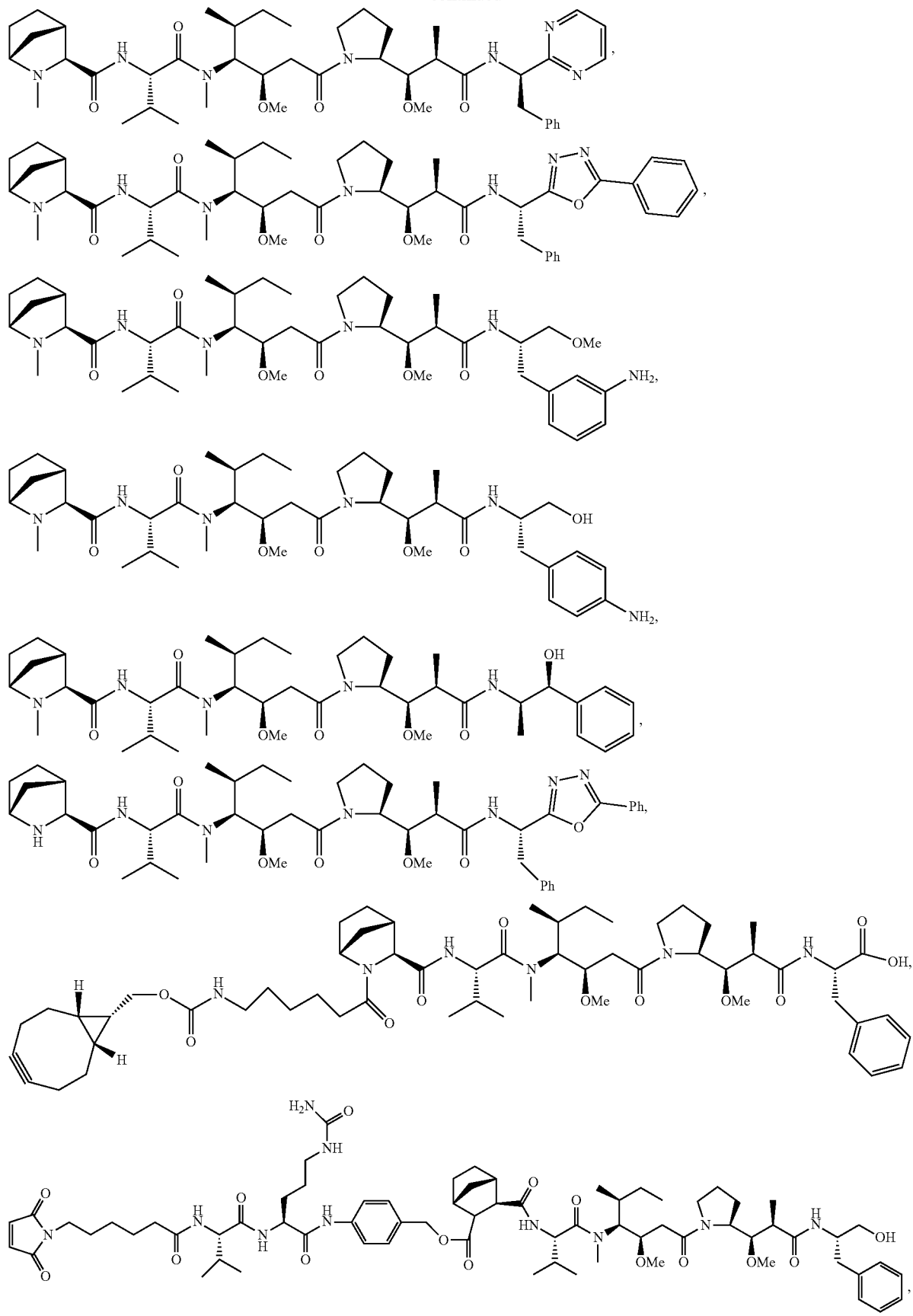

-continued
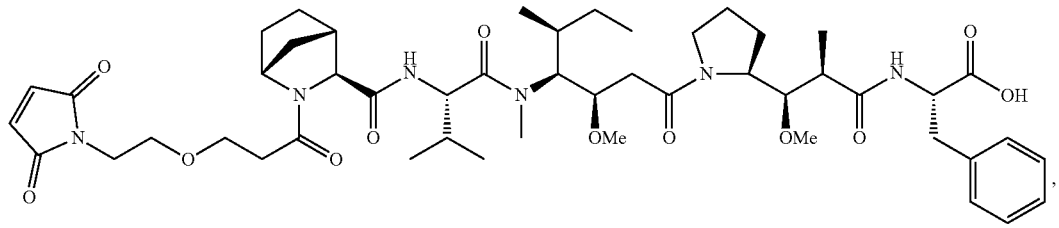
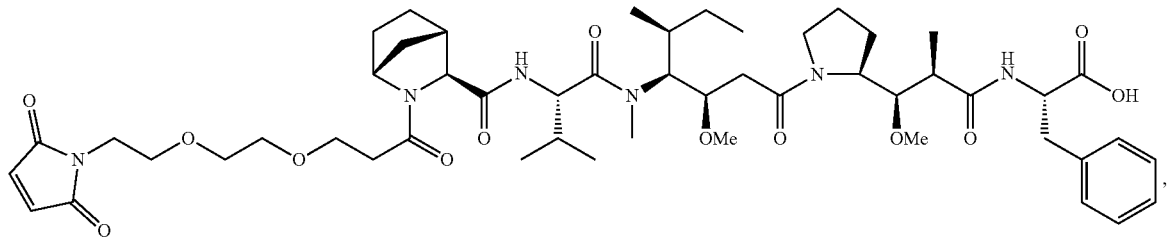
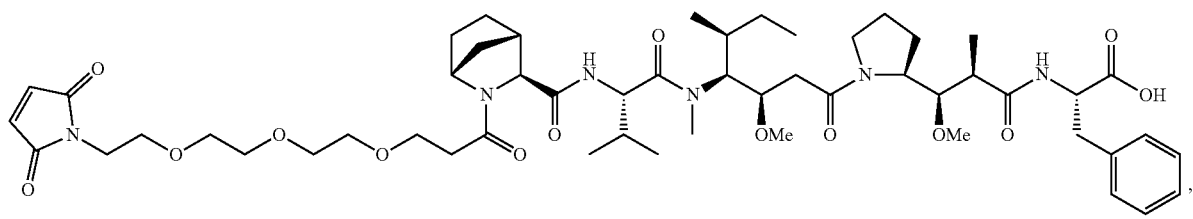
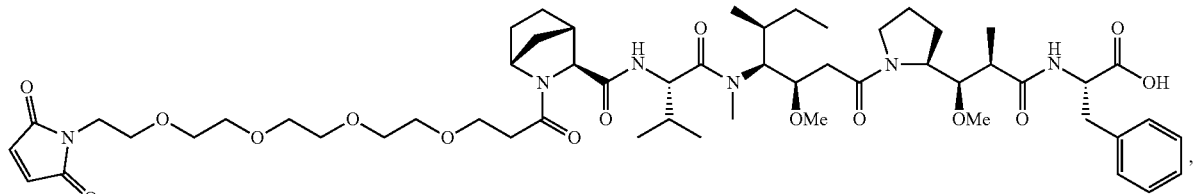
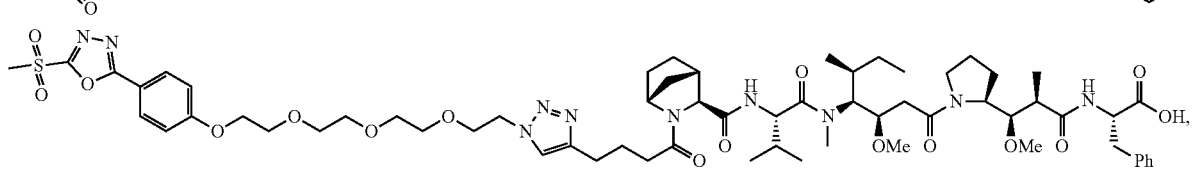
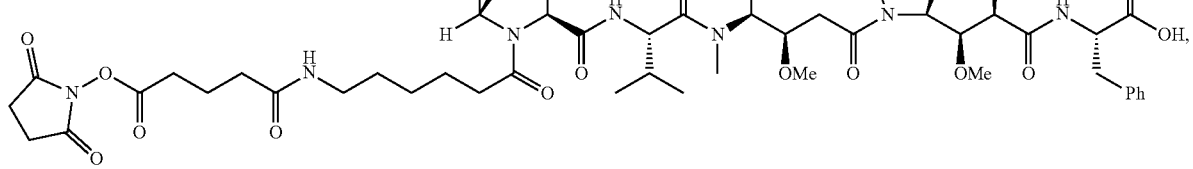
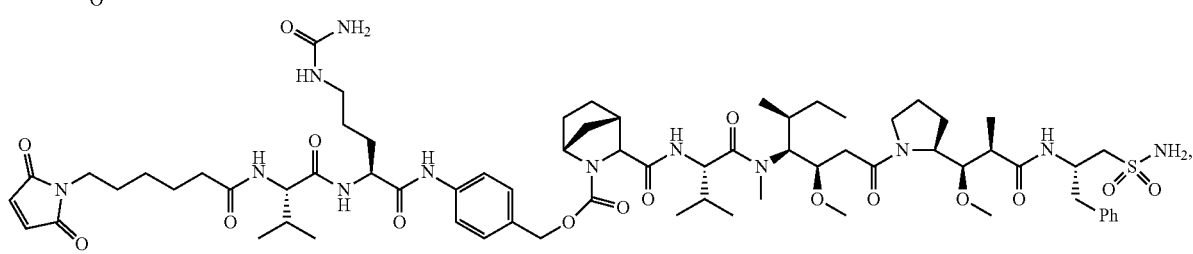

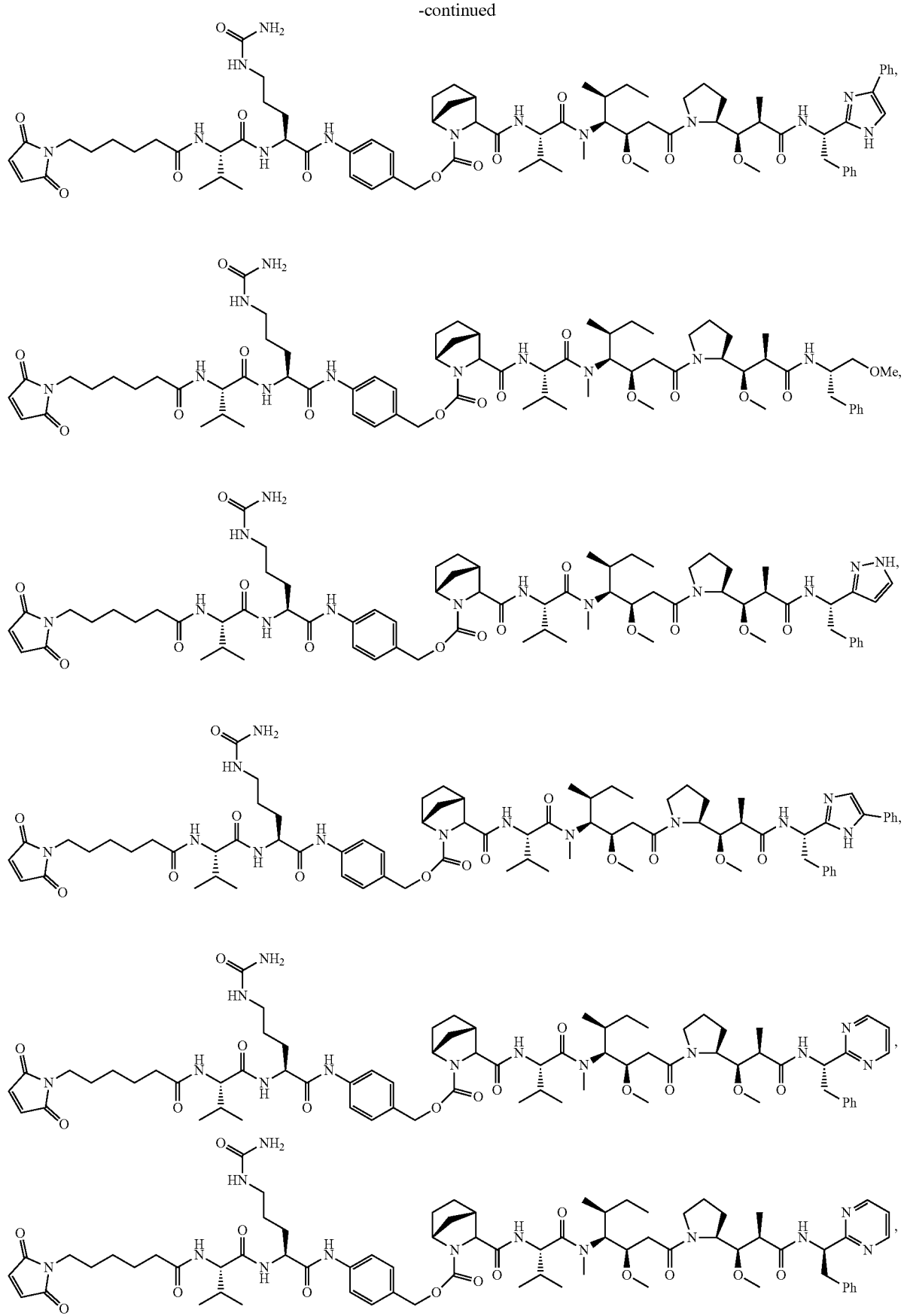

-continued

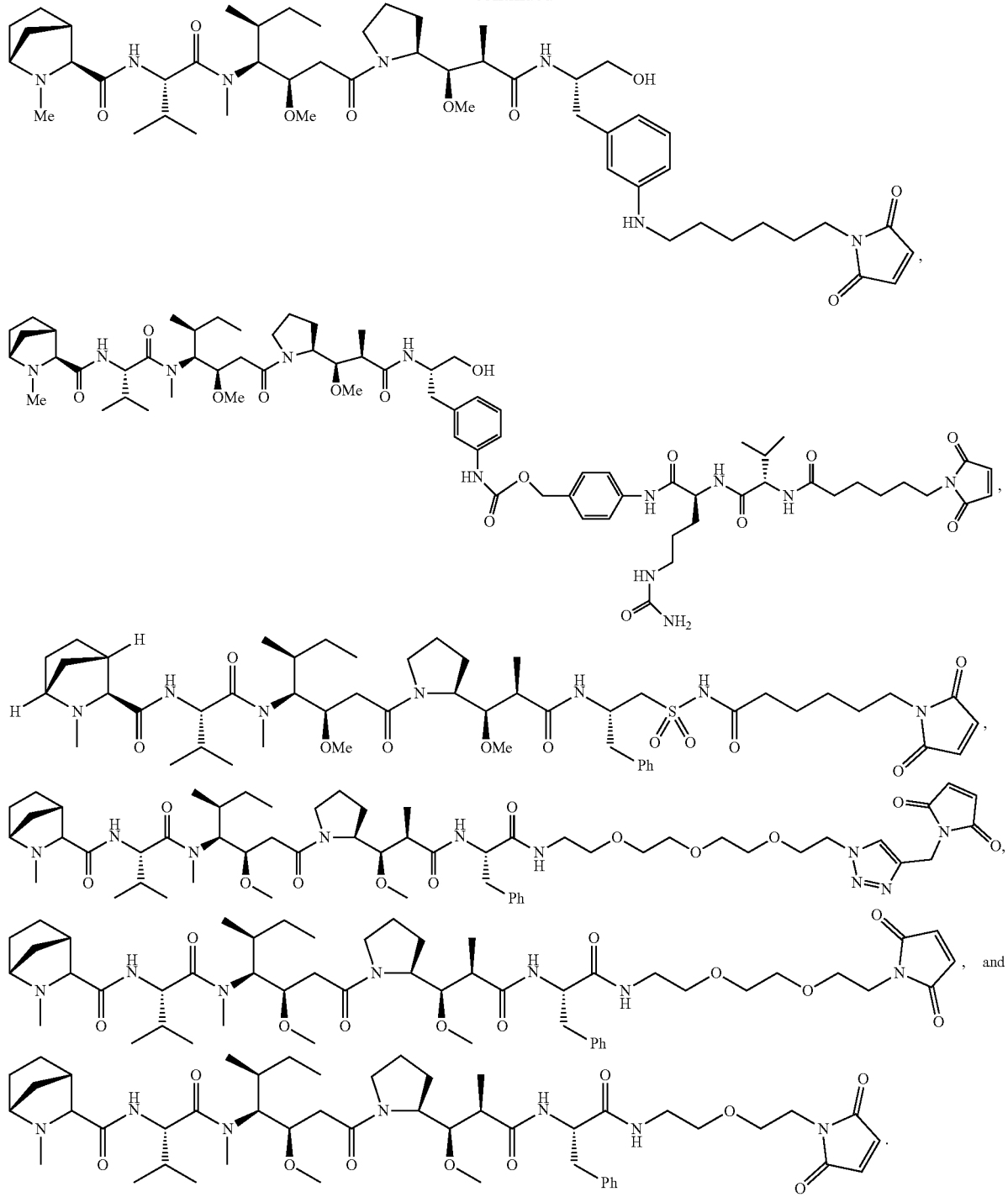

Embodiment 104. A pharmaceutical composition comprising an immunoconjugate of any one of embodiments 46 to 102, and one or more pharmaceutically acceptable carriers.

Embodiment 105. A combination comprising a therapeutically effective amount of an immunoconjugate of any one of embodiments 46 to 102, and one or more therapeutically active co-agents.

Embodiment 106. A method of treating a cell proliferation disorder, comprising administering to a subject in need thereof a therapeutically effective amount of an immunoconjugate of any one of embodiments 46 to 102.

Embodiment 107. An immunoconjugate of any one of embodiments 46 to 102 for use as a medicament.

Embodiment 108. The immunoconjugate according to embodiment 107, wherein the medicament is for use in the treatment of cancer.

Embodiment 109. An immunoconjugate of any one of embodiments 46 to 102 for use to treat cancer.
Embodiment 110. An immunoconjugate according to embodiments 46 to 102, having a formula selected from:
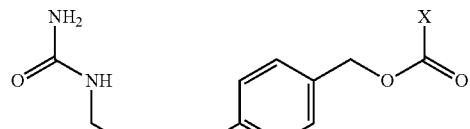
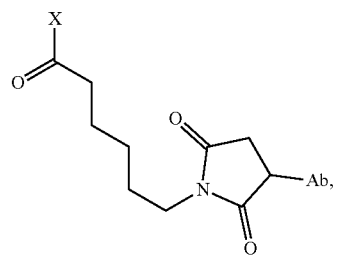 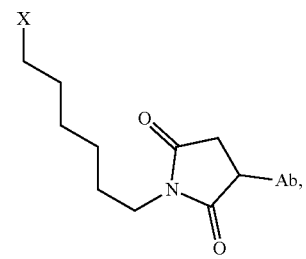
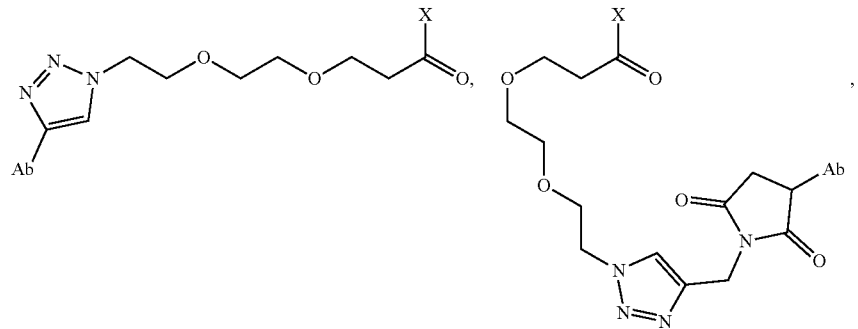
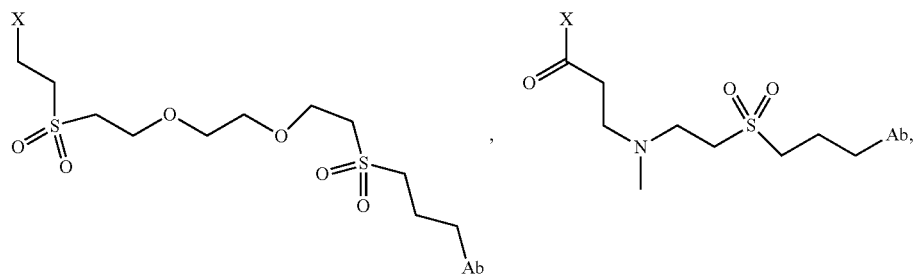
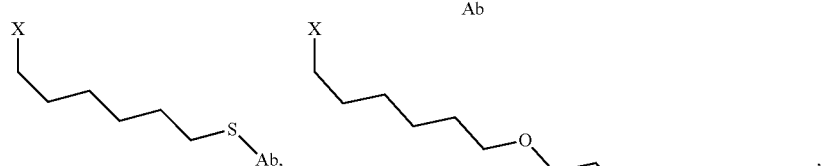
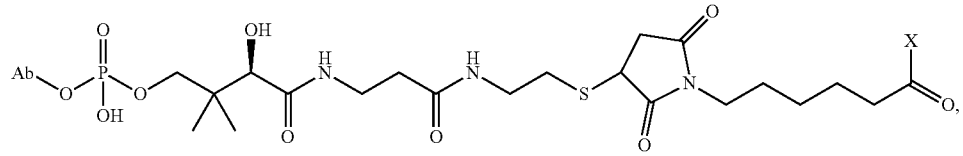

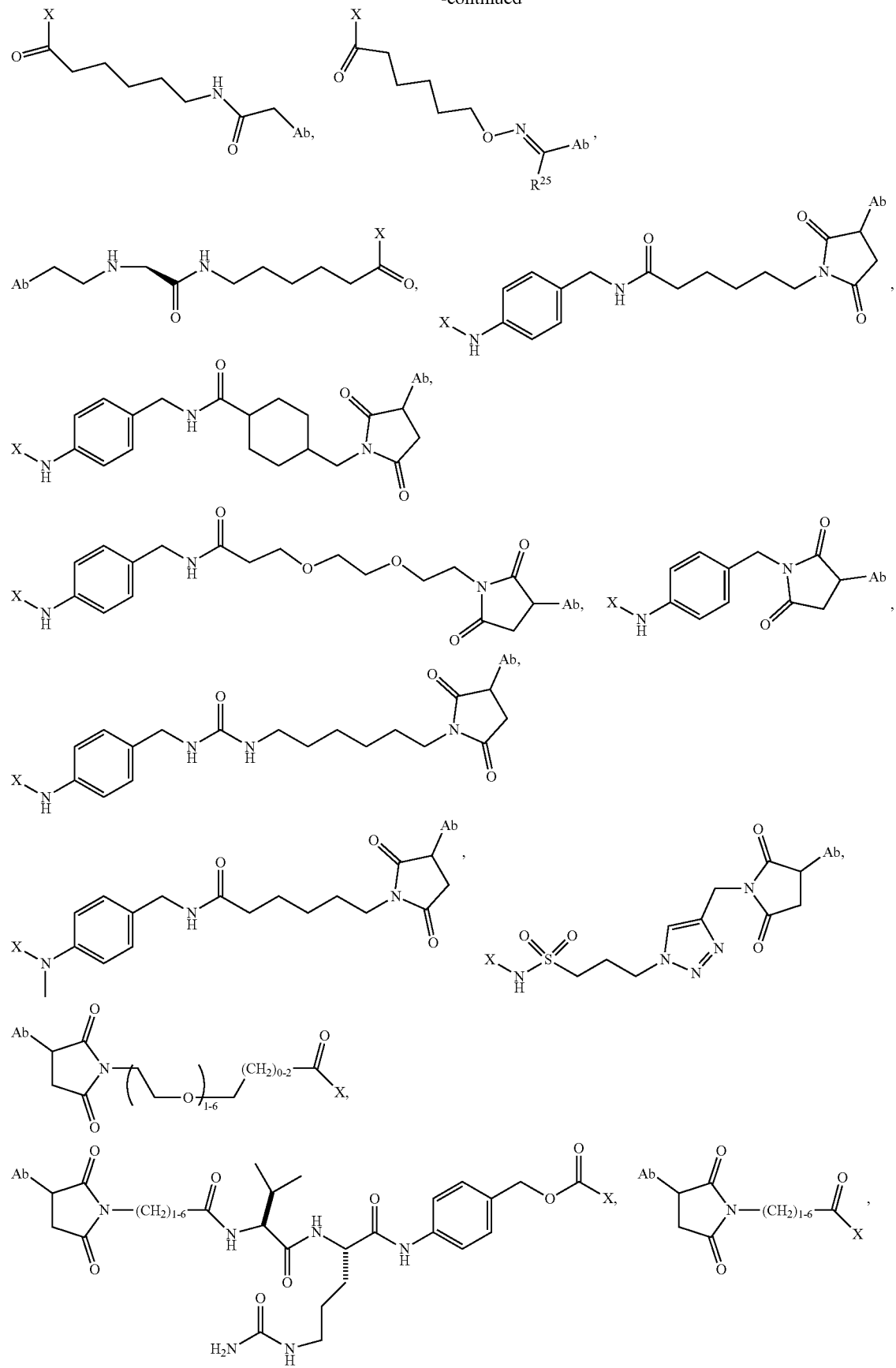

497 498
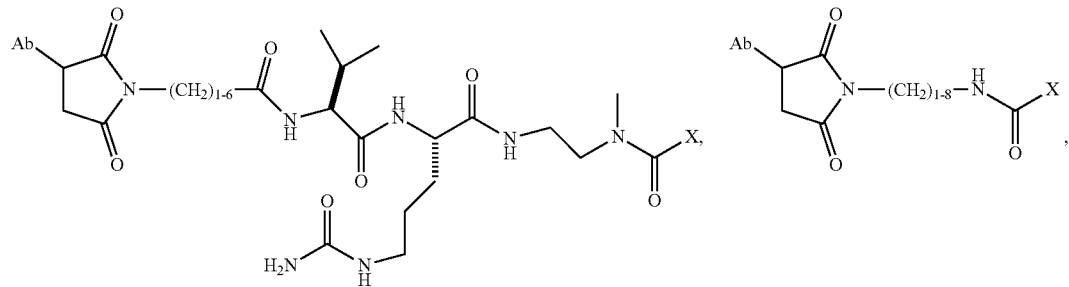
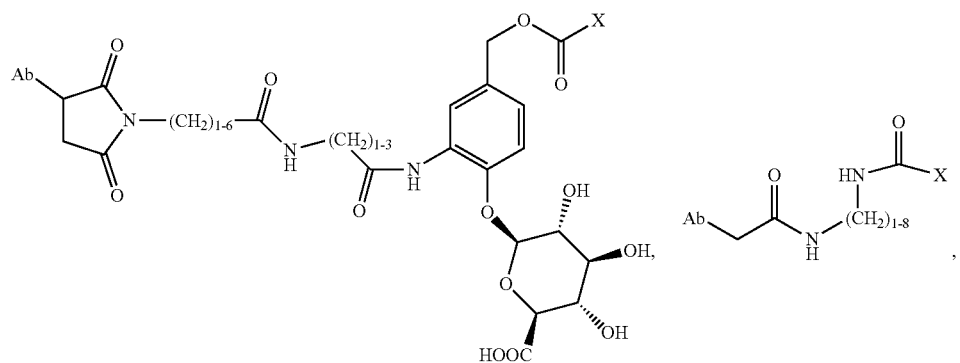
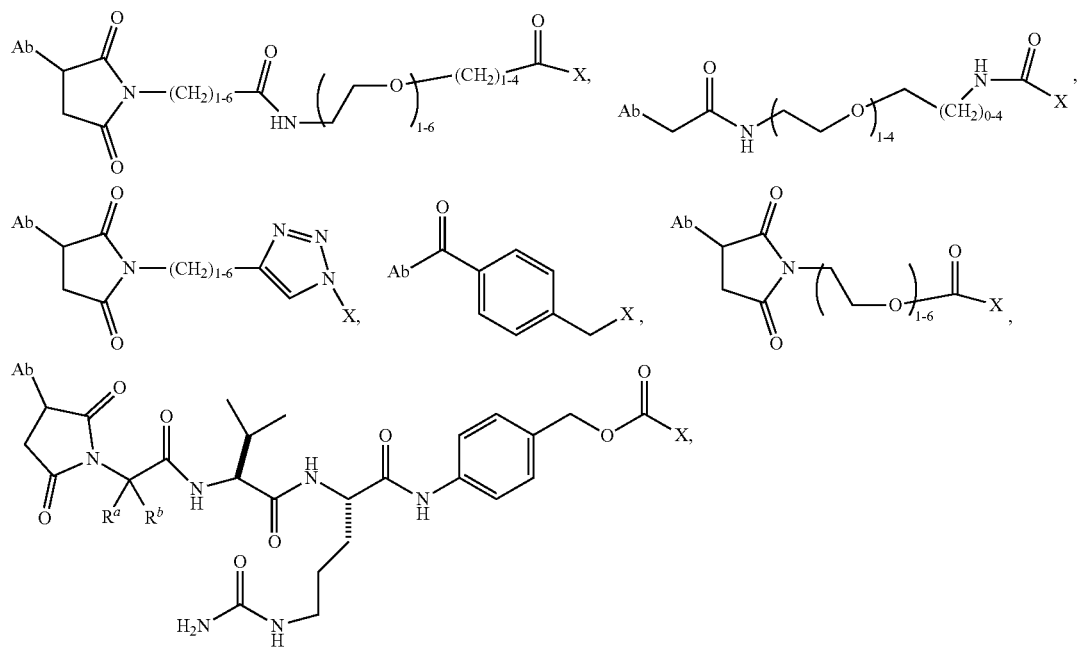
$R^a$ = H, $R^b$ = CH$_2$Ph
$R^a$ = H, $R^b$ = CH$_2$-(4-hydroxyphenyl)
$R^a$ = Me, $R^b$ = Me
$R^a$ = H, $R^b$ = CH$_2$COOH
$R^a$ = H, $R^b$ = CH$_2$CH$_2$NH$_2$
$R^a$ = H, $R^b$ = COOH
$R^a$ = H, $R^b$ = H
$R^a$ = $R^b$ together = cyclopropane
$R^a$ = $R^b$ together = cyclopentane
$R^a$ = H, $R^b$ = Ph
$R^a$ = H, $R^b$ = 3-indolyl -continued
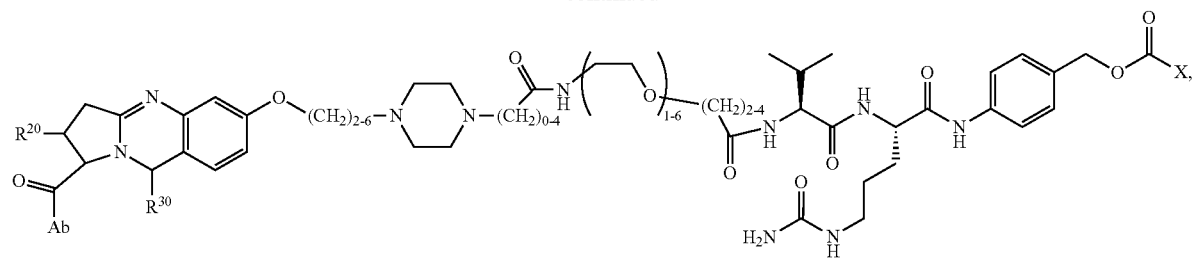
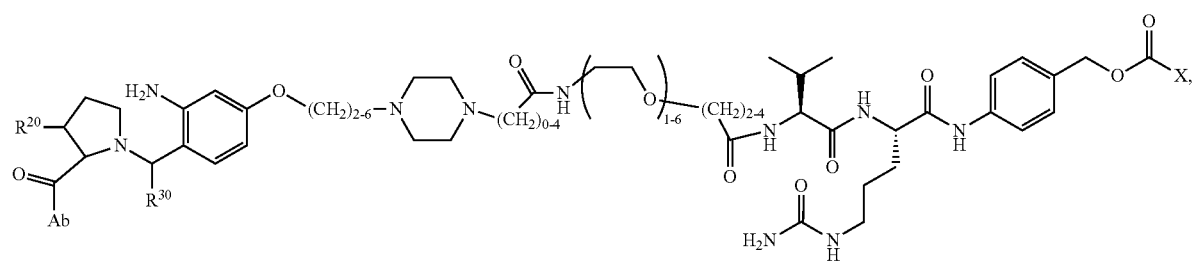
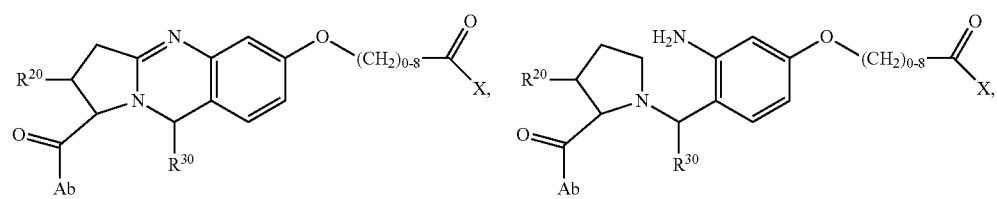
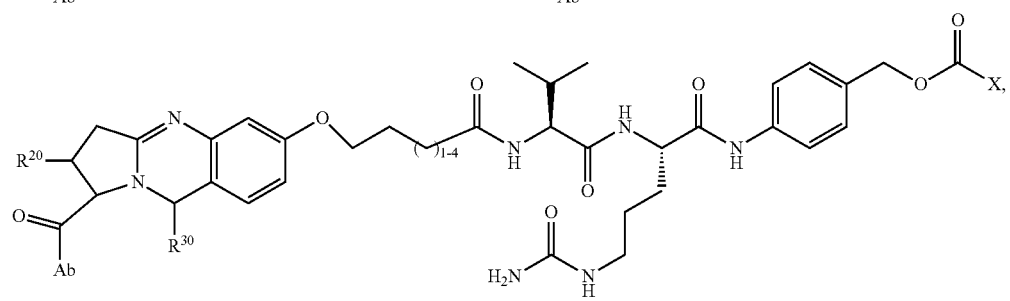
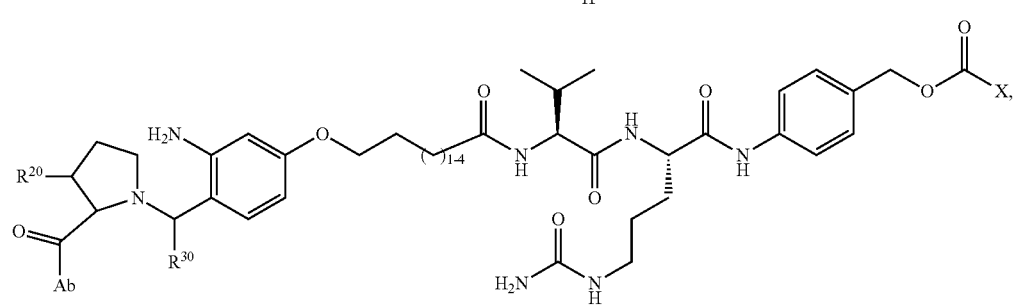
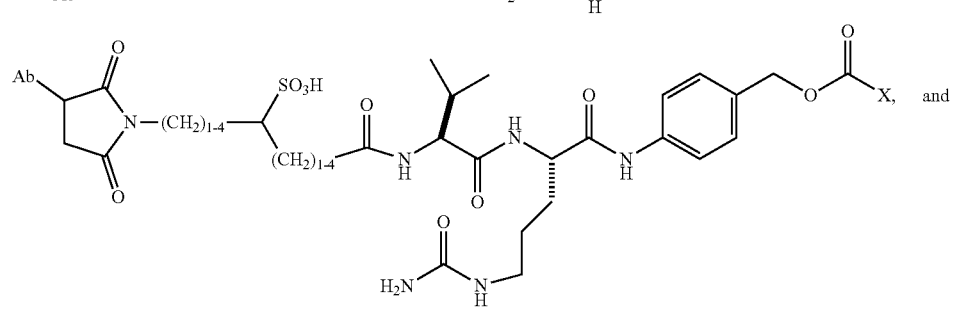

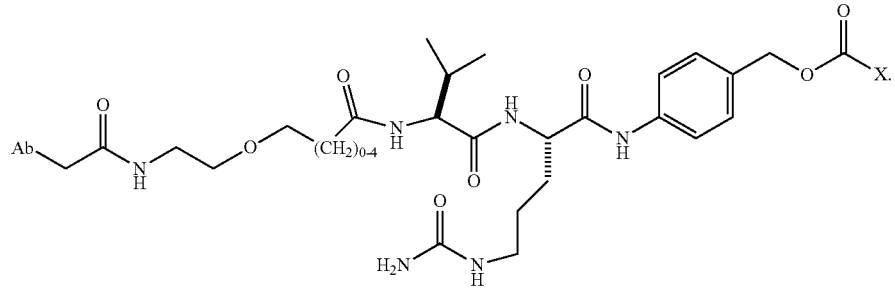

Embodiment 111. In embodiment 110, X is

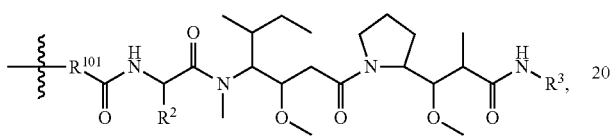

wherein $R^{101}$, $R^2$ and $R^3$ are as defined in embodiments 46, 47, 54 to 59, and 80.

Embodiment 112. In embodiment 111, X is

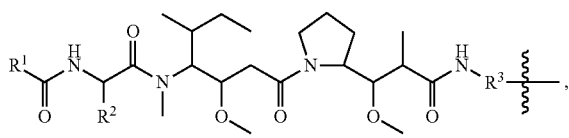

wherein $R^1$, $R^2$ and $R^3$ are as defined in embodiments 65, 66, 73 to 78 and 81.

Embodiment 113. In embodiment 112, X is any one of the species in embodiments 1 or 2.

Embodiment 114. In any one of embodiments 46 to 113, unless otherwise described, Ab can be any antigen binding moiety, and is preferably an antigen or antigen fragment that recognizes a cell surface marker such as those described herein that is characteristic of a targeted cell, such as a cancer cell.

Embodiment 115. In any one of embodiments 46 to 113, unless otherwise described, Ab can be any antigen binding moiety, typically one that recognizes an antigen characteristic of cells to be targeted for pharmaceutical intervention, such as cancer cells. Many suitable antigens are well known in the art; specific ones of special interest are described herein. Typically, Ab is an antibody, which may be isolated or constructed, and may be natural or modified (engineered), or an antibody fragment that retains antigen binding activity similar to the antibody.

Embodiment 116. In any one of the above embodiments, each m is independently selected from 1, 2, 3, 4, 5 and 6. In any of the above embodiments, each m is independently selected from 1, 2, 3, 4 and 5. In any of the above embodiments, each m is independently selected from 1, 2, 3 and 4. In any of the above embodiments, each m is independently selected from 1, 2 and 3. In any of the above embodiments, each m is independently selected from 1 and 2.

Embodiment 117. In any of the above embodiments, each n is independently selected from 1, 2, 3, 4, 5, 6, 7, 8, 9, 10, 11 and 12. In any of the above embodiments, each n is independently selected from 1, 2, 3, 4, 5, 6, 7, 8, 9, 10 and 11. In any of the above embodiments, each n is independently selected from 1, 2, 3, 4, 5, 6, 7, 8, 9 and 10. In any of the above embodiments, each n is independently selected from 1, 2, 3, 4, 5, 6, 7, 8 and 9. In any of the above embodiments, each n is independently selected from 1, 2, 3, 4, 5, 6, 7 and 8. In any of the above embodiments, each n is independently selected from 1, 2, 3, 4, 5, 6 and 7. In any of the above embodiments, each n is independently selected from 1, 2, 3, 4, 5 and 6. In any of the above embodiments, each n is independently selected from 1, 2, 3, 4 and 5. In any of the above embodiments, each n is independently selected from 1, 2, 3 and 4. In any of the above embodiments, each n is independently selected from 1, 2 and 3. In any of the above embodiments, each n is independently selected from 1 and 2.

Embodiment 118. In any one of embodiments 46 to 114, each y is independently selected from 1, 2, 3, 4, 5, 6, 7, 8, 9, 10, 11 and 12. In any of the above embodiments, each y is independently selected from 1, 2, 3, 4, 5, 6, 7, 8, 9, 10 and 11. In any of the above embodiments, each y is independently selected from 1, 2, 3, 4, 5, 6, 7, 8, 9 and 10. In any of the above embodiments, each y is independently selected from 1, 2, 3, 4, 5, 6, 7, 8 and 9. In any of the above embodiments, each y is independently selected from 1, 2, 3, 4, 5, 6, 7 and 8. In any of the above embodiments, each y is independently selected from 1, 2, 3, 4, 5, 6 and 7. In any of the above embodiments, each y is independently selected from 1, 2, 3, 4, 5 and 6. In any of the above embodiments, each y is independently selected from 1, 2, 3, 4 and 5. In any of the above embodiments, each y is independently selected from 1, 2, 3 and 4. In any of the above embodiments, each y is independently selected from 1, 2 and 3. In any of the above embodiments, each y is independently selected from 1 and 2.

Embodiment 119. The compound according to embodiment 3, wherein $R^3$ is

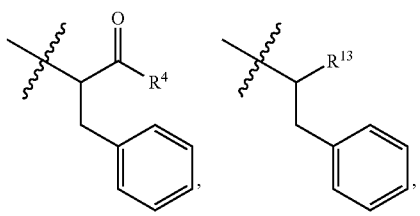

503
-continued

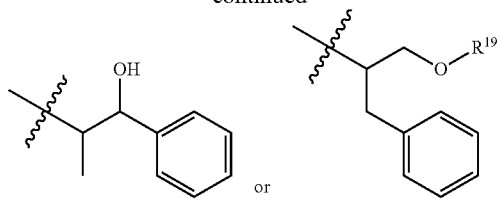

and $R^{19}$ is H.

Embodiment 120. The compound according to any one of embodiments 3 to 6, 18-26, 32, 33, 45 and 81 to 87, wherein:

$R^1$ is

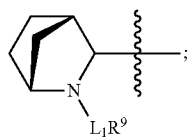

$R^2$ is methyl, ethyl, isopropyl or sec-butyl; $R^3$ is

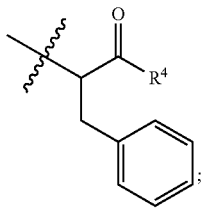

$R^4$ is —OH; $R^9$ is

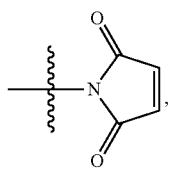

L is $L_1$, wherein $L_1$ is selected from —$(CH_2)_m C(\!=\!O)$—, —$C(\!=\!O)(CH_2)_m$—, —$(CH_2)_m(O(CH_2)_m)_n C(\!=\!O)$—, and —$C(\!=\!O)((CH_2)_m O)_n(CH_2)_m$—;

each m is independently selected from 1, 2, 3, 4, 5, 6, 7, 8, 9 and 10, and each n is independently selected from 1, 2, 3, 4, 5, 6, 7, 8, 9, 10, 11, 12, 13, 14, 15, 16, 17 and 18.

Embodiment 121. The compound according to any one of embodiments 3 to 6, 18-26, 32, 33, 45 and 81 to 87, wherein:

504

$R^1$ is

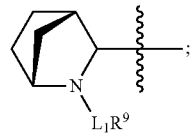

$R^2$ is methyl, ethyl, isopropyl or sec-butyl;

L is $L_1$, wherein $L_1$ is selected from —$(CH_2)_m C(\!=\!O)$—, —$C(\!=\!O)(CH_2)_m$—, —$(CH_2)_m(O(CH_2)_m)_n C(\!=\!O)$—, —$C(\!=\!O)((CH_2)_m O)_n(CH_2)_m$—, —$(CH_2)_m X_3(CH_2)_m (O(CH_2)_m)_n C(\!=\!O)$— and —$C(\!=\!O)((CH_2)_m O)_n (CH_2)_m X_3(CH_2)_m$—;

$R^3$ is

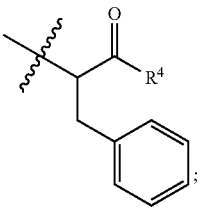

$R^4$ is —OH; $R^9$ is

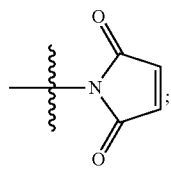 [SMILES: *N1C(=O)C=CC1=O]

$X_3$ is

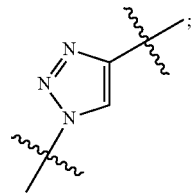 [SMILES: *c1cn(*)nn1]

each m is independently selected from 1, 2, 3, 4, 5, 6, 7, 8, 9 and 10, and each n is independently selected from 1, 2, 3, 4, 5, 6, 7, 8, 9, 10, 11, 12, 13, 14, 15, 16, 17 and 18.

---

We claim:
1. An immunoconjugate of Formula (III):

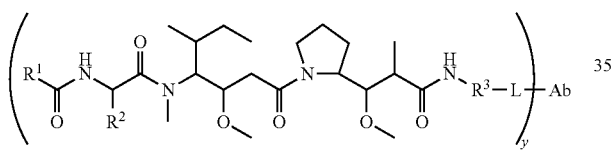

Formula (III)

wherein:
Ab represents an antigen binding moiety;
L is selected from -$L_1 L_2 L_3 L_4 L_5 L_6$-, -$L_6 L_5 L_4 L_3 L_2 L_1$-, -$L_1 L_2 L_3 L_4 L_5$-, -$L_5 L_4 L_3 L_2 L_1$-, -$L_1 L_2 L_3 L_4$-, -$L_4 L_3 L_2 L_1$-, -$L_1 L_2 L_3$-, -$L_3 L_2 L_1$-, -$L_1 L_2$-, -$L_2 L_1$- and -$L_1$,
wherein
$L_1$ is selected from —$(CH_2)_m$—, —$C(=O)(CH_2)_m$—, —$C(=O)X_1 X_2 C(=O)(CH_2)_m$—, —$C(=O)X_1 X_2 C(=O)(CH_2)_m NR^{12} C(=O)(CH_2)_m$—, —$C(=O)X_1 X_2 C(=O)(CH_2)_m X_3 (CH_2)_m$—, —$C(=O)X_1 X_2 C(=O)((CH_2)_m O)_n (CH_2)_m$—, —$C(=O)X_1 X_2 C(=O)((CH_2)_m O)_n (CH_2)_m NR^{12} C(=O)(CH_2)_m$—, —$C(=O)X_1 X_2 C(=O)((CH_2)_m O)_n (CH_2)_m NR^{12} C(=O)(CH_2)_m X_3 (CH_2)_m$—, —$C(=O)X_1 X_2 C(=O)(CH_2)_m$—, —$C(=O)X_1 X_2 C(=O)(CH_2)_m NR^{12} C(=O)((CH_2)_m O)_n (CH_2)_m$—, —$C(=O)X_1 X_2 C(=O)(CH_2)_m NR^{12} C(=O)((CH_2)_m O)_n (CH_2)_m X_3 (CH_2)_m$—, —$C(=O)X_1 X_2 (CH_2)_m X_3 (CH_2)_m$—, —$C(=O)X_1 X_2 ((CH_2)_m O)_n (CH_2)_m$—, —$C(=O)X_1 X_2 ((CH_2)_m O)_n (CH_2)_m NR^{12} C(=O)(CH_2)_m$—, —$C(=O)X_1 X_2 ((CH_2)_m O)_n (CH_2)_m NR^{12} C(=O)(CH_2)_m X_3 (CH_2)_m$—, —$C(=O)X_1 X_2 ((CH_2)_m O)_n (CH_2)_m X_3 (CH_2)_m$—, —$C(=O)X_1 X_2 (CH_2)_m NR^{12} ((CH_2)_m O)_n (CH_2)_m$—, —$C(=O)X_1 X_2 C(=O)NR^{12} ((CH_2)_m O)_n (CH_2)_m X_3 (CH_2)_m$—, —$(CH_2)_m NR^{12} C(=O)(CH_2)_m$—, —$C(=O)((CH_2)_m O)_n (CH_2)_m$—, —$(CH_2)_m S(=O)_2 ((CH_2)_m O)_n (CH_2)_m$—, —$C(=O)(CH_2)_m NR^{12}(CH_2)_m$—, —$C(=O)NR^{12}(CH_2)_m$—, —$C(=O)NR^{12}(CH_2)_m X_3 (CH_2)_m$—, —$C(=O)NH(CH_2)_m NR^{12} C(=O)X_2 X_2 C(=O)(CH_2)_m$—, —$C(=O)X_1 C(=O)NR^{12}(CH_2)_m NR^{12} C(=O)(CH_2)_m$—, —$C(=O)X_1 C(=O)NR^{12}(CH_2)_m X_3 (CH_2)_m$—, —$C(=O)NR^{12}(CH_2)_m NR^{12} C(=O)(CH_2)_m$—, —$C(=O)NR^{12}(CH_2)_m NR^{12} C(=O)(CH_2)_m X_3 (CH_2)_m$—,

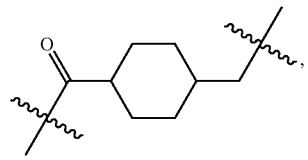

—$(CH_2)_m C(=O)NR^{12}(CH_2)_m NR^{12} C(=O)(CH_2)_m$—, —$(CH_2)_m C(=O)$—, —$(CH_2)_m C(=O)X_2 X_1 C(=O)$—, —$(CH_2)_m X_3 (CH_2)_m C(=O)X_2 X_1 C(=O)$—, —$(CH_2)_m C(=O)NR^{12}(CH_2)_m$—, —$(CH_2)_m X_3 (CH_2)_m C(=O)NR^{12}(CH_2)_m$—, —$(CH_2)_m NR^{12} C(=O)(CH_2)_m X_3 (CH_2)_m$—, —$(CH_2)_m (O(CH_2)_m)_n C(=O)$—, —$(CH_2)_m (O(CH_2)_m)_n S(=O)_2 (CH_2)_m$—, —$(CH_2)_m NR^{12}(CH_2)_m C(=O)$—, —$(CH_2)_m NR^{12} C(=O)$—, —$(CH_2)_m C(=O)X_2 X_1 C(=O)NR^{12}(CH_2)_m NHC(=O)$—, —$(CH_2)_m C(=O)NR^{12}(CH_2)_m NR^{12} C(=O)X_1$—, —$(CH_2)_m C(=O)NR^{12}(CH_2)_m NR^{12} C(=O)$—,

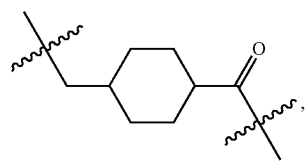 [SMILES: *CC1CCC(C(*)=O)CC1]

-$((CH_2)_m O)_n (CH_2)_m$—, —$(CH_2)_m (O(CH_2)_m)_n$-, —$(CH_2)_m (O(CH_2)_m)_n X_3 (CH_2)_m$—, —$(CH_2)_m X_3 ((CH_2)_m O)_n (CH_2)_m$—, —$(CH_2)_m X_3 (CH_2)_m C(=O)$—,

—C(=O)(CH$_2$)$_m$X$_3$(CH$_2$)$_m$—, —(CH$_2$)$_m$X$_3$(CH$_2$)$_m$(O(CH$_2$)$_m$)$_n$C(=O)—, —C(=O)((CH$_2$)$_m$O)$_n$(CH$_2$)$_m$X$_3$(CH$_2$)$_m$—, —(CH$_2$)$_m$C(=O)NR$^{12}$(CH$_2$)$_m$C(=O)—, —C(=O)(CH$_2$)$_m$NR$^{12}$C(=O)(CH$_2$)$_m$—, —(CH$_2$)$_m$OC(=O)NR$^{12}$(CH$_2$)$_m$C(=O)O(CH$_2$)$_m$—, —S(=O)$_2$(CH$_2$)$_m$NR$^{12}$C(=O)O(CH$_2$)$_m$—, —(CH$_2$)$_m$OC(=O)NR$^{12}$(CH$_2$)$_m$S(=O)$_2$—, —(CH$_2$)$_m$C(=O)NR$^{12}$(CH$_2$)$_m$(O(CH$_2$)$_m$)$_n$C(=O)—, —C(=O)((CH$_2$)$_m$O)$_n$(CH$_2$)$_m$NR$^{12}$C(=O)(CH$_2$)$_m$—, —(CH$_2$)$_m$C(=O)NR$^{12}$(CH$_2$)$_m$C(=O)NR$^{12}$(CH$_2$)$_m$—, —(CH$_2$)$_m$NR$^{12}$C(=O)(CH$_2$)$_m$NR$^{12}$C(=O)(CH$_2$)$_m$—, —C(=O)NR$^{12}$(CH$_2$)$_m$NR$^{12}$C(=O)—, —(CH$_2$)$_m$S(CH$_2$)$_m$—, —NR$^{12}$C(=O)(CH$_2$)$_m$—, —NR$^{12}$C(=O)(CH$_2$)$_m$X$_3$(CH$_2$)$_m$—, —(CH$_2$)$_m$X$_3$(CH$_2$)$_m$C(=O)NR$^{12}$—, —(CH$_2$)$_m$C(=O)NR$^{12}$—, —(CH$_2$)$_m$NR$^{12}$(CH$_2$)$_m$—, —(CH$_2$)$_m$X$_3$(CH$_2$)$_m$—, —((CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$-, —NR$^{12}$(CH$_2$)$_m$—, —NR$^{12}$C(R$^{12}$)$_2$(CH$_2$)$_m$—, —(CH$_2$)$_m$C(R$^{12}$)$_2$NR$^{12}$—, —(CH$_2$)$_m$C(=O)NR$^{12}$(CH$_2$)$_m$NR$^{12}$—, —NR$^{12}$(CH$_2$)$_m$NR$^{12}$C(=O)(CH$_2$)$_m$—, —NR$^{12}$C(R$^{12}$)$_2$(CH$_2$)$_m$NR$^{12}$C(=O)(CH$_2$)$_m$—, —(CH$_2$)$_m$C(=O)NR$^{12}$(CH$_2$)$_m$C(R$^{12}$)$_2$NR$^{12}$—, —NR$^{12}$(CH$_2$)$_m$X$_3$(CH$_2$)$_m$—, —NR$^{12}$C(R$^{12}$)$_2$(CH$_2$)$_m$X$_3$(CH$_2$)$_m$—, —(CH$_2$)$_m$X$_3$(CH$_2$)$_m$C(R$^{12}$)$_2$NR$^{12}$—, —NR$^{12}$C(R$^{12}$)$_2$(CH$_2$)$_m$OC(=O)NR$^{12}$(CH$_2$)$_m$—, —(CH$_2$)$_m$NR$^{12}$C(=O)O(CH$_2$)$_m$C(R$^{12}$)$_2$NR$^{12}$—, —NR$^{12}$C(R$^{12}$)$_2$(CH$_2$)$_m$OC(=O)NR$^{12}$(CH$_2$)$_m$X$_3$(CH$_2$)$_m$—, —NR$^{12}$(CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NR$^{12}$—, —NR$^{12}$(CH$_2$)$_m$O)$_n$(CH$_2$)$_m$—, —(CH$_2$)$_m$(O(CH$_2$)$_m$)$_n$NR$^{12}$—, —NR$^{12}$(CH$_2$)$_m$O)$_n$(CH$_2$)$_m$—, —(CH$_2$)$_m$X$_3$(CH$_2$)$_m$NR$^{12}$C(=O)O(CH$_2$)$_m$C(R$^{12}$)$_2$NR$^{12}$—, —NR$^{12}$C(R$^{12}$)$_2$(CH$_2$)$_m$OC(=O)NR$^{12}$((CH$_2$)$_m$O)$_n$(CH$_2$)$_m$—, —(CH$_2$)$_m$(O(CH$_2$)$_m$)$_n$NR$^{12}$C(=O)O(CH$_2$)$_m$C(R$^{12}$)$_2$NR$^{12}$—, —(CH$_2$)$_m$X$_3$(CH$_2$)$_m$NR$^{12}$—, —NR$^{12}$((CH$_2$)$_m$O)$_n$(CH$_2$)$_m$X$_3$(CH$_2$)$_m$—, —(CH$_2$)$_m$X$_3$(CH$_2$)$_m$(O(CH$_2$)$_m$)$_n$NR$^{12}$—, —(CH$_2$)$_m$NR$^{12}$—, —NR$^{12}$((CH$_2$)$_m$O)$_n$(CH$_2$)$_m$—, —NR$^{12}$((CH$_2$)$_m$O)$_n$(CH$_2$)$_m$NR$^{12}$C(=O)(CH$_2$)$_m$—, —(CH$_2$)$_m$C(=O)NR$^{12}$(CH$_2$)$_m$(O(CH$_2$)$_m$)$_n$NR$^{12}$—, —(CH$_2$)$_m$(O(CH$_2$)$_m$)$_n$NR$^{12}$—, —(C(R$_{12}$)$_2$)$_m$—, —(CH$_2$CH$_2$O)$_n$—, —(OCH$_2$CH$_2$)$_n$—, —(CH$_2$)$_m$O(CH$_2$)$_m$—, —S(=O)$_2$(CH$_2$)$_m$—, —(CH$_2$)$_m$S(=O)$_2$—, —S(=O)$_2$(CH$_2$)$_m$NR$^{12}$C(=O)(CH$_2$)$_m$—, —(CH$_2$)$_m$C(=O)NR$^{12}$(CH$_2$)$_m$S(=O)$_2$—, —S(=O)$_2$(CH$_2$)$_m$X$_3$(CH$_2$)$_m$—, —(CH$_2$)$_m$X$_3$(CH$_2$)$_m$S(=O)$_2$—, —(CH$_2$)$_m$X$_2$X$_1$C(=O)—, —C(=O)X$_2$X$_1$(CH$_2$)$_m$—, —(CH$_2$)$_m$(O(CH$_2$)$_m$)$_n$C(=O)X$_2$X$_1$C(=O)—, —C(=O)X$_1$X$_2$C(=O)((CH$_2$)$_m$O)$_n$(CH$_2$)$_m$—, —(CH$_2$)$_m$(O(CH$_2$)$_m$)$_n$X$_2$X$_1$C(=O)—, —(CH$_2$)$_m$X$_3$(CH$_2$)$_m$X$_2$X$_1$C(=O)—, —C(=O)X$_2$X$_1$(CH$_2$)$_m$X$_3$(CH$_2$)$_m$—, —(CH$_2$)$_m$X$_3$(CH$_2$)$_m$(O(CH$_2$)$_m$)$_n$X$_2$X$_1$C(=O)—, —(CH$_2$)$_m$X$_3$(CH$_2$)$_m$C(=O)NR$^{12}$(CH$_2$)$_m$NR$^{12}$C(=O)—, —(CH$_2$)$_m$X$_3$(CH$_2$)$_m$C(=O)NR$^{12}$(CH$_2$)$_m$C(=O)—, —C(=O)(CH$_2$)$_m$NR$^{12}$C(=O(CH$_2$)$_m$X$_3$(CH$_2$)$_m$—, —(CH$_2$)$_m$X$_3$(CH$_2$)$_m$C(=O)NR$^{12}$(CH$_2$)$_m$(O(CH$_2$)$_m$)$_n$C(=O)—, —C(=O)((CH$_2$)$_m$O)$_n$(CH$_2$)$_m$NR$^{12}$C(=O)(CH$_2$)$_m$X$_3$(CH$_2$)$_m$—, —(CH$_2$)$_m$NR$^{12}$C(=O)X$_1$X$_2$C(=O)(CH$_2$)$_m$—, —(CH$_2$)$_m$C(=O)X$_2$X$_1$C(=O)NR$^{12}$(CH$_2$)$_m$—, —X$_4$X$_1$X$_2$C(=O)(CH$_2$)$_m$—, —(CH$_2$)$_m$C(=O)X$_2$X$_1$X$_4$—, —X$_1$C(=O)(CH$_2$)$_m$NHC(=O)(CH$_2$)$_m$—, —(CH$_2$)$_m$C(=O)NH(CH$_2$)$_m$C(=O)X$_1$—, —C(=O)CHR$^{aa}$NR$^{12}$—, —CHR$^{aa}$C(=O)—, —C(=O)NR$^{12}$—, —C(=O)O—, —S—, —SCH$_2$C(=O)NR$^{12}$—, —NR$^{12}$C(=O)CH$_2$S—, —S(=O)$_2$CH$_2$CH$_2$S—, —SCH$_2$CH$_2$S(=O)$_2$—, —(CH$_2$)$_2$S(=O)$_2$CH$_2$CH$_2$S—, —SCH$_2$CH$_2$S(=O)$_2$CH$_2$CH$_2$—, —NR$^{12}$C(=S)—, —(CH$_2$)$_m$X$_3$(O(CH$_2$)$_m$)$_n$C(=O)—, —C(=O)((CH$_2$)$_m$O)$_n$X$_3$(CH$_2$)$_m$—, —(CH$_2$)$_m$NR$^{12}$C(=O)((CH$_2$)$_m$O)$_n$(CH$_2$)$_m$—, —(CH$_2$)$_m$(O(CH$_2$)$_m$)$_n$C(=O)NR$^{12}$(CH$_2$)$_m$—, —(CH$_2$)$_m$NR$^{12}$C(=O)NR$^{12}$(CH$_2$)$_m$—, —(CH$_2$)$_m$X$_3$(CH$_2$)$_m$NR$^{12}$C(=O)—, —C(=O)NR$^{12}$(CH$_2$)$_m$X$_3$(CH$_2$)$_m$—, —NR$_{12}$S(=O)$_2$(CH$_2$)$_m$X$_3$(CH$_2$)$_m$—, —(CH$_2$)$_m$X$_3$(CH$_2$)$_m$S(=O)$_2$NR$_{12}$—,

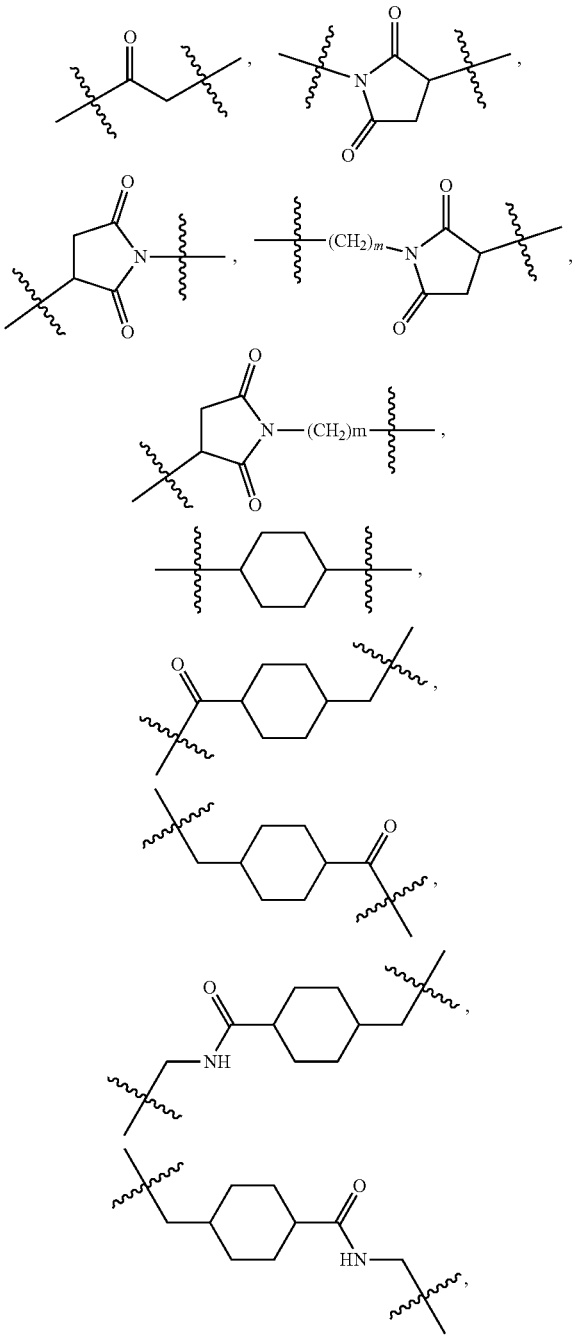

533
-continued
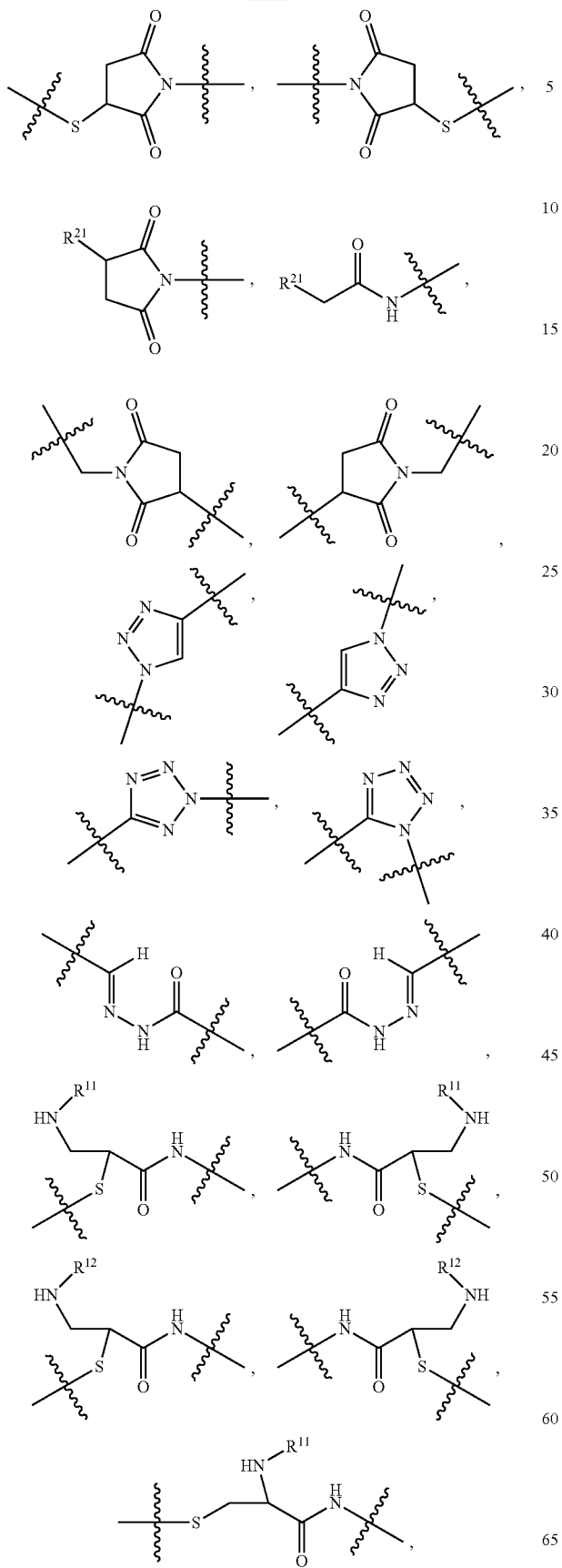
534
-continued
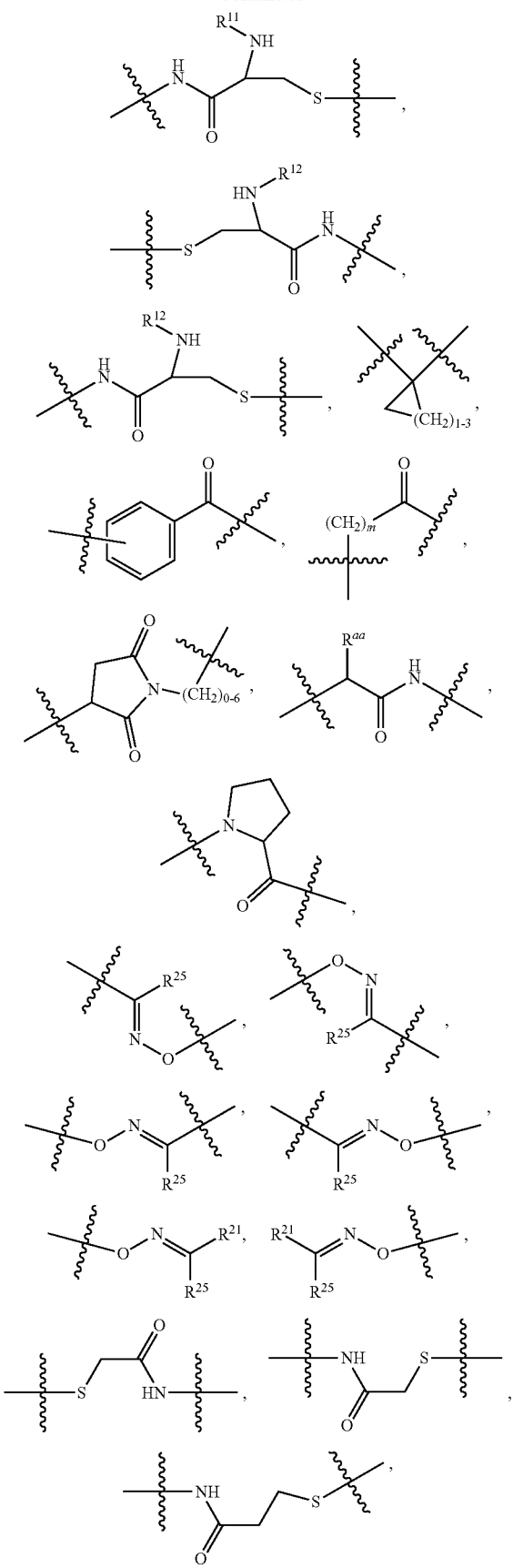

535
-continued
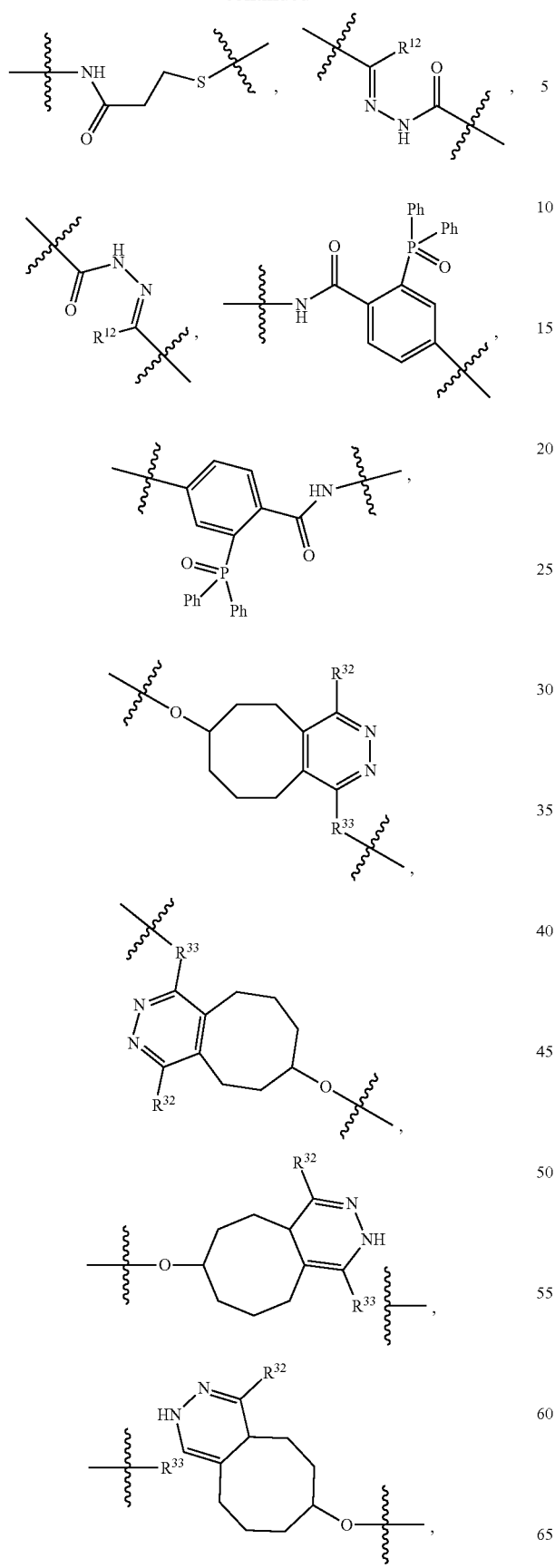
536
-continued
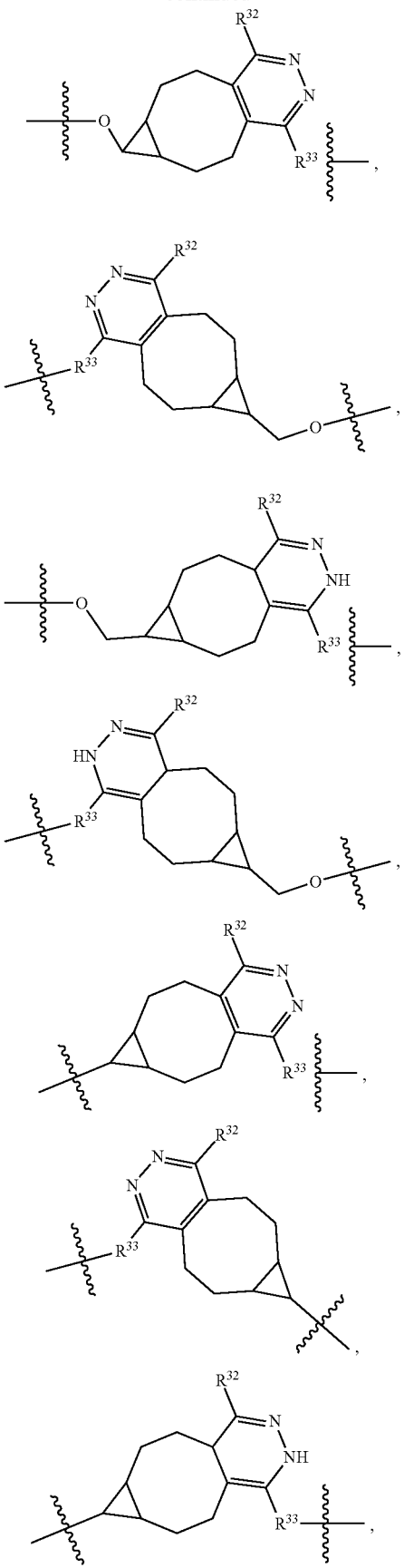

537
-continued
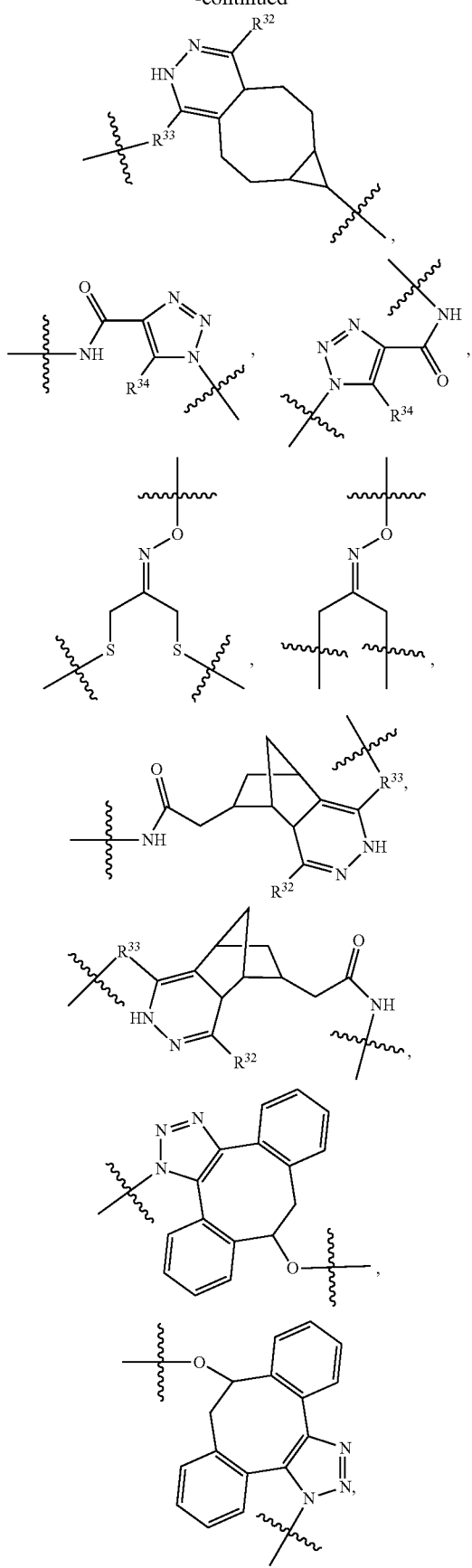
538
-continued
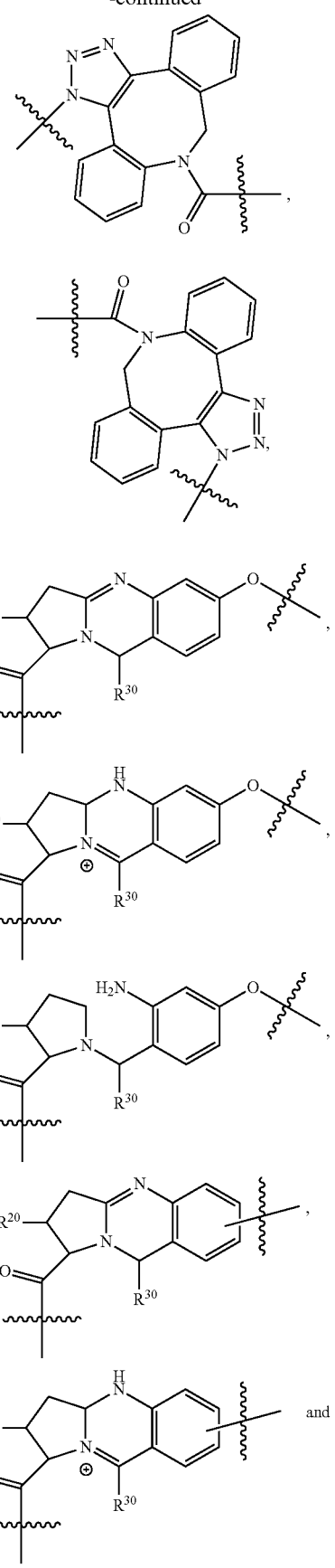

-continued

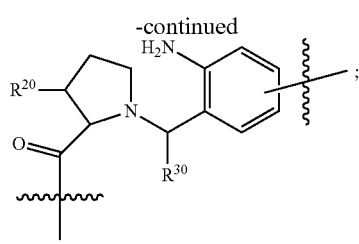

$R^{20}$ is H or Me, and $R^{30}$ is H, —CH₃ or phenyl;
$R^{21}$ is each $R^{25}$ is independently selected from H or $C_{1-4}$ alkyl;

$R^{aa}$ is a side chain of an amino acid selected from glycine, alanine, tryptophan, tyrosine, phenylalanine, leucine, isoleucine, valine, asparagine, glutamic acid, glutamine, aspatic acid, histidine, arginine, lysine, cysteine, methionine, serine, threonine, phenylglycine and t-butylglycine;

$R^{32}$ is independently selected from H, $C_{1-4}$ alkyl, phenyl, pyrimidine and pyridine;

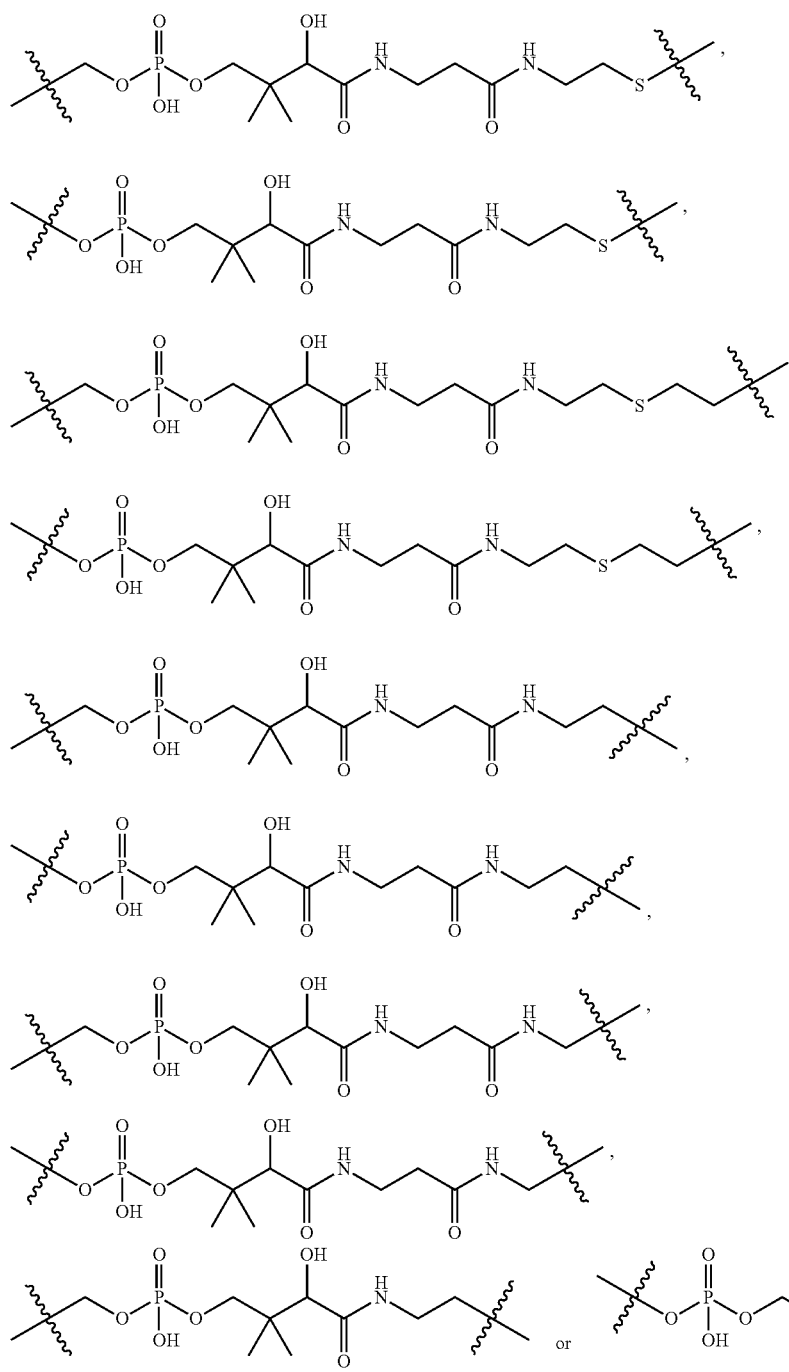

$R^{33}$ is independently selected from
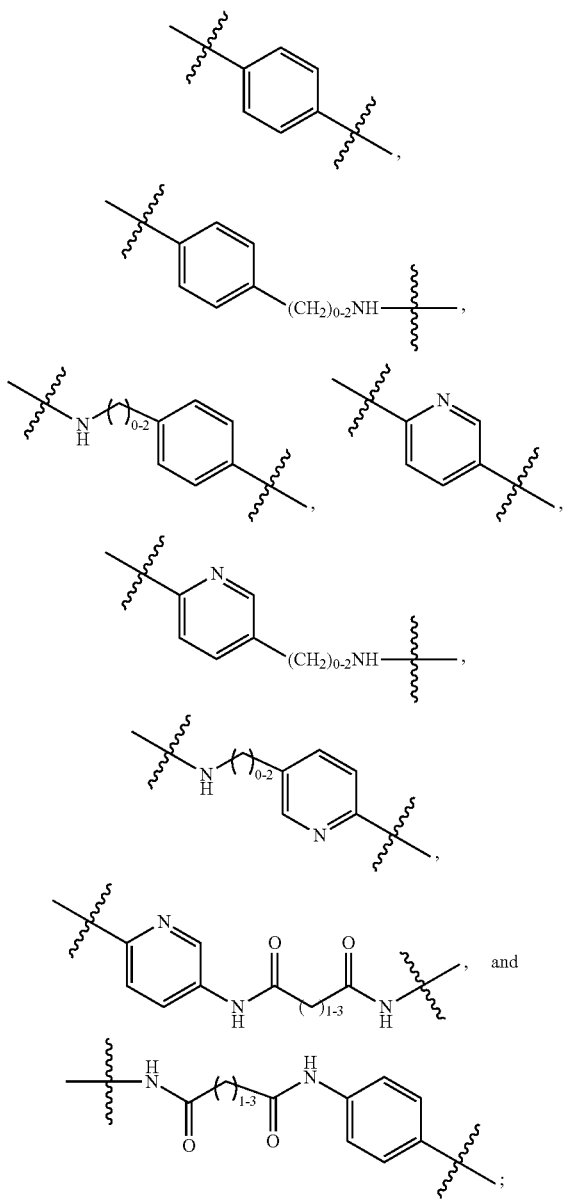
$R^{34}$ is independently selected from H, $C_{1-4}$ alkyl, and $C_{1-6}$ haloalkyl;
$X_1$ is self immolative spacer selected from
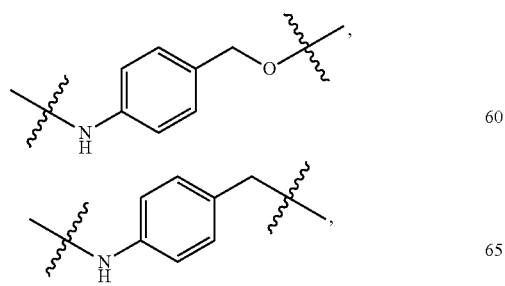
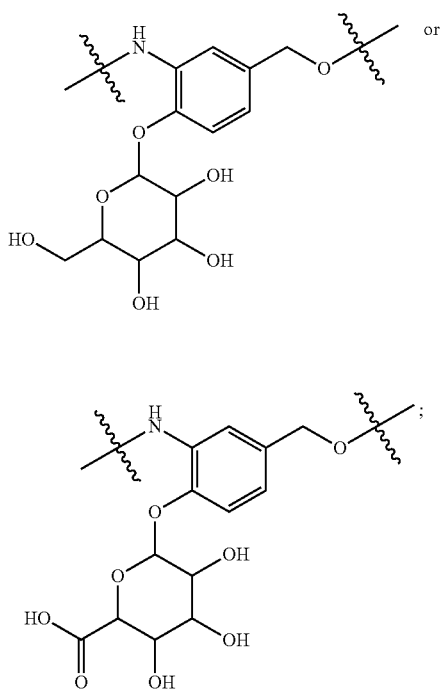
$X_2$ is dipeptide selected from
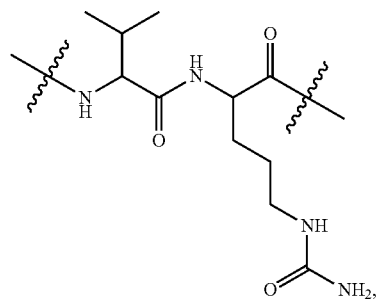
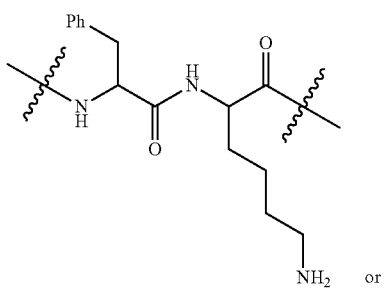
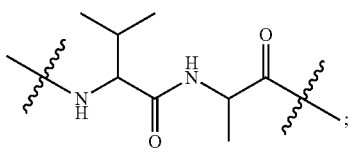

$X_3$ is

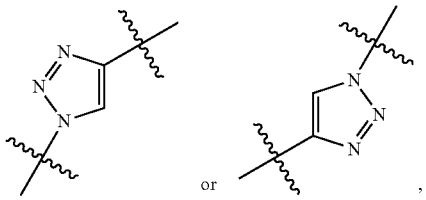 [SMILES: *c1cn(*)nn1 ; *c1cn(*)nn1]

or and $X_4$ is

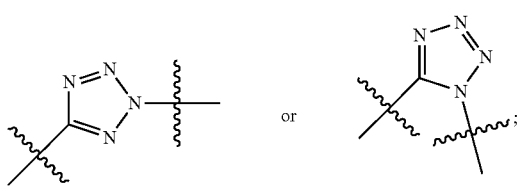 [SMILES: *c1nnn(*)n1 ; *c1nnnn1*]

or and $L_2$, $L_3$, $L_4$, $L_5$, and $L_6$ are each independently selected from a bond and $L_1$;

y is an integer from 1 to 16;

$R^1$ is a 6 membered heterocycloalkyl containing 1-2 N heteroatoms and a $C_1$-$C_2$alkylene bridge, wherein the 6 membered heterocycloalkyl is unsubstituted or substituted with 1 to 3 substituents independently selected from $R^5$ and $R^6$;

or $R^1$ is a 5-8 membered fused bicyclic heterocycloalkyl containing 1-2 N heteroatoms, wherein the 5-8 membered fused bicyclic heterocycloalkyl is unsubstituted or substituted with 1 to 3 substituents independently selected from $R^5$ and $R^6$;

$R^2$ is —$C_1$-$C_6$alkyl;

$R^3$ is

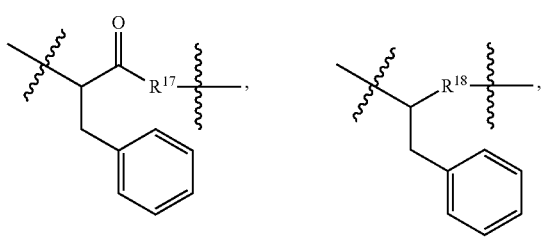

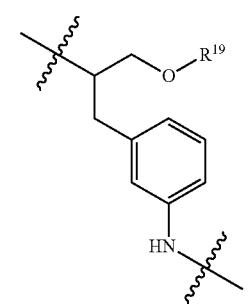

or

-continued

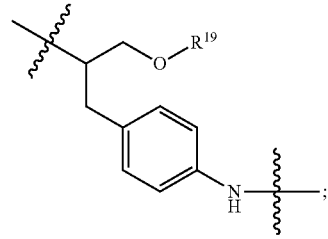

$R^5$ is $C_1$-$C_6$alkyl, —C(=O)$R^{11}$, —(CH$_2$)$_m$OH, —C(=O)(CH$_2$)$_m$OH, —C(=O)((CH$_2$)$_m$O)$_n$$R^{12}$, —((CH$_2$)$_m$O)$_n$$R^{12}$, or $C_1$-$C_6$alkyl which is optionally substituted with —CN, —C(=O)NH$_2$ or 1 to 5 hydroxyl;

$R^6$ is halo, oxo, OH, $C_1$-$C_6$alkyl, —N($R^{14}$)$_2$, —$R^{16}$ and —NR$^{12}$C(=O)$R^{11}$;

$R^{11}$ is $C_1$-$C_6$alkyly or $C_1$-$C_6$alkyl which is optionally substituted with 1 to 5 hydroxyl;

each $R^{12}$ is independently selected from H and $C_1$-$C_6$alkyly;

each $R^{14}$ is independently selected from H and $C_1$-$C_6$alkyly;

$R^{16}$ is an N-linked 4-8 membered heterocycloalkyl containing 1-2 heteroatoms independently selected from N and O;

$R^{17}$ is a bond, —NH—, —NHS(=O)$_2$—,

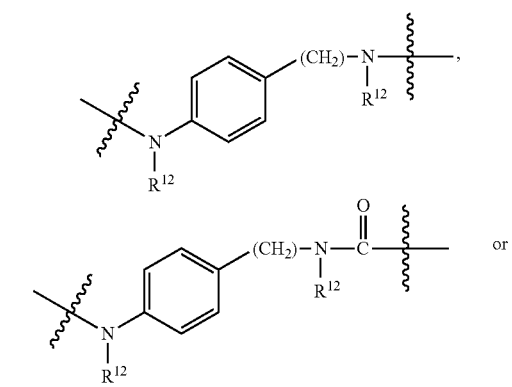

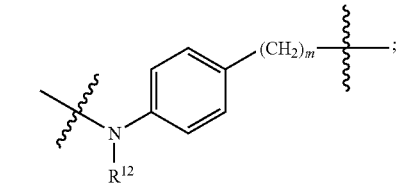

$R^{18}$ is a bond,

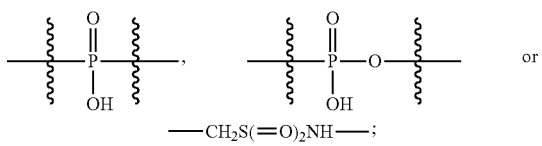

—CH$_2$S(=O)$_2$NH—;

$R^{19}$ is H or $C_1$-$C_6$alkyly;

each m is independently selected from 1, 2, 3, 4, 5, 6, 7, 8, 9 and 10, and each n is independently selected from 1, 2, 3, 4, 5, 6, 7, 8, 9, 10, 11, 12, 13, 14, 15, 16, 17 and 18.

2. The immunoconjugate of claim 1, wherein the immunoconjugate of Formula (III) is an immunoconjugate of Formula (IIIb) or Formula (IIIc):
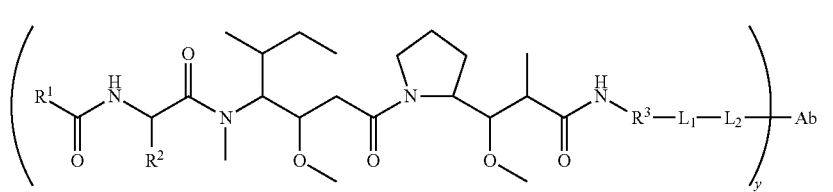
Formula (IIIb)
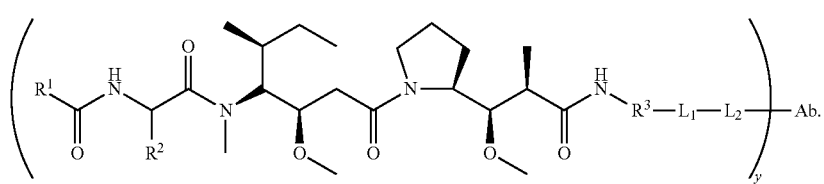
Formula (IIIc)
3. The immunoconjugate of claim 2, wherein $R^1$ is
4. The immunoconjugate of claim 3, wherein $R^3$ is
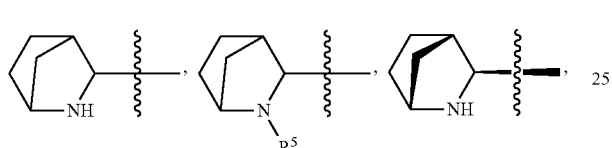
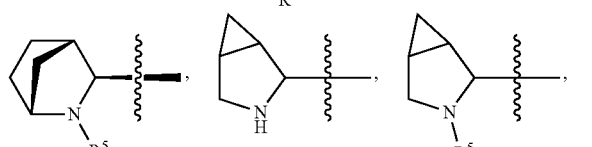
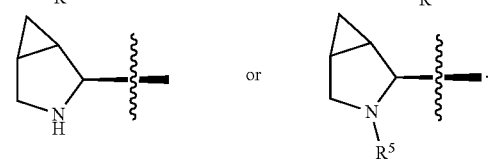
or
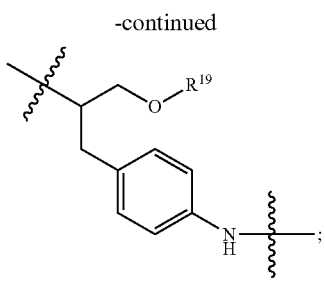
-continued
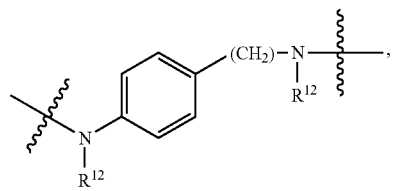
$R^{17}$ is —NH—, —NHS(=O)$_2$—,
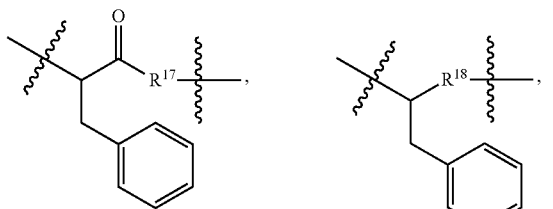
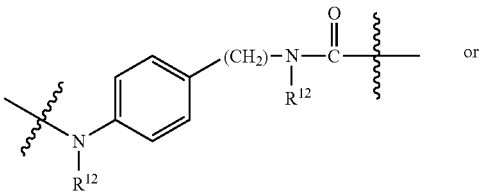
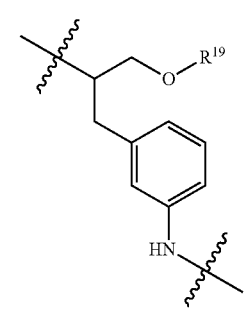
or
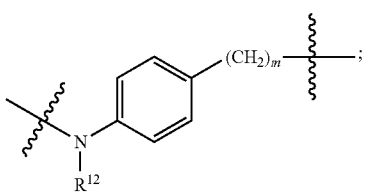

$R^{18}$ is

[structure: phosphate group with OH] or —CH$_2$S(=O)$_2$NH—, and $R^{19}$ is H or —CH$_3$.

5. The immunoconjugate of claim 4, wherein $R^5$ is —CH$_3$, —C(=O)CH$_3$, —C(=O)((CH$_2$)$_2$O)$_{12}$R$^{12}$, —C(=O)((CH$_2$)$_2$O)$_8$R$^{12}$, or —C(=O)((CH$_2$)$_2$O)$_4$R$^{12}$.

6. The immunoconjugate of claim 5, wherein $R^{12}$ is H, —CH$_3$ or —CH$_2$CH$_3$.

7. The immunoconjugate of claim 6, wherein $R^2$ is methyl, ethyl, isopropyl or sec-butyl.

8. The immunoconjugate of claim 7, wherein:

$L_1$ is selected from —*C(=O)(CH$_2$)$_m$—, —(CH$_2$)$_m$—, —*(CH$_2$)$_m$X$_3$(CH$_2$)$_m$—, —*(CH$_2$)$_m$NHC(=O)X$_1$X$_2$C(=O)(CH$_2$)$_m$—, —*X$_4$X$_1$X$_2$C(=O)(CH$_2$)$_m$—, —*X$_1$C(=O)(CH$_2$)$_m$NHC(=O)(CH$_2$)$_m$—, —*(CH$_2$)$_m$C(=O)NH(CH$_2$)$_m$NHC(=O)(CH$_2$)$_m$—, —*S(=O)$_2$(CH$_2$)$_m$X$_3$(CH$_2$)$_m$—,

[structure: cyclohexane with carbonyl]

—*C(=O)NH (CH$_2$)$_m$—, —*C(=O)X$_1$X$_2$C(=O)(CH$_2$)$_m$—, —*C(=O)((CH$_2$)$_m$O)$_n$(CH$_2$)$_m$—, —*((CH$_2$)$_m$O)$_n$(CH$_2$)$_m$—, —*(CH$_2$)$_m$S(=O)$_2$((CH$_2$)$_m$O)$_n$(CH$_2$)$_m$—, —*C(=O)(CH$_2$)$_m$NR$^{12}$(CH$_2$)$_m$—, —*C(=O)(CH$_2$)$_m$NH(CH$_2$)$_m$—, —*(CH$_2$)$_m$(O(CH$_2$)$_m$)$_n$—, —*C(=O)(CH$_2$)$_m$X$_3$(CH$_2$)$_m$—, —*C(=O)NH(CH$_2$)$_m$—, —*C(=O)((CH$_2$)$_m$O)$_n$(CH$_2$)$_m$X$_3$(CH$_2$)$_m$—, —*(CH$_2$)$_m$NHC(=O)(CH$_2$)$_m$—, —*C(=O)NH(CH$_2$)$_m$NHC(=O)(CH$_2$)$_m$—, —*C(=O)(CH$_2$)$_m$NHC(=O)(CH$_2$)$_m$—, —*C(=O)((CH$_2$)$_m$O)$_n$(CH$_2$)$_m$NHC(=O)(CH$_2$)$_m$—, —*((CH$_2$)$_m$O)$_n$(CH$_2$)$_m$X$_3$(CH$_2$)$_m$—, —(CH$_2$)$_m$C(=O)NH (CH$_2$)$_m$NHC(=O)(CH$_2$)$_m$—, —*NHS(=O)$_2$(CH$_2$)$_m$X$_3$(CH$_2$)$_m$—, —*(CH$_2$)$_m$NHC(=O)(CH$_2$)$_m$NHC(=O)(CH$_2$)$_m$— and —C(=O)NH(CH$_2$)$_m$NHC(=O)—, wherein the * indicates the point of attachment to $R^3$;

$L_2$ is a bond,

[structures: maleimide, maleimide-thioether, substituted maleimide, amide with R$^{21}$, succinimide-N-CH$_2$, triazole (two isomers), —S—, —SCH$_2$(C=O)NH—, —NHC(=O)CH$_2$S—, hydrazone structures, oxime structures with R$^{25}$, cysteine-linked amides with R$^{11}$, pyrrolo-quinazoline structures with R$^{30}$, R$^{31}$, —S(=O)$_2$CH$_2$CH$_2$S—, —SCH$_2$CH$_2$S(=O)$_2^-$]

$(CH_2)_2S(=O)_2CH_2CH_2S$— or —$SCH_2CH_2S(=O)_2$$CH_2CH_2$—, wherein the * indicates the point of attachment to $L_1$,
and $L_3$, $L_4$, $L_5$ and $L_6$ are a bond.

9. The immunoconjugate of claim 8, wherein:
$L_1$ is selected from —*$C(=O)(CH_2)_m$—, —$(CH_2)_m$—, —*$(CH_2)_mX_3(CH_2)_m$—, —*$C(=O)X_1X_2C(=O)(CH_2)_m$—, —*$((CH_2)_mO)_n(CH_2)_mX_3(CH_2)_m$—, —*$(CH_2)_mNHC(=O)X_1X_2C(=O)(CH_2)_m$—, —*$X_4X_1X_2C(=O)(CH_2)_m$—, —*$X_1C(=O)(CH_2)_mNHC(=O)(CH_2)_m$—, —*$(CH_2)_mC(=O)NH(CH_2)_mNHC(=O)(CH_2)_m$—, —*$S(=O)_2(CH_2)_mX_3(CH_2)_m$—,

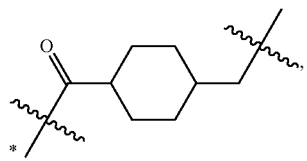 [SMILES: *CC1CCC(C(*)=O)CC1]

*$NHS(=O)_2(CH_2)_mX_3(CH_2)_m$—, —*$C(=O)((CH_2)_mO)_n(CH_2)_m$— and —*$C(=O)NH(CH_2)_m$—,
wherein the * indicates the point of attachment to $R^3$;
$L_2$ is

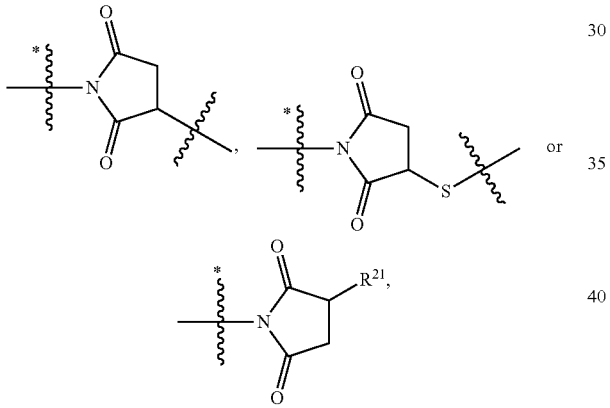

wherein the * indicates the point of attachment to $L_1$, and $L_3$, $L_4$, $L_5$ and $L_6$ are a bond.

10. The immunoconjugate of claim 9, wherein:
$L_1$ is selected from —*$C(=O)(CH_2)_m$—, —$(CH_2)_m$—, —*$(CH_2)_mX_3(CH_2)_m$—, —*$C(=O)X_1X_2C(=O)(CH_2)_m$—, —*$((CH_2)_mO)_n(CH_2)_mX_3(CH_2)_m$—, —*$S(=O)_2(CH_2)_mX_3(CH_2)_m$—,

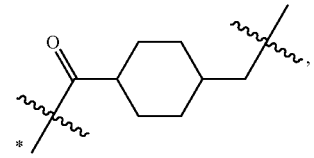

—*$NHS(=O)_2(CH_2)_mX_3(CH_2)_m$—, —*$C(=O)((CH_2)_mO)_n(CH_2)_m$— and —*$C(=O)NH(CH_2)_m$—,
wherein the * indicates the point of attachment to $R^3$;
$L_2$ is

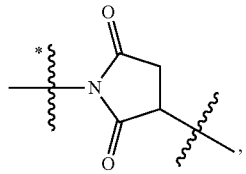 [SMILES: *C1CC(=O)N(*)C1=O]

wherein the * indicates the point of attachment to $L_1$, and $L_3$, $L_4$, $L_5$ and $L_6$ are a bond.

11. A pharmaceutical composition comprising an immunoconjugate of claim 1, and one or more pharmaceutically acceptable carriers.

12. A method of treating cancer, comprising administering to a subject in need thereof a therapeutically effective amount of an immunoconjugate of claim 1.

* * * * *